US007378492B2

(12) United States Patent
Chawla et al.

(10) Patent No.: US 7,378,492 B2

(45) Date of Patent: May 27, 2008

(54) CD40-RELATED RECEPTOR THAT BINDS CD40L

(75) Inventors: Narinder K. Chawla, Union City, CA (US); Henry Yue, Sunnyvale, CA (US); Thomas W. Richardson, Redwood City, CA (US); Joseph P. Marquis, San Jose, CA (US); Patricia M. Lehr-Mason, Morgan Hill, CA (US); Ann E. Gorvad, Livermore, CA (US); Shanya D. Becha, Castro Valley, CA (US); Amy E. Kable, San Francisco, CA (US); Anita Swarnakar, San Francisco, CA (US); Pei Jin, Palo Alto, CA (US); Phillip R. Hawkins, Mountain View, CA (US); David Chien, Los Altos, CA (US); Jayalaxmi Ramkumar, Freemont, CA (US); Uyen K. Tran, San Jose, CA (US); April J. A. Hafalia, Santa Clara, CA (US); Mariah R. Baughn, San Leandro, CA (US); Soo Yeun Lee, Daly City, CA (US); Xin Jiang, Saratoga, CA (US); Alan A. Jackson, Los Gatos, CA (US); Reena Khare, Saratoga, CA (US); Sean A. Bulloch, Cupertino, CA (US)

(73) Assignee: Incyte Corporation, Wilmington, DE (US)

( * ) Notice: Subject to any disclaimer, the term of this patent is extended or adjusted under 35 U.S.C. 154(b) by 0 days.

(21) Appl. No.: 10/504,973

(22) PCT Filed: Feb. 18, 2003

(86) PCT No.: PCT/US03/04902

§ 371 (c)(1),
(2), (4) Date: Aug. 17, 2005

(87) PCT Pub. No.: WO03/070902

PCT Pub. Date: Aug. 28, 2003

(65) Prior Publication Data

US 2006/0121459 A1 Jun. 8, 2006

Related U.S. Application Data

(60) Provisional application No. 60/379,853, filed on May 10, 2002, provisional application No. 60/379,837, filed on May 10, 2002, provisional application No. 60/376,669, filed on Apr. 29, 2002, provisional application No. 60/375,657, filed on Apr. 25, 2002, provisional application No. 60/364,338, filed on Mar. 13, 2002, provisional application No. 60/358,279, filed on Feb. 20, 2002.

(51) Int. Cl.
*C07K 14/705* (2006.01)
*C07K 19/00* (2006.01)

(52) U.S. Cl. .................... 530/350; 435/69.1; 435/69.7; 536/23.4; 536/23.5

(58) Field of Classification Search .................... 435/6, 435/7.21, 69.1, 252.3, 320.1; 530/350; 514/2; 536/23.5
See application file for complete search history.

(56) References Cited

U.S. PATENT DOCUMENTS

| | | | |
|---|---|---|---|
| 5,175,383 A | 12/1992 | Leder et al. | |
| 5,270,163 A | 12/1993 | Gold et al. | |
| 5,474,796 A | 12/1995 | Brennan | |
| 5,605,662 A | 2/1997 | Heller et al. | |
| 5,686,242 A | 11/1997 | Bruice et al. | |
| 5,707,618 A | 1/1998 | Armentano et al. | |
| 5,767,337 A | 6/1998 | Roses et al. | |
| 5,804,413 A | 9/1998 | DeLuca | |
| 5,807,522 A | 9/1998 | Brown et al. | |
| 5,837,458 A | 11/1998 | Minshull et al. | |
| 5,840,484 A | 11/1998 | Seilhamer et al. | |
| 5,910,434 A | 6/1999 | Rigg et al. | |
| 5,914,236 A | 6/1999 | Monsma, Jr. et al. | |
| 5,932,435 A | 8/1999 | Atkins et al. | |
| 5,997,848 A | 12/1999 | Patton et al. | |
| 6,022,691 A | 2/2000 | Bruice et al. | |
| 6,057,101 A | 5/2000 | Nandabalan et al. | |
| 6,372,724 B1 | 4/2002 | Pelleg et al. | |
| 7,063,846 B2 * | 6/2006 | Rikihisa et al. | 424/153.1 |

FOREIGN PATENT DOCUMENTS

| | | |
|---|---|---|
| WO | WO84/03564 | 9/1984 |
| WO | WO95/25116 | 9/1995 |
| WO | WO95/35505 | 12/1995 |

OTHER PUBLICATIONS

Ackerman, S.L. et al., "The mouse rostral cerebellar malformation gene encodes an UNC-5-like protein," (1997) Nature 386:838-842.
Adam, M.A. et al., "Identification of a signal in a murine retrovirus that is sufficient for packaging of nonretroviral RNA into virions," (1988) J. Virol. 62:3802-3806.
Aisenberg, A.C. et al., "Rearrangement of the gene for the beta chain of the T-cell receptor in T-cell chronic lymphocytic leukemia and related disorders," (1985) N. Engl. J. Med. 313:529-533.
Altschul, S.F. et al., "Basic local alignment search tool," (1990) J. Mol. Biol. 215:403-410.
Anderson, N.L. et al., "A comparison of selected mRNA and protein abundances in human liver," (1997) Electrophoresis 18:533-537.
Antinozzi, P.A. et al., "Metabolic engineering with recombinant adenoviruses," (1999) Annu. Rev. Nutr. 19:511-544.

(Continued)

*Primary Examiner*—John Ulm
(74) *Attorney, Agent, or Firm*—Foley & Lardner LLP

(57) ABSTRACT

Various embodiments of the invention provide human receptors and membrane-associated proteins (REMAP) and Q polynucleotides which identify and encode REMAP. Embodiments of the invention also provide expression vectors, host cells, antibodies, agonists, and antagonists. Other embodiments provide methods for diagnosing, treating, or preventing disorders associated with aberrant expression of REMAP.

6 Claims, No Drawings

OTHER PUBLICATIONS

Arap, W. et al., "Cancer treatment by targeted drug delivery to tumor vasculature in a mouse model," (1998) Science, 279:377-380.
Armentano, D. et al., "Effect of internal viral sequences on the utility of retroviral vectors," (1987) J. Virol. 61:1647-1650.
Arndt, G.M. et al., "A rapid genetic screening system for identifying gene-specific suppression constructs for use in human cells," (2000) Nucleic Acids Res. 28:E15.
Ashkenazi, A. et al., "Apoptosis control by death and decoy receptors," (1999) Curr. Opin. Cell Biol. 11:255-260.
Baldwin, A.M., "Structure and function of receptors coupled to G proteins," (1994) Curr. Opin. Cell Biol. 6:180-190.
Baltimore, D., "Intracellular Immunization," (1988) Nature 335:395-396.
Bauer, G. et al., "Inhibition of human immunodeficiency virus-1 (HIV-1) replication after transduction of granulocyte colony-stimulating factor-mobilized D34+cells from HIV-1-Infected donors using retroviral vectors containing anti-HIV genes," (1997) Blood 89:2259-2267.
Bender, M.A. et al., "Evidence that the packaging signal of Moloney murine leukemia virus extends into the gag region," (1987) J. Virol. 61:1639-1646.
Bitter, G.A. et al., "Expression and secretion vectors for yeast," (1987) Methods Enzymol. 153:516-544.
Blaese, R.M. et al., "T lymphocyte-directed gene therapy for ADA-SCID: initial trial results after 7 years," (1995) Science 270:475-480.
Blind, M. et al., "Cytoplasmic RNA modulators of an inside-out signal-transduction cascade," (1999) Proc. Nat. Acad. Sci. USA 96:3606-3610.
Boado, R.J. et al., "Drug delivery of antisense molecules to the brain for treatment of Alzheimer's disease and cerebral AIDS," (1998) J. Pharm. Sci. 87:1308-1315.
Bolton, A.E. et al., "The labelling of proteins to high specific radioactivities by conjugation to a 1251-containing acylating agent," (1973) Biochem. J. 133:529-539.
Bonyhadi, M.L., "RevM10-expressing T cells derived in vivo from transduced human hematopoietic stem-progenitor cells inhibit human immunodeficiency virus replication," (1997) J. Virol. 71:4707-4716.
Bordignon, C. et al., "Gene therapy in peripheral blood lymphocytes and bone marrow for ADA-immunodeficient patients," (1995) Science 270:470-475.
Boulay, J.-L. et al., "Expression vectors and delivery systems," (1998) Curr. Opin. Biotechnol. 9:445-450.
Brody, E.N. et al., "Aptamers as therapeutic and diagnosis agents," (2000) J. Biotechnol. 74:5-13.
Broglie, R. et al., "Light-regulated expression of a pea Ribulose-1,5-Bisphosphate Carboxylase small subunit gene in transformed plant cells," (1984) Science 334:838-843.
Brose, K. et al., "Slit proteins bind robo receptors and have an evolutionarily conserved role in repulsive axon guidance," (1999) Cell 96:795-806.
Brummelkamp, T.R. et al., "A system for stable expression of short interfering RNAs in mammalian cells," (2002) Science 296:550-553.
Buller, R.M. et al., "Decreased virulence of recombinant Vaccinia virus expression vectors is associated with a thymidine kinase-negative phenotype," (1985) Nature 317:813-815.
Burge, C. et al., "Finding the genes in genomic DNA," (1997) J. Mol. Biol. 268:78-94.
Burge, C. et al., "Prediction of complete gene structures in human genomic DNA," (1998) Curr. Opin. Struct. Biol. 8:346-354.
Burton, D.R., "A large array of human monoclonal antibodies to type 1 human immunodeficiency virus from combinatorial libraries of asymptomatic seropositive individuals," (1991) Proc. Natl. Acad. Sci. USA 88:10134-10137.
Capecchi, M.R., "Altering the genome by homologous recombination," (1989) Science 244:1288-1291.
Caruthers, M.H. et al., "New chemical methods for synthesi in polynucleotides," (1980) Nucleic Acids Symp. Ser. 7:215-223.
Cavazzano-Calvo, M. et al., "Gene therapy of human severe combined immunodeficiency (SCID)-X1 disease," (2000) Science 288:669-672.
Chang, C.-C. et al., "Evolution of a cytokine using DNA family shuffling," (1999) Nat. Biotechnol. 17:793-797.
Charng, M.J. et al., "A novel protein distinguishes between quiescent and activated forms of the type I transforming growth factor β Receptor," (1998) J. Biol. Chem. 273:9365-9368.
Chen, L. et al., "Overexpression of matrix Gla protein mRNA in malignant human breast cells: isolation by differential cDNA hybridization," (1990) Oncogene 5:1391-1395.
Chicz, R.M. et al., "High-performance liquid chromatography: effective protein purification by various chromatographic modes," (1990) Methods Enzymol. 182:392-421.
Christians, F.C. et al., "Directed evolution of thymidine kinase for AZT phosphorylation using DNA family shuffling," (1999) Nat. Biotechnol. 17:259-264.
Clarke, M.L. et al., "Comparative analysis of artificial antisense RNA regulation in fussion yeast and human cells," (2000) Biochem. Biophys. Res. Commun. 268:8-13.
Colbere-Garapin, F. et al., "A new dominant hybrid selective marker for higher eukaryotic cells," (1981) J. Mol. Biol. 150:1-14.
Cole, S.P. et al., "Human monoclonal antibodies," (1984) Mol. Cell Biol. 62:109-120.
Coruzzi, G. et al., "Tissue-specific and light-regulated expression of a pea nuclear gene encoding the small subunit of rebulose-1,5-bisphoshpate carboxylase," (1984) EMBO J. 3:1671-1680.
Cote, R.J. et al., "Generation of human monoclonal antibodies reactive with cellular antigene," (1983) Proc. Natl. Acad. Sci. USA 80:2026-2030.
Crameri, A. et al., "Improved green fluorescent protein by molecular evoluation using DNA shuffling," (1996) Nat. Biotechnol. 14:315-319.
Crystal, R.G. et al., "A Phase 1 study, in cystic fibrosis patients, of the safety, toxicity, and biological efficacy of a single administration of a replication deficient, recombinant adenovirus carrying the cDNA of the normal cystic fibrosis transmembrane conductance regulator gene in the lung," (1995) Hum. Gene Therapy 6:643-666.
Crystal, R.G. et al., "Evaluation of repeat administration of a replication deficient, recombinant adenovirus containing the normal cystic fibrosis transmembrane conductance regulator cDNA to the airways of individuals with cystic fibrosis," (1995) Hum. Gene Therapy 6:667-703.
Crystal, R.G., "Transfer of genes to humans: Early lessons and obstacles to success," (1995) Science 270:404-410.
Csete, M.E. et al., "Efficient gene transfer to pancreatic islets mediated by adenoviral vectors," (1995) Transplantation 27:263-268.
Cunningham, B.C. et al., "Rational design of receptor-specific variants of human growth hormone," (1991) Proc. Natl. Acad. Sci. USA 88:3407-3411.
de la Fuenta, M.A. et al., "CD84 leukocyte antigen is a new member of the Ig superfamily," (1997) Blood 90:2398-2405.
Dryga, S.A. et al., "Identification of mutations in a sindbis virus variant able to establish persisent infection in BHK cells: The importance of a mutation in the nsP2 gene," (1997) Virology 228:74-83.
Dull, T. et al., "A third-generation lentivirus vector with a conditional packaging system," (1998) J. Virol. 72:8463-8471.
Duplaa, C. et al., "Quantitative analysis of polymerase chain reaction products using biotinylated dUTP incorporation," (1993) Anal. Biochem. 212:229-236.
Eddy, S.R., "Hidden markov models," (1996) Curr. Opin. Struct. Biol. 6:361-365.
Elbashir, S.M. et al., "Duplexes of 21-nucleotide RNAs mediate RNA interference in cultured mammalian cells," (2001) Nature 411:494-498.
Elomaa, O. et al., "Cloning of a novel bacteria-binding receptor structurally related to scavenger receptors and expressed in a subset of macrophages," (1995) Cell 80:603-609.
Engelhard, E.K. et al., "The insect tracheal system: a conduit for the systemic spread of Autographa californica M nuclear polyhedrosis virus," (1994) Proc. Natl. Acad. Sci. USA 91:3224-3227.

Fields, S. et al., "A novel genetic system to detect protein-protein interactions," (1989) Nature 340:245-246.
Fire, A. et al., "Potent and specific genetic interference by double-stranded RNA in *Caenorhabditis elegans*," (1998) Nature 391:806-811.
Fournier, A.E. et al., "Identification of a receptor mediating Nogo-66 inhibition of axonal regeneration," (2001) Nature 409:341-346.
Garoff, H. et al., "Recent advances in gene expression using alphavirus vectors," (1998) Curr. Opin. Biotechnol. 9:464-469.
Gartner, J. et al., "The 22-kD peroxisomal integral membrane protein in Zellweger Syndrome—presence, abundance, and association with a peroxisomal thiolase precursor protein," (1991) Pediatr. Res. 29:141-146.
Gatti, R.A. et al., "Localization of an ataxia-telangiectasia gene to chromosome," (1988) Nature 336:577-580.
Gaudin, P. et al., "Constitutive activation of the human vasoactive intestinal peptide 1 receptor, a member of the new Class II family of G protein-coupled receptors," (1998) J. Biol. Chem. 273:4990-4996.
Goins, W.F. et al., "Herpes simplex virus type 1 vector-mediated expression of nerve growth factor protects dorsal root ganglion neurons from peroxide toxicity," (1999) J. Virol. 73:519-532.
Goldman, C.K. et al., "In vitro and in vivo gene delivery mediated by a synthetic polycationic amino polymer," (1997) Nat. Biotechnol. 15:462-466.
Gossen, M. et al, "Tight control of gene expression in mammalian cells by tetracycline-responsive promoters," (1992) Proc. Natl. Acad. Sci. USA 89:5547-5551.
Gossen, M. et al., "Transcriptional activation by tetracyclines in mammalian cells," (1995) Science 268:1766-1769.
Graham, F.L., "A new technique for the assay of infectivity of human adenovirus 5 DNA," (1973) Virology 52:456-467.
Gura, T., "A silence that speaks volumes," (2000) Nature 404:804-808.
Guy, G.R. et al., "Dockers at the crossroads," (2002) Cell Signal. 14:11-20.
Haft, D.H. et al., "TIGRFAMs: a protein family resource for the functional identification of proteins," (2001) Nucleic Acids Res. 29:41-43.
Harrington, M.G., "Elution of protein from gels," (1990) Methods Enzymol. 182:488-495.
Harrington, J.J. et al., "Formation of de novo centromere and construction of first-generation human artificial microchromosomes," (1997) Nat. Genet. 15:345-355.
Hartman, S.C. et al., "Two dominant-acting selectable markers for gene transfer studies in mammalian cells," (1988) Proc. Natl. Acad. Sci. USA 85:8047-8051.
Heller, R.A. et al., "Discovery and analysis of inflammatory disease-related genes using cDNA microarrays," (1997) Proc. Natl. Acad. Sci. USA 94:2150-2155.
Hermey, G. et al., "Identification and characterization of SorCS, a third member of a novel receptor family," (1999) Biochem. Biophys. Res. Commun. 266:347-351.
Hermey, G. et al., "Transient expression of SorCS in developing telencephalic and mesencephalic structures of the mouse," (2001) Neuroreport 12:29-32.
Higgins, D.G. et al., "Fast and sensitive multiple sequence alignments on a microcomputer," (1989) CABIOS 5:151-153.
Higgins, D.G. et al., "CLUSTAL V: Improved software for multiple sequence alignment," (1992) CABIOS 8:189-191.
Horn, F. et al., "G protein-coupled receptors in silico," (1998) J. Mol. Med. 76:464-468.
Horn, T. et al., "Synthesis of oligonucleotides on cellulose. Part II: design and synthetic strategy to the synthesis of 22 oligodeoxynucleotides coding for Gastric Inhibitory Polypeptide (GIP)," (1980) Nucleic Acids Symp. Ser. 7:225-232.
Hoshi, N. et al., "KCR1, a membrane protein that facilitates functional expression of non-inactivating K+ currents associates with rat EAG voltage-dependent K+ channels," (1998) J. Biol. Chem. 273:23080-23085.
Howard, A.D. et al., "Orphan G-protein-coupled receptors and natural ligand discovery," (2001) Trends Pharmacol. Sci.22:132-140.
Huse, W.D. et al., "Generation of a large combinatorial library of the immunoglobulin repertoire in Phage Lambda," (1989) Science 246:1275-1281.
Ivics, Z., "Molecular reconstruction of sleeping beauty, a Tc1-like transposon from fish, and its transposition in human cells," (1997) Cell 91:501-510.
Jankowski, S.A., "SAS, a gene amplified in human sarcomas, encodes a new member of the transmembrane 4 superfamily of proteins," (1994) Oncogene 9:1205-1211.
Karcher, R.L. et al., "Motor-cargo interactions: the key to transport specificity," (2002) Trends in Cell Biology vol. 12(1):21-7.
Kimmel, A.R., "Identification and characterization of specific clones: Strategy for confirming the validity of presumptive clones," (1987) Methods Enzymol. 152:507-511.
Kohler, G. et al., "Continuous cultures of fused cells secreting antibody of predefined specificity," (1975) Nature 256:495-497.
Kozbor, D. et al., "Specific immunoglobulin production and enhanced tumorigenicity following ascites growth of human hybridomas," (1985) J. Immunol. Methods 81:31-42.
Kumar, J. et al., "Kinectin, an essential anchor for kinesin-driven vesicle motility," (1995) Science 267, 1834-137.
Kwok, P.-Y. et al., "Single nucleotide polymorphism libraries: why and how are we building them?," (1999) Mol. Med. Today 5:538-543.
Lagerstrom, M. et al., "Capture PCR: efficient amplification of DNA fragments adjacent to a known sequence in human and YAC DNA," (1991) PCR Methods Applic. 1:111-119.
Lander, E.S. et al., "Strategies for studying heterogeneous genetic traits in humans by using a linkage map of restriction fragment length polymorphisms," (1986) Proc. Natl. Acad. Sci. USA 83:7353-7357.
Lee, SW et al., "Down-regulation of a member of the S100 gene family in mammary carcinoma cells and reexpression by azadeoxycytidine treatment," (1992) Proc Natl Acad Sci USA 89:2504-2508.
Leonardo, E.D. et al., "Vertebrate homologues of C. elegans UNC-5 are candidate netrin receptors," (1997) Nature 386:833-838.
Letunic, I. et al., "Recent improvements to the SMART domain-based sequence annotation resource," (2002) Nucleic Acids Res. 30:242-244.
Li, J. et al., "The FHA domain mediates phosphoprotein interactions," (2000) J. Cell Sci. 113:4143-4149.
Liu, E. et al., "The HER2 (c-erbB-2) oncogene is frequently amplified in in situ carcenomas of the breast," (1992) Oncogene 7:1027-1032.
Liu, X. et al., "Herpes simplex virus mediated gene transfer to primate ocular tissues," (1999) Exp. Eye Res. 169:385-395.
Logan, J. et al., "Adenovirus tripartite leader sequence enhances translation of mRNAs late after infection," (1984) Proc. Natl. Acad. Sci. USA 81:3655-3659.
Lois, C. et al., "Germline transmission and tissue-specific expression of transgenes delivered by lentiviral vectors," (2000) Science 295:868-872.
Lowenstein, E.J. et al., "The SH2 and SH3 domain-containing protein GRB2 links receptor tyrosine kinases to ras signaling," (1992) Cell 70:431-442.
Lowman, H.B. et al., "Mutational analysis and protein engineering of receptor-binding determinants in human placental lactogen," (1991) J. Biol. Chem. 266:10982-10988.
Lowy, I. et al., "Isolation of tranforming DNA: cloning the hamster aprt gene," (1980) Cell 22:817-823.
Lueking, A. et al., "Protein microarrays for gene expression and antibody screening," (1999) Anal. Biochem. 270:103-111.
Manda et al., "Identification of genes (SPON2 and C20orf2) differentially expressed between cancerous and noncancerous lung cells by mRNA differential display," (1999; Genomics 51:5-14.
Mantovani, A. et al., "Decoy receptors: a strategy to regulate inflammatory cytokines and chemokines," (2001) Trends Immunol. 22:328-336.
Marshall, A. et al., "DNA Chips: an array of possibilities," (1998) Nat. Biotechnol. 16:27-31.
Marth, J.D., "Recent advances in gene mutagenesis by site-directed recombination," (1996) Clin. Invest. 97:1999-2002.

Mather, J.P. et al., "Activins, inhibins, and follistatins: further thoughts on a growing family of regulators," (1997) Proc. Soc. Exp. Biol. Med. 215:209-222.
Matsumoto, A. et al., "Human macrophage scavenger receptors: primary structure, expression, and localization in atherosclerotic lesions," (1990) Proc. Natl. Acad. Sci. USA 87:9133-9137.
Matthews, D.J. et al., "Engineering an interfacial zinc site to increase hormone-receptor affinity," (1994) Chem. Biol. 1:25-30.
Mayer, R.J. et al., "Endosome-lysosomes, ubiquitin and neurodegeneration," (1996) Adv. Exp. Med. Biol. 389:261-269.
McGregor, D.P. et al., "Spontaneous assembly of bivalent single chain antibody fragments in *Escherichia coli*," (1994) Mol. Immunol. 31:219-226.
Melby, P.C. et al., "Quantitative measurement of human cytokine gene expression by polymerase chain reaction," (1993) J. Immunol. Methods 159:235-244.
Mendoza, L.G. et al., "High-throughput microarray-based enzyme-linked immunosorbent assay (ELISA)," (1999) Biotechniques 27:778-788.
Mestek A. et al., "The human μ opioid receptor: modulation of functional desensitization by calcium/calmodulin-dependent protein kinase and protein kinase C," (1995) J. Neurosci. 15:2396-2406.
Mikhailenko, I. et al., "Cellular internalization and degradation of thrombospondin-1 is mediated by the amino-terminal heparin binding domain (HBD).," (1997) J. Biol. Chem. 272:6784-6791.
Miller, A.D., "Progress toward human gene therapy," (1990) Blood 76:271.
Milligan, G. et al., "G16 as a universal G protein adapter: implications for agonist screening strategies," (1996) Trends Pharmacol. Sci. 17:235-237.
Morgan, R.A. et al., "Human gene therapy," (1993) Annu. Rev. Biochem. 61:191-217.
Morris, M.C. et al., "A new peptide vector for efficient delivery of oligonucleotides into mammalian cells," (1997) Nucleic Acids Res. 25:2730-2736.
Morrison, S.L. et al., "Chimeric human antibody molecules: mouse antigen-binding domains with human constant region domains," (1984) Proc. Natl. Acad. Sci. USA 81:6851-6855.
Moser, H.W. et al., "Peroxisomal disorders: overview," (1996) Ann. NY Acad. Sci. 804:427-441.
Muyldermans, S., "Single domain camel antibodies: current status," (2001) J. Biotechnol. 74:277-302.
Neuberger, M.S. et al., "Recombinant antibodies possessing novel effector functions," (1984) Nature 312:604-608.
Neumann, E. et al., "Gene transfer into mouse lyoma cells by electroporation in high electric fields," (1982) EMBO J. 1:841-845.
Nowotny, P. et al., "SNP analysis to dissect human traits," (2001) Curr. Opin. Neurobiol. 11:637-641.
Nuwaysir, E.F. et al., "Microarrays and toxicology: the advent of toxicogenomics," (1999) Mol. Carcinog. 24:153-159.
Oba, K. et al., "Two putative tumor suppressor genes on chromosome arem 8p may ply different roles inprostate cancer," (2001) Cancer Genet. Cytogenet. 124: 20-26.
Offermanns, S. et al., "Gα15 and Gα16 couple a wide variety of receptors to phospholipase C," (1995) J. Biol. Chem. 270:15175-15180.
Orlandi, R. et al., "Cloning immunoglobulin variable domains for expression by the polymerase chain reaction," (1989) Proc. Natl. Acad. Sci. USA 86:3833-3837.
Paddison, P.J. et al., "Short hairpin RNAs (shRNAs) induce sequence-specific silencing in mammalian cells," (2002) Genes Dev. 16:948-958.
Pan, Y.X. et al., "Identification and characterization of three new alternatively spliced μ-opioid receptor isoforms," (1999) Mol. Pharm. 56:396-403.
Parker, J.D. et al., "Targeted gene walking polymerase chain reaction," (1991) Nucleic Acids Res. 19:3055-3060.
Parma, J. et al., "Somatic mutations in the thyrotropin receptor gene cause hyperfunctioning thyroid adenomas," (1993) Nature 365:649-651.
Perou CM et al., "Molecular portraits of human breast tumours," (2000) Nature 406:747-752.
Petersen et al., "Gene therapy expression profiling of advanced lung cancer," (2000) Int J. Cancer, 86:512-517.
Petraglia, F., Inhibin, activin and follistatin in the human placenta—a new family of regulatory proteins (1997) Placenta 18:3-8.
Poeschla, E. et al. (1996) Proc. Natl. Acad. Sci. USA 93:11395-11399.
Ranga, U. et al., "Cell and viral regulatory elements enhance the expression and function of a human immunodeficiency virus inhibitory gene," (1997) J. Virol. 71:7020-7029.
Ranga, U. et al., "Enhanced T cell engraftment after retroviral delivery of an antiviral gene in HIV-infected individuals," (1998) Proc. Natl. Acad. Sci. USA 95:1201-1206.
Rao, V.B., "Direct sequencing of polymerase chain reaction-amplified DNA," (1994) Anal. Biochem. 216:1-14.
Raper, J.A., "Semaphorins and their receptors in vertebrates and invertebrates," (2000) Curr. Opin. Neurobiol. 10:88-94.
Rezgaoui, M., "Identification of SorCS2, a novel member of the VPS10 domain containing receptor family, prominently expressed in the developing mouse brain," (2001) Mech. Dev. 100:335-338.
Rhodes, C.A., "Transformation of maize by electroporation of embryos," (1995) Methods Mol. Biol. 55:121-131.
Riviere, I. et al., "Effects of retroviral vector design on expression of human adenosine deaminase in murine bone marrow transplant recipients engrafted with genetically modified cells," (1995) Proc. Natl. Acad. Sci. USA 92:6733-6737.
Roberge, J.Y. et al., "A strategy for a convergent synthesis of N-linked glycopeptides on a solid support," (1995) Science 269:202-204.
Rossi, F.M.V. et al., "Recent advances in inducible gene expression systems," (1998) Curr. Opin. Biotechnol. 9:451-456.
Rossi, J.J., "Therapeutic antisense and ribozymes," (1995) Br. Med. Bull. 51:217-225.
Rothman, J.E. et al., "Proteins sorting by transport vesicles," (1996) Science 272:227-234.
Sager, R et al., Maspin: a tumor suppressing serpin (1996) Curr Top Microbiol Immunol 213:51-64.
Saito, H. et al., "Complete primary structure of a heterodimeric T-cell receptor deduced from cDNA sequences," (1984) Nature 309:757-762.
Sadig, V. et al., "Gene transfer into hepatocytes and human liver tissue by baculorius vectors," (1996) Hum. Gene Ther. 7:1935-1945.
Sarkar, G., "Restriction-site PCR: a direct method of unknown sequence retrieval adjacent to a known locus by using universal primers," (1993) PCR Methods Applic. 2:318-322.
Scanlon, K.J. et al., "Oligonucleotide-mediated modulation of mammalian gene expression," (1995) 9:1288-1296.
Scharf, D. et al., "Heat stress promoters and transcription factors," (1994) Results Probl. Cell Differ. 20:125-162.
Schena, M. et al., "Parallel human genome analysis: microarray-based expression monitoring of 1000 genes," (1996) Proc. Natl. Acad. Sci. USA 93:10614-10619.
Schena, M. et al., "Quantitative monitoring of gene expression patterns with a complementary DNA microarray," (1995) Science 270:467-470.
Schultz, J. et al., "SMART, a simple modular architecture research tool: Identification of signaling domains," (1998) Proc. Natl. Acad. Sci. USA 95:5857-5864.
Schwarze, S.R. et al., "In vivo protein transduction: delivery of a biologically active protein into the mouse," (1999) Science 285:1569-1572.
Scorer, C.A. et al., "Rapid selection using G418 of high copy number transformants of Pichia Pastoris for high-level foreign gene expression," (1994) Bio/Technology 12:181-184.
Scott, L.M. et al., "E3, a hematopoietic-specific transcript directly regulated by the retinoic acid receptor alpha," (1996) Blood 88:2517-2530.
Shalon, D. et al., "A DNA microarray system for analyzing complex DNA samples using two-color fluorescent probe hybridization," (1996) Genome Res. 6:639-645.
Singer, S.J., "The structure and insertion of integral proteins in membranes," (1990) Annu. Rev. Cell Biol. 6:247-296.

Skerra, A., "Anticalins: A new class of engineered ligand-binding proteins with antibody-like properties," (2001) J. Biotechnol. 74:257-275.
Slater, J.E et al., "Environmental and occupational disorders," (1998) J. Allergy Clin. Immunol. 102:469-475.
Stadel, J.M. et al., "Orphan G protein-coupled receptors: a neglected opportunity for pioneer drug discovery," (1997) Trends Pharmacol. Sci. 18:430-437.
Steiner, S. et al., "Expression profiling in toxicology—potentials and limitations," (2000) Toxicol. Lett. 112-113:467-471.
Strosberg, A.D., "Structure/function relationship of proteins belonging to the family of receptors coupled to GTP-binding proteins," (1991) Eur. J. Biochem. 196:1-10.
Su, L., "Hematopoietic stem cell-based gene therapy for acquired immunodeficiency syndrome: efficient transduction and expression of RevM10 in myeloid cells in vivo and in vitro," (1997) Blood 89:2283-2290.
Takagi, S. et al., "Identification of a highly specific surface marker of T-cell acute lymphoblastic leukemia and neuroblastoma as a new member of the transmembrane 4 superfamily," (1995) Int. J. Cancer 61:706-715.
Takamatsu, N., "Expression of bacterial chloramphenicol acetyltransferase gene in tobacco plants mediated by TRV-RNA," (1987) EMBO J. 6:307-311.
Takeda, S. et al., "Construction of chimaeric processed immunoglobulin genes containing mouse variable and human constant region sequences," (1985) Nature 314:452-454.
Taylor, J.G. et al., "Deconstructing type 2 diabetes," (2001) Trends Mol. Med. 7:507-512.
Taylor, P.C. et al., "Immunotherapy for rheumatoid arthritis," (2001) Curr. Opin. Immunol. 13:611-616.
Thomson, J.A. et al., "Embryonic stem cell lines derived from human blastocysts," (1998) Science 282:1145-1147.
Trask, B.J., "Fluorescence in situ hybridization," (1991) Trends Genet. 7:149-154.
Triglia, T. et al., "A procedure for in vitro amplification of DNA segments that lie outside the boundaries of known sequences," (1988) Nucleic Acids Res. 16:8186.
Uckert, W. et al., "Retrovirus-mediated gene transfer in cancer therapy," (1994) Pharmacol. Ther. 63:323-347.
Ulrix W et al., "The differentiation-related gene 1, Drg1, is markedly upregulated by androgens in LNCaP prostatic adenocarcinoma cells," (1999) FEBS Lett 455:23-26.
Van Heeke, G. et al., "Expression of human synthetase in *Escherichia coli*," (1989) J. Biol. Chem. 264:5503-5509.
Verma, I.M. et al., "Gene therapy—promises, problems and prospects," (1997) Nature 18 389:239-242.
Vidal, M. et al., "SH2 and SH3 domains as targets for anti-proliferative agents," (2001) Crit. Rev. Oncol. Hematol. 40:175-186.
Wagner, K.U. et al., "Cre-mediated gene deletion the mammary gland," (1997) Nucleic Acids Res. 25:4323-4330.
Wahl, G.M. et al., "Molecular hybridization of immobilized nucleic acids: theoretical concepts and practical considerations," (1987) Methods Enzymol. 152:399-407.
Wang et al., "Identification of genes differentially over-expressed in lung squamous cell carcinoma using combination of cDNA substraction and microarray analysis," (2000) Oncogene 19:1519-1528.
Waterham, H.R. et al., Orphan G-protein-coupled receptors: the next generation of drug targets? (1997) BioEssays 19:57-66.
Weiss, G.A. et al., "Anticalins versus antibodies: made-to-order binding proteins for small molecules," (2000) Chem. Biol. 7:R177-R184.
Wigler, M. et al., "Transfer of purified herpes virus thymidine kinase gene to cultured mouse cells," (1977) Cell 11:223-232.
Wigler, M. et al., "Transformation of mammalian cells with an amplifiable dominant-acting gene," (1980) Proc. Natl. Acad. Sci. USA 77:3567-3570.
Wilson, S. et al., "Orphan G-protein-coupled receptors: the next generation of drug targets?," (1998) Br. J. Pharmocol. 125:1387-1392.
Winter, G. et al., "Man-made antibodies," (1991) Nature 349:293-299.
Winter, J. et al., "The expression of heat shock protein and cognate genes during plant development," (1991) Results Probl. Cell Differ. 17:85-105.
Wise, A. et al., "Target validation of G-protein coupled receptors," (2002) Drug Discovery Today 7:235-246.
Wistuba II et al., "Comparison of features of human breast cancer cell lines and their corresponding tumors," (1998) Clin Cancer Res 4:2931-2938.
Wright, M.D. et al., "The ins and outs of the transmembrane 4 superfamily," (1994) Immunol. Today 15:588-594.
Xu, H. et al., "Viral transduction of trkA into cultured nodose and spinal motor newrons conveys NGF responsiveness," (1994) Dev. Biol. 163:152-161.
Yu, M. et al., "A hairpin ribozyme inhibits expression of diverse strains of human immunodeficiency virus Type 1," (1993) Proc. Natl. Acad. Sci. USA 90:6340-6344.
Zabner, J. et al., "Adenovirus-mediated gene transfer transiently corrects the chloride transport defect in masal epithelia of patients with cystic fibrosis," (1993) Cell 75:207-216.
Zhou Z et al., "Up-regulation of human secreted frizzled homolog in apoptosis and its down-regulation in breat tumors," (1998) Int J Cancer 78:95-99.
Zufferey, R. et al., "Self-inactivating lentivirus vector for safe and efficient in vivo gene delivery," (1998) J. Virol. 72:9873-9880.

* cited by examiner

CD40-RELATED RECEPTOR THAT BINDS CD40L

TECHNICAL FIELD

The invention relates to novel nucleic acids, receptors and membrane-associated proteins encoded by these nucleic acids, and to the use of these nucleic acids and proteins in the diagnosis, treatment, and prevention of cell proliferative, autoimmune/inflammatory, neurological, metabolic, developmental, and endocrine disorders. The invention also relates to the assessment of the effects of exogenous compounds on the expression of nucleic acids and receptors and membrane-associated proteins.

BACKGROUND OF THE INVENTION

Signal transduction is the general process by which cells respond to extracellular signals. Signal transduction across the plasma membrane begins with the binding of a signal molecule, e.g., a hormone, neurotransmitter, or growth factor, to a cell membrane receptor. The receptor, thus activated, triggers an intracellular biochemical cascade that ends with the activation of an intracellular target molecule, such as a transcription factor. This process of signal transduction regulates all types of cell functions including cell proliferation, differentiation, and gene transcription.

Biological membranes surround organelles, vesicles, and the cell itself. Membranes are highly selective permeability barriers made up of lipid bilayer sheets composed of phosphoglycerides, fatty acids, cholesterol, phospholipids, glycolipids, proteoglycans, and proteins. Membranes contain ion pumps, ion channels, and specific receptors for external stimuli which transmit biochemical signals across the membranes. These membranes also contain second messenger proteins which interact with these pumps, channels, and receptors to amplify and regulate transmission of these signals.

Plasma Membrane Proteins

Plasma membrane proteins (MPs) are divided into two groups based upon methods of protein extraction from the membrane. Extrinsic or peripheral membrane proteins can be released using extremes of ionic strength or pH, urea, or other disruptors of protein interactions. Intrinsic or integral membrane proteins are released only when the lipid bilayer of the membrane is dissolved by detergent.

The majority of known integral membrane proteins are transmembrane proteins (TM) which are characterized by an extracellular, a transmembrane, and an intracellular domain. TM domains are typically comprised of 15 to 25 hydrophobic amino acids which are predicted to adopt an α-helical conformation. TM proteins are classified as bitopic (Types I and II) and polytopic (Types III and IV) (Singer, S. J. (1990) Annu. Rev. Cell Biol. 6:247-296). Bitopic proteins span the membrane once while polytopic proteins contain multiple membrane-spanning segments. TM proteins carry out a variety of important cellular functions, including acting as cell-surface receptor proteins involved in signal transduction. These functions are represented by growth and differentiation factor receptors, and receptor-interacting proteins such as *Drosophila* pecanex and frizzled proteins, LIV-1 protein, NF2 protein, and GNS1/SUR4 eukaryotic integral membrane proteins. TM proteins also act as transporters of ions or metabolites, such as gap junction channels (connexins), and ion channels, and as cell anchoring proteins, such as lectins, integrins, and fibronectins. TM proteins may be vesicle organelle-forming molecules, such as caveolins, or cell recognition molecules, such as cluster of differentiation (CD) antigens, glycoproteins, and mucins.

Many MPs contain amino acid sequence motifs that serve to localize proteins to specific subcellular sites. Examples of these motifs include PDZ domains, KDEL, ROD, NGR, and GSL sequence motifs, von Willebrand factor A (vWFA) domains, and EGF-like domains. RGD, NGR, and GSL motif-containing peptides have been used as drug delivery agents in targeted cancer treatment of tumor vasculature (Arap, W. et al. (1998) Science, 279:377-380). Furthermore, MPs may also contain amino acid sequence motifs that serve to interact with extracellular or intracellular molecules, such as carbohydrate recognition domains (CRD).

Chemical modification of amino acid residue side chains alters the manner in which MPs interact with other molecules, for example, phospholipid membranes. Examples of such chemical modifications to amino acid residue side chains are covalent bond formation with glycosaminoglycans, oligosaccharides, phospholipids, acetyl and palmitoyl moieties, ADP-ribose, phosphate, and sulphate groups.

RNA encoding membrane proteins may have alternative splice sites which give rise to proteins encoded by the same gene but with different messenger RNA and amino acid sequences. Splice variant membrane proteins may interact with other ligand and protein isoforms.

Receptors

The term receptor describes proteins that specifically recognize other molecules. The category is broad and includes proteins with a variety of functions. The bulk of receptors are cell surface proteins which bind extracellular ligands and produce cellular responses in the areas of growth, differentiation, endocytosis, and immune response. Other receptors facilitate the selective transport of proteins out of the endoplasmic reticulum and localize enzymes to particular locations in the cell. The term may also be applied to proteins which act as receptors for ligands with known or unknown chemical composition and which interact with other cellular components. For example, the steroid hormone receptors bind to and regulate transcription of DNA.

Cell surface receptors are typically integral plasma membrane proteins. These receptors recognize hormones such as catecholamines; peptide hormones; growth and differentiation factors; small peptide factors such as thyrotropin-releasing hormone; galanin, somatostatin, and tachykinins; and circulatory system-borne signaling molecules. Cell surface receptors on immune system cells recognize antigens, antibodies, and major histocompatibility complex (MHC)-bound peptides. Other cell surface receptors bind ligands to be internalized by the cell. This receptor-mediated endocytosis functions in the uptake of low density lipoproteins (LDL), transferrin, glucose- or mannose-terminal glycoproteins, galactose-terminal glycoproteins, immunoglobulins, phosphovitellogenins, fibrin, proteinase-inhibitor complexes, plasminogen activators, and thrombospondin (Lodish, H. et al. (1995) *Molecular Cell Biology*, Scientific American Books, New York N.Y., p. 723; Mikhailenko, I. et al. (1997) J. Biol. Chem. 272:6784-6791).

Receptor Protein Kinases

Many growth factor receptors, including receptors for epidermal growth factor, platelet-derived growth factor, fibroblast growth factor, as well as the growth modulator α-thrombin, contain intrinsic protein kinase activities. When growth factor binds to the receptor, it triggers the autophosphorylation of a serine, threonine, or tyrosine residue on the receptor. These phosphorylated sites are recognition sites for the binding of other cytoplasmic signaling proteins. These proteins participate in signaling pathways that eventually link the initial receptor activation at the cell surface to the activation of a specific intracellular target molecule. In the case of tyrosine residue autophosphorylation, signaling proteins can bind these motifs using several common domains, for example Src homology-2 (SH2) domains, phosphotyrosine-binding (PTB) domains, and forkhead-associated (FHA) domains. These domains, alone or in combination, are found in many signaling proteins, such as phospholipase C-γ (PLC-γ), the p85 regulatory subunit of PI-3 kinase, $pp60^{c-crc}$,Ras-GTPase activating protein, Chk2, AF-6, insulin receptor substrate-i (IRS-1), and Shc (Li, J. et al. (2000) J. Cell Sci. 113:4143-4149; Guy, G. R. et al. (2002) Cell Signal. 14:11-20; Vidal, M. et al. (2001) Crit. Rev. Oncol. Hematol. 40:175-186; Lowenstein, E. J. et al. (1992) Cell 70:431-442). The cytoline family of receptors share a different common binding domain and include transmembrane receptors for growth hormone (GH), interleukins, erythropoietin, and prolactin.

Other receptors and second messenger-binding proteins have intrinsic serine/threonine protein kinase activity. These include activin/TGF-β/BMP-superfamily receptors, calcium- and diacylglycerol-activated/phospholipid-dependant protein kinase (PK-C), and RNA-dependant protein kinase (PK-R). In addition, other serine/threonine protein kinases, including nematode Twitchin, have fibronectin-like, immunoglobulin C2-like domains.

G-Protein Coupled Receptors

The G-protein coupled receptors (GPCRs), encoded by one of the largest families of genes yet identified, play a central role in the transduction of extracellular signals across the plasma membrane. GPCRs have a proven history of being successful therapeutic targets.

GPCRs are integral membrane proteins characterized by the presence of seven hydrophobic transmembrane domains which together form a bundle of antiparallel alpha (α) helices. GPCRs range in size from under 400 to over 1000 amino acids (Strosberg, A. D. (1991) Eur. J. Biochem. 196:1-10; Cougllin, S. R. (1994) Curr. Opin. Cell Biol. 6:191-197). The amino-terminus of a GPCR is extracellular, is of variable length, and is often glycosylated. The carboxy-terminus is cytoplasmic and generally phosphorylated. Extracellular loops alternate with intracellular loops and link the transmembrane domains. Cysteine disulfide bridges linking the second and third extracellular loops may interact with agonists and antagonists. The most conserved domains of GPCRs are the transmembrane domains and the first two cytoplasmic loops. The transmembrane domains account, in part, for structural and functional features of the receptor. In most cases, the bundle of a helices forms a ligand-binding pocket The extracellular N-terminal segment, or one or more of the three extracellular loops, may also participate in ligand binding. Ligand binding activates the receptor by inducing a conformational change in intracellular portions of the receptor. In turn, the large, third intracellular loop of the activated receptor interacts with a heterotrimeric guanine nucleotide binding (G) protein complex which mediates further intracellular signaling activities, including the activation of second messengers such as cyclic AMP (cAMP), phospholipase C, and inositol triphosphate, and the interaction of the activated GPCR with ion channel proteins. (See, e.g., Watson, S. and S. Arkinstall (1994) *The G-protein Linked Receptor Facts Book*, Academic Press,. San Diego Calif., pp. 2-6; Bolander, F. F. (1994) *Molecular Endocrinology*, Academic Press, San Diego Calif., pp. 162-176; Baldwin, J. M. (1994) Curr. Opin. Cell Biol. 6:180-190.)

GPCRs include receptors for sensory signal mediators (e.g., light and olfactory stimulatory molecules); adenosine, γ-aminobutyric acid (GABA), hepatocyte growth factor, melanocortins, neuropeptide Y, opioid peptides, opsins, somatostatin, tachykinins, vasoactive intestinal polypeptide family, and vasopressin; biogenic amines (e.g., dopamine, epinephrine and norepinephrine, histamine, glutamate (metabotropic effect), acetylcholine (muscarinic effect), and serotonin); chemokines; lipid mediators of inflammation (e.g., prostaglandins and prostanoids, platelet activating factor, and leukotrienes); and peptide hormones (e.g., bombesin, bradykinin, calcitonin, C5a anaphylatoxin, endothelin, follicle-stimulating hormone (FSH), gonadotropic-releasing hormone (GnRH), neurokinin, and thyrotropin-releasing hormone (TRH), and oxytocin). GPCRs which act as receptors for stimuli that have yet to be identified are known as orphan receptors.

GPCR mutations, which may cause loss of function or constitutive activation, have been associated with numerous human diseases (Coughlin, supra). For instance, retinitis pigmentosa may arise from mutations in the rhodopsin gene. Furthermore, somatic activating mutations in the thyrotropin receptor have been reported to cause hyperfunctioning thyroid adenomas, suggesting that certain GPCRs susceptible to constitutive activation may behave as protooncogenes (Parma, J. et al. (1993) Nature 365:649-651). GPCR receptors for the following ligands also contain mutations associated with human disease: luteinizing hormone (precocious puberty); vasopressin $V_2$ (X-linked nephrogenic diabetes); glucagon (diabetes and hypertension); calcium (hyperparathyroidism, hypocalcuria, hypercalcemia); parathyroid hormone (short limbed dwarfism); $\beta_3$-adrenoceptor (obesity, non-insulin-dependent diabetes mellitus); growth hormone releasing hormone (dwarfism); and adrenocorticotropin (glucocorticoid deficiency) (Wilson, S. et al. (1998) Br. J. Pharmocol. 125:1387-1392; Stadel, J. M. et al. (1997) Trends Pharmacol. Sci. 18:430-437). GPCRs are also involved in depression, schizophrenia, sleeplessness, hypertension, anxiety, stress, renal failure, and several cardiovascular disorders (Horn, F. and G. Vriend (1998) J. Mol. Med. 76:464468).

In addition, within the past 20 years several hundred new drugs have been recognized that are directed towards activating or inhibiting GPCRs. The therapeutic targets of these drugs span a wide range of diseases and disorders, including cardiovascular, gastrointestinal, and central nervous system disorders as well as cancer, osteoporosis and endometriosis (Wilson et al., supra; Stadel et al., supra). For example, the dopamine agonist L-dopa is used to treat Parkinson's disease, while a dopamine antagonist is used to treat schizophrenia and the early stages of Huntington's disease. Agonists and antagonists of adrenoceptors have been used for the treatment of asthma, high blood pressure, other cardiovascular disorders, and anxiety; muscarinic agonists are used in the treatment of glaucoma and tachycardia; serotonin 5HT1D antagonists are used against migraine; and histamine Hi antagonists are used against allergic and anaphylactic reactions, hay fever, itching, and motion sickness (Horn et al., supra).

Nuclear Receptors

Nuclear receptors bind small molecules such as hormones or second messengers, leading to increased receptor-binding affinity to specific chromosomal DNA elements. In addition the affinity for other nuclear proteins may also be altered. Such binding and protein-protein interactions may regulate and modulate gene expression. Examples of such receptors include the steroid hormone receptors family, the retinoic acid receptors family, and the thyroid hormone receptors family.

Ligand-Gated Receptor Ion Channels

Ligand-gated receptor ion channels fall into two categories. The first category, extracellular ligand-gated receptor ion channels (ELGs), rapidly transduce neurotransmitter-binding events into electrical signals, such as fast synaptic neurotransmission. ELG function is regulated by post-translational modification. The second category, intracellular ligand-gated receptor ion channels (ILGs), are activated by many intracellular second messengers and do not require post-translational modification(s) to effect a channel-opening response.

ELGs depolarize excitable cells to the threshold of action potential generation. In non-excitable cells, ELGs permit a limited calcium ion-influx during the presence of agonist ELGs include channels directly gated by neurotransmitters such as acetylcholine, L-glutamate, glycine, ATP, serotonin, GABA, and histamine. ELG genes encode proteins having strong structural and functional similarities. ELGs are encoded by distinct and unrelated gene families and include receptors for cAMP, cGMP, calcium ions, ATP, and metabolites of arachidonic acid.

Macrophage Scavenger Receptors

Macrophage scavenger receptors with broad ligand specificity may participate in the binding of low density lipoproteins (LDL) and foreign antigens. Scavenger receptors types I and II are trimeric membrane proteins with each subunit containing a small N-terminal intracellular domain, a transmembrane domain, a large extracellular domain, and a C-terminal cysteine-rich domain. The extracellular domain contains a short spacer domain, an α-helical coiled-coil domain, and a triple helical collagenous domain. These receptors have been shown to bind a spectrum of ligands, including chemically modified lipoproteins and albumin, polyribonucleotides, polysaccharides, phospholipids, and asbestos (Matsumoto, A. et al. (1990) Proc. Natl. Acad. Sci. USA 87:9133-9137; Elomaa, O. et al. (1995) Cell 80:603-609). The scavenger receptors are thought to play a key role in atherogenesis by mediating uptake of modified LDL in arterial walls, and in host defense by binding bacterial endotoxins, bacteria, and protozoa.

T-Cell Receptors

T cells play a dual role in the immune system as effectors and regulators, coupling antigen recognition with the transmission of signals that induce cell death in infected cells and stimulate proliferation of other immune cells. Although a population of T cells can recognize a wide range of different antigens, an individual T cell can only recognize a single antigen and only when it is presented to the T cell receptor (TCR) as a peptide complexed with a major histocompatibility molecule (MHC) on the surface of an antigen presenting cell. The TCR on most T cells consists of immunoglobulin-like integral membrane glycoproteins containing two polypeptide subunits, a and p, of similar molecular weight. Both TCR subunits have an extracellular domain containing both variable and constant regions, a transmembrane domain that traverses the membrane once, and a short intracellular domain (Saito, H. et al. (1984) Nature 309:757-762). The genes for the TCR subunits are constructed through somatic rearrangement of different gene segments. Interaction of antigen in the proper MHC context with the TCR initiates signaling cascades that induce the proliferation, maturation, and function of cellular components of the immune system (Weiss, A. (1991) Annu. Rev. Genet. 25:487-510). Rearrangements in TCR genes and alterations in TCR expression have been noted in lymphomas, leukemias, autoimmune disorders, and immunodeficiency disorders (Aisenberg, A. C. et al. (1985) N. Engl. J. Med. 313:529-533; Weiss, supra).

Netrin Receptors

The netrins are a family of molecules that function as diffusible attractants and repellants to guide migrating cells and axons to their targets within the developing nervous system. The netrin receptors include the *C. elegans* protein UNC-5, as well as homologues recently identified in vertebrates (Leonardo, E. D. et al. (1997) Nature 386:833-838). These receptors are members of the immunoglobulin superfamily, and also contain a characteristic domain called the ZU5 domain. Mutations in the mouse member of the netrin receptor family, Rcm (rostral cerebellar malformation) result in cerebellar and midbrain defects as an apparent result of abnormal neuronal migration (Ackerman, S. L. et al. (1997) Nature 386:838-842).

VPS10 Domain Containing Receptors

The members of the VPS10 domain containing receptor family all contain a domain with homology to the yeast vacuolar sorting protein 10 (VPS10) receptor. This family includes the mosaic receptor SorLA, the neurotensin receptor sortilin, and SorCS, which is expressed during mouse embryonal and early postnatal nervous system development (Hermey, G. et al. (1999) Biochem. Biophys. Res. Commun. 266:347-351; Hermey, G. et al. (2001) Neuroreport 12:29-32). A recently identified member of this family, SorCS2, is highly expressed in the developing and mature mouse central nervous system. Its main site of expression is the floor plate, and high levels are also detected transiently in brain regions including the dopaminergic brain nuclei and the dorsal thalamus (Rezgaoui, M. (2001) Mech. Dev. 100:335-338).

Membrane-Associated Proteins

Tetraspan Family Proteins

The transmembrane 4 superfamily (TM4SF) or tetraspan family is a multigene family encoding type mi integral membrane proteins (Wright, M. D. and M. G. Tomlinson (1994) Immunol. Today 15:588-594). The TM4SF is comprised of membrane proteins which traverse the cell membrane four times. Members of the TM4SF include platelet and endothelial cell membrane proteins, melanoma-associated antigens, leukocyte surface glycoproteins, colonal carcinoma antigens, tumor-associated antigens, and surface proteins of the schistosome parasites (Jankowski, S. A. (1994) Oncogene 9:1205-1211). Members of the TM4SF share about 25-30% amino acid sequence identity with one another. A number of TM4SF members have been implicated in signal transduction, control of cell adhesion, regulation of cell growth and proliferation, including development and oncogenesis, and cell motility, including tumor cell metastasis. Expression of TM4SF proteins is associated with a variety of tumors and the level of expression may be altered when cells are growing or activated.

Tumor Antigens

Tumor antigens are surface molecules that are differentially expressed in tumor cells relative to normal cells. Tumor antigens distinguish tumor cells immunologically from normal cells and provide diagnostic and therapeutic targets for human cancers (Takagi, S. et al. (1995) Int. J. Cancer 61:706-715; Liu, E. et al. (1992) Oncogene 7:1027-1032).

Ion Channels

Ion channels are found in the plasma membranes of virtually every cell in the body. For example, chloride channels mediate a variety of cellular functions including regulation of membrane potentials and absorption and secretion of ions across epithelial membranes. When present in intracellular membranes of the Golgi apparatus and endocytic vesicles, chloride channels also regulate organelle pH. (See, e.g., Greger, R. (1988) Annu. Rev. Physiol. 50:111-122.) Electrophysiological and pharmacological properties of chloride channels, including ion conductance, current-voltage relationships, and sensitivity to modulators, suggest that different chloride channels exist in muscles, neurons, fibroblasts, epithelial cells, and lymphocytes. Many channels have sites for phosphorylation by one or more protein kinases including protein kinase A, protein kinase C, tyrosine kinase, and casein kinase II, all of which regulate ion channel activity in cells. Inappropriate phosphorylation of proteins in cells has been linked to changes in cell cycle progression and cell differentiation. Changes in the cell cycle have been linked to induction of apoptosis or cancer. Changes in cell differentiation have been linked to diseases and disorders of the reproductive system, immune system, and skeletal muscle.

Cerebellar granule neurons possess a non-inactivating potassium current which modulates firing frequency upon receptor stimulation by neurotransmitters and controls the resting membrane potential. Potassium channels that exhibit non-inactivating currents include the ether a go-go (EAG) channel. A membrane protein designated KCR1 specifically binds to rat EAG by means of its C-terminal region and regulates the cerebellar non-inactivating potassium current. KCR1 is predicted to contain 12 transmembrane domains, with intracellular amino and carboxyl termini. Structural characteristics of these transmembrane regions appear to be similar to those of the transporter superfamily, but no homology between KCR1 and known transporters was found, suggesting that KCR1 belongs to a novel class of transporters. KCR1 appears to be the regulatory component of non-inactivating potassium channels (Hoshi, N. et al. (1998) J. Biol. Chem. 273:23080-23085).

ABC Transporters

ATP-binding cassette (ABC) transporters, also called the "traffic ATPases", are a superfamily of membrane proteins that mediate transport and channel functions in prokaryotes and eukaryotes (Higgins, C. F. (1992) Annu. Rev. Cell Biol. 8:67-113). ABC proteins share a similar overall structure and significant sequence homology. All ABC proteins contain a conserved domain of approximately two hundred amino acid residues which includes one or more nucleotide binding domains. Mutations in ABC transporter genes are associated with various disorders, such as hyperbilirubinemia II/Dubin-Johnson syndrome, recessive Stargardt's disease, X-linked adrenoleukodystrophy, multidrug resistance, celiac disease, and cystic fibrosis.

Semaphorins and Neuropilins

Semaphorins are a large group of axonal guidance molecules consisting of at least 30 different members and are found in vertebrates, invertebrates, and even certain viruses. All semaphorins contain the sema domain which is approximately 500 amino acids in length. Neuropilin, a semaphorin receptor, has been shown to promote neurite outgrowth in vitro. The extracellular region of neuropilins consists of three different domains: CUB, discoidin, and MAM domains. The CUB and the MAM motifs of neuropilin have been suggested to have roles in protein-protein interactions and are thought to be involved in the binding of semaphorins through the sema and the C-terminal domains (reviewed in Raper, J. A. (2000) Curr. Opin. Neurobiol. 10:88-94).

Membrane Proteins Associated with Intercellular Communication

Intercellular communication is essential for the development and survival of multicellular organisms. Cells communicate with one another through the secretion and uptake of protein signaling molecules. The uptake of proteins into the cell is achieved by endocytosis, in which the interaction of signaling molecules with the plasma membrane surface, often via binding to specific receptors, results in the formation of plasma membrane-derived vesicles that enclose and transport the molecules into the cytosol. The secretion of proteins from the cell is achieved by exocytosis, in which molecules inside of the cell are packaged into membrane-bound transport vesicles derived from the trans Golgi network. These vesicles fuse with the plasma membrane and release their contents into the surrounding extracellular space. Endocytosis and exocytosis result in the removal and addition of plasma membrane components, and the recycling of these components is essential to maintain the integrity, identity, and functionality of both the plasma membrane and internal membrane-bound compartments.

Nogo has been identified as a component of the central nervous system myelin that prevents axonal regeneration in adult vertebrates. Cleavage of the Nogo-66 receptor and other glycophosphatidylinositol-linked proteins from axonal surfaces renders neurons insensitive to Nogo-66, facilitating potential recovery from CNS damage (Fournier, A. E. et al. (2001) Nature 409:341-346).

The slit proteins are extracellular matrix proteins expressed by cells at the ventral midline of the nervous system. Slit proteins are ligands for the repulsive guidance receptor Roundabout (Robo) and thus play a role in repulsive axon guidance (Brose, K. et al. (1999) Cell 96:795-806).

Lysosomes are the site of degradation of intracellular material during autophagy and of extracellular molecules following endocytosis. Lysosomal enzymes are packaged into vesicles which bud from the trans-Golgi network. These vesicles fuse with endosomes to form the mature lysosome in which hydrolytic digestion of endocytosed material occurs. Lysosomes can fuse with autophagosomes to form a unique compartment in which the degradation of organelles and other intracellular components occurs.

Protein sorting by transport vesicles, such as the endosome, has important consequences for a variety of physiological processes including cell surface growth, the biogenesis of distinct intracellular organelles, endocytosis, and the controlled secretion of hormones and neurotransmitters (Rothman, J. E. and F. T. Wieland (1996) Science 272:227-234). In particular, neurodegenerative disorders and other neuronal pathologies are associated with biochemical flaws during endosomal protein sorting or endosomal biogenesis (Mayer, R. J. et al. (1996) Adv. Exp. Med. Biol. 389:261-269).

Three classes of molecular motors—kinesins, dyneins and myosins—are involved in a variety of biological movements, such as mitosis, axoplasmic transport and secretion. Structurally, motor proteins consist of two functional parts: a motor domain that reversibly binds to the cytoskeleton and converts chemical energy into motion; and the rest of the molecule, often referred to as the tail, that interacts with cargo directly or through accessory light chains. These movements are required for the spatial organization of cytoplasm and, as a consequence, are crucial for cell division, embryonic development, and the formation of specialized areas of cytoplasm such as cilia and flagella. The ability of these proteins to transport a wide array of cargo is due, in part, to the fact that the tail domains are quite divergent from one another. This has allowed them to evolve into adaptors, linking themselves to cargo through interactions with receptor proteins on the cargo surface (Karcher, R. L. et al. (2002) TRENDS in Cell Biology Vol. 12 No. 1).

Kinesin is the most abundant motor in many cell types and is responsible for movement of a variety of different cargoes. The best characterized of kinesin receptors is kinectin, a receptor isolated as an endoplasmic-reticulum specific protein (Kumar, J. et al. (1995) Science 267, 1834-1837). Kinesin exists as a tetramer of two heavy chains, which contain the N-terminal motor domain and C-terminal tail, as well as two light chains, which bind to the heavy chain tail. Kinectin binds to the heavy chain of kinesin and is considered an ER-specific receptor for this motor protein. Interactions between motor proteins and corresponding receptors may be verified using a yeast two-hybrid system or co-immunoprecipitation assays.

Peroxisomes are organelles independent from the secretory pathway. They are the site of many peroxide-generating oxidative reactions in the cell. Peroxisomes are unique among eukaryotic organelles in that their size, number, and enzyme content vary depending upon organism, cell type, and metabolic needs (Waterham, H. R. and J. M. Cregg (1997) BioEssays 19:57-66). Genetic defects in peroxisome proteins which result in peroxisomal deficiencies have been linked to a number of human pathologies, including Zellweger syndrome, rhizomelic chonrodysplasia punctata, X-linked adrenoleukodystrophy, acyl-CoA oxidase deficiency, bifunctional enzyme deficiency, classical Refsum's disease, DHAP alkyl transferase deficiency, and acatalasemia (Moser, H. W. and A. B. Moser (1996) Ann. NY Acad. Sci. 804:427-441). In addition, Gartner, J. et al. (1991; Pediatr. Res. 29:141-146) found a 22 kDa integral membrane protein associated with lower density peroxisome-like subcellular fractions in patients with Zellweger syndrome.

Normal embryonic development and control of germ cell maturation is modulated by a number of secretory proteins which interact with their respective membrane-bound receptors. Cell fate during embryonic development is determined by members of the activin/TGF-β superfamily, cadherins, IGF-2, and other morphogens. In addition, proliferation, maturation, and redifferentiation of germ cell and reproductive tissues are regulated, for example, by IGF-2, inhibins, activins, and follistatins (Petraglia, F. (1997) Placenta 18:3-8; Mather, J. P. et al. (1997) Proc. Soc. Exp. Biol. Med. 215:209-222). Transforming growth factor beta (TGFβ) signal transduction is mediated by two receptor Ser/Thr kinases acting in series, type II TGFβ receptor and (TβR-II) phosphorylating type I TGFβ receptor (TβR-I). Signaling is initiated when the ligand binds to the TβR-II which is followed by recruitment of TβR-I into a heteromeric complex. Within the complex, TβR-II transphosphorylates and activates TβR-I kinase, which phosphorylates and activates downstream signaling components of the pathway. TβR-I-associated protein-1 (TRECAP-1), which distinguishes between quiescent and activated forms of the type I transforming growth factor beta receptor, has been associated with TGFβ signaling (Charng, M. J. et al. (1998) J. Biol. Chem. 273:9365-9368).

Retinoic acid receptor alpha (RAR alpha) mediates retinoic-acid induced maturation and has been implicated in myeloid development. Genes induced by retinoic acid during granulocytic differentiation include E3, a hematopoietic-specific gene that is an immediate target for the activated RAR alpha during myelopoiesis (Scott, L. M. et al. (1996) Blood 88:2517-2530).

The μ-opioid receptor (MOR) mediates the actions of analgesic agents including morphine, codeine, methadone, and fentanyl as well as heroin. MOR is functionally coupled to a G-protein-activated potassium channel (Mestek A. et al. (1995) J. Neurosci. 15:2396-2406). A variety of MOR subtypes exist. Alternative splicing has been observed with MOR-1 as with a number of G protein-coupled receptors including somatostatin 2, dopamine D2, prostaglandin EP3, and serotonin receptor subtypes 5-hydroxytryptamine4 and 5-hydroxytryptamine7 (Pan, Y. X. et al. (1999) Mol. Pharm. 56:396403).

Peripheral and Anchored Membrane Proteins

Some membrane proteins are not membrane-spanning but are attached to the plasma membrane via membrane anchors or interactions with integral membrane proteins. Membrane anchors are covalently joined to a protein post-translationally and include such moieties as prenyl, myristyl, and glycosylphosphatidyl inositol groups. Membrane localization of peripheral and anchored proteins is important for their function in processes such as receptor-mediated signal transduction. For example, prenylation of Ras is required for its localization to the plasma membrane and for its normal and oncogenic functions in signal transduction.

Expression Profiling

Microarrays are analytical tools used in bioanalysis. A microarray has a plurality of molecules spatially distributed over, and stably associated with, the surface of a solid support. Microarrays of polypeptides, polynucleotides, and/or antibodies have been developed and find use in a variety of applications, such as gene sequencing, monitoring gene expression, gene mapping, bacterial identification, drug discovery, and combinatorial chemistry.

One area in particular in which microarrays find use is in gene expression analysis. Array technology can provide a simple way to explore the expression of a single polymorphic gene or the expression profile of a large number of related or unrelated genes. When the expression of a single gene is examined, arrays are employed to detect the expression of a specific gene or its variants. When an expression profile is examined, arrays provide a platform for identifying genes that are tissue specific, are affected by a substance being tested in a toxicology assay, are part of a signaling cascade, carry out housekeeping functions, or are specifically related to a particular genetic predisposition, condition, disease, or disorder.

Breast Cancer

Breast cancer is the most frequently diagnosed type of cancer in American women and the second most frequent cause of cancer death. There are more than 180,000 new cases of breast cancer diagnosed each year, and the mortality rate for breast cancer approaches 10% of all deaths in females between the ages of 45-54 (K. Gish (1999) AWIS Magazine 28:7-10). The lifetime risk of an American woman developing breast cancer is 1 in 8, and one-third of women diagnosed with breast cancer die of the disease. However the survival rate based on early diagnosis of localized breast cancer is extremely high (97%), compared with the advanced stage of the disease in which the tumor has spread beyond the breast (22%). A number of risk factors have been identified, including hormonal and genetic factors. Current procedures for clinical breast examination are lacking in sensitivity and specificity, and efforts are underway to develop comprehensive gene expression profiles for breast cancer that may be used in conjunction with conventional screening methods to improve diagnosis and prognosis of this disease (Perou C M et al. (2000) Nature 406:747-752).

Breast cancer evolves through a multi-step process whereby premalignant mammary epithelial cells undergo a relatively defined sequence of events leading to tumor formation. An early event in tumor development is ductal hyperplasia. Cells undergoing rapid neoplastic growth gradually progress to invasive carcinoma and become metastatic to the lung, bone, and potentially other organs. Variables that may influence the process of tumor progression and malignant transformation include genetic factors, environmental factors, growth factors, and hormones.

Breast cancer is a genetic disease commonly caused by mutations in cellular disease. One genetic defect associated with breast cancer results in a loss of heterozygosity (LOH) at multiple loci such as p53, Rb, BRCA1, and BRCA2. Another genetic defect is gene amplification involving genes such as c-myc and c-erbB2 (Her2-neu gene). Steroid and growth factor pathways are also altered in breast cancer, notably the estrogen, progesterone, and epidermal growth factor (EGF) pathways. Mutations in two genes, BRCA1 and BRCA2, are known to greatly predispose a woman to breast cancer and may be passed on from parents to children (Gish, supra). However, this type of hereditary breast cancer accounts for only about 5% to 9% of breast cancers, while the vast majority of breast cancer is due to noninherited mutations that occur in breast epithelial cells.

A good deal is already known about the expression of specific genes associated with breast cancer. For example, the relationship between expression of epidermal growth factor (EGF) and its receptor, EGFR, to human mammary carcinoma has been particularly well studied. (See Khazaie et al., supra, and references cited therein for a review of this area.) Overexpression of EGFR, particularly coupled with down-regulation of the estrogen receptor, is a marker of poor prognosis in breast cancer patients. In addition, EGFR expression in breast tumor metastases is frequently elevated relative to the primary tumor, suggesting that EGFR is involved in tumor progression and metastasis. This is supported by accumulating evidence that EGF has effects on cell functions related to metastatic potential, such as cell motility, chemotaxis, secretion and differentiation. Changes in expression of other members of the erbB receptor family, of which EGFR is one, have also been implicated in breast cancer. The abundance of erbB receptors, such as HER-2/neu, HER-3, and HER-4, and their ligands in breast cancer points to their functional importance in the pathogenesis of the disease, and may therefore provide targets for therapy of the disease (Bacus, S S et al. (1994) Am J Clin Pathol 102:S13S24). Other known markers of breast cancer include a human secreted frizzled protein mRNA that is downregulated in breast tumors; the matrix G1a protein which is overexpressed is human breast carcinoma cells; Drg1 or RTP, a gene whose expression is diminished in colon, breast, and prostate tumors; maspin, a tumor suppressor gene down-regulated in invasive breast carcinomas; and CaN19, a member of the S100 protein family, all of which are down regulated in mammary carcinoma cells relative to normal mammary epithelial cells (Zhou Z et al. (1998) Int J Cancer 78:95-99; Chen, L et al. (1990) Oncogene 5:1391-1395; Ulrix W et al (1999) FEBS Lett 455:23-26; Sager, R et al. (1996) Curr Top Microbiol Immunol 213:51-64; and Lee, S W et al. (1992) Proc Natl Acad Sci USA 89:2504-2508).

Cell lines derived from human mammary epithelial cells at various stages of breast cancer provide a useful model to study the process of malignant transformation and tumor progression as it has been shown that these cell lines retain many of the properties of their parental tumors for lengthy culture periods (Wistuba II et al. (1998) Clin Cancer Res 4:2931-2938). Such a model is particularly useful for comparing phenotypic and molecular characteristics of human mammary epithelial cells at various stages of malignant transformation.

Prostate Cancer

As with most tumors, prostate cancer develops through a multistage progression ultimately resulting in an aggressive tumor phenotype. The initial step in tumor progression involves the hyperproliferation of normal luminal and/or basal epithelial cells. Androgen responsive cells become hyperplastic and evolve into early-stage tumors. Although early-stage tumors are often androgen sensitive and respond to androgen ablation, a population of androgen independent cells evolve from the hyperplastic population. These cells represent a more advanced form of prostate tumor that may become invasive and potentially become metastatic to the bone, brain, or lung. A variety of genes may be differentially expressed during tumor progression. For example, loss of heterozygosity (LOH) is frequently observed on chromosome 8p in prostate cancer. Fluorescence in situ hybridization (FISH) revealed a deletion for at least 1 locus on 8p in 29 (69%) tumors, with a significantly higher frequency of the deletion on 8p21.2-p21.1 in advanced prostate cancer than in localized prostate cancer, implying that deletions on 8p22-p21.3 play an important role in tumor differentiation, while 8p21.2-p21.1 deletion plays a role in progression of prostate cancer (Oba, K. et al. (2001) Cancer Genet. Cytogenet. 124: 20-26). As with breast cancer, there is a need for diagnostic and therapeutic agents that will improve treatment options for prostate cancer patients that can be fulfilled by the use of microarray expression analysis.

Colon Cancer

While soft tissue sarcomas are relatively rare, more than 50% of new patients diagnosed with the disease will die from it. The molecular pathways leading to the development of sarcomas are relatively unknown, due to the rarity of the disease and variation in pathology. Colon cancer evolves through a multi-step process whereby pre-malignant colonocytes undergo a relatively defined sequence of events leading to tumor formation. Several factors participate in the process of tumor progression and malignant transformation including genetic factors, mutations, and selection.

To understand the nature of gene alterations in colorectal cancer, a number of studies have focused on the inherited syndromes. The first, Familial Adenomatous Polyposis (FAP), is caused by mutations in the Adenomatous Polyposis Coli gene (APC), resulting in truncated or inactive forms of the protein. This tumor suppressor gene has been mapped to chromosome 5q. The second known inherited syndrome is hereditary nonpolyposis colorectal cancer (HNPCC), which is caused by mutations in mismatch repair genes.

Although hereditary colon cancer syndromes occur in a small percentage of the population, and most colorectal cancers are considered sporadic, knowledge from studies of the hereditary syndromes can be applied broadly. For instance, somatic mutations in APC occur in at least 80% of sporadic colon tumors. APC mutations are thought to be the initiating event in disease progression. Other mutations occur subsequently. Approximately 50% of colorectal cancers contain activating mutations in ras, while 85% contain inactivating mutations in p53. Changes in all of these genes lead to gene expression changes in colon cancer. Less is understood about downstream targets of these mutations and the role they may play in cancer development and progression.

Lung Cancer

Lung cancer is the leading cause of cancer death in the United States, affecting more than 100,000 men and 50,000 women each year. Nearly 90% of the patients diagnosed with lung cancer are cigarette smokers. Tobacco smoke contains thousands of noxious substances that induce carcinogen metabolizing enzymes and covalent DNA adduct formation in the exposed bronchial epithelium. In nearly 80% of patients diagnosed with lung cancer, metastasis has already occurred. Most commonly lung cancers metastasize to pleura, brain, bone, pericardium, and liver. The decision to treat with surgery, radiation therapy, or chemotherapy is made on the basis of tumor histology, response to growth factors or hormones, and sensitivity to inhibitors or drugs. With current treatments, most patients die within one year of diagnosis. Earlier diagnosis and a systematic approach to identification, staging, and treatment of lung cancer could positively affect patient outcome.

Lung cancers progress through a series of morphologically distinct stages from hyperplasia to invasive carcinoma. Malignant lung cancers are divided into two groups comprising four histopathological classes. The Non Small Cell Lung Carcinoma (NSCLC) group includes squamous cell carcinomas, adenocarcinomas, and large cell carcinomas and accounts for about 70% of all lung cancer cases. Adenocarcinomas typically arise in the peripheral airways and often form mucin secreting glands. Squamous cell carcinomas typically arise in proximal airways. The histogenesis of squamous cell carcinomas may be related to chronic inflammation and injury to the bronchial epithelium, leading to squamous metaplasia. The Small Cell Lung Carcinoma (SCLC) group accounts for about 20% of lung cancer cases. SCLCs typically arise in proximal airways and exhibit a number of paraneoplastic syndromes including inappropriate production of adrenocorticotropin and anti-diuretic hormone.

Lung cancer cells accumulate numerous genetic lesions, many of which are associated with cytologically visible chromosomal aberrations. The high frequency of chromosomal deletions associated with lung cancer may reflect the role of multiple tumor suppressor loci in the etiology of this disease. Deletion of the short arm of chromosome 3 is found in over 90% of cases and represents one of the earliest genetic lesions leading to lung cancer. Deletions at chromosome arms 9p and 17p are also common. Other frequently observed genetic lesions include overexpression of telomerase, activation of oncogenes such as K-ras and c-myc, and inactivation of tumor suppressor genes such as RB, p53 and CDKN2.

Genes differentially regulated in lung cancer have been identified by a variety of methods. Using mRNA differential display technology, Manda et al. (1999; Genomics 51:5-14) identified five genes differentially expressed in lung cancer cell lines compared to normal bronchial epithelial cells. Among the known genes, pulmonary surfactant apoprotein A and alpha 2 macroglobulin were down regulated whereas nm23H1 was upregulated. Petersen et al. (2000; Int J. Cancer, 86:512-517) used suppression subtractive hybridization to identify 552 clones differentially expressed in lung tumor derived cell lines, 205 of which represented known genes. Among the known genes, thrombospondin-1, fibronectin, intercellular adhesion molecule 1, and cytokeratins 6 and 18 were previously observed to be differentially expressed in lung cancers. Wang et al. (2000; Oncogene 19:1519-1528) used a combination of microarray analysis and subtractive hybridization to identify 17 genes differentially overexpresssed in squamous cell carcinoma compared with normal lung epithelium. Among the known genes they identified were keratin isoform 6, KOC, SPRC, IGFb2, connexin 26, plakofillin 1 and cytokeratin 13.

Ovarian Cancer

Ovarian cancer is the leading cause of death from a gynecologic cancer. The majority of ovarian cancers are derived from epithelial cells, and 70% of patients with epithelial ovarian cancers present with late-stage disease. As a result, the long-term survival rates for this disease is very low. Identification of early-stage markers for ovarian cancer would significantly increase the survival rate. Genetic variations involved in ovarian cancer development include mutation of p53 and microsatellite instability. Gene expression patterns likely vary when normal ovary is compared to ovarian tumors.

Immune Response

Tumor cells stimulate the formation of stroma that secretes various mediators, such as growth factors, cytokines, and proteases, all of which are pivotal for tumor growth. One such cytokine, interferon gamma (IFN-γ) induces growth arrest in normal human mammary epithelial cells by establishing a block during mid-G1 phase. EFN-γ inhibits the kinase activities of cdk2, cdk4 and cdk6 within 24 h of treatment. IFN-γ-mediated growth inhibition requires signal transducers and activators of transcrip-tion (STAT)-1 activation and may require induction of the cyclin-dependent kinase inhibitor p21. IFN-γ, maybe through the elevation of caspase-8 levels, sensitizes human breast tumor cells to a death receptor-mediated, mitochondria-operated pathway of apoptosis.

IFN-γ, also known as Type U interferon or immune interferon, is produced primarily by T-lympho-cytes and natural killer cells. IFN-γ was originally characterized based on its antiviral characteristics. The protein exhibits antiproliferative, immunoregulatory and proinflammatory activities and is thus important in host defense mechanisms. IFN-γ induces the production of cytokines, upregulates the expression of class I and II MHC antigens, Fc receptor, and leukocyte adhesion molecules. It modulates macrophage effector functions, influences isotype switching and potentiates the secretion of immunoglobulins by B cells. IFN-γ also augments TH1 cell expansion and may be required for TH1 cell differentiation. The IFN-γ receptor has been cloned and characterized, and is structurally related to the recently cloned IL-10 receptor. It is present on almost all cell types except mature erythrocytes.

Human Peripheral Blood Mononuclear Cells (PBMCs)

Human peripheral blood mononuclear cells (PBMCs) represent the major cellular components of the immune system. PBMCs contain about 52% lymphocytes (12% B lymphocytes, 40% T lymphocytes {25% CD4+ and 15% CD8+}), 20% NK cells, 25% monocytes, and 3% various cells that include dendritic cells and progenitor cells. The proportions, as well as the biology of these cellular components tend to vary slightly between healthy individuals, depending on factors such as age, gender, past medical history, and genetic background. These cells are responsible for immune responses and fighting infections, and thus represent a crucial system designed to maintain human health. Understanding the factors that activate and maintain this system requires analysis of cellular responses to stimuli, examining differences in the gene expression patterns of the various cell types, and determination of potential therapeutic targets that could be exploited for bolstering the immune response in individuals with deficiencies in this system. Microarray expression analysis can play an important role in achieving these goals.

Leukocytes comprise lymphocytes, granulocytes, and monocytes. Lymphocytes include T and B cells, which specifically recognize and respond to foreign pathogens. T cells fight viral infections and activate other leukocytes, while B cells secrete antibodies that neutralize bacteria and other microbes. Lymphoblast cell lines can be used to study signaling in human B cells and identify factors produced by those cells. An example is the RPMI 6666 B cell lymphoblast cell line derived from the peripheral blood of a male donor with Hodgkin's disease, which produces immunoglobulins and presents cell-associated Epstein-Barr virus (EBV) particles. Granulocytes and monocytes are primarily migratory, phagocytic cells that exit the bloodstream to fight infection in tissues. Monocytes, which are derived from immature promonocytes, further differentiate into macrophages that engulf and digest microorganisms and damaged or dead cells. Monocytes and macrophages modulate the immune response by secreting signaling molecules such as growth factors and cytokines. Tumor necrosis factor-α (TNF-α), for example, is a macrophage-secreted protein with anti-tumor and anti-viral activity. In addition, monocytes and macrophages are recruited to sites of infection and inflammation by signaling proteins secreted by other leukocytes. The differentiation of the monocyte blood cell lineage can be studied in vitro using cultured cell lines. For example, THP-1 is a human promonocyte cell line that can be activated by treatment with both phorbol ester such as phorbol myristate acetate (PMA) and ionomycin, a calcium ionophore that permits the entry of calcium in the cell, which increases the intracellular concentration of calcium. PMA is a broad activator of the protein kinase C-dependent pathways. The combination of PMA and ionomycin activates two of the major signaling pathways used by mammalian cells to interact with their environment. In T cells, the combination of PMA and ionomycin mimics the type of secondary signaling events elicited during optimal B cell activation. THP-1 can also be activated by treatment with both phorbol ester such as phorbol myristate acetate (PMA), and lipopolysaccharide (LPS). In another example, K-562 is a myeloid precursor cell line derived from the pleural effusion of a 53-year-old female with chronic myelogenous leukemia. The K-562 cell line has been extensively used to study differentiation of the erythrocytic, granulocytic, and monocytic lineage in humans. In addition, the K-562 cell line is widely used as an extremely sensitive target to the cytolytic activity of human natural killer cells in vitro. Another cell line, Jurkat, is an acute T cell leukemia cell line that grows actively in the absence of external stimuli and has been extensively used to study signaling in human T cells. In T cells, the combination of PMA and ionomycin mimics the type of secondary signaling events elicited during optimal B cell activation.

Monocytes are involved in the initiation and maintenance of inflammatory immune responses. The outer membrane of gram-negative bacteria expresses lipopolysaccharide (LPS) complexes called endotoxins. Toxicity is associated with the lipid component (Lipid A) of LPS, and immunogenicity is associated with the polysaccharide components of LPS. LPS elicits a variety of inflammatory responses, and because it activates complement by the alternative (properdin) pathway, it is often part of the pathology of gram-negative bacterial infections. For the most part, endotoxins remain associated with the cell wall until the bacteria disintegrate. LPS released into the bloodstream by lysing gram-negative bacteria is first bound by certain plasma proteins identified as LPS-binding proteins. The LPS-binding protein complex interacts with CD14 receptors on monocytes, macrophages, B cells, and other types of receptors on endothelial cells. Activation of human B cells with LPS results in mitogenesis as well as immunoglobulin synthesis. In monocytes and macrophages three types of events are triggered during their interaction with LPS: 1) Production of cytokines, including IL-1, IL6, IL-8, TNF-α, and platelet-activating factor, which stimulate production of prostaglandins and leukotrienes that mediate inflammation and septic shock; 2) Activation of the complement cascade; and 3) Activation of the coagulation cascade. Thus, LPS stimulation of lymphocytic cells can be used to examine changes in gene expression that occur in response to infectious stimuli, and can be analyzed by microarray expression analysis.

Functional interaction of the cell types involved in immune responses involves transfer of signals via soluble messenger molecules known as cytokines. Both hematopoietic cells and non-hematopoietic cells produce cytokines, which stimulate the activation, differentiation and proliferation of T cells, B cells, macrophages, and granulocytes during an active immune response. Cytokines bind to specific receptors expressed on cellular membranes and transduce a signal through the cell. Depending on the type of cytokine and the cell to which it binds, this signal initiates activation, differentiation, growth, and/or apoptosis. IL-10 is a pleiotrophic cytoline that can exert either immunostimulatory or immunosupressive effects on a variety of cell types. IL-10 suppresses the accessory cell function of macrophages and dendritic cells in part by downregulating class II MHC expression, preventing antigen presentation. IL-10 directly suppresses macrophage and monocyte production of inflammatory molecules such as tumor necrosis factor alpha (TNF-α), EL-1α, and IL6, while maintaining production of transforming growth factor beta (TGF-β) which curbs Th1 responses. In contrast to its suppressive activities on T cells and macrophages, IL-10 boosts proliferation and differentiation of activated B cells into plasma cells.

Staphylococcal exotoxins specifically activate human T cells, expressing an appropriate TCR-Vbeta chain. Although polyclonal in nature, T cells activated by Staphylococcal exotoxins require antigen presenting cells (APCs) to present the exotoxin molecules to the T cells and deliver the costimulatory signals required for optimum T cell activation. Although, Staphylococcal exotoxins must be presented to T cells by APCs, these molecules are not required to be processed by APC. Indeed, Staphylococcal exotoxins directly bind to a non-polymorphic portion of the human MHC class II molecules, bypassing the need for capture, cleavage, and binding of the peptides to the polymorphic antigenic groove of the MHC class II molecules.

There is a need in the art for new compositions, including nucleic acids and proteins, for the diagnosis, prevention, and treatment of cell proliferative, autoimmune/inflammatory, neurological, metabolic, developmental, and endocrine disorders.

SUMMARY OF THE INVENTION

The present invention relates to novel receptors and membrane-associated proteins, referred to collectively as "REMAPs." The present invention relates to isolated polypeptides encoding REMAPs, REMAP variants, REMAP fragments, REMAP fusion polypeptides, polynucleotides encoding such polypeptides and methods of producing such polypeptides. One exemplary REMAP, termed REMAP-22, corresponds to SEQ ID NO: 22.

In some embodiments, an isolated REMAP polypeptide may be biologically active. For example, an isolated REMAP polypeptide may be capable of binding a ligand, such as CD40L. Such an isolated polypeptide may include the amino acid of SEQ ID NO: 22 or an amino acid sequence that is 90% identical to SEQ ID NO: 22. In some embodiments, the isolated polypeptide may share one or more antigenic determinants with a polypeptide encoded by SEQ ID NO: 22. In still other embodiments, the isolated polypeptide may be biologically active, e.g., may bind CD40L, and share one or more antigenic determinants with the polypeptide encoded by SEQ ID NO: 22.

In further embodiments, the isolated polypeptide may be encoded by (i) a polynucleotide such as SEQ ID NO: 60, (ii) an RNA equivalent of SEQ ID NO: 60, or (iii) a polynucleotide which varies from (i) or (ii) due to the genetic code. In some embodiments, the polynucleotide may be operably linked to a regulatory or expression sequence, such as a promoter sequence.

In further embodiments, an isolated polypeptide may include a REMAP fragment or a biologically active REMAP fragment. In still other embodiments, the isolated polypeptide may comprise a fusion protein that includes a portion of a REMAP polypeptide. For example, in some embodiments, an isolated polypeptide may include amino acids 188-237 of SEQ ID NO:22. In other embodiments, an isolated peptide may include an amino acid sequence of SEQ ID NO: 22 fused to a heterologous fusion polypeptide.

The polypeptides of the present invention may be isolated and produced by any number of methods known in the art. For example, such polypeptides may be produced recombinantly. In some embodiments, such polypeptides may be produced by culturing cells under conditions suitable for expression of the polypeptide, and recovering the polypeptide so expressed. In some embodiments, cells may be transformed with a polynucleotide including, for example, SEQ ID NO: 60, an RNA equivalent of SEQ ID NO: 60 or a polynucleotide which varies from SEQ ID NO: 60 due to the genetic code; in some embodiments, the polynucleotides may be operably linked to a promoter sequence.

BRIEF DESCRIPTION OF THE TABLES

Table 1 summarizes the nomenclature for full length polynucleotide and polypeptide embodiments of the invention.

Table 2 shows the GenBank identification number and annotation of the nearest GenBank homolog, and the PROTEOME database identification numbers and annotations of PROTEOME database homologs, for polypeptide embodiments of the invention. The probability scores for the matches between each polypeptide and its homolog(s) are also shown.

Table 3 shows structural features of polypeptide embodiments, including predicted motifs and domains, along with the methods, algorithms, and searchable databases used for analysis of the polypeptides.

Table 4 lists the cDNA and/or genomic DNA fragments which were used to assemble polynucleotide embodiments, along with selected fragments of the polynucleotides.

Table 5 shows representative cDNA libraries for polynucleotide embodiments.

Table 6 provides an appendix which describes the tissues and vectors used for construction of the cDNA libraries shown in Table 5.

Table 7 shows the tools, programs, and algorithms used to analyze polynucleotides and polypeptides, along with applicable descriptions, references, and threshold parameters.

Table 8 shows single nucleotide polymorphisms found in polynucleotide sequences of the invention, along with allele frequencies in different human populations.

DESCRIPTION OF THE INVENTION

Before the present proteins, nucleic acids, and methods are described, it is understood that embodiments of the invention are not limited to the particular machines, instruments, materials, and methods described, as these may vary. It is also to be understood that the terminology used herein is for the purpose of describing particular embodiments only, and is not intended to limit the scope of the invention.

As used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any machines, materials, and methods similar or equivalent to those described herein can be used to practice or test the present invention, the preferred machines, materials and methods are now described. All publications mentioned herein are cited for the purpose of describing and disclosing the cell lines, protocols, reagents and vectors which are reported in the publications and which might be used in connection with various embodiments of the invention. Nothing herein is to be construed as an admission that the invention is not entitled to antedate such disclosure by virtue of prior invention.

Definitions

"REMAP" refers to the amino acid sequences of substantially purified REMAP obtained from any species, particularly a mammalian species, including bovine, ovine, porcine, murine, equine, and human, and from any source, whether natural, synthetic, semi-synthetic, or recombinant.

The term "agonist" refers to a molecule which intensifies or mimics the biological activity of REMAP. Agonists may include proteins, nucleic acids, carbohydrates, small molecules, or any other compound or composition which modulates the activity of REMAP either by directly interacting with REMAP or by acting on components of the biological pathway in which REMAP participates.

An "allelic variant" is an alternative form of the gene encoding REMAP Allelic variants may result from at least one mutation in the nucleic acid sequence and may result in altered mRNAs or in polypeptides whose structure or function may or may not be altered. A gene may have none, one, or many allelic variants of its naturally occurring form. Common mutational changes which give rise to allelic variants are generally ascribed to natural deletions, additions, or substitutions of nucleotides. Each of these types of changes may occur alone, or in combination with the others, one or more times in a given sequence.

"Altered" nucleic acid sequences encoding REMAP include those sequences with deletions, insertions, or substitutions of different nucleotides, resulting in a polypeptide the same as REMAP or a polypeptide with at least one functional characteristic of REMAP. Included within this definition are polymorphisms which may or may not be readily detectable using a particular oligonucleotide probe of the polynucleotide encoding REMAP, and improper or unexpected hybridization to allelic variants, with a locus other than the normal chromosomal locus for the polynucleotide encoding REMAP. The encoded protein may also be "altered," and may contain deletions, insertions, or substitutions of amino acid residues which produce a silent change and result in a functionally equivalent REMAP. Deliberate amino acid substitutions may be made on the basis of one or more similarities in polarity, charge, solubility, hydrophobicity, hydrophilicity, and/or the amphipathic nature of the residues, as long as the biological or immunological activity of REMAP is retained. For example, negatively charged amino acids may include aspartic acid and glutamic acid, and positively charged amino acids may include lysine and arginine. Amino acids with uncharged polar side chains having similar hydrophilicity values may include: asparagine and glutamine; and serine and threonine. Amino acids with uncharged side chains having similar hydrophilicity values may include: leucine, isoleucine, and valine; glycine and alanine; and phenylalanine and tyrosine.

The terms "amino acid" and "amino acid sequence" can refer to an oligopeptide, a peptide, a polypeptide, or a protein sequence, or a fragment of any of these, and to naturally occurring or synthetic molecules. Where "amino acid sequence" is recited to refer to a sequence of a naturally occurring protein molecule, "amino acid sequence" and like terms are not meant to limit the amino acid sequence to the complete native amino acid sequence associated with the recited protein molecule.

"Amplification" relates to the production of additional copies of a nucleic acid. Amplification may be carried out using polymerase chain reaction (PCR) technologies or other nucleic acid amplification technologies well known in the art.

The term "antagonist" refers to a molecule which inhibits or attenuates the biological activity of REMAP. Antagonists may include proteins such as antibodies, anticalins, nucleic acids, carbohydrates, small molecules, or any other compound or composition which modulates the activity of REMAP either by directly interacting with REMAP or by acting on components of the biological pathway in which REMAP participates.

The term "antibody" refers to intact immunoglobulin molecules as well as to fragments thereof, such as Fab, $F(ab')_2$, and Fv fragments, which are capable of binding an epitopic determinant. Antibodies that bind REMAP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant" refers to that region of a molecule (i.e., an epitope) that makes contact with a particular antibody. When a protein or a fragment of a protein is used to immunize a host animal, numerous regions of the protein may induce the production of antibodies which bind specifically to antigenic determinants (particular regions or three-dimensional structures on the protein). An antigenic determinant may compete with the intact antigen (i.e., the immunogen used to elicit the immune response) for binding to an antibody.

The term "aptamer" refers to a nucleic acid or oligonucleotide molecule that binds to a specific molecular target. Aptamers are derived from an in vitro evolutionary process (e.g., SELEX (Systematic Evolution of Ligands by EXponential Enrichment), described in U.S. Pat. No. 5,270,163), which selects for target-specific aptamer sequences from large combinatorial libraries. Aptamer compositions may be double-stranded or single-stranded, and may include deoxyribonucleotides, ribonucleotides, nucleotide derivatives, or other nucleotide-like molecules. The nucleotide components of an aptamer may have modified sugar groups (e.g., the 2'-OH group of a ribonucleotide may be replaced by 2'-F or 2'-$NH_2$), which may improve a desired property, e.g., resistance to nucleases or longer lifetime in blood. Aptamers may be conjugated to other molecules, e.g., a high molecular weight carrier to slow clearance of the aptamer from the circulatory system. Aptamers may be specifically cross-linked to their cognate ligands, e.g., by photo-activation of a cross-linker (Brody, E. N. and L. Gold (2000) J. Biotechnol. 74:5-13).

The term "intramer" refers to an aptamer which is expressed in vivo. For example, a vaccinia virus-based RNA expression system has been used to express specific RNA aptamers at high levels in the cytoplasm of leukocytes (Blind, M. et al. (1999) Proc. Natl. Acad. Sci. USA 96:3606-3610).

The term "spiegelmer" refers to an aptamer which includes L-DNA, L-RNA, or other left-handed nucleotide derivatives or nucleotide-like molecules. Aptamers containing left-handed nucleotides are resistant to degradation by naturally occurring enzymes, which normally act on substrates containing right-handed nucleotides.

The term "antisense" refers to any composition capable of base-pairing with the "sense" (coding) strand of a polynucleotide having a specific nucleic acid sequence. Antisense compositions may include DNA; RNA; peptide nucleic acid (PNA); oligonucleotides having modified backbone linkages such as phosphorothioates, methylphosphonates, or benzylphosphonates; oligonucleotides having modified sugar groups such as 2'-methoxyethyl sugars or 2'-methoxyethoxy sugars; or oligonucleotides having modified bases such as 5-methyl cytosine, 2'-deoxyuracil, or 7-deaza-2'-deoxyguanosine. Antisense molecules may be produced by any method including chemical synthesis or transcription. Once introduced into a cell, the complementary antisense molecule base-pairs with a naturally occurring nucleic acid sequence produced by the cell to form duplexes which block either transcription or translation. The designation "negative" or "minus" can refer to the antisense strand, and the designation "positive" or "plus" can refer to the sense strand of a reference DNA molecule.

The term "biologically active" refers to a protein having structural, regulatory, or biochemical functions of a naturally occurring molecule. Likewise, "immunologically active" or "immunogenic" refers to the capability of the natural, recombinant, or synthetic REMAP, or of any oligopeptide thereof, to induce a specific immune response in appropriate animals or cells and to bind with specific antibodies.

"Complementary" describes the relationship between two single-stranded nucleic acid sequences that anneal by base-pairing. For example, 5'-AGT-3' pairs with its complement, 3'-TCA-5'.

A "composition comprising a given polynucleotide" and a "composition comprising a given polypeptide" can refer to any composition containing the given polynucleotide or polypeptide. The composition may comprise a dry formulation or an aqueous solution. Compositions comprising polynucleotides encoding REMAP or fragments of REMAP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., sodium dodecyl sulfate; SDS), and other components (e.g., Denhardt's solution, dry milk, salmon sperm DNA, etc.).

"Consensus sequence" refers to a nucleic acid sequence which has been subjected to repeated DNA sequence analysis to resolve uncalled bases, extended using the XL-PCR kit (Applied Biosystems, Foster City Calif.) in the 5' and/or the 3' direction, and resequenced, or which has been assembled from one or more overlapping cDNA, EST, or genomic DNA fragments using a computer program for fragment assembly, such as the GELVIEW fragment assembly system (Accelrys,. Burlington Mass.) or Phrap (University of Washington, Seattle Wash.). Some sequences have been both extended and assembled to produce the consensus sequence.

"Conservative amino acid substitutions" are those substitutions that are predicted to least interfere with the properties of the original protein, i.e., the structure and especially the function of the protein is conserved and not significantly changed by such substitutions. The table below shows amino acids which may be substituted for an original amino acid in a protein and which are regarded as conservative amino acid substitutions.

| Original Residue | Conservative Substitution |
|---|---|
| Ala | Gly, Ser |
| Arg | His, Lys |
| Asn | Asp, Gln, His |
| Asp | Asn, Glu |
| Cys | Ala, Ser |
| Gln | Asn, Glu, His |
| Glu | Asp, Gln, His |
| Gly | Ala |
| His | Asn, Arg, Gln, Glu |
| Ile | Leu, Val |
| Leu | Ile, Val |
| Lys | Arg, Gln, Glu |
| Met | Leu, Ile |
| Phe | His, Met, Leu, Trp, Tyr |
| Ser | Cys, Thr |
| Thr | Ser, Val |
| Trp | Phe, Tyr |
| Tyr | His, Phe, Trp |
| Val | Ile, Leu, Thr |

Conservative amino acid substitutions generally maintain (a) the structure of the polypeptide backbone in the area of the substitution, for example, as a beta sheet or alpha helical conformation, (b) the charge or hydrophobicity of the molecule at the site of the substitution, and/or (c) the bulk of the side chain.

A "deletion" refers to a change in the amino acid or nucleotide sequence that results in the absence of one or more amino acid residues or nucleotides.

The term "derivative" refers to a chemically modified polynucleotide or polypeptide. Chemical modifications of a polynucleotide can include, for example, replacement of hydrogen by an alkyl, acyl, hydroxyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

A "detectable label" refers to a reporter molecule or enzyme that is capable of generating a measurable signal and is covalently or noncovalently joined to a polynucleotide or polypeptide.

"Differential expression" refers to increased or upregulated; or decreased, downregulated, or absent gene or protein expression, determined by comparing at least two different samples. Such comparisons may be carried out between, for example, a treated and an untreated sample, or a diseased and a normal sample.

"Exon shuffling" refers to the recombination of different coding regions (exons). Since an exon may represent a structural or functional domain of the encoded protein, new proteins may be assembled through the novel reassortment of stable substructures, thus allowing acceleration of the evolution of new protein functions.

A "fragment" is a unique portion of REMAP or a polynucleotide encoding REMAP which can be identical in sequence to, but shorter in length than, the parent sequence. A fragment may comprise up to the entire length of the defined sequence, minus one nucleotide/amino acid residue. For example, a fragment may comprise from about 5 to about 1000 contiguous nucleotides or amino acid residues. A fragment used as a probe, primer, antigen, therapeutic molecule, or for other purposes, may be at least 5, 10, 15, 16, 20, 25, 30, 40, 50, 60, 75, 100, 150, 250 or at least 500 contiguous nucleotides or amino acid residues in length. Fragments may be preferentially selected from certain regions of a molecule. For example, a polypeptide fragment may comprise a certain length of contiguous amino acids selected from the first 250 or 500 amino acids (or first 25% or 50%) of a polypeptide as shown in a certain defined sequence. Clearly these lengths are exemplary, and any length that is supported by the specification, including the Sequence Listing, tables, and figures, may be encompassed by the present embodiments.

A fragment of SEQ ID NO:39-76 can comprise a region of unique polynucleotide sequence that specifically identifies SEQ ID NO:39-76, for example, as distinct from any other sequence in the genome from which the fragment was obtained. A fragment of SEQ ID NO:39-76 can be employed in one or more embodiments of methods of the invention, for example, in hybridization and amplification technologies and in analogous methods that distinguish SEQ ID NO:39-76 from related polynucleotides. The precise length of a fragment of SEQ ID NO:39-76 and the region of SEQ ID NO:39-76 to which the fragment corresponds are routinely determinable by one of ordinary skill in the art based on the intended purpose for the fragment.

A fragment of SEQ ID NO:1-38 is encoded by a fragment of SEQ ID NO:39-76. A fragment of SEQ ID NO:1-38 can comprise a region of unique amino acid sequence that specifically identifies SEQ ID NO:1-38. For example, a fragment of SEQ ID NO:1-38 can be used as an immunogenic peptide for the development of antibodies that specifically recognize SEQ ID NO:1-38. The precise length of a fragment of SEQ ID NO:1-38 and the region of SEQ ID NO:1-38 to which the fragment corresponds can be determined based on the intended purpose for the fragment using one or more analytical methods described herein or otherwise known in the art.

A "full length" polynucleotide is one containing at least a translation initiation codon (e.g., methionine) followed by an open reading frame and a translation termination codon. A "full length" polynucleotide sequence encodes a "full length" polypeptide sequence.

"Homology" refers to sequence similarity or, alternatively, sequence identity, between two or more polynucleotide sequences or two or more polypeptide sequences.

The terms "percent identity" and "% identity," as applied to polynucleotide sequences, refer to the percentage of identical nucleotide matches between at least two polynucleotide sequences aligned using a standardized algorithm. Such an algorithm may insert, in a standardized and reproducible way, gaps in the sequences being compared in order to optimize alignment between two sequences, and therefore achieve a more meaningful comparison of the two sequences.

Percent identity between polynucleotide sequences may be determined using one or more computer algorithms or programs known in the art or described herein. For example, percent identity can be determined using the default parameters of the CLUSTAL V algorithm as incorporated into the MEGALIGN version 3.12e sequence alignment program. This program is part of the LASERGENE software package, a suite of molecular biological analysis programs (DNASTAR, Madison Wis.). CLUSTAL V is described in Higgins, D. G. and P. M. Sharp (1989; CABIOS 5:151-153) and in Higgins, D. G. et al. (1992; CABIOS 8:189-191). For pairwise alignments of polynucleotide sequences, the default parameters are set as follows: Ktuple=2, gap penalty=5, window=4, and "diagonals saved"=4. The "weighted" residue weight table is selected as the default.

Alternatively, a suite of commonly used and freely available sequence comparison algorithms which can be used is provided by the National Center for Biotechnology Information (NCBI) Basic Local Alignment Search Tool (BLAST) (Altschul, S. F. et al. (1990) J. Mol. Biol. 215: 403-410), which is available from several sources, including the NCBI, Bethesda, Md., and on the NCBI World Wide Web site available on the Internet. The BLAST software suite includes various sequence analysis programs including "blastn," that is used to align a known polynucleotide sequence with other polynucleotide sequences from a variety of databases. Also available is a tool called "BLAST 2 Sequences" that is used for direct pairwise comparison of two nucleotide sequences. "BLAST 2 Sequences" can be accessed and used interactively on the Internet via the NCBI World Wide Web site as well. The "BLAST 2 Sequences" tool can be used for both blastn and blastp (discussed below). BLAST programs are commonly used with gap and other parameters set to default settings. For example, to compare two nucleotide sequences, one may use blastn with the "BLAST 2 Sequences" tool Version 2.0.12 (Apr. 21, 2000) set at default parameters. Such default parameters may be, for example:

Matrix: BLOSUM62
Reward for match: 1
Penalty for mismatch: −2
Open Gap: 5 and Extension Gap: 2 penalties
Gap x drop-off: 50
Expect: 10
Word Size: 11
Filter: on Percent identity may be measured over the length of an entire defined sequence, for example, as defined by a particular SEQ ID number, or may be measured over a shorter length, for example, over the length of a fragment taken from a larger, defined sequence, for instance, a fragment of at least 20, at least 30, at least 40, at least 50, at least 70, at least 100, or at least 200 contiguous nucleotides. Such lengths are exemplary only, and it is understood that any fragment length supported by the sequences shown herein, in the tables, figures, or Sequence Listing, may be used to describe a length over which percentage identity may be measured.

Nucleic acid sequences that do not show a high degree of identity may nevertheless encode similar amino acid sequences due to the degeneracy of the genetic code. It is understood that changes in a nucleic acid sequence can be made using this degeneracy to produce multiple nucleic acid sequences that all encode substantially the same protein.

The phrases "percent identity" and "% identity," as applied to polypeptide sequences, refer to the percentage of identical residue matches between at least two polypeptide sequences aligned using a standardized algorithm. Methods of polypeptide sequence alignment are well-known. Some alignment methods take into account conservative amino acid substitutions. Such conservative substitutions, explained in more detail above, generally preserve the charge and hydrophobicity at the site of substitution, thus preserving the structure (and therefore function) of the polypeptide. The phrases "percent similarity" and "% similarity," as applied to polypeptide sequences, refer to the percentage of residue matches, including identical residue matches and conservative substitutions, between at least two polypeptide sequences aligned using a standardized algorithm. In contrast, conservative substitutions are not included in the calculation of percent identity between polypeptide sequences.

Percent identity between polypeptide sequences may be determined using the default parameters of the CLUSTAL V algorithm as incorporated into the MEGALIGN version 3.12e sequence alignment program (described and referenced above). For pairwise alignments of polypeptide sequences using CLUSTAL V, the default parameters are set as follows: Ktuple=1, gap penalty=3, window=5, and "diagonals saved"=5. The PAM250 matrix is selected as the default residue weight table.

Alternatively the NCBI BLAST software suite may be used. For example, for a pairwise comparison of two polypeptide sequences, one may use the "BLAST 2 Sequences" tool Version 2.0.12 (Apr. 21, 2000) with blastp set at default parameters. Such default parameters may be, for example:

Matrix: BLOSUM62
Open Gap: 11 and Extension Gap: 1 penalties
Gap x drop-off: 50
Expect: 10
Word Size: 3
Filter: on Percent identity may be measured over the length of an entire defined polypeptide sequence, for example, as defined by a particular SEQ ID number, or may be measured over a shorter length, for example, over the length of a fragment taken from a larger, defined polypeptide sequence, for instance, a fragment of at least 15, at least 20, at least 30, at least 40, at least 50, at least 70 or at least 150 contiguous residues. Such lengths are exemplary only, and it is understood that any fragment length supported by the sequences shown herein, in the tables, figures or Sequence Listing, may be used to describe a length over which percentage identity may be measured.

"Human artificial chromosomes" (HACs) are linear microchromosomes which may contain DNA sequences of about 6 kb to 10 Mb in size and which contain all of the elements required for chromosome replication, segregation and maintenance.

The term "humanized antibody" refers to an antibody molecule in which the amino acid sequence in the non-antigen binding regions has been altered so that the antibody more closely resembles a human antibody, and still retains its original binding ability.

"Hybridization" refers to the process by which a polynucleotide strand anneals with a complementary strand through base pairing under defined hybridization conditions. Specific hybridization is an indication that two nucleic acid sequences share a high degree of complementarity. Specific hybridization complexes form under permissive annealing conditions and remain hybridized after the "washing" step(s). The washing step(s) is particularly important in determining the stringency of the hybridization process, with more stringent conditions allowing less non-specific binding, i.e., binding between pairs of nucleic acid strands that are not perfectly matched. Permissive conditions for annealing of nucleic acid sequences are routinely determinable by one of ordinary skill in the art and may be consistent among hybridization experiments, whereas wash conditions may be varied among experiments to achieve the desired stringency, and therefore hybridization specificity. Permissive annealing conditions occur, for example, at 68° C. in the presence of about 6×SSC, about 1% (w/v) SDS, and about 100 μg/ml sheared, denaturedsalmon sperm DNA.

Generally, stringency of hybridization is expressed, in part, with reference to the temperature under which the wash step is carried out. Such wash temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. An equation for calculating $T_m$ and conditions for nucleic acid hybridization are well known and can be found in Sambrook, J. and D. W. Russell (2001; *Molecular Cloning: A Laboratory Manual,* 3rd ed., vol. 1-3, Cold Spring Harbor Press, Cold Spring Harbor N.Y., ch. 9).

High stringency conditions for hybridization between polynucleotides of the present invention include wash conditions of 68° C. in the presence of about 0.2×SSC and about 0.1% SDS, for 1 hour. Alternatively, temperatures of about 65° C., 60° C., 55° C., or 42° C. may be used. SSC concentration may be varied from about 0.1 to 2×SSC, with SDS being present at about 0.1%. Typically, blocking reagents are used to block non-specific hybridization. Such blocking reagents include, for instance, sheared and denatured salmon sperm DNA at about 100-200 μg/ml. Organic solvent, such as formamide at a concentration of about 35-50% v/v, may also be used under particular circumstances, such as for RNA:DNA hybridizations. Useful variations on these wash conditions will be readily apparent to those of ordinary skill in the art. Hybridization, particularly under high stringency conditions, may be suggestive of evolutionary similarity between the nucleotides. Such similarity is strongly indicative of a similar role for the nucleotides and their encoded polypeptides.

The term "hybridization complex" refers to a complex formed between two nucleic acids by virtue of the formation of hydrogen bonds between complementary bases. A hybridization complex may be formed in solution (e.g., $C_0t$ or $R_0t$ analysis) or formed between one nucleic acid present in solution and another nucleic acid immobilized on a solid support (e.g., paper, membranes, filters, chips, pins or glass slides, or any other appropriate substrate to which cells or their nucleic acids have been fixed).

The words "insertion" and "addition" refer to changes in an amino acid or polynucleotide sequence resulting in the addition of one or more amino acid residues or nucleotides, respectively.

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

An "immunogenic fragment" is a polypeptide or oligopeptide fragment of REMAP which is capable of eliciting an immune response when introduced into a living organism, for example, a mammal. The term "immunogenic fragment" also includes any polypeptide or oligopeptide fragment of REMAP which is useful in any of the antibody production methods disclosed herein or known in the art.

The term "microarray" refers to an arrangement of a plurality of polynucleotides, polypeptides, antibodies, or other chemical compounds on a substrate.

The terms "element" and "array element" refer to a polynucleotide, polypeptide, antibody, or other chemical compound having a unique and defined position on a microarray.

The term "modulate" refers to a change in the activity of REMAP. For example, modulation may cause an increase or a decrease in protein activity, binding characteristics, or any other biological, functional, or immunological properties of REMAP.

The phrases "nucleic acid" and "nucleic acid sequence" refer to a nucleotide, oligonucleotide, polynucleotide, or any fragment thereof. These phrases also refer to DNA or RNA of genomic or synthetic origin which may be single-stranded or double-stranded and may represent the sense or the antisense strand, to peptide nucleic acid (PNA), or to any DNA-like or RNA-like material.

"Operably linked" refers to the situation in which a first nucleic acid sequence is placed in a functional relationship with a second nucleic acid sequence. For instance, a promoter is operably linked to a coding sequence if the promoter affects the transcription or expression of the coding sequence. Operably linked DNA sequences may be in close proximity or contiguous and, where necessary to join two protein coding regions, in the same reading frame.

"Peptide nucleic acid" (PNA) refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA or RNA and stop transcript elongation, and may be pegylated to extend their lifespan in the cell.

"Post-translational modification" of an REMAP may involve lipidation, glycosylation, phosphorylation, acetylation, racemization, proteolytic cleavage, and other modifications known in the art. These processes may occur synthetically or biochemically. Biochemical modifications will vary by cell type depending on the enzymatic milieu of REMAP.

"Probe" refers to nucleic acids encoding REMAP, their complements, or fragments thereof, which are used to detect identical, allelic or related nucleic acids. Probes are isolated oligonucleotides or polynucleotides attached to a detectable label or reporter molecule. Typical labels include radioactive isotopes, ligands, chemiluminescent agents, and enzymes. "Primers" are short nucleic acids, usually DNA oligonucleotides, which may be annealed to a target polynucleotide by complementary base-pairing. The primer may then be extended along the target DNA strand by a DNA polymerase enzyme. Primer pairs can be used for amplification (and identification) of a nucleic acid, e.g., by the polymerase chain reaction (PCR).

Probes and primers as used in the present invention typically comprise at least 15 contiguous nucleotides of a known sequence. In order to enhance specificity, longer probes and primers may also be employed, such as probes and primers that comprise at least 20, 25, 30, 40, 50, 60, 70, 80, 90, 100, or at least 150 consecutive nucleotides of the disclosed nucleic acid sequences. Probes and primers may be considerably longer than these examples, and it is understood that any length supported by the specification, including the tables, figures, and Sequence Listing, may be used.

Methods for preparing and using probes and primers are described in, for example, Sambrook, J. and D. W. Russell (2001; *Molecular Cloning: A Laboratory Manual,* 3rd ed., vol. 1-3, Cold Spring Harbor Press, Cold Spring Harbor N.Y.), Ausubel, F. M. et al. (1999; *Short Protocols in Molecular Biology,* $4^{th}$ ed., John Wiley & Sons, New York N.Y.), and Innis, M. et al. (1990; *PCR Protocols, A Guide to Methods and Applications*, Academic Press, San Diego Calif.). PCR primer pairs can be derived from a known sequence, for example, by using computer programs intended for that purpose such as Primer (Version 0.5, 1991, Whitehead Institute for Biomedical Research, Cambridge Mass.).

Oligonucleotides for use as primers are selected using software known in the art for such purpose. For example, OLIGO 4.06 software is useful for the selection of PCR primer pairs of up to 100 nucleotides each, and for the analysis of oligonucleotides and larger polynucleotides of up to 5,000 nucleotides from an input polynucleotide sequence of up to 32 kilobases. Similar primer selection programs have incorporated additional features for expanded capabilities. For example, the PrimOU primer selection program (available to the public from the Genome Center at University of Texas South West Medical Center, Dallas Tex.) is capable of choosing specific primers from megabase sequences and is thus useful for designing primers on a genome-wide scope. The Primer3 primer selection program (available to the public from the Whitehead Institute/MIT Center for Genome Research, Cambridge Mass.) allows the user to input a "mispriming library," in which sequences to avoid as primer binding sites are user-specified. Primer3 is useful, in particular, for the selection of oligonucleotides for microarrays. (The source code for the latter two primer selection programs may also be obtained from their respective sources and modified to meet the user's specific needs.) The PrimeGen program (available to the public from the UK Human Genome Mapping Project Resource Centre, Cambridge UK) designs primers based on multiple sequence alignments, thereby allowing selection of primers that hybridize to either the most conserved or least conserved regions of aligned nucleic acid sequences. Hence, this program is useful for identification of both unique and conserved oligonucleotides and polynucleotide fragments. The oligonucleotides and polynucleotide fragments identified by any of the above selection methods are useful in hybridization technologies, for example, as PCR or sequencing primers, microarray elements, or specific probes to identify fully or partially complementary polynucleotides in a sample of nucleic acids. Methods of oligonucleotide selection are not limited to those described above.

A "recombinant nucleic acid" is a nucleic acid that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques such as those described in Sambrook and Russell (supra). The term recombinant includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Alternatively, such recombinant nucleic acids may be part of a viral vector, e.g., based on a vaccinia virus, that could be use to vaccinate a mammal wherein the recombinant nucleic acid is expressed, inducing a protective immunological response in the mammal.

A "regulatory element" refers to a nucleic acid sequence usually derived from untranslated regions of a gene and includes enhancers, promoters, introns, and 5' and 3' untranslated regions (UTRs). Regulatory elements interact with host or viral proteins which control transcription, translation, or RNA stability.

"Reporter molecules" are chemical or biochemical moieties used for labeling a nucleic acid, amino acid, or antibody. Reporter molecules include radionuclides; enzymes; fluorescent, chemiluminescent, or chromogenic agents; substrates; cofactors; inhibitors; magnetic particles; and other moieties known in the art.

An "RNA equivalent," in reference to a DNA molecule, is composed of the same linear sequence of nucleotides as the reference DNA molecule with the exception that all occurrences of the nitrogenous base thymine are replaced with uracil, and the sugar backbone is composed of ribose instead of deoxyribose.

The term "sample" is used in its broadest sense. A sample suspected of containing REMAP, nucleic acids encoding REMAP, or fragments thereof may comprise a bodily fluid; an extract from a cell, chromosome, organelle, or membrane isolated from a cell; a cell; genomic DNA, RNA, or cDNA, in solution or bound to a substrate; a tissue; a tissue print; etc.

The terms "specific binding" and "specifically binding" refer to that interaction between a protein or peptide and an agonist, an antibody, an antagonist, a small molecule, or any natural or synthetic binding composition. The interaction is dependent upon the presence of a particular structure of the protein, e.g., the antigenic determinant or epitope, recognized by the binding molecule. For example, if an antibody is specific for epitope "A," the presence of a polypeptide comprising the epitope A, or the presence of free unlabeled A, in a reaction containing free labeled A and the antibody will reduce the amount of labeled A that binds to the antibody.

The term "substantially purified" refers to nucleic acid or amino acid sequences that are removed from their natural environment and are isolated or separated, and are at least about 60% free, preferably at least about 75% free, and most preferably at least about 90% free from other components with which they are naturally associated.

A "substitution" refers to the replacement of one or more amino acid residues or nucleotides by different amino acid residues or nucleotides, respectively.

"Substrate" refers to any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which polynucleotides or polypeptides are bound.

A "transcript image" or "expression profile" refers to the collective pattern of gene expression by a particular cell type or tissue under given conditions at a given time.

"Transformation" describes a process by which exogenous DNA is introduced into a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, bacteriophage or viral infection, electroporation, heat shock, lipofection, and particle bombardment. The term "transformed cells" includes stably transformed cells in which the inserted DNA is capable of replication either as an autonomously replicating plasmid or as part of the host chromosome, as well as transiently transformed cells which express the inserted DNA or RNA for limited periods of time.

A "transgenic organism," as used herein, is any organism, including but not limited to animals and plants, in which one or more of the cells of the organism contains heterologous nucleic acid introduced by way of human intervention, such as by transgenic techniques well known in the art. The nucleic acid is introduced into the cell, directly or indirectly by introduction into a precursor of the cell, by way of deliberate genetic manipulation, such as by microinjection or by infection with a recombinant virus. In another embodiment, the nucleic acid can be introduced by infection with a recombinant viral vector, such as a lentiviral vector (Lois, C. et al. (2002) Science 295:868-872). The term genetic manipulation does not include classical cross-breeding, or in vitro fertilization, but rather is directed to the introduction of a recombinant DNA molecule. The transgenic organisms contemplated in accordance with the present invention include bacteria, cyanobacteria, fungi, plants and animals. The isolated DNA of the present invention can be introduced into the host by methods known in the art, for example infection, transfection, transformation or transconjugation. Techniques for transferring the DNA of the present invention into such organisms are widely known and provided in references such as Sambrook and Russell (supra).

A "variant" of a particular nucleic acid sequence is defined as a nucleic acid sequence having at least 40% sequence identity to the particular nucleic acid sequence over a certain length of one of the nucleic acid sequences using blastn with the "BLAST 2 Sequences" tool Version 2.0.9 (May 7, 1999) set at default parameters. Such a pair of nucleic acids may show, for example, at least 50%, at least 60%, at least 70%, at least 80%, at least 85%, at least 90%, at least 91%, at least 92%, at least 93%, at least 94%, at least 95%, at least 96%, at least 97%, at least 98%, or at least 99% or greater sequence identity over a certain defined length. A variant may be described as, for example, an "allelic" (as defined above), "splice," "species," or "polymorphic" variant. A splice variant may have significant identity to a reference molecule, but will generally have a greater or lesser number of polynucleotides due to alternate splicing during mRNA processing. The corresponding polypeptide may possess additional functional domains or lack domains that are present in the reference molecule. Species variants are polynucleotides that vary from one species to another. The resulting polypeptides will generally have significant amino acid identity relative to each other. A polymorphic variant is a variation in the polynucleotide sequence of a particular gene between individuals of a given species. Polymorphic variants also may encompass "single nucleotide polymorphisms" (SNPs) in which the polynucleotide sequence varies by one nucleotide base. The presence of SNPs may be indicative of, for example, a certain population, a disease state, or a propensity for a disease state.

A "variant" of a particular polypeptide sequence is defined as a polypeptide sequence having at least 40% sequence identity or sequence similarity to the particular polypeptide sequence over a certain length of one of the polypeptide sequences using blastp with the "BLAST 2 Sequences" tool Version 2.0.9 (May 7, 1999) set at default parameters. Such a pair of polypeptides may show, for example, at least 50%, at least 60%, at least 70%, at least 80%, at least 85%, at least 90%, at least 91%,.at least 92%, at least 93%, at least 94%, at least 95%, at least 96%, at least97%, at least 98%, or at least 99% or greater sequence identity or sequence similarity over a certain defined length of one of the polypeptides.

The Invention

Various embodiments of the invention include new human receptors and membrane-associated proteins (REMAP), the polynucleotides encoding REMAP, and the use of these compositions for the diagnosis, treatment, or prevention of cell proliferative, autoimmune/inflammatory, neurological, metabolic, developmental, and endocrine disorders.

Table 1 summarizes the nomenclature for the full length polynucleotide and polypeptide embodiments of the invention. Each polynucleotide and its corresponding polypeptide are correlated to a single Incyte project identification number (Incyte Project ID). Each polypeptide sequence is denoted by both a polypeptide sequence identification number (Polypeptide SEQ ID NO:) and an Incyte polypeptide sequence number (Incyte Polypeptide ID) as shown. Each polynucleotide sequence is denoted by both a polynucleotide sequence identification number (Polynucleotide SEQ ID NO:) and an Incyte polynucleotide consensus sequence number (Incyte Polynucleotide ID) as shown. Column 6 shows the Incyte ID numbers of physical, full length clones corresponding to the polypeptide and polynucleotide sequences of the invention. The full length clones encode polypeptides which have at least 95% sequence identity to the polypeptide sequences shown in column 3.

Table 2 shows sequences with homology to polypeptide embodiments of the invention as identified by BLAST analysis against the GenBank protein (genpept) database and the PROTEOME database. Columns 1 and 2 show the polypeptide sequence identification number (Polypeptide SEQ ID NO:) and the corresponding Incyte polypeptide sequence number (Incyte Polypeptide ID) for polypeptides of the invention. Column 3 shows the GenBank identification number (GenBank ID NO:) of the nearest GenBank homolog and the PROTEOME database identification numbers (PROTEOME ID NO:) of the nearest PROTEOME database homologs. Column 4 shows the probability scores for the matches between each polypeptide and its homolog(s). Column 5 shows the annotation of the GenBank and PROTEOME database homolog(s) along with relevant citations where applicable, all of which are expressly incorporated by reference herein.

Table 3 shows various structural features of the polypeptides of the invention. Columns 1 and 2 show the polypeptide sequence identification number (SEQ ID NO:) and the corresponding Incyte polypeptide sequence number (Incyte Polypeptide ID) for each polypeptide of the invention. Column 3 shows the number of amino acid residues in each polypeptide. Column 4 shows potential phosphorylation sites, and column 5 shows potential glycosylation sites, as determined by the MOTIFS program of the GCG sequence analysis software package (Accelrys, Burlington Mass.). Column 6 shows amino acid residues comprising signature sequences, domains, and motifs. Column 7 shows analytical methods for protein structure/function analysis and in some cases, searchable databases to which the analytical methods were applied.

Together, Tables 2 and 3 summarize the properties of polypeptides of the invention, and these properties establish that the claimed polypeptides are receptors and membrane-associated proteins. For example, SEQ ID NO:6 is 100% identical, from residue M1 to residue S208, to human tumor necrosis factor receptor 1 (GenBank ID g339750) as determined by the Basic Local Alignment Search Tool (BLAST). (See Table 2.) The BLAST probability score is 4.5e-119, which indicates the probability of obtaining the observed polypeptide sequence alignment by chance. SEQ ID NO:6 also has homology to proteins that are localized to the plasma membrane, function as receptors, and are tumor necrosis factor receptors, type 1, as determined by BLAST analysis using the PROTEOME database. SEQ ID NO:6 also contains a TNF-receptor internal cysteine rich domain, a TNFR/NGFR cysteine-rich region domain, and a tumor necrosis factor receptor/nerve domain as determined by searching for statistically significant matches in the hidden Markov model (HMM)-based PFAM, INCY, and SMART databases of conserved protein family domains. (See Table 3.) Data from BUMPS, MOTIFS, and other BLAST analyses provide further corroborative evidence that SEQ ID NO:6 is a type 1 tumor necrosis factor receptor. In another example, SEQ ID NO:8 is 99% identical, from residue M1 to residue A272, to human gastrin receptor (GenBank ID g406076) as determined by the Basic Local Alignment Search Tool (BLAST). The BLAST probability score is 3.2e-206, which indicates the probability of obtaining the observed polypeptide sequence alignment by chance. SEQ ID NO:8 also has homology to cholecystolcnin B (gastrin) receptors that are localized to the basolateral plasma membrane, as determined by BLAST analysis using the PROTEOME database. These receptors are G protein-coupled receptors. They are involved in stimulating phospholipase C and intracellular calcium flux, regulating digestion, gastric mucosal cell proliferation, and opioidergic and dopaminergic signaling. The human CCKBR variant is associated with colorectal cancer. SEQ ID NO:8 also contains a 7 transmembrane receptor (rhodopsin family) domain as determined by searching for statistically significant matches in the hidden Markov model (HM)-based PFAM database of conserved protein families/domains. (See Table 3.) Data from BLIMPS, MOTIFS, and PROFHLESCAN analyses provide further corroborative evidence that SEQ ID NO:8 is a G-protein coupled gastrin receptor. In another example, SEQ ID NO:22 is 99% identical, from residue Ml to residue G187, to human CDw40 (GenBank ID g29851) as determined by the Basic Local Alignment Search Tool (BLAST). (See Table 2.) The BLAST probability score is 2.7e-107, which indicates the probability of obtaining the observed polypeptide sequence alignment by chance. SEQ ID NO:22 is also a member of the tumor necrosis factor receptor superfamily, binds the ligand CD40L, and is expressed specifically in B lymphocytes. It also has a role in B lymphocyte maturation, as determined by BLAST analysis using the PROTEOME database. SEQ ID NO:22 also contains a TNF-receptor internal cysteine rich, Tumor necrosis factor receptor/nerve, and TNFR/NGFR cysteine-rich region domains as determined by searching for statistically significant matches in the hidden Markov model (HMM)-based PFAM, SMART, and INCY databases of conserved protein families/domains. (See Table 3.) Data from BLIMPS and MOTIFS analyses, and BLAST analyses against the PRODOM and DOMO databases, provide further corroborative evidence that SEQ ID NO:22 is a CDw40. In another example, SEQ ID NO:27 is 100% identical, from residue M1 to residue M224, to *Homo sapiens* ocular melanoma-associated antigen (GenBank ID g246539) as determined by the Basic Local Alignment Search Tool (BLAST). (See Table 2.) The BLAST probability score is 1.8e-115, which indicates the probability of obtaining the observed polypeptide sequence alignment by chance. SEQ ID NO:27 also has homology to proteins that are members of the tetraspanning superfamily and specifically CD63 antigen, form complexes with integrins and MHC class II molecules, and act to limit the invasion and progression of melanoma, as determined by BLAST analysis using the PROTEOME database. SEQ ID NO:27 also contains a tetraspanin family domain as determined by searching for statistically significant matches in the hidden Markov model (HMM)-based PFAM database of conserved protein families/domains. (See Table 3.) Data from BLIMPS, MOTIFS, and PROFILESCAN analyses, and BLAST analyses against the PRODOM and DOMO databases, provide further corroborative evidence that SEQ ID NO:27 is a transmembrane 4 family or tetraspanning family member. In another example, SEQ ID NO:31 is 85% identical, from residue F6 to residue I786, to human CD97 (GenBank ID g1685051) as determined by the Basic Local Alignment Search Tool (BLAST). (See Table 2.) The BLAST probability score is 0, which indicates the probability of obtaining the observed polypeptide sequence alignment by chance. SEQ ID NO:31 also has homology to proteins that are localized to the plasma membrane and are members of the EGF TM7 family of class II seven-span transmembrane receptors, as determined by BLAST analysis using the PROTEOME database. SEQ ID NO:31 also contains a 7 transmembrane receptor (secretin family) domain, an EGF-like domain, a G-protein coupled receptor proteolytic site domain, and a latrophilin/CL-1-like GPS domain as determined by searching for statistically significant matches in the hidden Markov model (HMM)-based PFAM and SMART databases of conserved protein families/domains. (See Table 3.) Data from BLIMPS, MOTIFS, and TMHMMER analyses, and BLAST analyses against the PRODOM and DOMO databases, provide further corroborative evidence that SEQ ID NO:31 is a CD97 antigen. In another example, SEQ ID NO:38 is 99% identical, from residue M1 to residue K792, to *H. sapiens* CD97 (GenBank ID g1685051) as determined by the Basic Local Alignment Search Tool (BLAST). (See Table 2.) The BLAST probability score is 0.0, which indicates the probability of obtaining the observed polypeptide sequence alignment by chance. SEQ ID NO:38 also has homology to proteins that are localized to the plasma membrane, are receptors for the complement cascade regulator, CD55 (Daf1), may play a role in lymphocyte activation, and are CD97 antigens as determined by BLAST analysis using the PROTEOME database. SEQ ID NO:38 also contains a 7 transmembrane receptor domain, an EGF-like domain, and a Latrophilin/CL-1-like GPS domain, as determined by searching for statistically significant matches in the hidden Markov model (HMM)-based PFAM and SMART databases of conserved protein families/domains. (See Table 3.) Data from BLIMPS and MOTIFS analyses, and BLAST analyses against the PRODOM and DOMO databases, provide further corroborative evidence that SEQ ID NO:38 is a CD97 antigen. SEQ ID NO:1-5, SEQ ID NO:7, SEQ ID NO:9-21, SEQ ID NO:23-26, SEQ ID NO:28-30, and SEQ ID NO:32-37 were analyzed and annotated in a similar manner. The algorithms and parameters for the analysis of SEQ ID NO:1-38 are described in Table 7.

As shown in Table 4, the full length polynucleotide embodiments were assembled using cDNA sequences or coding (exon) sequences derived from genomic DNA, or any combination of these two types of sequences. Column 1 lists the polynucleotide sequence identification number (Polynucleotide SEQ ID NO:), the corresponding Incyte polynucleotide consensus sequence number (Incyte ID) for each polynucleotide of the invention, and the length of each polynucleotide sequence in basepairs. Column 2 shows the nucleotide start (5') and stop (3') positions of the cDNA and/or genomic sequences used to assemble the full length polynucleotide embodiments, and of fragments of the polynucleotides which are useful, for example, in hybridization or amplification technologies that identify SEQ ID NO:39-76 or that distinguish between SEQ ID NO:39-76 and related polynucleotides.

The polynucleotide fragments described in Column 2 of Table 4 may refer specifically, for example, to Incyte cDNAs derived from tissue-specific cDNA libraries or from pooled cDNA libraries. Alternatively, the polynucleotide fragments described in column 2 may refer to GenBank cDNAs or ESTs which contributed to the assembly of the full length polynucleotides. In addition, the polynucleotide fragments described in column 2 may identify sequences derived from the ENSEMBL (The Sanger Centre, Cambridge, UK) database (i.e., those sequences including the designation "ENST"). Alternatively, the polynucleotide fragments described in column 2 may be derived from the NCBI RefSeq Nucleotide Sequence. Records Database (i.e., those sequences including the designation "NM" or "NT") or the NCBI RefSeq Protein Sequence Records (i.e., those sequences including the designation "NP"). Alternatively, the polynucleotide fragments described in column 2 may refer to assemblages of both cDNA and Genscan-predicted exons brought together by an "exon stitching" algorithm. For example, a polynucleotide sequence identified as $FL\_XXXXXX\_N_1\_N_2\_YYYYY\_N_3\_N_4$ represents a "stitched" sequence in which XXXXXX is the identification number of the cluster of sequences to which the algorithm was applied, and YYYYY is the number of the prediction generated by the algorithm, and $N_{1,2,3}$ . . . , if present, represent specific exons that may have been manually edited during analysis (See Example V). Alternatively, the polynucleotide fragments in column 2 may refer to assemblages of exons brought together by an "exon-stretching" algorithm. For example, a polynucleotide sequence identified as FL_XXXXXX_gAAAAA_gBBBBB_1_N is a "stretched" sequence, with XXXXXX being the Incyte project identification number, gAAAAA being the GenBank identification number of the human genomic sequence to which the "exon-stretching" algorithm was applied, gBBBBB being the GenBank identification number or NCBI RefSeq identification number of the nearest GenBank protein homolog, and N referring to specific exons (See Example V). In instances where a RefSeq sequence was used as a protein homolog for the "exon-stretching" algorithm, a RefSeq identifier (denoted by "NM," "NP," or "NT") may be used in place of the GenBank identifier (i.e., gBBBBB).

Alternatively, a prefix identifies component sequences that were hand-edited, predicted from genomic DNA sequences, or derived from a combination of sequence analysis methods. The following Table lists examples of component sequence prefixes and corresponding sequence analysis methods associated with the prefixes (see Example IV and Example V).

| Prefix | Type of analysis and/or examples of programs |
|---|---|
| GNN, GFG, ENST | Exon prediction from genomic sequences using, for example, GENSCAN (Stanford University, CA, USA) or FGENES (Computer Genomics Group, The Sanger Centre, Cambridge, UK). |
| GBI | Hand-edited analysis of genomic sequences. |
| FL | Stitched or stretched genomic sequences (see Example V). |
| INCY | Full length transcript and exon prediction from mapping of EST sequences to the genome. Genomic location and EST composition data are combined to predict the exons and resulting transcript. |

In some cases, Incyte cDNA coverage redundant with the sequence coverage shown in Table 4 was obtained to confirm the final consensus polynucleotide sequence, but the relevant Incyte cDNA identification numbers are not shown.

Table 5 shows the representative cDNA libraries for those full length polynucleotides which were assembled using Incyte cDNA sequences. The representative cDNA library is the Incyte cDNA library which is most frequently represented by the Incyte cDNA sequences which were used to assemble and confirm the above polynucleotides. The tissues and vectors which were used to construct the cDNA libraries shown in Table 5 are described in Table 6.

Table 8 shows single nucleotide polymorphisms (SNPs) found in polynucleotide sequences of the invention, along with allele frequencies in different human populations. Columns 1 and 2 show the polynucleotide sequence identification number (SEQ ID NO:) and the corresponding Incyte project identification number (PID) for polynucleotides of the invention. Column 3 shows the Incyte identification number for the EST in which the SNP was detected (EST ID), and column 4 shows the identification number for the SNP (SNP ID). Column 5 shows the position within the EST sequence at which the SNP is located (EST SNP), and column 6 shows the position of the SNP within the full-length polynucleotide sequence (CB1 SNP). Column 7 shows the allele found in the EST sequence. Columns 8 and 9 show the two alleles found at the SNP site. Column 10 shows the amino acid encoded by the codon including the SNP site, based upon the allele found in the EST. Columns 11-14 show the frequency of allele 1 in four different human populations. An entry of n/d (not detected) indicates that the frequency of allele 1 in the population was too low to be detected, while n/a (not available) indicates that the allele frequency was not determined for the population.

The invention also encompasses REMAP variants. Various embodiments of REMAP variants can have at least about 80%, at least about 90%, or at least about 95% amino acid sequence identity to the REMAP amino acid sequence, and can contain at least one functional or structural characteristic of REMAP.

Various embodiments also encompass polynucleotides which encode REMAP. In a particular embodiment, the invention encompasses a polynucleotide sequence comprising a sequence selected from the group consisting of SEQ ID NO:39-76, which encodes REMAP. The polynucleotide sequences of SEQ ID NO:39-76, as presented in the Sequence Listing, embrace the equivalent RNA sequences, wherein occurrences of the nitrogenous base thymine are replaced with uracil, and the sugar backbone is composed of ribose instead of deoxyribose.

The invention also encompasses variants of a polynucleotide encoding REMAP. In particular, such a variant polynucleotide will have at least about 70%, or alternatively at least about 85%, or even at least about 95% polynucleotide sequence identity to a polynucleotide encoding REMAP. A particular aspect of the invention encompasses a variant of a polynucleotide comprising a sequence selected from the group consisting of SEQ ID NO:39-76 which has at least about 70%, or alternatively at least about 85%, or even at least about 95% polynucleotide sequence identity to a nucleic acid sequence selected from the group consisting of SEQ ID NO:39-76. Any one of the polynucleotide variants described above can encode a polypeptide which contains at least one functional or structural characteristic of REMAP.

In addition, or in the alternative, a polynucleotide variant of the invention is a splice variant of a polynucleotide encoding REMAP. A splice variant may have portions which have significant sequence identity to a polynucleotide encoding REMAP, but will generally have a greater or lesser number of polynucleotides due to additions or deletions of blocks of sequence arising from alternate splicing during mRNA processing. A splice variant may have less than about 70%, or alternatively less than about 60%, or alternatively less than about 50% polynucleotide sequence identity to a polynucleotide encoding REMAP over its entire length; however, portions of the splice variant will have at least about 70%, or alternatively at least about 85%, or alternatively at least about 95%, or alternatively 100% polynucleotide sequence identity to portions of the polynucleotide encoding REMAP. For example, a polynucleotide comprising a sequence of SEQ ID NO:69 and a polynucleotide comprising a sequence of SEQ ID NO:76 are splice variants of each other. Any one of the splice variants described above can encode a polypeptide which contains at least one functional or structural characteristic of REMAP.

It will be appreciated by those skilled in the art that as a result of the degeneracy of the genetic code, a multitude of polynucleotide sequences encoding REMAP, some bearing minimal similarity to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring REMAP, and all such variations are to be considered as being specifically disclosed.

Although polynucleotides which encode REMAP and its variants are generally capable of hybridizing to polynucleotides encoding naturally occurring REMAP under appropriately selected conditions of stringency, it may be advantageous to produce polynucleotides encoding REMAP or its derivatives possessing a substantially different codon usage, e.g., inclusion of non-naturally occurring codons. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding REMAP and its derivatives without altering the encoded amino acid sequences include the production of RNA transcripts having more desirable properties, such as a greater half-life, than transcripts produced from the naturally occurring sequence.

The invention also encompasses production of polynucleotides which encode REMAP and REMAP derivatives, or fragments thereof, entirely by synthetic chemistry. After production, the synthetic polynucleotide may be inserted into any of the many available expression vectors and cell systems using reagents well known in the art. Moreover, synthetic chemistry may be used to introduce mutations into a polynucleotide encoding REMAP or any fragment thereof.

Embodiments of the invention can also include polynucleotides that are capable of hybridizing to the claimed polynucleotides, and, in particular, to those having the sequences shown in SEQ ID NO:39-76 and fragments thereof, under various conditions of stringency (Wahl, G. M. and S. L. Berger (1987) Methods Enzymol. 152:399-407; Kimmel, A. R. (1987) Methods Enzymol. 152:507-511). Hybridization conditions, including annealing and wash conditions, are described in "Definitions."

Methods for DNA sequencing are well known in the art and may be used to practice any of the embodiments of the invention. The methods may employ such enzymes as the Klenow fragment of DNA polymerase I, SEQUENASE (US Biochemical, Cleveland Ohio), Taq polymerase (Applied Biosystems), thermostable T7 polymerase (Amersham Biosciences, Piscataway N.J.), or combinations of polymerases and proofreading exonucleases such as those found in the ELONGASE amplification system (Invitrogen, Carlsbad Calif.). Preferably, sequence preparation is automated with machines such as the MICROLAB 2200 liquid transfer system (Hamilton, Reno Nev.), PTC200 thermal cycler (MJ Research, Watertown Mass.) and ABI CATALYST 800 thermal cycler (Applied Biosystems). Sequencing is then carried out using either the ABI 373 or 377 DNA sequencing system (Applied Biosystems), the MEGABACE 1000 DNA sequencing system (Amersham Biosciences), or other systems known in the art. The resulting sequences are analyzed using a variety of algorithms which are well known in the art (Ausubel et al., supra, ch. 7; Meyers, R. A. (1995) *Molecular Biology and Biotechnology*, Wiley VCH, New York N.Y., pp. 856-853).

The nucleic acids encoding REMAP may be extended utilizing a partial nucleotide sequence and employing various PCR-based methods known in the art to detect upstream sequences, such as promoters and regulatory elements. For example, one method which may be employed, restriction-site PCR, uses universal and nested primers to amplify unknown sequence from genomic DNA within a cloning vector (Sarkar, G. (1993) PCR Methods Applic. 2:318-322). Another method, inverse PCR, uses primers that extend in divergent directions to amplify unknown sequence from a circularized template. The template is derived from restriction fragments comprising a known genomic locus and surrounding sequences (Triglia, T. et al. (1988) Nucleic Acids Res. 16:8186). A third method, capture PCR, involves PCR amplification of DNA fragments adjacent to known sequences in human and yeast artificial chromosome DNA (Lagerstrom, M. et al. (1991) PCR Methods Applic. 1:111-119). In this method, multiple restriction enzyme digestions and ligations may be used to insert an engineered double-stranded sequence into a region of unknown sequence before performing PCR. Other methods which may be used to retrieve unknown sequences are known in the art (Parker, J. D. et al. (1991) Nucleic Acids Res. 19:3055-3060). Additionally, one may use PCR, nested primers, and PROMOTERFINDER libraries (Clontech, Palo Alto Calif.) to walk genomic DNA. This procedure avoids the need to screen libraries and is useful in finding intron/exon junctions. For all PCR-based methods, primers may be designed using commercially available software, such as OLIGO 4.06 primer analysis software (National Biosciences, Plymouth Minn.) or another appropriate program, to be about 22 to 30 nucleotides in length, to have a GC content of about 50% or more, and to anneal to the template at temperatures of about 68° C. to 72° C.

When screening for full length cDNAs, it is preferable to use libraries that have been size-selected to include larger cDNAs. In addition, random-primed libraries, which often include sequences containing the 5' regions of genes, are preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different nucleotide-specific, laser-stimulated fluorescent dyes, and a charge coupled device camera for detection of the emitted wavelengths. Output/light intensity may be converted to electrical signal using appropriate software (e.g., GENOTYPER and SEQUENCE NAVIGATOR, Applied Biosystems), and the entire process from loading of samples to computer analysis and electronic data display may be computer controlled. Capillary electrophoresis is especially preferable for sequencing small DNA fragments which may be present in limited amounts in a particular sample.

In another embodiment of the invention, polynucleotides or fragments thereof which encode REMAP may be cloned in recombinant DNA molecules that direct expression of REMAP, or fragments or functional equivalents thereof, in appropriate host cells. Due to the inherent degeneracy of the genetic code, other polynucleotides which encode substantially the same or a functionally equivalent polypeptides may be produced and used to express REMAP.

The polynucleotides of the invention can be engineered using methods generally known in the art in order to alter REMAP-encoding sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

The nucleotides of the present invention may be subjected to DNA shuffling techniques such as MOLECULARBREEDING (Maxygen Inc., Santa Clara Calif.; described in U.S. Pat. No. 5,837,458; Chang, C.-C. et al. (1999) Nat. Biotechnol. 17:793-797; Christians, F. C. et al. (1999) Nat. Biotechnol. 17:259-264; and Crameri, A. et al. (1996) Nat. Biotechnol. 14:315-319) to alter or improve the biological properties of REMAP, such as its biological or enzymatic activity or its ability to bind to other molecules or compounds. DNA shuffling is a process by which a library of gene variants is produced using PCR-mediated recombination of gene fragments. The library is then subjected to selection or screening procedures that identify those gene variants with the desired properties. These preferred variants may then be pooled and further subjected to recursive rounds of DNA shuffling and selection/screening. Thus, genetic diversity is created through "artificial" breeding and rapid molecular evolution. For example, fragments of a single gene containing random point mutations may be recombined, screened, and then reshuffled until the desired properties are optimized. Alternatively, fragments of a given gene may be recombined with fragments of homologous genes in the same gene family, either from the same or different species, thereby maximizing the genetic diversity of multiple naturally occurring genes in a directed and controllable manner.

In another embodiment, polynucleotides encoding REMAP may be synthesized, in whole or in part, using one or more chemical methods well known in the art (Caruthers, M. H. et al. (1980) Nucleic Acids Symp. Ser. 7:215-223; Horn, T. et al. (1980) Nucleic Acids Symp. Ser. 7:225-232). Alternatively, REMAP itself or a fragment thereof may be synthesized using chemical methods known in the art. For example, peptide synthesis can be performed using various solution-phase or solid-phase techniques (Creighton, T. (1984) Proteins. Structures and Molecular Properties, WH Freeman, New York N.Y., pp. 55-60; Roberge, J. Y. et al. (1995) Science 269:202-204). Automated synthesis may be achieved using the ABI 431A peptide synthesizer (Applied Biosystems). Additionally, the amino acid sequence of REMAP, or any part thereof, may be altered during direct synthesis and/or combined with sequences from other proteins, or any part thereof, to produce a variant polypeptide or a polypeptide having a sequence of a naturally occurring polypeptide.

The peptide may be substantially purified by preparative high performance liquid chromatography (Chiez, R. M. and F. Z. Regnier (1990) Methods Enzymol. 182:392-421). The composition of the synthetic peptides may be confirmed by amino acid analysis or by sequencing (Creighton, supra, pp. 28-53).

In order to express a biologically active REMAP, the polynucleotides encoding REMAP or derivatives thereof may be inserted into an appropriate expression vector, i.e., a vector which contains the necessary elements for transcriptional and translational control of the inserted coding sequence in a suitable host. These elements include regulatory sequences, such as enhancers, constitutive and inducible promoters, and 5' and 3' untranslated regions in the vector and in polynucleotides encoding REMAP. Such elements may vary in their strength and specificity. Specific initiation signals may also be used to achieve more efficient translation of polynucleotides encoding REMAP. Such signals include the ATG initiation codon and adjacent sequences, e.g. the Kozak sequence. In cases where a polynucleotide sequence encoding REMAP and its initiation codon and upstream regulatory sequences are inserted into the appropriate expression vector, no additional transcriptional or translational control signals may be needed. However, in cases where only coding sequence, or a fragment thereof, is inserted, exogenous translational control signals including an in-frame ATG initiation codon should be provided by the vector. Exogenous translational elements and initiation codons may be of various origins, both natural and synthetic. The efficiency of expression may be enhanced by the inclusion of enhancers appropriate for the particular host cell system used (Scharf, D. et al. (1994) Results Probl. Cell Differ. 20:125-162).

Methods which are well known to those skilled in the art may be used to construct expression vectors containing polynucleotides encoding REMAP and appropriate transcriptional and translational control elements. These methods include in vitro recombinant DNA techniques, synthetic techniques, and in vivo genetic recombination (Sambrook and Russell, supra, ch. 14, and 8; Ausubel et al., supra, ch. 1, 3, and 15).

A variety of expression vector/host systems may be utilized to contain and express polynucleotides encoding REMAP. These include, but are not limited to, microorganisms such as bacteria transformed with recombinant bacteriophage, plasmid, or cosmid DNA expression vectors; yeast transformed with yeast expression vectors; insect cell systems infected with viral expression vectors (e.g., baculovirus); plant cell systems transformed with viral expression vectors (e.g., cauliflower mosaic virus, CaMV, or tobacco mosaic virus, TMV) or with bacterial expression vectors (e.g., Ti or pBR322 plasmids); or animal cell systems (Sambrook and Russell, supra; Ausubel et al., supra; Van Heeke, G. and S. M. Schuster (1989) J. Biol. Chem. 264:5503-5509; Engelhard, E. K. et al. (1994) Proc. Natl. Acad. Sci. USA 91:3224-3227; Sandig, V. et al. (1996) Hum. Gene Ther. 7:1937-1945; Takamatsu, N. (1987) EMBO J. 6:307-311; *The McGraw Hill Yearbook of Science and Technology l (*1992) McGraw Hill, New York N.Y., pp. 191-196; Logan, J. and T. Shenk (1984) Proc. Natl. Acad. Sci. USA 81:3655-3659; Harrington, J. J. et al. (1997) Nat. Genet. 15:345-355). Expression vectors derived from retroviruses, adenoviruses, or herpes or vaccinia viruses, or from various bacterial plasmids, may be used for delivery of polynucleotides to the targeted organ, tissue, or cell population (Di Nicola, M. et al. (1998) Cancer Gen. Ther. 5:350-356; Yu, M. et al. (1993) Proc. Natl. Acad. Sci. USA 90:6340-6344; Buller, R. M. et al. (1985) Nature 317:813-815; McGregor, D. P. et al. (1994) Mol. Immunol. 31:219-226; Verma, I. M. and N. Somia (1997) Nature 389:239-242). The invention is not limited by the host cell employed.

In bacterial systems, a number of cloning and expression vectors may be selected depending upon the use intended for polynucleotides encoding REMAP. For example, routine cloning, subcloning, and propagation of polynucleotides encoding REMAP can be achieved using a multifunctional *E. coli* vector such as PBLUESCRIPT (Stratagene, La Jolla Calif.) or PSPORT1 plasmid (Invitrogen). Ligation of polynucleotides encoding REMAP into the vector's multiple cloning site disrupts the lacZ gene, allowing a colorimetric screening procedure for identification of transformed bacteria containing recombinant molecules. In addition, these vectors may be useful for in vitro transcription, dideoxy sequencing, single strand rescue with helper phage, and creation of nested deletions in the cloned sequence (Van Heeke, G. and S. M. Schuster (1989) J. Biol. Chem. 264:5503-5509). When large quantities of REMAP are needed, e.g. for the production of antibodies, vectors which direct high level expression of REMAP may be used. For example, vectors containing the strong, inducible SP6 or T7 bacteriophage promoter may be used.

Yeast expression systems may be used for production of REMAP. A number of vectors containing constitutive or inducible promoters, such as alpha factor, alcohol oxidase, and PGH promoters, may be used in the yeast *Saccharomyces cerevisiae* or *Pichia pastoris*. In addition, such vectors direct either the secretion or intracellular retention of expressed proteins and enable integration of foreign polynucleotide sequences into the host genome for stable propagation (Ausubel et al., supra; Bitter, G. A. et al. (1987) Methods Enzymol. 153:516-544; Scorer, C. A. et al. (1994) Bio/Technology 12:181-184).

Plant systems may also be used for expression of REMAP. Transcription of polynucleotides encoding REMAP may be driven by viral promoters, e.g., the 35S and 19S promoters of CaMV used alone or in combination with the omega leader sequence from TMV (Takamatsu, N. (1987) EMBO J. 6:307-311). Alternatively, plant promoters such as the small subunit of RUBISCO or heat shock promoters may be used (Coruzzi, G. et al. (1984) EMBO J. 3:1671-1680; Broglie, R. et al. (1984) Science 224:838-843; Winter, J. et al. (1991) Results Probl. Cell Differ. 17:85-105). These constructs can be introduced into plant cells by direct DNA transformation or pathogen-mediated transfection (*The McGraw Hill Yearbook of Science and Technology* (1992) McGraw Hill, New York N.Y., pp. 191-196).

In mammalian cells, a number of viral-based expression systems may be utilized. In cases where an adenovirus is used as an expression vector, polynucleotides encoding REMAP may be ligated into an adenovirus transcription/translation complex consisting of the late promoter and tripartite leader sequence. Insertion in a non-essential E1 or E3 region of the viral genome may be used to obtain infective virus which expresses REMAP in host cells (Logan, J. and T. Shenk (1984) Proc. Natl. Acad. Sci. USA 81:3655-3659). In addition, transcription enhancers, such as the Rous sarcoma virus (RSV) enhancer, may be used to increase expression in mammalian host cells. SV40 or EBV-based vectors may also be used for high-level protein expression.

Human artificial chromosomes (HACs) may also be employed to deliver larger fragments of DNA than can be contained in and expressed from a plasmid. HACs of about 6 kb to 10 Mb are constructed and delivered via conventional delivery methods (liposomes, polycationic amino polymers, or vesicles) for therapeutic purposes (Harrington, J. J. et al. (1997) Nat. Genet. 15:345-355).

For long term production of recombinant proteins in mammalian systems, stable expression of REMAP in cell lines is preferred. For example, polynucleotides encoding REMAP can be transformed into cell lines using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to a selective agent, and its presence allows growth and recovery of cells which successfully express the introduced sequences. Resistant clones of stably transformed cells may be propagated using tissue culture techniques appropriate to the cell type.

Any number of selection systems may be used to recover transformed cell lines. These include, but are not limited to, the herpes simplex virus thymidine kinase and adenine phosphoribosyltransferase genes, for use in tk and apr cells, respectively (Wigler, M. et al. (1977) Cell 11:223-232; Lowy, I. et al. (1980) Cell 22:817-823). Also, antimetabolite, antibiotic, or herbicide resistance can be used as the basis for selection. For example, dhfr confers resistance to methotrexate; neo confers resistance to the aminoglycosides neomycin and G418; and als and pat confer resistance to chlorsulfuron and phosphinotricin acetyltransferase, respectively (Wigler, M. et al. (1980) Proc. Natl. Acad. Sci. USA 77:3567-3570; Colbere-Garapin, F. et al. (1981) J. Mol. Biol. 150:1-14). Additional selectable genes have been described, e.g., trpB and hisD, which alter cellular requirements for metabolites (Hartan, S. C. and R. C. Mulligan (1988) Proc. Natl. Acad. Sci. USA 85:8047-8051). Visible markers, e.g., anthocyanins, green fluorescent proteins (GFP; Clontech), β-glucuronidase and its substrate β-glucuronide, or luciferase and its substrate luciferin may be used. These markers can be used not only to identify transformants, but also to quantify the amount of transient or stable protein expression attributable to a specific vector system (Rhodes, C. A. (1995) Methods Mol. Biol. 55:121-131).

Although the presence/absence of marker gene expression suggests that the gene of interest is also present, the presence and expression of the gene may need to be confirmed. For example, if the sequence encoding REMAP is inserted within a marker gene sequence, transformed cells containing polynucleotides encoding REMAP can be identified by the absence of marker gene function. Alternatively, a marker gene can be placed in tandem with a sequence encoding REMAP under the control of a single promoter. Expression of the marker gene in response to induction or selection usually indicates expression of the tandem gene as well.

In general, host cells that contain the polynucleotide encoding REMAP and that express REMAP may be identified by a variety of procedures known to those of skill in the art. These procedures include, but are not limited to, DNA-DNA or DNA-RNA hybridizations, PCR amplification, and protein bioassay or immunoassay techniques which include membrane, solution, or chip based technologies for the detection and/or quantification of nucleic acid or protein sequences.

Immunological methods for detecting and measuring the expression of REMAP using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on REMAP is preferred, but a competitive binding assay may be employed. These and other assays are well known in the art (Hampton, R. et al. (1990) *Serological Methods, a Laboratory Manual*, APS Press, St. Paul Minn., Sect. IV; Coligan, J. E. et al. (1997) *Current Protocols in Immunology*, Greene Pub. Associates and Wiley-Interscience, New York N.Y.; Pound, J. D. (1998) *Immunochemical Protocols*, Humana Press, Totowa N.J.).

A wide variety of labels and conjugation techniques are known by those skilled in the art and may be used in various nucleic acid and amino acid assays. Means for producing labeled hybridization or PCR probes for detecting sequences related to polynucleotides encoding REMAP include oligolabeling, nick translation, end-labeling, or PCR amplification using a labeled nucleotide. Alternatively, polynucleotides encoding REMAP, or any fragments thereof, may be cloned into a vector for the production of an mRNA probe. Such vectors are known in the art, are commercially available, and may be used to synthesize RNA probes i t vitro by addition of an appropriate RNA polymerase such as T7, T3, or SP6 and labeled nucleotides. These procedures may be conducted using a variety of commercially available kits, such as those provided by Amersham Biosciences, Promega (Madison Wis.), and US Biochemical. Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with polynucleotides encoding REMAP may be cultured under conditions suitable for the expression and recovery of the protein from cell culture. The protein produced by a transformed cell may be secreted or retained intracellularly depending on the sequence and/or the vector used. As will be understood by those of skill in the art, expression vectors containing polynucleotides which encode REMAP may be designed to contain signal sequences which direct secretion of REMAP through a prokaryotic or eukaryotic cell membrane.

In addition, a host cell strain may be chosen for its ability to modulate expression of the inserted polynucleotides or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" or "pro" form of the protein may also be used to specify protein targeting, folding, and/or activity. Different host cells which have specific cellular machinery and characteristic mechanisms for post-translational activities (e.g., CHO, HeLa, MDCK, HEK293, and WI38) are available from the American Type Culture Collection (ATCC, Manassas Va.) and may be chosen to ensure the correct modification and processing of the foreign protein.

In another embodiment of the invention, natural, modified, or recombinant polynucleotides encoding REMAP may be ligated to a heterologous sequence resulting in translation of a fusion protein in any of the aforementioned host systems. For example, a chimeric REMAP protein containing a heterologous moiety that can be recognized by a commercially available antibody may facilitate the screening of peptide libraries for inhibitors of REMAP activity. Heterologous protein and peptide moieties may also facilitate purification of fusion proteins using commercially available affinity matrices. Such moieties include, but are not limited to, glutathione S-transferase (GST), maltose binding protein (MBP), thioredoxin (Trx), calmodulin binding peptide (CBP), 6-His, FLAG, c-myc, and hemagglutinin (HA). GST, MBP, Trx, CBP, and 6-His enable purification of their cognate fusion proteins on immobilized glutathione, maltose, phenylarsine oxide, calmodulin, and metal-chelate resins, respectively. FLAG, c-nyc, and hemagglutinin (HA) enable immunoaffinity purification of fusion proteins using commercially available monoclonal and polyclonal antibodies that specifically recognize these epitope tags. A fusion protein may also be engineered to contain a proteolytic cleavage site located between the REMAP encoding sequence and the heterologous protein sequence, so that REMAP may be cleaved away from the heterologous moiety following purification. Methods for fusion protein expression and purification are discussed in Ausubel et al. (supra, ch. 10 and 16). A variety of commercially available kits may also be used to facilitate expression and purification of fusion proteins.

In another embodiment, synthesis of radiolabeled REMAP may be achieved in vitro using the TNT rabbit reticulocyte lysate or wheat germ extract system (Promega).

These systems couple transcription and translation of protein-coding sequences operably associated with the T7, T3, or SP6 promoters. Translation takes place in the presence of a radiolabeled amino acid precursor, for example, $^{35}$S-methionine.

REMAP, fragments of REMAP, or variants of REMAP may be used to screen for compounds that specifically bind to REMAP. One or more test compounds may be screened for specific binding to REMAP. In various embodiments, 1, 2, 3, 4, 5, 10, 20, 50, 100, or 200 test compounds can be screened for specific binding to REMAP. Examples of test compounds can include antibodies, anticalins, oligonucleotides, proteins (e.g., ligands or receptors), or small molecules.

In related embodiments, variants of REMAP can be used to screen for binding of test compounds, such as antibodies, to REMAP, a variant of REMAP, or a combination of REMAP and/or one or more variants REMAP. In an embodiment, a variant of REMAP can be used to screen for compounds that bind to a variant of REMAP, but not to REMAP having the exact sequence of a sequence of SEQ ID NO:1-38. REMAP variants used to perform such screening can have a range of about 50% to about 99% sequence identity to REMAP, with various embodiments having 60%, 70%, 75%, 80%, 85%, 90%, and 95% sequence identity.

In an embodiment, a compound identified in a screen for specific binding to REMAP can be closely related to the natural ligand of REMAP, e.g., a ligand or fragment thereof, a natural substrate, a structural or functional mimetic, or a natural binding partner (Coligan, J. E. et al. (1991) *Current Protocols in Immunology* 1(2):Chapter 5). In another embodiment, the compound thus identified can be a natural ligand of a receptor REMAP (Howard, A. D. et al. (2001) Trends Pharmacol. Sci. 22: 132-140; Wise, A. et al. (2002) Drug Discovery Today 7:235-246).

In other embodiments, a compound identified in a screen for specific binding to REMAP can be closely related to the natural receptor to which REMAP binds, at least a fragment of the receptor, or a fragment of the receptor including all or a portion of the ligand binding site or binding pocket For example, the compound may be a receptor for REMAP which is capable of propagating a signal, or a decoy receptor for REMAP which is not capable of propagating a signal (Ashkenazi, A. and V. M. Divit (1999) Curr. Opin. Cell Biol. 11:255-260; Mantovani, A. et al. (2001) Trends Immunol. 22:328-336). The compound can be rationally designed using known techniques. Examples of such techniques include those used to construct the compound etanercept (ENBREL; Amgen Inc., Thousand Oaks Calif.), which is efficacious for treating rheumatoid arthritis in humans. Etanercept is an engineered p75 tumor necrosis factor (CNE) receptor dimer linked to the Fc portion of human $IgG_1$ (Taylor, P. C. et al. (2001) Curr. Opin. Immunol. 13:611-616).

In one embodiment, two or more antibodies having similar or, alternatively, different specificities can be screened for specific binding to REMAP, fragments of REMAP, or variants of REMAP. The binding specificity of the antibodies thus screened can thereby be selected to identify particular fragments or variants of REMAP. In one embodiment, an antibody can be selected such that its binding specificity allows for preferential identification of specific fragments or variants of REMAP. In another embodiment, an antibody can be selected such that its binding specificity allows for preferential diagnosis of a specific disease or condition having increased, decreased, or otherwise abnormal production of REMAP.

In an embodiment, anticalins can be screened for specific binding to REMAP, fragments of REMAP, or variants of REMAP. Anticalins are,ligand-binding proteins that have been constructed based on a lipocalin scaffold (Weiss, G. A. and H. B. Lowman (2000) Chem. Biol. 7:R177-R184; Skerra, A. (2001) J. Biotechnol. 74:257-275). The protein architecture of lipocalins can include a beta-barrel having eight antiparallel beta-strands, which supports four loops at its open end. These loops form the natural ligand-binding site of the lipocalins, a site which can be re-engineered in vitro by amino acid substitutions to impart novel binding specificities. The amino acid substitutions can be made using methods known in the art or described herein, and can include conservative substitutions (e.g., substitutions that do not alter binding specificity) or substitutions that modestly, moderately, or significantly alter binding specificity.

In one embodiment, screening for compounds which specifically bind to, stimulate, or inhibit REMAP involves producing appropriate cells which express REMAP, either as a secreted protein or on the cell membrane. Preferred cells can include cells from mammals, yeast, *Drosophila*, or *E. coli*. Cells expressing REMAP or cell membrane fractions which contain REMAP are then contacted with a test compound and binding, stimulation, or inhibition of activity of either REMAP or the compound is analyzed.

An assay may simply test binding of a test compound to the polypeptide, wherein binding is detected by a fluorophore, radioisotope, enzyme conjugate, or other detectable label. For example, the assay may comprise the steps of combining at least one test compound with REMAP, either in solution or affixed to a solid support, and detecting the binding of REMAP to the compound. Alternatively, the assay may detect or measure binding of a test compound in the presence of a labeled competitor. Additionally, the assay may be carried out using cell-free preparations, chemical libraries, or natural product mixtures, and the test compound(s) may be free in solution or affixed to a solid support.

An assay can be used to assess the ability of a compound to bind to its natural ligand and/or to inhibit the binding of its natural ligand to its natural receptors. Examples of such assays include radio-labeling assays such as those described in U.S. Pat. No. 5,914,236 and U.S. Pat. No. 6,372,724. In a related embodiment, one or more amino acid substitutions can be introduced into a polypeptide compound (such as a receptor) to improve or alter its ability to bind to its natural ligands (Matthews, D. J. and J. A. Wells. (1994) Chem. Biol. 1:25-30). In another related embodiment, one or more amino acid substitutions can be introduced into a polypeptide compound (such as a ligand) to improve or alter its ability to bind to its natural receptors (Cunningham, B. C. and J. A. Wells (1991) Proc. Natl. Acad. Sci. USA 88:3407-3411; Lowman, H. B. et al. (1991) J. Biol. Chem. 266:10982-10988).

REMAP, fragments of REMAP, or variants of REMAP may be used to screen for compounds that modulate the activity of REMAP. Such compounds may include agonists, antagonists, or partial or inverse agonists. In one embodiment, an assay is performed under conditions permissive for REMAP activity, wherein REMAP is combined with at least one test compound, and the activity of REMAP in the presence of a test compound is compared with the activity of REMAP in the absence of the test compound. A change in the activity of REMAP in the presence of the test compound is indicative of a compound that modulates the activity of REMAP. Alternatively, a test compound is combined with an in vitro or cell-free system comprising REMAP under conditions suitable for REMAP activity, and the assay is performed. In either of these assays, a test compound which modulates the activity of REMAP may do so indirectly and need not come in direct contact with the test compound. At least one and up to a plurality of test compounds may be screened.

In another embodiment, polynucleotides encoding REMAP or their mammalian homologs may be "knocked out" in an animal model system using homologous recombination in embryonic stem (ES) cells. Such techniques are well known in the art and are useful for the generation of animal models of human disease (see, e.g., U.S. Pat. No. 5,175,383 and U.S. Pat. No. 5,767,337). For example, mouse ES cells, such as the mouse 129/SvJ cell line, are derived from the early mouse embryo and grown in culture. The ES cells are transformed with a vector containing the gene of interest disrupted by a marker gene, e.g., the neomycin phosphotransferase gene (neo; Capecchi, M. R. (1989) Science 244:1288-1292). The vector integrates into the corresponding region of the host genome by homologous recombination. Alternatively, homologous recombination takes place using the Cre-loxP system to knockout a gene of interest in a tissue- or developmental stage-specific manner (Marth, J. D. (1996) Clin. Invest. 97:1999-2002; Wagner, K. U. et al. (1997) Nucleic Acids Res. 25:4323-4330). Transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains. Transgenic animals thus generated may be tested with potential therapeutic or toxic agents.

Polynucleotides encoding REMAP may also be manipulated in vitro in ES cells derived from human blastocysts. Human ES cells have the potential to differentiate into at least eight separate cell lineages including endoderm, mesoderm, and ectodermal cell types. These cell lineages differentiate into, for example, neural cells, hematopoietic lineages, and cardiomyocytes (Thomson, J. A. et al. (1998) Science 282:1145-1147).

Polynucleotides encoding REMAP can also be used to create "knockin" humanized animals (pigs) or transgenic animals (mice or rats) to model human disease. With knockin technology, a region of a polynucleotide encoding REMAP is injected into animal ES cells, and the injected sequence integrates into the animal cell genome. Transformed cells are injected into blastulae, and the blastulae are implanted as described above. Transgenic progeny or inbred lines are studied and treated with potential pharmaceutical agents to obtain information on treatment of a human disease. Alternatively, a mammal inbred to overexpress REMAP, e.g., by secreting REMAP in its milk, may also serve as a convenient source of that protein (Janne, J. et al. (1998) Biotechnol. Annu. Rev. 4:55-74).

Therapeutics

Chemical and structural similarity, e.g., in the context of sequences and motifs, exists between regions of REMAP and receptors and membrane-associated proteins. In addition, examples of tissues expressing REMAP can be found in Table 6 and can also be found in Example XI. Therefore, REMAP appears to play a role in cell proliferative, autoimmune/inflammatory, neurological, metabolic, developmental, and endocrine disorders. In the treatment of disorders associated with increased REMAP expression or activity, it is desirable to decrease the expression or activity of REMAP. In the treatment of disorders associated with decreased REMAP expression or activity, it is desirable to increase the expression or activity of REMAP.

Therefore, in one embodiment, REMAP or a fragment or derivative thereof may be administered to a subject to treat or prevent a disorder associated with decreased expression or activity of REMAP. Examples of such disorders include, but are not limited to, a cell proliferative disorder such as actinic keratosis, arteriosclerosis, atherosclerosis, bursitis, cirrhosis, hepatitis, mixed connective tissue disease (MCrD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kuru, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a metabolic disorder such as Addison's disease, cerebrotendinous xanthomatosis, congenital adrenal hyperplasia, coumarin resistance, cystic fibrosis, fatty hepatocirrhosis, fructose-1,6-diphosphatase deficiency, galactosemia, goiter, glucagonoma, glycogen storage diseases, hereditary fructose intolerance, hyperadrenalism, hypoadrenalism, hyperparathyroidism, hypoparathyroidism, hypercholesterolemia, hyperthyroidism, hypoglycemia, hypothyroidism, hyperlipidemia, hyperlipemia, lipid myopathies, lipodystrophies, lysosomal storage diseases, mannosidosis, neuraminidase deficiency, obesity, osteoporosis, phenylketonuria, pseudovitamin D-deficiency rickets, disorders of carbohydrate metabolism such as congenital type II dyserythropoietic anemia, diabetes, insulin-dependent diabetes mellitus, non-insulin-dependent diabetes mellitus, galactose epimerase deficiency, glycogen storage diseases, lysosomal storage diseases, fructosuria, pentosuria, and inherited abnormalities of pyruvate metabolism, disorders of lipid metabolism such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoff's disease, hyperlipidemia, hyperlipemia, and lipid myopathies, and disorders of copper metabolism such as Menke's disease, Wilson's disease, and Ehlers-Danlos syndrome type IX diabetes; a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, a seizure disorder such as Syndenham's chorea and cerebral palsy, spina bifida, anencephaly, craniorachischisis, congenital glaucoma, cataract, and sensorineural hearing loss; and an endocrine disorder such as a disorder of the hypothalamus and/or pituitary resulting from lesions such as a primary brain tumor, adenoma, infarction associated with pregnancy, hypophysectomy, aneurysm, vascular malformation, thrombosis, infection, immunological disorder, and complication due to head trauma, a disorder associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism, a disorder associated with hyperpituitarism including acromegaly, giantism, and syndrome of inappropriate antidiuretic hormone (ADH) secretion (SIADH) often caused by benign adenoma, a disorder associated with hypothyroidism including goiter, myxedema, acute thyroiditis associated with bacterial infection, subacute thyroiditis associated with viral infection, autoimmune thyroiditis (Hashimoto's disease), and cretinism, a disorder associated with hyperthyroidism including thyrotoxicosis and its various forms, Grave's disease, pretibial myxedema, toxic multinodular goiter, thyroid carcinoma, and Plummer' s disease, a disorder associated with hyperparathyroidism including Conn disease (chronic hypercalemia), a pancreatic disorder such as Type I or Type II diabetes mellitus and associated complications, a disorder associated with the adrenals such as hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease, a disorder associated with gonadal steroid hormones such as: in women, abnormal prolactin production, infertility, endometriosis, perturbation of the menstrual cycle, polycystic ovarian disease, hyperprolactinemia, isolated gonadotropin deficiency, amenorrhea, galactorrhea, hermaphroditism, hirsutism and virilization, breast cancer, and, in post-menopausal women, osteoporosis, and, in men, Leydig cell deficiency, male climacteric phase, and germinal cell aplasia, a hypergonadal disorder associated with Leydig cell tumors, androgen resistance associated with absence of androgen receptors, syndrome of 5 $\alpha$-reductase, and gynecomastia.

In another embodiment, a vector capable of expressing REMAP or a fragment or derivative thereof may be administered to a subject to treat or prevent a disorder associated with decreased expression or activity of REMAP including, but not limited to, those described above.

In a further embodiment, a composition comprising a substantially purified REMAP in conjunction with a suitable pharmaceutical carrier may be administered to a subject to treat or prevent a disorder associated with decreased expression or activity of REMAP including, but not limited to, those provided above.

In still another embodiment, an agonist which modulates the activity of REMAP may be administered to a subject to treat or prevent a disorder associated with decreased expression or activity of REMAP including, but not limited to, those listed above.

In a further embodiment, an antagonist of REMAP may be administered to a subject to treat or prevent a disorder associated with increased expression or activity of REMAP. Examples of such disorders include, but are not limited to, those cell proliferative, autoimmune/inflammatory, neurological, metabolic, developmental, and endocrine disorders described above. In one aspect, an antibody which specifically binds REMAP may be used directly as an antagonist or indirectly as a targeting or delivery mechanism for bringing a pharmaceutical agent to cells or tissues which express REMAP.

In an additional embodiment, a vector expressing the complement of the polynucleotide encoding REMAP may be administered to a subject to treat or prevent a disorder associated with increased expression or activity of REMAP including, but not limited to, those described above.

In other embodiments, any protein, agonist, antagonist, antibody, complementary sequence, or vector embodiments may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of REMAP may be produced using methods which are generally known in the art. In particular, purified REMAP may be used to produce antibodies or to screen libraries of pharmaceutical agents to identify those which specifically bind REMAP. Antibodies to REMAP may also be generated using methods that are well known in the art. Such antibodies may include, but are not limited to, polyclonal, monoclonal, chimeric, and single chain antibodies, Fab fragments, and fragments produced by a Fab expression library. In an embodiment, neutralizing antibodies (i.e., those which inhibit dimer formation) can be used therapeutically. Single chain antibodies (e.g., from camels or llamas) may be potent enzyme inhibitors and may have application in the design of peptide mimetics, and in the development of immuno-adsorbents and biosensors (Muyldermans, S. (2001) J. Biotechnol. 74:277-302).

For the production of antibodies, various hosts including goats, rabbits, rats, mice, camels, dromedaries, llamas, humans, and others may be immunized by injection with REMAP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to REMAP have an amino acid sequence consisting of at least about 5 amino acids, and generally will consist of at least about 10 amino acids. It is also preferable that these oligopeptides, peptides, or fragments are substantially identical to a portion of the amino acid sequence of the natural protein. Short stretches of REMAP amino acids may be fused with those of another protein, such as KLH, and antibodies to the chimeric molecule may be produced.

Monoclonal antibodies to REMAP may be prepared using any technique which provides for the production of antibody molecules by continuous cell lines in culture. These include, but are not limited to, the hybridoma technique, the human B-ell hybridoma technique, and the EBV-hybridoma technique (Kohler, G. et al. (1975) Nature 256:495-497; Kozbor, D. et al. (1985) J. Immunol. Methods 81:31-42; Cote, R. J. et al. (1983) Proc. Natl. Acad. Sci. USA 80:2026-2030; Cole, S. P. et al. (1984) Mol. Cell Biol. 62:109-120).

In addition, techniques developed for the production of "chimeric antibodies," such as the splicing of mouse antibody genes to human antibody genes to obtain a molecule with appropriate antigen specificity and biological activity, can be used (Morrison, S. L. et al. (1984) Proc. Natl. Acad. Sci. USA 81:6851-6855; Neuberger, M. S. et al. (1984) Nature 312:604-608; Takeda, S. et al. (1985) Nature 314: 452-454). Alternatively, techniques described for the production of single chain antibodies may be adapted, using methods known in the art, to produce REMAP-specific single chain antibodies. Antibodies with related specificity, but of distinct idiotypic composition, may be generated by chain shuffling from random combinatorial immunoglobulin libraries (Burton, D. R. (1991) Proc. Natl. Acad. Sci. USA 88:10134-10137).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. USA 86:3833-3837; Winter, G. et al. (1991) Nature 349:293-299).

Antibody fragments which contain specific binding sites for REMAP may also be generated. For example, such fragments include, but are not limited to, $F(ab')_2$ fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 246:1275-1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between REMAP and its specific antibody. A two-site, monoclonal-based immunoassay utilizing monoclonal antibodies reactive to two non-interfering REMAP epitopes is generally used, but a competitive binding assay may also be employed (Pound, supra).

Various methods such as Scatchard analysis in conjunction with radioimmunoassay techniques may be used to assess the affinity of antibodies for REMAP. Affinity is expressed as an association constant, $K_a$, which is defined as the molar concentration of REMAP-antibody complex divided by the molar concentrations of free antigen and free antibody under equilibrium conditions. The $K_a$ determined for a preparation of polyclonal antibodies, which are heterogeneous in their affinities for multiple REMAP epitopes, represents the average affinity, or avidity, of the antibodies for REMAP. The $K_a$ determined for a preparation of monoclonal antibodies, which are monospecific fdr a particular REMAP epitope, represents a true measure of affinity. High-affinity antibody preparations with $K_a$ ranging from about $10^9$ to $10^{12}$ L/mole are preferred for use in immunoassays in which the REMAP-antibody complex must withstand rigorous manipulations. Low-affinity antibody preparations with $K_a$ ranging from about $10^6$ to $10^7$ L/mole are preferred for use in immunopurification and similar procedures which ultimately require dissociation of REMAP, preferably in active form, from the antibody (Catty, D. (1988) *Antibodies, Volume I: A Practical Approach*, IRL Press, Washington D.C.; Liddell, J. E. and A. Cryer (1991) *A Practical Guide to Monoclonal Antibodies*, John Wiley & Sons, New York N.Y.).

The titer and avidity of polyclonal antibody preparations may be further evaluated to determine the quality and suitability of such preparations for certain downstream applications. For example, a polyclonal antibody preparation containing at least 1-2 mg specific antibody/ml, preferably 5-10 mg specific antibody/ml, is generally employed in procedures requiring precipitation of REMAP-antibody complexes. Procedures for evaluating antibody specificity, titer, and avidity, and guidelines for antibody quality and usage in various applications, are generally available (Catty, supra; Coligan et al., supra).

In another embodiment of the invention, polynucleotides encoding REMAP, or any fragment or complement thereof, may be used for therapeutic purposes. In one aspect, modifications of gene expression can be achieved by designing complementary sequences or antisense molecules (DNA, RNA, PNA, or modified oligonucleotides) to the coding or regulatory regions of the gene encoding REMAP. Such technology is well known in the art, and antisense oligonucleotides or larger fragments can be designed from various locations along the coding or control regions of sequences encoding REMAP (Agrawal, S., ed. (1996) *Antisense Therapeutics*, Humana Press, Totawa N.J.).

In therapeutic use, any gene delivery system suitable for introduction of the antisense sequences into appropriate target cells can be used. Antisense sequences can be delivered intracellularly in the form of an expression plasmid which, upon transcription, produces a sequence complementary to at least a portion of the cellular sequence encoding the target protein (Slater, J. E. et al. (1998) J. Allergy Clin. Immunol. 102:469-475; Scanlon, K. J. et al. (1995) 9:1288-1296). Antisense sequences can also be introduced intracellularly through the use of viral vectors, such as retrovirus and adeno-associated virus vectors (Miller, A. D. (1990) Blood 76:271; Ausubel et al., supra; Uckert, W. and W. Walther (1994) Pharmacol. Ther. 63:323-347). Other gene delivery mechanisms include liposome-derived systems, artificial viral envelopes, and other systems known in the art (Rossi, J. J. (1995) Br. Med. Bull. 51:217-225; Boado, R. J. et al. (1998) J. Pharm. Sci. 87:1308-1315; Morris, M. C. et al. (1997) Nucleic Acids Res. 25:2730-2736).

In another embodiment of the invention, polynucleotides encoding REMAP may be used for somatic or germline gene therapy. Gene therapy may be performed to (i) correct a genetic deficiency (e.g., in the cases of severe combined immunodeficiency (SCID)-X1 disease characterized by X-linked inheritance (Cavazzana-Calvo, M. et al. (2000) Science 288:669-672), severe combined immunodeficiency syndrome associated with an inherited adenosine deaminase (ADA) deficiency (Blaese, R. M. et al. (1995) Science 270:475-480; Bordignon, C. et al. (1995) Science 270:470-475), cystic fibrosis (Zabner, J. et al. (1993) Cell 75:207-216; Crystal, R. G. et al. (1995) Hum. Gene Therapy 6:643-666; Crystal, R. G. et al. (1995) Hum. Gene Therapy 6:667-703), thalassamias, familial hypercholesterolemia, and hemophilia resulting from Factor VIII or Factor IX deficiencies (Crystal, R. G. (1995) Science 270:404-410; Verma, I. M. and N. Somia (1997) Nature 389:239-242)), (ii) express a conditionally lethal gene product (e.g., in the case of cancers which result from unregulated cell proliferation), or (iii) express a protein which affords protection against intracellular parasites (e.g., against human retroviruses, such as human immunodeficiency virus (HI) (Baltimore, D. (1988) Nature 335:395-396; Poeschla, E. et al. (1996) Proc. Natl. Acad. Sci. USA 93:11395-11399), hepatitis B or C virus (HBV, HCV); fungal parasites, such as *Candida albicans* and *Paracoccidioides brasiliensis*; and protozoan parasites such as *Plasmodium falciparum* and *Trypanosoma cruzi*). In the case where a genetic deficiency in REMAP expression or regulation causes disease, the expression of REMAP from an appropriate population of transduced cells may alleviate the clinical manifestations caused by the genetic deficiency.

In a further embodiment of the invention, diseases or disorders caused by deficiencies in REMAP are treated by constructing mammalian expression vectors encoding REMAP and introducing these vectors by mechanical means into REMAP-deficient cells. Mechanical transfer technologies for use with cells in vivo or ex vitro include (i) direct DNA microinjection into individual cells, (ii) ballistic gold particle delivery, (iii) liposome-mediated transfection, (iv) receptor-mediated gene transfer, and (v) the use of DNA transposons (Morgan, R. A. and W. F. Anderson (1993) Annu. Rev. Biochem. 62:191-217; Ivics, Z. (1997) Cell 91:501-510; Boulay, J.-L. and H. Recipon (1998) Curr. Opin. Biotechnol. 9:445450).

Expression vectors that may be effective for the expression of REMAP include, but are not limited to, the PCDNA 3.1, EPITAG, PRCCMV2, PREP, PVAX, PCR2-TOPOTA vectors (Invitrogen, Carlsbad Calif.), PCMV-SCRIPT, PCMV-TAG, PEGSH/PERV (Stratagene, La Jolla Calif.), and PTET-OFF, PTET-ON, PTRE2, PTRE2-LUC, PTK-HYG (Clontech, Palo Alto Calif.). REMAP may be expressed using (i) a constitutively active promoter, (e.g., from cytomegalovirus (CMV), Rous sarcoma virus (RSV), SV40 virus, thymidine kinase (TK), or β-actin genes), (ii) an inducible promoter (e.g., the tetracycline-regulated promoter (Gossen, M. and H. Bujard (1992) Proc. Natl. Acad. Sci. USA 89:5547-5551; Gossen, M. et al. (1995) Science 268:1766-1769; Rossi, F. M. V. and H. M. Blau (1998) Curr. Opin. Biotechnol. 9:451-456), commercially available in the T-REX plasmid (Invitrogen)); the ecdysone-inducible promoter (available in the plasmids PVGRXR and PIND; Invitrogen); the FK506/rapamycin inducible promoter; or the RU486/mifepristone inducible promoter (Rossi, F. M. V. and H. M. Blau, supra)), or (iii) a tissue-specific promoter or the native promoter of the endogenous gene encoding REMAP from a normal individual.

Commercially available liposome transformation kits (e.g., the PERFECT LIPID TRANSPECTION KIT, available from Invitrogen) allow one with ordinary skill in the art to deliver polynucleotides to target cells in culture and require minimal effort to optimize experimental parameters. In the alternative, transformation is performed using the calcium phosphate method (Graham, F. L. and A. J. Eb (1973) Virology 52:456467), or by electroporation (Neumann, E. et al. (1982) EMBO J. 1:841-845). The introduction of DNA to primary cells requires modification of these standardized mammalian transfection protocols.

In another embodiment of the invention, diseases or disorders caused by genetic defects with respect to REMAP expression are treated by constructing a retrovirus vector consisting of (i) the polynucleotide encoding REMAP under the control of an independent promoter or the retrovirus long terminal repeat (LTR) promoter, (ii) appropriate RNA packaging signals, and (iii) a Rev-responsive element (RRE) along with additional retrovirus cis-acting RNA sequences and coding sequences required for efficient vector propagation. Retrovirus vectors (e.g., PFB and PFBNEO) are commercially available (Stratagene) and are based on published data (Riviere, L. et al. (1995) Proc. Natl. Acad. Sci. USA 92:6733-6737), incorporated by reference herein. The vector is propagated in an appropriate vector producing cell line (VPCL) that expresses an envelope gene with a tropism for receptors on the target cells or a promiscuous envelope protein such as VSVg (Armentano, D. et al. (1987) J. Virol. 61:1647-1650; Bender, M. A. et al. (1987) J. Virol. 61:1639-1646; Adam, M. A. and A. D. Miller (1988) J. Virol. 62:3802-3806; Dull, T. et al. (1998) J. Virol. 72:8463-8471; Zufferey, R. et al. (1998) J. Virol. 72:9873-9880). U.S. Pat. No. 5,910,434 to Rigg ("Method for obtaining retrovirus packaging cell lines producing high transducing efficiency retroviral supernatant") discloses a method for obtaining retrovirus packaging cell lines and is hereby incorporated by reference. Propagation of retrovirus vectors, transduction of a population of cells (e.g., CD4+T-cells), and the return of transduced cells to a patient are procedures well known to persons skilled in the art of gene therapy and have been well documented (Ranga, U. et al. (1997) J. Virol. 71:7020-7029; Bauer, G. et al. (1997) Blood 89:2259-2267; Bonyhadi, M.

L. (1997) J. Virol. 71:4707-4716; Ranga, U. et al. (1998) Proc. Natl. Acad. Sci. USA 95:1201-1206; Su, L. (1997) Blood 89:2283-2290).

In an embodiment, an adenovirus-based gene therapy delivery system is used to deliver polynucleotides encoding REMAP to cells which have one or more genetic abnormalities with respect to the expression of REMAP. The construction and packaging of adenovirus-based vectors are well known to those with ordinary skill in the art. Replication defective adenovirus vectors have proven to be versatile for importing genes encoding immunoregulatory proteins into intact islets in the pancreas (Csete, M. E. et al. (1995) Transplantation 27:263-268). Potentially useful adenoviral vectors are described in U.S. Pat. No. 5,707,618 to Armentano ("Adenovirus vectors for gene therapy"), hereby incorporated by reference. For adenoviral vectors, see also Antinozzi, P. A. et al. (1999; Annu. Rev. Nutr. 19:511-544) and Verma, I. M. and N. Somia (1997; Nature 18:389:239-242).

In another embodiment, a herpes-based, gene therapy delivery system is used to deliver polynucleotides encoding REMAP to target cells which have one or more genetic abnormalities with respect to the expression of REMAP. The use of herpes simplex virus (HSV)-based vectors may be especially valuable for introducing REMAP to cells of the central nervous system, for which HSV has a tropism. The construction and packaging of herpes-based vectors are well known to those with ordinary skill in the art. A replication-competent herpes simplex virus (HSV) type 1-based vector has been used to deliver a reporter gene to the eyes of primates (Liu, X. et al. (1999) Exp. Eye Res. 169:385-395). The construction of a HSV-1 virus vector has also been disclosed in detail in U.S. Pat. No. 5,804,413 to DeLuca ("Herpes simplex virus strains for gene transfer"), which is hereby incorporated by reference. U.S. Pat. No. 5,804,413 teaches the use of recombinant HSV d92 which consists of a genome containing at least one exogenous gene to be transferred to a cell under the control of the appropriate promoter for purposes including human gene therapy. Also taught by this patent are the construction and use of recombinant HSV strains deleted for ICP4, ICP27 and ICP22. For HSV vectors, see also Goins, W. F. et al. (1999; J. Virol. 73:519-532) and Xu, H. et al. (1994; Dev. Biol. 163:152-161). The manipulation of cloned herpesvirus sequences, the generation of recombinant virus following the transfection of multiple plasmids containing different segments of the large herpesvirus genomes, the growth and propagation of herpesvirus, and the infection of cells with herpesvirus are techniques well known to those of ordinary skill in the art.

In another embodiment, an alphavirus (positive, single-stranded RNA virus) vector is used to deliver polynucleotides encoding REMAP to target cells. The biology of the prototypic alphavirus, Senilti Forest Virus (SFV), has been studied extensively and gene transfer vectors have been based on the SFV genome (Garoff, H. and K.-J. Li (1998) Curr. Opin. Biotechnol. 9:464-469). During alphavirus RNA replication, a subgenomic RNA is generated that normally encodes the viral capsid proteins. This subgenomic RNA replicates to higher levels than the full length genomic RNA, resulting in the overproduction of capsid proteins relative to the viral proteins with enzymatic activity (e.g., protease and polymerase). Similarly, inserting the coding sequence for REMAP into the alphavirus genome in place of the capsid-coding region results in the production of a large number of REMAP-coding RNAs and the synthesis of high levels of REMAP in vector transduced cells. While alphavirus infection is typically associated with cell lysis within a few days, the ability to establish a persistent infection in hamster normal kidney cells (BHK-21) with a variant of Sindbis virus (SIN) indicates that the lytic replication of alphaviruses can be altered to suit the needs of the gene therapy application (Dryga, S. A. et al. (1997) Virology 228:74-83). The wide host range of alphaviruses will allow the introduction of REMAP into a variety of cell types. The specific transduction of a subset of cells in a population may require the sorting of cells prior to transduction. The methods of manipulating infectious cDNA clones of alphaviruses, performing alphavirus cDNA and RNA transfections, and performing alphavirus infections, are well known to those with ordinary skill in the art.

Oligonucleotides derived from the transcription initiation site, e.g., between about positions −10 and +10 from the start site, may also be employed to inhibit gene expression. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) in Huber, B. E. and B. I. Carr, *Molecular and Immunologic Approaches*, Futura Publishing, Mt. Kisco N.Y., pp. 163-177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules may specifically and efficiently catalyze endonucleolytic cleavage of RNA molecules encoding REMAP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides, corresponding to the region of the target gene containing the cleavage site, may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA molecules encoding REMAP. Such DNA sequences may be incorporated into a wide variety of vectors with suitable RNA polymerase promoters such as T7 or SP6. Alternatively, these cDNA constructs that synthesize complementary RNA, constitutively or inducibly, can be introduced into cell lines, cells, or tissues.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

In other embodiments of the invention, the expression of one or more selected polynucleotides of the present invention can be altered, inhibited, decreased, or silenced using RNA interference (RNAi) or post-transcriptional gene silencing (PTGS) methods known in the art. RNAi is a post-transcriptional mode of gene silencing in which double-stranded RNA (dsRNA) introduced into a targeted cell specifically suppresses the expression of the homologous gene (i.e., the gene bearing the sequence complementary to the dsRNA). This effectively knocks out or substantially reduces the expression of the targeted gene. PTGS can also be accomplished by use of DNA or DNA fragments as well. RNAi methods are described by Fire, A. et al. (1998; Nature 391:806-811) and Gura, T. (2000; Nature 404:804-808). PTGS can also be initiated by introduction of a complementary segment of DNA into the selected tissue using gene delivery and/or viral vector delivery methods described herein or known in the art.

RNAi can be induced in mammalian cells by the use of small interfering RNA also known as siRNA. SiRNA are shorter segments of dsRNA (typically about 21 to 23 nucleotides in length) that result in vivo from cleavage of introduced dsRNA by the action of an endogenous ribonuclease. SiRNA appear to be the mediators of the RNAi effect in mammals. The most effective siRNAs appear to be 21 nucleotide dsRNA& with 2 nucleotide 3' overhangs. The use of siRNA for inducing RNAi in mammalian cells is described by Elbashir, S. M. et al. (2001; Nature 411:494-498).

SiRNA can either be generated indirectly by introduction of dsRNA into the targeted cell, or directly by mammalian transfection methods and agents described herein or known in the art. (such as liposome-mediated transfection, viral vector methods, or other polynucleotide delivery/introductory methods). Suitable SiRNAs can be selected by examining a transcript of the target polynucleotide (e.g., mRNA) for nucleotide sequences downstream from the AUG start codon and recording the occurrence of each nucleotide and the 3' adjacent 19 to 23 nucleotides as potential siRNA target sites, with sequences having a 21 nucleotide length being preferred. Regions to be avoided for target siRNA sites include the 5' and 3' untranslated regions (UTRs) and regions near the start codon (within 75 bases), as these may be richer in regulatory protein binding sites. UTR-binding proteins and/or translation initiation complexes may interfere with binding of the siRNP endonuclease complex. The selected target sites for siRNA can then be compared to the appropriate genome database (e.g., human, etc.) using BLAST or other sequence comparison algorithms known in the art. Target sequences with significant homology to other coding sequences can be eliminated from consideration. The selected SiRNAs can be produced by chemical synthesis methods known in the art or by in vitro transcription using commercially available methods and kits such as the SILENCER siRNA construction kit (Ambion, Austin Tex.).

In alternative embodiments, long-term gene silencing and/or RNAi effects can be induced in selected tissue using expression vectors that continuously express siRNA. This can be accomplished using expression vectors that are engineered to express hairpin RNAs (shRNAs) using methods known in the art (see, e.g., Brummelkamp, T. R. et al. (2002) Science 296:550-553; and Paddison, P. J. et al. (2002) Genes Dev. 16:948-958). In these and related embodiments, shRNAs can be delivered to target cells using expression vectors known in the art. An example of a suitable expression vector for delivery of siRNA is the PSILENCER1.0-U6 (circular) plasmid (Ambion). Once delivered to the target tissue, shRNAs are processed in vivo into siRNA-like molecules capable of carrying out gene-specific silencing.

In various embodiments, the expression levels of genes targeted by RNAi or PTGS methods can be determined by assays for mRNA and/or protein analysis. Expression levels of the mRNA of a targeted gene, can be determined by northern analysis methods using, for example, the NORTHERNMAX-GLY kit (Ambion); by microarray methods; by PCR methods; by real time PCR methods; and by other RNA/polynucleotide assays known in the art or described herein. Expression levels of the protein encoded by the targeted gene can be determined by Western analysis using standard techniques known in the art.

An additional embodiment of the invention encompasses a method for screening for a compound which is effective in altering expression of a polynucleotide encoding REMAP. Compounds which may be effective in altering expression of a specific polynucleotide may include, but are not limited to, oligonucleotides, antisense oligonucleotides, triple helix-forming oligonucleotides, transcription factors and other polypeptide transcriptional regulators, and non-macromolecular chemical entities which are capable of interacting with specific polynucleotide sequences. Effective compounds may alter polynucleotide expression by acting as either inhibitors or promoters of polynucleotide expression. Thus, in the treatment of disorders associated with increased REMAP expression or activity, a compound which specifically inhibits expression of the polynucleotide encoding REMAP may be therapeutically useful, and in the treatment of disorders associated with decreased REMAP expression or activity, a compound which specifically promotes expression of the polynucleotide encoding REMAP may be therapeutically useful.

In various embodiments, one or more test compounds may be screened for effectiveness in altering expression of a specific polynucleotide. A test compound may be obtained by any method commonly known in the art, including chemical modification of a compound known to be effective in altering polynucleotide expression; selection from an existing, commercially-available or proprietary library of naturally-occurring or non-natural chemical compounds; rational design of a compound based on chemical and/or structural properties of the target polynucleotide; and selection from a library of chemical compounds created combinatorially or randomly. A sample comprising a polynucleotide encoding REMAP is exposed to at least one test compound thus obtained. The sample may comprise, for example, an intact or permeabilized cell, or an in vitro cell-free or reconstituted biochemical system. Alterations in the expression of a polynucleotide encoding REMAP are assayed by any method commonly known in the art. Typically, the expression of a specific nucleotide is detected by hybridization with a probe having a nucleotide sequence complementary to the sequence of the polynucleotide encoding REMAP. The amount of hybridization may be quantified, thus forming the basis for a comparison of the expression of the polynucleotide both with and without exposure to one or more test compounds. Detection of a change in the expression of a polynucleotide exposed to a test compound indicates that the test compound is effective in altering the expression of the polynucleotide. A screen for a compound effective in altering expression of a specific polynucleotide can be carried out, for example, using a Schizosaccharomyces pombe gene expression system (Atkins, D. et al. (1999) U.S. Pat. No. 5,932,435; Arndt, G. M. et al. (2000) Nucleic Acids Res. 28:E15) or a human cell line such as HeLa cell (Clarke, M. L. et al. (2000) Biochem. Biophys. Res. Commun. 268:8-13). A particular embodiment of the present invention involves screening a combinatorial library of oligonucleotides (such as deoxyribonucleotides, ribonucleotides, peptide nucleic acids, and modified oligonucleotides) for antisense activity against a specific polynucleotide sequence (Bruice, T. W. et al. (1997) U.S. Pat. No. 5,686,242; Bruice, T. W. et al. (2000) U.S. Pat. No. 6,022,691).

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art (Goldman, C. K. et al. (1997) Nat. Biotechnol. 15:462-466).

Any of the therapeutic methods described above may be applied to any subject in need of such therapy, including, for example, mammals such as humans, dogs, cats, cows, horses, rabbits, and monkeys.

An additional embodiment of the invention relates to the administration of a composition which generally comprises an active ingredient formulated with a pharmaceutically acceptable excipient. Excipients may include, for example, sugars, starches, celluloses, gums, and proteins. Various formulations are commonly known and are thoroughly discussed in the latest edition of *Remington's Pharmaceutical Sciences* (Maack Publishing, Easton Pa.). Such compositions may consist of REMAP, antibodies to REMAP, and mimetics, agonists, antagonists, or inhibitors of REMAP.

In various embodiments, the compositions described herein, such as pharmaceutical compositions, may be administered by any number of routes including, but not limited to, oral, intravenous, intramuscular, intra-arterial, intramedullary, intrathecal, intraventricular, pulmonary, transdermal, subcutaneous, intraperitoneal, intranasal, enteral, topical, sublingual, or rectal means.

Compositions for pulmonary administration may be prepared in liquid or dry powder form. These compositions are generally aerosolized immediately prior to inhalation by the patient In the case of small molecules (e.g. traditional low molecular weight organic drugs), aerosol delivery of fast-acting formulations is well-known in the art. In the case of macromolecules (e.g. larger peptides and proteins), recent developments in the field of pulmonary delivery via the alveolar region of the lung have enabled the practical delivery of drugs such as insulin to blood circulation (see, e.g., Patton, J. S. et al., U.S. Pat. No. 5,997,848). Pulmonary delivery allows administration without needle injection, and obviates the need for potentially toxic penetration enhancers.

Compositions suitable for use in the invention include compositions wherein the active ingredients are contained in an effective amount to achieve the intended purpose. The determination of an effective dose is well within the capability of those skilled in the art.

Specialized forms of compositions may be prepared for direct intracellular delivery of macromolecules comprising REMAP or fragments thereof. For example, liposome preparations containing a cell-impermeable macromolecule may promote cell fusion and intracellular delivery of the macromolecule. Alternatively, REMAP or a fragment thereof may be joined to a short cationic N-terminal portion from the HIV Tat-1 protein. Fusion proteins thus generated have been found to transduce into the cells of all tissues, including the brain, in a mouse model system (Schwarze, S. R. et al. (1999) Science 285:1569-1572).

For any compound, the therapeutically effective dose can be estimated initially either in cell culture assays, e.g., of neoplastic cells, or in animal models such as mice, rats, rabbits, dogs, monkeys, or pigs. An animal model may also be used to determine the appropriate concentration range and route of administration. Such information can then be used to determine useful doses and routes for administration in humans.

A therapeutically effective dose refers to that amount of active ingredient, for example REMAP or fragments thereof, antibodies of REMAP, and agonists, antagonists or inhibitors of REMAP, which ameliorates the symptoms or condition. Therapeutic efficacy and toxicity may be determined by standard pharmaceutical procedures in cell cultures or with experimental animals, such as by calculating the $ED_{50}$ (the dose therapeutically effective in 50% of the population) or $LD_{50}$ (the dose lethal to 50% of the population) statistics. The dose ratio of toxic to therapeutic effects is the therapeutic index, which can be expressed as the $LD_{50}/ED_{50}$ ratio. Compositions which exhibit large therapeutic indices are preferred. The data obtained from cell culture assays and animal studies are used to formulate a range of dosage for human use. The dosage contained in such compositions is preferably within a range of circulating concentrations that includes the $ED_{50}$ with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, time and frequency of administration, drug combination(s), reaction sensitivities, and response to therapy. Long-acting compositions may be administered every 3 to 4 days, every week, or biweekly depending on the half-life and clearance rate of the particular formulation.

Normal dosage amounts may vary from about 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind REMAP may be used for the diagnosis of disorders characterized by expression of REMAP, or in assays to monitor patients being treated with REMAP or agonists, antagonists, or inhibitors of REMAP. Antibodies useful for diagnostic purposes may be prepared in the same manner as described above for therapeutics. Diagnostic assays for REMAP include methods which utilize the antibody and a label to detect REMAP in human body fluids or in extracts of cells or tissues. The antibodies may be used with or without modification, and may be labeled by covalent or non-covalent attachment of a reporter molecule. A wide variety of reporter molecules, several of which are described above, are known in the art and may be used.

A variety of protocols for measuring REMAP, including ELISAs, RIAs, and FACS, are known in the art and provide a basis for diagnosing altered or abnormal levels of REMAP expression. Normal or standard values for REMAP expression are established by combining body fluids or cell extracts taken from normal mammalian subjects, for example, human subjects, with antibodies to REMAP under conditions suitable for complex formation. The amount of standard complex formation may be quantitated by various methods, such as photometric means. Quantities of REMAP expressed in subject, control, and disease samples from biopsied tissues are compared with the standard values. Deviation between standard and subject values establishes the parameters for diagnosing disease.

In another embodiment of the invention, polynucleotides encoding REMAP may be used for diagnostic purposes. The polynucleotides which may be used include oligonucleotides, complementary RNA and DNA molecules, and PNAs. The polynucleotides may be used to detect and quantify gene expression in biopsied tissues in which expression of REMAP may be correlated with disease. The diagnostic assay may be used to determine absence, presence, and excess expression of REMAP, and to monitor regulation of REMAP levels during therapeutic intervention.

In one aspect, hybridization with PCR probes which are capable of detecting polynucleotides, including genomic sequences, encoding REMAP or closely related molecules may be used to identify nucleic acid sequences which encode REMAP. The specificity of the probe, whether it is made from a highly specific region, e.g., the 5' regulatory region, or from a less specific region, e.g., a conserved motif, and the stringency of the hybridization or amplification will determine whether the probe identifies only naturally occurring sequences encoding REMAP, allelic variants, or related sequences.

Probes may also be used for the detection of related sequences, and may have at least 50% sequence identity to any of the REMAP encoding sequences. The hybridization probes of the subject invention may be DNA or RNA and may be derived from the sequence of SEQ ID NO:39-76 or from genomic sequences including promoters, enhancers, and introns of the REMAP gene.

Means for producing specific hybridization probes for polynucleotides encoding REMAP include the cloning of polynucleotides encoding REMAP or REMAP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}P$ or $^{35}S$, or by enzymatic labels, such as alkaline phosphatase coupled to the probe via avidin/biotin coupling systems, and the like.

Polynucleotides encoding REMAP may be used for the diagnosis of disorders associated with expression of REMAP. Examples of such disorders include, but are not limited to, a cell proliferative disorder such as actinic keratosis, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, colon, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; an autoimmune/inflammatory disorder such as acquired immunodeficiency syndrome (AIDS), Addison's disease, adult respiratory distress syndrome, allergies, ankylosing spondylitis, amyloidosis, anemia, asthma, atherosclerosis, autoimmune hemolytic anemia, autoimmune thyroiditis, autoimmune polyendocrinopathy-candidiasis-ectodermal dystrophy (APECED), bronchitis, cholecystitis, contact dermatitis, Crohn's disease, atopic dermatitis, dermatomyositis, diabetes mellitus, emphysema, episodic lymphopenia with lymphocytotoxins, erythroblastosis fetalis, erythema nodosum, atrophic gastritis, glomerulonephritis, Goodpasture's syndrome, gout, Graves' disease, Hashimoto's thyroiditis, hypereosinophilia, irritable bowel syndrome, multiple sclerosis, myasthenia gravis, myocardial or pericardial inflammation, osteoarthritis, osteoporosis, pancreatitis, polymyositis, psoriasis, Reiter's syndrome, rheumatoid arthritis, scleroderma, Sjögren's syndrome, systemic anaphylaxis, systemic lupus erythematosus, systemic sclerosis, thrombocytopenic purpura, ulcerative colitis, uveitis, Werner syndrome, complications of cancer, hemodialysis, and extracorporeal circulation, viral, bacterial, fungal, parasitic, protozoal, and helminthic infections, and trauma; a neurological disorder such as epilepsy, ischemic cerebrovascular disease, stroke, cerebral neoplasms, Alzheimer's disease, Pick's disease, Huntington's disease, dementia, Parkinson's disease and other extrapyramidal disorders, amyotrophic lateral sclerosis and other motor neuron disorders, progressive neural muscular atrophy, retinitis pigmentosa, hereditary ataxias, multiple sclerosis and other demyelinating diseases, bacterial and viral meningitis, brain abscess, subdural empyema, epidural abscess, suppurative intracranial thrombophlebitis, myelitis and radiculitis, viral central nervous system disease, prion diseases including kurui, Creutzfeldt-Jakob disease, and Gerstmann-Straussler-Scheinker syndrome, fatal familial insomnia, nutritional and metabolic diseases of the nervous system, neurofibromatosis, tuberous sclerosis, cerebelloretinal hemangioblastomatosis, encephalotrigeminal syndrome, mental retardation and other developmental disorders of the central nervous system, cerebral palsy, neuroskeletal disorders, autonomic nervous system disorders, cranial nerve disorders, spinal cord diseases, muscular dystrophy and other neuromuscular disorders, peripheral nervous system disorders, dermatomyositis and polymyositis, inherited, metabolic, endocrine, and toxic myopathies, myasthenia gravis, periodic paralysis, mental disorders including mood, anxiety, and schizophrenic disorders, seasonal affective disorder (SAD), akathesia, amnesia, catatonia, diabetic neuropathy, tardive dyskinesia, dystonias, paranoid psychoses, postherpetic neuralgia, Tourette's disorder, progressive supranuclear palsy, corticobasal degeneration, and familial frontotemporal dementia; a metabolic disorder such as Addison's disease, cerebrotendinous xanthomatosis, congenital adrenal hyperplasia, coumarin resistance, cystic fibrosis, fatty hepatocirrhosis, fructose-1,6-diphosphatase deficiency, galactosemia, goiter, glucagonoma, glycogen storage diseases, hereditary fructose intolerance, hyperadrenalism, hypoadrenalism, hyperparathyroidism, hypoparathyroidism, hypercholesterolemia, hyperthyroidism, hypoglycemia, hypothyroidism, hyperlipidemia, hyperlipemia, lipid myopathies, lipodystrophies, lysosomal storage diseases, mannosidosis, neuraminidase deficiency, obesity, osteoporosis, phenylketonuria, pseudovitamin D-deficiency rickets, disorders of carbohydrate metabolism such as congenital type II dyserythropoietic anemia, diabetes, insulin-dependent diabetes mellitus, non-insulin-dependent diabetes mellitus, galactose epimerase deficiency, glycogen storage diseases, lysosomal storage diseases, fructosuria, pentosuria, and inherited abnormalities of pyruvate metabolism, disorders of lipid metabolism such as fatty liver, cholestasis, primary biliary cirrhosis, carnitine deficiency, carnitine palmitoyltransferase deficiency, myoadenylate deaminase deficiency, hypertriglyceridemia, lipid storage disorders such Fabry's disease, Gaucher's disease, Niemann-Pick's disease, metachromatic leukodystrophy, adrenoleukodystrophy, $GM_2$ gangliosidosis, and ceroid lipofuscinosis, abetalipoproteinemia, Tangier disease, hyperlipoproteinemia, lipodystrophy, lipomatoses, acute panniculitis, disseminated fat necrosis, adiposis dolorosa, lipoid adrenal hyperplasia, minimal change disease, lipomas, atherosclerosis, hypercholesterolemia, hypercholesterolemia with hypertriglyceridemia, primary hypoalphalipoproteinemia, hypothyroidism, renal disease, liver disease, lecithin:cholesterol acyltransferase deficiency, cerebrotendinous xanthomatosis, sitosterolemia, hypocholesterolemia, Tay-Sachs disease, Sandhoffs disease, hyperlipidemia, hyperlipemia, and lipid myopathies, and disorders of copper metabolism such as Menke's disease, Wilson's disease, and Ehlers-Danlos syndrome type DX diabetes; a developmental disorder such as renal tubular acidosis, anemia, Cushing's syndrome, achondroplastic dwarfism, Duchenne and Becker muscular dystrophy, epilepsy, gonadal dysgenesis, WAGR syndrome (Wilms' tumor, aniridia, genitourinary abnormalities, and mental retardation), Smith-Magenis syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, a seizure disorder such as Syndenham's chorea and cerebral palsy, spina bifida, anencephaly, craniorachischisis, congenital glaucoma, cataract, and sensorineural hearing loss; and an endocrine disorder such as a disorder of the hypothalamus and/or pituitary resulting from lesions such as a primary brain tumor, adenoma, infarction associated with pregnancy, hypophysectomy, aneurysm, vascular malformation, thrombosis, infection, immunological disorder, and complication due to head trauma, a disorder associated with hypopituitarism including hypogonadism, Sheehan syndrome, diabetes insipidus, Kallman's disease, Hand-Schuller-Christian disease, Letterer-Siwe disease, sarcoidosis, empty sella syndrome, and dwarfism, a disorder associated with hyperpituitarism including acromegaly, giantism, and syndrome of inappropriate antidiuretic hormone (ADH) secretion (SIADH) often caused by benign adenoma, a disorder associated with hypothyroidism including goiter, myxedema, acute thyroiditis associated with bacterial infection, subacute thyroiditis associated with viral infection, autoimmune thyroiditis (Hashimoto's disease), and cretinism, a disorder associated with hyperthyroidism including thyrotoxicosis and its various forms, Grave's disease, pretibial myxedema, toxic multinodular goiter, thyroid carcinoma, and Plummer's disease, a disorder associated with hyperparathyroidism including Conn disease (chronic hypercalemia), a pancreatic disorder such as Type I or Type II diabetes mellitus and associated complications, a disorder associated with the adrenals such as hyperplasia, carcinoma, or adenoma of the adrenal cortex, hypertension associated with alkalosis, amyloidosis, hypokalemia, Cushing's disease, Liddle's syndrome, and Arnold-Healy-Gordon syndrome, pheochromocytoma tumors, and Addison's disease, a disorder associated with gonadal steroid hormones such as: in women, abnormal prolactin production, infertility, endometriosis, perturbation of the menstrual cycle, polycystic ovarian disease, hyperprolactinemia, isolated gonadotropin deficiency, amenorrhea, galactorrhea, hermaphroditism, hirsutism and virilization, breast cancer, and, in post-menopausal women, osteoporosis, and, in men, Leydig cell deficiency, male climacteric phase, and germinal cell aplasia, a hypergonadal disorder associated with Leydig cell tumors, androgen resistance associated with absence of androgen receptors, syndrome of 5 $\alpha$-reductase, and gynecomastia. Polynucleotides encoding REMAP may be used in Southern or northern analysis, dot blot, or other membrane-based technologies; in PCR technologies; in dipstick, pin, and multiformat ELISA-like assays; and in microarrays utilizing fluids or tissues from patients to detect altered REMAP expression. Such qualitative or quantitative methods are well known in the art.

In a particular embodiment, polynucleotides encoding REMAP may be used in assays that detect the presence of associated disorders, particularly those mentioned above. Polynucleotides complementary to sequences encoding REMAP may be labeled by standard methods and added to a fluid or tissue sample from a patient under conditions suitable for the formation of hybridization complexes. After a suitable incubation period, the sample is washed and the signal is quantified and compared with a standard value. If the amount of signal in the patient sample is significantly altered in comparison to a control sample then the presence of altered levels of polynucleotides encoding REMAP in the sample indicates the presence of the associated disorder. Such assays may also be used to evaluate the efficacy of a particular therapeutic treatment regimen in animal studies, in clinical trials, or to monitor the treatment of an individual patient.

In order to provide a basis for the diagnosis of a disorder associated with expression of REMAP, a normal or standard profile for expression is established. This may be accomplished by combining body fluids or cell extracts taken from normal subjects, either animal or human, with a sequence, or a fragment thereof, encoding REMAP, under conditions suitable for hybridization or amplification. Standard hybridization may be quantified by comparing the values obtained from normal subjects with values from an experiment in which a known amount of a substantially purified polynucleotide is used. Standard values obtained in this manner may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to determine if the level of expression in the patient begins to approximate that which is observed in the normal subject. The results obtained from successive assays may be used to show the efficacy of treatment over a period ranging from several days to months.

With respect to cancer, the presence of an abnormal amount of transcript (either under- or overexpressed) in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier, thereby preventing the development or further progression of the cancer.

Additional diagnostic uses for oligonucleotides designed from the sequences encoding REMAP may involve the use of PCR. These oligomers may be chemically synthesized, generated enzymatically, or produced in vitro. Oligomers will preferably contain a fragment of a polynucleotide encoding REMAP, or a fragment of a polynucleotide complementary to the polynucleotide encoding REMAP, and will be employed under optimized conditions for identification of a specific gene or condition. Oligomers may also be employed under less stringent conditions for detection or quantification of closely related DNA or RNA sequences.

In a particular aspect, oligonucleotide primers derived from polynucleotides encoding REMAP may be used to detect single nucleotide polymorphisms (SNPs). SNPs are substitutions, insertions and deletions that are a frequent cause of inherited or acquired genetic disease in humans. Methods of SNP detection include, but are not limited to, single-stranded conformation polymorphism (SSCP) and fluorescent SSCP (FSSCP) methods. In SSCP, oligonucleotide primers derived from polynucleotides encoding REMAP are used to amplify DNA using the polymerase chain reaction (PCR). The DNA may be derived, for example, from diseased or normal tissue, biopsy samples, bodily fluids, and the like. SNPs in the DNA cause differences in the secondary and tertiary structures of PCR products in single-stranded form, and these differences are detectable using gel electrophoresis in non-denaturing gels. In fSCCP, the oligonucleotide primers are fluorescently labeled, which allows detection of the amplimers in high-throughput equipment such as DNA sequencing machines. Additionally, sequence database analysis methods, termed in silico SNP (isSNP), are capable of identifying polymorphisms by comparing the sequence of individual overlapping DNA fragments which assemble into a common consensus sequence. These computer-based methods filter out sequence variations due to laboratory preparation of DNA and sequencing errors using statistical models and automated analyses of DNA sequence chromatograms. In the alternative, SNPs may be detected and characterized by mass spectrometry using, for example, the high throughput MASSARRAY system (Sequenom, Inc., San Diego Calif.).

SNPs may be used to study the genetic basis of human disease. For example, at least 16 common SNPs have been associated with non-insulin-dependent diabetes mellitus. SNPs are also useful for examining differences in disease outcomes in monogenic disorders, such as cystic fibrosis, sickle cell anemia, or chronic granulomatous disease. For example, variants in the mannose-binding lectin, MBL2, have been shown to be correlated with deleterious pulmonary outcomes in cystic fibrosis. SNPs also have utility in pharmacogenomics, the identification of genetic variants that influence a patient's response to a drug, such as life-threatening toxicity. For example, a variation in N-acetyl transferase is associated with a high incidence of peripheral neuropathy in response to the anti-tuberculosis drug isoniazid, while a variation in the core promoter of the ALOX5 gene results in diminished clinical response to treatment with an anti-asthma drug that targets the 5-lipoxygenase pathway. Analysis of the distribution of SNPs in different populations is useful for investigating genetic drift, mutation, recombination, and selection, as well as for tracing the origins of populations and their migrations (Taylor, J. G. et al. (2001) Trends Mol. Med. 7:507-512; Kwok, P.-Y. and Z. Gu (1999) Mol. Med. Today 5:538-543; Nowotny, P. et al. (2001) Curr. Opin. Neurobiol. 11:637-641).

Methods which may also be used to quantify the expression of REMAP include radiolabeling or biotinylating nucleotides, coamplification of a control nucleic acid, and interpolating results from standard curves (Melby, P. C. et al. (1993) J. Immunol. Methods 159:235-244; Duplaa, C. et al. (1993) Anal. Biochem. 212:229-236). The speed of quantitation of multiple samples may be accelerated by running the assay in a high-throughput format where the oligomer or polynucleotide of interest is presented in various dilutions and a spectrophotometric or calorimetric response gives rapid quantitation.

In further embodiments, oligonucleotides or longer fragments derived from any of the polynucleotides described herein may be used as elements on a microarray. The microarray can be used in transcript imaging techniques which monitor the relative expression levels of large numbers of genes simultaneously as described below. The microarray may also be used to identify genetic variants, mutations, and polymorphisms. This information may be used to determine gene function, to understand the genetic basis of a disorder, to diagnose a disorder, to monitor progression/regression of disease as a function of gene expression, and to develop and monitor the activities of therapeutic agents in the treatment of disease. In particular, this information may be used to develop a pharmacogenomic profile of a patient in order to select the most appropriate and effective treatment regimen for that patient. For example, therapeutic agents which are highly effective and display the fewest side effects may be selected for a patient based on his/her pharmacogenomic profile.

In another embodiment, REMAP, fragments of REMAP, or antibodies specific for REMAP may be used as elements on a microarray. The microarray may be used to monitor or measure protein-protein interactions, drug-target interactions, and gene expression profiles, as described above.

A particular embodiment relates to the use of the polynucleotides of the present invention to generate a transcript image of a tissue or cell type. A transcript image represents the global pattern of gene expression by a particular tissue or cell type. Global gene expression patterns are analyzed by quantifying the number of expressed genes and their relative abundance under given conditions and at a given time (Seilhamer et al., "Comparative Gene Transcript Analysis," U.S. Pat. No. 5,840,484; hereby expressly incorporated by reference herein). Thus a transcript image may be generated by hybridizing the polynucleotides of the present invention or their complements to the totality of transcripts or reverse transcripts of a particular tissue or cell type. In one embodiment, the hybridization takes place in high-throughput format, wherein the polynucleotides of the present invention or their complements comprise a subset of a plurality of elements on a microarray. The resultant transcript image would provide a profile of gene activity.

Transcript images may be generated using transcripts isolated from tissues, cell lines, biopsies, or other biological samples. The transcript image may thus reflect gene expression in vivo, as in the case of a tissue or biopsy sample, or in vitro, as in the case of a cell line.

Transcript images which profile the expression of the polynucleotides of the present invention may also be used in conjunction with in vitro model systems and preclinical evaluation of pharmaceuticals, as well as toxicological testing of industrial and naturally-occurring environmental compounds. All compounds induce characteristic gene expression patterns, frequently termed molecular fingerprints or toxicant signatures, which are indicative of mechanisms of action and toxicity (Nuwaysir, E. F. et al. (1999) Mol. Carcinog. 24:153-159; Steiner, S. and N. L. Anderson (2000) Toxicol. Lett. 112-113:467-471). If a test compound has a signature similar to that of a compound with known toxicity, it is likely to share those toxic properties. These fingerprints or signatures are most useful and refined when they contain expression information from a large number of genes and gene families. Ideally, a genome-wide measurement of expression provides the highest quality signature. Even genes whose expression is not altered by any tested compounds are important as well, as the levels of expression of these genes are used to normalize the rest of the expression data. The normalization procedure is useful for comparison of expression data after treatment with different compounds. While the assignment of gene function to elements of a toxicant signature aids in interpretation of toxicity mechanisms, knowledge of gene function is not necessary for the statistical matching of signatures which leads to prediction of toxicity (see, for example, Press Release 00-02 from the National Institute of Environmental Health Sciences, released Feb. 29, 2000, available on the Internet at the National Institute of Environmental Health Sciences ("NIEHS") government World Wide Web site. Therefore, it is important and desirable in toxicological screening using toxicant signatures to include all expressed gene sequences.

In an embodiment, the toxicity of a test compound can be assessed by treating a biological sample containing nucleic acids with the test compound. Nucleic acids that are expressed in the treated biological sample are hybridized with one or more probes specific to the polynucleotides of the present invention, so that transcript levels corresponding to the polynucleotides of the present invention may be quantified. The transcript levels in the treated biological sample are compared with levels in an untreated biological sample. Differences in the transcript levels between the two samples are indicative of a toxic response caused by the test compound in the treated sample.

Another embodiment relates to the use of the polypeptides disclosed herein to analyze the proteome of a tissue or cell type. The term proteome refers to the global pattern of protein expression in a particular tissue or cell type. Each protein component of a proteome can be subjected individually to further analysis. Proteome expression patterns, or profiles, are analyzed by quantifying the number of expressed proteins and their relative abundance under given conditions and at a given time. A profile of a cell's proteome may thus be generated by separating and analyzing the polypeptides of a particular tissue or cell type. In one embodiment, the separation is achieved using two-dimensional gel electrophoresis, in which proteins from a sample are separated by isoelectric focusing in the first dimension, and then according to molecular weight by sodium dodecyl sulfate slab gel electrophoresis in the second dimension (Steiner and Anderson, supra). The proteins are visualized in the gel as discrete and uniquely positioned spots, typically by staining the gel with an agent such as Coomassie Blue or silver or fluorescent stains. The optical density of each protein spot is generally proportional to the level of the protein in the sample. The optical densities of equivalently positioned protein spots from different samples, for example, from biological samples either treated or untreated with a test compound or therapeutic agent, are compared to identify any changes in protein spot density related to the treatment. The proteins in the spots are partially sequenced using, for example, standard methods employing chemical or enzymatic cleavage followed by mass spectrometry. The identity of the protein in a spot may be determined by comparing its partial sequence, preferably of at least 5 contiguous amino acid residues, to the polypeptide sequences of interest. In some cases, further sequence data may be obtained for definitive protein identification.

A proteomic profile may also be generated using antibodies specific for REMAP to quantify the levels of REMAP expression. In one embodiment, the antibodies are used as elements on a microarray, and protein expression levels are quantified by exposing the microarray to the sample and detecting the levels of protein bound to each array element (Lueking, A. et al. (1999) Anal. Biochem. 270:103-111; Mendoze, L. G. et al. (1999) Biotechniques 27:778-788). Detection may be performed by a variety of methods known in the art, for example, by reacting the proteins in the sample with a thiol- or amino-reactive fluorescent compound and detecting the amount of fluorescence bound at each array element.

Toxicant signatures at the proteome level are also useful for toxicological screening, and should be analyzed in parallel with toxicant signatures at the transcript level. There is a poor correlation between transcript and protein abundances for some proteins in some tissues (Anderson, N. L. and J. Seilhamer (1997) Electrophoresis 18:533-537), so proteome toxicant signatures may be useful in the analysis of compounds which do not significantly affect the transcript image, but which alter the proteomic profile. In addition, the analysis of transcripts in body fluids is difficult, due to rapid degradation of mRNA, so proteomic profiling may be more reliable and informative in such cases.

In another embodiment, the toxicity of a test compound is assessed by treating a biological sample containing proteins with the test compound. Proteins that are expressed in the treated biological sample are separated so that the amount of each protein can be quantified. The amount of each protein is compared to the amount of the corresponding protein in an untreated biological sample. A difference in the amount of protein between the two samples is indicative of a toxic response to the test compound in the treated sample. Individual proteins are identified by sequencing the amino acid residues of the individual proteins and comparing these partial sequences to the polypeptides of the present invention.

In another embodiment, the toxicity of a test compound is assessed by treating a biological sample containing proteins with the test compound. Proteins from the biological sample are incubated with antibodies specific to the polypeptides of the present invention. The amount of protein recognized by the antibodies is quantified. The amount of protein in the treated biological sample is compared with the amount in an untreated biological sample. A difference in the amount of protein between the two samples is indicative of a toxic response to the test compound in the treated sample.

Microarrays may be prepared, used, and analyzed using methods known in the art (Brennan, T. M. et al. (1995) U.S. Pat. No. 5,474,796; Schena, M. et al. (1996) Proc. Natl. Acad. Sci. USA 93:10614-10619; Baldeschweiler et al. (1995) PCT application WO95/25116; Shalon, D. et al. (1995) PCT application WO95/35505; Heller, R. A. et al. (1997) Proc. Natl. Acad. Sci. USA 94:2150-2155; Heller, M. J. et al. (1997) U.S. Pat. No. 5,605,662). Various types of microarrays are well known and thoroughly described in Schena, M., ed. (1999; *DNA Microarrays: A Practical Approach*, Oxford University Press, London).

In another embodiment of the invention, nucleic acid sequences encoding REMAP may be used to generate hybridization probes useful in mapping the naturally occurring genomic sequence. Either coding or noncoding sequences may be used, and in some instances, noncoding sequences may be preferable over coding sequences. For example, conservation of a coding sequence among members of a multi-gene family may potentially cause undesired cross hybridization during chromosomal mapping. The sequences may be mapped to a particular chromosome, to a specific region of a chromosome, or to artificial chromosome constructions, e.g., human artificial chromosomes (HACs), yeast artificial chromosomes (YACs), bacterial artificial chromosomes (BACs), bacterial P1 constructions, or single chromosome cDNA libraries (Harrington, J. J. et al. (1997) Nat. Genet. 15:345-355; Price, C. M. (1993) Blood Rev. 7:127-134; Trask, B. J. (1991) Trends Genet. 7:149-154). Once mapped, the nucleic acid sequences may be used to develop genetic linkage maps, for example, which correlate the inheritance of a disease state with the inheritance of a particular chromosome region or restriction fragment length polymorphism (RFLP) (Lander, E. S. and D. Botstein (1986) Proc. Natl. Acad. Sci. USA 83:7353-7357).

Fluorescent in situ hybridization (FISH) may be correlated with other physical and genetic map data (Heinz-Ulrich, et al. (1995) in Meyers, supra, pp. 965-968). Examples of genetic map data can be found in various scientific journals or at the Online Mendelian Inheritance in Man (OMIM) World Wide Web site. Correlation between the location of the gene encoding REMAP on a physical map and a specific disorder, or a predisposition to a specific disorder, may help define the region of DNA associated with that disorder and thus may further positional cloning efforts.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the exact chromosomal locus is not known. This information is valuable to investigators searching for disease genes using positional cloning or other gene discovery techniques. Once the gene or genes responsible for a disease or syndrome have been crudely localized by genetic linkage to a particular genomic region, e.g., ataxia-telangiectasia to 11q22-23, any sequences mapping to that area may represent associated or regulatory genes for further investigation (Gatti, R. A. et al. (1988) Nature 336:577-580). The nucleotide sequence of the instant invention may also be used to detect differences in the chromosomal location due to translocation, inversion, etc., among normal, carrier, or affected individuals.

In another embodiment of the invention, REMAP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between REMAP and the agent being tested may be measured.

Another technique for drug screening provides for high throughput screening of compounds having suitable binding affinity to the protein of interest (Geysen, et al. (1984) PCT application W084/03564). In this method, large numbers of different small test compounds are synthesized on a solid substrate. The test compounds are reacted with REMAP, or fragments thereof, and washed. Bound REMAP is then detected by methods well known in the art. Purified REMAP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding REMAP specifically compete with a test compound for binding REMAP. In this manner, antibodies can be used to detect the presence of any peptide which shares one or more antigenic determinants with REMAP.

In additional embodiments, the nucleotide sequences which encode REMAP may be used in any molecular biology techniques that have yet to be developed, provided the new techniques rely on properties of nucleotide sequences that are currently known, including, but not limited to, such properties as the triplet genetic code and specific base pair interactions.

Without further elaboration, it is believed that one skilled in the art can, using the preceding description, utilize the present invention to its fullest extent. The following embodiments are, therefore, to be construed as merely illustrative, and not limitative of the remainder of the disclosure in any way whatsoever.

The disclosures of all patents, applications, and publications mentioned above and below, including U.S. Ser. No. 60/358,279, U.S. Ser. No. 60/364,338, U.S. Ser. No. 60/375,657, U.S. Ser. No. 60/376,669, U.S. Ser. No. 60/379,837, and U.S. Ser. No. 60/379,853, are hereby expressly incorporated by reference.

EXAMPLES

I. Construction of cDNA Libraries

Incyte cDNAs were derived from cDNA libraries described in the LIFESEQ GOLD database (Incyte Genomics, Palo Alto Calif.). Some tissues were homogenized and lysed in guanidinium isothiocyanate, while others were homogenized and lysed in phenol or in a suitable mixture of denaturants, such as TRIZOL (Invitrogen), a monophasic solution of phenol and guanidine isothiocyanate. The resulting lysates were centrifuged over CsCl cushions or extracted with chloroform. RNA was precipitated from the lysates with either isopropanol or sodium acetate and ethanol, or by other routine methods.

Phenol extraction and precipitation of RNA were repeated as necessary to increase RNA purity. In some cases, RNA was treated with DNase. For most libraries, poly(A)+RNA was isolated using oligo d(T)-coupled paramagnetic particles (Promega), OLIGOTEX latex particles (QIAGEN, Chatsworth Calif.), or an OLIGOTEX mRNA purification kit (QIAGEN). Alternatively, RNA was isolated directly from tissue lysates using other RNA isolation kits, e.g., the POLY(A)PURE mRNA purification kit (Ambion, Austin Tex.).

In some cases, Stratagene was provided with RNA and constructed the corresponding cDNA libraries. Otherwise, cDNA was synthesized and cDNA libraries were constructed with the UNIZAP vector system (Stratagene) or SUPERSCRIPT plasmid system (Invitrogen), using the recommended procedures or similar methods known in the art (Ausubel et al., supra, ch. 5). Reverse transcription was initiated using oligo d(T) or random primers. Synthetic oligonucleotide adapters were ligated to double stranded cDNA, and the cDNA was digested with the appropriate restriction enzyme or enzymes. For most libraries, the cDNA was size-selected (300-1000 bp) using SEPHACRYL S1000, SEPHAROSE CL2B, or SEPHAROSE CLAB column chromatography (Amersham Biosciences) or preparative agarose gel electrophoresis. cDNAs were ligated into compatible restriction enzyme sites of the polylinker of a suitable plasmid, e.g., PBLUESCRIPT plasmid (Stratagene), PSPORT1 plasmid (Invitrogen, Carlsbad Calif.), PCDNA2.1 plasmid (Invitrogen), PBK-CMV plasmid (Stratagene), PCR2-TOPOTA plasmid (Invitrogen), PCMV-ICIS plasmid (Stratagene), pIGEN (Incyte Genomics, Palo Alto Calif.), pRARE (Incyte Genomics), or pINCY (Incyte Genomics), or derivatives thereof. Recombinant plasmids were transformed into competent *E. coli* cells including XL1-Blue, XL1-BlueMRF, or SOLR from Stratagene or DH5α, DH10B, or ElectroMAX DH10B from Invitrogen.

II. Isolation of cDNA Clones

Plasmids obtained as described in Example I were recovered from host cells by in vivo excision using the UNIZAP vector system (Stratagene) or by cell lysis. Plasmids were purified using at least one of the following: a Magic or WIZARD Minipreps DNA purification system (Promega); an AGTC Miniprep purification kit (Edge Biosystems, Gaithersburg Md.); and QIAWELL 8 Plasmid, QIAWELL 8 Plus Plasmid, QIAWELL 8 Ultra Plasmid purification systems or the R.E.A.L. PREP 96 plasmid purification kit from QIAGEN. Following precipitation, plasmids were resuspended in 0.1 ml of distilled water and stored, with or without lyophilization, at 4° C.

Alternatively, plasmid DNA was amplified from host cell lysates using direct link PCR in a high-throughput format (Rao, V. B. (1994) Anal. Biochem. 216:1-14). Host cell lysis and thermal cycling steps were carried out in a single reaction mixture. Samples were processed and stored in 384-well plates, and the concentration of amplified plasmid DNA was quantified fluorometrically using PICOGREEN dye (Molecular Probes, Eugene Oreg.) and a FLUOROSKAN II fluorescence scanner (Labsystems Oy, Helsinki, Finland).

III. Sequencing and Analysis

Incyte cDNA recovered in plasmids as described in Example II were sequenced as follows. Sequencing reactions were processed using standard methods or high-throughput instrumentation such as the ABI CATALYST 800 (Applied Biosystems) thermal cycler or the PTC-200 thermal cycler (MJ Research) in conjunction with the HYDRA microdispenser (Robbins Scientific) or the MICROLAB 2200 (Hamilton) liquid transfer system. cDNA sequencing reactions were prepared using reagents provided by Amersham Biosciences or supplied in ABI sequencing kits such as the ABI PRISM BIGDYE Terminator cycle sequencing ready reaction kit (Applied Biosystems). Electrophoretic separation of cDNA sequencing reactions and detection of labeled polynucleotides were carried out using the MEGABACE 1000 DNA sequencing system (Amersham Biosciences); the ABI PRISM 373 or 377 sequencing system (Applied Biosystems) in conjunction with standard ABI protocols and base calling software; or other sequence analysis systems known in the art. Reading frames within the cDNA sequences were identified using standard methods (Ausubel et al., supra, ch. 7). Some of the cDNA sequences were selected for extension using the techniques disclosed in Example VIII.

The polynucleotide sequences derived from Incyte cDNAs were validated by removing vector, linker, and poly(A) sequences and by masking ambiguous bases, using algorithms and programs based on BLAST, dynamic programming, and dinucleotide nearest neighbor analysis. The Incyte cDNA sequences or translations thereof were then queried against a selection of public databases such as the GenBank primate, rodent, mammalian, vertebrate, and eukaryote databases, and BLOCKS, PRINTS, DOMO, PRODOM; PROTEOME databases with sequences from *Homo sapiens, Rattus norvegicus, Mus musculus, Caenorhabditis elegans, Saccharomyces cerevisiae, Schizosaccharomyces pombe*, and *Candida albicans* (Incyte Genomics, Palo Alto Calif.); hidden Markov model WMM)-based protein family databases such as PFAM, INCY, and TIGRFAM (Haft, D. H. et al. (2001) Nucleic Acids Res. 29:41-43); and HMM-based protein domain databases such as SMART (Schultz, J. et al. (1998) Proc. Natl. Acad. Sci. USA 95:5857-5864; Letunic, I. et al. (2002) Nucleic Acids Res. 30:242-244). (HHM is a probabilistic approach which analyzes consensus primary structures of gene families; see, for example, Eddy, S. R. (1996) Curr. Opin. Struct. Biol. 6:361-365.) The queries were performed using programs based on BLAST, FASTA, BLIMPS, and HMMER. The Incyte cDNA sequences were assembled to produce full length polynucleotide sequences. Alternatively, GenBank cDNAs, GenBank ESTs, stitched sequences, stretched sequences, or Genscan-predicted coding sequences (see Examples IV and V) were used to extend Incyte cDNA assemblages to full length. Assembly was performed using programs based on Phred, Phrap, and Consed, and cDNA assemblages were screened for open reading frames using programs based on GeneMark, BLAST, and FASTA. The full length polynucleotide sequences were translated to derive the corresponding full length polypeptide sequences. Alternatively, a polypeptide may begin at any of the methionine residues of the full length translated polypeptide. Full length polypeptide sequences were subsequently analyzed by querying against databases such as the GenBank protein databases (genpept), SwissProt, the PROTEOME databases, BLOCKS, PRINTS, DOMO, PRODOM, Prosite, hidden Markov model (HM)-based protein family databases such as PFAM, INCY, and TIGRFAM; and HMM-based protein domain databases such as SMART. Full length polynucleotide sequences are also analyzed using MACDNASIS PRO software (MiraiBio, Alameda Calif.) and LASERGENE software (DNASTAR). Polynucleotide and polypeptide sequence alignments are generated using default parameters specified by the CLUSTAL algorithm as incorporated into the MEGALIGN multisequence alignments program (DNASTAR), which also calculates the percent identity between aligned sequences.

Table 7 summarizes the tools, programs, and algorithms used for the analysis and assembly of Incyte cDNA and full length sequences and provides applicable descriptions, references, and threshold parameters. The first column of Table 7 shows the tools, programs, and algorithms used, the second column provides brief descriptions thereof, the third column presents appropriate references, all of which are incorporated by reference herein in their entirety, and the fourth column presents, where applicable, the scores, probability values, and other parameters used to evaluate the strength of a match between two sequences (the higher the score or the lower the probability value, the greater the identity between two sequences).

The programs described above for the assembly and analysis of full length polynucleotide and polypeptide sequences were also used to identify polynucleotide sequence fragments from SEQ ID NO:39-76. Fragments from about 20 to about 4000 nucleotides which are useful in hybridization and amplification technologies are described in Table 4, column 2.

IV. Identification and Editing of Coding Sequences from Genomic DNA

Putative receptors and membrane-associated proteins were initially identified by running the Genscan gene identification program against public genomic sequence databases (e.g., gbpri and gbhtg). Genscan is a general-purpose gene identification program which analyzes genomic DNA sequences from a variety of organisms (Burge, C. and S. Karlin (1997) J. Mol. Biol. 268:78-94; Burge, C. and S. Karlin (1998) Curr. Opin. Struct. Biol. 8:346-354). The program concatenates predicted exons to form an assembled cDNA sequence extending from a methionine to a stop codon. The output of Genscan is a FASTA database of polynucleotide and polypeptide sequences. The maximum range of sequence for Genscan to analyze at once was set to 30 kb. To determine which of these Genscan predicted cDNA sequences encode receptors and membrane-associated proteins, the encoded polypeptides were analyzed by querying against PFAM models for receptors and membrane-associated proteins. Potential receptors and membrane-associated proteins were also identified by homology to Incyte cDNA sequences that had been annotated as receptors and membrane-associated proteins. These selected Genscan-predicted sequences were then compared by BLAST analysis to the genpept and gbpri public databases. Where necessary, the Genscan-predicted sequences were then edited by comparison to the top BLAST hit from genpept to correct errors in the sequence predicted by Genscan, such as extra or omitted exons. BLAST analysis was also used to find any Incyte cDNA or public cDNA coverage of the Genscan-predicted sequences, thus providing evidence for transcription. When Incyte cDNA coverage was available, this information was used to correct or confirm the Genscan predicted sequence. Full length polynucleotide sequences were obtained by assembling Genscan-predicted coding sequences with Incyte cDNA sequences and/or public cDNA sequences using the assembly process described in Example III. Alternatively, full length polynucleotide sequences were derived entirely from edited or unedited Genscan-predicted coding sequences.

V. Assembly of Genomic Sequence Data with cDNA Sequence Data

"Stitched" Sequences

Partial cDNA sequences were extended with exons predicted by the Genscan gene identification program described in Example IV. Partial cDNAs assembled as described in Example III were mapped to genomic DNA and parsed into clusters containing related cDNAs and Genscan exon predictions from one or more genomic sequences. Each cluster was analyzed using an algorithm based on graph theory and dynamic programming to integrate cDNA and genomic information, generating possible splice variants that were subsequently confirmed, edited, or extended to create a full length sequence. Sequence intervals in which the entire length of the interval was present on more than one sequence in the cluster were identified, and intervals thus identified were considered to be equivalent by transitivity. For example, if an interval was present on a cDNA and two genomic sequences, then all three intervals were considered to be equivalent. This process allows unrelated but consecutive genomic sequences to be brought together, bridged by cDNA sequence. Intervals thus identified were then "stitched" together by the stitching algorithm in the order that they appear along their parent sequences to generate the longest possible sequence, as well as sequence variants. Linkages between intervals which proceed along one type of parent sequence (cDNA to cDNA or genomic sequence to genomic sequence) were given preference over linkages which change parent type (cDNA to genomic sequence). The resultant stitched sequences were translated and compared by BLAST analysis to the genpept and gbpri public databases. Incorrect exons predicted by Genscan were corrected by comparison to the top BLAST hit from genpept. Sequences were further extended with additional cDNA sequences, or by inspection of genomic DNA, when necessary.

"Stretched" Sequences

Partial DNA sequences were extended to full length with an algorithm based on BLAST analysis. First, partial cDNAs assembled as described in Example III were queried against public databases such as the GenBank primate, rodent, mammalian, vertebrate, and eukaryote databases using the BLAST program. The nearest GenBank protein homolog was then compared by BLAST analysis to either Incyte cDNA sequences or GenScan exon predicted sequences described in Example IV. A chimeric protein was generated by using the resultant high-scoring segment pairs (HSPs) to map the translated sequences onto the GenBank protein homolog. Insertions or deletions may occur in the chimeric protein with respect to the original GenBank protein homolog. The GenBank protein homolog, the chimeric protein, or both were used as probes to search for homologous genomic sequences from the public human genome databases. Partial DNA sequences were therefore "stretched" or extended by the addition of homologous genomic sequences. The resultant stretched sequences were examined to determine whether it contained a complete gene.

VI. Chromosomal Mapping of REMAP Encoding Polynucleotides

The sequences which were used to assemble SEQ ID NO:39-76 were compared with sequences from the Incyte LIFESEQ database and public domain databases using BLAST and other implementations of the Smith-Waterman algorithm. Sequences from these databases that matched SEQ ID NO:39-76 were assembled into clusters of contiguous and overlapping sequences using assembly algorithms such as Phrap (Table 7). Radiation hybrid and genetic mapping data available from public resources such as the Stanford Human Genome Center (SHGC), Whitehead Institute for Genome Research (WIGR), and Genethon were used to determine if any of the clustered sequences had been previously mapped. Inclusion of a mapped sequence in a cluster resulted in the assignment of all sequences of that cluster, including its particular SEQ ID NO:, to that map location.

Map locations are represented by ranges, or intervals, of human chromosomes. The map position of an interval, in centiMorgans, is measured relative to the terminus of the chromosome's p-arm. (The centiMorgan (cM) is a unit of measurement based on recombination frequencies between chromosomal markers. On average, 1 cM is roughly equivalent to 1 megabase (Mb) of DNA in humans, although this can vary widely due to hot and cold spots of recombination.) The cM distances are based on genetic markers mapped by Genethon which provide boundaries for radiation hybrid markers whose sequences were included in each of the clusters. Human genome maps and other resources available to the public, such as the NCBI "GeneMap'99" World Wide Web site, can be employed to determine if previously identified disease genes map within or in proximity to the intervals indicated above.

VII. Analysis of Polynucleotide Expression

Northern analysis is a laboratory technique used to detect the presence of a transcript of a gene and involves the hybridization of a labeled nucleotide sequence to a membrane on which RNAs from a particular cell type or tissue have been bound (Sambrook and Russell, supra, ch. 7; Ausubel et al., supra, ch. 4).

Analogous computer techniques applying BLAST were used to search for identical or related molecules in databases such as GenBank or LIFESEQ (Incyte Genomics). This analysis is much faster than multiple membrane-based hybridizations. In addition, the sensitivity of the computer search can be modified to determine whether any particular match is categorized as exact or similar. The basis of the search is the product score, which is defined as:

$$\frac{BLAST\ \text{Score} \times \text{Percent Identity}}{5 \times \text{minimum } \{\text{length(Seq.1)}, \text{length(Seq.2)}\}}$$

The product score takes into account both the degree of similarity between two sequences and the length of the sequence match. The product score is a normalized value between 0 and 100, and is calculated as follows: the BLAST score is multiplied by the percent nucleotide identity and the product is divided by (5 times the length of the shorter of the two sequences). The BLAST score is calculated by assigning a score of +5 for every base that matches in a high-scoring segment pair (HSP), and −4 for every mismatch. Two sequences may share more than one HSP (separated by gaps). If there is more than one HSP, then the pair with the highest BLAST score is used to calculate the product score. The product score represents a balance between fractional overlap and quality in a BLAST alignment. For example, a product score of 100 is produced only for 100% identity over the entire length of the shorter of the two sequences being compared. A product score of 70 is produced either by 100% identity and 70% overlap at one end, or by 88% identity and 100% overlap at the other. A product score of 50 is produced either by 100% identity and 50% overlap at one end, or 79% identity and 100% overlap.

Alternatively, polynucleotides encoding REMAP are analyzed with respect to the tissue sources from which they were derived. For example, some fill length sequences are assembled, at least in part, with overlapping Incyte cDNA sequences (see Example III). Each cDNA sequence is derived from a cDNA library constructed from a human tissue. Each human tissue is classified into one of the following organ/tissue categories: cardiovascular system; connective tissue; digestive system; embryonic structures; endocrine system; exocrine glands; genitalia, female; genitalia, male; germ cells; hemic and immune system; liver; musculoskeletal system; nervous system; pancreas; respiratory system; sense organs; skin; stomatognathic system; unclassified/mixed; or urinary tract. The number of libraries in each category is counted and divided by the total number of libraries across all categories. Similarly, each human tissue is classified into one of the following disease/condition categories: cancer, cell line, developmental, inflammation, neurological, trauma, cardiovascular, pooled, and other, and the number of libraries in each category is counted and divided by the total number of libraries across all categories. The resulting percentages reflect the tissue- and disease-specific expression of cDNA encoding REMAP. cDNA sequences and cDNA library/tissue information are found in the LIESEQ GOLD database (Incyte Genomics, Palo Alto Calif.).

VIII. Extension of REMAP Encoding Polynucleotides

Full length polynucleotides are produced by extension of an appropriate fragment of the full length molecule using oligonucleotide primers designed from this fragment. One primer was synthesized to initiate 5' extension of the known fragment, and the other primer was synthesized to initiate 3' extension of the known fragment. The initial primers were designed using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries were used to extend the sequence. If more than one extension was necessary or desired, additional or nested sets of primers were designed.

High fidelity amplification was obtained by PCR using methods well known in the art. PCR was performed in 96-well plates using the PTC-200 thermal cycler (MJ Research, Inc.). The reaction mix contained DNA template, 200 nmol of each primer, reaction buffer containing $Mg^{2+}$, $(NH_4)_2SO_4$, and 2-mercaptoethanol, Taq DNA polymerase (Amersham Biosciences), ELONGASE enzyme (Invitrogen), and Pfu DNA polymerase (Stratagene), with the following parameters for primer pair PCI A and PCI B: Step 1: 94° C., 3 min; Step 2: 94° C., 15 sec; Step 3: 60° C., 1 min; Step 4: 68° C., 2 min; Step 5: Steps 2, 3, and 4 repeated 20 times; Step 6: 68° C., 5 min; Step 7: storage at 4° C. In the alternative, the parameters for primer pair T7 and SK+ were as follows: Step 1: 94° C., 3 min; Step 2: 94° C., 15 sec; Step 3: 57° C., 1 min; Step 4: 68° C., 2 min; Step 5: Steps 2, 3, and 4 repeated 20 times; Step 6: 68° C., 5 min; Step 7: storage at 4° C.

The concentration of DNA in each well was determined by dispensing 100 μl PICOGREEN quantitation reagent (0.25% (v/v) PICOGREEN; Molecular Probes, Eugene Oreg.) dissolved in 1×TE and 0.5 μl of undiluted PCR product into each well of an opaque fluorimeter plate (Corning Costar, Acton Mass.), allowing the DNA to bind to the reagent. The plate was scanned in a Fluoroskan II (Labsysterns Oy, Helsinki, Finland) to measure the fluorescence of the sample and to quantify the concentration of DNA. A 5 μl to 10 μl aliquot of the reaction mixture was analyzed by electrophoresis on a 1% agarose gel to determine which reactions were successful in extending the sequence.

The extended nucleotides were desalted and concentrated, transferred to 384-well plates, digested with CviJI cholera virus endonuclease (Molecular Biology Research, Madison Wis.), and sonicated or sheared prior to religation into pUC 18 vector (Amersham Biosciences). For shotgun sequencing, the digested nucleotides were separated on low concentration (0.6 to 0.8%) agarose gels, fragments were excised, and agar digested with Agar ACE (Promega). Extended clones were religated using T4 ligase (New England Biolabs, Beverly Mass.) into pUC 18 vector (Amersham Biosciences), treated with Pfu DNA polymerase (Stratagene) to fill-in restriction site overhangs, and transfected into competent *E. coli* cells. Transformed cells were selected on antibiotic-containing media, and individual colonies were picked and cultured overnight at 37OC in 384-well plates in LB/2×carb liquid media.

The cells were lysed, and DNA was amplified by PCR using Taq DNA polymerase (Amersham Biosciences) and Pfu DNA polymerase (Stratagene) with the following parameters: Step 1: 94° C., 3 min; Step 2: 94° C., 15 sec; Step 3: 60° C., 1 min; Step 4: 72° C., 2 min; Step 5: steps 2, 3, and 4 repeated 29 times; Step 6: 72° C., 5 min; Step 7: storage at 4° C. DNA was quantified by PICOGREEN reagent (Molecular Probes) as described above. Samples with low DNA recoveries were reamplified using the same conditions as described above. Samples were diluted with 20% dimethysulfoxide (1:2, v/v), and sequenced using DYENAMIC energy transfer sequencing primers and the DYENAMIC DIRECT kit (Amersham Biosciences) or the ABI PRISM BIGDYE Terminator cycle sequencing ready reaction kit (Applied Biosystems).

In like manner, full length polynucleotides are verified using the above procedure or are used to obtain 5' regulatory sequences using the above procedure along with oligonucleotides designed for such extension, and an appropriate genomic library.

IX. Identification of Single Nucleotide Polymorphisms in REMAP Encoding Polynucleotides Common DNA sequence variants known as single nucleotide polymorphisms (SNPS) were identified in SEQ ID NO:39-76 using the LIFESEQ database (Incyte Genomics). Sequences from the same gene were clustered together and assembled as described in Example III, allowing the identification of all sequence variants in the gene. An algorithm consisting of a series of filters was used to distinguish SNPs from other sequence variants. Preliminary filters removed the majority of basecall errors by requiring a minimum Phred quality score of 15, and removed sequence alignment errors and errors resulting from improper trimming of vector sequences, chimeras, and splice variants. An automated procedure of advanced chromosome analysis analysed the original chromatogram files in the vicinity of the putative SNP. Clone error filters used statistically generated algorithms to identify errors introduced during laboratory processing, such as those caused by reverse transcriptase, polymerase, or somatic mutation. Clustering error filters used statistically generated algorithms to identify errors resulting from clustering of close homologs or pseudogenes, or due to contamination by non-human sequences. A final set of filters removed duplicates and SNPs found in immunoglobulinsor T-cell receptors.

Certain SNPs were selected for further characterization by mass spectrometry using the high throughput MASSARRAY system (Sequenom, Inc.) to analyze allele frequencies at the SNP sites in four different human populations. The Caucasian population comprised 92 individuals (46 male, 46 female), including 83 from Utah, four French, three Venezualan, and two Amish individuals. The African population comprised 194 individuals (97 male, 97 female), all African Americans. The Hispanic population comprised 324 individuals (162 male, 162 female), all Mexican Hispanic. The Asian population comprised 126 individuals (64 male, 62 female) with a reported parental breakdown of 43% Chinese, 31% Japanese, 13% Korean, 5% Vietnamese, and 8% other Asian. Allele frequencies were first analyzed in the Caucasian population; in some cases those SNPs which showed no allelic variance in this population were not further tested in the other three populations.

X. Labeling and Use of Individual Hybridization Probes

Hybridization probes derived from SEQ ID NO:39-76 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer, 250 μCi of [$\gamma$-$^{32}$P] adenosine triphosphate (Amersham Biosciences), and T4 polynucleotide kinase (DuPont NEN, Boston Mass.). The labeled oligonucleotides are substantially purified using a SEPHADEX G-25 superfine size exclusion dextran bead column (Amersham Biosciences). An aliquot containing $10^7$ counts per minute of the labeled probe is used in a typical membrane-based hybridization analysis of human genomic DNA digested with one of the following endonucleases: AseI, BglII, EcoRI, PstI, XbaI, or PvuII (DuPont NEN).

The DNA from each digest is fractionated on a 0.7% agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under conditions of up to, for example, 0.1×saline sodium citrate and 0.5% sodium dodecyl sulfate. Hybridization patterns are visualized using autoradiography or an alternative imaging means and compared.

XI. Microarrays

The linkage or synthesis of array elements upon a microarray can be achieved utilizing photolithography, piezoelectric printing (ink-jet printing; see, e.g., Baldeschweiler et al., supra), mechanical microspotting technologies, and derivatives thereof. The substrate in each of the aforementioned technologies should be uniform and solid with a non-porous surface (Schena, M., ed. (1999) *DNA Microarrays: A Practical Approach*, Oxford University Press, London). Suggested substrates include silicon, silica, glass slides, glass chips, and silicon wafers. Alternatively, a procedure analogous to a dot or slot blot may also be used to arrange and link elements to the surface of a substrate using thermal, UV, chemical, or mechanical bonding procedures. A typical array may be produced using available methods and machines well known to those of ordinary skill in the art and may contain any appropriate number of elements (Schena, M. et al. (1995) Science 270:467470; Shalon, D. et al. (1996) Genome Res. 6:639-645; Marshall, A. and J. Hodgson (1998) Nat. Biotechnol. 16:27-31).

Full length cDNAs, Expressed Sequence Tags (ESTs), or fragments or oligomers thereof may comprise the elements of the microarray. Fragments or oligomers suitable for hybridization can be selected using software well known in the art such as LASERGENE software (DNASTAR). The array elements are hybridized with polynucleotides in a biological sample. The polynucleotides in the biological sample are conjugated to a fluorescent label or other molecular tag for ease of detection. After hybridization, nonhybridized nucleotides from the biological sample are removed, and a fluorescence scanner is used to detect hybridization at each array element. Alternatively, laser desorbtion and mass spectrometry may be used for detection of hybridization. The degree of complementarity and the relative abundance of each polynucleotide which hybridizes to an element on the microarray may be assessed. In one embodiment, microarray preparation and usage is described in detail below.

Tissue or Cell Sample Preparation

Total RNA is isolated from tissue samples using the guanidinium thiocyanate method and poly(A)$^+$ RNA is purified using the oligo-(dT) cellulose method. Each poly (A)$^+$ RNA sample is reverse transcribed using MMLV reverse-transcriptase, 0.05 pg/μl oligo-(dT) primer (21mer), 1×first strand buffer, 0.03 units/μl RNase inhibitor, 500 μM DATP, 500 μM dGTP, 500 μM dTTP, 40 ηM dCTP, 40 μM dCTP-Cy3 (BDS) or dCTP-Cy5 (Amersham Biosciences). The reverse transcription reaction is performed in a 25 ml volume containing 200 ng poly(A)$^+$ RNA with GEM-BRIGHT kits (Incyte Genomics). Specific control poly(A)$^+$ RNAs are synthesized by in vitro transcription from non-coding yeast genomic DNA. After incubation at 37° C. for 2 hr, each reaction sample (one with Cy3 and another with Cy5 labeling) is treated with 2.5 ml of 0.5M sodium hydroxide and incubated for 20 minutes at 85° C. to the stop the reaction and degrade the RNA. Samples are purified using two successive CHROMA SPIN 30 gel filtration spin columns (Clontech, Palo Alto Calif.) and after combining, both reaction samples are ethanol precipitated using 1 ml of glycogen (1 mg/ml), 60 ml sodium acetate, and 300 ml of 100% ethanol. The sample is then dried to completion using a SpeedVAC (Savant Instruments Inc., Holbrook N.Y.) and resuspended in 14 μl 5×SSC/0.2% SDS.

Microarray Preparation

Sequences of the present invention are used to generate array elements. Each array element is amplified from bacterial cells containing vectors with cloned cDNA inserts. PCR amplification uses primers complementary to the vector sequences flanking the cDNA insert. Array elements are amplified in thirty cycles of PCR from an initial quantity of 1-2 ng to a final quantity greater than 5 μg. Amplified array elements are then purified using SEPHACRYL400 (Amersham Biosciences).

Purified array elements are immobilized on polymer-coated glass slides. Glass microscope slides (Corning) are cleaned by ultrasound in 0.1% SDS and acetone, with extensive distilled water washes between and after treatments. Glass slides are etched in 4% hydrofluoric acid (VWR Scientific Products Corporation (VWR), West Chester Pa.), washed extensively in distilled water, and coated with 0.05% aininopropyl silane (Sigma-Aldrich, St. Louis Mo.) in 95% ethanol. Coated slides are cured in a 110° C. oven.

Array elements are applied to the coated glass substrate using a procedure described in U.S. Pat. No. 5,807,522, incorporated herein by reference. 1 μl of the array element DNA, at an average concentration of 100 ng/μl, is loaded into the open capillary printing element by a high-speed robotic apparatus. The apparatus then deposits about 5 nl of array element sample per slide.

Microarrays are UV-crosslinked using a STRATALSKER UV-crosslinker (Stratagene). Microarrays are washed at room temperature once in 0.2% SDS and three times in distilled water. Non-specific binding sites are blocked by incubation of microarrays in 0.2% casein in phosphate buffered saline (PBS) (Tropix, Inc., Bedford Mass.) for 30 minutes at 60° C. followed by washes in 0.2% SDS and distilled water as before.

Hybridization

Hybridization reactions contain 9 μl of sample mixture consisting of 0.2 μg each of Cy3 and Cy5 labeled cDNA synthesis products in 5×SSC, 0.2% SDS hybridization buffer. The sample mixture is heated to 65° C. for 5 minutes and is aliquoted onto the microarray surface and covered with an 1.8 $cm^2$ coverslip. The arrays are transferred to a waterproof chamber having a cavity just slightly larger than a microscope slide. The chamber is kept at 100% humidity internally by the addition of 140 μl of 5×SSC in a corner of the chamber. The chamber containing the arrays is incubated for about 6.5 hours at 60° C. The arrays are washed for 10 min at 45° C. in a first wash buffer (1×SSC, 0.1% SDS), three times for 10 minutes each at 45° C. in a second wash buffer (0.1×SSC), and dried.

Detection

Reporter-labeled hybridization complexes are detected with a microscope equipped with an Innova 70 mixed gas 10 W laser (Coherent, Inc., Santa Clara Calif.) capable of generating spectral lines at 488 nm for excitation of Cy3 and at 632 nm for excitation of Cy5. The excitation laser light is focused on the array using a 20× microscope objective (Nikon, Inc., Melville N.Y.). The slide containing the array is placed on a computer-controlled X-Y stage on the microscope and raster-scanned past the objective. The 1.8 cm×1.8 cm array used in the present example is scanned with a resolution of 20 micrometers.

In two separate scans, a mixed gas multiline laser excites the two fluorophores sequentially. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. Each array is typically scanned twice, one scan per fluorophore using the appropriate filters at the laser source, although the apparatus is capable of recording the spectra from both fluorophores simultaneously.

The sensitivity of the scans is typically calibrated using the signal intensity generated by a cDNA control species added to the sample mixture at a known concentration. A specific location on the array contains a complementary DNA sequence, allowing the intensity of the signal at that location to be correlated with a weight ratio of hybridizing species of 1:100,000. When two samples from different sources (e.g., representing test and control cells), each labeled with a different fluorophore, are hybridized to a single array for the purpose of identifying genes that are differentially expressed, the calibration is done by labeling samples of the calibrating cDNA with the two fluorophores and adding identical amounts of each to the hybridization mixture.

The output of the photomultiplier tube is digitized using a 12-bit RTI-835H analog-to-digital (A/D) conversion board (Analog Devices, Inc., Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using each fluorophore's emission spectrum.

A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS gene expression analysis program (Incyte Genomics). Array elements that exhibit at least about a two-fold change in expression, a signal-to-background ratio of at least about 2.5, and an element spot size of at least about 40%, are considered to be differentially expressed.

Expression

For example, T-47D is a breast carcinoma cell line isolated from a pleural effusion obtained from a 54-year-old female with an infiltrating ductal carcinoma of the breast. T-47D cells were treated with interferon gamma for from one hour to three days and then compared to untreated T-47D cells. Expression of SEQ ID NO:39 was decreased from 2- to 5.8-fold in treated T-47D cells when compared to untreated T-47D cells. Therefore, SEQ ID NO:39 is useful as a diagnostic marker or as a potential therapeutic target for breast cancer and inflammatory and immune diseases.

In another example, SEQ ID NO:65 demonstrated differential expression in a number of breast cancer and prostate cancer cell lines, as determined by microarray expression analysis. Normal breast cancer cells were represented by the HMEC (human mammary epithelial cells) cell line, and the fibrocystic cell line MCF-10A, derived from a donor with fibrocystic breast disease, was also used as a control, non-cancerous cell line. SEQ ID NO:65 showed at least a 2-fold decrease in expression in Sk-Br-3 cells, a Her2-positive cell line derived from a malignant adenocarcinoma of the breast, when compared to expression levels in either HMEC or MCF-10A cells. In addition, the BT-20 cell line, a cell line that forms stage II adenocarcinomas in mice derived from a donor with malignant adenocarcinoma of the breast, had at least a 2-fold decrease in SEQ ID NO:65 gene expression levels when compared to MCF-10A expression levels. Interestingly, the MCF-10A cell line showed at least a 2-fold decrease in expression of SEQ ID NO:65 when compared to the expression profile in HMEC normal epithelial cell line.

In another example, expression levels of SEQ ID NO:65 were compared in prostate cancer cell lines and in the normal prostate epithelial cell line PrEC. SEQ ID NO:9 showed a 2-fold increase in expression in PC3 cells (a adenocarcinoma cell line isolated from a bone metastasis of a donor with grade IV prostate cancer) when compared to starved PrEC cells. In other experiments, there was a 2-fold decrease in expression in DU 145 cells (derived from a brain metastasis of a donor with metastatic prostatic carcinoma), and a 2-fold decrease in expression in LNCaP cells (derived from a metastatic site in the lymph node of a prostate cancer donor), when compared to gene expression levels in PrEC cells grown in defined media LNCaP cells also showed at least a 2-fold decrease in SEQ ID NO:65 gene expression levels when compared to levels in another control prostate cell line, PZ-HPV-7. Additionally, treatment of LNCaP cells with PMA and ionomycin, activating PKC and calcium influx into the cells, lead to a time-dependent increase in expression of SEQ ID NO:65 (at least 2-fold after 4 hours, and at least 3-fold after 8 hours) when compared to untreated cells. Therefore, SEQ ID NO:65 is useful for staging of, monitoring treatment of, and diagnostic assays for breast and prostate cancer.

In another example, SEQ ID NO:62 and SEQ ID NO:65 were shown to have differential expression patterns in a number of lymphocyte cell models upon treatment with various stimuli, as determined by microarray expression analysis. Human peripheral blood mononuclear cells (PBMCs) were treated with PMA and ionomycin, to activate PKC- and calcium-dependent signaling pathways, and SEQ ID NO:62 expression levels were compared to levels in untreated cells. SEQ ID NO:62 showed a time-dependent increase in expression, at least 2.5-fold above untreated cell levels at 1 hour, peaking at 4.8-fold after 2 hours, then declining back to at least 2.5-fold at the 4 hour time point. Also, PBMCs from a number of different donors were treated with LPS for 4 to 24 hours, and these cells showed a general decrease in expression of SEQ ID NO:65 of between 2- and 4.5-fold when compared to untreated cells. In addition, RPMI 6666 cells (B cells derived from a donor with Hodgkin's disease) showed at least a 2-fold decrease in expression of SEQ ID NO:65 upon LPS treatment for 8 hours, when compared to expression levels in untreated RPMI 6666 cells. Treatment of donor PBMCs with SEB (staphylococcal endotoxin), however, resulted in a 2- to 4-fold increase in expression after 24 to 72 hours of SEQ ID NO:65, when compared to untreated cells.

In another example, THP-1 cells, a monocytic cell line, demonstrated differential expression of SEQ ID NO:62 and SEQ ID NO:65 upon differentiation into macrophage-like cells or foam cells, as determined by microarray expression analysis. Stimulation of THP-1 cells with PMA induces differentiation into a macrophage-like cell that displays many characteristics of peripheral human macrophages. The gene expression levels of SEQ ID NO:65 were shown to increase in PMA-treated cells from 2- to 6-fold, when compared to untreated THP-1 cells. Further treatment of THP-1 cells with oxidized LDL (oxLDL) induces differentiation into foam cells. Upon LPS treatment of macrophage-like or foam cells, the expression of SEQ ID NO:62 increased at least 2-fold when compared to untreated cells. Therefore, SEQ ID NO:62 and SEQ ID NO:65 are useful for study of activated immune system cells, and for monitoring treatment of and diagnostic assays for diseases of the immune system.

In another example, SEQ ID NO:70 and SEQ ID NO:73 showed differential expression in association with breast cancer, as determined by microarray analysis. Gene expression profiles were obtained by comparing the results of competitive hybridization experiments. The gene expression profile of cells isolated from a tumor in the right breast was compared to the gene expression profile of cells originating from grossly uninvolved breast tissue from the same donor, a 43-year-old female diagnosed with invasive lobular carcinoma (Huntsman Cancer Institute, Salt Lake City, Utah). The tumor was described as well differentiated and metastatic to 2 out of 13 lymph nodes. SEQ ID NO:73 showed decreased gene expression by at least two-fold in the tumorous tissue sample as compared to the uninvolved tissue sample from the same donor. In another example, the gene expression profile of a breast carcinoma cell line treated with interferon gamma (IFN-γ) was compared to the gene expression profile of untreated cells from the same line. T-47D is a breast carcinoma cell line isolated from a pleural effusion obtained from a 54-year-old female with an infiltrating ductal carcinoma of the breast. T-47D cells were treated with IFN-γ for 1, 4, 8, 24, 48 hours and 3 days. The expression of SEQ ID NO:70 was decreased by at least two-fold in the treated breast carcinoma cell lines as compared to the untreated T-47D population. Thus, SEQ ID NO:70 and SEQ ID NO:73 are useful as diagnostic markers for breast cancer, as well as for monitoring the progression and treatment of breast cancer.

In another example, SEQ ID NO:73 and SEQ ID NO:76 showed differential expression in association with colon cancer, as determined by microarray analysis. Gene expression profiles were obtained by comparing the results of competitive hybridization experiments between normal colon tissue and tumorous rectal tissue from the same donor. Different pieces of normal tissue were also compared against a pool of normal tissue from the same donor to determine gene expression variation in normal colon tissue. The expression of SEQ ID NO:73 was decreased by at least two-fold in tumorous rectal tissue as compared to normal rectal tissue from the same donor. In addition, the gene expression profiles of 6 different colon cancer tissues were analyzed by comparing one individual sample to 5 others, keeping one element in common between the various pairs of comparisons. The reference tissue sample is a metastatic adenocarcinoma of ovarian origin, which distinguishes this sample from the others and may be of special interest. The other five samples include tumorous colon tissue collected from an 85-year-old male, an 81-year-old male, an 83-year-old female, as well as a mucinous adenocarcinoma from a 58-year-old female, and a poorly differentiated metastatic adenocarcinoma from a 56-year-old female. The gene expression of SEQ ID NO:76 was decreased by two-fold in the tumorous rectal tissue samples as compared to the reference tissue. Therefore, SEQ ID NO:73 and SEQ ID NO:76 are useful as diagnostic markers for colon cancer, as well as for monitoring the progression and treatment of colon cancer.

In another example, SEQ ID NO:73 showed differential expression in association with lung cancer. Gene expression profiles were obtained by comparing the results of competitive hybridization experiments. Messenger RNA isolated from grossly uninvolved lung tissue with no visible abnormalities, from a 73-year-old male, was compared to lung squamous cell adenocarcinoma tissue from the same donor (Roy Castle International Centre for Lung Cancer Research, Liverpool, UK). The expression of SEQ ID NO:73 was decreased by at least two-fold in tumorous lung tissue as compared to normal lung tissue from the same donor. Therefore, SEQ ID NO:73 is useful as a diagnostic marker for lung cancer, as well as for monitoring the progression and treatment of lung cancer.

In another example, SEQ ID NO:73 showed differential expression in association with inflammatory and immune responses, as determined by microarray analysis. Gene expression profiles were obtained by comparing the results of competitive hybridization experiments. Human peripheral blood mononuclear cells (PBMCs) from seven healthy donors were stimulated in vitro with Staphylococal extoxin B (SEB) for 24 and 72 hours. The SEB treated PBMCs from each donor were compared to PBMCs from the same donor, kept in culture for 24 hours, in the absence of SEB. The gene expression of SEQ ID NO:73 was decreased by at least two-fold in SEB treated PBMCs as compared to untreated PBMCs from the same donors. In another example, SEQ ID NO:73 showed differential expression in treated versus untreated cells in a promonocyte cell line. THP-1 was isolated from the peripheral blood of a 1-year-old male with acute monocytic leukemia. PMA is a broad activator of the protein kinase C-dependent pathways. Upon stimulation with PMA, THP-1 differentiates into a macrophagelike cell that displays many characteristics of peripheral human macrophages. Promonocytes and monocytes to LPS, PMA-activated THP-1 cells (monocytic) and untreated THP-1 cells (promonocytic) were stimulated in vitro with LPS for 4 hours. LPS-treated THP-1 cells were compared to untreated THP-1 cells. In addition, PMA-activated THP-1 cells were compared to untreated THP-1 cells. The expression of SEQ ID NO:73 was decreased by at least two-fold in treated cells as compared to untreated cells. Therefore, SEQ ID NO:73 is useful as a diagnostic marker for inflammatory and immune response diseases, as well as for monitoring the progression and treatment of inflammatory and immune response diseases.

XII. Complementary Polynucleotides

Sequences complementary to the REMAP-encoding sequences, or any parts thereof, are used to detect, decrease, or inhibit expression of naturally occurring REMAP. Although use of oligonucleotides comprising from about 15 to 30 base pairs is described, essentially the same procedure is used with smaller or with larger sequence fragments. Appropriate oligonucleotides are designed using OLIGO 4.06 software (National Biosciences) and the coding sequence of REMAP. To inhibit transcription, a complementary oligonucleotide is designed from the most unique 5' sequence and used to prevent promoter binding to the coding sequence. To inhibit translation, a complementary oligonucleotide is designed to prevent ribosomal binding to the REMAP-encoding transcript.

XIII. Expression of REMAP

Expression and purification of REMAP is achieved using bacterial or virus-based expression systems. For expression of REMAP in bacteria, cDNA is subcloned into an appropriate vector containing an antibiotic resistance gene and an inducible promoter that directs high levels of cDNA transcription. Examples of such promoters include, but are not limited to, the trp-lac (tac) hybrid promoter and the T5 or T7 bacteriophage promoter in conjunction with the lac operator regulatory element. Recombinant vectors are transformed into suitable bacterial hosts, e.g., BL21(DE3). Antibiotic resistant bacteria express REMAP upon induction with isopropyl beta-D-thiogalactopyranoside (IPTG). Expression of REMAP in eukaryotic cells is achieved by infecting insect or mammalian cell lines with recombinant *Autographica californica* nuclear polyhedrosis virus (AcMNPV), commonly known as baculovirus. The nonessential polyhedrin gene of baculovirus is replaced with cDNA encoding REMAP by either homologous recombination or bacterial-mediated transposition involving transfer plasmid intermediates. Viral infectivity is maintained and the strong polyhedrin promoter drives high levels of cDNA transcription. Recombinant baculovirus is used to infect *Spodoptera frugiperda* (Sf9) insect cells in most cases, or human hepatocytes, in some cases. Infection of the latter requires additional genetic modifications to baculovirus (Engelhard, E. K. et al. (1994) Proc. Natl. Acad. Sci. USA 91:3224-3227; Sandig, V. et al. (1996) Hum. Gene Ther. 7:1937-1945).

In most expression systems, REMAP is synthesized as a fusion protein with, e.g., glutathione S-transferase (GST) or a peptide epitope tag, such as FLAG or 6-His, permitting rapid, single-step, affinity-based purification of recombinant fusion protein from crude cell lysates. GST, a 26-kilodalton enzyme from *Schistosoma japonicum*, enables the purification of fusion proteins on immobilized glutathione under conditions that maintain protein activity and antigenicity (Amersham Biosciences). Following purification, the GST moiety can be proteolytically cleaved from REMAP at specifically engineered sites. FLAG, an 8-amino acid peptide, enables immunoaffinity purification using commercially available monoclonal and polyclonal anti-FLAG antibodies (Eastman Kodak). 6-His, a stretch of six consecutive histidine residues, enables purification on metal-chelate resins (QIAGEN). Methods for protein expression and purification are discussed in Ausubel et al. (supra, ch. 10 and 16). Purified REMAP obtained by these methods can be used directly in the assays shown in Examples XVII, XVIII, and XIX, where applicable.

XIV. Functional Assays

REMAP function is assessed by expressing the sequences encoding REMAP at physiologically elevated levels in mammalian cell culture systems. cDNA is subcloned into a mammalian expression vector containing a strong promoter that drives high levels of cDNA expression. Vectors of choice include PCMV SPORT plasmid (Invitrogen, Carlsbad Calif.) and PCR3.1 plasmid (Invitrogen), both of which contain the cytomegalovirus promoter. 5-10 μg of recombinant vector are transiently transfected into a human cell line, for example, an endothelial or hematopoietic cell line, using either liposome formulations or electroporation. 1-2 μg of an additional plasmid containing sequences encoding a marker protein are co-transfected. Expression of a marker protein provides a means to distinguish transfected cells from nontransfected cells and is a reliable predictor of cDNA expression from the recombinant vector. Marker proteins of choice include, e.g., Green Fluorescent Protein (GFP; Clontech), CD64, or a CD64-GFP fusion protein. Flow cytometry (FCM), an automated, laser optics-based technique, is used to identify transfected cells expressing GFP or CD64-GFP and to evaluate the apoptotic state of the cells and other cellular properties. FCM detects and quantifies the uptake of fluorescent molecules that diagnose events preceding or coincident with cell death. These events include changes in nuclear DNA content as measured by staining of DNA with propidium iodide; changes in cell size and granularity as measured by forward light scatter and 90 degree side light scatter; down-regulation of DNA synthesis as measured by decrease in bromodeoxyuridine uptake; alterations in expression of cell surface and intracellular proteins as measured by reactivity with specific antibodies; and alterations in plasma membrane composition as measured by the binding of fluorescein-conjugated Annexin V protein to the cell surface. Methods in flow cytometry are discussed in Ormerod, M. G. (1994; *Flow Cytometry*, Oxford, New York N.Y.).

The influence of REMAP on gene expression can be assessed using highly purified populations of cells transfected with sequences encoding REMAP and either CD64 or CD64-GFP. CD64 and CD64-GFP are expressed on the surface of transfected cells and bind to conserved regions of human immunoglobulin G (IgG). Transfected cells are efficiently separated from nontransfected cells using magnetic beads coated with either human IgG or antibody against CD64 (DYNAL, Lake Success N.Y.). mRNA can be purified from the cells using methods well known by those of skill in the art. Expression of mRNA encoding REMAP and other genes of interest can be analyzed by northern analysis or microarray techniques.

XV. Production of REMAP Specific Antibodies

REMAP substantially purified using polyacrylamide gel electrophoresis (PAGE; see, e.g., Harrington, M. G. (1990) Methods Enzymol. 182:488-495), or other purification techniques, is used to immunize animals (e.g., rabbits, mice, etc.) and to produce antibodies using standard protocols.

Alternatively, the REMAP amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art (Ausubel et al., supra, ch. 11).

Typically, oligopeptides of about 15 residues in length are synthesized using an ABI 431A peptide synthesizer (Applied Biosystems) using FMOC chemistry and coupled to KLH (Sigma-Aldrich, St. Louis Mo.) by reaction with N-maleimidobenzoyl-N-hydroxysuccinimide ester (MBS) to increase immunogenicity (Ausubel et al., supra). Rabbits are immunized with the oligopeptide-KLH complex in complete Freund's adjuvant. Resulting antisera are tested for antipeptide and anti-REMAP activity by, for example, binding the peptide or REMAP to a substrate, blocking with 1% BSA, reacting with rabbit antisera, washing, and reacting with radio-iodinated goat anti-rabbit IgG.

XVI. Purification of Naturally Occurring REMAP Using Specific Antibodies

Naturally occurring or recombinant REMAP is substantially purified by immunoaffinity chromatography using antibodies specific for REMAP. An immunoaffinity column is constructed by covalently coupling anti-REMAP antibody to an activated chromatographic resin, such as CNBr-activated SEPHAROSE (Amersham Biosciences). After the coupling, the resin is blocked and washed according to the manufacturer's instructions.

Media containing REMAP are passed over the immunoaffinity column, and the column is washed under conditions that allow the preferential absorbance of REMAP (e.g., high ionic strength buffers in the presence of detergent). The column is eluted under conditions that disrupt antibody/REMAP binding (e.g., a buffer of pH 2 to pH 3, or a high concentration of a chaotrope, such as urea or thiocyanate ion), and REMAP is collected.

XVII. Identification of Molecules which Interact with REMAP

REMAP, or biologically active fragments thereof, are labeled with $^{125}I$ Bolton-Hunter reagent (Bolton, A. E. and W. M. Hunter (1973) Biochem. J. 133:529-539). Candidate molecules previously arrayed in the wells of a multi-well plate are incubated with the labeled REMAP, washed, and any wells with labeled REMAP complex are assayed. Data obtained using different concentrations of REMAP are used to calculate values for the number, affinity, and association of REMAP with the candidate molecules.

Alternatively, molecules interacting with REMAP are analyzed using the yeast two-hybrid system as described in Fields, S. and O. Song (1989; Nature 340:245-246), or using commercially available kits based on the two-hybrid system, such as the MATCHMAKER system (Clontech).

REMAP may also be used in the PATHCALLING process (CuraGen Corp., New Haven Conn.) which employs the yeast two-hybrid system in a high-throughput manner to determine all interactions between the proteins encoded by two large libraries of genes (Nandabalan, K. et al. (2000) U.S. Pat. No. 6,057,101).

XVIII. Demonstration of REMAP Activity

An assay for REMAP activity measures the expression of REMAP on the cell surface. cDNA encoding REMAP is transfected into an appropriate mammalian cell line. Cell surface proteins are labeled with biotin as described (de la Fuente, M. A. et al. (1997) Blood 90:2398-2405). Immunoprecipitations are performed using REMAP-specific antibodies, and immunoprecipitated samples are analyzed using sodium dodecyl sulfate polyacrylamide gel electrophoresis (SDS-PAGE) and immunoblotting techniques. The ratio of labeled immunoprecipitant to unlabeled immunoprecipitant is proportional to the amount of REMAP expressed on the cell surface.

In the alternative, an assay for REMAP activity is based on a prototypical assay for ligand/receptor-mediated modulation of cell proliferation. This assay measures the rate of DNA synthesis in Swiss mouse 3T3 cells. A plasmid containing polynucleotides encoding REMAP is added to quiescent 3T3 cultured cells using transfection methods well known in the art. The transiently transfected cells are then incubated in the presence of [$^3$H]thymidine, a radioactive DNA precursor molecule. Varying amounts of REMAP ligand are then added to the cultured cells. Incorporation of [$^3$H]thymidine into acid-precipitable DNA is measured over an appropriate time interval using a radioisotope counter, and the amount incorporated is directly proportional to the amount of newly synthesized DNA. A linear dose-response curve over at least a hundred-fold REMAP ligand concentration range is indicative of receptor activity. One unit of activity per milliliter is defined as the concentration of REMAP producing a 50% response level, where 100% represents maximal incorporation of [$^3$H]thymidine into acid-precipitable DNA (McKay, L. and I. Leigh, eds. (1993) *Growth Factors: A Practical Approach*, Oxford University Press, New York NY, p. 73.)

In a further alternative, the assay for REMAP activity is based upon the ability of GPCR family proteins to modulate G protein-activated second messenger signal transduction pathways (e.g., cAMP; Gaudin, P. et al. (1998) J. Biol. Chem. 273:4990-4996). A plasmid encoding full length REMAP is transfected into a mammalian cell line (e.g., Chinese hamster ovary (CHO) or human embryonic kidney (HEK-293) cell lines) using methods well-known in the art. Transfected cells are grown in 12-well trays in culture medium for 48 hours, then the culture medium is discarded, and the attached cells are gently washed with PBS. The cells are then incubated in culture medium with or without ligand for 30 minutes, then the medium is removed and cells lysed by treatment with 1 M perchloric acid. The cAMP levels in the lysate are measured by radioimmunoassay using methods well-known in the art. Changes in the levels of cAMP in the lysate from cells exposed to ligand compared to those without ligand are proportional to the amount of REMAP present in the transfected cells.

To measure changes in inositol phosphate levels, the cells are grown in 24-well plates containing $1\times10^5$ cells/well and incubated with inositol-free media and [$^3$H]myoinositol, 2 μCi/well, for 48 hr. The culture medium is removed, and the cells washed with buffer containing 10 mM LiCl followed by addition of ligand. The reaction is stopped by addition of perchloric acid. Inositol phosphates are extracted and separated on Dowex AG1-X8 (Bio-Rad) anion exchange resin, and the total labeled inositol phosphates counted by liquid scintillation. Changes in the levels of labeled inositol phosphate from cells exposed to ligand compared to those without ligand are proportional to the amount of REMAP present in the transfected cells.

In a further alternative, the ion conductance capacity of REMAP is demonstrated using an electrophysiological assay. REMAP is expressed by transforming a mammalian cell line such as COS7, HeLa or CHO with a eukaryotic expression vector encoding REMAP. Eukaryotic expression vectors are commercially available, and the techniques to introduce them into cells are well known to those skilled in the art. A small amount of a second plasmid, which expresses any one of a number of marker genes such as β-galactosidase, is co-transformed into the cells in order to allow rapid identification of those cells which have taken up and expressed the foreign DNA. The cells are incubated for 48-72 hours after transformation under conditions appropriate for the cell line to allow expression and accumulation of REMAP and β-galactosidase. Transformed cells expressing β-galactosidase are stained blue when a suitable colorimetric substrate is added to the culture media under conditions that are well known in the art. Stained cells are tested for differences in membrane conductance due to various ions by electrophysiological techniques that are well known in the art. Untransformed cells, and/or cells transformed with either vector sequences alone or β-galactosidase sequences alone, are used as controls and tested in parallel. The contribution of REMAP to cation or anion conductance can be shown by incubating the cells using antibodies specific for either REMAP. The respective antibodies will bind to the extracellular side of REMAP, thereby blocking the pore in the ion channel, and the associated conductance.

In a further alternative, REMAP transport activity is assayed by measuring uptake of labeled substrates into *Xenopus laevis* oocytes. Oocytes at stages V and VI are injected with REMAP mRNA (10 ng per oocyte) and incubated for 3 days at 18° C. in OR2 medium (82.5 mM NaCl, 2.5 mM KCl, 1 mM $CaCd_2$, 1 mM $MgCl_2$, 1 mM $Na_2OPO_4$, 5 mM Hepes, 3.8 mM NaOH, 50 μg/ml gentamycin, pH 7.8) to allow expression of REMAP protein. Oocytes are then transferred to standard uptake medium (100 mM NaCl, 2 mM KCl, 1 mM $CaCl_2$, 1 mM $MgCl_2$, 10 mM Hepes/Tris pH 7.5). Uptake of various substrates (e.g., amino acids, sugars, drugs, and neurotransmitters) is initiated by adding a $^3$H substrate to the oocytes. After incubating for 30 minutes, uptake is terminated by washing the oocytes three times in $Na^+$-free medium, measuring the incorporated $^3$H, and comparing with controls. REMAP activity is proportional to the level of internalized $^3$H substrate.

In a further alternative, REMAP protein kinase (PK) activity is measured by phosphorylation of a protein substrate using gamma-labeled [$^{32}$P]-ATP and quantitation of the incorporated radioactivity using a gamma radioisotope counter. REMAP is incubated with the protein substrate, [$^{32}$P]-ATP, and an appropriate kinase buffer. The $^{32}$P incorporated into the product is separated from free [$^{32}$P]-ATP by electrophoresis and the incorporated $^{32}$P is counted. The amount of $^{32}$P recovered is proportional to the PK activity of REMAP in the assay. A determination of the specific amino acid residue phosphorylated is made by phosphoamino acid analysis of the hydrolyzed protein.

XIX. Identification of REMAP Ligands

REMAP is expressed in a eukaryotic cell line such as CHO (Chinese Hamster Ovary) or BEK (Human Embryonic Kidney) 293 which have a good history of GPCR expression and which contain a wide range of G-proteins allowing for functional coupling of the expressed REMAP to downstream effectors. The transformed cells are assayed for activation of the expressed receptors in the presence of candidate ligands. Activity is measured by changes in intracellular second messengers, such as cyclic AMP or $Ca^{2+}$. These may be measured directly using standard methods well known in the art, or by the use of reporter gene assays in which a luminescent protein (e.g. firefly luciferase or green fluorescent protein) is under the transcriptional control of a promoter responsive to the stimulation of protein kinase C by the activated receptor (Milligan, G. et al. (1996) Trends Pharmacol. Sci. 17:235-237). Assay technologies are available for both of these second messenger systems to allow high throughput readout in multi-well plate format, such as the adenylyl cyclase activation FlashPlate Assay (NEN Life Sciences Products), or fluorescent $Ca^{2+}$ indicators such as Fluo-4 AM (Molecular Probes) in combination with the FLIPR fluorimetric plate reading system (Molecular Devices). In cases where the physiologically relevant second messenger pathway is not known, REMAP may be coexpressed with the G-proteins $G_{\alpha 15/16}$ which have been demonstrated to couple to a wide range of G-proteins (Offermanns, S. and M. I. Simon (1995) J. Biol. Chem. 270:15175-15180), in order to funnel the signal transduction of the REMAP through a pathway involving phospholipase C and $Ca^{2+}$ mobilization. Alternatively, REMAP may be expressed in engineered yeast systems which lack endogenous GPCRs, thus providing the advantage of a null background for REMAP activation screening. These yeast systems substitute a human GPCR and $G_{\alpha}$ protein for the corresponding components of the endogenous yeast pheromone receptor pathway. Downstream signaling pathways are also modified so that the normal yeast response to the signal is converted to positive growth on selective media or to reporter gene expression (Broach, J. R. and J. Thorner (1996) Nature 384 (supp.): 14-16). The receptors are screened against putative ligands including known GPCR ligands and other naturally occurring bioactive molecules. Biological extracts from tissues, biological fluids and cell supernatants are also screened.

XX. Other Embodiments

Various embodiments of the invention provide purified polypeptides, receptors and membrane-associated proteins, referred to collectively as 'REMAP' and individually as 'REMAP-1,' 'REMAP-2,' 'REMAP-3,' 'REMAP4,' 'REMAP-5,' 'REMAP-6,' 'REMAP-7,' 'REMAP-8,' 'REMAP-9,' 'REMAP-10,' 'REMAP-11,' 'REMAP-12,' 'REMAP-13,' 'REMAP-14,' 'REMAP-15,' 'REMAP-16,' 'REMAP-17,' 'REMAP-18,' 'REMAP-19,' 'REMAP-20,' 'REMAP-21,' 'REMAP-22,' 'REMAP-23,' 'REMAP-24,' 'REMAP-25,' 'REMAP-26,' 'REMAP-27,' 'REMAP-28,' 'REMAP-29,' 'REMAP-30,' 'REMAP-31,' 'REMAP-32,' 'REMAP-33,' 'REMAP-34,' 'REMAP-35,' 'REMAP-36,' 'REMAP-37,' and 'REMAP-38,' and methods for using these proteins and their encoding polynucleotides for the detection, diagnosis, and treatment of diseases and medical conditions. Embodiments also provide methods for utilizing the purified receptors and membrane-associated proteins and/or their encoding polynucleotides for facilitating the drug discovery process, including determination of efficacy, dosage, toxicity, and pharmacology. Related embodiments provide methods for utilizing the purified receptors and membrane-associated proteins and/or their encoding polynucleotides for investigating the pathogenesis of diseases and medical conditions.

An embodiment provides an isolated polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. Another embodiment provides an isolated polypeptide comprising an amino acid sequence of SEQ ID NO:1-38.

Still another embodiment provides an isolated polynucleotide encoding a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. In another embodiment, the polynucleotide encode& a polypeptide selected from the group consisting of SEQ ID NO:1-38. In an alternative embodiment, the polynucleotide is selected from the group consisting of SEQ ID NO:39-76.

Still another embodiment provides a recombinant polynucleotide comprising a promoter sequence operably linked to a polynucleotide encoding a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. Another embodiment provides a cell transformed with the recombinant polynucleotide. Yet another embodiment provides a transgenic organism comprising the recombinant polynucleotide.

Another embodiment provides a method for producing a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. The method comprises a) culturing a cell under conditions suitable for expression of the polypeptide, wherein said cell is transformed with a recombinant polynucleotide comprising a promoter sequence operably linked to a polynucleotide encoding the polypeptide, and b) recovering the polypeptide so expressed.

Yet another embodiment provides an isolated antibody which specifically binds to a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38.

Still yet another embodiment provides an isolated polynucleotide selected from the group consisting of a) a polynucleotide comprising a polynucleotide sequence selected from the group consisting of SEQ ID NO:39-76, b) a polynucleotide comprising a naturally occurring polynucleotide sequence at least 90% identical or at least about 90% identical to a polynucleotide sequence selected from the group consisting of SEQ ID NO:39-76, c) a polynucleotide complementary to the polynucleotide of a), d) a polynucleotide complementary to the polynucleotide of b), and e) an RNA equivalent of a)-d). In other embodiments, the polynucleotide can comprise at least about 20, 30, 40, 60, 80, or 100 contiguous nucleotides.

Yet another embodiment provides a method for detecting a target polynucleotide in a sample, said target polynucleotide being selected from the group consisting of a) a polynucleotide comprising a polynucleotide sequence selected from the group consisting of SEQ ID NO:39-76, b) a polynucleotide comprising a naturally occurring polynucleotide sequence at least 90% identical or at least about 90% identical to a polynucleotide sequence selected from the group consisting of SEQ ID NO:39-76, c) a polynucleotide complementary to the polynucleotide of a), d) a polynucleotide complementary to the polynucleotide of b), and e) an RNA equivalent of a)-d). The method comprises a) hybridizing the sample with a probe comprising at least 20 contiguous nucleotides comprising a sequence complementary to said target polynucleotide in the sample, and which probe specifically hybridizes to said target polynucleotide, under conditions whereby a hybridization complex is formed between said probe and said target polynucleotide or fragments thereof, and b) detecting the presence or absence of said hybridization complex. In a related embodiment, the method can include detecting the amount of the hybridization complex. In still other embodiments, the probe can comprise at least about 20, 30, 40, 60, 80, or 100 contiguous nucleotides.

Still another embodiment provides a method for detecting a target polynucleotide in a sample, said target polynucleotide being selected from the group consisting of a) a polynucleotide comprising a polynucleotide sequence selected from the group consisting of SEQ ID NO:39-76, b) a polynucleotide comprising a naturally occurring polynucleotide sequence at least 90% identical or at least about 90% identical to a polynucleotide sequence selected from the group consisting of SEQ ID NO:39-76, c) a polynucleotide complementary to the polynucleotide of a), d) a polynucleotide complementary to the polynucleotide of b), and e) an RNA equivalent of a)-d). The method comprises a) amplifying said target polynucleotide or fragment thereof using polymerase chain reaction amplification, and b) detecting the presence or absence of said amplified target polynucleotide or fragment thereof. In a related embodiment, the method can include detecting the amount of the amplified target polynucleotide or fragment thereof.

Another embodiment provides a composition comprising an effective amount of a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38, and a pharmaceutically acceptable excipient. In one embodiment, the composition can comprise an amino acid sequence selected from the group consisting of SEQ ID NO:1-38. Other embodiments provide a method of treating a disease or condition associated with decreased or abnormal expression of functional REMAP, comprising administering to a patient in need of such treatment the composition.

Yet another embodiment provides a method for screening a compound for effectiveness as an agonist of a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. The method comprises a) exposing a sample comprising the polypeptide to a compound, and b) detecting agonist activity in the sample. Another embodiment provides a composition comprising an agonist compound identified by the method and a pharmaceutically acceptable excipient. Yet another embodiment provides a method of treating a disease or condition associated with decreased expression of functional REMAP, comprising administering to a patient in need of such treatment the composition.

Still another embodiment provides a method for screening a compound for effectiveness as an antagonist of a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. The method comprises a) exposing a sample comprising the polypeptide to a compound, and b) detecting antagonist activity in the sample. Another embodiment provides a composition comprising an antagonist compound identified by the method and a pharmaceutically acceptable excipient. Yet another embodiment provides a method of treating a disease or condition associated with overexpression of functional REMAP, comprising administering to a patient in need of such treatment the composition.

Another embodiment provides a method of screening for a compound that specifically binds to a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. The method comprises a) combining the polypeptide with at least one test compound under suitable conditions, and b) detecting binding of the polypeptide to the test compound, thereby identifying a compound that specifically binds to the polypeptide.

Yet another embodiment provides a method of screening for a compound that modulates the activity of a polypeptide selected from the group consisting of a) a polypeptide comprising an amino acid sequence selected from the group consisting of SEQ ID NO:1-38, b) a polypeptide comprising a naturally occurring amino acid sequence at least 90% identical or at least about 90% identical to an amino acid sequence selected from the group consisting of SEQ ID NO:1-38, c) a biologically active fragment of a polypeptide having an amino acid sequence selected from the group consisting of SEQ ID NO:1-38, and d) an immunogenic fragment of a polypeptide having an amino acid sequence selected from the group consisting of SEQ ID NO:1-38. The method comprises a) combining the polypeptide with at least one test compound under conditions permissive for the activity of the polypeptide, b) assessing the activity of the polypeptide in the presence of the test compound, and c) comparing the activity of the polypeptide in the presence of the test compound with the activity of the polypeptide in the absence of the test compound, wherein a change in the activity of the polypeptide in the presence of the test compound is indicative of a compound that modulates the activity of the polypeptide.

Still another embodiment provides a method for screening a compound for effectiveness in altering expression of a target polynucleotide, wherein said target polynucleotide comprises a polynucleotide sequence selected from the group consisting of SEQ ID NO:39-76, the method comprising a) exposing a sample comprising the target polynucleotide to a compound, b) detecting altered expression of the target polynucleotide, and c) comparing the expression of the target polynucleotide in the presence of varying amounts of the compound and in the absence of the compound.

Another embodiment provides a method for assessing toxicity of a test compound, said method comprising a) treating a biological sample containing nucleic acids with the test compound; b) hybridizing the nucleic acids of the treated biological sample with a probe comprising at least 20 contiguous nucleotides of a polynucleotide selected from the group consisting of i) a polynucleotide comprising a polynucleotide sequence selected from the group consisting of SEQ ID NO:39-76, ii) a polynucleotide comprising a naturally occurring polynucleotide sequence at least 90% identical or at least about 90% identical to a polynucleotide sequence selected from the group consisting of SEQ ID NQ:39-76, iii) a polynucleotide having a sequence complementary to i), iv) a polynucleotide complementary to the polynucleotide of ii), and v) an RNA equivalent of i)-iv). Hybridization occurs under conditions whereby a specific hybridization complex is formed between said probe and a target polynucleotide in the biological sample, said target polynucleotide selected from the group consisting of i) a polynucleotide comprising a polynucleotide sequence selected from the group consisting of SEQ ID NO:39-76, ii) a polynucleotide comprising a naturally occurring polynucleotide sequence at least 90% identical or at least about 90% identical to a polynucleotide sequence selected from the group consisting of SEQ ID NO:39-76, iii) a polynucleotide complementary to the polynucleotide of i), iv) a polynucleotide complementary to the polynucleotide of ii), and v) an RNA equivalent of i)-iv). Alternatively, the target polynucleotide can comprise a fragment of a polynucleotide selected from the group consisting of i)-v) above; c) quantifying the amount of hybridization complex; and d) comparing the amount of hybridization complex in the treated biological sample with the amount of hybridization complex in an untreated biological sample, wherein a difference in the amount of hybridization complex in the treated biological sample is indicative of toxicity of the test compound.

TABLE 1

| Incyte Project ID | Polypeptide SEQ ID NO: | Incyte Polypeptide ID | Polynucleotide SEQ ID NO: | Incyte Polynucleotide ID | Incyte Full Length Clones |
|---|---|---|---|---|---|
| 3048626 | 1 | 3048626CD1 | 39 | 3048626CB1 | |
| 2684425 | 2 | 2684425CD1 | 40 | 2684425CB1 | |
| 7505960 | 3 | 7505960CD1 | 41 | 7505960CB1 | |
| 7507021 | 4 | 7507021CD1 | 42 | 7507021CB1 | 90122224CA2 |
| 7509099 | 5 | 7509099CD1 | 43 | 7509099CB1 | 90137914CA2 |
| 7509361 | 6 | 7509361CD1 | 44 | 7509361CB1 | 90134650CA2 |
| 7506815 | 7 | 7506815CD1 | 45 | 7506815CB1 | 90115637CA2 |
| 7506814 | 8 | 7506814CD1 | 46 | 7506814CB1 | 90115621CA2 |
| 7506852 | 9 | 7506852CD1 | 47 | 7506852CB1 | 90123356CA2, 90123372CA2, 90123380CA2, 90123571CA2 |
| 7503782 | 10 | 7503782CD1 | 48 | 7503782CB1 | |
| 7504647 | 11 | 7504647CD1 | 49 | 7504647CB1 | 6352669CA2, 90036485CA2, 90036561CA2, 95121338CA2, 95121529CA2, 95121605CA2, 95121637CA2, 95121653CA2, 95121693CA2, 95121745CA2, 95121761CA2, 95121812CA2, 95121868CA2, 95121884CA2, 95121905CA2 |
| 7500424 | 12 | 7500424CD1 | 50 | 7500424CB1 | 90030465CA2, 90030473CA2, 90030573CA2, 90030581CA2 |
| 7500449 | 13 | 7500449CD1 | 51 | 7500449CB1 | |
| 7503281 | 14 | 7503281CD1 | 52 | 7503281CB1 | 90041241CA2, 90041301CA2, 90041317CA2, 90041341CA2 |
| 7503292 | 15 | 7503292CD1 | 53 | 7503292CB1 | |

TABLE 1-continued

| Incyte Project ID | Polypeptide SEQ ID NO: | Incyte Polypeptide ID | Polynucleotide SEQ ID NO: | Incyte Polynucleotide ID | Incyte Full Length Clones |
|---|---|---|---|---|---|
| 7503311 | 16 | 7503311CD1 | 54 | 7503311CB1 | |
| 7510384 | 17 | 7510384CD1 | 55 | 7510384CB1 | |
| 7509976 | 18 | 7509976CD1 | 56 | 7509976CB1 | |
| 7510454 | 19 | 7510454CD1 | 57 | 7510454CB1 | 55062756CA2, 90005113CA2, 90005121CA2, 90005137CA2, 90005145CA2, 90005205CA2, 90005213CA2, 90005221CA2, 90005237CA2, 90082826CA2, 90208706CA2, 90208714CA2, 90208785CA2, 90208793CA2 |
| 8017335 | 20 | 8017335CD1 | 58 | 8017335CB1 | |
| 7510197 | 21 | 7510197CD1 | 59 | 7510197CB1 | 3833001CA2 |
| 7510055 | 22 | 7510055CD1 | 60 | 7510055CB1 | 95110475CA2 |
| 7501754 | 23 | 7501754CD1 | 61 | 7501754CB1 | 3576444CA2 |
| 7510517 | 24 | 7510517CD1 | 62 | 7510517CB1 | |
| 7511014 | 25 | 7511014CD1 | 63 | 7511014CB1 | 90115446CA2 |
| 7506687 | 26 | 7506687CD1 | 64 | 7506687CB1 | |
| 7510621 | 27 | 7510621CD1 | 65 | 7510621CB1 | |
| 7505533 | 28 | 7505533CD1 | 66 | 7505533CB1 | 95136216CA2, 95136264CA2 |
| 7511220 | 29 | 7511220CD1 | 67 | 7511220CB1 | |
| 7510967 | 30 | 7510967CD1 | 68 | 7510967CB1 | |
| 7511298 | 31 | 7511298CD1 | 69 | 7511298CB1 | 90171160CA2 |
| 7510937 | 32 | 7510937CD1 | 70 | 7510937CB1 | 90051283CA2 |
| 7511852 | 33 | 7511852CD1 | 71 | 7511852CB1 | 95001926CA2 |
| 7511077 | 34 | 7511077CD1 | 72 | 7511077CB1 | 1929803CA2 |
| 7511576 | 35 | 7511576CD1 | 73 | 7511576CB1 | |
| 7511492 | 36 | 7511492CD1 | 74 | 7511492CB1 | |
| 7511141 | 37 | 7511141CD1 | 75 | 7511141CB1 | 2776443CA2, 95021920CA2 |
| 7511300 | 38 | 7511300CD1 | 76 | 7511300CB1 | |

TABLE 2

| Polypeptide SEQ ID NO: | Incyte Polypeptide ID | GenBank ID NO: or PROTEOME ID NO: | Probability Score | Annotation |
|---|---|---|---|---|
| 1 | 3048626CD1 | g6523391 | 8.1E−210 | [*Mus musculus*] phtf protein<br>Manuel, A. et al. (2000) Molecular characterization of a novel gene family (PHTF) conserved from *drosophila* to mammals. Genomics 64: 216-220 |
| | | 587245\|Phtf | 6.8E−211 | [*Mus musculus*][Transcription factor; DNA-binding protein] Putative homeodomain transcription factor; expressed in testis<br>Manuel, A. et al. (2000) Molecular characterization of a novel gene family (PHTF) conserved from *drosophila* to mammals. Genomics 64: 216-220 |
| | | 432628\|PHTF1 | 2.1E−209 | [*Homo sapiens*][Transcription factor; DNA-binding protein] Putative homeodomain transcription factor; may play role in development<br>Raich, N. et al. (1999) PHTF, A novel atypical homeobox gene on chromosome 1p13, is evolutionarily conserved. Genomics 59: 108-109 |
| 2 | 2684425CD1 | g8439531 | 0.0 | [*Homo sapiens*] transmembrane molecule with thrombospondin module |
| | | 599850\|LOC55901 | 0.0 | [*Homo sapiens*] Protein containing a type 1 thrombospondin domain |
| 3 | 7505960CD1 | g4529890 | 0.0 | [*Homo sapiens*] NG22 |
| | | 692052\|NG22 | 0.0 | [*Homo sapiens*] Protein of unknown function, has strong similarity to uncharacterized mouse 2210409B01Rik |
| | | 664607\|2210409B01Rik | 2.3E−294 | [*Mus musculus*] RIKEN cDNA 2210409B01 gene |
| 4 | 7507021CD1 | g2338292 | 1.4E−78 | [*Homo sapiens*] proline-rich Gla protein 2<br>Kulman, J. D. et al. (1997) Primary structure and tissue distribution of two novel proline-rich gamma-carboxyglutamic acid proteins. Proc. Natl. Acad. Sci. U.S.A. 94: 9058-9062 |
| 5 | 7509099CD1 | g307046 | 2.4E−274 | [*Homo sapiens*] interleukin 1 receptor precursor |
| | | 336000\|IL1R1 | 2.0E−275 | [*Homo sapiens*][Receptor (signalling)][Plasma membrane] Type I interleukin-1 receptor, a member of the IL1R like protein family regulated by IL1R associated kinase IRAK1, involve in immune and inflammatory responses, involved in leukemia, atherosclerosis, sepsis and growth of solid tumors<br>Chen, G. et al. (2000) Selection of insulinoma cell lines with resistance to interleukin-1beta- and gamma-interferon-induced cytotoxicity. Diabetes 49: 562-570 |
| | | 583367\|Il1r1 | 2.4E−193 | [*Mus musculus*][Receptor (signalling)][Plasma membrane] Type I interleukin-1 receptor, a member of the IL1R like protein family regulated by IL1R associated kinase IRAK (Il1rak), involved in immune and inflammatory resposes and signal transduction<br>Parnet, P. et al. (1994) Expression of type I and type II interleukin-1 receptors in mouse brain. Brain Res. Mol. Brain Res. 27: 63-70 |

TABLE 2-continued

| Polypeptide SEQ ID NO: | Incyte Polypeptide ID | GenBank ID NO: or PROTEOME ID NO: | Probability Score | Annotation |
|---|---|---|---|---|
| 6 | 7509361CD1 | g339750 | 4.5E−119 | [*Homo sapiens*] tumor necrosis factor receptor 1<br>Fuchs, P. et al. (1992) Structure of the human TNF receptor 1 (p60) gene (TNFR1) and localization to chromosome 12p13 [corrected] [published erratum appears in (1992) Genomics 13: 1384] Genomics 13: 219-224 |
| | | 338586\|TNFRSF1A | 3.8E−120 | [*Homo sapiens*][Receptor (signalling)][Plasma membrane] FPF Type I tumor necrosis factor receptor, mediates proinflammatory cellular responses, juxtamembrane domain interacts with phosphatidylinositol-4-phosphate 5-kinase<br>Baranzini, S. E. et al. (2000) Transcriptional analysis of multiple sclerosis brain lesions reveals a complex pattern of cytokine expression. J. Immunol. 165: 6576-6582 |
| | | 723062\|1ext_A | 3.0E−95 | [Protein Data Bank] Tumor Necrosis Factor Receptor |
| | | 590719\|Tnfrsf1a | 1.1E−85 | [*Rattus norvegicus*][Receptor (signalling)] Type I tumor necrosis factor receptor, a glycoprotein that mediates proinflammatory cellular responses, contains an extracellular domain that is proteolytically cleaved to yield a tumor necrosis factor binding protein<br>Laabich, A. et al. (2001) Characterization of apoptosis-genes associated with NMDA mediated cell death in the adult rat retina. Brain Res. Mol. Brain Res. 91: 34-42 |
| 7 | 7506815CD1 | g12653895 | 1.1E−194 | [*Homo sapiens*] cholecystokinin B receptor |
| | | 334486\|CCKBR | 9.0E−196 | [*Homo sapiens*][Regulatory subunit; Receptor (signalling)] [Basolateral plasma membrane; Cytoplasmic; Plasma membrane] Cholecystokinin B (gastrin) receptor, G protein-coupled receptor stimulating phospholipase C and intracellular calcium flux, associated with anxiety and likely digestion and dopamine signaling, constitutively active form is expressed in colorectal cancers<br>Smith, A. M. and Watson, S. A. (2000) Gastrin and gastrin receptor activation: an early event in the adenoma-carcinoma sequence. Gut 4: 820-824 |
| | | 589913\|Cckbr | 1.3E−170 | [*Rattus norvegicus*][Receptor (signalling)] [Nuclear; Cytoplasmic; Plasma membrane] Cholecystokinin B (gastrin) receptor, G protein-coupled receptor stimulating phospholipase C and intracellular calcium flux, associated with digestion and opioidergic and dopaminergic signaling; a human CCKBR variant is associated with colorectal cancer<br>Coudore-Civiale, M. A. et al. (2000) Spinal effect of the cholecystokinin-B receptor antagonist CI-988 on hyperalgesia, allodynia and morphine-induced analgesia in diabetic and mononeuropathic rats. Pain 88: 15-22 |
| 8 | 7506814CD1 | g12653895 | 3.20E−206 | [*Homo sapiens*] cholecystokinin B receptor |
| | 7506814CD1 | 334486\|CCKBR | 2.70E−207 | [*Homo sapiens*][Regulatory subunit; Receptor (signalling)][Basolateral plasma membrane; Cytoplasmic; Plasma membrane] Cholecystokinin B (gastrin) receptor, G protein-coupled receptor stimulating phospholipase C and intracellular calcium flux, associated with anxiety and likely digestion and dopamine signaling, constitutively active form is expressed in colorectal cancers (Desbois, C. et al. (1999) Eur J Biochem 266, 1003-10) |
| | 7506814CD1 | 589913\|Cckbr | 3.50E−194 | [*Rattus norvegicus*][Receptor (signalling)][Nuclear; Cytoplasmic; Plasma membrane] Cholecystokinin B (gastrin) receptor, G protein-coupled receptor stimulating phospholipase C and intracellular calcium flux, associated with digestion and opioidergic and dopaminergic signaling; a human CCKBR variant is associated with colorectal cancer (Wank, S. A. et al. (1992) Proc Natl Acad Sci USA 89, 8691-5) |
| 9 | 7506852CD1 | g400450 | 1.80E−53 | [*Homo sapiens*] A1 adenosine receptor |
| | 7506852CD1 | 334066\|ADORA1 | 1.50E−54 | [*Homo sapiens*][Receptor (signalling)][Cytoplasmic; Plasma membrane] Adenosine A1 receptor, a glycoprotein and G protein-coupled receptor that selectively binds adenosine; stimulates cell death of thymocytes and phagocytosis; density is reduced in hippocampus from Alzheimer's disease patients; may play a role in obesity (Libert, F. et al. (1992) Biochem Biophys Res Commun 187, 919-26) |
| | 7506852CD1 | 590847\|Adoral | 6.40E−54 | [*Rattus norvegicus*][Receptor (signalling)][Plasma membrane] Adenosine A1 receptor, a G protein-coupled receptor that selectively binds adenosine; modulates adenosine effects in neural and endocrine systems; may play a role in inherited obesity (Mahan, L. C. et al. (1991) Mol Pharmacol 40, 1-7) |
| 10 | 7503782CD1 | g7209574 | 4.20E−19 | [*Homo sapiens*] LAK-4p |
| 11 | 7504647CD1 | g533184 | 3.60E−23 | [*Homo sapiens*] 50 kD dystrophin-associated glycoprotein (McNally, E. et al. (1994) Proc. Natl. Acad. Sci. U.S.A. 11; 91(21): 9690-4) |
| | 7504647CD1 | 337978\|SGCA | 3.00E−24 | [*Homo sapiens*][Anchor Protein][Extracellular matrix (cuticle and basement membrane); Basement membrane (extracellular matrix); Plasma membrane] Alpha-sarcoglycan (adhalin), a dystrophin-associated glycoprotein required for normal striated muscle development, protects against contraction-induced sarcolemmal damage; mutations in the corresponding gene cause limb girdle muscular dystrophy type 2D (Barresi, R. et al. (2000) J Biol Chem 275, 38554-60) |
| | 7504647CD1 | 581329\|Sgca | 5.80E−15 | [*Mus musculus*][Structural protein][Extracellular matrix (cuticle and basement membrane); Basement membrane (extracellular matrix); Cytoplasmic; Plasma membrane] Alpha-sarcoglycan (adhalin), a dystrophin-associated glycoprotein required for normal striated muscle development, protects against contraction-induced sarcolemmal damage; mutations in the human SGCA gene cause limb girdle muscular dystrophy type 2D (Coral-Vazquez, R. et al. (1999) Cell 98, 465-74). |
| 12 | 7500424CD1 | g14250620 | 4.50E−66 | [*Homo sapiens*] G protein-coupled receptor 56 |
| | 7500424CD1 | 342484\|GPR56 | 3.70E−67 | [*Homo sapiens*][Receptor (signalling)][Plasma membrane] G protein-coupled receptor 56, a putative G protein-coupled receptor that may function in cell adhesion, cell-cell signaling, and is differentially expressed during metastatic progression of melanomas (Zendman, A. J. et al. (1999) FEBS Lett 446, 292-8) |

TABLE 2-continued

| Poly-pep-tide SEQ ID NO: | Incyte Polypeptide ID | GenBank ID NO: or PROTEOME ID NO: | Probability Score | Annotation |
|---|---|---|---|---|
| | 7500424CD1 | 732759\| Gpr56 | 6.10E−38 | [*Mus musculus*][Receptor (signalling)][Plasma membrane] G protein-coupled receptor 56 |
| 13 | 7500449CD1 | g456353 | 1.50E-131 | [*Homo sapiens*] intestinal VIP receptor related protein (Couvineau, A. et al. (1994) Biochem. Biophys. Res. Commun. 200, 769-776) |
| | 7500449CD1 | 749162\| VIPR1 | 4.80E−97 | [*Homo sapiens*][Receptor (signalling)][Plasma membrane] Vasoactive intestinal activating polypeptide receptor 1, a stimulatory G protein coupled receptor; mediates gastrointestinal, nervous system, pulmonary, vascular and immune functions, inhibits inflammation (Sreedharan, S. P. et al. (1995) Proc Natl Acad Sci USA 92, 2939-43) |
| | 7500449CD1 | 590753\|Vipr1 | 3.50E−78 | [*Rattus norvegicus*][Receptor (signalling)][Plasma membrane] Vasoactive intestinal activating polypeptide receptor 1, a stimulatory G protein coupled receptor; inhibits inflammatory responses and may mediate central and peripheral nervous system functions (Ishihara, T. et al (1992). Neuron 8, 811-9) |
| 14 | 7503281CD1 | g178198 | 1.40E−112 | [*Homo sapiens*] alpha-2-adrenergic receptor (alpha-2 C2) old gene name 'ADRA2RL1' (Lomasney, J. W. et al. (1990) Proc. Natl. Acad. Sci. U.S.A. 87, 5094-5098) |
| | 7503281CD1 | 343936\| ADRA2B | 1.10E−113 | [*Homo sapiens*][Receptor (signalling)][Plasma membrane] Adrenergic alpha-2B receptor, a G protein-coupled receptor that binds epinephrine and norepinephrine, signals through regulation of adenylyl cyclase and MAPK pathways to mediate cell-cell signaling, may have a role in fat metabolism (Smith, M. S. et al. (1995) Brain Res Mol Brain Res 34, 109-17) |
| | 7503281CD1 | 429618\| Adra2b | 3.90E−102 | [*Mus musculus*][Receptor (signalling)][Endosome/Endosomal vesicles; Cytoplasmic; Plasma membrane] Adrenergic receptor alpha 2b, a G protein-coupled receptor that binds epinephrine and norepinephrine, signals through regulation of adenylyl cyclase activity, involved in blood pressure regulation, sensory perception, synaptic transmission, and analgesia (Link, R. E. et al. (1996) Science 273, 803-5) |
| 15 | 7503292CD1 | g3901028 | 1.70E−144 | [*Homo sapiens*] neurotensin receptor 2 (Vita, N. et al. (1998) Eur. J. Pharmacol. 360, 265-272) |
| | 7503292CD1 | 428880\| NTSR2 | 1.40E−145 | [*Homo sapiens*][Receptor (signalling)][Plasma membrane] Levocabastine-sensitive neurotensin receptor, a low affinity putative G protein-coupled receptor that binds, but is not activated by, neurotensin; activation by SR48692 and SR142948A stimulates IP formation, Ca2+ mobilization, and arachidonic acid release (Mazella, J. et al. (1996) J Neurosci 16, 5613-20) |
| | 7503292CD1 | 659258\|Ntsr2 | 7.10E−119 | [*Rattus norvegicus*][Receptor (signalling)][Plasma membrane] Levocabastine-sensitive neurotensin receptor, a G protein-coupled receptor that binds neurotensin, and the H1 antihistaminic drug levocabastine, activation by SR48692 induces Ca2+ mobilization, may help modulate neuronal osmosensitivity (Botto, J. M. et al. (1998) Biochem Biophys Res Commun 243, 585-90) |
| 16 | 7503311CD1 | g1785516 | 3.50E−146 | [*Homo sapiens*] gastric inhibitory polypeptide receptor (Yamada, Y. et al. (1995) Genomics 29, 773-776) |
| | 7503311CD1 | 335524\|GIPR | 2.80E−147 | [*Homo sapiens*][Receptor (signalling)][Plasma membrane] Gastric inhibitory polypeptide receptor, a G protein-coupled receptor that increases intracellular cAMP levels and MAPK kinase activity, may be associated with Gushing's syndrome (Lacroix, A. et al. (1998) Endocr Res 24, 835-43) |
| | 7503311CD1 | 590141\|Gipr | 5.70E−117 | [*Rattus norvegicus*][Receptor (signalling)][Plasma membrane] Gastric inhibitory polypeptide receptor, a G protein-coupled receptor that increases intracellular cAMP and calcium levels, mediates effects of glucose-dependent insulinotropic polypeptide (GIP) on insulin secretion, may be associated with type 2 diabetes (Usdin, T. B. et al. (1993) Endocrinology 133, 2861-70) |
| 17 | 7510384CD1 | g3242762 | 1.10E−110 | [*Homo sapiens*] growth hormone-releasing hormone receptor |
| | 7510384CD1 | 335522\| GHRHR | 3.00E−111 | [*Homo sapiens*][Receptor (signalling)][Plasma membrane] Growth hormone releasing hormone receptor, a G protein-coupled receptor that regulates pituitary growth hormone synthesis and secretion, may act through increasing intracellular cAMP levels; deficiency is a cause of dwarfism (Wajnrajch, M. P. et al. (1996) Nat Genet 12, 88-90) |
| | 7510384CD1 | 590139\|Ghrhr | 3.10E−86 | [*Rattus norvegicus*][Receptor (signalling)][Plasma membrane] Growth hormone releasing hormone receptor, a member of the G protein-coupled receptor family expressed primarily in pituitary, has probable roles in regulating growth; has strong similarity to human GHRHR, deficiency of which is associated with dwarfism (Zeitler, P. et al. (1998) J Mol Endocrinol 21, 363-71) |
| 18 | 7509976CD1 | g1200235 | 0 | [*Homo sapiens*] SEX protein |
| | 7509976CD1 | 599756\| HSSEXGENE | 0 | [*Homo sapiens*][Receptor (signalling)][Plasma membrane] Protein with strong similarity to murine Plxn3, which is a member of the plexin family of semaphorin receptors involved in cell guidance (Kameyama, T. et al. (1996) Biochem Biophys Res Commun 226, 396-402) |
| | 7509976CD1 | 582527\|Plxn3 | 0 | [*Mus musculus*][Receptor (signalling)][Plasma membrane] Plexin 3, a member of the plexin family of semaphorin receptors, may play a role in the regulation of neuronal development (Kameyama, T. et al. (supra)) |
| 19 | 7510454CD1 | g17481324 | 1.10E−21 | [*Mus musculus*] vomeronasal receptor 1 E9 |
| | 7510454CD1 | 613285\| V1RL1 | 2.50E−11 | [*Homo sapiens*][Receptor (signalling)] V1R-like 1, a predicted member of the G-protein coupled receptor family and a putative olfactory mucosal pheromone receptor (Rodriguez, I. et al. (2000) Nat Genet 26, 18-9) |
| 20 | 8017335CD1 | g15082375 | 6.7E−81 | [*Homo sapiens*] Similar to transmembrane 7 superfamily member 1 (upregulated in kidney) |
| | 8017335CD1 | 338556\| TM7SF1 | 5.5E−82 | [*Homo sapiens*][Plasma membrane] Transmembrane 7 superfamily member 1, may be a member of the G protein-coupled receptor family, contains seven alpha helical transmembrane domains; expression is upregulated during kidney development Spangenberg, C. et al. Cloning and characterization of a novel gene (TM7SF1) encoding a putative seven-pass |

TABLE 2-continued

| Polypeptide SEQ ID NO: | Incyte Polypeptide ID | GenBank ID NO: or PROTEOME ID NO: | Probability Score | Annotation |
|---|---|---|---|---|
| | | | | transmembrane protein that is upregulated during kidney development.<br>Genomics 48, 178-85 (1998). |
| | 8017335CD1 | 746563\|<br>Tm7sf1 | 1E−80 | [*Mus musculus*] Transmembrane 7 superfamily member 1, may be a member of the G protein-coupled receptor family, contains seven alpha helical transmembrane domains; expression is upregulated during kidney development |
| 22 | 7510055CD1 | g29851 | 2.7E−107 | [*Homo sapiens*] CDw40<br>Stamenkovic, I. et al.<br>A B-lymphocyte activation molecule related to the nerve growth factor receptor and induced by cytokines in carcinomas<br>EMBO J. 8, 1403-1410 (1989) |
| | 7510055CD1 | 338592\|<br>TNFRSF5 | 2.2E−108 | [*Homo sapiens*][Receptor (signalling)][Plasma membrane] Member of the tumor necrosis factor receptor superfamily, binds the ligand CD40L and is expressed specifically in B lymphocytes, has a role in B lymphocyte maturation<br>Stamenkovic, I. et al.<br>A B-lymphocyte activation molecule related to the nerve growth factor receptor and induced by cytokines in carcinomas.<br>Embo Journal 8, 1403-10 (1989).<br>Mach, F. et al.<br>Reduction of atherosclerosis in mice by inhibition of CD40 signalling.<br>Nature 394, 200-3 (1998). |
| | 7510055CD1 | 586037\|<br>Tnfrsf5 | 4.1E−68 | [*Mus musculus*][Receptor (signalling)][Plasma membrane] Member of the tumor necrosis factor receptor superfamily, binds the ligand CD40L and is expressed specifically in B lymphocytes, has a role in B lymphocyte maturation<br>Torres, R. M. et al.<br>Differential increase of an alternatively polyadenylated mRNA species of murine CD40 upon B lymphocyte activation.<br>J Immunol 148, 620-6 (1992). |
| 23 | 7501754CD1 | g9944291 | 2.5E−223 | [*Homo sapiens*] TTYH1<br>Campbell, H. D. et al.<br>Human and mouse homologues of the *drosophila melanogaster* tweety (tty) gene: A novel gene family encoding predicted transmembrane proteins<br>Genomics 68, 89-92 (2000) |
| | 7501754CD1 | 613379\|<br>TTYH1 | 2E−224 | [*Homo sapiens*][Active transporter, secondary; Transporter] Tweety homolog 1 (*Drosophila*), a member of a family of putative membrane proteins with five potential transmembrane domains<br>Campbell, H. D. et al.<br>Human and mouse homologues of the *drosophila melanogaster* tweety (tty) gene; A novel gene family encoding predicted transmembrane proteins<br>Genomics 68, 89-92 (2000). |
| | 7501754CD1 | 618612\|<br>Ttyh1 | 4E−203 | [*Mus musculus*] Tweety homolog 1 (*Drosophila*), a member of a family of putative membrane proteins with five potential transmembrane domains<br>Campbell, H. D. et al. (supra) |
| 24 | 7510517CD1 | g1359731 | 1.0E−98 | [*Homo sapiens*] EP4 prostaglandin receptor<br>Foord, S. M. et al. (1996) The structure of the prostaglandin EP4 receptor gene and related pseudogenes. Genomics 35: 182-188. |
| | | 337370\|<br>PTGER4 | 8.6E−100 | [*Homo sapiens*][Receptor (signaling)][Plasma membrane] Prostaglandin E receptor 4, a G protein-coupled receptor that signals through stimulatory G-protein, mediates a variety of physiological effects including inflammatory response and cell motility, may increase invasive growth of colorectal carcinoma cells<br>Bastien, L. et al. (1994) Cloning, functional expression and characterization of the human Prostaglandin E2 receptor EP2 subtype. J. Biol. Chem. 269: 11873-11877.<br>An, S. et al. (1993) Cloning and expression of the EP2 subtype of human receptors for prostaglandin E2. Biochem. Biophys. Res. Commun. 197: 263-270.<br>Dumais, N. et al. (1998) Prostaglandin E2 up-regulates HIV-1 long terminal repeat-driven gene activity in T cells via NF-kappaB-dependent and -independent signaling pathways. J. Biol. Chem. 273: 27306-27314.<br>Pai, R. et al. (2002) Prostaglandin E2 transactivates EGF receptor: a novel mechanism for promoting colon cancer growth and gastrointestinal hypertrophy. Nat. Med. 8: 289-293.<br>Mutoh, M. et al. (2002) Involvement of prostaglandin E receptor subtype EP(4) in colon carcinogenesis. Cancer Res. 62: 28-32.<br>Sheng, H. et al. (2001) Prostaglandin E2 increases growth and motility of colorectal carcinoma cells. J. Biol. Chem. 276: 18075-18081. |
| | | 582643\|<br>Ptger4 | 8.8E−91 | [*Mus musculus*][Receptor (signaling)][Plasma membrane] Prostaglandin E receptor 4, a G protein-coupled receptor that signals through a stimulatory G-protein, mediates a variety of physiological and pathophysiological effects including immune and inflammatory responses and heart and skeletal development<br>Honda, A. et al. (1993) Cloning and expression of a cDNA for mouse prostaglandin E receptor EP2 subtype. J. Biol. Chem. 268: 7759-7762.<br>Suzawa, T. et al. (2000) The role of prostaglandin E receptor subtypes (EP1, EP2, EP3, and EP4) in bone resorption: an analysis using specific agonists for the respective Eps. Endocrinology 14: 1554-1559. |

TABLE 2-continued

| Polypeptide SEQ ID NO: | Incyte Polypeptide ID | GenBank ID NO: or PROTEOME ID NO: | Probability Score | Annotation |
|---|---|---|---|---|
| | | | | Miyaura, C. et al. (2000) Impaired bone resorption to prostaglandin E2 in prostaglandin E receptor EP4-knockout mice. J. Biol. Chem. 275: 19819-19823. |
| 25 | 7511014CD1 | g456564 | 9.9E−140 | [*Homo sapiens*] prostanoid FP receptor<br>Abramovitz, M. et al. (1994) Cloning and expression of a cDNA for the human prostanoid FP receptor. J. Biol. Chem. 269: 2632-2636. |
| | | 337372\|PTGFR | 8.5E−141 | [*Homo sapiens*][Receptor (signaling)][Plasma membrane] Prostanoid FP receptor (prostaglandin F2-alpha receptor), activation induces calcium flux, regulates smooth muscle contraction, and predicted to be necessary for luteolysis; mutations in the corresponding gene are associated with breast cancer<br>Sossey-Alaoui, K. et al. (2001) Fine mapping of the PTGFR gene to 1p31 region and mutation analysis in human breast cancer. Int. J. Mol. Med 7: 543-546.<br>Sugimoto, Y. et al. (1997) Failure of parturition in mice lacking the prostaglandin F receptor. Science 277: 681-683. |
| | | 582645\|Ptgfr | 4.3E−130 | [Mus musculus][Receptor (signaling)][Plasma membrane] Prostanoid FP receptor (prostaglandin F2-alpha receptor), a G protein-coupled receptor that mediates intracellular signaling, necessary for luteolysis; mutations in human PTGFR gene are associated with breast cancer<br>Sugimoto, Y. et al. (1994) Cloning and expression of a cDNA for mouse prostaglandin F receptor. J. Biol. Chem. 269: 1356-1360. |
| 26 | 7506687CD1 | g6010211 | 0.0 | [*Homo sapiens*] semaphorin receptor<br>Tamagnone, L. et al. (1999) Plexins are a large family of receptors for transmembrane, secreted, and GPI-anchored semaphorins in vertebrates. Cell 99: 71-80. |
| | | 568412\|PLXNB1 | 0.0 | [*Homo sapiens*][Receptor (signaling)][Plasma membrane] Plexin 5, member of the plexin family of semaphorin receptors involved in mediating cell guidance, expressed in the brain<br>Maestrini, E. et al. (1996) A family of transmembrane proteins with homology to the MET-hepatocyte growth factor receptor. Proc. Natl. Acad. Sci. USA 93: 674-678. |
| | | 608600\|Plxn6 | 2.5E−149 | [*Mus musculus*] Protein containing a plexin repeat, a Sema domain, and three IPT/TIG domains, all of which are found in receptors |
| 27 | 7510621CD1 | g246539 | 1.8E−115 | [*Homo sapiens*] ocular melanoma-associated antigen; OMA81H<br>Wang, M. X. et al. (1992) An ocular melanoma-associated antigen. Molecular characterization. Arch. Ophthalmol. 110: 399-404. |
| | | 344036\|CD63 | 1.6E−116 | [*Homo sapiens*][Lysosome/vacuole; Cytoplasmic; Plasma membrane] Melanoma 1 antigen, a member of the tetraspanning superfamily (TM4SF), forms multicomponent complexes with beta 1 integrins, associates with peptide-loaded MHC class II molecules; acts to limit the invasion and progression of melanoma<br>Metzelaar, M. J. et al. (1991) CD63 antigen. A novel lysosomal membrane glycoprotein, cloned by a screening procedure for intracellular antigens in eukaryotic cells. J. Biol. Chem. 266: 3239-3245.<br>Gwynn, B. et al. (1996) Genetic localization of Cd63, a member of the transmembrane 4 superfamily, reveals two distinct loci in the mouse genome. Genomics 35: 389-391.<br>Radford, K. J. et al. (1996) CD63 associates with transmembrane 4 superfamily members, CD9 and CD81, and with beta 1 integrins in human melanoma. Biochem. Biophys. Res. Commun. 222: 13-18.<br>Smith, D. A. et al. (1995) Antibodies against human CD63 activate transfected rat basophilic leukemia (RBL-2H3) cells. Mol. Immunol. 32: 1339-1344. |
| | | 583753\|Cd63 | 2.3E−92 | [*Mus musculus*][Plasma membrane] Melanoma 1 antigen, a member of the tetraspanning superfamily (TM4SF), may play a role in maintaining normal renal function, highly expressed in activated macrophages<br>Miyamoto, H. et al. (1994) Molecular cloning of the murine homologue of CD63/ME491 and detection of its strong expression in the kidney and activated macrophages. Biochim. Biophys. Acta 1217: 312-316. |
| 28 | 7505533CD1 | g7768496 | 6.9E−13 | [*Schizosaccharomyces pombe*] putative ER-derived vesicles protein similar to yeast erv14 |
| | | 569856\|HSPC163 | 8.9E−43 | [*Homo sapiens*] Protein of unknown function, has moderate similarity to S. cerevisiae Erv14p, which is a protein of ER-derived vesicles that is required for efficient degradation of soluble ER quality control substrates |
| | | 6677\|ERV14 | 4.0E−15 | [*Saccharomyces cerevisiae*][Vesicle coat protein; Docking protein][Endoplasmic reticulum; Other vesicles of the secretory/endocytic pathways]Protein of ER-derived vesicles that is required for efficient degradation of soluble ER quality control substrates, has similarity to *Drosophila melanogaster* cni protein<br>Powers, J. et al. (1998) Transport of Ax12p depends on Erv14p, an ER-vesicle protein related to the *Drosophila cornichon* gene product. J. Cell Biol. 142: 1209-1222. |
| 29 | 7511220CD1 | g7259234 | 1.0E−75 | [*Mus musculus*] contains transmembrane (TM) region<br>Inoue, S. et al.<br>Growth suppression of *Escherichia coli* by induction of expression of mammalian genes with transmembrane or ATPase domains<br>Biochem. Biophys. Res. Commun. 268, 553-561 (2000) |
| 30 | 7510967CD1 | g14091952 | 0.0 | [*Rattus norvegicus*] KIDINS220<br>Iglesias, T. et al.<br>Identification and cloning of Kidins220, a novel neuronal substrate of protein kinase D<br>J. Biol. Chem. 275, 40048-40056 (2000) |

TABLE 2-continued

| Poly-pep-tide SEQ ID NO: | Incyte Polypeptide ID | GenBank ID NO: or PROTEOME ID NO: | Probability Score | Annotation |
|---|---|---|---|---|
| | 7510967CD1 | 735217\| KIDINS220 | 0.0 | [*Homo sapiens*] Protein containing eleven ankyrin (Ank) repeats, which may mediate protein-protein interactions, has a region of low similarity to a region of ankyrin 1 (human ANK1), which is a a cytoskeletal anchor protein and is associated with hereditary spherocytosis |
| | 7510967CD1 | 244565\| F36H1.2 | 9.6E−181 | [*Caenorhabditis elegans*] Ankyrin repeat-containing protein with similarity to *C. elegans* UNC-44 and human and *D. melanogaster* ankyrins<br>Iglesias, T. et al. (supra) |
| 31 | 7511298CD1 | g1685051 | 0.0 | [*Homo sapiens*] CD97<br>Gray, J. X. et al.<br>CD97 is a processed, seven-transmembrane, heterodimeric receptor associated with inflammation<br>J Immunol 157, 5438-47 (1996). |
| | 7511298CD1 | 762597\|CD97 | 0.0 | [*Homo sapiens*][Receptor (signalling)][Plasma membrane] CD97 antigen, a leukocyte activation antigen that binds CD55 (DAF), may be involved in cell-cell signaling, cell adhesion, immune and inflammatory responses, expressed in thyroid and gastrointestinal tract cancer<br>Zendman, A. J. et al.<br>TM7XN1, a novel human EGF-TM7-like cDNA, detected with mRNA differential display using human melanoma cell lines with different metastatic potential.<br>FEBS Lett 446, 292-8 (1999).<br>Aust, G. et al.<br>CD97: a dedifferentiation marker in human thyroid carcinomas.<br>Cancer Res 57, 1798-806 (1997). |
| | 7511298CD1 | 584465\|Cd97 | 5.4E−213 | [*Mus musculus*][Adhesin/agglutinin; Receptor (signalling)][Plasma membrane] CD97 antigen, a member of the EGF TM7 family that is a group of class II seven-span transmembrane receptors, receptor for the complement cascade regulator, CD55(Daf1), plays a role in cell adhesion, may play a role in lymphocyte activation<br>Qian, Y. M. et al.<br>Structural characterization of mouse CD97 and study of its specific interaction with the murine decay-accelerating factor (DAF, CD55).<br>Immunology 98, 303-11 (1999). |
| 32 | 7510937CD1 | g3766232 | 0.0 | [*Vulpes vulpes*] kinectin |
| | | 341688\| KTN1 | 0.0 | [*Homo sapiens*][Anchor Protein; Activator][Endoplasmic reticulum; Cytoplasmic] Kinectin, functions as a receptor for the microtubule-motor protein kinesin and plays a role in intracellular movement of organelles; mutations in the corresponding gene are associated with childhood papillary thyroid carcinoma.<br>Salassidis, K. et al. Translocation t(10; 14)(q11.2:q22.1) fusing the kinetin to the RET gene creates a novel rearranged form (PTC8) of the RET proto-oncogene in radiation-induced childhood papillary thyroid carcinoma. Cancer Res 60, 2786-9. (2000). |
| | | 581915\|Ktn1 | 0.0 | [*Mus musculus*][Anchor Protein][Endoplasmic reticulum; Cytoplasmic; Plasma membrane] Kinectin, functions as a receptor for the microtubule-motor protein kinesin and plays a role in intracellular movement of organelles; mutations in the human KTN1 gene are associated with childhood papillary thyroid carcinoma.<br>Leung, E. et al. Cloning of novel kinectin splice variants with alternative C-termini: structure, distribution and evolution of mouse kinectin. Immunol Cell Biol 74, 421-33 (1996). |
| 33 | 7511852CD1 | g189186 | 8.1E−149 | [*Homo sapiens*] tumor necrosis factor receptor<br>Smith, C. A. et al. A receptor for tumor necrosis factor defines an unusual family of cellular and viral proteins. Science 248, 1019-1023 (1990). |
| | | 338588\| TNFRSF1B | 6.5E−150 | [*Homo sapiens*][Receptor (signalling)][Plasma membrane] Tumor necrosis factor receptor 1b, a receptor for tumor necrosis factor (TNF), mediates proinflammatory responses associated with wounding and immunity; mutation in gene is associated familial combined hyperlipidemia and narcolepsy.<br>Chan, F. K. et al. A domain in TNF receptors that mediates ligand-independent receptor assembly and signaling. Science 288, 2351-4 (2000). |
| | | 586035\| Tnfrsf1b | 1.5E−81 | [*Mus musculus*][Receptor (signalling)][Extracellular (excluding cell wall); Plasma membrane] Tumor necrosis factor receptor 1b, a receptor for tumor necrosis factor (TNF), mediates proinflammatory responses; mutation in human TNFRSF1B gene is associated familial combined hyperlipidemia and narcolepsy.<br>Kurrelmeyer, K. M., Michael, L. H., Baumgarten, G., Taffet, G. E., Peschon, J. J., Sivasubramanian, N., Entman, M. L., and Mann, D. L. Endogenous tumor necrosis factor protects the adult cardiac myocyte against ischemic-induced apoptosis in a murine model of acute myocardial infarction. Proc Natl Acad Sci U S A 97, 5456-61 (2000).<br>Azuma, Y., Kaji, K., Katogi, R., Takeshita, S., and Kudo, A. Tumor necrosis factor-alpha induces differentiation of and bone resorption by osteoclasts. J Biol Chem 275, 4858-64. (2000). |
| 34 | 7511077CD1 | g15079236 | 3.3E−81 | [*Mus musculus*] Similar to tumor differentially expressed 1 |
| | | 585979\|Tde1 | 3.0E−81 | [*Mus musculus*] Tumor differentially expressed 1, a putative membrane protein that is overexpressed in testicular tumor cells.<br>Bossolasco, M. et al. The human TDE gene homologue: localization to 20q13.1-13.3 and variable expression in human tumor cell lines and tissue. Mol Carcinog 26, 189-200 (1999). |
| | | 428528\| | 3.7E−76 | [*Homo sapiens*] Tumor differentially expressed 1, a putative membrane protein that is |

TABLE 2-continued

| Poly-pep-tide SEQ ID NO: | Incyte Polypeptide ID | GenBank ID NO: or PROTEOME ID NO: | Probability Score | Annotation |
|---|---|---|---|---|
| | | TDE1 | | overexpressed in lung tumors and colorectal tumor cells.<br>Bossolasco, M. et al. (supra)<br>Nimmrich, I. et al. Seven genes that are differentially transcribed in colorectal tumor cell lines. Cancer Lett 160, 37-43 (2000). |
| 35 | 7511576CD1 | g13661645 | 1.3E−77 | [*Homo sapiens*] MS4A6A-polymorph<br>Liang, Y. et al. Identification of a CD2O-, FcepsilonRIbeta-, and HTm4-related gene family: sixteen new MS4a family members expressed in human and mouse. Genomics 72, 119-127 (2001). |
| | | 697394\|MS4A6A | 4.1E−61 | [*Homo sapiens*][Plasma membrane]Member 6 of the membrane-spanning four-domains, subfamily A group of proteins, has similarity to CD20, HTm4 (CD20L), and high affinity IgE receptor beta chain (FCER1B).<br>Ishibashi, K. et al., Identification of a new multigene four-transmembrane family (MS4A) related to CD20, HTm4 and beta subunit of the high-affinity IgE receptor., Gene 264, 87-93. (2001). |
| 36 | 7511492CD1 | g506861 | 1.1E−46 | [*Homo sapiens*] BST-2<br>Ishikawa, J. et al., Molecular cloning and chromosomal mapping of a bone marrow stromal cell surface gene, BST2, that may be involved in pre-B-cell growth, Genomics 26, 527-534 (1995). |
| | | 340100\|BST2 | 9.3E−48 | [*Homo sapiens*][Plasma membrane] Bone marrow stromal antigen 2, a cell surface antigen that may play a role in proliferation and cell-cell communication, likely to be involved in humoral defense; elevated levels are associated with myeloma.<br>Ohtomo, T. et al. Molecular cloning and characterization of a surface antigen preferentially overexpressed on multiple myeloma cells. Biochem Biophys Res Commun 258, 583-91. (1999). |
| 37 | 7511141CD1 | g974282 | 2.9E−73 | [*Homo sapiens*] secretin receptor<br>Chow, B. K. Molecular cloning and functional characterization of a human secretin receptor. Biochem. Biophys. Res. Commun. 212, 204-211 (1995). |
| | | 337902\|SCTR | 2.3E−74 | [*Homo sapiens*][Receptor (signalling)][Plasma membrane] Secretin receptor, a class II G protein-coupled receptor that can couple the cAMP and phosphatisylinositol intracellular signaling pathways and is involved in the control of water, bicarbonate and enzyme secretion in pancreas, gall bladder and stomach.<br>Shetzline, M. A. et al. A role for receptor kinases in the regulation of class II G protein-coupled receptors. Phosphorylation and desensitization of the secretin receptor. J Biol Chem 273, 6756-62 (1998). |
| | | 705026\|Sctr | 5.9E−46 | [Rattus norvegicus][Receptor (signalling)][Plasma membrane] Secretin receptor, a class II G protein-coupled receptor that couples to a stimulatory G protein, activates the cAMP signaling pathway and is involved in the control of water, bicarbonate and enzyme secretion in pancreas, gall bladder and stomach.<br>Dong, M., Wang, Y., Hadac, E. M., Pinon, D. I., Holicky, E., and Miller, L. J. Identification of an interaction between residue 6 of the natural peptide ligand and a distinct residue within the amino-terminal tail of the secretin receptor. J Biol Chem 274, 19161-7 (1999). |
| 38 | 7511300CD1 | g1685051 | 0.0 | [*Homo sapiens*] CD97<br>Gray, J. X. et al. CD97 is a processed, seven-transmembrane, heterodimeric receptor associated with inflammation. J. Immunol. 157(12): 5438-47 (1996). |
| | | 762597\|CD97 | 0.0 | [*Homo sapiens*][Receptor (signalling)][Plasma membrane] CD97 antigen, a leukocyte activation antigen that binds CD55 (DAF), may be involved in cell-cell signaling, cell adhesion, immune and inflammatory responses, expressed in thyroid and gastrointestinal tract cancer.<br>Gray, J. X. et al. (supra)<br>Aust, G. et al. CD97: a dedifferentiation marker in human thyroid carcinomas. Cancer Res 57, 1798-806 (1997). |
| | | 584465\|Cd97 | 2.1E−242 | [*Mus musculus*][Adhesin/agglutinin; Receptor (signalling)][Plasma membrane] CD97 antigen, a member of the EGF TM7 family that is a group of class II seven-span transmembrane receptors, receptor for the complement cascade regulator, CD55 (Daf1), plays a role in cell adhesion, may play a role in lymphocyte activation.<br>Caminschi, I., Lucas, K. M., O'Keeffe, M. A., Hochrein, H., Laabi, Y., Kontgen, F., Lew, A. M., Shortman, K., and Wright, M. D. Molecular cloning of F4/80-like-receptor, a seven-span membrane protein expressed differentially by dendritic cell and monocyte-macrophage subpopulations. J Immunol 167, 3570-6. (2001). |

TABLE 3

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 1 | 3048626CD1 | 747 | S150 S184 S222 S250 S297 S307 S345 S350 S351 | N291 N659 N718 | Cytosolic domains: M1-K97, S150-I456, C534-D595, T648-P714<br>Transmembrane domains: V98-F117, | TMHMMER |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | S357 S362 S384 S440 S494 S505 S555 S580 S654 S658 T74 T95 T153 T233 T247 T264 T276 T285 T386 T485 T539 T653 | | I132-V149, P457-F479, V511-L533, V596-H618, Y628-V647, L715-G737 Non-cytosolic domains: C118-V131, R480-I510, V619-H627, F738-S747 | |
| | | | | | Class IA and IB cytochrome C signature PR00604: H374-S381 | BLIMPS_PRINTS |
| | | | | | Cytochrome c family heme-binding site signature: C375-S380 | MOTIFS |
| 2 | 2684425CD1 | 799 | S137 S174 S182 S191 S254 S322 S328 S405 S410 S424 S435 S458 S476 S523 S545 S552 S587 S602 S629 S713 S718 S722 S726 S782 T55 T73 T85 T190 T306 T444 T495 T509 T621 T752 T767 Y779 | N39 N53 N58 N69 N80 N135 N304 N557 N761 | signal_cleavage: M1-A24 | SPSCAN |
| | | | | | Signal Peptide: M1-G22 | HMMER |
| | | | | | Signal Peptide: M1-A24 | HMMER |
| | | | | | Cytosolic domain: M1-N360 Transmembrane domain: I361-W383 Non-cytosolic domain: R384-I799 | TMHMMER |
| 3 | 7505960CD1 | 663 | S22 S31 S102 S119 S218 S304 S430 S526 S572 T135 T447 Y13 | N29 N69 N155 N197 N298 N393 N405 N416 N631 | signal_cleavage: M1-G52 | SPSCAN |
| | | | | | Cytosolic domains: M1-V35, R251-R251, R331-M355, E473-D549, S610-K663 Transmembrane domains: I36-Y58, S228-L250, L252-Y274, T308-L330, F356-Y378, Y450-L472, L550-S572, L587-F609 Non-cytosolic domains: G59-Q227, Y275-E307, L379-R449, G573-H586 | TMHMMER |
| | | | | | Leucine zipper pattern: L245-L266 | MOTIFS |
| 4 | 7507021CD1 | 150 | S21 S73 T16 T26 T85 T87 Y96 | | signal_cleavage: M1-D19 | SPSCAN |
| | | | | | Signal Peptide: M1-D19 | HMMER |
| | | | | | Signal Peptide: M1-P22 | HMMER |
| | | | | | Signal Peptide: M1-E25 | HMMER |
| | | | | | Signal Peptide: M1-S23 | HMMER |
| | | | | | Signal Peptide: M1-T20 | HMMER |
| | | | | | Vitamin K-dependent carboxylation/gamma-carb: L55-Y96 | HMMER_PFAM |
| | | | | | Cytosolic domain: R133-L150 Transmembrane domain: L110-L132 Non-cytosolic domain: M1-S109 | TMHMMER |
| | | | | | Vitamin K-dependent carboxylation domain: V30-A111 | PROFILESCAN |
| | | | | | Coagulation factor GLA domain signature PR00001: D54-C67, L68-F81, E82-Y96 | BLIMPS_PRINTS |
| | | | | | PROLINERICH GLA PROTEIN 2 PD059428: M1-D54 | BLAST_PRODOM |
| | | | | | PROLINERICH GLA PROTEIN 2 PD059430: I95-E146 | BLAST_PRODOM |
| | | | | | GLA DOMAIN DM00454 \|P25155\|2-80: L9-W91 \|P19221\|5-91: Q28-Y94 \|P18292\|5-91: Q28-Y94 \|S49075\|2-80: L7-W91 | BLAST_DOMO |
| | | | | | Vitamin K-dependent carboxylation domain: D54-W91 | MOTIFS |
| 5 | 7509099CD1 | 504 | S16 S35 S200 S225 S234 S305 S334 S336 S382 S402 S437 S460 S481 T152 T226 T329 Y94 Y320 | N128 N168 N184 N198 N232 | signal_cleavage: M1-A20 | SPSCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Signal Peptide: M1-S16 | HMMER |
| | | | | | Signal Peptide: M1-E19 | HMMER |
| | | | | | Signal Peptide: M1-A20 | HMMER |
| | | | | | Signal Peptide: M1-K22 | HMMER |
| | | | | | Signal Peptide: M1-C23 | HMMER |
| | | | | | Signal Peptide: M1-S17 | HMMER |
| | | | | | TIR domain: A322-H472 | HMMER_PFAM |
| | | | | | Cytosolic domain: K295-G504<br>Transmembrane domain: H272-F294<br>Non-cytosolic domain: M1-K271 | TMHMMER |
| | | | | | RECEPTOR INTERLEUKIN-1 P PD02870: L116-F150, E169-V185, N268-K292 | BLIMPS_PRODOM |
| | | | | | RECEPTOR PROTEIN PRECURSOR SIGNAL INTERLEUKIN1 TRANSMEMBRANE GLYCOPROTEIN I IMMUNOGLOBULIN FOLD PD002366: G317-V475 | BLAST_PRODOM |
| | | | | | RECEPTOR INTERLEUKIN1 I PRECURSOR TRANSMEMBRANE SIGNAL TYPE IL1R1 P80<br>IMMUNOGLOBULIN PD011274: V216-G317 | BLAST_PRODOM |
| | | | | | RECEPTOR TYPE I INTERLEUKIN1 PRECURSOR IL1R1 P80 IMMUNOGLOBULIN FOLD TRANSMEMBRANE PD015419: N168-Y213 | BLAST_PRODOM |
| | | | | | RECEPTOR PRECURSOR SIGNAL INTERLEUKIN1 IMMUNOGLOBULIN FOLD GLYCOPROTEIN TRANSMEMBRANE TYPE PROTEIN PD006063: L4-V97 | BLAST_PRODOM |
| | | | | | INTERLEUKIN; ACCESSORY; INTRLEUKIN; ST2L; DM02304<br>\|P14778\|323-562: A258-E498<br>\|P13504\|326-565: A258-K494<br>\|JQ1526\|326-555: A258-S488 | BLAST_DOMO |
| | | | | | IG-LIKE C2-TYPE DOMAIN DM01362\|P14778\|11-227: I11-I163, D98-I163 | BLAST_DOMO |
| 6 | 7509361CD1 | 247 | S42 S157 S208 S221 S237 S244 T5 T90 | N54 N145 N151 | signal_cleavage: M1-G21 | SPSCAN |
| | | | | | Signal Peptide: M1-G21 | HMMER |
| | | | | | Signal Peptide: M1-P24 | HMMER |
| | | | | | Signal Peptide: M1-G29 | HMMER |
| | | | | | TNF-receptor internal cysteine rich dom: C84-C125, C127-C166, C44-C81, C168-C195 | HMMER_INCY |
| | | | | | TNFR/NGFR cysteine-rich region: C84-C125, C44-C81, C127-C166, C168-C195 | HMMER_PFAM |
| | | | | | Tumor necrosis factor receptor/nerve: C84-C125, C44-C81, C127-C166, C168-C195 | HMMER_SMRT |
| | | | | | Cytosolic domain: H33-A247<br>Transmembrane domain: L10-P32<br>Non-cytosolic domain: M1-L9 | TMHMMER |
| | | | | | TNFR/NGFR family cysteine-rich region proteins BL00652: L9-L15, C58-L68, C117-C127 | BLIMPS_BLOCKS |
| | | | | | TUMOR NECROSIS FACTOR RECEPTOR PRECURSOR P60 TNFR1 P55 TRANSMEMBRANE GLYCOPROTEIN PD013401: C168-S208, P214-R236 | BLAST_PRODOM |
| | | | | | TUMOR NECROSIS FACTOR RECEPTOR TYPE 1 DM04395<br>\|P19438\|120-454: D120-S208<br>\|P50555\|120-460: D120-S208, N201-A247 | BLAST_DOMO |
| | | | | | TNFR/NGFR FAMILY CYSTEINE-RICH REGION DM00218<br>\|P19438\|39-118: K39-V119<br>\|P50555\|39-118: K39-V119 | BLAST_DOMO |
| | | | | | Cytochrome c family heme-binding site signature: C59-K64 | MOTIFS |
| | | | | | EGF-like domain signature 2: C166-C179 | MOTIFS |
| | | | | | TNFR/NGFR family cysteine-rich region signature: C44-C81, C84-C125, C125-C166, C127-C166 | MOTIFS |
| 7 | 7506815CD1 | 363 | S127 S171 T270 | N7 N30 N36 | 7 transmembrane receptor (rhodopsin family): V52-Y306 | HMMER_PFAM |
| | | | | | Cytosolic domains: M1-H86, S158-R246, M309-G363 Transmembrane domains: A87-T109, S135-I157, V247-Y266, A286-F308Non-cytosolic domains: V110-W134, S267-G285 | TMHMMER |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | G-protein coupled receptors proteins BL00237: N36-P75, F143-Y154, L242-A268, S298-R314 | BLIMPS_BLOCKS |
| | | | | | G-protein coupled receptors family 2 proteins BL00649: R129-M150 | BLIMPS_BLOCKS |
| | | | | | Gastrin receptor signature PR00527: S20-N36, L37-S53, P75-R89, M102-P116, R117-S135, I157-D174, A201-R217, R323-P342 | BLIMPS_PRINTS |
| | | | | | Neuropeptide Y receptor PR01012: R50-A65, L293-N302, L304-C317 | BLIMPS_PRINTS |
| | | | | | Rhodopsin-like GPCR superfamily PR00237: R50-I72, H86-V107, S135-S158, V247-W271, I288-R314 | BLIMPS_PRINTS |
| | | | | | G-protein coupled receptors signature: G48-T94 | PROFILESCAN |
| | | | | | Visual pigments (opsins) retinal binding site: G276-P341 | PROFILESCAN |
| | | | | | RECEPTOR GPROTEIN COUPLED TRANSMEMBRANE GLYCOPROTEIN LIPOPROTEIN PALMITATE GASTRIN/CHOLECYSTOKININ TYPE B PD005216: T109-G208 | BLAST_PRODOM |
| | | | | | GASTRIN/CHOLECYSTOKININ TYPE B RECEPTOR CCKB CCKBR G-PROTEIN COUPLED TRANSMEMBRANE GLYCOPROTEIN PD009141: C307-G363 | BLAST_PRODOM |
| | | | | | GASTRIN/CHOLECYSTOKININ TYPE B RECEPTOR CCKB CCKBR G-PROTEIN COUPLED TRANSMEMBRANE GLYCOPROTEIN PD007211: M1-I64 | BLAST_PRODOM |
| | | | | | G-PROTEIN COUPLED RECEPTORS DM00013 \|P30552\|48-412: G51-A322 \|P32238\|35-386: G51-T320 \|S17783\|95-396: V52-Q182, P236-R314 \|P30975\|95-396: V52-Q182, P236-R314 | BLAST_DOMO |
| | | | | | G-protein coupled receptors signature: V56-I72 | MOTIFS |
| 8 | 7506814CD1 | 392 | S82 S211 S255 T299 | N7 N30 N36 | 7 transmembrane receptor (rhodopsin family): G71-Y335 | HMMER_PFAM |
| | | | | | Cytosolic domains: L81-A91, R152-A171, S242-R275, M338-G392 Transmembrane domains: I58-G80, F92-P114, A129-E151, A172-V194, S219-I241, V276-Y295, A315-F337 Non-cytosolic domains: M1-R57, N115-K128, V195-W218, S296-G314 | TMHMMER |
| | | | | | G-protein coupled receptors proteins BL00237: F120-P159, F227-Y238, G271-A297, S327-R343 | BLIMPS_BLOCKS |
| | | | | | G-protein coupled receptors signature: S131-T178 | PROFILESCAN |
| | | | | | Visual pigments (opsins) retinal binding site: G305-P370 | PROFILESCAN |
| | | | | | Rhodopsin-like GPCR superfamily signature PR00237: I56-G80, T89-F110, M134-I156, H170-V191, S219-S242, V276-W300, I317-R343 | BLIMPS_PRINTS |
| | | | | | Gastrin receptor signature PR00527: S20-N36, L37-E53, F110-I125, P159-R173, M186-P200, R201-S219, I241-D258, R352-P371 | BLIMPS_PRINTS |
| | | | | | Neuropeptide Y receptor signature PR01012: L81-L93, T111-G123, M134-A149, L322-N331, L333-C346 | BLIMPS_PRINTS |
| | | | | | GASTRIN/CHOLECYSTOKININ TYPE B RECEPTOR CCKB CCKBR GPROTEIN COUPLED TRANSMEMBRANE GLYCOPROTEIN PD007211: M1-R83 | BLAST_PRODOM |
| | | | | | RECEPTOR GPROTEIN COUPLED TRANSMEMBRANE GLYCOPROTEIN LIPOPROTEIN PALMITATE GASTRIN/CHOLECYSTOKININ TYPE B PD005216: T193-G271 | BLAST_PRODOM |
| | | | | | GASTRIN/CHOLECYSTOKININ TYPE B RECEPTOR CCKB CCKBR GPROTEIN COUPLED TRANSMEMBRANE GLYCOPROTEIN PD009141: C336-G392 | BLAST_PRODOM |
| | | | | | RECEPTOR COUPLED GPROTEIN | BLAST_PRODOM |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | TRANSMEMBRANE GLYCOPROTEIN PHOSPHORYLATION LIPOPROTEIN PALMITATE PROTEIN FAMILY PD000009: R83-P188 | |
| | | | | | G-PROTEIN COUPLED RECEPTORS DM00013\|P30552\|48-412: G48-G271, A272-A351, R8-R45 | BLAST_DOMO |
| | | | | | G-PROTEIN COUPLED RECEPTORS DM00013\|P32238\|35-386: T49-R262, L247-T349 | BLAST_DOMO |
| | | | | | G-PROTEIN COUPLED RECEPTORS DM00013\|P25929\|34-335: L52-Q344 | BLAST_DOMO |
| | | | | | G-PROTEIN COUPLED RECEPTORS DM00013\|P25931\|84-384: L60-E348 | BLAST_DOMO |
| | | | | | G-protein coupled receptors signature: V140-I156 | MOTIFS |
| 9 | 7506852CD1 | 125 | S117 S122 | | signal_cleavage: M1-G59 | SPSCAN |
| | | | | | 7 transmembrane receptor (rhodopsin family): G26-R114 | HMMER_PFAM |
| | | | | | Cytosolic domains: A33-T44, V103-S125<br>Transmembrane domains: A10-W32, F45-I67, C80-A102<br>Non-cytosolic domains: M1-Q9, L68-T79 | TMHMMER |
| | | | | | G-protein coupled receptors proteins BL00237: P73-P112 | BLIMPS_BLOCKS |
| | | | | | G-protein coupled receptors signature: A84-S125 | PROFILESCAN |
| | | | | | Rhodopsin-like GPCR superfamily signature PR00237: A11-K35, T44-L65, V87-V109 | BLIMPS_PRINTS |
| | | | | | Adenosine receptor signature PR00424: A10-I19, T79-T91 | BLIMPS_PRINTS |
| | | | | | Adenosine A1 receptor signature PR00552: I5-I15, V34-C46, L68-C80 | BLIMPS_PRINTS |
| | | | | | RECEPTOR A1 GPROTEIN COUPLED TRANSMEMBRANE GLYCOPROTEIN ADENOSINE LIPOPROTEIN PALMITATE AS PD007911: M1-A39 | BLAST_PRODOM |
| | | | | | G-PROTEIN COUPLED RECEPTORS DM00013\|I48096\|3-304: S4-R114 | BLAST_DOMO |
| | | | | | G-PROTEIN COUPLED RECEPTORS DM00013\|P28190\|3-303: P3-R114 | BLAST_DOMO |
| | | | | | G-PROTEIN COUPLED RECEPTORS DM00013\|P49892\|3-304: S4-R114 | BLAST_DOMO |
| | | | | | G-PROTEIN COUPLED RECEPTORS DM00013\|S55231\|3-304: S4-R114 | BLAST_DOMO |
| | | | | | G-protein coupled receptors signature: S93-V109 | MOTIFS |
| 10 | 7503782CD1 | 728 | S9 S200 S243 S248 S419 S437 S472 S536 S573 S666 T60 T72 T175 T220 T261 T342 T528 Y426 | N148 N386 N582 | Cytosolic domains: M1-F115, R222-S298, Q375-N386, D469-W501, S569-Q728<br>Transmembrane domains: L116-L138, Y199-L221, Y299-T321, Q352-V374, L387-Q409, S446-V468, M502-I524, T546-V568<br>Non-cytosolic domains: R139-V198, K322-L351, T410-L445, K525-S545 | TMHMMER |
| | | | | | Leucine zipper pattern: L207-L228, L347-L368, L445-L466 | MOTIFS |
| 11 | 7504647CD1 | 61 | S47 | | signal_cleavage: M1-A23 | SPSCAN |
| | | | | | Signal Peptide: M1-G19 | HMMER |
| | | | | | Signal Peptide: M1-T21 | HMMER |
| | | | | | Signal Peptide: M1-A23 | HMMER |
| | | | | | Signal Peptide: M1-Q25 | HMMER |
| | | | | | PRECURSOR SIGNAL ADHALIN ALPHASARCOGLYCAN GLYCOPROTEIN EPSILONSARCOGLYCAN ADHALIN35 A DYSTROPHINASSOCIATED PD009878: M1-H51 | BLAST_PRODOM |
| 12 | 7500424CD1 | 152 | | | Signal Peptide: M1-G22 | HMMER |
| | | | | | Signal Peptide: M1-G25 | HMMER |
| | | | | | Signal Peptide: M1-G27 | HMMER |
| 13 | 7500449CD1 | 283 | S8 S67 S139 S165 S176 T111 T146 | N93 N104 N135 | Domain present in hormone receptors: E94-L166 | HMMER_SMART |
| | | | | | Hormone receptor domain: T95-K162 | HMMER_PFAM |
| | | | | | Cytosolic domain: R203-S283 Transmembrane domain: G180-F202<br>Non-cytosolic domain: M1-T179 | TMHMMER |
| | | | | | G-protein coupled receptors proteins BL00237: W78-A117, F181-Y192 | BLIMPS_BLOCKS |
| | | | | | G-protein coupled receptors family 2 signatures: Y74-G144 | PROFILESCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Secretin-like GPCR superfamily signature PR00249: T179-R203, Y211-F235 | BLIMPS_PRINTS |
| | | | | | Vasoactive intestinal peptide receptor signature PR00491: P122-G133, N135-P150, P152-K162 | BLIMPS_PRINTS |
| | | | | | RECEPTOR TRANSMEMBRANE GPROTEIN COUPLED GLYCOPROTEIN PRECURSOR SIGNAL TYPE POLYPEPTIDE ALTERNATIVE PD000752: C98-S244 | BLAST_PRODOM |
| | | | | | G-PROTEIN COUPLED RECEPTORS FAMILY 2 DM00378\|P32241\|25-434: L68-S247 | BLAST_DOMO |
| | | | | | G-PROTEIN COUPLED RECEPTORS FAMILY 2 DM00378\|Q02643\|16-422: S62-S244 | BLAST_DOMO |
| | | | | | G-PROTEIN COUPLED RECEPTORS FAMILY 2 DM00378\|P41586\|13-446: Q81-Q132, V136-C243 | BLAST_DOMO |
| | | | | | G-PROTEIN COUPLED RECEPTORS FAMILY 2 DM00378\|A53471\|12-420: S66-G257 | BLAST_DOMO |
| | | | | | G-protein coupled receptors family 2 signature 1: C98-P122 | MOTIFS |
| 14 | 7503281CD1 | 246 | S42 S122 S202 S222 T39 T83 T125 T226 Y172 | | signal_cleavage: M1-R44 | SPSCAN |
| | | | | | 7 transmembrane receptor (rhodopsin family): G29-H246 | HMMER_PFAM |
| | | | | | Cytosolic domains: L38-N48, D109-R128, R194-H246 Transmembrane domains: I15-V37, L49-A71, E86-L108, I129-K151, W171-L193 Non-cytosolic domains: M1-A14, N72-C85, G152-A170 | TMHMMER |
| | | | | | G-protein coupled receptors signature: A90-V136 | PROFILESCAN |
| | | | | | Rhodopsin-like GPCR superfamily signature PR00237: A14-L38, Q47-F68, D92-V114, R128-I149, I173-Y196 | BLIMPS_PRINTS |
| | | | | | RECEPTOR COUPLED GPROTEIN TRANSMEMBRANE GLYCOPROTEIN PHOSPHORYLATION LIPOPROTEIN PALMITATE PROTEIN FAMILY PD000009: R41-Y150 | BLAST_PRODOM |
| | | | | | ADRENERGIC RECEPTOR ADRENOCEPTOR GPROTEIN COUPLED TRANSMEMBRANE MULTIGENE FAMILY PHOSPHORYLATION GLYCOPROTEIN PD003999: M1-S42 | BLAST_PRODOM |
| | | | | | G-PROTEIN COUPLED RECEPTORS DM00013\|P18089\|6-442: P6-S238 | BLAST_DOMO |
| | | | | | G-PROTEIN COUPLED RECEPTORS DM00013\|I49481\|27-442: P6-A218, R205-S240 | BLAST_DOMO |
| | | | | | G-PROTEIN COUPLED RECEPTORS DM00013\|P08913\|27-442: P6-R228 | BLAST_DOMO |
| | | | | | G-PROTEIN COUPLED RECEPTORS DM00013\|P18825\|45-452: Y7-T217, K200-A245 | BLAST_DOMO |
| | | | | | G-protein coupled receptors signature: S98-V114 | MOTIFS |
| 15 | 7503292CD1 | 319 | S5 S252 T148 | | signal_cleavage: M1-S53 | SPSCAN |
| | | | | | 7 transmembrane receptor (rhodopsin family): G49-T318 | HMMER_PFAM |
| | | | | | Cytosolic domains: L58-R69, E132-R151, T229-W319 Transmembrane domains: F35-V57, H70-Y92, Y112-A131, T152-M174, F206-V228 Non-cytosolic domains: M1-L34, S93-Y111, G175-V205 | TMHMMER |
| | | | | | G-protein coupled receptors signature: F113-L158 | PROFILESCAN |
| | | | | | Rhodopsin-like GPCR superfamily signature PR00237: L34-L58, L68-V89, H115-V137, R151-V172, I207-V230 | BLIMPS_PRINTS |
| | | | | | NEUROTENSIN RECEPTOR TYPE NTR2 LEVOCABASTINE SENSITIVE GPROTEIN COUPLED TRANSMEMBRANE LIPOPROTEIN PD027448: M1-G66 | BLAST_PRODOM |
| | | | | | NEUROTENSIN RECEPTOR TYPE 2 NTR2 LOWAFFINITY LEVOCABASTINE SENSITIVE NTRL GPROTEIN COUPLED TRANSMEMBRANE LIPOPROTEIN PALMITATE PD016080: I173-G261 | BLAST_PRODOM |
| | | | | | G-PROTEIN COUPLED RECEPTORS DM00013\|P30989\|57-380: D26-Q239 | BLAST_DOMO |
| | | | | | G-PROTEIN COUPLED RECEPTORS DM00013\|P20905\|156-522: L34-L225 | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | G-PROTEIN COUPLED RECEPTORS DM00013\|P31391\|41-326: D26-L219 | BLAST_DOMO |
| | | | | | G-PROTEIN COUPLED RECEPTORS DM00013\|P35371\|41-345: Y39-S242 | BLAST_DOMO |
| | | | | | G-protein coupled receptors signature: A121-V137 | MOTIFS |
| 16 | 7503311CD1 | 284 | T31 T79 T116 | N62 N77 N230 | Signal Peptide: M1-T25 | HMMER |
| | | | | | Domain present in hormone receptors: S57-F127 | HMMER_SMART |
| | | | | | 7 transmembrane receptor (Secretin family): L134-S284 | HMMER_PFAM |
| | | | | | Hormone receptor domain: G58-K123 | HMMER_PFAM |
| | | | | | Cytosolic domain: R163-C226 Transmembrane domains: M140-F162, V227-G249 Non-cytosolic domains: M1-V139, G250-S284 | TMHMMER |
| | | | | | G-protein coupled receptors family 2 proteins BL00649: C61-L88, G144-S189, C216-L241 | BLIMPS_BLOCKS |
| | | | | | G-protein coupled receptors family 2 signatures: W39-G107 | PROFILESCAN |
| | | | | | Secretin-like GPCR superfamily signature PR00249: V139-R163, Y171-P195, T218-L241, F256-P281 | BLIMPS_PRINTS |
| | | | | | RECEPTOR TRANSMEMBRANE GPROTEIN COUPLED GLYCOPROTEIN PRECURSOR SIGNAL TYPE POLYPEPTIDE ALTERNATIVE PD000752: C61-G265 | BLAST_PRODOM |
| | | | | | GASTRIC INHIBITORY POLYPEPTIDE RECEPTOR PRECURSOR GIPR GLUCOSE DEPENDENT INSULINOTROPIC G PROTEIN PD022939: Q21-L59 | BLAST_PRODOM |
| | | | | | G-PROTEIN COUPLED RECEPTORS FAMILY 2 DM00378\|P48546\|21-438: Q21-A266 | BLAST_DOMO |
| | | | | | G-PROTEIN COUPLED RECEPTORS FAMILY 2 DM00378\|P47871\|18-444: L35-A266 | BLAST_DOMO |
| | | | | | G-PROTEIN COUPLED RECEPTORS FAMILY 2 DM00378\|P43220\|21-448: E34-G265 | BLAST_DOMO |
| | | | | | G-PROTEIN COUPLED RECEPTORS FAMILY 2 DM00378\|P25107\|23-499: L20-G265 | BLAST_DOMO |
| | | | | | G-protein coupled receptors family 2 signature 1: C61-P85 | MOTIFS |
| 17 | 7510384CD1 | 400 | T128 T347 | N50 | signal_cleavage: M1-G22 | SPSCAN |
| | | | | | Signal Peptide: M5-G22 | HMMER |
| | | | | | Signal Peptide: M48-G71 | HMMER |
| | | | | | Domain present in hormone receptors: T51-E121 | HMMER_SMART |
| | | | | | Hormone receptor domain: T52-E117 | HMMER_PFAM |
| | | | | | Cytosolic domain: M1-K130 Transmembrane domain: I131-A153 Non-cytosolic domain: L154-D400 | TMHMMER |
| | | | | | G-protein coupled receptors family 2 proteins BL00649: C55-F82, G136-L181 | BLIMPS_BLOCKS |
| | | | | | G-protein coupled receptors family 2 signatures: L34-G100 | PROFILESCAN |
| | | | | | Secretin-like GPCR superfamily signature PR00249: I131-R155, Y163-F187 | BLIMPS_PRINTS |
| | | | | | Vasoactive intestinal peptide receptor signature PR00491: P79-G90, A91-P106 | BLIMPS_PRINTS |
| | | | | | RECEPTOR TRANSMEMBRANE GPROTEIN COUPLED GLYCOPROTEIN PRECURSOR SIGNAL TYPE POLYPEPTIDE ALTERNATIVE PD000752: C55-V200 | BLAST_PRODOM |
| | | | | | GROWTH HORMONERELEASING HORMONE RECEPTOR PRECURSOR GHRH GRF GRFR GPROTEIN COUPLED PD016970: M1-G54 | BLAST_PRODOM |
| | | | | | G-PROTEIN COUPLED RECEPTORS FAMILY 2 DM00378\|Q02643\|16-422: P16-M201 | BLAST_DOMO |
| | | | | | G-PROTEIN COUPLED RECEPTORS FAMILY 2 DM00378\|P32241\|25-434: M24-V200 | BLAST_DOMO |
| | | | | | G-PROTEIN COUPLED RECEPTORS FAMILY 2 DM00378\|P41587\|13-421: M24-C195 | BLAST_DOMO |
| | | | | | G-PROTEIN COUPLED RECEPTORS FAMILY 2 DM00378\|JC2532\|20-434: C28-C195 | BLAST_DOMO |
| | | | | | G-protein coupled receptors family 2 signature 1: C55-P79 | MOTIFS |
| 18 | 7509976CD1 | 893 | S82 S182 S183 S188 S274 S283 S436 S479 S598 S671 S778 S831 T169 T248 T252 | N59 N548 N637 N738 N746 | signal_cleavage: M1-G19 | SPSCAN |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | T259 T421 T614 T664 T703 T759 | | | |
| | | | | | Signal Peptide: M1-A17 | HMMER |
| | | | | | Signal Peptide: M1-G19 | HMMER |
| | | | | | Signal Peptide: M1-R21 | HMMER |
| | | | | | Signal Peptide: M1-P22 | HMMER |
| | | | | | Signal Peptide: M1-A25 | HMMER |
| | | | | | Domain found in Plexins, Semaphorins and Int: T490-V540, N637-P684, K785-S838 | HMMER_SMRT |
| | | | | | Plexin repeat: T490-V540, K785-S838, N637-P684 | HMMER_PFAM |
| | | | | | Sema domain: L33-Y357, A415-D471 | HMMER_PFAM |
| | | | | | Tyrosinase CuA-binding region proteins BL00497: P461-K481 | BLIMPS_BLOCKS |
| | | | | | PLEXIN PROTEIN PRECURSOR SIGNAL KIAA0407 K04B12.1 TRANSMEMBRANE SEX RECEPTOR GLYCOPROTEIN PD010132: S496-H819 | BLAST_PRODOM |
| | | | | | PLEXIN PRECURSOR SIGNAL TRANSMEMBRANE PROTEIN SEX RECEPTOR GLYCOPROTEIN PD003973: R352-H474 | BLAST_PRODOM |
| | | | | | SEMAPHORIN PROTEIN PRECURSOR RECEPTOR KINASE SIGNAL TYROSINE TYROSINEPROTEIN FAMILY HEPATOCYTE PD001844: T34-W284, I96-V454 | BLAST_PRODOM |
| | | | | | do KINASE; TYROSINE; ATP; GROWTH; DM01368\|P51805\|796-899: C796-R893 | BLAST_DOMO |
| | | | | | do KINASE; TYROSINE; HEPATOCYTE; ATP; DM03653\|P08581\|14-526: D30-A498 | BLAST_DOMO |
| | | | | | do KINASE; TYROSINE; HEPATOCYTE; ATP; DM03653\|Q04912\|17-533: V45-C497 | BLAST_DOMO |
| | | | | | do KINASE; TYROSINE; HEPATOCYTE; ATP; DM03653\|A48196\|13-528: H35-L365 | BLAST_DOMO |
| | | | | | ATP/GTP-binding site motif A (P-loop): G168-S175 | MOTIFS |
| 19 | 7510454CD1 | 203 | S53 S198 T45 Y128 | N117 | Signal Peptide: M1-A15 | HMMER |
| | | | | | Signal Peptide: M1-M19 | HMMER |
| | | | | | Cytosolic domain: K27-D56 Transmembrane domains: F4-L26, I57-I75 Non-cytosolic domains: M1-S3, C76-P203 | TMHMMER |
| | | | | | Leucine zipper pattern: L127-L148 | MOTIFS |
| 20 | 8017335CD1 | 429 | S80 S258 S287 S296 S343 S357 S366 S413 T157 | N181 N208 N285 | Cytosolic domains: L73-S83, L144-K163, C224-V247, R323-N429 Transmembrane domains: S50-L72, L84-L106, F121-N143, I164-M186, V201-I223, V248-I270, Y300-F322 Non-cytosolic domains: M1-L49, S107-H120, L187-T200, S271-E299 | TMHMMER |
| | | | | | PUTATIVE SEVEN PASS TRANSMEMBRANE PROTEIN TRANSMEMBRANE PD138976: M1-L361 | BLAST_PRODOM |
| 21 | 7510197CD1 | 101 | S40 | | signal_cleavage: M1-F16 | SPSCAN |
| | | | | | Signal Peptide: M1-F16 | HMMER |
| | | | | | Signal Peptide: M1-D18 | HMMER |
| | | | | | Cytosolic domain: T68-L101 Transmembrane domain: A45-L67 Non-cytosolic domain: M1-C44 | TMHMMER |
| | | | | | Leucine zipper pattern: L39-L60, L46-L67, L53-L74 | MOTIFS |
| | | | | | Prenyl group binding site (CAAX box): C99-L101 | MOTIFS |
| 22 | 7510055CD1 | 237 | S97 S156 T55 T104 T141 T165 T179 | N153 N180 | signal_cleavage: M1-P20 | SPSCAN |
| | | | | | Signal Peptide: M1-P20 | HMMER |
| | | | | | Signal Peptide: M1-E28 | HMMER |
| | | | | | Signal Peptide: M1-A25 | HMMER |
| | | | | | Signal Peptide: M1-C26 | HMMER |
| | | | | | TNF-receptor internal cysteine rich domain: C62-C103, C146-C186, C105-C143, C26-C59 | HMMER_INCY |
| | | | | | Tumor necrosis factor receptor/nerve: C105-C143, C62-C103, C146-C186, C26-C59 | HMMER_SMART |
| | | | | | TNFR/NGFR cysteine-rich region: C26-C59, C62-C103, C105-C143, C146-C186 | HMMER_PFAM |
| | | | | | TNFR/NGFR family cysteine-rich region proteins BL00652: C37-L47, G95-C105 | BLIMPS_BLOCKS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | CD40L RECEPTOR PRECURSOR BCELL SURFACE ANTIGEN CD40 BP50 CDW40 GLYCOPROTEIN PD154353: P61-T104 | BLAST_PRODOM |
| | | | | | CD40L RECEPTOR PRECURSOR BCELL SURFACE ANTIGEN CD40 BP50 CDW40 GLYCOPROTEIN TRANSMEMBRANE REPEAT SIGNAL PD059682: M1-C59 | BLAST_PRODOM |
| | | | | | RECEPTOR ACTIVATOR OF NFKAPPAB RANK PD173848: C8-C103 | BLAST_PRODOM |
| | | | | | RECEPTOR FACTOR TUMOR NECROSIS HOMOLOG II PROTEIN PRECURSOR REPEAT SIGNAL PD149629: C105-T165 | BLAST_PRODOM |
| | | | | | TNFR/NGFR FAMILY CYSTEINE-RICH REGION DM00218\|P25942\|99-178: C99-T179 | BLAST_DOMO |
| | | | | | TNFR/NGFR FAMILY CYSTEINE-RICH REGION DM00218\|P25942\|22-97: P22-E98 | BLAST_DOMO |
| | | | | | TNFR/NGFR FAMILY CYSTEINE-RICH REGION DM00218\|P27512\|99-178: T99-T179 | BLAST_DOMO |
| | | | | | TNFR/NGFR FAMILY CYSTEINE-RICH REGION DM00218\|P27512\|22-97: C26-E98 | BLAST_DOMO |
| | | | | | EGF-like domain signature 2: C103-C116 | MOTIFS |
| | | | | | TNFR/NGFR family cysteine-rich region signature: C26-C59 | MOTIFS |
| 23 | 7501754CD1 | 460 | S134 S207 S276 S318 S349 T156 T157 T286 | N130 N205 N284 N355 | signal_cleavage: M1-G56 | SPSCAN |
| | | | | | Cytosolic domains: R68-G87, K237-K240, P414-H460<br>Transmembrane domains: L45-I67, G88-Y110, W214-A236, W241-L263, G391-L413Non-cytosolic<br>domains: M1-L44, G111-R213, E264-E390 | TMHMMER |
| | | | | | TWEETY F42E11.2 PROTEIN PD043235: L19-S426 | BLAST_PRODOM |
| 24 | 7510517CD1 | 218 | S45 S160 S187 S202 S205 Y55 | N7 N177 | signal_cleavage: M27-A78 | SPSCAN |
| | | | | | 7 transmembrane receptor (rhodopsin family): G34-L218 | HMMER_PFAM |
| | | | | | Cytosolic domains: C43-T53, E116-L135<br>Transmembrane domains: P20-L42, F54-T76, T96-V115, A136-L158<br>Non-cytosolic domains: M1-S19, I77-S95, G159-L218 | TMHMMER |
| | | | | | G-protein coupled receptors proteins BL00237: W85-A124" | BLIMPS_BLOCKS |
| | | | | | G-protein coupled receptors signature: F97-Y144 | PROFILESCAN |
| | | | | | Prostaglandin receptor signature PR00428: T22-V33, G68-Y80, A136-L149 | BLIMPS_PRINTS |
| | | | | | Prostanoid EP4 receptor signature PR00586: S2-T22, C43-G60, M81-F102, N122-T139, F171-Y191 | BLIMPS_PRINTS |
| | | | | | RECEPTOR PROSTAGLANDIN E2 EP4 SUBTYPE<br>PROSTANOID PGE G-PROTEIN COUPLED TRANSMEMBRANE<br>PD014814: M1-E51 | BLAST_PRODOM |
| | | | | | PROSTAGLANDIN; SUBTYPE; EP3; PROSTACYCLIN<br>DM00355\|P35408\|11-344: S11-V200<br>DM00355\|P43119\|7-307: P20-R212<br>DM00355\|P43253\|36-335: P20-C211<br>DM00355\|S52078\|36-335: P20-C211 | BLAST_DOMO |
| | | | | | G-protein coupled receptors signature: S105-I121 | MOTIFS |
| 25 | 7511014CD1 | 297 | S94 S144 T148 Y201 | N4 N19 | Signal Peptide: M3-C22, M3-T24 | HMMER |
| | | | | | 7 transmembrane receptor (rhodopsin family): S43-Y281 | HMMER_PFAM |
| | | | | | Cytosolic domains: M1-L28, V89-C108, H174-L202, L272-E297<br>Transmembrane domains: S29-L51, F66-A88, S109-I131, H151-G173, L203-I225, I249-I271 | TMHMMER |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | Non-cytosolic domains: M52-S65, E132-K150, T226-V248 | |
| | | | | | G-protein coupled receptors proteins BL00237: F101-P140, S242-Y268 | BLIMPS_BLOCKS |
| | | | | | G-protein coupled receptors signature: F111-F162 | PROFILESCAN |
| | | | | | Prostaglandin receptor signature PR00428: G80-Y92, S206-C219 | BLIMPS_PRINTS |
| | | | | | Thromboxane receptor signature PR00429: G72-G85, F111-G126, H174-N189, E197-G214 | BLIMPS_PRINTS |
| | | | | | Prostaglandin F receptor signature PR00855: S2-Q23, E25-V39, K53-L68, I171-T184, Y188-F205, L228-H244 | BLIMPS_PRINTS |
| | | | | | PROSTAGLANDIN F2-ALPHA RECEPTOR PROSTANOID FP PGF PGF2 ALPHA G-PROTEIN COUPLED PD012201: M1-F66 PD012850: H174-Y201 | BLAST_PRODOM |
| | | | | | PROSTAGLANDIN; SUBTYPE; EP3; PROSTACYCLIN DM00355\|P43118\|20-319: T20-W293 DM00355\|S51281\|20-319: T20-W293 DM00355\|P37289\|20-319: T20-L266 DM00355\|P34995\|26-365: I35-R238, R238-L266 | BLAST_DOMO |
| | | | | | G-protein coupled receptors signature: C121-V137 | MOTIFS |
| 26 | 7506687CD1 | 917 | S199 S260 S509 S545 S555 S625 S646 S793 S834 S870 T173 T185 T203 T283 T411 T661 T720 T783 T856 Y142 Y341 | N31 N334 N543 | Signal Peptide: M1-T19 | HMMER |
| | | | | | Plexin repeat: S481-L534, R636-P682 | HMMER_PFAM |
| | | | | | domain found in Plexins, Semaphorins and Integrins: S481-L534, D628-P678 | HMMER_SMART |
| | | | | | RECEPTOR KIAA0407 SEMAPHORIN PD184600: M1-H465 PD145279: K663-L882 | BLAST_PRODOM |
| | | | | | PLEXIN PROTEIN PRECURSOR SIGNAL KIAA0407 K04B12.1 TRANSMEMBRANE SEX RECEPTOR GLYCOPROTEIN PD010132: P541-T708 | BLAST_PRODOM |
| | | | | | RGD cell attachment sequence: R872-D874 | MOTIFS |
| 27 | 7510621CD1 | 224 | S120 S216 S219 T138 | N116 N136 N158 | signal_cleavage: M7-G74 | SPSCAN |
| | | | | | Signal Peptide: M1-A25, M1-G32, M1-A35, M7-A25, M7-G27, M7-A30, M7-V31 | HMMER |
| | | | | | Tetraspanin family: K11-I217 | HMMER_PFAM |
| | | | | | Cytosolic domains: M1-F12, C73-N188 Transmembrane domains: L13-A35, G50-C72, V189-C211 Non-cytosolic domains: Q36-P49, C212-M224 | TMHMMER |
| | | | | | Transmembrane 4 family proteins BL00421: K8-V26, V56-R94, M125-N136, V151-C156, N188-I217 | BLIMPS_BLOCKS |
| | | | | | Transmembrane 4 family signature: T48-E100 | PROFILESCAN |
| | | | | | Transmembrane four family signature PR00259: F12-A35, G50-C76, V191-I217 | BLIMPS_PRINTS |
| | | | | | TRANSMEMBRANE GLYCOPROTEIN SIGNAL ANCHOR PROTEIN ANTIGEN MEMBRANE PHOTORECEPTOR VISION CD9 CELL PD000920: K11-S145, Y80-C163, C163-I217 | BLAST_PRODOM |
| | | | | | TRANSMEMBRANE 4 FAMILY DM00947\|P08962\|1-232: A2-G220 DM00947\|S43511\|2-233: A2-G220 DM00947\|P41732\|2-238: C9-I217 DM00947\|P27591\|3-214: G6-I217 | BLAST_DOMO |
| | | | | | Transmembrane 4 family signature: G61-M83 | MOTIFS |
| 28 | 7505533CD1 | 114 | S9 S28 T26 | | Signal Peptide: M1-S20 | HMMER |
| | | | | | Cornichon protein: E2-L110 | HMMER_PFAM |
| | | | | | Cytosolic domains: M1-V4, P76-L114 Transmembrane domains: V5-L27, I53-L75 Non-cytosolic domain: S28-L52 | TMHMMER |
| | | | | | C5A-anaphylatoxin receptor signature PR00426: L11-F23 | BLIMPS_PRINTS |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | PROTEIN TRANSMEMBRANE CORNICHON DEVELOPMENTAL CORNICHON-LIKE T09E8.3 ER-DERIVED VESICLES ERV14 ENDOPLASMIC PD008226: F6-R84 | BLAST_PRODOM |
| | | | | | CORNICHON DM04292\|P53173\|1-137: M1-Q87 DM04292\|P38312\|1-141: V5-T8 | BLAST_DOMO |
| 29 | 7511220CD1 | 181 | S5 S143 T172 Y32 | | signal_cleavage: M1-A21 | SPSCAN |
| | | | | | Signal Peptide: M1-A21, M1-L22, M1-R24, M1-D28 | HMMER |
| | | | | | Cytosolic domains: M1-C4, I55-R60, T172-K181 Transmembrane domains: S5-L22, Y32-T54, Y61-Y83, H149-F171 Non-cytosolic domains: E23-G31, L84-L148 | TMHMMER |
| 30 | 7510967CD1 | 1753 | S167 S219 S363 S381 S430 S471 S562 S614 S722 S883 S886 S1034 S1164 S1291 S1311 S1350 S1377 S1389 S1411 S1448 S1453 S1479 S1503 S1508 S1565 S1589 S1605 S1634 S1643 S1644 S1719 T233 T432 T434 T590 T621 T791 T862 T904 T939 T950 T998 T1001 T1012 T1148 T1218 T1254 T1336 T1358 T1459 T1715 Y409 Y1442 | N71 N165 N231 N303 N315 N766 N971 N1309 N1329 N1578 N1669 | Ankyrin repeat: C37-L69, G103-L135, D236-R268, Y170-A202, D335-K367, S269-Q301, D70-M102, Y137-K169, N203-K235, D302-K334, K368-R400 | HMMER_PFAM |
| | | | | | ankyrin repeats: C37-L66, G103-V132, Y170-Q199, D236-I265, D335-A364, S269-I298, Y137-C166, D70-H99, D302-I331, N203-L232, K368-Y399 | HMMER_SMART |
| | | | | | Cytosolic domains: F519-N524, R682-H687 Transmembrane domains: F496-A518, L525-G547, P659-F681, L688-L707 Non-cytosolic domains: M1-L495, G548-L658, N708-L1753 | TMHMMER |
| | | | | | Ankyrin repeat signature PR01415: G171-H183, N348-A360 | BLIMPS_PRINTS |
| | | | | | Ank repeat proteins. PF00023: L42-L57, G369-R378 | BLIMPS_PFAM |
| | | | | | Domain present in ZO-1 and Unc5-like netrin receptor PF00791: L42-N96, L354-P392, L983-D1025 | BLIMPS_PFAM |
| | | | | | REPEAT PROTEIN ANK NUCLEAR ANKYR. PD00078: D366-R378 | BLIMPS_PRODOM |
| | | | | | F36H1.2 PROTEIN PD148722: D267-K304 K361-P1082 L1189-R1252 | BLAST_PRODOM |
| | | | | | Cell attachment sequence: R1436-D1438 | MOTIFS |
| | | | | | ATP/GTP-binding site motif A (P-loop): A467-S474 | MOTIFS |
| 31 | 7511298CD1 | 786 | S50 S185 S243 S283 S307 S329 S371 S384 S394 S418 S423 S451 S453 S602 T57 T61 T105 T113 T159 T205 T670 | N33 N38 N108 N322 N357 N364 N404 N471 N774 | signal_cleavage: M1-T20 | SPSCAN |
| | | | | | Signal Peptide: M1-T20 | HMMER |
| | | | | | 7 transmembrane receptor (Secretin family): D495-V744 | HMMER_PFAM |
| | | | | | EGF-like domain: C120-C158, C164-G197, | HMMER_PFAM |

TABLE 3-continued

<table>
<tr><th>SEQ ID NO:</th><th>Incyte Polypeptide ID</th><th>Amino Acid Residues</th><th>Potential Phosphorylation Sites</th><th>Potential Glycosylation Sites</th><th>Signature Sequences, Domains and Motifs</th><th>Analytical Methods and Databases</th></tr>
<tr><td></td><td></td><td></td><td></td><td></td><td>C68-G102, C26-P58</td><td></td></tr>
<tr><td></td><td></td><td></td><td></td><td></td><td>Latrophilin/CL-1-like GPS domain: Q442-V493</td><td>HMMER_PFAM</td></tr>
<tr><td></td><td></td><td></td><td></td><td></td><td>Epidermal growth factor-like domain: E119-T159, E163-E208, E67-Q115, G25-D63</td><td>HMMER_SMART</td></tr>
<tr><td></td><td></td><td></td><td></td><td></td><td>Calcium-binding EGF-like domain: D116-T159, D160-E208, D64-Q115</td><td>HMMER_SMART</td></tr>
<tr><td></td><td></td><td></td><td></td><td></td><td>G-protein-coupled receptor proteolytic site: Q442-V493</td><td>HMMER_SMART</td></tr>
<tr><td></td><td></td><td></td><td></td><td></td><td>Cytosolic domains: Q527-T532, F590-L601, W667-K685, N741-I786<br>Transmembrane domains: V504-I526, I533-I552, A567-Y589, S602-I624, L644-V666, A686-L708, L718-L740<br>Non-cytosolic domains: M1-R503, E553-V566, Y625-F643, F709-V717</td><td>TMHMMER</td></tr>
<tr><td></td><td></td><td></td><td></td><td></td><td>G-protein coupled receptors family 2 (secretin-like) IPB000832: G505-A550, C563-L588, G610-Y634, W645-S674, L689-I710, C727-V755</td><td>BLIMPS_BLOCKS</td></tr>
<tr><td></td><td></td><td></td><td></td><td></td><td>Calcium-binding EGF-like domain IPB001881: C42-S52, C133-C144</td><td>BLIMPS_BLOCKS</td></tr>
<tr><td></td><td></td><td></td><td></td><td></td><td>Laminin-type EGF-like (LE) domain IPB002049: A41-F51, T132-F148</td><td>BLIMPS_BLOCKS</td></tr>
<tr><td></td><td></td><td></td><td></td><td></td><td>EMR1 hormone receptor signature PR01128: K450-G468, V523-C540, S621-C635, D679-L700</td><td>BLIMPS_PRINTS</td></tr>
<tr><td></td><td></td><td></td><td></td><td></td><td>CD97 protein signature PR01278: C26-C42, G96-Q115, D204-H222, H222-D239, Q280-P297, K298-E317, R331-E343, M358-K373, V388-T406, H480-D495, E553-H571, R594-I609, K668-L683</td><td>BLIMPS_PRINTS</td></tr>
<tr><td></td><td></td><td></td><td></td><td></td><td>CD97 LEUCOCYTE ANTIGEN PRECURSOR G-PROTEIN-COUPLED RECEPTOR TRANSMEMBRANE GLYCOPROTEIN EGF-LIKE<br>PD040384: W192-Q389<br>PD028353: M1-C114<br>PD005792: A752-I786</td><td>BLAST_PRODOM</td></tr>
<tr><td></td><td></td><td></td><td></td><td></td><td>RECEPTOR TRANSMEMBRANE G-PROTEIN-COUPLED GLYCOPROTEIN PRECURSOR SIGNAL TYPE POLYPEPTIDE ALTERNATIVE<br>PD000752: Q477-W751</td><td>BLAST_PRODOM</td></tr>
<tr><td></td><td></td><td></td><td></td><td></td><td>HORMONE; EMR1; LEUCOCYTE; ANTIGEN;<br>DM05221|I37225|347-738: R391-E783<br>DM05221|P48960|347-738: R391-E783<br>DM05221|A57172|465-886: E408-T768</td><td>BLAST_DOMO</td></tr>
<tr><td></td><td></td><td></td><td></td><td></td><td>LEUCOCYTE; ANTIGEN; CD97;<br>DM08257|P48960|171-254: W215-G299</td><td>BLAST_DOMO</td></tr>
<tr><td></td><td></td><td></td><td></td><td></td><td>Aspartic acid and asparagine hydroxylation site: C82-C93, C133-C144, C177-C188</td><td>MOTIFS</td></tr>
<tr><td></td><td></td><td></td><td></td><td></td><td>Calcium-binding EGF-like domain pattern signature: D64-C91, D116-C142, D160-C186</td><td>MOTIFS</td></tr>
<tr><td></td><td></td><td></td><td></td><td></td><td>G-protein coupled receptors family 2 signature 2: Q729-V744</td><td>MOTIFS</td></tr>
<tr><td>32</td><td>7510937CD1</td><td>1328</td><td>S75 S110 S161<br>S188 S206 S212</td><td>N172 N435 N772<br>N904 N1059<br>N1234</td><td>Cytosolic domain: M1-S6 Transmembrane domain: A7-M29 Non-cytosolic domain: K30-E1328</td><td>TMHMMER</td></tr>
<tr><td></td><td></td><td></td><td>S213 S290 S297<br>S322 S323 S397</td><td>N1300</td><td>Tropomyosin IPB000533: L462-E498, K612-Q655, H511-E565</td><td>BLIMPS_BLOCKS</td></tr>
<tr><td></td><td></td><td></td><td>S625 S632 S694<br>S794 S812 S906</td><td></td><td>PROTEIN KINECTIN CG1 KIAA0004 A COILEDCOIL PD017436: M1-K283</td><td>BLAST_PRODOM</td></tr>
<tr><td></td><td></td><td></td><td>S926 S957 S975<br>S1002 S1017<br>S1061 S1081</td><td></td><td>PROTEIN KINECTIN ES/130 RIBOSOME RECEPTOR CG1 KIAA0004 A COILEDCOIL PD013824: Q264-E400</td><td>BLAST_PRODOM</td></tr>
<tr><td></td><td></td><td></td><td>S1142 S1156<br>S1215 S1290</td><td></td><td>ES/130 RIBOSOME RECEPTOR PD074881: E1040-E1235</td><td>BLAST_PRODOM</td></tr>
<tr><td></td><td></td><td></td><td>T32 T50 T52<br>T200 T268<br>T273 T275</td><td></td><td>PROTEIN KINECTIN CG1 KIAA0004 A COILEDCOIL PD151414: T401-G467</td><td>BLAST_PRODOM</td></tr>
<tr><td></td><td></td><td></td><td>T364 T463 T466<br>T508 T631 T746<br>T760 T830 T859</td><td></td><td>RIBOSOME; 160K; 180K; DM05457<br>|S32763|1-529: M1-S531<br>|A56734|660-1039: P165-E510</td><td>BLAST_DOMO</td></tr>
<tr><td></td><td></td><td></td><td>T878 T893 T1145<br>T1154 T1276<br>Y503<br>Y1194 Y1216</td><td></td><td>RIBOSOME; 160K; 180K; DM05456<br>|A56734|1041-1479: Q901-E1235<br>|S32763|1001-1356: S1002-L1327<br>|S32763|1001-1356: W1012-E1328</td><td>BLAST_DOMO</td></tr>
<tr><td></td><td></td><td></td><td></td><td></td><td>Leucine zipper pattern: L935-L956, L942-L963</td><td>MOTIFS</td></tr>
</table>

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| 33 | 7511852CD1 | 355 | S77 S129 S174 S221 S254 S283 S305 S309 S318 S326 S337 T39 T73 T119 T298 | N171 N193 N274 | signal_cleavage: M1-A22 | SPSCAN |
| | | | | | Signal Peptide: M1-A20, M1-A22, M1-P24 | HMMER |
| | | | | | TNFR/NGFR cysteine-rich region: C40-C75, C78-C118, C120-C161, C164-C200 | HMMER_PFAM |
| | | | | | Tumor necrosis factor receptor/nerve growth factor receptor: C120-C161, C78-C118, C40-C75, C164-C200 | HMMER_SMART |
| | | | | | TNF-receptor internal cysteine rich domain: C120-C161, C40-C75, C78-C118, C164-C200 | HMMER_INCY |
| | | | | | EGF-like domain IPB000561: C118-C126 | BLIMPS_BLOCKS |
| | | | | | TNFR/NGFR family cysteine-rich region IPB001368: C53-A63, C110-C120 | BLIMPS_BLOCKS |
| | | | | | RECEPTOR TUMOR NECROSIS FACTOR P80 PRECURSOR TNFR2 P75 TRANSMEMBRANE GLYCOPROTEIN PD024155: V149-P166, I190-S355, Q183-T330 | BLAST_PRODOM |
| | | | | | RECEPTOR FACTOR TUMOR NECROSIS HOMOLOG II PROTEIN PRECURSOR REPEAT SIGNAL PD149629: C120-H182 | BLAST_PRODOM |
| | | | | | RECEPTOR P80 TNFALPHA TUMOR NECROSIS FACTOR PRECURSOR TNFR2 P75 TRANSMEMBRANE PD059688: M1-Q51 | BLAST_PRODOM |
| | | | | | TUMOR NECROSIS FACTOR RECEPTOR PRECURSOR BINDING PROTEIN TBPII P80 TNFR2 PD153238: L23-Q51 | BLAST_PRODOM |
| | | | | | TUMOR NECROSIS FACTOR RECEPTOR TYPE 2 DM06946 \|P20333\|195-460: V199-S355 \|P25119\|197-473: S195-V262, D263-S355 | BLAST_DOMO |
| | | | | | TNFR/NGFR FAMILY CYSTEINE-RICH REGION DM00218 \|P20333\|113-193: E113-A194 \|P20333\|35-111: E35-R112 | BLAST_DOMO |
| | | | | | TNFR/NGFR family cysteine-rich region signature: C40-C75, C78-C118 | MOTIFS |
| 34 | 7511077CD1 | 295 | S120 T286 | N34 N243 | TMS membrane protein/tumour differentially expressed protein (TDE): S15-L295 | HMMER_PFAM |
| | | | | | Cytosolic domains: C28-R39, S119-N130, H183-W201, P257-L295 Transmembrane domains: L5-S27, L40-L57, A96-V118, G131-I150, F160-A182, Y202-F224, F239-L256 Non-cytosolic domains: M1-C4, S58-R95, P151-W159, M225-V238 | TMHMMER |
| | | | | | PROTEIN PLACENTAL DIFF33 DEVELOPMENTALLY REGULATED R11H6.2 PD011773: D87-P266 PD018175: C13-E73 | BLAST_PRODOM |
| 35 | 7511576CD1 | 203 | S22 S36 S91 S188 T60 T65 T132 T148 Y197 | N8 N20 | Cytosolic domains: M1-K66, T158-S203 Transmembrane domains: L67-I89, A135-L157 Non-cytosolic domain: L90-K134 | TMHMMER |
| 36 | 7511492CD1 | 156 | S146 T4 T45 T94 | N65 N92 | signal_cleavage: M1-G38 | SPSCAN |
| | | | | | Cytosolic domain: M1-K21 Transmembrane domain: L22-F44 Non-cytosolic domain: T45-A156 | TMHMMER |
| | | | | | BONE MARROW STROMAL ANTIGEN 2 BST2 TRANSMEMBRANE GLYCOPROTEIN SIGNALANCHOR PD095137: M1-G116. | BLAST_PRODOM |
| 37 | 7511141CD1 | 170 | S130 T97 | N72 N100 N106 N128 | signal_cleavage: M1-A27 | SPSCAN |
| | | | | | Signal Peptide: M1-A22, M1-S24, M1-A27, M1-A19 | HMMER |
| | | | | | Hormone receptor domain: V63-N128 | HMMER_PFAM |
| | | | | | Domain present in hormone receptors: P62-N132 | HMMER_SMART |
| | | | | | G-protein coupled receptors family 2 (secretin-like) IPB000832: C66-L93 | BLIMPS_BLOCKS |
| | | | | | Vasoactive intestinal peptide receptor 1 signature PR01154: L31-E52, W76-F92 | BLIMPS_PRINTS |
| | | | | | G-protein coupled receptors family 2 signatures: C45-G111 | PROFILESCAN |
| | | | | | Secretin receptor signature PR00490: R2-L14, L18-V34, V37-E52, E52-V63, P90-F104, C123-E136 | BLIMPS_PRINTS |
| | | | | | G-PROTEIN COUPLED RECEPTORS FAMILY 2 DM00378 | BLAST_DOMO |

TABLE 3-continued

| SEQ ID NO: | Incyte Polypeptide ID | Amino Acid Residues | Potential Phosphorylation Sites | Potential Glycosylation Sites | Signature Sequences, Domains and Motifs | Analytical Methods and Databases |
|---|---|---|---|---|---|---|
| | | | | | \|JC2532\|20-434: C20-L139<br>\|P47872\|20-434: C20-L139<br>\|S47631\|30-491: L12-M95 R105-S130<br>\|P41586\|13-446: E40-M95 G101-S130 | |
| | | | | | G-protein coupled receptors family 2 signature 1: C66-P90 | MOTIFS |
| 38 | 7511300CD1 | 801 | S50 S234 S292 S332 S356 S378 S420 S433 S443 S467 S472 S500 S502 S651 T57 T61 T105 T113 T205 T254 T719 | N33 N38 N108 N203 N371 N406 N413 N453 N520 | signal_cleavage: M1-T20 | SPSCAN |
| | | | | | Signal Peptide: M1-T20 | HMMER |
| | | | | | 7 transmembrane receptor (Secretin family): D544-A793 | HMMER_PFAM |
| | | | | | EGF-like domain: C120-C158, C213-G246, C164-P199, C68-G102, C26-P58 | HMMER_PFAM |
| | | | | | Latrophilin/CL-1-like GPS domain: Q491-V542 | HMMER_PFAM |
| | | | | | Epidermal growth factor-like domain.: E119-T159, E163-E208, G25-D63, E67-Q115, E212-E257 | HMMER_SMART |
| | | | | | Calcium-binding EGF-like domain: D116-T159, D160-E208, D209-E257, D64-Q115 | HMMER_SMART |
| | | | | | G-protein-coupled receptor proteolytic site: Q491-V542 | HMMER_SMART |
| | | | | | Cytosolic domains: Q576-T581, Q646-S651, K717-R736, C787-I801<br>Transmembrane domains: V553-I575, I582-I601, F623-F645, T652-Y674, W694-W716, A737-I759, S764-H786 Non-cytosolic domains: M1-R552, E602-C622, S675-L693, F760-R763 | TMHMMER |
| | | | | | Calcium-binding EGF-like domain IPB001881: C142-P152, C133-C144 | BLIMPS_BLOCKS |
| | | | | | Laminin-type EGF-like (LE) domain IPB002049: A41-F51 A41-F51 | BLIMPS_BLOCKS |
| | | | | | G-protein coupled receptors family IPB000832: G554-A599, C612-L637, G659-S683, W694-S723, L738-I759, C776-I801 | BLIMPS_BLOCKS |
| | | | | | Type II EGF-like signature PR00010: D116-C127, G138-F148 | BLIMPS_PRINTS |
| | | | | | EMR1 hormone receptor signature PR01128: K499-G517, V572-C589, S670-C684, D728-L749 | BLIMPS_PRINTS |
| | | | | | CD97 protein signature PR01278: C26-C42, G96-Q115, D253-H271, H271-D288, Q329-P346, K347-E366, R380-E392, M407-K422, V437-T455, H529-D544, E602-H620, R643-I658, K717-L732 | BLIMPS_PRINTS |
| | | | | | CD97 LEUCOCYTE ANTIGEN PRECURSOR GPROTEIN COUPLED RECEPTOR TRANSMEMBRANE GLYCOPROTEIN EGF-LIKE; PD028353: M1-C114<br>PD040384: W192-V210 W241-Q438 | BLAST_PRODOM |
| | | | | | RECEPTOR TRANSMEMBRANE GPROTEIN COUPLED GLYCOPROTEIN PRECURSOR SIGNAL TYPE POLYPEPTIDE ALTERNATIVE PD000752: Q526-K792 | BLAST_PRODOM |
| | | | | | HORMONE; EMR1; LEUCOCYTE; ANTIGEN; DM05221<br>\|I37225\|347-738: R440-K792<br>\|A57172\|465-886: E457-N790<br>\|P48960\|347-738: R440-K792 | BLAST_DOMO |
| | | | | | LEUCOCYTE; ANTIGEN; CD97; DM08257<br>\|P48960\|171-254: W264-G348 | BLAST_DOMO |
| | | | | | Calcium-binding EGF-like domain pattern signature: D64-C91, D116-C142, D160-C186, D209-C235 | MOTIFS |

TABLE 4

| Polynucleotide SEQ ID NO:/ Incyte ID/Sequence Length | Sequence Fragments |
|---|---|
| 39/3048626CB1/ 2714 | 1-631, 10-543, 15-646, 80-703, 157-686, 190-754, 205-683, 205-714, 205-741, 218-917, 224-720, 236-885, 256-871, 310-981, 335-894, 335-1009, 351-998, 372-915, 374-1057, 375-948, 378-883, 378-1017, |

TABLE 4-continued

| Polynucleotide SEQ ID NO:/ Incyte ID/Sequence Length | Sequence Fragments |
|---|---|
| | 382-1063, 384-1049, 385-1037, 396-1028, 404-1011, 431-1040, 438-1035, 460-1045, 462-898, 492-1178, 502-1222, 519-1154, 527-714, 533-1174, 553-1057, 558-1195, 566-1041, 566-1190, 575-895, 586-869, 586-1187, 586-1253, 605-1039, 605-1305, 616-1324, 623-1248, 625-1251, 638-1215, 641-1230, 649-1061, 650-1170, 662-1329, 665-1253, 668-1220, 682-1265, 685-845, 687-1258, 695-1360, 703-1354, 704-1230, 709-1240, 724-1314, 726-1402, 735-1335, 747-1435, 751-1329, 777-1430, 781-1263, 787-1233, 789-1532, 794-1549, 804-1351, 812-1353, 824-1138, 824-1375, 824-1386, 824-1399, 824-1402, 858-1314, 861-1378, 911-1556, 916-1547, 930-1551, 935-1427, 935-1643, 936-1617, 946-1628, 968-1639, 974-1481, 977-1549, 1001-1671, 1017-1671, 1031-1640, 1037-1588, 1038-1217, 1038-1361, 1043-1558, 1044-1651, 1087-1669, 1095-1463, 1096-1671, 1102-1671, 1109-1408, 1109-1523, 1151-1671, 1576-2268, 2045-2308, 2178-2714 |
| 40/2684425CB1/ 2858 | 1-298, 19-268, 29-320, 37-883, 55-575, 55-704, 94-356, 99-613, 110-755, 237-1049, 445-1099, 509-1105, 533-785, 533-954, 541-785, 541-813 541-1174, 544-1223, 546-809, 664-955, 666-1270, 668-1274, 719-1337, 723-1303, 783-1358, 797-1357, 802-1274, 813-1417, 820-1134, 832-1439, 854-1362, 881-1235, 916-1412, 920-1100, 984-1630, 1013-1675, 1015-1272, 1047-1664, 1087-1706, 1106-1704, 1119-1621, 1129-1722, 1215-1749, 1235-1533, 1235-1815, 1304-1886, 1329-1921, 1347-1587, 1360-1621, 1362-1638, 1362-1740, 1369-1872, 1443-1934, 1443-1984, 1445-2045, 1569-2199, 1596-1761, 1599-1980, 1627-1898, 1632-1861, 1639-2223, 1649-2167, 1675-1938, 1675-2151, 1681-1950, 1746-1901, 1753-2427, 1770-2010, 1787-2397, 1904-2180, 1904-2581, 1951-2331, 2181-2777, 2224-2782, 2275-2521, 2310-2790, 2317-2817, 2317-2832, 2413-2819, 2610-2858, 2650-2858, 2714-2855 |
| 41/7505960CB1/ 2445 | 1-315, 1-340, 1-457, 1-479, 1-487, 1-640, 1-646, 1-2239, 2-597, 3-330, 3-626, 5-518, 5-551, 5-620, 8-260, 8-493, 8-521, 8-637, 10-536, 11-571, 12-281, 14-111, 17-274, 18-285, 19-194, 19-259, 19-620, 19-630, 19-636, 20-273, 22-305, 22-584, 24-288, 24-479, 25-288, 25-397, 77-325, 91-364, 91-578, 104-561, 106-868, 131-433, 141-676, 161-784, 171-487, 171-489, 188-330, 194-708, 197-784, 210-411, 210-853, 219-485, 266-879, 269-625, 271-901, 282-814, 294-561, 294-899, 295-805, 298-531, 300-581, 312-861, 335-920, 335-927, 343-962, 387-1114, 418-1146, 450-1185, 450-1289, 454-1009, 457-703, 461-1147, 464-1051, 478-827, 479-611, 482-1072, 532-1163, 534-1057, 538-1216, 545-1070, 583-1165, 585-1107, 602-1241, 630-1190, 645-1202, 656-1237, 657-1243, 658-1054, 663-859, 673-1270, 691-1289, 691-1302, 695-1223, 720-1301, 770-1062, 776-1242, 787-1028, 808-991, 843-976, 865-1275, 902-1017, 903-1276, 922-1190, 932-1073, 955-1253, 961-1222, 964-1246, 966-1214, 971-1208, 985-1245, 1013-1286, 1028-1313, 1040-1313, 1058-1313, 1067-1297, 1247-1515, 1247-1592, 1247-1643, 1247-1646, 1247-1803, 1247-1836, 1254-1876, 1310-1603, 1310-1780, 1310-1785, 1310-1880, 1310-1949, 1312-1586, 1312-1808, 1313-1534, 1313-1877, 1324-1642, 1345-1848, 1356-1717, 1357-1749, 1359-1618, 1369-1637, 1369-1808, 1369-1917, 1371-1884, 1373-2020, 1375-1649, 1379-1588, 1379-1918, 1382-1586, 1385-1946, 1390-1619, 1398-1935, 1400-1777, 1405-1671, 1405-1943, 1408-1775, 1410-1902, 1413-1902, 1428-2133, 1431-2018, 1435-1622, 1442-1758, 1448-2178, 1456-1719, 1456-1764, 1467-1738, 1467-1758, 1474-1967, 1474-2071, 1477-1891, 1479-1603, 1483-1753, 1487-2007, 1492-1762, 1497-2191, 1498-1923, 1507-1769, 1507-1888, 1510-1776, 1511-1758, 1516-1792, 1521-2143, 1526-1853, 1536-1808, 1540-2085, 1542-2053, 1544-2231, 1548-2011, 1548-2083, 1551-1951, 1551-2218, 1552-1991, 1552-2124, 1554-1822, 1554-2378, 1570-1859, 1580-1780, 1580-2360, 1604-1928, 1607-2098, 1608-2229, 1610-1824, 1620-1885, 1626-1895, 1632-1996, 1634-1890, 1634-1898, 1636-2284, 1637-1904, 1637-1915, 1638-2231, 1655-2372, 1658-2207, 1673-2202, 1673-2241, 1677-2269, 1686-2273, 1690-1931, 1691-1934, 1693-2015, 1697-2355, 1701-2147, 1703-2063, 1705-1922, 1706-2141, 1713-2321, 1714-2359, 1715-2146, 1731-1963, 1743-2032, 1744-2102, 1755-1960, 1759-2271, 1760-2163, 1761-2012, 1765-2039, 1765-2040, 1767-2176, 1776-2251, 1782-2421, 1787-2046, 1787-2278, 1788-2187, 1791-2244, 1794-1985, 1796-2375, 1799-2060, 1799-2101, 1815-2388, 1818-2419, 1820-2359, 1821-2417, 1823-2443, 1827-2061, 1828-2383, 1830-2416, 1831-2358, 1835-2422, 1844-2101, 1849-2062, 1849-2434, 1853-2157, 1862-2357, 1862-2442, 1862-2444, 1873-2283, 1877-2158, 1878-2419, 1886-2033, 1888-2438, 1898-2187, 1903-2444, 1911-2221, 1916-2418, 1927-2101, 1929-2324, 1931-2324, 1933-2101, 1936-2445, 1937-2417, 1941-2101, 1941-2182, 1944-2239, 1959-2161, 1961-2222, 1966-2233, 1981-2399, 1983-2101, 1989-2222, 1989-2425, 1991-2101, 1996-2212, 2002-2101, 2008-2101, 2017-2101, 2021-2077, 2021-2087, 2023-2135, |

TABLE 4-continued

| Polynucleotide SEQ ID NO:/ Incyte ID/Sequence Length | Sequence Fragments |
|---|---|
| | 2028-2101, 2029-2101, 2030-2101, 2031-2101, 2033-2101, 2040-2101, 2043-2322, 2046-2101, 2046-2125, 2118-2147 |
| 42/7507021CB1/ 1248 | 1-137, 1-223, 1-250, 1-357, 1-390, 1-424, 1-433, 1-532, 1-545, 1-573, 1-1248, 3-584, 4-584, 5-224, 5-585, 11-244, 11-299, 11-530, 11-538, 11-554, 11-579, 24-585, 28-585, 56-537, 93-585, 115-328, 115-565, 115-715, 115-767, 116-258, 117-258, 137-359, 137-585, 144-585, 152-566, 203-501, 210-456, 251-513, 292-448, 577-1108, 585-730, 585-816, 585-854, 590-1226, 593-1248, 627-1156, 628-841, 629-1248, 640-1248, 647-868, 648-767, 657-1082, 661-767, 677-1132, 678-912, 678-1197, 699-908, 702-836, 715-1119, 726-1246, 741-767, 743-1248, 746-1228, 748-1247, 755-1248, 762-1248, 804-944, 818-1248, 829-1248, 830-1248, 838-1248, 839-1248, 845-1069, 853-1248, 862-928, 892-1228, 894-1248, 906-1248, 918-1248, 926-1248, 928-1248, 962-1248, 973-1248, 979-1248, 1023-1238, 1025-1248, 1048-1248, 1104-1248 |
| 43/7509099CB1/ 1989 | 1-243, 1-1842, 10-761, 10-767, 37-242, 92-365, 374-712, 385-1112, 409-1028, 409-1130, 425-945, 453-1317, 466-1051, 585-1182, 588-1290, 691-1682, 698-1682, 734-1681, 751-1368, 757-1018, 770-1438, 788-1682, 821-1681, 825-1352, 837-1682, 838-1682, 840-1682, 841-1682, 842-1681, 843-1681, 847-1438, 856-1682, 863-1682, 877-1681, 878-1110, 890-1681, 890-1682, 899-1681, 905-1681, 906-1681, 906-1682, 918-1438, 985-1681, 991-1677, 993-1384, 1041-1438, 1055-1752, 1134-1729, 1172-1736, 1317-1910, 1383-1686, 1412-1675, 1429-1633, 1475-1989, 1681-1924, 1686-1855, 1733-1989, 1833-1866 |
| 44/7509361CB1/ 1863 | 1-242, 1-268, 1-361, 1-1863, 3-207, 4-242, 4-261, 5-105, 5-241, 6-258, 7-193, 7-263, 7-284, 7-303, 7-445, 8-294, 8-433, 9-256, 12-237, 15-270, 25-232, 28-736, 28-815, 28-843, 28-863, 29-755, 39-275, 39-282, 39-321, 39-323, 40-280, 40-730, 46-309, 46-321, 46-434, 47-475, 48-694, 50-536, 50-607, 50-632, 53-662, 54-286, 54-357, 54-363, 54-367, 54-639, 55-302, 57-272, 57-329, 57-684, 59-171, 60-305, 61-324, 61-340, 61-364, 62-300, 64-363, 69-317, 69-347, 70-540, 72-445, 74-359, 74-745, 76-712, 79-210, 79-372, 79-382, 80-276, 82-198, 82-303, 83-207, 83-301, 84-651, 90-294, 90-372, 92-281, 96-626, 97-391, 99-400, 102-406, 103-645, 110-702, 111-294, 113-253, 123-703, 129-420, 136-445, 146-347, 153-630, 183-816, 200-261, 206-396, 207-581, 239-734, 239-780, 239-876, 239-877, 239-952, 257-445, 271-679, 280-869, 294-877, 311-532, 354-590, 446-465, 446-800, 446-825, 446-877, 467-722, 467-746, 527-833, 554-679, 566-803, 573-784, 573-786, 585-816, 612-841, 612-856, 658-1441, 692-860, 875-1040, 875-1085, 875-1118, 875-1191, 875-1306, 875-1523, 875-1569, 875-1577, 880-1034, 881-1149, 884-1441, 897-1441, 899-1154, 900-1173, 918-1152, 920-1159, 935-1167, 942-1148, 952-1159, 952-1219, 957-1117, 961-1557, 962-1205, 968-1270, 973-1596, 974-1243, 994-1258, 997-1089, 1000-1259, 1011-1315, 1028-1403, 1040-1275, 1058-1299, 1078-1337, 1085-1351, 1112-1309, 1117-1335, 1123-1388, 1154-1815, 1155-1846, 1160-1848, 1175-1441, 1180-1778, 1187-1853, 1203-1457, 1209-1482, 1213-1514, 1219-1510, 1223-1496, 1238-1501, 1240-1502, 1240-1507, 1253-1478, 1264-1824, 1271-1848, 1276-1772, 1281-1855, 1291-1565, 1297-1537, 1302-1594, 1302-1776, 1304-1777, 1304-1851, 1314-1539, 1314-1658, 1315-1539, 1315-1557, 1316-1466, 1319-1612, 1323-1562, 1323-1797, 1324-1579, 1327-1863, 1328-1790, 1337-1577, 1337-1585, 1337-1594, 1339-1718, 1340-1579, 1342-1602, 1347-1514, 1347-1584, 1351-1789, 1354-1790, 1357-1658, 1365-1847, 1366-1837, 1367-1718, 1369-1862, 1377-1526, 1377-1851, 1379-1609, 1379-1806, 1386-1633, 1386-1847, 1386-1855, 1387-1859, 1387-1863, 1389-1655, 1389-1700, 1391-1674, 1394-1657, 1398-1777, 1400-1654, 1402-1854, 1406-1850, 1413-1853, 1418-1682, 1418-1850, 1419-1663, 1421-1669, 1422-1654, 1422-1674, 1424-1851, 1425-1857, 1427-1849, 1432-1825, 1433-1848, 1435-1685, 1436-1850, 1438-1848, 1440-1848, 1443-1848, 1447-1602, 1452-1689, 1457-1848, 1457-1851, 1460-1715, 1469-1715, 1472-1650, 1474-1839, 1482-1851, 1483-1862, 1487-1863, 1491-1848, 1492-1863, 1495-1850, 1502-1789, 1513-1848, 1513-1853, 1514-1851, 1520-1863, 1522-1776, 1522-1809, 1522-1848, 1523-1848, 1526-1846, 1526-1848, 1531-1848, 1537-1848, 1537-1850, 1544-1803, 1550-1863, 1554-1785, 1559-1851, 1562-1846, 1562-1848, 1562-1849, 1564-1800, 1565-1848, 1567-1848, 1572-1852, 1575-1778, 1577-1848, 1584-1843, 1589-1799, 1593-1851, 1602-1848, 1604-1848, 1605-1846, 1605-1848, 1605-1855, 1609-1797, 1620-1863, 1625-1855, 1627-1731, 1631-1846, 1633-1861, 1662-1848, 1662-1850, 1662-1858, 1673-1848, 1678-1848, 1678-1850, 1683-1848, 1687-1848, 1688-1848, 1689-1818, 1689-1851, 1689-1863, 1692-1826, 1692-1848, 1693-1863, 1696-1848, 1696-1861, 1708-1838, 1709-1814, 1711-1853, 1712-1851, 1720-1855, 1723-1840, 1752-1858, 1753-1862, |

TABLE 4-continued

| Polynucleotide SEQ ID NO:/ Incyte ID/Sequence Length | Sequence Fragments |
|---|---|
| | 1753-1863, 1757-1860, 1757-1863, 1765-1863, 1768-1850, 1777-1849, 1784-1851, 1785-1863, 1786-1851, 1794-1848 |
| 45/7506815CB1/ 1734 | 1-1734, 123-827, 309-1275, 443-1275, 464-1274, 466-1274, 540-1275, 547-1274, 613-1274, 866-1096, 866-1180, 866-1348, 866-1363, 866-1395, 866-1431, 866-1484, 866-1543, 866-1650, 866-1658, 904-1221, 940-1731, 971-1541, 973-1367, 974-1371, 975-1222, 975-1331, 975-1440, 975-1595, 988-1284, 988-1563, 998-1607, 1020-1427, 1020-1517, 1051-1566, 1071-1427, 1099-1734, 1103-1362, 1109-1604, 1115-1432, 1152-1408, 1159-1694, 1180-1365, 1206-1635, 1228-1734, 1263-1675, 1264-1560, 1293-1691, 1322-1510, 1331-1734, 1352-1620, 1428-1575, 1466-1709, 1507-1702 |
| 46/7506814CB1/ 1786 | 1-785, 1-825, 1-883, 1-901, 1-902, 1-1786, 87-758, 87-804, 87-813, 87-824, 87-904, 87-980, 88-900, 242-820, 363-1327, 740-1328, 918-1148, 918-1232, 918-1400, 918-1415, 918-1447, 918-1483, 918-1536, 918-1595, 918-1702, 918-1710, 956-1273, 992-1783, 1023-1593, 1025-1419, 1026-1423, 1027-1274, 1027-1383, 1027-1492, 1027-1647, 1040-1336, 1040-1615, 1050-1659, 1072-1479, 1072-1569, 1103-1618, 1123-1479, 1151-1786, 1155-1414, 1161-1656, 1167-1484, 1204-1460, 1211-1746, 1232-1417, 1258-1687, 1280-1786, 1315-1727, 1316-1612, 1345-1743, 1374-1562, 1383-1786, 1404-1672, 1480-1627, 1518-1761, 1559-1754 |
| 47/7506852CB1/ 2193 | 1-2193, 56-668, 56-787, 56-793, 532-1066 |
| 48/7503782CB1/ 3696 | 1-3673, 532-1000, 716-895, 1524-2351, 1525-1791, 1863-2448, 1863-2471, 1888-2305, 1903-2671, 1904-2671, 1939-2201, 1979-2671, 2023-2671, 2187-2671, 2211-2453, 2211-2471, 2321-2671, 2321-2735, 2321-2792, 2366-2627, 2371-2786, 2379-2623, 2420-2503, 2421-2696, 2501-2830, 2575-2752, 2735-3211, 2784-3282, 2848-3200, 2899-3384, 2966-3536, 3033-3535, 3037-3671, 3038-3650, 3040-3289, 3064-3673, 3067-3521, 3095-3194, 3104-3682, 3129-3535, 3132-3696, 3140-3668, 3147-3662, 3149-3673, 3185-3420, 3185-3642, 3187-3659, 3191-3535, 3205-3391, 3205-3673, 3281-3535, 3595-3647 |
| 49/7504647CB1/ 1283 | 1-132, 1-169, 1-297, 1-439, 1-442, 4-814, 4-1260, 10-166, 12-168, 169-419, 169-552, 169-630, 169-702, 180-777, 235-919, 235-1034, 271-791, 277-497, 277-967, 278-501, 286-520, 313-846, 324-882, 332-844, 339-1004, 342-1151, 346-838, 350-806, 354-625, 357-1121, 362-855, 384-949, 412-1250, 418-1250, 424-1087, 431-893, 434-1175, 457-1132, 465-1159, 466-1101, 469-954, 471-872, 472-599, 472-1000, 480-1011, 487-844, 492-933, 502-763, 502-1075, 521-1170, 537-1214, 555-1151, 562-1222, 563-1050, 570-1218, 595-1110, 596-849, 596-1259, 597-1255, 602-883, 603-1175, 612-1222, 614-1067, 622-1065, 626-1218, 628-1207, 652-1143, 653-1182, 685-1222, 690-1222, 694-1153, 698-1222, 701-1222, 704-1010, 705-1148, 707-1222, 713-971, 718-1208, 718-1222, 723-1214, 725-978, 736-1218, 737-1222, 751-1197, 791-1226, 795-1283, 808-1057, 809-833, 810-1226, 811-1275, 836-1222, 841-1222, 875-1275, 891-1133, 910-1250, 910-1254, 951-1257, 999-1221, 1003-1258, 1099-1224 |
| 50/7500424CB1/ 1142 | 1-245, 1-248, 1-325, 1-377, 1-441, 1-463, 1-1142, 7-61, 18-437, 59-134, 59-283, 59-753, 59-761, 59-879, 59-944, 59-955, 60-732, 100-392, 126-1040, 164-1040, 199-1040, 241-1040, 290-563, 388-1040, 401-1040, 425-1040, 467-678, 467-699, 467-714, 467-882, 467-956, 467-968, 467-1040, 467-1058, 467-1083, 467-1119, 467-1123, 468-718, 468-1116, 469-1086, 469-1116, 469-1122, 471-721, 471-1065, 474-1040, 480-658, 484-707, 484-922, 490-750, 490-761, 491-1092, 493-796, 494-760, 495-710, 495-1065, 496-943, 496-1034, 499-694, 500-851, 503-851, 513-1125, 514-720, 514-1072, 515-1118, 516-1002, 528-792, 528-805, 528-1113, 530-745, 530-967, 531-976, 531-1080, 531-1136, 535-1113, 535-1118, 536-820, 539-818, 540-768, 541-784, 543-849, 544-877, 549-867, 552-1116, 556-1142, 559-851, 559-1114, 561-851, 566-1114, 567-853, 575-1142, 579-832, 579-891, 579-1142, 580-851, 585-1123, 586-1114, 587-885, 596-1119, 598-834, 601-1078, 606-851, 608-1117, 609-1040, 611-1129, 614-949, 615-833, 615-865, 615-1142, 622-1121, 623-861, 624-1123, 625-1123, 626-898, 635-979, 636-1115, 636-1142, 644-851, 646-1112, 648-940, 650-1138, 652-1142, 654-1142, 656-1132, 657-1133, 658-851, 662-1131, 664-1142, 668-1142, 679-1142, 680-1142, 686-1132, 690-989, 690-1131, 691-1114, 697-1138, 697-1142, 700-932, 704-1121, 704-1134, 705-1139, 709-1142, 710-1131, 711-1133, 712-1084, 714-1131, 715-1130, 715-1132, 716-1129, 716-1135, 717-1129, 718-1127, 719-1042, 720-1129, 721-1123, 721-1129, 721-1142, 722-1133, 722-1136, 723-1121, 724-1121, 724-1133, 725-984, 726-1132, 727-1132, 729-1129, 729-1132, 730-1128, 733-946, 734-851, 736-1130, 739-983, 739-1042, 739-1121, 740-1000, 741-1120, 742-1129, 744-1114, 745-1135, 750-851, 753-1002, 755-1142, 756-1113, 756-1114, 756-1132, |

TABLE 4-continued

| Polynucleotide SEQ ID NO:/ Incyte ID/Sequence Length | Sequence Fragments |
|---|---|
| | 756-1142, 762-1129, 764-1142, 766-1128, 769-1123, 770-1142, 773-1134, 777-1025, 780-1137, 782-1141, 783-1022, 784-1128, 787-1142, 800-1130, 801-1130, 802-1075, 804-1042, 804-1133, 806-1130, 808-1114, 808-1132, 808-1133, 815-1132, 823-1111, 823-1123, 836-1086, 837-1042, 842-1042, 847-1132, 849-1042, 851-1132, 859-1042, 862-1142, 863-1124, 865-1042, 870-1048, 870-1130, 870-1132, 873-1132, 874-1042, 884-1130, 886-1119, 886-1142, 887-1132, 893-1142, 895-1142, 902-1129, 904-1129, 904-1142, 905-1123, 905-1130, 910-1142, 912-1132, 913-1132, 915-1075, 915-1129, 918-1132, 920-1137, 925-1132, 932-1132, 933-1137, 934-1132, 936-1142, 938-1142, 939-1129, 972-1132, 984-1142, 988-1130, 989-1129, 994-1136, 995-1125, 1004-1142, 1005-1132, 1006-1132, 1022-1142, 1030-1132, 1040-1142, 1068-1142 |
| 51/7500449CB1/ 1477 | 1-261, 7-270, 44-271, 47-1477, 52-163, 52-183, 52-199, 52-271, 60-183, 109-217, 273-761, 447-514, 513-1237, 515-757, 515-923, 515-928, 515-970, 515-1000, 515-1033, 515-1074, 515-1173, 515-1210, 515-1211, 515-1212, 515-1332, 515-1344, 515-1350, 517-1236, 519-1107, 809-1364, 899-1448, 1030-1319, 1177-1417, 1211-1400, 1269-1477, 1282-1477 |
| 52/7503281CB1/ 1097 | 1-665, 1-687, 1-696, 1-719, 1-730, 1-731, 1-738, 1-739, 1-775, 1-817, 1-838, 1-1097, 139-523, 293-1059, 298-1059, 311-1059, 334-1059, 419-1059, 432-1059 |
| 53/7503292CB1/ 1501 | 1-1493, 173-754, 173-769, 173-786, 173-812, 173-822, 173-1016, 175-840, 333-1159, 356-674, 405-1140, 484-1101, 548-715, 661-849, 686-1221, 800-1344, 806-1384, 848-1498, 849-1154, 849-1287, 849-1337, 849-1341, 849-1348, 849-1416, 849-1475, 936-1497, 940-1428, 955-1465, 965-1498, 967-1234, 968-1245, 975-1498, 978-1498, 982-1497, 987-1498, 994-1497, 996-1387, 998-1490, 999-1495, 1019-1501, 1025-1501, 1035-1491, 1037-1418, 1042-1497, 1045-1501, 1052-1495, 1057-1374, 1059-1413, 1062-1245, 1069-1496, 1075-1498, 1091-1501, 1115-1424, 1141-1388, 1144-1462, 1146-1497, 1147-1501, 1157-1424, 1172-1416, 1173-1390, 1179-1487, 1190-1496, 1215-1459, 1231-1380, 1242-1494, 1300-1501, 1310-1424 |
| 54/7503311CB1/ 1613 | 1-1613, 240-338, 240-555, 240-570, 240-632, 240-690, 240-715, 240-739, 240-899, 255-1038, 465-729, 584-1466, 628-723, 902-1132, 913-1441, 968-1499, 1050-1152, 1092-1584 |
| 55/7510384CB1/ 1523 | 1-1523, 68-557, 181-329, 224-318, 237-449, 243-418, 527-1059, 532-1059, 1062-1185 |
| 56/7509976CB1/ 6826 | 1-6826, 693-1218, 709-1289, 866-1146, 866-1217, 1001-1539, 1258-1887, 1857-2171, 1960-2223, 2291-2502, 2419-3005, 2419-3012, 2864-3322, 5428-5856, 5452-5888, 5452-5949, 5454-5984, 5471-5969, 5477-5746, 5494-5753, 5515-6064, 5518-5766, 5528-6062, 5540-6086, 5551-5692, 5553-5800, 5559-6119, 5566-6097, 5570-5821, 5578-5842, 5581-5975, 5589-5848, 5594-6130, 5612-5819, 5612-5881, 5614-6218, 5621-5863, 5645-6069, 5655-6226, 5657-5952, 5720-6221, 5742-6119, 5749-5980, 5780-5954, 5788-6179, 5795-6072, 5826-6004, 5834-6071, 5868-6219, 5871-6150, 5884-5985, 5913-6207, 5935-6232, 5944-6491, 5945-6222, 5952-6542, 5970-6209, 6009-6216, 6013-6272, 6033-6242, 6034-6229, 6054-6573, 6064-6333, 6094-6322, 6101-6408, 6101-6750, 6105-6361, 6147-6424, 6165-6431, 6171-6439, 6183-6406, 6194-6816, 6198-6550, 6200-6759, 6201-6796, 6207-6818, 6210-6467, 6210-6498, 6210-6503, 6212-6822, 6213-6516, 6219-6458, 6248-6501, 6254-6684, 6267-6500, 6267-6795, 6272-6611, 6278-6826, 6317-6570, 6317-6801, 6319-6815, 6326-6532, 6333-6546, 6333-6594, 6341-6778, 6352-6826, 6356-6816, 6362-6820, 6372-6821, 6378-6825, 6387-6816, 6394-6817, 6394-6820, 6397-6645, 6398-6661, 6399-6816, 6401-6542, 6406-6816, 6407-6816, 6409-6815, 6411-6824, 6423-6826, 6431-6703, 6432-6821, 6434-6655, 6435-6821, 6446-6815, 6451-6815, 6456-6746, 6458-6824, 6459-6803, 6460-6739, 6461-6741, 6491-6816, 6505-6821, 6521-6823, 6539-6816, 6558-6826, 6595-6819, 6601-6815, 6614-6818, 6627-6816, 6631-6826, 6638-6821, 6643-6816, 6668-6816, 6669-6808, 6669-6809, 6721-6819, 6724-6826 |
| 57/7510454CB1/ 2481 | 1-270, 1-423, 1-432, 1-447, 1-520, 1-532, 1-535, 1-552, 1-565, 1-568, 1-571, 1-602, 1-605, 1-611, 1-623, 1-631, 1-634, 1-663, 1-2481, 309-1087, 334-1085, 393-1006, 402-1085, 406-1085, 423-1085, 431-1085, 454-1212, 455-1085, 455-1179, 456-1085, 459-1085, 475-1075, 475-1085, 479-1085, 482-733, 482-1085, 497-1073, 530-1465, 531-1347, 531-1409, 558-1343, 558-1437, 558-1505, 562-1417, 720-1661, 748-1661, 752-1661, 825-1661, 825-1663, 827-1661, 827-1663, 829-1661, 886-1663, 895-1136, 895-1195, 895-1302, 895-1391, 895-1475, 895-1477, 895-1485, 895-1513, 895-1523, 898-1595, 905-1544, 964-1165, 965-1523, 976-1661, 988-1563, 1077-1609, 1102-1682, 1150-1706, 1160-1800, 1210-1865, 1277-1856, 1334-1917, 1347-1941, 1351-2015, |

TABLE 4-continued

| Polynucleotide SEQ ID NO:/ Incyte ID/Sequence Length | Sequence Fragments |
|---|---|
| | 1384-1934, 1386-1952, 1390-1978, 1393-1960, 1423-2010, 1463-2048, 1464-2112, 1477-2096, 1482-1992, 1491-2031, 1504-2170, 1517-1912, 1522-2023, 1537-2162, 1547-2481, 1549-1723, 1549-1977, 1549-2251, 1550-2010, 1562-2104, 1614-2282, 1616-2114, 1624-2191, 1626-2218, 1626-2219, 1633-1900, 1637-2170, 1658-1962, 1667-2299, 1670-2043, 1811-2064, 2214-2324, 2222-2313 |
| 58/8017335CB1/ 2512 | 1-2498, 34-594, 62-374, 544-862, 544-932, 544-1013, 544-1021, 544-1063, 544-1073, 544-1082, 544-1092, 544-1114, 544-1120, 544-1123, 544-1131, 560-1147, 856-1581, 856-1589, 907-1529, 909-1500, 1065-1926, 1084-1925, 1092-1926, 1099-1926, 1106-1924, 1106-1926, 1114-1925, 1114-1926, 1135-1924, 1180-1892, 1182-1924, 1208-1549, 1230-1926, 1239-1926, 1304-1925, 1495-1841, 1737-2008, 1747-2330, 1763-2324, 1814-2134, 1823-2345, 1904-2427, 1941-2218, 1966-2461, 1968-2512, 1996-2397, 2039-2512, 2061-2504, 2203-2512, 2206-2484 |
| 59/7510197CB1/ 754 | 1-270, 1-343, 1-552, 1-754 |
| 60/7510055CB1/ 1660 | 1-1660, 113-420, 430-480, 472-685, 544-751, 545-826, 585-1147, 585-1259, 676-817, 676-848, 681-931, 690-883, 720-984, 732-951, 763-1204, 775-1071, 792-1207, 793-1045, 794-1163, 806-1015, 806-1026, 858-1368, 886-1147, 886-1160, 923-1143, 923-1355, 923-1358, 923-1405, 976-1398, 976-1405, 983-1210, 983-1239, 990-1246, 991-1219, 1031-1204, 1039-1207, 1048-1422, 1070-1315, 1092-1295, 1115-1356, 1167-1405, 1228-1315, 1298-1377, 1369-1453, 1400-1489, 1404-1453, 1406-1453, 1410-1453, 1424-1453, 1449-1475, 1449-1479, 1449-1481 |
| 61/7501754CB1/ 2118 | 1-241, 1-271, 1-340, 1-486, 1-625, 2-645, 4-291, 6-667, 13-527, 14-625, 19-678, 19-685, 21-261, 21-1822, 28-272, 33-612, 35-287, 35-656, 45-741, 74-306, 80-309, 146-597, 193-451, 193-705, 233-512, 248-457, 249-833, 260-829, 280-951, 302-583, 318-528, 363-932, 369-813, 385-898, 390-977, 413-978, 415-595, 423-632, 423-632, 423-940, 428-668, 428-693, 429-912, 463-937, 476-1151, 493-953, 498-621, 524-1192, 543-1113, 548-1116, 548-1151, 552-1125, 578-1229, 591-1187, 598-1248, 603-886, 606-1146, 649-1239, 651-900, 664-914, 664-1023, 666-1177, 668-1027, 671-1163, 690-1171, 693-958, 704-1223, 707-1140, 707-1239, 714-1362, 715-1132, 726-1142, 729-1316, 737-1184, 738-1266, 750-1035, 754-1176, 763-1039, 764-1389, 771-1298, 780-1023, 793-1046, 799-1313, 804-1281, 814-1029, 814-1116, 814-1347, 815-895, 815-927, 819-1240, 819-1425, 821-1099, 836-1143, 840-1444, 847-1365, 861-1084, 865-993, 885-1348, 891-1287, 891-1316, 897-1170, 897-1325, 906-1389, 914-1161, 914-1167, 914-1177, 926-1372, 928-1207, 937-1195, 940-1179, 942-1190, 942-1195, 942-1226, 942-1243, 942-1344, 945-1286, 950-1209, 950-1217, 950-1520, 953-1428, 953-1629, 969-1230, 972-1073, 972-1228, 972-1407, 976-1418, 982-1290, 983-1609, 984-1537, 993-1250, 997-1238, 998-1515, 1024-1300, 1024-1506, 1026-1331, 1055-1579, 1070-1323, 1071-1356, 1073-1277, 1080-1569, 1082-1325, 1084-1755, 1091-1545, 1110-1664, 1131-1349, 1133-1617, 1151-1410, 1151-1416, 1167-1811, 1174-1747, 1179-1779, 1184-1698, 1188-1825, 1213-1761, 1217-1482, 1220-1543, 1265-1707, 1280-1546, 1324-1807, 1340-1464, 1347-1632, 1347-1746, 1347-1780, 1347-1792, 1347-1808, 1347-1824, 1350-1551, 1351-1830, 1354-1469, 1355-1611, 1355-1782, 1355-1814, 1356-1824, 1357-1602, 1358-1814, 1362-1814, 1365-1601, 1368-1814, 1369-1814, 1369-1844, 1377-1796, 1380-1833, 1382-1812, 1384-1881, 1385-1812, 1389-1823, 1391-1616, 1391-1812, 1392-1873, 1393-1592, 1393-1679, 1394-1831, 1399-1809, 1400-1636, 1401-1631, 1404-1650, 1404-1882, 1412-1812, 1414-1825, 1419-1540, 1419-1715, 1430-1620, 1430-1811, 1434-1666, 1434-1670, 1444-1874, 1451-1814, 1454-2118, 1456-1725, 1457-1798, 1459-1725, 1459-1791, 1463-1813, 1467-1814, 1468-1743, 1484-1814, 1485-1811, 1499-1811, 1502-1826, 1507-1816, 1509-1735, 1509-1756, 1511-1811, 1512-1903, 1523-1815, 1526-1810, 1548-1810, 1555-1877, 1560-1854, 1569-1778, 1569-1789, 1569-1797, 1569-1827, 1572-1811, 1572-1814, 1575-1814, 1576-1803, 1578-1810, 1580-1814, 1581-1843, 1588-1793, 1592-1803, 1593-1831, 1594-1826, 1606-1811, 1634-1812, 1639-1814, 1652-1814, 1657-1814, 1660-1817, 1696-1810, 1697-1800, 1697-1827, 1718-1830, 1718-1904 |
| 62/7510517CB1/ 2800 | 1-224, 1-286, 1-416, 1-437, 1-454, 1-465, 1-524, 1-587, 1-603, 1-616, 1-697, 4-287, 4-2800, 16-831, 22-466, 22-606, 22-640, 22-793, 22-818, 22-821, 22-831, 25-831, 32-803, 35-778, 59-546, 60-619, 61-205, 62-516, 62-569, 73-499, 82-638, 86-577, 134-453, 149-705, 208-683, 219-653, 220-647, 228-520, 259-486, 263-484, 360-668, 427-578, 454-885, 847-1295, 879-1327, 891-1152, 900-1114, 900-1150, 900-1224, 900-1473, 900-1532, 900-1775, 977-1269, 1006-1241, 1006-1511, 1008-1322, |

TABLE 4-continued

| Polynucleotide SEQ ID NO:/ Incyte ID/Sequence Length | Sequence Fragments |
| --- | --- |
| | 1008-1345, 1095-1677, 1151-2034, 1223-1470, 1223-1653, 1227-1887, 1235-1430, 1287-1530, 1297-1582, 1308-1607, 1436-1677, 1439-1702, 1441-2064, 1467-1793, 1469-1989, 1475-1988, 1485-1744, 1492-1758, 1497-2397, 1498-1989, 1509-1748, 1542-1772, 1554-1787, 1579-1850, 1589-1827, 1596-1808, 1596-2112, 1600-1988, 1602-2177, 1665-1934, 1679-2129, 1679-2196, 1682-1977, 1713-1958, 1714-1932, 1721-1974, 1728-1950, 1730-2150, 1733-2256, 1734-2397, 1735-2237, 1741-2394, 1762-2010, 1785-2608, 1799-2286, 1799-2517, 1800-2209, 1800-2220, 1800-2321, 1800-2364, 1800-2394, 1805-2293, 1824-2394, 1826-2607, 1833-2394, 1843-2102, 1843-2344, 1868-2395, 1871-2608, 1877-2604, 1881-2149, 1899-2133, 1899-2145, 1918-2394, 1934-2205, 1947-2604, 1952-2229, 1963-2092, 1969-2273, 1971-2534, 1976-2538, 1991-2493, 1992-2608, 1995-2537, 2003-2537, 2011-2575, 2033-2239, 2038-2291, 2038-2329, 2040-2296, 2040-2553, 2050-2456, 2050-2566, 2052-2245, 2067-2570, 2075-2637, 2081-2791, 2083-2536, 2091-2214, 2116-2309, 2166-2382, 2174-2758, 2177-2793, 2187-2462, 2210-2784, 2215-2760, 2233-2720, 2253-2523, 2272-2752, 2291-2754, 2300-2751, 2301-2789, 2311-2791, 2322-2575, 2322-2600, 2322-2731, 2322-2793, 2324-2606, 2325-2800, 2336-2452, 2350-2798, 2353-2800, 2362-2791, 2374-2794, 2445-2794, 2455-2800, 2480-2789, 2550-2800, 2702-2800 |
| 63/7511014CB1/ 1750 | 1-477, 9-1750, 10-295, 611-1452, 890-1719 |
| 64/7506687CB1/ 7106 | 1-487, 88-7106, 246-807, 446-710, 578-852, 662-1293, 688-1178, 694-1282, 797-1490, 925-1439, 931-1292, 950-1288, 1131-1378, 1131-1426, 1395-1422, 1921-2491, 2447-2687, 2475-2787, 2508-3180, 2613-3272, 2701-3232, 2712-3395, 2742-3405, 2764-3021, 2789-3203, 2814-3396, 2828-3402, 2861-3457, 2873-3235, 2873-3237, 2899-3296, 2924-3464, 3124-3265, 3141-3395, 3251-3801, 3358-4003, 3361-3957, 3491-4067, 3508-4096, 3530-4167, 3555-4093, 3588-4004, 3612-4174, 3678-3977, 3706-3977, 3735-4136, 3771-4055, 3775-4476, 3782-4000, 3804-4067, 3810-4563, 3846-4297, 3847-4297, 3848-4545, 3853-4195, 3853-4238, 3859-4331, 3861-4490, 3900-4056, 3913-4617, 3917-4433, 3919-4307, 3946-4297, 3967-4793, 3992-4328, 4004-4518, 4086-4355, 4124-4714, 4165-4765, 4169-4404, 4169-4413, 4171-4417, 4175-4829, 4251-4856, 4269-4831, 4319-4666, 4322-4729, 4352-4956, 4355-4950, 4372-4869, 4383-4957, 4392-5302, 4479-5089, 4499-4750, 4525-4709, 4528-4811, 4533-5128, 4543-4686, 4557-5004, 4562-4763, 4576-4812, 4597-5169, 4599-4885, 4645-4864, 4646-5190, 4653-5233, 4720-4933, 4735-5016, 4765-4921, 4779-5160, 4780-5137, 4785-5089, 4785-5132, 4785-5144, 4787-5227, 4792-5158, 4798-5153, 4800-5070, 4810-5634, 4816-5062, 4816-5066, 4829-5044, 4850-5348, 4850-5553, 4851-5150, 4855-5561, 4861-5104, 4861-5466, 4869-5460, 4869-5507, 4873-5166, 4878-5561, 4897-5540, 4920-5248, 4937-5253, 4959-5180, 4960-5521, 4965-5217, 4969-5130, 4971-5214, 4979-5166, 4996-5203, 4996-5274, 5014-5666, 5033-5296, 5033-5546, 5038-5271, 5043-5309, 5050-5184, 5070-5723, 5076-5594, 5089-5510, 5094-5291, 5095-5653, 5096-5707, 5101-5498, 5110-5292, 5110-5311, 5116-5773, 5127-5328, 5127-5344, 5141-5412, 5143-5838, 5148-5743, 5148-5753, 5151-5462, 5152-5434, 5156-5333, 5156-5385, 5157-5718, 5159-5747, 5161-5510, 5193-5838, 5194-5736, 5221-6083, 5232-5710, 5260-5697, 5263-5571, 5316-5562, 5336-5874, 5341-5969, 5342-5608, 5342-5989, 5345-5906, 5350-5594, 5377-5989, 5380-5628, 5380-5647, 5382-5495, 5390-5632, 5390-5637, 5390-5830, 5423-5652, 5425-5602, 5425-5698, 5429-5695, 5444-6079, 5450-5546, 5450-5740, 5460-5691, 5463-5820, 5473-5830, 5515-5763, 5521-5770, 5526-5918, 5526-6214, 5535-5773, 5551-5847, 5562-6071, 5566-6041, 5572-5838, 5575-5831, 5585-5816, 5600-6032, 5601-5856, 5605-5833, 5615-5801, 5634-5882, 5634-5964, 5642-6345, 5651-6071, 5655-6151, 5658-5950, 5673-5964, 5685-5968, 5712-6184, 5715-6362, 5716-5964, 5725-6042, 5738-5808, 5744-6089, 5751-6014, 5761-6116, 5762-5923, 5765-5886, 5765-5922, 5767-6109, 5776-6061, 5776-6464, 5776-6648, 5784-6151, 5785-6041, 5795-6082, 5812-5990, 5812-6035, 5820-6094, 5842-6129, 5859-6100, 5860-6134, 5869-6147, 5877-6167, 5877-6183, 5878-6144, 5888-6109, 5907-6145, 5908-6637, 5916-6548, 5917-6183, 5926-6184, 5926-6508, 5928-6119, 5929-6209, 5943-6221, 5945-6371, 5945-6533, 5961-6220, 5971-6210, 5971-6301, 5971-6450, 5978-6271, 5984-6192, 5987-6628, 5991-6149, 6011-6245, 6012-6256, 6012-6337, 6027-6656, 6029-6281, 6038-6613, 6048-6479, 6053-6378, 6064-6295, 6068-6340, 6072-6348, 6081-6536, 6081-6656, 6106-6372, 6107-6336, 6107-6393, 6108-6382, 6113-6298, 6116-6464, 6119-6406, 6128-6246, 6128-6345, 6134-6545, 6135-6758, 6137-6800, 6171-6388, 6171-6779, 6176-6497, 6186-6453, 6190-6827, 6192-6624, 6193-6387, |

TABLE 4-continued

| Polynucleotide SEQ ID NO:/ Incyte ID/Sequence Length | Sequence Fragments |
|---|---|
| | 6193-6436, 6193-6439, 6193-6713, 6197-6430, 6202-6468, 6209-6480, 6220-6426, 6224-6485, 6225-6455, 6225-7023, 6228-6457, 6228-6459, 6228-6479, 6228-6497, 6234-6429, 6235-6500, 6235-6780, 6241-6455, 6248-6526, 6250-6762, 6257-6540, 6268-6547, 6277-7011, 6287-6665, 6288-6488, 6288-6772, 6290-7023, 6292-6531, 6293-6946, 6296-6561, 6298-6538, 6300-6429, 6300-6551, 6310-6566, 6317-6551, 6317-6558, 6318-6968, 6318-6979, 6325-6544, 6326-6868, 6327-6583, 6327-6587, 6332-6635, 6337-6570, 6337-6622, 6338-6679, 6340-6913, 6348-6575, 6351-6520, 6361-6639, 6366-6607, 6366-6611, 6366-6679, 6366-6929, 6366-6939, 6369-6877, 6369-6943, 6370-6981, 6375-7001, 6376-6966, 6377-6617, 6379-6581, 6387-6600, 6390-6701, 6394-6956, 6397-6946, 6397-6983, 6400-6905, 6402-6637, 6404-6675, 6405-6649, 6405-6918, 6405-7016, 6406-6675, 6407-7013, 6413-6653, 6413-6656, 6414-6948, 6416-6997, 6425-7014, 6431-6586, 6436-6767, 6437-6685, 6437-6987, 6443-6727, 6445-7019, 6453-6876, 6459-6991, 6468-6770, 6475-6755, 6482-7010, 6487-6742, 6488-6784, 6488-7020, 6488-7029, 6489-6999, 6493-6750, 6493-6895, 6498-6792, 6499-6732, 6500-6779, 6500-6784, 6503-7029, 6506-6676, 6512-7029, 6515-6956, 6516-6768, 6516-6798, 6516-7027, 6526-7027, 6527-6697, 6535-6768, 6535-6839, 6539-6787, 6539-6788, 6542-6802, 6543-6768, 6553-6784, 6553-7002, 6557-7027, 6558-6985, 6560-7027, 6566-6994, 6570-7027, 6574-7027, 6576-6819, 6576-6838, 6578-7021, 6585-6802, 6585-6849, 6587-7027, 6590-7029, 6590-7033, 6593-7029, 6594-7027, 6595-6845, 6595-7032, 6600-7029, 6602-6861, 6602-7029, 6603-6868, 6603-6915, 6605-6986, 6606-7028, 6607-7021, 6607-7027, 6613-6890, 6614-7027, 6615-7027, 6619-7029, 6623-6845, 6623-6906, 6623-7027, 6624-7027, 6627-7029, 6629-6836, 6634-7026, 6635-6919, 6635-7021, 6644-7021, 6647-6765, 6648-6922, 6650-7028, 6654-7027, 6656-6896, 6656-7028, 6658-7028, 6659-6894, 6659-7021, 6659-7023, 6659-7028, 6678-6948, 6683-6907, 6687-6952, 6688-6850, 6689-6944, 6689-6953, 6690-6951, 6690-6952, 6690-7027, 6691-7027, 6692-6922, 6696-7023, 6700-7027, 6714-6967, 6714-7026, 6721-7000, 6724-7020, 6725-7029, 6728-7027, 6730-6989, 6730-6990, 6730-7009, 6733-7028, 6735-6940, 6737-6940, 6737-7026, 6737-7029, 6743-7028, 6760-7027, 6764-7027, 6766-7027, 6767-7027, 6774-7029, 6775-7024, 6782-7029, 6784-7027, 6786-7029, 6790-7027, 6801-7029, 6827-7027, 6831-7029, 6832-7028, 6833-7027, 6860-7029, 6882-7106, 6918-7027, 6928-7028, 6947-7008 |
| 65/7510621CB1/ 1187 | 1-182, 1-212, 1-248, 1-301, 1-334, 1-339, 1-497, 1-590, 1-591, 1-613, 1-628, 1-1114, 2-251, 4-233, 4-252, 8-263, 29-561, 43-204, 59-278, 91-573, 107-652, 169-475, 190-323, 191-414, 191-435, 210-360, 213-567, 239-446, 239-478, 266-470, 272-564, 291-475, 309-417, 317-584, 318-564, 318-594, 334-446, 336-607, 336-630, 336-650, 337-548, 337-551, 337-567, 343-585, 362-586, 362-631, 377-527, 377-528, 377-549, 377-588, 377-595, 377-605, 377-607, 377-617, 377-618, 377-631, 377-636, 377-637, 377-652, 378-652, 379-649, 379-652, 380-649, 381-590, 381-621, 381-624, 381-652, 382-609, 383-652, 386-1058, 392-652, 399-634, 402-649, 402-652, 403-652, 408-652, 409-652, 410-608, 410-652, 411-620, 411-624, 417-566, 417-652, 418-652, 422-632, 422-652, 424-652, 428-641, 429-652, 433-652, 443-644, 444-588, 444-645, 446-652, 447-647, 449-652, 468-652, 490-1114, 494-640, 511-638, 516-581, 524-648, 526-652, 538-649, 564-1114, 613-646, 648-759, 648-781, 648-797, 648-838, 648-842, 648-848, 648-855, 648-858, 648-861, 648-862, 648-864, 648-867, 648-869, 648-870, 648-872, 648-874, 648-875, 648-876, 648-879, 648-881, 648-882, 648-883, 648-884, 648-885, 648-886, 648-887, 648-888, 648-892, 648-895, 648-897, 648-899, 648-902, 648-903, 648-906, 648-907, 648-908, 648-913, 648-918, 648-920, 648-927, 648-928, 648-935, 648-940, 648-942, 648-944, 648-950, 648-954, 648-956, 648-959, 648-962, 648-965, 648-971, 648-989, 648-1052, 648-1096, 648-1114, 649-918, 650-837, 650-863, 650-889, 650-921, 650-927, 650-946, 650-1027, 651-897, 651-1114, 652-1043, 654-870, 654-988, 645-884, 655-1114, 656-891, 658-787, 662-901, 662-916, 665-942, 665-970, 666-1114, 668-917, 668-937, 668-964, 668-1110, 669-953, 669-960, 670-875, 670-919, 670-923, 671-909, 672-924, 672-934, 672-1114, 673-855, 673-959, 673-960, 674-1114, 675-961, 676-904, 676-937, 676-945, 676-1114, 677-938, 677-958, 678-838, 678-884, 678-895, 678-918, 678-1004, 678-1114, 679-891, 679-934, 680-851, 682-935, 683-845, 683-958, 683-994, 685-990, 685-1114, 687-925, 687-958, 687-967, 687-1077, 687-1114, 688-1114, 689-852, 689-909, 689-910, 689-934, 689-940, 689-942, 689-956, 689-968, 690-897, 694-1114, 695-1016, 695-1030, 695-1114, 696-893, 696-904, 696-911, 696-968, 696-970, 696-1114, 697-931, 697-943, 697-947, 697-948, 697-957, |

TABLE 4-continued

| Polynucleotide SEQ ID NO:/ Incyte ID/Sequence Length | Sequence Fragments |
|---|---|
| | 697-1114, 698-923, 698-1114, 699-851, 699-974, 699-1005, 700-1114, 701-974, 706-928, 706-1114, 708-967, 708-981, 708-992, 709-972, 709-978, 709-983, 709-1114, 710-920, 710-946, 710-976, 710-987, 710-997, 711-978, 711-1070, 711-1114, 714-1114, 715-1114, 716-810, 716-832, 716-924, 716-927, 716-952, 716-971, 716-989, 716-995, 716-996, 716-1002, 716-1009, 716-1012, 717-979, 718-852, 718-949, 719-1015, 719-1023, 719-1089, 722-1114, 724-1008, 724-1114, 725-1114, 726-928, 726-934, 726-998, 726-1006, 726-1022, 726-1114, 727-878, 727-922, 727-944, 727-957, 727-967, 727-982, 727-989, 731-851, 731-1038, 731-1114, 732-1114, 734-858, 734-936, 734-961, 734-991, 734-1008, 734-1030, 734-1114, 735-881, 735-973, 738-851, 738-963, 738-992, 738-1114, 739-1107, 739-1114, 740-1114, 741-1114, 742-953, 742-1014, 742-1114, 743-972, 743-1114, 744-1029, 744-1114, 745-1025, 745-1026, 745-1043, 746-1043, 746-1114, 747-1017, 748-997, 748-1114, 749-1114, 750-974, 751-851, 751-964, 751-1114, 752-995, 753-1016, 753-1114, 754-1114, 755-980, 755-997, 755-998, 755-1019, 755-1114, 756-998, 756-1030, 757-1059, 757-1113, 757-1114, 758-889, 759-1114, 761-974, 761-1011, 761-1018, 761-1026, 761-1114, 762-1039, 763-1063, 763-1114, 764-1114, 765-959, 765-982, 765-1114, 766-851, 767-1000, 767-1004, 767-1049, 767-1114, 768-1010, 768-1018, 768-1066, 768-1114, 770-1114, 771-1028, 771-1056, 771-1114, 772-851, 772-891, 773-956, 773-996, 773-997, 773-1114, 774-864, 774-981, 774-1112, 775-1114, 776-1114, 777-1114, 778-1114, 779-897, 779-1114, 781-1104, 782-1060, 782-1066, 782-1114, 783-918, 783-1114, 785-1114, 786-1036, 786-1114, 787-1039, 789-1029, 790-1016, 790-1114, 791-1056, 792-922, 792-1034, 792-1038, 792-1039, 792-1046, 792-1114, 793-1021, 793-1062, 799-1114, 800-964, 800-1027, 800-1029, 800-1114, 801-1033, 803-1028, 804-1114, 807-1114, 810-1114, 811-930, 811-1007, 811-1022, 811-1048, 811-1069, 811-1114, 812-1000, 812-1031, 812-1087, 812-1089, 812-1114, 813-1093, 813-1114, 814-1064, 814-1067, 814-1114, 816-1114, 818-1114, 819-1114, 820-1083, 820-1100, 820-1114, 822-1114, 823-1114, 827-1025, 827-1114, 828-1045, 829-1055, 829-1080, 829-1097, 829-1114, 830-926, 830-1063, 830-1068, 830-1084, 831-1024, 833-1074, 833-1097, 834-1040, 834-1090, 836-1114, 837-1067, 837-1114, 840-1076, 840-1077, 843-1068, 843-1073, 843-1096, 844-1085, 844-1114, 845-1114, 846-1114, 849-1080, 851-1114, 852-1114, 853-1114, 858-1114, 861-1114, 862-1114, 864-1094, 864-1111, 864-1114, 865-1109, 865-1114, 866-988, 866-1040, 866-1114, 870-1089, 871-1114, 872-1114, 874-1114, 876-1114, 877-1048, 877-1088, 877-1108, 877-1114, 879-978, 879-1052, 879-1071, 879-1105, 880-1114, 881-1114, 882-1031, 882-1070, 882-1099, 882-1114, 883-1114, 885-1114, 886-1087, 886-1114, 887-1114, 889-1114, 890-1098, 890-1114, 893-1114, 894-1014, 895-1114, 899-1114, 901-1114, 902-1114, 905-1114, 907-1114, 909-1076, 909-1114, 913-1114, 915-1114, 916-1187, 917-1114, 919-1114, 920-1114, 921-1114, 924-1114, 925-1103, 925-1114, 926-1114, 928-1114, 930-1100, 930-1114, 933-1114, 934-1114, 935-1114, 936-1114, 937-1114, 939-1114, 941-1114, 942-1114, 944-1114, 949-1100, 949-1114, 950-1114, 951-1114, 953-1114, 954-1114, 958-1114, 961-1114, 962-1114, 967-1114, 969-1083, 969-1114, 978-1114, 979-1114, 981-1114, 982-1112, 982-1114, 985-1114, 986-1114, 988-1114, 993-1114, 995-1114, 996-1114, 998-1114, 1004-1114, 1006-1114, 1011-1114, 1020-1096, 1020-1114, 1021-1114, 1027-1114, 1029-1114, 1032-1114, 1034-1114, 1035-1114, 1037-1114, 1042-1083, 1045-1114, 1047-1083, 1048-1083, 1049-1083, 1051-1083, 1052-1083, 1110-1175, 1110-1177, 1110-1181, 1110-1184, 1110-1187, 1112-1175, 1113-1187, 1123-1177, 1140-1163, 1140-1168, 1140-1181, 1141-1160, 1141-1162, 1141-1163, 1141-1164, 1141-1165, 1141-1168, 1141-1169, 1141-1170, 1141-1171, 1141-1172, 1141-1173, 1141-1174, 1141-1175, 1141-1176, 1141-1178, 1141-1180, 1141-1181, 1141-1182, 1141-1183, 1141-1184, 1141-1185, 1141-1186, 1141-1187, 1144-1174, 1144-1175 |
| 66/7505533CB1/ 570 | 1-237, 1-261, 1-283, 12-154, 12-195, 12-249, 12-250, 12-259, 12-268, 12-271, 12-275, 12-276, 12-283, 12-570, 13-278, 14-245, 14-266, 16-236, 21-233, 25-252, 26-248, 26-272, 29-100, 29-261, 37-207, 59-157, 177-563, 223-563, 295-563, 308-442, 467-562 |
| 67/7511220CB1 685 | 1-280, 1-685, 2-554, 170-685 |
| 68/7510967CB1/ 5723 | 1-136, 1-168, 1-203, 1-241, 1-258, 1-359, 1-471, 1-501, 1-612, 1-626, 1-763, 1-5723, 41-631, 201-417, 282-531, 282-536, 282-658, 333-723, 407-581, 505-1142, 505-1143, 505-1181, 505-1192, 505-1197, 505-1238, 505-1254, 505-1255, 505-1263, 505-1296, 505-1297, 505-1302, 505-1319, 563-826, 563-835, 563-1008, 588-1313, 627-1049, 692-819, |

TABLE 4-continued

| Polynucleotide SEQ ID NO:/ Incyte ID/Sequence Length | Sequence Fragments |
|---|---|
| | 759-1077, 791-1440, 811-1615, 867-1615, 869-1615, 876-1615, 879-1615, 889-1615, 898-1615, 902-1615, 929-1615, 944-1615, 945-1391, 1051-1334, 1051-1621, 1199-1727, 1199-1738, 1205-1716, 1221-1504, 1243-1709, 1376-1901, 1381-1641, 1492-1851, 1590-2092, 1628-2218, 1737-2086, 1737-2100, 1737-2155, 1805-2269, 1974-2822, 2011-2683, 2014-2656, 2027-2626, 2027-2633, 2027-2657, 2129-2855, 2138-2390, 2138-2677, 2145-2855, 2203-2905, 2220-2771, 2220-2844, 2243-2845, 2251-2989, 2252-2848, 2257-2888, 2310-2846, 2432-2741, 2484-3162, 2552-3106, 2613-3135, 2620-3166, 2713-3225, 2834-3274, 2857-3496, 2918-3543, 2946-3296, 2948-3447, 3013-3559, 3178-3510, 3233-3807, 3242-3428, 3439-4105, 3445-3839, 3828-4236, 3828-4238, 3832-4076, 3863-4088, 3913-4491, 3923-4387, 3928-4462, 3936-4217, 3975-4479, 3991-4560, 4035-4269, 4045-4234, 4056-4555, 4100-4715, 4113-4296, 4115-4386, 4131-4791, 4149-4727, 4151-4378, 4197-4451, 4223-4874, 4248-4647, 4257-4505, 4269-4856, 4290-4958, 4310-4789, 4354-4616, 4365-4446, 4406-4586, 4434-4731, 4434-4785, 4464-4824, 4492-4764, 4527-4838, 4561-5159, 4573-4816, 4624-4869, 4629-4889, 4646-5059, 4651-5159, 4697-5326, 4727-5267, 4732-5415, 4736-5334, 4748-5029, 4750-5036, 4752-5177, 4758-5009, 4758-5078, 4778-5131, 4786-5323, 4793-5051, 4814-5267, 4815-5116, 4818-5227, 4823-5127, 4828-4941, 4835-5365, 4836-5164, 4862-5164, 4868-5075, 4875-5199, 4881-5080, 4881-5455, 4891-5428, 4934-5215, 4950-5231, 5050-5418, 5072-5491, 5072-5504, 5130-5514, 5167-5476, 5178-5530, 5201-5267, 5201-5582, 5203-5452, 5203-5485, 5205-5510, 5236-5518, 5237-5510, 5241-5501, 5245-5531, 5256-5526, 5264-5570, 5306-5573 |
| 69/7511298CB1/ 3044 | 1-157, 1-202, 1-237, 1-262, 1-275, 1-386, 1-513, 1-528, 1-550, 1-553, 1-3043, 2-241, 2-248, 2-303, 6-273, 6-455, 9-466, 11-259, 11-552, 11-670, 13-313, 13-417, 16-239, 16-250, 18-257, 18-269, 19-629, 25-243, 27-407, 28-553, 33-310, 63-392, 63-445, 107-221, 107-394, 107-456, 145-495, 215-346, 547-1098, 547-1193, 556-1203, 587-1135, 603-989, 625-1000, 637-1105, 645-1299, 645-1364, 655-989, 655-1174, 672-1268, 699-1156, 700-1292, 711-1380, 760-985, 773-969, 777-1283, 794-1269, 796-1451, 798-1065, 805-1264, 829-1475, 830-1297, 840-1631, 859-1550, 862-1493, 869-1022, 869-1034, 869-1353, 871-1122, 873-1275, 892-1141, 937-1237, 937-1248, 937-1538, 937-1568, 937-1720, 937-1770, 937-1812, 937-1817, 939-1683, 941-1186, 941-1189, 945-1192, 947-1194, 947-1355, 950-1195, 950-1454, 951-1220, 972-1817, 993-1647, 1001-1281, 1006-1597, 1008-1692, 1009-1241, 1009-1881, 1025-1700, 1028-1262, 1031-1283, 1031-1319, 1031-1428, 1043-1644, 1053-1653, 1055-1554, 1064-1333, 1072-1937, 1073-1535, 1075-1749, 1076-1560, 1080-1506, 1084-1344, 1106-1548, 1108-1706, 1123-1731, 1127-1977, 1128-1864, 1131-1644, 1137-1540, 1139-1443, 1139-1619, 1139-1652, 1139-1727, 1139-1790, 1141-1402, 1143-1349, 1146-1375, 1168-1701, 1178-2001, 1180-1814, 1181-1750, 1201-1452, 1205-1467, 1207-2001, 1222-1488, 1222-1501, 1222-1749, 1224-1850, 1227-1367, 1227-1457, 1250-1853, 1253-1531, 1253-1854, 1281-1485, 1282-1486, 1288-1792, 1290-2001, 1295-1978, 1297-1607, 1319-1824, 1334-1713, 1338-1508, 1338-1850, 1349-1853, 1350-2030, 1359-1853, 1367-1603, 1371-1652, 1387-1750, 1416-2094, 1423-1619, 1426-1707, 1428-1682, 1428-1686, 1435-1920, 1444-1707, 1451-1539, 1476-1726, 1480-2142, 1498-2119, 1527-1869, 1535-2358, 1536-1815, 1539-2272, 1552-1761, 1552-1784, 1552-2111, 1552-2112, 1554-2272, 1555-1821, 1555-1823, 1560-2165, 1563-2002, 1567-2238, 1574-2093, 1578-2072, 1581-2136, 1582-2321, 1588-1853, 1596-2099, 1597-2099, 1598-1846, 1600-1876, 1600-2196, 1603-1987, 1605-1882, 1610-2097, 1620-2138, 1620-2194, 1632-2150, 1638-2241, 1643-1912, 1643-1918, 1643-2254, 1654-1877, 1656-1909, 1657-1866, 1664-1958, 1664-2254, 1674-1953, 1686-2555, 1687-1937, 1687-1948, 1695-2375, 1715-1947, 1718-1974, 1719-1952, 1721-1904, 1726-1968, 1727-2036, 1730-1955, 1730-1965, 1730-2265, 1751-2111, 1752-2642, 1763-2025, 1770-1971, 1782-2322, 1782-2323, 1788-2182, 1790-2372, 1793-2214, 1795-2078, 1804-2358, 1811-2410, 1811-2412, 1812-2264, 1816-2089, 1816-2442, 1816-2513, 1817-2067, 1817-2070, 1817-2089, 1817-2304, 1824-2064, 1837-2083, 1838-2394, 1839-2126, 1839-2247, 1840-2256, 1850-2033, 1852-1936, 1852-2115, 1852-2155, 1852-2294, 1852-2370, 1852-2382, 1854-2348, 1855-2094, 1858-2104, 1858-2443, 1868-2421, 1870-2132, 1871-2119, 1872-2242, 1874-2172, 1891-2486, 1893-2465, 1899-2133, 1899-2458, 1901-2187, 1928-2473, 1954-2465, 1954-2585, 1957-2074, 1961-2591, 1964-2615, 1981-2231, 1984-2250, 2011-2246, 2011-2298, 2011-2600, 2019-2265, 2021-2541, 2023-2158, 2028-2683, 2030-2307, 2033-2310, 2037-2585, 2043-2334, 2048-2248, 2048-2344, 2048-2636, 2054-2305, 2058-2312, |

TABLE 4-continued

| Polynucleotide SEQ ID NO:/ Incyte ID/Sequence Length | Sequence Fragments |
|---|---|
| | 2058-2319, 2061-2310, 2061-2394, 2068-2752, 2072-2645, 2072-2657, 2079-2349, 2089-2236, 2091-2341, 2095-2362, 2095-2700, 2102-2375, 2102-2700, 2103-2343, 2110-2374, 2111-2702, 2113-2358, 2114-2404, 2115-2294, 2116-2388, 2127-2301, 2127-2386, 2127-2406, 2127-2545, 2132-2559, 2133-2685, 2137-2435, 2143-2413, 2156-2570, 2159-2700, 2159-3000, 2160-2630, 2165-2700, 2171-2700, 2180-2700, 2181-2343, 2188-2453, 2189-2452, 2189-2462, 2189-2792, 2203-2651, 2203-2691, 2209-2809, 2210-2700, 2214-2489, 2215-2506, 2215-2803, 2217-2837, 2227-2943, 2230-2700, 2231-2497, 2231-2500, 2232-2709, 2236-2361, 2241-2505, 2243-2521, 2250-2517, 2251-2700, 2261-2594, 2268-2513, 2268-2516, 2273-2506, 2273-2559, 2273-2650, 2277-2826, 2282-2623, 2282-3027, 2283-2526, 2283-2615, 2283-3027, 2284-2700, 2289-3027, 2290-2508, 2293-2666, 2293-2910, 2303-2701, 2303-3027, 2304-2880, 2306-3025, 2306-3027, 2311-2989, 2311-3027, 2318-3028, 2321-3025, 2330-2908, 2353-2557, 2357-2862, 2362-2911, 2363-2609, 2363-3027, 2366-2799, 2369-2569, 2369-2928, 2373-2570, 2373-2913, 2373-2926, 2374-2548, 2374-2881, 2375-2771, 2376-2568, 2376-2613, 2376-2619, 2376-2632, 2378-2868, 2378-2928, 2380-2700, 2381-2639, 2383-2667, 2386-2729, 2387-2966, 2389-2864, 2391-2662, 2391-2912, 2391-2935, 2393-2678, 2394-2927, 2396-2863, 2396-2881, 2396-2999, 2398-3028, 2400-2926, 2405-2702, 2405-3029, 2406-3002, 2410-2949, 2411-2921, 2415-2631, 2423-2606, 2428-2685, 2430-2649, 2432-2585, 2432-2715, 2435-2915, 2435-3029, 2439-3030, 2439-3044, 2441-2695, 2441-2821, 2447-2994, 2448-2697, 2448-2830, 2448-2927, 2451-3044, 2455-2721, 2455-2880, 2458-2808, 2462-3044, 2472-2774, 2472-2948, 2476-3006, 2478-2996, 2484-2992, 2485-2772, 2485-3031, 2496-2775, 2504-2996, 2520-2779, 2521-2923, 2521-2993, 2522-3040, 2533-2745, 2537-2681, 2543-3006, 2544-2880, 2551-2994, 2552-2776, 2552-2781, 2552-2830, 2553-3036, 2556-2994, 2557-2823, 2558-2637, 2561-2822, 2564-2955, 2565-2796, 2573-2839, 2584-2834, 2584-2873, 2584-2991, 2587-3044, 2590-2991, 2590-3035, 2591-2871, 2591-2916, 2592-2854, 2592-2861, 2593-2846, 2593-2859, 2593-3031, 2594-3037, 2596-3030, 2597-2865, 2601-2846, 2609-3033, 2610-2884, 2613-3040, 2616-3034, 2621-3033, 2633-2993, 2633-3031, 2633-3033, 2633-3034, 2634-3043, 2638-2852, 2638-2875, 2639-3040, 2648-2872, 2649-2854, 2653-2873, 2653-2909, 2653-2933, 2653-3031, 2659-3031, 2661-3023, 2661-3029, 2663-2900, 2663-3032, 2665-3039, 2666-3031, 2667-3035, 2669-3031, 2670-2891, 2673-2909, 2673-2962, 2673-3025, 2673-3036, 2677-3043, 2677-3044, 2678-3032, 2678-3035, 2681-2995, 2682-3033, 2689-2923, 2693-2982, 2701-2923, 2701-2993, 2709-3031, 2716-2776, 2725-2994, 2726-3044, 2727-3044, 2728-3023, 2729-3035, 2737-2994, 2739-2996, 2740-3043, 2740-3044, 2741-2985, 2742-3043, 2747-2999, 2758-3041, 2760-3029, 2760-3031, 2765-3044, 2772-2981, 2776-2993, 2786-3030, 2788-3030, 2790-3029, 2794-3040, 2802-3028, 2803-3034, 2812-3044, 2814-3034, 2817-3029, 2817-3030, 2820-3031, 2821-2970, 2821-3030, 2825-3036, 2826-3033, 2827-3040, 2847-3038, 2879-3044, 2880-3037, 2893-3044, 2918-3044, 2955-3044 |
| 70/7510937CB1/ 4455 | 1-191, 1-4449, 33-482, 35-298, 36-487, 37-917, 38-326, 40-338, 41-297, 41-322, 41-491, 41-494, 41-497, 42-828, 46-315, 49-119, 49-321, 49-322, 49-326, 49-327, 49-332, 49-486, 49-487, 52-323, 53-325, 54-246, 54-307, 59-178, 60-327, 64-327, 65-327, 68-325, 72-487, 74-323 75-166, 75-300, 75-307, 75-487, 76-325, 77-329, 77-371, 77-604, 78-328, 81-317, 84-145, 88-322, 88-803, 91-444, 92-333, 100-327, 105-487, 108-490, 108-537, 109-487, 110-487, 119-370, 120-487, 124-320, 124-488, 125-487, 125-652, 125-811, 130-475, 140-488, 141-475 145-487, 154-507, 156-487, 169-320, 173-355, 173-382, 173-419, 173-491, 198-486, 199-322, 199-479, 212-487, 219-480, 225-491, 242-497, 252-710, 319-606, 330-604, 346-794, 351-578, 351-601, 351-619, 364-714, 374-670, 378-1113, 392-1192, 401-1135, 409-644, 416-703, 441-1161, 465-1050, 486-779, 499-895, 504-808, 507-774, 513-790, 522-901, 583-1225, 598-880, 618-925, 620-1199, 648-893, 653-1252, 674-1146, 696-951, 707-1214, 708-1199, 733-1286, 772-1241, 776-1241, 852-1191, 871-1245, 884-1199, 894-1346, 898-1216, 903-1241, 935-1211, 1001-1200, 1006-1232, 1006-1272, 1032-1600, 1063-1844, 1065-1500, 1073-1835, 1084-1218, 1089-1447, 1104-1382, 1137-1976, 1151-1245, 1153-1766, 1167-1425, 1184-1817, 1200-1730, 1220-1530, 1228-1406, 1231-1991, 1256-1830, 1259-1730, 1284-1554, 1293-2080, 1300-1570, 1354-1591, 1361-1595, 1394-1550, 1398-1634, 1403-2014, 1403-2033, 1422-1942, 1429-2190 1472-1953, 1494-1827, 1496-1765, 1505-1779, 1568-1985, 1585-2219, 1611-1883, 1615-1874, 1615-1895, 1675-1892, 1692-1942, 1704-2227, 1709-1954, 1711-2568, 1711-2654, 1711-2679, 1712-2074, |

TABLE 4-continued

| Polynucleotide SEQ ID NO:/ Incyte ID/Sequence Length | Sequence Fragments |
|---|---|
| | 1718-2363, 1718-2562, 1728-2281, 1732-2319, 1745-1864, 1756-2331, 1780-1997, 1805-2337, 1811-2582, 1815-2122, 1830-2387, 1840-2076, 1840-2100, 1844-2690, 1851-2567, 1867-2681, 1875-2452, 1877-2166, 1883-2125, 1887-2201, 1892-2160, 1921-2528, 1942-2212, 1981-2215, 1981-2597, 1985-2273, 2001-2223, 2019-2286, 2032-2255, 2035-2626, 2045-2269, 2054-2503, 2070-2168, 2093-2346, 2101-2338, 2102-2682, 2106-2374, 2147-2329, 2158-2410, 2164-2424, 2188-2435, 2198-2419, 2198-2477, 2210-2520, 2211-2457, 2216-2839, 2233-2478, 2243-2494, 2268-2498, 2268-2547, 2288-2439, 2300-2454, 2311-2580, 2317-2556, 2342-2721, 2348-2616, 2354-2647, 2359-2588, 2359-2594, 2363-2753, 2391-2635, 2479-3076, 2480-3047, 2480-3100, 2481-2871, 2510-2805, 2531-3133, 2542-2798, 2545-2801, 2554-2833, 2563-2833, 2563-2876, 2565-2826, 2571-2762, 2571-2876, 2585-2824, 2585-2839, 2589-2799, 2593-2817, 2595-3266, 2599-2899, 2604-2863, 2648-2914, 2648-2915, 2674-3076, 2694-2948, 2722-2970, 2734-3002, 2742-3320, 2754-3015, 2755-2991, 2765-3023, 2794-3059, 2794-3064, 2801-3010, 2803-3057, 2803-3091, 2809-3112, 2815-3109, 2819-3231, 2830-3069, 2843-3440, 2867-3110, 2875-3032, 2884-3144, 2893-3132, 2893-3167, 2893-3169, 2893-3236, 2904-3171, 2904-3206, 2905-3178, 2916-3222, 2934-3358, 2957-3222, 2961-3365, 2964-3207, 2964-3220, 2964-3559, 2964-3755, 2973-3240, 2978-3491, 2982-3244, 2982-3537, 2991-3226, 2998-3637, 3011-3316, 3011-3358, 3013-3291, 3014-3141, 3015-3373, 3046-3547, 3063-3314, 3074-3208, 3074-3333, 3074-3591, 3088-3297, 3093-3668, 3116-3373, 3131-3538, 3133-3541, 3161-3477, 3166-3419, 3172-3755, 3179-3402, 3181-3460, 3192-3432, 3237-3369, 3237-3490, 3237-3510, 3242-3503, 3242-3733, 3243-3512, 3246-3511, 3246-3550, 3248-3710, 3251-3527, 3255-3492, 3256-3433, 3258-3350, 3258-3532, 3260-3514, 3268-3687, 3270-3559, 3278-3498, 3294-3540, 3316-3607, 3318-3566, 3320-3484, 3320-3555, 3320-3584, 3322-3430, 3322-3571, 3338-3639, 3340-3613, 3341-3641, 3344-3602, 3354-3650, 3372-3635, 3378-3755, 3378-3966, 3382-3675, 3383-3606, 3392-3755, 3396-3642, 3411-3664, 3415-3602, 3417-3764, 3421-3732, 3426-3671, 3427-3683, 3428-3722, 3434-3684, 3456-3755, 3494-3746, 3498-3749, 3504-3776, 3508-3673, 3513-3746, 3559-3755, 3591-3863, 3598-4390, 3599-3755, 3602-4391, 3606-3865, 3607-3860, 3611-4387, 3614-3734, 3617-3911, 3617-3972, 3631-3894, 3632-3814, 3641-4141, 3641-4186, 3641-4216, 3643-3843, 3643-3933, 3654-4391, 3660-4091, 3674-3931, 3702-3973, 3714-3978, 3716-4250, 3718-4269, 3721-4195, 3777-3977, 3789-4391, 3805-4096, 3812-4390, 3819-3934, 3826-4306, 3833-4287, 3833-4388, 3834-3886, 3834-3935, 3834-3956, 3834-4042, 3834-4055, 3837-4241, 3840-4390, 3841-4288, 3849-4152, 3851-4162, 3851-4178, 3859-4165, 3859-4277, 3859-4328, 3861-4100, 3863-4305, 3863-4395, 3865-4304, 3868-4140, 3869-4261, 3875-4364, 3875-4388, 3878-4080, 3879-4305, 3882-4375, 3886-4157, 3889-4291, 3896-4291, 3903-4288, 3904-4278, 3905-4175, 3912-4015, 3914-4423, 3927-4204, 3931-4185, 3931-4188, 3933-4227, 3940-4171, 3940-4212, 3944-4194, 3944-4288, 3945-4288, 3955-4424, 3959-4239, 3961-4233, 3962-4249, 3975-4391, 3977-4245, 3977-4306, 3992-4227, 3993-4266, 3995-4436, 3997-4271, 4004-4134, 4012-4435, 4025-4455, 4027-4313, 4027-4320, 4032-4435, 4037-4308, 4038-4276, 4042-4443, 4043-4299, 4045-4434, 4049-4291, 4061-4339, 4073-4288, 4094-4333, 4095-4340, 4099-4310, 4109-4272, 4114-4410, 4121-4377, 4136-4288, 4138-4385, 4139-4424, 4141-4402, 4141-4418, 4153-4435, 4174-4357, 4183-4448, 4185-4435, 4186-4435, 4202-4432, 4207-4417, 4214-4435, 4220-4388, 4228-4435, 4261-4372 |
| 71/7511852CB1/ 1949 | 1-252, 1-502, 1-505, 1-548, 1-551, 1-555, 1-570, 1-578, 1-581, 1-594, 1-621, 1-622, 1-626, 1-633, 1-636, 1-640, 1-641, 1-656, 1-657, 1-658, 1-678, 1-680, 1-689, 1-705, 1-711, 1-714, 1-731, 1-735, 1-738, 1-746, 1-751, 1-752, 1-753, 1-755, 1-785, 1-786, 1-790, 1-814, 2-409, 2-509, 2-643, 2-679, 2-738, 2-745, 2-762, 2-1949, 4-640, 21-250, 82-250, 126-767, 154-250, 161-249, 161-251, 215-492, 217-490, 217-500, 320-554, 320-694, 320-757, 331-583, 368-1085, 388-650, 800-1037, 800-1410, 809-1083, 818-1300, 869-1418, 888-1037, 910-1158, 937-1207, 993-1084, 1010-1683, 1037-1321, 1099-1374, 1099-1560, 1107-1313, 1110-1386, 1119-1420, 1179-1469, 1191-1449, 1258-1495, 1299-1565, 1319-1530, 1319-1680, 1339-1472, 1361-1613, 1361-1619, 1361-1624, 1366-1619, 1409-1644, 1432-1860, 1444-1667, 1459-1685, 1491-1693, 1515-1766, 1521-1756, 1524-1805, 1526-1782, 1577-1845, 1591-1693 |

TABLE 4-continued

| Polynucleotide SEQ ID NO:/ Incyte ID/Sequence Length | Sequence Fragments |
|---|---|
| 72/7511077CB1/ 1322 | 1-280, 1-341, 127-588, 330-685, 377-1066, 383-953, 392-941, 398-858, 411-1128, 475-1137, 490-943, 499-947, 516-1187, 533-1024, 538-980, 538-1075, 565-1066, 575-1296, 613-1025, 625-1042, 654-1088, 663-1248, 847-1322, 854-1319, 854-1322, 899-1322, 1011-1282, 1062-1292 |
| 73/7511576CB1/ 1381 | 1-244, 1-339, 5-292, 6-1364, 15-230, 15-265, 15-281, 16-298, 42-286, 46-249, 46-310, 47-191, 47-297, 50-339, 52-331, 52-339, 54-303, 54-309, 54-315, 59-307, 61-339, 62-339, 62-340, 63-339, 65-295, 65-339, 71-339, 72-339, 75-217, 84-333, 84-381, 86-307, 86-333, 90-212, 90-219, 90-334, 90-339, 91-339, 93-328, 95-174, 95-244, 95-306, 95-312, 95-323, 95-327, 95-339, 96-319, 96-320, 96-330, 97-339, 99-327, 99-339, 100-332, 103-339, 104-339, 115-339, 116-320, 117-324, 148-339, 194-339, 339-499, 340-538, 340-540, 340-557, 340-569, 340-583, 340-607, 340-799, 340-814, 340-921, 340-930, 340-948, 343-948, 346-605, 346-621, 348-588, 348-596, 348-614, 348-941, 348-948, 349-546, 353-583, 353-879, 357-948, 359-551, 360-575, 361-943, 367-948, 369-909, 371-667, 374-609, 383-795, 387-662, 387-784, 397-933, 398-905, 403-653, 406-903, 418-687, 418-948, 419-668, 420-679, 421-841, 431-670, 437-670, 445-684, 447-691, 451-947, 453-942, 460-745, 461-948, 468-658, 469-741, 476-948, 483-948, 484-948, 485-948, 486-947, 489-947, 489-951, 492-947, 492-948, 493-947, 494-947, 496-947, 497-948, 498-927, 498-948, 499-923, 504-947, 506-943, 507-948, 508-942, 509-950, 512-948, 514-943, 515-947, 515-948, 516-798, 517-941, 518-952, 526-942, 531-733, 531-948, 532-947, 534-947, 536-948, 539-948, 539-951, 540-951, 541-947, 541-948, 542-947, 543-917, 543-947, 544-948, 545-945, 546-941, 547-947, 547-948, 548-910, 550-941, 553-941, 558-948, 563-875, 568-857, 574-828, 579-830, 579-893, 579-923, 581-800, 590-947, 592-941, 595-771, 595-948, 607-948, 611-872, 611-899, 611-947, 615-946, 617-948, 618-947, 622-939, 622-948, 623-947, 627-769, 627-907, 629-948, 630-946, 637-941, 670-948, 682-911, 695-948, 700-947, 708-947, 713-943, 759-948, 798-947, 807-947, 811-948, 821-953, 822-948, 839-947, 843-948, 867-951, 878-948, 885-948, 922-1381, 1058-1084, 1112-1138 |
| 74/7511492CB1/ 1027 | 1-162, 1-265, 1-269, 1-270, 1-275, 1-289, 1-314, 1-316, 1-1027, 10-238, 10-263, 10-291, 11-254, 11-304, 14-184, 14-214, 14-337, 16-249, 16-281, 19-247, 19-287, 19-300, 20-249, 20-261, 20-271, 20-282, 25-229, 25-250, 25-269, 25-341, 27-254, 27-263, 27-270, 27-278, 27-285, 27-287, 27-310, 27-321, 27-349, 28-328, 30-229, 30-269, 31-323, 32-298, 33-199, 33-325, 34-313, 35-295, 35-301, 36-263, 36-299, 37-246, 37-264, 37-275, 37-319, 39-267, 40-273, 40-294, 40-296, 40-322, 40-325, 40-328, 42-242, 45-212, 45-325, 45-346, 46-226, 46-240, 46-285, 46-294, 46-297, 46-298, 46-302, 46-309, 46-312, 46-316, 46-319, 46-333, 46-334, 47-197, 47-282, 47-292, 47-295, 47-300, 47-320, 47-322, 47-329, 47-333, 47-334, 47-335, 47-338, 47-342, 47-349, 48-248, 48-322, 48-323, 48-324, 48-325, 48-328, 48-343, 48-346, 48-349, 49-279, 49-293, 49-322, 51-248, 51-301, 51-349, 52-190, 52-202, 52-294, 52-306, 52-310, 52-317, 52-319, 52-320, 52-325, 52-326, 52-332, 52-339, 52-349, 53-178, 53-205, 53-271, 53-274, 53-282, 53-283, 53-286, 53-293, 53-294, 53-300, 53-302, 53-304, 53-306, 53-310, 53-311, 53-317, 53-318, 53-323, 53-328, 53-335, 53-349, 54-139, 54-257, 54-264, 54-265, 54-271, 54-280, 54-307, 54-310, 54-316, 54-323, 54-349, 55-250, 55-270, 55-288, 55-295, 55-305, 55-318, 55-346, 55-348, 55-349, 56-349, 57-197, 57-211, 57-250, 57-258, 57-292, 57-295, 57-298, 57-304, 57-306, 57-308, 57-310, 57-318, 57-320, 57-324, 57-325, 57-326, 57-328, 57-330, 57-337, 57-341, 57-349, 58-250, 58-253, 58-275, 58-282, 58-286, 58-295, 58-296, 58-306, 58-309, 58-313, 58-322, 58-329, 58-336, 58-346, 58-349, 59-298, 59-304, 59-315, 59-316, 59-326, 59-349, 60-183, 60-226, 60-253, 60-264, 60-277, 60-282, 60-292, 60-293, 60-294, 60-296, 60-297, 60-298, 60-301, 60-302, 60-307, 60-308, 60-309, 60-311, 60-316, 60-317, 60-327, 60-334, 60-335, 60-338, 60-339, 60-342, 60-349 61-223, 61-251, 61-295, 61-300, 61-304, 61-319, 61-337, 61-342, 61-347, 61-349, 62-266, 62-304, 62-306, 62-314, 62-318, 62-321, 62-331 62-346, 62-349, 63-314, 64-215, 64-264, 64-343, 64-349, 66-285, 66-315, 66-329, 66-338, 66-343, 67-321, 67-345, 69-315, 69-329 69-338, 70-296, 70-329, 70-343, 70-349, 72-201, 72-294, 72-336, 74-296, 86-311, 86-341, 89-166, 89-317, 89-326, 89-333, 89-337, 89-348 90-309, 94-271, 102-294, 102-349, 102-392, 105-295, 108-337, 108-349, 108-356, 109-289, 112-349, 118-327, 132-349, 141-304 142-251, 166-338, 183-310, 343-460, 343-481, 343-483, 343-490, 343-503, 343-525, 343-545, 343-546, 343-549, 343-554, 343-555, 343-565 343-569, 343-575, 343-577, 343-580, 343-585, 343-586, 343-598, 343-599, 343-601, 343-608, 343-610, 343-611, 343-642, 343-647 343-712, 343-718, 344-588, 344-633, 348-585, 348-603, 348-615, 351-610, 353-584, 353-635, 358-618, 369-607, 371-654, 371-688, 372-559 |

TABLE 4-continued

| Polynucleotide SEQ ID NO:/ Incyte ID/Sequence Length | Sequence Fragments |
|---|---|
| | 377-633, 377-636, 377-643, 380-659, 381-636, 381-648, 382-655, 383-614, 385-625, 394-496, 406-604, 406-654, 409-642, 409-711 412-717, 414-670, 416-717, 421-691, 443-557, 446-562, 458-696, 460-680, 460-683, 460-693, 460-694, 460-717, 461-653, 462-716, 463-717 469-626, 469-637, 486-675, 489-717, 506-672, 510-717, 512-644, 530-679, 535-637, 578-717, 593-677 |
| 75/7511141CB1/ 3040 | 1-228, 1-518, 1-538, 5-710, 250-824, 250-826, 292-1101, 343-914, 359-903, 450-1096, 528-1167, 561-1252, 673-1397, 773-1481, 776-1427, 828-1553, 829-1557, 837-1461, 846-1436, 851-1469, 853-1707, 919-1605, 930-1670, 958-1752, 959-1514, 970-1544, 986-1588 1116-1494, 1270-1832, 1389-2037, 1402-2184, 1554-2212, 1602-2231, 1676-2200, 1780-2403, 1799-2294, 2053-2619, 2053-2621, 2270-2736, 2271-3040, 2376-2807 |
| 76/7511300CB1/ 3158 | 1-157, 1-202, 1-237, 1-262, 1-275, 1-386, 1-513, 1-528, 1-550, 1-555, 1-619, 1-3088, 2-241, 2-248, 2-303, 6-273, 6-455, 6-627, 6-666, 9-466 13-313, 13-417, 16-239, 16-250, 18-257, 18-269, 25-243, 27-407, 28-556, 33-310, 63-392, 63-445, 107-382, 107-445, 107-456, 139-629, 145-609, 174-677, 188-823, 215-346, 217-672, 336-594, 356-1261, 378-886, 393-885, 411-710, 466-697, 466-931, 545-1467, 547-615 547-646, 554-1077, 560-646, 560-752, 560-808, 582-953, 587-646, 690-1245, 690-1416, 694-793, 697-793, 703-1350, 707-793, 732-793 734-1282, 750-1136, 772-1147, 784-1252, 792-1511, 792-1630, 802-1136, 802-1321, 819-1415, 846-1116, 846-1303, 847-1439, 858-1527 907-1132, 924-1430, 935-1640, 941-1416, 943-1598, 945-1212, 952-1411, 976-1622, 977-1444, 987-1778, 1006-1697, 1016-1169 1016-1181, 1016-1500, 1018-1269, 1020-1422, 1039-1288, 1084-1384, 1084-1395, 1084-1685, 1084-1715, 1084-1867, 1084-1917, 1084-1959 1084-1964, 1086-1830, 1088-1333, 1088-1336, 1092-1339, 1094-1341, 1094-1502, 1097-1342, 1097-1601, 1098-1367, 1106-1839 1119-1964, 1140-1794, 1148-1428, 1153-1744, 1156-1388, 1156-2028, 1172-1847, 1175-1409, 1178-1430, 1178-1466, 1178-1575, 1190-1791, 1194-1425, 1200-1800, 1202-1701, 1211-1480, 1219-2084, 1220-1682, 1222-1896, 1223-1707, 1227-1653, 1231-1491, 1253-1695, 1255-1853, 1270-1878, 1274-2124, 1275-2011, 1278-1791, 1284-1841, 1286-1590, 1286-1766, 1286-1799, 1286-1874, 1286-1937, 1288-1549, 1290-1496, 1293-1522, 1315-1848, 1325-2148, 1327-1961, 1328-1897, 1348-1599, 1352-1614, 1354-2148, 1369-1635, 1369-1648, 1369-1896, 1371-2031, 1374-1514, 1374-1604, 1397-2059, 1400-1678, 1400-2001, 1428-1632, 1429-1633, 1435-1939, 1437-2148, 1442-2125, 1444-1754, 1452-2177, 1466-1971, 1481-1860, 1485-1655, 1485-2175, 1496-2111, 1506-2000, 1514-1750, 1518-1799, 1534-1897, 1563-2241, 1570-1766, 1573-1854, 1575-1829, 1575-1833, 1582-2067, 1591-1854, 1598-1686, 1623-1873, 1627-2289, 1645-2266, 1674-2016, 1683-1962, 1686-2419, 1699-1908, 1699-1931, 1699-2258, 1699-2259, 1701-2419, 1702-1968, 1702-1970, 1707-2312, 1710-2149, 1714-2385, 1721-2240, 1725-2219, 1728-2283, 1729-2445, 1735-2080, 1738-2403, 1743-2246, 1744-2246, 1745-1993, 1747-2023, 1747-2343, 1750-2134, 1752-2029, 1757-2244, 1767-2285, 1767-2341, 1779-2297, 1785-2388, 1790-2059, 1790-2065, 1790-2401, 1801-2024, 1803-2056, 1804-2013, 1811-2105, 1811-2401, 1821-2100, 1834-2084, 1834-2095, 1862-2094, 1865-2121, 1866-2099, 1868-2051, 1873-2115, 1874-2183, 1877-2102, 1877-2112, 1877-2412, 1898-2258, 1910-2172, 1917-2118, 1935-2329, 1940-2361, 1942-2225, 1959-2411, 1963-2236, 1964-2214, 1964-2217, 1964-2236, 1964-2447, 1971-2211, 1984-2230, 1986-2273, 1986-2394, 1997-2180, 1999-2083, 1999-2262, 1999-2302, 1999-2441, 2002-2241, 2005-2251, 2017-2279, 2018-2266, 2019-2389, 2021-2319, 2046-2280, 2048-2334, 2128-2378, 2131-2397, 2158-2393, 2158-2445, 2166-2412, 2170-2305, 2177-2447, 2180-2447, 2195-2395, 2201-2447, 2205-2447, 2208-2447, 2236-2383, 2262-2441, 2274-2447, 2328-2447, 2425-2711, 2446-2593, 2446-2613, 2446-2615, 2446-2658, 2446-2664, 2446-2677, 2446-2684, 2446-2707, 2446-2712, 2446-2723, 2446-2774, 2446-2909, 2446-2926, 2446-2971, 2446-2972, 2446-2973, 2446-2980, 2446-3011, 2446-3034, 2446-3044, 2446-3072, 2446-3073, 2446-3088, 2450-2747, 2450-3074, 2451-3047, 2455-2994, 2456-2966, 2460-2676, 2468-2651, 2473-2730, 2475-2696, 2477-2630, 2477-2760, 2480-2960, 2480-3074, 2484-3075, 2484-3089, 2486-2740, 2486-2866, 2492-3039, 2493-2742, 2493-2875, 2493-2972, 2496-3089, 2500-2766, 2500-2925, 2503-2853, 2507-3091, 2517-2819, 2517-2993, 2521-3051, 2523-3041, 2529-3037, 2530-2817, 2530-3076, 2541-2820, 2547-2884, 2549-3041, 2565-2824, 2566-2968, 2566-3038, 2567-3085, 2578-2790, 2582-2726, 2588-3051, 2589-2925, 2596-3039, 2597-2821, 2597-2826, 2597-2875, 2598-3081, 2601-3039, 2602-2868, 2603-2682, 2606-2867, 2609-3000, 2610-2841, 2629-2879, 2629-2918, 2629-3036, 2632-3110, 2635-3036, 2635-3080, 2636-2916, 2636-2961, 2637-2899, |

TABLE 4-continued

| Polynucleotide SEQ ID NO:/ Incyte ID/Sequence Length | Sequence Fragments |
|---|---|
| | 2637-2906, 2638-2891, 2638-2904, 2638-3076, 2639-3082, 2641-3075, 2642-2910, 2646-2891, 2654-3078, 2655-2929, 2658-3085, 2661-3079, 2666-3078, 2676-3076, 2676-3079, 2678-3038, 2678-3078, 2679-3088, 2683-2897, 2683-2920, 2684-3085, 2693-2917, 2694-2899, 2698-2918, 2698-2954, 2698-2978, 2698-3076, 2704-3076, 2706-3068, 2706-3074, 2708-2945, 2708-3077, 2710-3084, 2711-3076, 2712-3080, 2714-3076, 2715-2936, 2718-2954, 2718-3007, 2718-3070, 2718-3081, 2722-3093, 2723-3077, 2723-3080, 2726-3040, 2727-3078, 2734-2968, 2738-3027, 2746-2968, 2746-3038, 2754-3076, 2761-2946, 2770-3039, 2771-3093, 2772-3092, 2773-3068, 2774-3080, 2782-3039, 2784-3041, 2785-3088, 2785-3089, 2786-3030, 2787-3088, 2792-3044, 2803-3086, 2805-3074, 2805-3076, 2810-3090, 2817-3026, 2821-3038, 2831-3075, 2833-3075, 2835-3074, 2839-3085, 2847-3073, 2848-3079, 2857-3097, 2859-3079, 2862-3074, 2862-3075, 2865-3076, 2866-3015, 2866-3075, 2870-3081, 2871-3078, 2872-3085, 2892-3083, 2924-3158, 2925-3095, 2938-3090, 2963-3143, 3000-3137 |

TABLE 5

| Polynucleotide SEQ ID NO: | Incyte Project ID: | Representative Library |
|---|---|---|
| 39 | 3048626CB1 | FIBRUNT02 |
| 40 | 2684425CB1 | PONSAZT01 |
| 41 | 7505960CB1 | PROSTUT20 |
| 42 | 7507021CB1 | THYRNOT02 |
| 43 | 7509099CB1 | MIXDTUE01 |
| 44 | 7509361CB1 | LIVRTUE01 |
| 45 | 7506815CB1 | BRAINOT11 |
| 46 | 7506814CB1 | BRAINOT11 |
| 47 | 7506852CB1 | BRAINOT20 |
| 48 | 7503782CB1 | TMLR2DT01 |
| 49 | 7504647CB1 | COLNNOT23 |
| 50 | 7500424CB1 | THYRNOT03 |
| 51 | 7500449CB1 | BRSTNOT16 |
| 53 | 7503292CB1 | BRAINOT18 |
| 54 | 7503311CB1 | CONNNOT01 |
| 55 | 7510384CB1 | PITUDIR01 |
| 56 | 7509976CB1 | FIBRTXS07 |
| 57 | 7510454CB1 | BRAINOT18 |
| 58 | 8017335CB1 | LATRTUT02 |
| 59 | 7510197CB1 | PANCNOT17 |
| 60 | 7510055CB1 | SINTBST01 |

TABLE 5-continued

| Polynucleotide SEQ ID NO: | Incyte Project ID: | Representative Library |
|---|---|---|
| 61 | 7501754CB1 | BRAITUT03 |
| 62 | 7510517CB1 | BRSTNOT01 |
| 63 | 7511014CB1 | BRAIFET01 |
| 64 | 7506687CB1 | CORPNOT02 |
| 65 | 7510621CB1 | FIBRUNT02 |
| 66 | 7505533CB1 | MIXDTME02 |
| 67 | 7511220CB1 | BRAITUT12 |
| 68 | 7510967CB1 | MLP000032 |
| 69 | 7511298CB1 | EOSINOT01 |
| 70 | 7510937CB1 | UTRSTMR01 |
| 71 | 7511852CB1 | SCOMDIT01 |
| 72 | 7511077CB1 | COLNTUT03 |
| 73 | 7511576CB1 | UCMCL5T01 |
| 74 | 7511492CB1 | PROSTUS23 |
| 75 | 7511141CB1 | PANCNOT15 |
| 76 | 7511300CB1 | BRAVUNT02 |

TABLE 6

| Library | Vector | Library Description |
|---|---|---|
| BRAIFET01 | pINCY | Library was constructed using RNA isolated from brain tissue removed from a Caucasian male fetus, who was stillborn with a hypoplastic left heart at 23 weeks' gestation. |
| BRAINOT11 | pINCY | Library was constructed using RNA isolated from brain tissue removed from the right temporal lobe of a 5-year-old Caucasian male during a hemispherectomy. Pathology indicated extensive polymicrogyria and mild to moderate gliosis (predominantly subpial and subcortical), consistent with chronic seizure disorder. Family history included a cervical neoplasm. |
| BRAINOT18 | pINCY | Library was constructed using RNA isolated from left temporal lobe brain tissue removed from a 34-year-old Caucasian male during cerebral meninges lesion excision. Pathology for the associated tumor tissue indicated metastatic malignant melanoma. Neoplastic cells strongly expressed HMB-45. Patient history included malignant melanoma of skin of the trunk. Family history included liver cancer, acute myocardial infarction, atherosclerotic coronary artery disease, and cerebrovascular disease. |

TABLE 6-continued

| Library | Vector | Library Description |
|---|---|---|
| BRAINOT20 | pINCY | Library was constructed using RNA isolated from diseased brain tissue removed from the left temporal lobe of a 27-year-old Caucasian male during a brain lobectomy. Pathology for the left temporal lobe, including the mesial temporal structures, indicated focal, marked pyramidal cell loss and gliosis in hippocampal sector CA1, consistent with mesial temporal sclerosis. The left frontal lobe showed a focal deep white matter lesion, characterized by marked gliosis, calcifications, and hemosiderin-laden macrophages, consistent with a remote perinatal injury. This frontal lobe tissue also showed mild to moderate generalized gliosis, predominantly subpial and subcortical, consistent with chronic seizure disorder. GFAP was positive for astrocytes. Family history included brain cancer. |
| BRAITUT03 | PSPORT1 | Library was constructed using RNA isolated from brain tumor tissue removed from the left frontal lobe of a 17-year-old Caucasian female during excision of a cerebral meningeal lesion. Pathology indicated a grade 4 fibrillary giant and small-cell astrocytoma. Family history included benign hypertension and cerebrovascular disease. |
| BRAITUT12 | pINCY | Library was constructed using RNA isolated from brain tumor tissue removed from the left frontal lobe of a 40-year-old Caucasian female during excision of a cerebral meningeal lesion. Pathology indicated grade 4 gemistocytic astrocytoma. |
| BRAVUNT02 | PSPORT1 | Library was constructed using pooled RNA isolated from separate populations of unstimulated astrocytes. |
| BRSTNOT01 | PBLUESCRIPT | Library was constructed using RNA isolated from the breast tissue of a 56-year-old Caucasian female who died in a motor vehicle accident. |
| BRSTNOT16 | pINCY | Library was constructed using RNA isolated from diseased breast tissue removed from a 59-year-old Caucasian female during a unilateral extended simple mastectomy. Pathology for the associated tumor tissue indicated an invasive lobular carcinoma with extension into ducts. Patient history included liver cirrhosis, esophageal ulcer, hyperlipidemia, and neuropathy. |
| COLNNOT23 | pINCY | Library was constructed using RNA isolated from diseased colon tissue removed from a 16-year-old Caucasian male during a total colectomy with abdominal/perineal resection. Pathology indicated gastritis and pancolonitis consistent with the acute phase of ulcerative colitis. Inflammation was more severe in the transverse colon, with inflammation confined to the mucosa. There was only mild involvement of the ascending and sigmoid colon, and no significant involvement of the cecum, rectum, or terminal ileum. Family history included irritable bowel syndrome. |
| COLNTUT03 | pINCY | Library was constructed using RNA isolated from colon tumor tissue obtained from the sigmoid colon of a 62-year-old Caucasian male during a sigmoidectomy and permanent colostomy. Pathology indicated invasive grade 2 adenocarcinoma. One lymph node contained metastasis with extranodal extension. Patient history included hyperlipidemia, cataract disorder, and dermatitis. Family history included benign hypertension, atherosclerotic coronary artery disease, hyperlipidemia, breast cancer, and prostate cancer. |
| CONNNOT01 | pINCY | Library was constructed using RNA isolated from mesentery fat tissue obtained from a 71-year-old Caucasian male during a partial colectomy and permanent colostomy. Family history included atherosclerotic coronary artery disease, myocardial infarction, and extrinsic asthma. |
| CORPNOT02 | pINCY | Library was constructed using RNA isolated from diseased corpus callosum tissue removed from the brain of a 74-year-old Caucasian male who died from Alzheimer's disease. |
| EOSTNOT01 | pINCY | Library was constructed using RNA isolated from microscopically normal eosinophils from 31 non-allergic donors. Donors abstained from prescription and over-the-counter drug use for at least one week prior to donating 200 ml of peripheral venous blood. |
| FTBRTXS07 | pINCY | This subtracted library was constructed using 1.3 million clones from a dermal fibroblast library and was subjected to two rounds of subtraction hybridization with 2.8 million clones from an untreated dermal fibroblast tissue library. The starting library for subtraction was constructed using RNA isolated from treated dermal fibroblast tissue removed from the breast of a 31-year-old Caucasian female. The cells were treated with 9CIS retinoic acid. The hybridization probe for subtraction was derived from a similarly constructed library from RNA isolated from untreated dermal fibroblast tissue from the same donor. Subtractive hybridization conditions were based on the methodologies |

TABLE 6-continued

| Library | Vector | Library Description |
|---|---|---|
| | | of Swaroop et al, NAR (1991) 19: 1954 and Bonaldo, et al., Genome Research (1996) 6: 791. |
| FIBRUNT02 | pINCY | Library was constructed using RNA isolated from an untreated MG-63 cell line derived from an osteosarcoma removed from a 14-year-old Caucasian male. |
| LATRTUT02 | pINCY | Library was constructed using RNA isolated from a myxoma removed from the left atrium of a 43-year-old Caucasian male during annuloplasty. Pathology indicated atrial myxoma. Patient history included pulmonary insufficiency, acute myocardial infarction, atherosclerotic coronary artery disease, hyperlipidemia, and tobacco use. Family history included benign hypertension, acute myocardial infarction, atherosclerotic coronary artery disease, and type II diabetes. |
| LIVRTUE01 | PCDNA2.1 | This 5' biased random primed library was constructed using RNA isolated from liver tumor tissue removed from a 72-year-old Caucasian male during partial hepatectomy. Pathology indicated metastatic grade 2 (of 4) neuroendocrine carcinoma forming a mass. The patient presented with metastatic liver cancer. Patient history included benign hypertension, type I diabetes, prostatic hyperplasia, prostate cancer, alcohol abuse in remission, and tobacco abuse in remission. Previous surgeries included destruction of a pancreatic lesion, closed prostatic biopsy, transurethral prostatectomy, removal of bilateral testes and total splenectomy. Patient medications included Eulexin, Hytrin, Proscar, Ecotrin, and insulin. Family history included atherosclerotic coronary artery disease and acute myocardial infarction in the mother; atherosclerotic coronary artery disease and type II diabetes in the father. |
| MIXDTME02 | PBK-CMV | This 5' biased random primed library was constructed using pooled cDNA from five donors. cDNA was generated using mRNA isolated from heart tissue removed from a Caucasian male fetus who died after 20 weeks gestation from Patau's syndrome (donor A); adrenal gland removed from a 43-year-old Caucasian male (donor B) during nephroureterectomy, regional lymph node excision and unilateral adrenalectomy; kidney cortex removed from a 65-year-old male (donor C) during nephroureterectomy; lung tissue removed from a 14-month-old Caucasian female who died from drowning (donor D); and kidney tissue removed from an 8-year-old Caucasian female who died from a motor vehicle accident (donor E). For donor B, pathology for the associated tumor indicated grade 2 (of 4) renal cell carcinoma in the left kidney with invasion into the renal pelvis. Patient presented with hematuria and anemia. Patient history included benign hypertension and obesity. Previous surgeries included adenotonsillectomy and indirect inguinal hernia repair. The patient was not taking any medications. Family history included benign hypertension and atherosclerotic coronary artery disease in the father. For donor C pathology for the associated tumor shows grade 3 (of 4) renal cell carcinoma, clear cell type, within the mid-portion of the kidney. For donor D, serologies were negative. For donor E, medications included respiradol. |
| MIXDTUE01 | PBK-CMV | This 5' biased random primed library was constructed using pooled cDNA from seven donors. cDNA was generated using mRNA isolated from placental tissue removed from a Caucasian fetus (A), who died after 16 weeks' gestation from fetal demise and hydrocephalus; from placental tissue removed from a Caucasian male fetus (B), who died after 18 weeks' gestation from fetal demise; from an untreated LNCaP cell line, derived from prostate carcinoma with metastasis to the left supraclavicular lymph nodes, removed from a 50-year-old Caucasian male (C); from endometrial tissue removed from a 32-year-old female (D); from diseased right ovary tissue removed from a 45-year-old Caucasian female (E); from diseased right ovary tissue removed from a 47-year-old Caucasian female (donor F) and from right fallopian tube tumor tissue removed from an 85-year-old Caucasian female (donor G). For donor A, patient history included umbilical cord wrapped around the head (3 times) and the shoulders (1 time). Serology was positive for anti-CMV. Family history included multiple pregnancies and live births, and an abortion in the mother. For donor B, serologies were negative. For donor D, pathology indicated the endometrium was in secretory phase. For donor E, pathology indicated stromal hyperthecosis of the right and left ovaries. For donor F, pathology indicated endometriosis. For donor G, pathology indicated poorly differentiated mixed endometrioid (80%) and serous (20%) |

TABLE 6-continued

| Library | Vector | Library Description |
| --- | --- | --- |
| | | adenocarcinoma of the right fallopian tube. Patient history included medullary carcinoma of the thyroid. |
| MLP000032 | PCR2-TOPOTA | Library was constructed using pooled cDNA from different donors. cDNA was generated using mRNA isolated from the following: aorta, cerebellum, lymph nodes, muscle, tonsil (lymphoid hyperplasia), bladder tumor (invasive grade 3 transitional cell carcinoma.), breast (proliferative fibrocystic changes without atypia characterized by epithelial ductal hyperplasia, testicle tumor (embryonal carcinoma), spleen, ovary, parathyroid, ileum, breast skin, sigmoid colon, penis tumor (fungating invasive grade 4 squamous cell carcinoma), fetal lung,, breast, fetal small intestine, fetal liver, fetal pancreas, fetal lung, fetal skin, fetal penis, fetal bone, fetal ribs, frontal brain tumor (grade 4 gemistocytic astrocytoma), ovary (stromal hyperthecosis), bladder, bladder tumor (invasive grade 3 transitional cell carcinoma), stomach, lymph node tumor (metastatic basaloid squamous cell carcinoma), tonsil (reactive lymphoid hyperplasia), periosteum from the tibia, fetal brain, fetal spleen, uterus tumor, endometrial (grade 3 adenosquamous carcinoma), seminal vesicle, liver, aorta, adrenal gland, lymph node (metastatic grade 3 squamous cell carcinoma), glossal muscle, esophagus, esophagus tumor (invasive grade 3 adenocarcinoma), ileum, pancreas, soft tissue tumor from the skull (grade 3 ependymoma), transverse colon, (benign familial polyposis), rectum tumor (grade 3 colonic adenocarcinoma), rib tumor, (metastatic grade 3 osteosarcoma), lung, heart, placenta, thymus, stomach, spleen (splenomegaly with congestion), uterus, cervix (mild chronic cervicitis with focal squamous metaplasia), spleen tumor (malignant lymphoma, diffuse large cell type, B-cell phenotype with abundant reactive T-cells and marked granulomatous response), umbilical cord blood mononuclear cells, upper lobe lung tumor, (grade 3 squamous cell carcinoma), endometrium (secretory phase), liver, liver tumor (metastatic grade 2 neuroendocrine carcinoma), colon, umbilical cord blood, Th1 cells, nonactivated, umbilical cord blood, Th2 cells, nonactivated, coronary artery endothelial cells (untreated), coronary artery smooth muscle cells, (untreated), coronary artery smooth muscle cells.(treated with TNF & IL-1 10 ng/ml each for 20 hours), bladder (mild chronic cystitis), epiglottis, breast skin, small intestine, fetal prostate stroma fibroblasts, prostate epithelial cells (PrEC cells), fetal adrenal glands, fetal liver, kidney transformed embryonal cell line (293-EBNA) (untreated), kidney transformed embryonal cell line (293-EBNA) (treated with 5Aza-2deoxycytidine for 72 hours), mammary epithelial cells, (HMEC cells), peripheral blood monocytes (treated with IL-10 at time 0, 10 ng/ml, LPS was added at 1 hour at 5 ng/ml. Incubation 24 hours), peripheral blood monocytes (treated with anti-IL-10 at time 0, 10 ng/ml, LPS was added at 1 hour at 5 ng/ml. Incubation 24 hours), spinal cord, base of medulla (Huntington's chorea), thigh and arm muscle (ALS), breast skin fibroblast (untreated), breast skin fibroblast (treated with 9CIS Retinoic Acid 1 μM for 20 hours), breast skin fibroblast (treated with TNF-alpha & IL-1 beta, 10 ng/ml each for 20 hours), fetal liver mast cells, hematopoietic (Mast cells prepared from human fetal liver hematopoietic progenitor cells (CD34+ stem cells) cultured in the presence of hIL-6 and hSCF for 18 days), epithelial layer of colon, bronchial epithelial cells (treated for 20hours with 20% smoke conditioned media), lymph node, pooled peripheral blood mononuclear cells (untreated), pooled brain segments: striatum, globus pallidus and posterior putamen (Alzheimer's Disease), pituitary gland, umbilical cord blood, CD34+ derived dendritic cells (treated with SCF, GM-CSF & TNF alpha, 13 days), umbilical cord blood, CD34+ derived dendritic cells (treated with SCF, GM-CSF & TNF alpha, 13 days followed by PMA/Ionomycin for 5 hours), small intestine, rectum, bone marrow neuroblastoma cell line (SH-SY5Y cells, treated with 6-Hydroxydopamine 100 uM for 8 hours), bone marrow, neuroblastoma cell line (SH-SY5Y cells, untreated), brain segments from one donor: amygdala, entorhinal cortex, globus pallidus, substantia innominata, striatum, dorsal caudate nucleus, dorsal putamen, ventral nucleus accumbens, archaecortex (hippocampus anterior and posterior), thalamus, nucleus raphe magnus, periaqueductal gray, midbrain, substantia nigra, and dentate nucleus, pineal gland (Alzheimer's Disease), preadipocytes (untreated), preadipocytes (treated with a peroxisome proliferator-activated receptor gamma agonist, 1microM, 4 hours), pooled prostate |

TABLE 6-continued

| Library | Vector | Library Description |
| --- | --- | --- |
| | | (adenofibromatous hyperplasia), pooled kidney, pooled adipocytes (untreated), pooled adipocytes (treated with human insulin), pooled mesentaric and abdomenal fat, pooled adrenal glands, pooled thyroid (normal and adenomatous hyperplasia), pooled spleen (normal and with changes consistent with idiopathic thrombocytopenic purpura), pooled right and left breast, pooled lung, pooled nasal polyps, pooled fat, pooled synovium (normal and rhumatoid arthritis), pooled brain (meningioma, gemistocytic astrocytoma. and Alzheimer's disease), pooled fetal colon, pooled colon: ascending, descending (chronic ulcerative colitis), and rectal tumor (adenocarcinoma), pooled esophagus, normal and tumor (invasive grade 3 adenocarcinoma), pooled breast skin fibroblast (one treated w/9CIS Retinoic Acid and the other with TNF-alpha & IL-1 beta), pooled gallbladder (acute necrotizing cholecystitis with cholelithiasis (clinically hydrops), acute hemorrhagic cholecystitis with cholelithiasis, chronic cholecystitis and cholelithiasis), pooled fetal heart, (Patau's and fetal demise), pooled neurogenic tumor cell line, SK-N-MC, (neuroepitelioma, metastasis to supra-orbital area, untreated) and neuron, NT-2 cell line, (treated with mouse leptin at 1 μg/ml and 9cis retinoic acid at 3.3 μM for 6 days), pooled ovary (normal and polycystic ovarian disease), pooled prostate, (adenofibromatous hyperplasia), pooled seminal vesicle, pooled small intestine, pooled fetal small intestine, pooled stomach and fetal stomach, prostate epithelial cells, pooled testis (normal and embryonal carcinoma), pooled uterus, pooled uterus tumor (grade 3 adenosquamous carcinoma and leiomyoma), pooled uterus, endometrium, and myometrium, (normal and adenomatous hyperplasia with squamous metaplasia and focal atypia), pooled brain: (temporal lobe meningioma, cerebellum and hippocampus (Alzheimer's Disease), pooled skin, fetal lung, adrenal tumor (adrenal cortical carcinoma), prostate tumor (adenocarcinoma), fetal heart, fetal small intestine, ovary tumor (mucinous cystadenoma), ovary, ovary tumor (transitional cell carcinoma), disease prostate (adenofibromatous hyperplasia), fetal colon, uterus tumor (leiomyoma), temporal brain, submandibular gland, colon tumor (adenocarcinoma), ascending and transverse colon, ovary tumor (endometrioid carcinoma), lung tumor (squamous cell carcinoma), fetal brain, fetal lung, ureter tumor (transitional cell carcinoma), untreated HNT cells, para-aortic soft tissue, testis, seminal vesicle, diseased ovary (endometriosis), temporal lobe, myometrium, diseased gallbladder (cholecystitis, cholelithiasis), placenta, breast tumor (ductal adenocarcinoma), breast, lung tumor (liposarcoma), endometrium, abdominal fat, cervical spine dorsal root ganglion, thoracic spine dorsal root ganglion, diseased thyroid (adenomatous hyperplasia), liver, kidney, fetal liver, NT-2 cells (treated with mouse leptin and 9cis RA), K562 cells (treated with 9cis RA), cerebellum, corpus callosum, hypothalamus, fetal brain astrocytes (treated with TNFa and IL-1b), inferior parietal cortex, posterior hippocampus, pons, thalamus, C3A cells (untreated), C3A cells (treated with 3-methylcholanthrene), testis, colon epithelial layer, pooled prostate, pooled liver, substantia nigra, thigh muscle, rib bone, fallopian tube tumor (endometrioid and serous adenocarcinoma), diseased lung (idiopathic pulmonary disease), cingulate anterior allocortex and neocortex, cingulate posterior allocortex, auditory neocortex, frontal neocortex, orbital inferior neocortex, parietal superior neocortex, visual primary neocortex, dentate nucleus, posterior cingulate, cerebellum, vermis, inferior temporal cortex, medulla, posterior parietal cortex, colon polyp, pooled breast, anterior and posterior hippocampus, mesenteric and abdominal fat, pooled esophagus, pooled fetal kidney, pooled fetal liver, ileum, small intestine, pooled gallbladder, frontal and superior temporal cortex, pooled ovary, pooled endometrium, pooled prostate, pooled kidney, fetal femur, sacrum tumor (giant cell tumor), pooled kidney and kidney tumor (renal cell carcinoma clear-cell type), pooled liver and liver tumor (neuroendocrine carcinoma), pooled fetal liver, pooled lung, fetal pancreas, pancreas, parotid gland, parotid tumor (sebaceous lymphadenoma), retroperitoneal and suprglottic soft tissue, spleen, fetal spleen, spleen tumor (malignant lymphoma), diseased spleen (idiopathic thrombocytopenic purpura), parathyroid, thyroid, thymus, tonsil ureter tumor (transitional cell carcinoma), pooled adrenal gland and adrenal tumor |

TABLE 6-continued

| Library | Vector | Library Description |
|---|---|---|
| | | (pheochromocytoma), pooled lymph node tumor (Hodgkin's disease and metastatic adenocarcinoma), pooled neck and calf muscles, and pooled bladder. |
| PANCNOT15 | pINCY | Library was constructed using RNA isolated from diseased pancreatic tissue removed from a 15-year-old Caucasian male during a exploratory laparotomy with distal pancreatectomy and total splenectomy. Pathology indicated islet cell hyperplasia. Family history included prostate cancer and cardiovacular disease. |
| PANCNOT17 | pINCY | Library was constructed using RNA isolated from pancreatic tissue removed from a 65-year-old female. Pathology for the associated tumor tissue indicated well-differentiated, metastatic, neuroendocrine carcinoma (nuclear grade 1). |
| PITUDIR01 | PCDNA2.1 | This random primed library was constructed using RNA isolated from pituitary gland tissue removed from a 70-year-old female who died from metastatic adenocarcinoma. |
| PONSAZT01 | pINCY | Library was constructed using RNA isolated from diseased pons tissue removed from the brain of a 74-year-old Caucasian male who died from Alzheimer's disease. |
| PROSTUS23 | pINCY | This subtracted prostate tumor library was constructed using 10 million clones from a pooled prostate tumor library that was subjected to 2 rounds of subtractive hybridization with 10 million clones from a pooled prostate tissue library. The starting library for subtraction was constructed by pooling equal numbers of clones from 4 prostate tumor libraries using mRNA isolated from prostate tumor removed from Caucasian males at ages 58 (A), 61 (B), 66 (C), and 68 (D) during prostatectomy with lymph node excision. Pathology indicated adenocarcinoma in all donors. History included elevated PSA, induration and tobacco abuse in donor A; elevated PSA, induration, prostate hyperplasia, renal failure, osteoarthritis, renal artery stenosis, benign HTN, thrombocytopenia, hyperlipidemia, tobacco/alcohol abuse and hepatitis C (carrier) in donor B; elevated PSA, induration, and tobacco abuse in donor C; and elevated PSA, induration, hypercholesterolemia, and kidney calculus in donor D. The hybridization probe for subtraction was constructed by pooling equal numbers of cDNA clones from 3 prostate tissue libraries derived from prostate tissue, prostate epithelial cells, and fibroblasts from prostate stroma from 3 different donors. Subtractive hybridization conditions were based on the methodologies of Swaroop et al., NAR 19 (1991): 1954 and Bonaldo, et al. Genome Research 6 (1996): 791. |
| PROSTUT20 | pINCY | The library was constructed using RNA isolated from prostate umor tissue removed from a 58-year-old Caucasian male during radical prostatectomy, regional lymph node excision, and prostate needle biopsy. Pathology indicated adenocarcinoma (Gleason grade 3 + 2) of the prostate, which formed a predominant mass involving primarily the right side and focally involved the left side, peripherally and anteriorly. The patient presented with elevated prostate specific antigen (PSA)and induration. Family history included breast cancer. |
| SCOMDIT01 | pINCY | Library was constructed using RNA isolated from diseased spinal cord tissue removed from the base of the medulla of a 57-year-old Caucasian male who died from a cerebrovascular accident. Patient history included Huntington's disease and emphysema. |
| SINTBST01 | pINCY | Library was constructed using RNA isolated from ileum tissue obtained from an 18-year-old Caucasian female during bowel anastomosis. Pathology indicated Crohn's disease of the ileum, involving 15 cm of the small bowel. Family history included cerebrovascular disease and atherosclerotic coronary artery disease. |
| THYRNOT02 | PSPORT1 | Library was constructed using RNA isolated from the diseased thyroid tissue of a 16-year-old Caucasian female with Graves' disease (hyperthyroidism). |
| THYRNOT03 | pINCY | Library was constructed using RNA isolated from thyroid tissue removed from the left thyroid of a 28-year-old Caucasian female during a complete thyroidectomy. Pathology indicated a small nodule of adenomatous hyperplasia present in the left thyroid. Pathology for the associated tumor tissue indicated dominant follicular adenoma, forming a well-encapsulated mass in the left thyroid. |
| TMLR2DT01 | PBLUESCRIPT | Library was constructed using RNA isolated from non-adherent peripheral blood mononuclear cells. The blood was obtained from unrelated male and female donors. Cells from each donor were purified on Ficoll Hypaque, then co-cultured for 24 hours in medium containing normal human serum at a cell density of 2million cells/ml. |

TABLE 6-continued

| Library | Vector | Library Description |
|---|---|---|
| UCMCL5T01 | PBLUESCRIPT | Library was constructed using RNA isolated from mononuclear cells obtained from the umbilical cord blood of 12 individuals. The cells were cultured for 12 days with IL-5 before RNA was obtained from the pooled lysates. |
| UTRSTMR01 | pINCY | Library was constructed using RNA isolated from uterine myometrial tissue removed from a 41-year-old Caucasian female during a vaginal hysterectomy. The endometrium was secretory and contained fragments of endometrial polyps. Pathology for associated tumor tissue indicated uterine leiomyoma. Patient history included ventral hernia and a benign ovarian neoplasm. |

TABLE 7

| Program | Description | Reference | Parameter Threshold |
|---|---|---|---|
| ABI FACTURA | A program that removes vector sequences and masks ambiguous bases in nucleic acid sequences. | Applied Biosystems, Foster City, CA. | |
| ABI/PARACEL FDF | A Fast Data Finder useful in comparing and annotating amino acid or nucleic acid sequences. | Applied Biosystems, Foster City, CA; Paracel Inc., Pasadena, CA. | Mismatch <50% |
| ABI AutoAssembler | A program that assembles nucleic acid sequences. | Applied Biosystems, Foster City, CA. | |
| BLAST | A Basic Local Alignment Search Tool useful in sequence similarity search for amino acid and nucleic acid sequences. BLAST includes five functions: blastp, blastn, blastx, tblastn, and tblastx. | Altschul, S. F. et al. (1990) J. Mol. Biol. 215: 403-410; Altschul, S. F. et al. (1997) Nucleic Acids Res. 25: 3389-3402. | ESTs: Probability value = 1.0E−8 or less; Full Length sequences: Probability value = 1.0E−10 or less |
| FASTA | A Pearson and Lipman algorithm that searches for similarity between a query sequence and a group of sequences of the same type. FASTA comprises as least five functions: fasta, tfasta, fastx, tfastx, and ssearch. | Pearson, W. R. and D. J. Lipman (1988) Proc. Natl. Acad Sci. USA 85: 2444-2448; Pearson, W. R. (1990) Methods Enzymol. 183: 63-98; and Smith, T. F. and M. S. Waterman (1981) Adv. Appl. Math. 2: 482-489. | ESTs: fasta E value = 1.06E−6; Assembled ESTs: fasta Identity = 95% or greater and Match length = 200 bases or greater; fastx E value = 1.0E−8 or less; Full Length sequences: fastx score = 100 or greater |
| BLIMPS | A BLocks IMProved Searcher that matches a sequence against those in BLOCKS, PRINTS, DOMO, PRODOM, and PFAM databases to search for gene families, sequence homology, and structural fingerprint regions. | Henikoff, S. and J. G. Henikoff (1991) Nucleic Acids Res. 19: 6565-6572; Henikoff, J. G. and S. Henikoff (1996) Methods Enzymol. 266: 88-105; and Attwood, T. K. et al. (1997) J. Chem. Inf. Comput. Sci. 37: 417-424. | Probability value = 1.0E−3 or less |
| HMMER | An algorithm for searching a query sequence against hidden Markov model (HMM)-based databases of protein family consensus sequences, such as PFAM, INCY, SMART and TIGRFAM. | Krogh, A. et al. (1994) J. Mol. Biol. 235: 1501-1531; Sonnhammer, E. L. L. et al. (1988) Nucleic Acids Res. 26: 320-322; Durbin, R. et al. (1998) Our World View, in a Nutshell, Cambridge Univ. Press, pp. 1-350. | PFAM, INCY, SMART or TIGRFAM hits: Probability value = 1.0E−3 or less; Signal peptide hits: Score = 0 or greater |
| ProfileScan | An algorithm that searches for structural and sequence motifs in protein sequences that match sequence patterns defined in Prosite. | Gribskov, M. et al. (1988) CABIOS 4: 61-66; Gribskov, M. et al. (1989) Methods Enzymol. 183: 146-159; Bairoch, A. et al. (1997) Nucleic Acids Res. 25: 217-221. | Normalized quality score ≧ GCG specified "HIGH" value for that particular Prosite motif. Generally, score = 1.4-2.1. |
| Phred | A base-calling algorithm that examines automated sequencer traces with high sensitivity and probability. | Ewing, B. et al. (1998) Genome Res. 8: 175-185; Ewing, B. and P. Green (1998) Genome Res. 8: 186-194. | |
| Phrap | A Phils Revised Assembly Program including SWAT and CrossMatch, programs based on efficient implementation of the Smith-Waterman algorithm, useful in searching sequence homology and assembling DNA sequences. | Smith, T. F. and M. S. Waterman (1981) Adv. Appl. Math. 2: 482-489; Smith, T. F. and M. S. Waterman (1981) J. Mol. Biol. 147: 195-197; and Green, P., University of Washington, Seattle, WA. | Score = 120 or greater; Match length = 56 or greater |

TABLE 7-continued

| Program | Description | Reference | Parameter Threshold |
|---|---|---|---|
| Consed | A graphical tool for viewing and editing Phrap assemblies. | Gordon, D. et al. (1998) Genome Res. 8: 195-202. | |
| SPScan | A weight matrix analysis program that scans protein sequences for the presence of secretory signal peptides. | Nielson, H. et al. (1997) Protein Engineering 10: 1-6; Claverie, J. M. and S. Audic (1997) CABIOS 12: 431-439. | Score = 3.5 or greater |
| TMAP | A program that uses weight matrices to delineate transmembrane segments on protein sequences and determine orientation. | Persson, B. and P. Argos (1994) J. Mol. Biol. 237: 182-192; Persson, B. and P. Argos (1996) Protein Sci. 5: 363-371. | |
| TMHMMER | A program that uses a hidden Markov model (HMM) to delineate transmembrane segments on protein sequences and determine orientation. | Sonnhammer, E. L. et al. (1998) Proc. Sixth Intl. Conf. On Intelligent Systems for Mol. Biol., Glasgow et al., eds., The Am. Assoc. for Artificial Intelligence (AAAI) Press, Menlo Park, CA, and MIT Press, Cambridge, MA, pp. 175-182. | |
| Motifs | A program that searches amino acid sequences for patterns that matched those defined in Prosite. | Bairoch, A. et al. (1997) Nucleic Acids Res. 25: 217-221; Wisconsin Package Program Manual, version 9, page M51-59, Genetics Computer Group, Madison, WI. | |

TABLE 8

| SEQ ID NO: | PID | EST ID | SNP ID | EST SNP | CB1 SNP | EST Allele | Allele 1 | Allele 2 | Amino acid | Caucasian Allele 1 frequency | African Allele 1 frequency | Asian Allele 1 fre-quency | Hispanic Allele 1 frequency |
|---|---|---|---|---|---|---|---|---|---|---|---|---|---|
| 39 | 3048626 | 3504115H1 | SNP00142220 | 215 | 249 | T | T | C | S68 | n/a | n/a | n/a | n/a |
| 39 | 3048626 | 3517533H1 | SNP00038815 | 179 | 382 | T | C | T | S113 | n/a | n/a | n/a | n/a |
| 39 | 3048626 | 7409370H1 | SNP00142220 | 376 | 252 | T | T | C | P69 | n/a | n/a | n/a | n/a |
| 40 | 2684425 | 2120782H1 | SNP00096166 | 164 | 709 | T | T | C | I165 | n/a | n/a | n/a | n/a |
| 40 | 2684425 | 2291826H1 | SNP00027861 | 175 | 2682 | T | C | T | noncoding | n/a | n/a | n/a | n/a |
| 40 | 2684425 | 4379356H1 | SNP00096166 | 169 | 708 | T | T | C | I165 | n/a | n/a | n/a | n/a |
| 40 | 2684425 | 4380813H1 | SNP00096166 | 165 | 706 | T | T | C | N164 | n/a | n/a | n/a | n/a |
| 40 | 2684425 | 4574989H1 | SNP00073769 | 107 | 2351 | T | C | T | C713 | n/d | n/d | n/d | n/d |
| 40 | 2684425 | 5814109H1 | SNP00105399 | 56 | 2524 | G | G | A | E770 | n/a | n/a | n/a | n/a |
| 40 | 2684425 | 5817776H1 | SNP00105399 | 57 | 2525 | G | G | A | E771 | n/a | n/a | n/a | n/a |
| 40 | 2684425 | 5821814H1 | SNP00105399 | 55 | 2523 | G | G | A | G770 | n/a | n/a | n/a | n/a |
| 40 | 2684425 | 6196749H1 | SNP00073769 | 105 | 2354 | C | C | T | H714 | n/d | n/d | n/d | n/d |
| 40 | 2684425 | 6725305H1 | SNP00105399 | 330 | 2527 | G | G | A | Q771 | n/a | n/a | n/a | n/a |
| 41 | 7505960 | 2699329H1 | SNP00113522 | 36 | 1589 | A | A | C | K528 | n/d | n/d | n/d | n/d |
| 41 | 7505960 | 2743044H1 | SNP00060643 | 34 | 820 | T | C | T | Y271 | n/a | n/a | n/a | n/a |
| 41 | 7505960 | 4443424H1 | SNP00113522 | 8 | 1587 | A | A | C | D527 | n/d | n/d | n/d | n/d |
| 41 | 7505960 | 4860526H1 | SNP00113522 | 79 | 1588 | A | A | C | A527 | n/d | n/d | n/d | n/d |
| 41 | 7505960 | 6298990H1 | SNP00122314 | 88 | 387 | G | G | A | G127 | n/d | n/d | n/d | n/d |
| 41 | 7505960 | 6455382H1 | SNP00122314 | 391 | 390 | G | G | A | G128 | n/d | n/d | n/d | n/d |
| 42 | 7507021 | 6041339H1 | SNP00058963 | 323 | 903 | C | T | C | noncoding | n/d | n/d | n/a | n/d |
| 43 | 7509099 | 7196339H1 | SNP00116698 | 483 | 1254 | A | A | C | R391 | 0.97 | 0.96 | n/d | 0.99 |
| 44 | 7509361 | 1307093H1 | SNP00076254 | 169 | 753 | C | C | G | T167 | n/a | n/a | n/a | n/a |
| 44 | 7509361 | 1314858H1 | SNP00148375 | 150 | 1207 | G | G | A | noncoding | n/a | n/a | n/a | n/a |
| 44 | 7509361 | 1442760H1 | SNP00011095 | 243 | 288 | G | G | A | P12 | n/a | n/a | n/a | n/a |
| 44 | 7509361 | 1554337H1 | SNP00011095 | 144 | 289 | A | G | A | M13 | n/a | n/a | n/a | n/a |
| 44 | 7509361 | 1560591H1 | SNP00148375 | 94 | 1205 | G | G | A | noncoding | n/a | n/a | n/a | n/a |
| 44 | 7509361 | 1620178H1 | SNP00148375 | 90 | 1206 | G | G | A | noncoding | n/a | n/a | n/a | n/a |
| 44 | 7509361 | 2697396H1 | SNP00011095 | 279 | 287 | G | G | A | R12 | n/a | n/a | n/a | n/a |
| 44 | 7509361 | 2841966H1 | SNP00100840 | 34 | 500 | G | G | C | G83 | n/d | n/d | n/a | n/d |
| 44 | 7509361 | 2842095H1 | SNP00100840 | 35 | 501 | G | G | C | E83 | n/d | n/d | n/a | n/d |
| 44 | 7509361 | 2848215H1 | SNP00011095 | 184 | 286 | G | G | A | A12 | n/a | n/a | n/a | n/a |
| 44 | 7509361 | 3112588H1 | SNP00011095 | 239 | 285 | G | G | A | L11 | n/a | n/a | n/a | n/a |
| 44 | 7509361 | 3498684H1 | SNP00148375 | 29 | 1200 | G | G | A | noncoding | n/a | n/a | n/a | n/a |
| 44 | 7509361 | 3551794H1 | SNP00076254 | 116 | 752 | C | C | G | T167 | n/a | n/a | n/a | n/a |
| 44 | 7509361 | 5120295H1 | SNP00076254 | 115 | 741 | G | C | G | K163 | n/a | n/a | n/a | n/a |
| 44 | 7509361 | 7432084H1 | SNP00148375 | 235 | 1198 | G | G | A | noncoding | n/a | n/a | n/a | n/a |
| 47 | 7506852 | 1401073H1 | SNP00036002 | 67 | 1691 | T | C | T | noncoding | n/a | n/a | n/a | n/a |
| 47 | 7506852 | 3724338H1 | SNP00036002 | 254 | 1687 | C | C | T | noncoding | n/a | n/a | n/a | n/a |
| 47 | 7506852 | 3854972H1 | SNP00036002 | 17 | 1689 | C | C | T | noncoding | n/a | n/a | n/a | n/a |
| 47 | 7506852 | 4205312H1 | SNP00036002 | 192 | 1677 | C | C | T | noncoding | n/a | n/a | n/a | n/a |
| 48 | 7503782 | 6366326H1 | SNP00096612 | 255 | 2675 | C | C | A | H627 | 0.45 | 0.28 | 0.50 | 0.38 |
| 48 | 7503782 | 6587229H1 | SNP00058173 | 320 | 3251 | A | A | G | noncoding | 0.62 | n/a | n/a | n/a |
| 48 | 7503782 | 7036138H1 | SNP00096612 | 125 | 2677 | A | C | A | Q628 | 0.45 | 0.28 | 0.50 | 0.38 |
| 49 | 7504647 | 5051517H1 | SNP00065898 | 155 | 1110 | A | A | G | noncoding | n/a | n/a | n/a | n/a |
| 49 | 7504647 | 5051533H1 | SNP00065898 | 155 | 1111 | A | A | G | noncoding | n/a | n/a | n/a | n/a |
| 50 | 7500424 | 1335968H1 | SNP00001367 | 118 | 696 | G | G | A | noncoding | n/a | n/a | n/a | n/a |
| 50 | 7500424 | 1335968H1 | SNP00149783 | 49 | 627 | A | A | G | noncoding | n/a | n/a | n/a | n/a |

TABLE 8-continued

| SEQ ID NO: | PID | EST ID | SNP ID | EST SNP | CB1 SNP | EST Allele | Allele 1 | Allele 2 | Amino acid | Caucasian Allele 1 frequency | African Allele 1 frequency | Asian Allele 1 fre-quency | Hispanic Allele 1 frequency |
|---|---|---|---|---|---|---|---|---|---|---|---|---|---|
| 50 | 7500424 | 1445563H1 | SNP00121362 | 107 | 574 | G | G | C | noncoding | n/a | n/a | n/a | n/a |
| 50 | 7500424 | 3407118H1 | SNP00001367 | 154 | 694 | G | G | A | noncoding | n/a | n/a | n/a | n/a |
| 50 | 7500424 | 3407118H1 | SNP00149783 | 85 | 625 | A | A | G | noncoding | n/a | n/a | n/a | n/a |
| 50 | 7500424 | 3484021H1 | SNP00148356 | 184 | 193 | C | C | T | P33 | n/a | n/a | n/a | n/a |
| 50 | 7500424 | 3614711H1 | SNP00148356 | 112 | 112 | C | C | T | P6 | n/a | n/a | n/a | n/a |
| 50 | 7500424 | 3646188H1 | SNP00001367 | 137 | 693 | G | G | A | noncoding | n/a | n/a | n/a | n/a |
| 50 | 7500424 | 3714764H1 | SNP00149783 | 131 | 624 | A | A | G | noncoding | n/a | n/a | n/a | n/a |
| 50 | 7500424 | 4201810H1 | SNP00121362 | 24 | 573 | G | G | C | noncoding | n/a | n/a | n/a | n/a |
| 50 | 7500424 | 4457406H1 | SNP00148356 | 18 | 117 | C | C | T | Q8 | n/a | n/a | n/a | n/a |
| 50 | 7500424 | 4822857H1 | SNP00121362 | 34 | 572 | G | G | C | noncoding | n/a | n/a | n/a | n/a |
| 50 | 7500424 | 4992535H1 | SNP00148356 | 129 | 109 | C | C | T | S5 | n/a | n/a | n/a | n/a |
| 50 | 7500424 | 5810876H1 | SNP00121362 | 204 | 571 | G | G | C | noncoding | n/a | n/a | n/a | n/a |
| 51 | 7500449 | 2376438H1 | SNP00037402 | 81 | 185 | T | T | C | R39 | n/a | n/a | n/a | n/a |
| 51 | 7500449 | 6880929J1 | SNP00142781 | 103 | 930 | C | C | A | noncoding | n/a | n/a | n/a | n/a |
| 53 | 7503292 | 7076246H1 | SNP00111578 | 128 | 1217 | G | A | G | noncoding | 0.03 | n/a | n/a | n/a |
| 54 | 7503311 | 7455178H2 | SNP00126507 | 378 | 1463 | C | C | A | noncoding | n/a | n/a | n/a | n/a |
| 54 | 7503311 | 8007727H1 | SNP00137525 | 212 | 1326 | G | G | A | noncoding | n/a | n/a | n/a | n/a |
| 55 | 7510384 | 6908872J1 | SNP00062894 | 404 | 528 | C | T | C | P165 | n/d | n/a | n/a | n/a |
| 55 | 7510384 | 6912987J1 | SNP00062894 | 374 | 520 | T | T | C | N162 | n/d | n/a | n/a | n/a |
| 58 | 8017335 | 1351856H1 | SNP00120957 | 54 | 1790 | C | C | T | noncoding | n/a | n/a | n/a | n/a |
| 58 | 8017335 | 4776360H1 | SNP00031314 | 199 | 2140 | C | A | C | noncoding | 0.87 | 0.87 | 0.88 | 0.84 |
| 58 | 8017335 | 6839382H1 | SNP00031314 | 379 | 2141 | A | A | C | noncoding | 0.87 | 0.87 | 0.88 | 0.84 |
| 60 | 7510055 | 1432995H1 | SNP00015901 | 1 | 1031 | G | G | A | noncoding | n/a | n/a | n/a | n/a |
| 60 | 7510055 | 1432995H1 | SNP00015902 | 56 | 1086 | C | C | G | noncoding | 0.91 | n/a | n/a | n/a |
| 60 | 7510055 | 1452055H1 | SNP00000585 | 7 | 77 | C | C | T | noncoding | 0.83 | 0.97 | 0.58 | 0.81 |
| 60 | 7510055 | 1536017H1 | SNP00000585 | 20 | 76 | C | C | T | noncoding | 0.83 | 0.97 | 0.58 | 0.81 |
| 60 | 7510055 | 2610356H1 | SNP00000585 | 59 | 75 | C | C | T | noncoding | 0.83 | 0.97 | 0.58 | 0.81 |
| 60 | 7510055 | 2970103H2 | SNP00015901 | 154 | 1032 | G | G | A | noncoding | n/a | n/a | n/a | n/a |
| 60 | 7510055 | 2970103H2 | SNP00015902 | 209 | 1087 | C | C | G | noncoding | 0.91 | n/a | n/a | n/a |
| 60 | 7510055 | 3520995H1 | SNP00000585 | 18 | 74 | C | C | T | noncoding | 0.83 | 0.97 | 0.58 | 0.81 |
| 60 | 7510055 | 3679678H1 | SNP00000585 | 44 | 73 | T | C | T | noncoding | 0.83 | 0.97 | 0.58 | 0.81 |
| 60 | 7510055 | 4689661H1 | SNP00000585 | 38 | 71 | C | C | T | noncoding | 0.83 | 0.97 | 0.58 | 0.81 |
| 61 | 7501754 | 1287052H1 | SNP00020471 | 223 | 1622 | C | C | T | noncoding | n/a | n/a | n/a | n/a |
| 61 | 7501754 | 1366741H1 | SNP00020470 | 16 | 957 | C | C | T | L292 | n/a | n/a | n/a | n/a |
| 61 | 7501754 | 1366741H1 | SNP00144758 | 230 | 1171 | T | T | C | L364 | n/a | n/a | n/a | n/a |
| 61 | 7501754 | 1412435H1 | SNP00020469 | 240 | 267 | C | C | T | I62 | n/a | n/a | n/a | n/a |
| 61 | 7501754 | 1416519H1 | SNP00020471 | 188 | 1621 | C | C | T | noncoding | n/a | n/a | n/a | n/a |
| 61 | 7501754 | 1477407H1 | SNP00115549 | 182 | 609 | A | A | G | R176 | n/a | n/a | n/a | n/a |
| 61 | 7501754 | 1592982H1 | SNP00144757 | 103 | 916 | G | G | A | D279 | n/a | n/a | n/a | n/a |
| 61 | 7501754 | 1593474H1 | SNP00060616 | 79 | 396 | T | T | G | I105 | n/a | n/a | n/a | n/a |
| 61 | 7501754 | 2110613H1 | SNP00002430 | 142 | 1269 | A | A | G | L396 | 0.55 | 0.30 | 0.67 | 0.69 |
| 61 | 7501754 | 2286353H1 | SNP00002429 | 69 | 732 | C | C | T | Y217 | n/a | n/a | n/a | n/a |
| 61 | 7501754 | 3268502H1 | SNP00020469 | 199 | 233 | C | C | T | A51 | n/a | n/a | n/a | n/a |
| 61 | 7501754 | 3603324H1 | SNP00020470 | 16 | 956 | C | C | T | P292 | n/a | n/a | n/a | n/a |
| 61 | 7501754 | 3603324H1 | SNP00144758 | 230 | 1170 | T | T | C | H363 | n/a | n/a | n/a | n/a |
| 61 | 7501754 | 3665554H1 | SNP00002430 | 31 | 1266 | G | A | G | L395 | 0.55 | 0.30 | 0.67 | 0.69 |
| 61 | 7501754 | 3782483H1 | SNP00002429 | 129 | 731 | T | C | T | F217 | n/a | n/a | n/a | n/a |
| 61 | 7501754 | 3782483H1 | SNP00115549 | 6 | 608 | A | A | G | Q176 | n/a | n/a | n/a | n/a |
| 61 | 7501754 | 3825869H1 | SNP00020469 | 249 | 251 | C | C | T | P57 | n/a | n/a | n/a | n/a |
| 61 | 7501754 | 4061686H1 | SNP00144757 | 220 | 913 | G | G | A | A278 | n/a | n/a | n/a | n/a |
| 61 | 7501754 | 4205282H1 | SNP00119977 | 113 | 1541 | A | A | C | noncoding | n/a | n/a | n/a | n/a |
| 61 | 7501754 | 4259242H1 | SNP00020470 | 15 | 955 | C | C | T | L292 | n/a | n/a | n/a | n/a |
| 61 | 7501754 | 4259242H1 | SNP00144758 | 229 | 1169 | T | T | C | L363 | n/a | n/a | n/a | n/a |
| 61 | 7501754 | 4753963H1 | SNP00020470 | 4 | 952 | C | C | T | R291 | n/a | n/a | n/a | n/a |
| 61 | 7501754 | 4753963H1 | SNP00144758 | 217 | 1165 | T | T | C | Y362 | n/a | n/a | n/a | n/a |
| 61 | 7501754 | 5269726H1 | SNP00144758 | 167 | 1163 | T | T | C | F361 | n/a | n/a | n/a | n/a |
| 61 | 7501754 | 5662745H1 | SNP00144757 | 129 | 915 | G | G | A | P278 | n/a | n/a | n/a | n/a |
| 61 | 7501754 | 5832111H1 | SNP00020471 | 101 | 1607 | C | C | T | noncoding | n/a | n/a | n/a | n/a |
| 61 | 7501754 | 5847218H1 | SNP00144757 | 93 | 914 | G | G | A | R278 | n/a | n/a | n/a | n/a |
| 61 | 7501754 | 5847579H1 | SNP00020470 | 164 | 940 | C | C | T | Q287 | n/a | n/a | n/a | n/a |
| 61 | 7501754 | 5847579H1 | SNP00144757 | 123 | 898 | G | G | A | D273 | n/a | n/a | n/a | n/a |
| 61 | 7501754 | 6882567J1 | SNP00119977 | 271 | 1543 | C | A | C | noncoding | n/a | n/a | n/a | n/a |
| 61 | 7501754 | 6997953H1 | SNP00020469 | 121 | 265 | C | C | T | L62 | n/a | n/a | n/a | n/a |
| 61 | 7501754 | 6997953H1 | SNP00060616 | 250 | 394 | T | T | G | F105 | n/a | n/a | n/a | n/a |
| 62 | 7510517 | 1252418F6 | SNP00053146 | 95 | 2574 | C | C | T | noncoding | n/a | n/a | n/a | n/a |
| 62 | 7510517 | 1252418T6 | SNP00053146 | 135 | 2575 | C | C | T | noncoding | n/a | n/a | n/a | n/a |
| 62 | 7510517 | 1253746H1 | SNP00016073 | 86 | 2252 | A | A | G | noncoding | n/a | n/a | n/a | n/a |
| 62 | 7510517 | 1560944H1 | SNP00016072 | 183 | 1896 | G | A | G | noncoding | 0.12 | n/a | n/a | n/a |
| 62 | 7510517 | 2137250T6 | SNP00053146 | 110 | 2600 | C | C | T | noncoding | n/a | n/a | n/a | n/a |
| 62 | 7510517 | 2771793T6 | SNP00053146 | 155 | 2581 | C | C | T | noncoding | n/a | n/a | n/a | n/a |
| 62 | 7510517 | 3009863T7 | SNP00053146 | 147 | 2594 | C | C | T | noncoding | n/a | n/a | n/a | n/a |
| 62 | 7510517 | 3472133T6 | SNP00053146 | 131 | 2579 | T | C | T | noncoding | n/a | n/a | n/a | n/a |
| 62 | 7510517 | 415685T6 | SNP00053146 | 138 | 2616 | C | C | T | noncoding | n/a | n/a | n/a | n/a |
| 62 | 7510517 | 461386T6 | SNP00053146 | 105 | 2605 | C | C | T | noncoding | n/a | n/a | n/a | n/a |

TABLE 8-continued

| SEQ ID NO: | PID | EST ID | SNP ID | EST SNP | CB1 SNP | EST Allele | Allele 1 | Allele 2 | Amino acid | Caucasian Allele 1 frequency | African Allele 1 frequency | Asian Allele 1 fre-quency | Hispanic Allele 1 frequency |
|---|---|---|---|---|---|---|---|---|---|---|---|---|---|
| 62 | 7510517 | 6521830H1 | SNP00053145 | 453 | 432 | C | C | T | T53 | 0.91 | n/a | n/a | n/a |
| 62 | 7510517 | 950639T6 | SNP00053146 | 160 | 2593 | C | C | T | noncoding | n/a | n/a | n/a | n/a |
| 63 | 7511014 | 1439526F7 | SNP00144232 | 42 | 1598 | C | C | T | noncoding | n/a | n/a | n/a | n/a |
| 63 | 7511014 | 1439526F7 | SNP00144233 | 87 | 1643 | A | G | A | noncoding | n/a | n/a | n/a | n/a |
| 63 | 7511014 | 1446257F6 | SNP00144233 | 389 | 1646 | G | G | A | noncoding | n/a | n/a | n/a | n/a |
| 63 | 7511014 | 7612633H1 | SNP00144232 | 444 | 1600 | C | C | T | noncoding | n/a | n/a | n/a | n/a |
| 64 | 7506687 | 1415884H1 | SNP00041797 | 78 | 5120 | T | T | C | noncoding | n/d | n/a | n/a | n/a |
| 64 | 7506687 | 1477444H1 | SNP00076239 | 52 | 4874 | T | T | C | noncoding | n/d | n/d | n/d | n/d |
| 64 | 7506687 | 1485053H1 | SNP00076240 | 117 | 5540 | C | C | T | noncoding | n/d | n/d | n/d | n/d |
| 64 | 7506687 | 1965096R6 | SNP00041797 | 87 | 5119 | T | T | C | noncoding | n/d | n/a | n/a | n/a |
| 64 | 7506687 | 3679061H1 | SNP00011057 | 18 | 6519 | C | C | T | noncoding | n/d | n/a | n/a | n/a |
| 65 | 7510621 | 076193H1 | SNP00039731 | 93 | 502 | T | T | C | V38 | n/d | n/a | n/a | n/a |
| 65 | 7510621 | 076193H1 | SNP00069420 | 159 | 568 | T | T | G | V60 | n/d | n/d | n/d | n/d |
| 65 | 7510621 | 076193H1 | SNP00135470 | 154 | 563 | C | C | T | I58 | n/a | n/a | n/a | n/a |
| 65 | 7510621 | 1002877H1 | SNP00069735 | 152 | 807 | T | T | G | W140 | n/a | n/a | n/a | n/a |
| 65 | 7510621 | 1281484H1 | SNP00074872 | 32 | 932 | T | T | G | I181 | n/a | n/a | n/a | n/a |
| 65 | 7510621 | 1636307H1 | SNP00132688 | 94 | 734 | C | C | T | N115 | n/a | n/a | n/a | n/a |
| 65 | 7510621 | 1731529F6 | SNP00124792 | 79 | 79 | C | C | T | noncoding | n/a | n/a | n/a | n/a |
| 65 | 7510621 | 3216409T6 | SNP00069735 | 269 | 823 | T | T | G | F145 | n/a | n/a | n/a | n/a |
| 65 | 7510621 | 3216409T6 | SNP00074872 | 144 | 948 | T | T | G | stop187 | n/a | n/a | n/a | n/a |
| 65 | 7510621 | 3905994H1 | SNP00039731 | 153 | 504 | T | T | C | L39 | n/d | n/a | n/a | n/a |
| 65 | 7510621 | 3905994H1 | SNP00069420 | 219 | 570 | T | T | G | C61 | n/d | n/d | n/d | n/d |
| 65 | 7510621 | 3905994H1 | SNP00135470 | 214 | 565 | C | C | T | A59 | n/a | n/a | n/a | n/a |
| 65 | 7510621 | 5020934T1 | SNP00074872 | 113 | 966 | T | T | G | S193 | n/a | n/a | n/a | n/a |
| 65 | 7510621 | 6804058J1 | SNP00069735 | 356 | 790 | G | T | G | G134 | n/a | n/a | n/a | n/a |
| 65 | 7510621 | 6804058J1 | SNP00074872 | 481 | 915 | G | T | G | G176 | n/a | n/a | n/a | n/a |
| 65 | 7510621 | 7618082H1 | SNP00132688 | 410 | 735 | C | C | T | H116 | n/a | n/a | n/a | n/a |
| 66 | 7505533 | 5210141H1 | SNP00152657 | 57 | 307 | T | T | C | D92 | n/a | n/a | n/a | n/a |
| 66 | 7505533 | 5210141H1 | SNP00152658 | 94 | 344 | A | A | G | T105 | n/a | n/a | n/a | n/a |
| 66 | 7505533 | 5210141H1 | SNP00152659 | 218 | 468 | T | T | C | noncoding | n/a | n/a | n/a | n/a |
| 66 | 7505533 | 5210183H1 | SNP00152657 | 56 | 304 | T | T | C | A91 | n/a | n/a | n/a | n/a |
| 66 | 7505533 | 5210183H1 | SNP00152658 | 93 | 340 | A | A | G | stop103 | n/a | n/a | n/a | n/a |
| 67 | 7511220 | 6863270H1 | SNP00062114 | 182 | 437 | A | A | C | D131 | 0.23 | 0.10 | 0.33 | 0.16 |
| 67 | 7511220 | 6863270H1 | SNP00065517 | 55 | 310 | A | C | A | I89 | n/a | n/a | n/a | n/a |
| 68 | 7510967 | 1269923F6 | SNP00068898 | 197 | 5398 | A | A | G | E1750 | n/a | n/a | n/a | n/a |
| 68 | 7510967 | 1269923F6 | SNP00116132 | 65 | 5265 | T | T | C | I1706 | n/d | n/d | n/d | n/d |
| 68 | 7510967 | 1269923F6 | SNP00116133 | 310 | 5511 | C | C | T | noncoding | n/a | n/a | n/a | n/a |
| 68 | 7510967 | 2215706F6 | SNP00004638 | 161 | 4918 | G | G | T | Q1590 | n/a | n/a | n/a | n/a |
| 68 | 7510967 | 2215706F6 | SNP00025482 | 195 | 4952 | G | G | C | D1602 | n/d | n/d | n/d | n/d |
| 68 | 7510967 | 4252319F6 | SNP00134721 | 171 | 452 | A | A | G | M102 | n/a | n/a | n/a | n/a |
| 68 | 7510967 | 5089321H1 | SNP00134719 | 13 | 7 | C | C | G | noncoding | n/a | n/a | n/a | n/a |
| 68 | 7510967 | 6977458H1 | SNP00134720 | 282 | 275 | A | A | G | M43 | n/a | n/a | n/a | n/a |
| 69 | 7511298 | 1359892H1 | SNP00114894 | 62 | 1791 | T | T | C | F574 | n/a | n/a | n/a | n/a |
| 69 | 7511298 | 1389872F6 | SNP00136492 | 371 | 2647 | C | C | A | noncoding | n/a | n/a | n/a | n/a |
| 69 | 7511298 | 1391007F6 | SNP00114895 | 532 | 2085 | A | A | G | K672 | n/d | n/d | n/d | n/d |
| 69 | 7511298 | 1391007F6 | SNP00148080 | 277 | 1828 | G | G | A | L586 | n/a | n/a | n/a | n/a |
| 69 | 7511298 | 1429445F6 | SNP00016801 | 294 | 1546 | C | C | T | D492 | n/a | n/a | n/a | n/a |
| 69 | 7511298 | 1429445F6 | SNP00151717 | 252 | 1504 | C | C | T | C478 | n/a | n/a | n/a | n/a |
| 69 | 7511298 | 1501745F6 | SNP00058189 | 420 | 2271 | C | C | T | S734 | n/a | n/a | n/a | n/a |
| 69 | 7511298 | 1519651F6 | SNP00123884 | 164 | 676 | A | A | G | Q202 | n/d | n/a | n/a | n/a |
| 69 | 7511298 | 1877054H1 | SNP00058189 | 23 | 2272 | C | C | T | Y734 | n/a | n/a | n/a | n/a |
| 69 | 7511298 | 1878525H1 | SNP00016803 | 213 | 2588 | T | C | T | noncoding | n/a | n/a | n/a | n/a |
| 69 | 7511298 | 2044874F6 | SNP00062888 | 285 | 596 | G | C | G | V176 | n/d | n/a | n/a | n/a |
| 69 | 7511298 | 2082962T6 | SNP00136492 | 332 | 2654 | C | C | A | noncoding | n/a | n/a | n/a | n/a |
| 69 | 7511298 | 2437515F6 | SNP00016802 | 456 | 2185 | C | C | T | V705 | n/a | n/a | n/a | n/a |
| 69 | 7511298 | 2803211H1 | SNP00126602 | 25 | 2370 | C | T | C | T767 | n/a | n/a | n/a | n/a |
| 69 | 7511298 | 5615830F6 | SNP00016801 | 407 | 1540 | T | C | T | H490 | n/a | n/a | n/a | n/a |
| 69 | 7511298 | 5615830F6 | SNP00151717 | 365 | 1498 | C | C | T | C476 | n/a | n/a | n/a | n/a |
| 69 | 7511298 | 7226075H1 | SNP00123884 | 182 | 675 | A | A | G | Q202 | n/d | n/a | n/a | n/a |
| 69 | 7511298 | 7607396J1 | SNP00062884 | 266 | 690 | C | C | A | S207 | n/d | n/a | n/a | n/a |
| 70 | 7510937 | 1213711H1 | SNP00001099 | 182 | 4086 | G | G | A | A1312 | n/a | n/a | n/a | n/a |
| 70 | 7510937 | 1233991H1 | SNP00046056 | 492 | 149 | G | G | C | E667 | n/a | n/a | n/a | n/a |
| 70 | 7510937 | 1294381H1 | SNP00016843 | 76 | 4277 | G | G | A | noncoding | n/d | n/a | n/a | n/a |
| 70 | 7510937 | 1702543F6 | SNP00108395 | 156 | 3932 | T | T | C | L1261 | n/a | n/a | n/a | n/a |
| 70 | 7510937 | 183926H1 | SNP00046055 | 148 | 1856 | T | T | C | M569 | n/a | n/a | n/a | n/a |
| 70 | 7510937 | 1867984H1 | SNP00108393 | 161 | 2808 | A | A | G | K886 | n/d | n/d | n/d | n/d |
| 70 | 7510937 | 2056164T6 | SNP00016843 | 279 | 4281 | G | G | A | noncoding | n/d | n/a | n/a | n/a |
| 70 | 7510937 | 2070471H1 | SNP00046057 | 28 | 2631 | G | G | A | K827 | n/a | n/a | n/a | n/a |
| 70 | 7510937 | 2705113T6 | SNP00016843 | 274 | 4279 | G | G | A | noncoding | n/d | n/a | n/a | n/a |
| 70 | 7510937 | 2786224T6 | SNP00001099 | 276 | 4087 | G | G | A | V1313 | n/a | n/a | n/a | n/a |
| 70 | 7510937 | 2903742T6 | SNP00016843 | 180 | 4374 | G | G | A | noncoding | n/d | n/a | n/a | n/a |
| 70 | 7510937 | 3773791H1 | SNP00046054 | 183 | 1287 | G | A | G | R379 | 0.86 | 0.93 | n/d | 0.95 |
| 70 | 7510937 | 3790871H1 | SNP00016841 | 4 | 3240 | G | G | C | K1030 | n/a | n/a | n/a | n/a |
| 70 | 7510937 | 6597222H1 | SNP00108394 | 384 | 3239 | A | A | C | N1030 | n/a | n/a | n/a | n/a |

TABLE 8-continued

| SEQ ID NO: | PID | EST ID | SNP ID | EST SNP | CB1 SNP | EST Allele | Allele 1 | Allele 2 | Amino acid | Caucasian Allele 1 frequency | African Allele 1 frequency | Asian Allele 1 fre-quency | Hispanic Allele 1 frequency |
|---|---|---|---|---|---|---|---|---|---|---|---|---|---|
| 70 | 7510937 | 7459195H1 | SNP00046054 | 99 | 1282 | A | A | G | N378 | 0.86 | 0.93 | n/d | 0.95 |
| 71 | 7511852 | 1674771H1 | SNP00124011 | 23 | 1466 | C | C | T | noncoding | n/a | n/a | n/a | n/a |
| 71 | 7511852 | 2330339H1 | SNP00004236 | 163 | 1261 | A | A | G | noncoding | 0.64 | 0.82 | 0.57 | n/a |
| 71 | 7511852 | 2330339H1 | SNP00004237 | 190 | 1288 | C | T | C | noncoding | 0.31 | 0.19 | 0.09 | 0.26 |
| 71 | 7511852 | 3555370H1 | SNP00024881 | 213 | 1393 | C | C | T | noncoding | n/a | n/a | n/a | n/a |
| 72 | 7511077 | 1223450H1 | SNP00124213 | 14 | 30 | G | G | A | noncoding | n/a | n/a | n/a | n/a |
| 72 | 7511077 | 1315226H1 | SNP00124215 | 130 | 1229 | G | G | A | noncoding | 0.98 | n/a | n/a | n/a |
| 72 | 7511077 | 1434590H1 | SNP00124214 | 208 | 399 | C | C | T | R122 | n/d | n/a | n/a | n/a |
| 72 | 7511077 | 1581204H1 | SNP00017009 | 17 | 524 | T | C | T | G163 | n/d | n/a | n/a | n/a |
| 72 | 7511077 | 1705518H1 | SNP00017008 | 155 | 485 | T | T | C | I150 | n/a | n/a | n/a | n/a |
| 72 | 7511077 | 1843956R6 | SNP00017008 | 328 | 486 | C | T | C | P151 | n/a | n/a | n/a | n/a |
| 72 | 7511077 | 1843956R6 | SNP00124214 | 242 | 400 | C | C | T | P122 | n/d | n/a | n/a | n/a |
| 72 | 7511077 | 4586519H1 | SNP00124216 | 223 | 1251 | C | C | T | noncoding | n/a | n/a | n/a | n/a |
| 72 | 7511077 | 6481807H1 | SNP00001218 | 40 | 1248 | G | G | C | noncoding | n/a | n/a | n/a | n/a |
| 72 | 7511077 | 7639431J2 | SNP00017008 | 354 | 457 | C | T | C | A141 | n/a | n/a | n/a | n/a |
| 72 | 7511077 | 7639431J2 | SNP00017009 | 393 | 496 | C | C | T | S154 | n/d | n/a | n/a | n/a |
| 72 | 7511077 | 7639431J2 | SNP00124214 | 269 | 371 | C | C | T | T112 | n/d | n/a | n/a | n/a |
| 73 | 7511576 | 034843H1 | SNP00098584 | 220 | 335 | T | T | C | I48 | n/a | n/a | n/a | n/a |
| 73 | 7511576 | 1493422H1 | SNP00034873 | 58 | 384 | G | A | G | L64 | n/a | n/a | n/a | n/a |
| 73 | 7511576 | 1520967H1 | SNP00033391 | 154 | 442 | C | C | T | L84 | n/a | n/a | n/a | n/a |
| 73 | 7511576 | 1724713F6 | SNP00033392 | 303 | 1128 | A | A | C | noncoding | n/a | n/a | n/a | n/a |
| 73 | 7511576 | 1724713T6 | SNP00033392 | 160 | 1134 | A | A | C | noncoding | n/a | n/a | n/a | n/a |
| 73 | 7511576 | 8588603T1 | SNP00154298 | 467 | 395 | G | A | G | W68 | n/a | n/a | n/a | n/a |
| 73 | 7511576 | 8588603T1 | SNP00154299 | 363 | 500 | G | A | G | R103 | n/a | n/a | n/a | n/a |
| 74 | 7511492 | 008076H1 | SNP00001520 | 204 | 306 | T | T | C | F81 | n/a | n/a | n/a | n/a |
| 74 | 7511492 | 1216191H1 | SNP00050705 | 215 | 565 | G | G | A | noncoding | n/a | n/a | n/a | n/a |
| 74 | 7511492 | 1693356H1 | SNP00064907 | 56 | 648 | C | C | A | noncoding | n/a | n/a | n/a | n/a |
| 74 | 7511492 | 1907176H1 | SNP00001521 | 222 | 703 | C | C | G | noncoding | n/a | n/a | n/a | n/a |
| 75 | 7511141 | 1435538T6 | SNP00003434 | 193 | 2614 | T | T | C | noncoding | n/a | n/a | n/a | n/a |
| 75 | 7511141 | 1435538T6 | SNP00065777 | 28 | 2777 | A | A | G | noncoding | n/a | n/a | n/a | n/a |
| 75 | 7511141 | 1513489T6 | SNP00003434 | 145 | 2602 | C | T | C | noncoding | n/a | n/a | n/a | n/a |
| 75 | 7511141 | 1631170F6 | SNP00003434 | 381 | 2601 | T | T | C | noncoding | n/a | n/a | n/a | n/a |
| 75 | 7511141 | 1631170F6 | SNP00065776 | 212 | 2432 | C | C | T | noncoding | n/a | n/a | n/a | n/a |
| 75 | 7511141 | 1631170T6 | SNP00003434 | 165 | 2629 | T | T | C | noncoding | n/a | n/a | n/a | n/a |
| 75 | 7511141 | 1631170T6 | SNP00065776 | 335 | 2459 | C | C | T | noncoding | n/a | n/a | n/a | n/a |
| 75 | 7511141 | 1632763T6 | SNP00003434 | 193 | 2605 | T | T | C | noncoding | n/a | n/a | n/a | n/a |
| 75 | 7511141 | 1632763T6 | SNP00065776 | 363 | 2435 | C | C | T | noncoding | n/a | n/a | n/a | n/a |
| 75 | 7511141 | 1632763T6 | SNP00065777 | 28 | 2769 | A | A | G | noncoding | n/a | n/a | n/a | n/a |
| 75 | 7511141 | 2091984H2 | SNP00065777 | 206 | 2767 | A | A | G | noncoding | n/a | n/a | n/a | n/a |
| 75 | 7511141 | 2216503T6 | SNP00003434 | 139 | 2654 | C | T | C | noncoding | n/a | n/a | n/a | n/a |
| 75 | 7511141 | 2640569T6 | SNP00003434 | 177 | 2631 | C | T | C | noncoding | n/a | n/a | n/a | n/a |
| 75 | 7511141 | 2640569T6 | SNP00065776 | 347 | 2461 | C | C | T | noncoding | n/a | n/a | n/a | n/a |
| 75 | 7511141 | 2640569T6 | SNP00065777 | 12 | 2794 | A | A | G | noncoding | n/a | n/a | n/a | n/a |
| 75 | 7511141 | 2676369F6 | SNP00065777 | 381 | 2766 | A | A | G | noncoding | n/a | n/a | n/a | n/a |
| 75 | 7511141 | 2676369T6 | SNP00003434 | 121 | 2685 | C | T | C | noncoding | n/a | n/a | n/a | n/a |
| 75 | 7511141 | 2676369T6 | SNP00065776 | 291 | 2515 | C | C | T | noncoding | n/a | n/a | n/a | n/a |
| 75 | 7511141 | 3835977T6 | SNP00065776 | 377 | 2431 | C | C | T | noncoding | n/a | n/a | n/a | n/a |
| 76 | 7511300 | 1359892H1 | SNP00114894 | 62 | 1938 | T | T | C | F623 | n/a | n/a | n/a | n/a |
| 76 | 7511300 | 1389872F6 | SNP00136492 | 371 | 2692 | C | C | A | noncoding | n/a | n/a | n/a | n/a |
| 76 | 7511300 | 1391007F6 | SNP00114895 | 532 | 2232 | A | A | G | K721 | n/d | n/d | n/d | n/d |
| 76 | 7511300 | 1391007F6 | SNP00148080 | 277 | 1975 | G | G | A | L635 | n/a | n/a | n/a | n/a |
| 76 | 7511300 | 1429445F6 | SNP00016801 | 294 | 1693 | C | C | T | D541 | n/a | n/a | n/a | n/a |
| 76 | 7511300 | 1429445F6 | SNP00151717 | 252 | 1651 | C | C | T | C527 | n/a | n/a | n/a | n/a |
| 76 | 7511300 | 1501745F6 | SNP00058189 | 420 | 2418 | C | C | T | S783 | n/a | n/a | n/a | n/a |
| 76 | 7511300 | 1519651F6 | SNP00123884 | 164 | 823 | A | A | G | Q251 | n/d | n/a | n/a | n/a |
| 76 | 7511300 | 1878525H1 | SNP00016803 | 213 | 2633 | T | C | T | noncoding | n/a | n/a | n/a | n/a |
| 76 | 7511300 | 2044874F6 | SN000062888 | 285 | 743 | G | C | G | V225 | n/d | n/a | n/a | n/a |
| 76 | 7511300 | 2082962T6 | SNP00136492 | 332 | 2699 | C | C | A | noncoding | n/a | n/a | n/a | n/a |
| 76 | 7511300 | 2242331H1 | SNP00058189 | 214 | 2419 | C | C | T | Y783 | n/a | n/a | n/a | n/a |
| 76 | 7511300 | 2437515F6 | SNP00016802 | 456 | 2332 | C | C | T | V754 | n/a | n/a | n/a | n/a |
| 76 | 7511300 | 5615830F6 | SNP00016801 | 407 | 1687 | T | C | T | H539 | n/a | n/a | n/a | n/a |
| 76 | 7511300 | 5615830F6 | SNP00151717 | 365 | 1645 | C | C | T | C525 | n/a | n/a | n/a | n/a |
| 76 | 7511300 | 7226075H1 | SNP00123884 | 182 | 822 | A | A | G | Q251 | n/d | n/a | n/a | n/a |

What is claimed is:

1. An isolated polypeptide comprising the amino acid sequence of SEQ ID NO: 22.

2. The isolated polypeptide of claim 1, wherein said polypeptide is biologically active.

3. The isolated polypeptide of claim 1, produced recombinantly.

4. An isolated polypeptide consisting of SEQ ID NO: 22.

5. An isolated polypeptide comprising amino acids 188-237 of SEQ ID NO: 22.

6. A polypeptide consisting of (a) an amino acid sequence comprising SEQ ID NO: 22; fused to (b) a heterologous fusion polypeptide.

* * * * *

SEQUENCE LISTING

<160> NUMBER OF SEQ ID NOS: 76

<210> SEQ ID NO 1
<211> LENGTH: 747
<212> TYPE: PRT
<213> ORGANISM: Homo sapiens
<220> FEATURE:
<221> NAME/KEY: misc_feature
<223> OTHER INFORMATION: Incyte ID No: 3048626CD1

<400> SEQUENCE: 1

```
Met Ala Ser Lys Val Thr Asp Ala Ile Val Trp Tyr Gln Lys Lys
  1               5                  10                  15

Ile Gly Ala Tyr Asp Gln Gln Ile Trp Glu Lys Ser Val Glu Gln
                 20                  25                  30

Arg Glu Ile Lys Gly Leu Arg Asn Lys Pro Lys Lys Thr Ala His
                 35                  40                  45

Val Lys Pro Asp Leu Ile Asp Val Asp Leu Val Arg Gly Ser Ala
                 50                  55                  60

Phe Ala Lys Ala Lys Pro Glu Ser Pro Trp Thr Ser Leu Thr Arg
                 65                  70                  75

Lys Gly Ile Val Arg Val Val Phe Phe Pro Phe Phe Phe Arg Trp
                 80                  85                  90

Trp Leu Gln Val Thr Ser Lys Val Ile Phe Phe Trp Leu Leu Val
                 95                 100                 105

Leu Tyr Leu Leu Gln Val Ala Ala Ile Val Leu Phe Cys Ser Thr
                110                 115                 120

Ser Ser Pro His Ser Ile Pro Leu Thr Glu Val Ile Gly Pro Ile
                125                 130                 135

Trp Leu Met Leu Leu Leu Gly Thr Val His Cys Gln Ile Val Ser
                140                 145                 150

Thr Arg Thr Pro Lys Pro Pro Leu Ser Thr Gly Gly Lys Arg Arg
                155                 160                 165

Arg Lys Leu Arg Lys Ala Ala His Leu Glu Val His Arg Glu Gly
                170                 175                 180

Asp Gly Ser Ser Thr Thr Asp Asn Thr Gln Glu Gly Ala Val Gln
                185                 190                 195

Asn His Gly Thr Ser Thr Ser His Ser Val Gly Thr Val Phe Arg
                200                 205                 210

Asp Leu Trp His Ala Ala Phe Phe Leu Ser Gly Ser Lys Lys Ala
                215                 220                 225

Lys Asn Ser Ile Asp Lys Ser Thr Glu Thr Asp Asn Gly Tyr Val
                230                 235                 240

Ser Leu Asp Gly Lys Lys Thr Val Lys Ser Gly Glu Asp Gly Ile
                245                 250                 255

Gln Asn His Glu Pro Gln Cys Glu Thr Ile Arg Pro Glu Glu Thr
                260                 265                 270

Ala Trp Asn Thr Gly Thr Leu Arg Asn Gly Pro Ser Lys Asp Thr
                275                 280                 285

Gln Arg Thr Ile Thr Asn Val Ser Asp Glu Val Ser Ser Glu Glu
                290                 295                 300

Gly Pro Glu Thr Gly Tyr Ser Leu Arg Arg His Val Asp Arg Thr
                305                 310                 315

Ser Glu Gly Val Leu Arg Asn Arg Lys Ser His His Tyr Lys Lys
```

-continued

```
                320                 325                 330

His Tyr Pro Asn Glu Asp Ala Pro Lys Ser Gly Thr Ser Cys Ser
                335                 340                 345

Ser Arg Cys Ser Ser Ser Arg Gln Asp Ser Glu Ser Ala Arg Pro
                350                 355                 360

Glu Ser Glu Thr Glu Asp Val Leu Trp Glu Asp Leu Leu His Cys
                365                 370                 375

Ala Glu Cys His Ser Ser Cys Thr Ser Glu Thr Asp Val Glu Asn
                380                 385                 390

His Gln Ile Asn Pro Cys Val Lys Lys Glu Tyr Arg Asp Asp Pro
                395                 400                 405

Phe His Gln Ser His Leu Pro Trp Leu His Ser Ser His Pro Gly
                410                 415                 420

Leu Glu Lys Ile Ser Ala Ile Val Trp Glu Gly Asn Asp Cys Lys
                425                 430                 435

Lys Ala Asp Met Ser Val Leu Glu Ile Ser Gly Met Ile Met Asn
                440                 445                 450

Arg Val Asn Ser His Ile Pro Gly Ile Gly Tyr Gln Ile Phe Gly
                455                 460                 465

Asn Ala Val Ser Leu Ile Leu Gly Leu Thr Pro Phe Val Phe Arg
                470                 475                 480

Leu Ser Gln Ala Thr Asp Leu Glu Gln Leu Thr Ala His Ser Ala
                485                 490                 495

Ser Glu Leu Tyr Val Ile Ala Phe Gly Ser Asn Glu Asp Val Ile
                500                 505                 510

Val Leu Ser Met Val Ile Ile Ser Phe Val Val Arg Val Ser Leu
                515                 520                 525

Val Trp Ile Phe Phe Phe Leu Leu Cys Val Ala Glu Arg Thr Tyr
                530                 535                 540

Lys Gln Arg Leu Leu Phe Ala Lys Leu Phe Gly His Leu Thr Ser
                545                 550                 555

Ala Arg Arg Ala Arg Lys Ser Glu Val Pro His Phe Arg Leu Lys
                560                 565                 570

Lys Val Gln Asn Ile Lys Met Trp Leu Ser Leu Arg Ser Tyr Leu
                575                 580                 585

Lys Arg Arg Gly Pro Gln Arg Ser Val Asp Val Ile Val Ser Ser
                590                 595                 600

Ala Phe Leu Leu Thr Ile Ser Val Val Phe Ile Cys Cys Ala Gln
                605                 610                 615

Val Leu His Val His Glu Ile Phe Leu Asp Cys His Tyr Asn Trp
                620                 625                 630

Glu Leu Val Ile Trp Cys Ile Ser Leu Thr Leu Phe Leu Leu Arg
                635                 640                 645

Phe Val Thr Leu Gly Ser Glu Thr Ser Lys Lys Tyr Ser Asn Thr
                650                 655                 660

Ser Ile Leu Leu Thr Glu Gln Ile Asn Leu Tyr Leu Lys Met Glu
                665                 670                 675

Lys Lys Pro Asn Lys Lys Glu Glu Leu Thr Leu Val Asn Asn Val
                680                 685                 690

Leu Lys Leu Ala Thr Lys Leu Leu Lys Glu Leu Asp Ser Pro Phe
                695                 700                 705

Arg Leu Tyr Gly Leu Thr Met Asn Pro Leu Leu Tyr Asn Ile Thr
                710                 715                 720
```

-continued

```
Gln Val Val Ile Leu Ser Ala Val Ser Gly Val Ile Ser Asp Leu
                725                 730                 735

Leu Gly Phe Asn Leu Lys Leu Trp Lys Ile Lys Ser
                740                 745


<210> SEQ ID NO 2
<211> LENGTH: 799
<212> TYPE: PRT
<213> ORGANISM: Homo sapiens
<220> FEATURE:
<221> NAME/KEY: misc_feature
<223> OTHER INFORMATION: Incyte ID No: 2684425CD1

<400> SEQUENCE: 2

Met Lys Pro Met Leu Lys Asp Phe Ser Asn Leu Leu Leu Val Val
  1               5                  10                  15

Leu Cys Asp Tyr Val Leu Gly Glu Ala Glu Tyr Leu Leu Leu Arg
                 20                  25                  30

Glu Pro Gly His Val Ala Leu Ser Asn Asp Thr Val Tyr Val Asp
                 35                  40                  45

Phe Gln Tyr Phe Asp Gly Ala Asn Gly Thr Leu Arg Asn Val Ser
                 50                  55                  60

Val Leu Leu Leu Glu Ala Asn Thr Asn Gln Thr Val Thr Thr Lys
                 65                  70                  75

Tyr Leu Leu Thr Asn Gln Ser Gln Gly Thr Leu Lys Phe Glu Cys
                 80                  85                  90

Phe Tyr Phe Lys Glu Ala Gly Asp Tyr Trp Phe Thr Met Thr Pro
                 95                 100                 105

Glu Ala Thr Asp Asn Ser Thr Pro Phe Pro Trp Trp Glu Lys Ser
                110                 115                 120

Ala Phe Leu Lys Val Glu Trp Pro Val Phe His Val Asp Leu Asn
                125                 130                 135

Arg Ser Ala Lys Ala Ala Glu Gly Thr Phe Gln Val Gly Leu Phe
                140                 145                 150

Thr Ser Gln Pro Leu Cys Pro Phe Pro Val Asp Lys Pro Asn Ile
                155                 160                 165

Val Val Asp Val Ile Phe Thr Asn Ser Leu Pro Glu Ala Arg Arg
                170                 175                 180

Asn Ser Arg Gln Pro Leu Glu Ile Arg Thr Ser Lys Arg Thr Glu
                185                 190                 195

Leu Ala Gln Gly Gln Trp Val Glu Phe Gly Cys Ala Pro Leu Gly
                200                 205                 210

Pro Glu Ala Tyr Val Thr Val Val Leu Lys Leu Leu Gly Arg Asp
                215                 220                 225

Ser Val Ile Thr Ser Thr Gly Pro Ile Asp Leu Ala Gln Lys Phe
                230                 235                 240

Gly Tyr Lys Leu Val Met Val Pro Glu Leu Thr Cys Glu Ser Gly
                245                 250                 255

Val Glu Val Thr Val Leu Pro Pro Pro Cys Thr Phe Val Gln Gly
                260                 265                 270

Val Val Thr Val Phe Lys Glu Ala Pro Arg Tyr Pro Gly Lys Arg
                275                 280                 285

Thr Ile His Leu Ala Glu Asn Ser Leu Pro Leu Gly Glu Arg Arg
                290                 295                 300

Thr Ile Phe Asn Cys Thr Leu Phe Asp Met Gly Lys Asn Lys Tyr
```

-continued

```
                305                 310                 315

Cys Phe Asp Phe Gly Ile Ser Ser Arg Ser His Phe Ser Ala Lys
                320                 325                 330

Glu Glu Cys Met Leu Ile Gln Arg Asn Thr Ala Phe Gln Pro Ser
                335                 340                 345

Ser Pro Ser Pro Leu Gln Pro Gln Gly Pro Val Lys Ser Asn Asn
                350                 355                 360

Ile Val Thr Val Thr Gly Ile Ser Leu Cys Leu Phe Ile Ile Ile
                365                 370                 375

Ala Thr Val Leu Ile Thr Leu Trp Arg Arg Phe Gly Arg Pro Ala
                380                 385                 390

Lys Cys Ser Thr Pro Ala Arg His Asn Ser Ile His Ser Pro Ser
                395                 400                 405

Phe Arg Lys Asn Ser Asp Glu Glu Asn Ile Cys Glu Leu Ser Glu
                410                 415                 420

Gln Arg Gly Ser Phe Ser Asp Gly Gly Asp Gly Pro Thr Gly Ser
                425                 430                 435

Pro Gly Asp Thr Gly Ile Pro Leu Thr Tyr Arg Arg Ser Gly Pro
                440                 445                 450

Val Pro Pro Glu Asp Asp Ala Ser Gly Ser Glu Ser Phe Gln Ser
                455                 460                 465

Asn Ala Gln Lys Ile Ile Pro Pro Leu Phe Ser Tyr Arg Leu Ala
                470                 475                 480

Gln Gln Gln Leu Lys Glu Met Lys Lys Lys Gly Leu Thr Glu Thr
                485                 490                 495

Thr Lys Val Tyr His Val Ser Gln Ser Pro Leu Thr Asp Thr Ala
                500                 505                 510

Ile Asp Ala Ala Pro Ser Ala Pro Leu Asp Leu Glu Ser Pro Glu
                515                 520                 525

Glu Ala Ala Ala Asn Lys Phe Arg Ile Lys Ser Pro Phe Pro Glu
                530                 535                 540

Gln Pro Ala Val Ser Ala Gly Glu Arg Pro Pro Ser Arg Leu Asp
                545                 550                 555

Leu Asn Val Thr Gln Ala Ser Cys Ala Ile Ser Pro Ser Gln Thr
                560                 565                 570

Leu Ile Arg Lys Ser Gln Ala Arg His Val Gly Ser Arg Gly Gly
                575                 580                 585

Pro Ser Glu Arg Ser His Ala Arg Asn Ala His Phe Arg Arg Thr
                590                 595                 600

Ala Ser Phe His Glu Ala Arg Gln Ala Arg Pro Phe Arg Glu Arg
                605                 610                 615

Ser Met Ser Thr Leu Thr Pro Arg Gln Ala Pro Ala Tyr Ser Ser
                620                 625                 630

Arg Thr Arg Thr Cys Glu Gln Ala Glu Asp Arg Phe Arg Pro Gln
                635                 640                 645

Ser Arg Gly Ala His Leu Phe Pro Glu Lys Leu Glu His Phe Gln
                650                 655                 660

Glu Ala Ser Gly Thr Arg Gly Pro Leu Asn Pro Leu Pro Lys Ser
                665                 670                 675

Tyr Thr Leu Gly Gln Pro Leu Arg Lys Pro Asp Leu Gly Asp His
                680                 685                 690

Gln Ala Gly Leu Val Ala Gly Ile Glu Arg Thr Glu Pro His Arg
                695                 700                 705
```

-continued

```
Ala Arg Arg Gly Pro Ser Pro Ser His Lys Ser Val Ser Arg Lys
                710                 715                 720

Gln Ser Ser Pro Ile Ser Pro Lys Asp Asn Tyr Gln Arg Val Ser
                725                 730                 735

Ser Leu Ser Pro Ser Gln Cys Arg Lys Asp Lys Cys Gln Ser Phe
                740                 745                 750

Pro Thr His Pro Glu Phe Ala Phe Tyr Asp Asn Thr Ser Phe Gly
                755                 760                 765

Leu Thr Glu Ala Glu Gln Arg Met Leu Asp Leu Pro Gly Tyr Phe
                770                 775                 780

Gly Ser Asn Glu Glu Asp Glu Thr Thr Ser Thr Leu Ser Val Glu
                785                 790                 795

Lys Leu Val Ile


<210> SEQ ID NO 3
<211> LENGTH: 663
<212> TYPE: PRT
<213> ORGANISM: Homo sapiens
<220> FEATURE:
<221> NAME/KEY: misc_feature
<223> OTHER INFORMATION: Incyte ID No: 7505960CD1

<400> SEQUENCE: 3

Met Gly Gly Lys Gln Arg Asp Glu Asp Asp Glu Ala Tyr Gly Lys
  1               5                  10                  15

Pro Val Lys Tyr Asp Pro Ser Phe Arg Gly Pro Ile Lys Asn Arg
                 20                  25                  30

Ser Cys Thr Asp Val Ile Cys Cys Val Leu Phe Leu Leu Phe Ile
                 35                  40                  45

Leu Gly Tyr Ile Val Val Gly Ile Val Ala Trp Leu Tyr Gly Asp
                 50                  55                  60

Pro Arg Gln Val Leu Tyr Pro Arg Asn Ser Thr Gly Ala Tyr Cys
                 65                  70                  75

Gly Met Gly Glu Asn Lys Asp Lys Pro Tyr Leu Leu Tyr Phe Asn
                 80                  85                  90

Ile Phe Ser Cys Ile Leu Ser Ser Asn Ile Ile Ser Val Ala Glu
                 95                 100                 105

Asn Gly Leu Gln Cys Pro Thr Pro Gln Val Cys Val Ser Ser Cys
                110                 115                 120

Pro Glu Asp Pro Trp Thr Val Gly Lys Asn Glu Phe Ser Gln Thr
                125                 130                 135

Val Gly Glu Val Phe Tyr Thr Lys Asn Arg Asn Phe Cys Leu Pro
                140                 145                 150

Gly Val Pro Trp Asn Met Thr Val Ile Thr Ser Leu Gln Gln Glu
                155                 160                 165

Leu Cys Pro Ser Phe Leu Leu Pro Ser Ala Pro Ala Leu Gly Arg
                170                 175                 180

Cys Phe Pro Trp Thr Asn Ile Thr Pro Pro Ala Leu Pro Gly Ile
                185                 190                 195

Thr Asn Asp Thr Thr Ile Gln Gln Gly Ile Ser Gly Leu Ile Asp
                200                 205                 210

Ser Leu Asn Ala Arg Asp Ile Ser Val Lys Ile Phe Glu Asp Phe
                215                 220                 225

Ala Gln Ser Trp Tyr Trp Ile Leu Val Ala Leu Gly Val Ala Leu
                230                 235                 240
```

-continued

```
Val Leu Ser Leu Leu Phe Ile Leu Leu Leu Arg Leu Val Ala Gly
                245                 250                 255

Pro Leu Val Leu Val Leu Ile Leu Gly Val Leu Gly Val Leu Ala
                260                 265                 270

Tyr Gly Ile Tyr Tyr Cys Trp Glu Glu Tyr Arg Val Leu Arg Asp
                275                 280                 285

Lys Gly Ala Ser Ile Ser Gln Leu Gly Phe Thr Thr Asn Leu Ser
                290                 295                 300

Ala Tyr Gln Ser Val Gln Glu Thr Trp Leu Ala Ala Leu Ile Val
                305                 310                 315

Leu Ala Val Leu Glu Ala Ile Leu Leu Leu Val Leu Ile Phe Leu
                320                 325                 330

Arg Gln Arg Ile Arg Ile Ala Ile Ala Leu Leu Lys Glu Ala Ser
                335                 340                 345

Lys Ala Val Gly Gln Met Met Ser Thr Met Phe Tyr Pro Leu Val
                350                 355                 360

Thr Phe Val Leu Leu Leu Ile Cys Ile Ala Tyr Trp Ala Met Thr
                365                 370                 375

Ala Leu Tyr Leu Ala Thr Ser Gly Gln Pro Gln Tyr Val Leu Trp
                380                 385                 390

Ala Ser Asn Ile Ser Ser Pro Gly Cys Glu Lys Val Pro Ile Asn
                395                 400                 405

Thr Ser Cys Asn Pro Thr Ala His Leu Val Asn Ser Ser Cys Pro
                410                 415                 420

Gly Leu Met Cys Val Phe Gln Gly Tyr Ser Ser Lys Gly Leu Ile
                425                 430                 435

Pro Thr Phe Pro Leu Ile Ser Ala Phe Ile Arg Thr Leu Arg Tyr
                440                 445                 450

His Thr Gly Ser Leu Ala Phe Gly Ala Leu Ile Leu Thr Leu Val
                455                 460                 465

Gln Ile Ala Arg Val Ile Leu Glu Tyr Ile Asp His Lys Leu Arg
                470                 475                 480

Gly Val Gln Asn Pro Val Ala Arg Cys Ile Met Cys Cys Phe Lys
                485                 490                 495

Cys Cys Leu Trp Cys Leu Glu Lys Phe Ile Lys Phe Leu Asn Arg
                500                 505                 510

Asn Ala Tyr Ile Met Ile Ala Ile Tyr Gly Lys Asn Phe Cys Val
                515                 520                 525

Ser Ala Lys Asn Ala Phe Met Leu Leu Met Arg Asn Ile Val Arg
                530                 535                 540

Val Val Val Leu Asp Lys Val Thr Asp Leu Leu Leu Phe Phe Gly
                545                 550                 555

Lys Leu Leu Val Val Gly Gly Val Gly Val Leu Ser Phe Phe Phe
                560                 565                 570

Phe Ser Gly Arg Ile Pro Gly Leu Gly Lys Asp Phe Lys Ser Pro
                575                 580                 585

His Leu Asn Tyr Tyr Trp Leu Pro Ile Met Thr Ser Ile Leu Gly
                590                 595                 600

Ala Tyr Val Ile Ala Ser Gly Phe Phe Ser Val Phe Gly Met Cys
                605                 610                 615

Val Asp Thr Leu Phe Leu Cys Phe Leu Glu Asp Leu Glu Arg Asn
                620                 625                 630
```

-continued

```
Asn Gly Ser Leu Asp Arg Pro Tyr Tyr Met Ser Lys Ser Leu Leu
                635                 640                 645

Lys Ile Leu Gly Lys Lys Asn Glu Ala Pro Pro Asp Asn Lys Lys
                650                 655                 660

Arg Lys Lys


<210> SEQ ID NO 4
<211> LENGTH: 150
<212> TYPE: PRT
<213> ORGANISM: Homo sapiens
<220> FEATURE:
<221> NAME/KEY: misc_feature
<223> OTHER INFORMATION: Incyte ID No: 7507021CD1

<400> SEQUENCE: 4

Met Arg Gly His Pro Ser Leu Leu Leu Leu Tyr Met Ala Leu Thr
  1               5                  10                  15

Thr Cys Leu Asp Thr Ser Pro Ser Glu Glu Thr Asp Gln Glu Val
                 20                  25                  30

Phe Leu Gly Pro Pro Glu Ala Gln Ser Phe Leu Ser Ser His Thr
                 35                  40                  45

Arg Ile Pro Arg Ala Asn His Trp Asp Leu Glu Leu Leu Thr Pro
                 50                  55                  60

Gly Asn Leu Glu Arg Glu Cys Leu Glu Glu Arg Cys Ser Trp Glu
                 65                  70                  75

Glu Ala Arg Glu Tyr Phe Glu Asp Asn Thr Leu Thr Glu Arg Phe
                 80                  85                  90

Trp Glu Ser Tyr Ile Tyr Asn Gly Lys Gly Gly Arg Gly Arg Val
                 95                 100                 105

Asp Val Ala Ser Leu Ala Val Gly Leu Thr Gly Gly Ile Leu Leu
                110                 115                 120

Ile Val Leu Ala Gly Leu Gly Ala Phe Trp Tyr Leu Arg Trp Arg
                125                 130                 135

Gln His Arg Gly Gln Gln Pro Cys Pro Gln Glu Pro Pro His Leu
                140                 145                 150


<210> SEQ ID NO 5
<211> LENGTH: 504
<212> TYPE: PRT
<213> ORGANISM: Homo sapiens
<220> FEATURE:
<221> NAME/KEY: misc_feature
<223> OTHER INFORMATION: Incyte ID No: 7509099CD1

<400> SEQUENCE: 5

Met Lys Val Leu Leu Arg Leu Ile Cys Phe Ile Ala Leu Leu Ile
  1               5                  10                  15

Ser Ser Leu Glu Ala Asp Lys Cys Lys Glu Arg Glu Glu Lys Ile
                 20                  25                  30

Ile Leu Val Ser Ser Ala Asn Glu Ile Asp Val Arg Pro Cys Pro
                 35                  40                  45

Leu Asn Pro Asn Glu His Lys Gly Thr Ile Thr Trp Tyr Lys Asp
                 50                  55                  60

Asp Ser Lys Thr Pro Val Ser Thr Glu Gln Ala Ser Arg Ile His
                 65                  70                  75

Gln His Lys Glu Lys Leu Trp Phe Val Pro Ala Lys Val Glu Asp
                 80                  85                  90

Ser Gly His Tyr Tyr Cys Val Asp Cys Lys Pro Leu Leu Leu Asp
```

-continued

```
                95                  100                 105

Asn Ile His Phe Ser Gly Val Lys Asp Arg Leu Ile Val Met Asn
                110                 115                 120

Val Ala Glu Lys His Arg Gly Asn Tyr Thr Cys His Ala Ser Tyr
                125                 130                 135

Thr Tyr Leu Gly Lys Gln Tyr Pro Ile Thr Arg Val Ile Glu Phe
                140                 145                 150

Ile Thr Leu Glu Glu Asn Lys Pro Thr Arg Pro Val Ile Val Ser
                155                 160                 165

Pro Ala Asn Glu Thr Met Glu Val Asp Leu Gly Ser Gln Ile Gln
                170                 175                 180

Leu Ile Cys Asn Val Thr Gly Gln Leu Ser Asp Ile Ala Tyr Trp
                185                 190                 195

Lys Trp Asn Gly Ser Val Ile Asp Glu Asp Asp Pro Val Leu Gly
                200                 205                 210

Glu Asp Tyr Tyr Ser Val Glu Asn Pro Ala Asn Lys Arg Arg Ser
                215                 220                 225

Thr Leu Ile Thr Val Leu Asn Ile Ser Glu Ile Glu Ser Arg Phe
                230                 235                 240

Tyr Lys His Pro Phe Thr Cys Phe Ala Lys Asn Thr His Gly Ile
                245                 250                 255

Asp Ala Ala Tyr Ile Gln Leu Ile Tyr Pro Val Thr Asn Phe Gln
                260                 265                 270

Lys His Met Ile Gly Ile Cys Val Thr Leu Thr Val Ile Ile Val
                275                 280                 285

Cys Ser Val Phe Ile Tyr Lys Ile Phe Lys Ile Asp Ile Val Leu
                290                 295                 300

Trp Tyr Arg Asp Ser Cys Tyr Asp Phe Leu Pro Ile Lys Ala Ser
                305                 310                 315

Asp Gly Lys Thr Tyr Asp Ala Tyr Ile Leu Tyr Pro Lys Thr Val
                320                 325                 330

Gly Glu Gly Ser Thr Ser Asp Cys Asp Ile Phe Val Phe Lys Val
                335                 340                 345

Leu Pro Glu Val Leu Glu Lys Gln Cys Gly Tyr Lys Leu Phe Ile
                350                 355                 360

Tyr Gly Arg Asp Asp Tyr Val Gly Glu Asp Ile Val Glu Val Ile
                365                 370                 375

Asn Glu Asn Val Lys Lys Ser Arg Arg Leu Ile Ile Ile Leu Val
                380                 385                 390

Arg Glu Thr Ser Gly Phe Ser Trp Leu Gly Gly Ser Ser Glu Glu
                395                 400                 405

Gln Ile Ala Met Tyr Asn Ala Leu Val Gln Asp Gly Ile Lys Val
                410                 415                 420

Val Leu Leu Glu Leu Glu Lys Ile Gln Asp Tyr Glu Lys Met Pro
                425                 430                 435

Glu Ser Ile Lys Phe Ile Lys Gln Lys His Gly Ala Ile Arg Trp
                440                 445                 450

Ser Gly Asp Phe Thr Gln Gly Pro Gln Ser Ala Lys Thr Arg Phe
                455                 460                 465

Trp Lys Asn Val Arg Tyr His Met Pro Val Gln Arg Arg Ser Pro
                470                 475                 480

Ser Ser Lys His Gln Leu Leu Ser Pro Ala Thr Lys Glu Lys Leu
                485                 490                 495
```

-continued

```
Gln Arg Glu Ala His Val Pro Leu Gly
                500


<210> SEQ ID NO 6
<211> LENGTH: 247
<212> TYPE: PRT
<213> ORGANISM: Homo sapiens
<220> FEATURE:
<221> NAME/KEY: misc_feature
<223> OTHER INFORMATION: Incyte ID No: 7509361CD1

<400> SEQUENCE: 6

Met Gly Leu Ser Thr Val Pro Asp Leu Leu Leu Pro Leu Val Leu
  1               5                  10                  15

Leu Glu Leu Leu Val Gly Ile Tyr Pro Ser Gly Val Ile Gly Leu
                 20                  25                  30

Val Pro His Leu Gly Asp Arg Glu Lys Arg Asp Ser Val Cys Pro
                 35                  40                  45

Gln Gly Lys Tyr Ile His Pro Gln Asn Asn Ser Ile Cys Cys Thr
                 50                  55                  60

Lys Cys His Lys Gly Thr Tyr Leu Tyr Asn Asp Cys Pro Gly Pro
                 65                  70                  75

Gly Gln Asp Thr Asp Cys Arg Glu Cys Glu Ser Gly Ser Phe Thr
                 80                  85                  90

Ala Ser Glu Asn His Leu Arg His Cys Leu Ser Cys Ser Lys Cys
                 95                 100                 105

Arg Lys Glu Met Gly Gln Val Glu Ile Ser Ser Cys Thr Val Asp
                110                 115                 120

Arg Asp Thr Val Cys Gly Cys Arg Lys Asn Gln Tyr Arg His Tyr
                125                 130                 135

Trp Ser Glu Asn Leu Phe Gln Cys Phe Asn Cys Ser Leu Cys Leu
                140                 145                 150

Asn Gly Thr Val His Leu Ser Cys Gln Glu Lys Gln Asn Thr Val
                155                 160                 165

Cys Thr Cys His Ala Gly Phe Phe Leu Arg Glu Asn Glu Cys Val
                170                 175                 180

Ser Cys Ser Asn Cys Lys Lys Ser Leu Glu Cys Thr Lys Leu Cys
                185                 190                 195

Leu Pro Gln Ile Glu Asn Val Lys Gly Thr Glu Asp Ser Glu Arg
                200                 205                 210

Trp His His Pro Ile Arg Gly Leu Thr Pro Ser Leu Arg Gln Pro
                215                 220                 225

Ser Pro Pro Thr Pro Ser Pro Thr Pro Phe Arg Ser Gly Arg Thr
                230                 235                 240

Ala Pro Thr Ser His Arg Ala
                245


<210> SEQ ID NO 7
<211> LENGTH: 363
<212> TYPE: PRT
<213> ORGANISM: Homo sapiens
<220> FEATURE:
<221> NAME/KEY: misc_feature
<223> OTHER INFORMATION: Incyte ID No: 7506815CD1

<400> SEQUENCE: 7

Met Glu Leu Leu Lys Leu Asn Arg Ser Val Gln Gly Thr Gly Pro
  1               5                  10                  15
```

-continued

```
Gly Pro Gly Ala Ser Leu Cys Arg Pro Gly Ala Pro Leu Leu Asn
                20                  25                  30

Ser Ser Ser Val Gly Asn Leu Ser Cys Glu Pro Pro Arg Ile Arg
                35                  40                  45

Gly Ala Gly Thr Arg Gly Val Ser Val Ser Val Ser Thr Leu Ser
                50                  55                  60

Leu Val Ala Ile Ala Leu Glu Arg Tyr Ser Ala Ile Cys Arg Pro
                65                  70                  75

Leu Gln Ala Arg Val Trp Gln Thr Arg Ser His Ala Ala Arg Val
                80                  85                  90

Ile Val Ala Thr Trp Leu Leu Ser Gly Leu Leu Met Val Pro Tyr
                95                  100                 105

Pro Val Tyr Thr Val Val Gln Pro Val Gly Pro Arg Val Leu Gln
                110                 115                 120

Cys Val His Arg Trp Pro Ser Ala Arg Val Arg Gln Thr Trp Ser
                125                 130                 135

Val Leu Leu Leu Leu Leu Leu Phe Phe Ile Pro Gly Val Val Met
                140                 145                 150

Ala Val Ala Tyr Gly Leu Ile Ser Arg Glu Leu Tyr Leu Gly Leu
                155                 160                 165

Arg Phe Asp Gly Asp Ser Asp Ser Asp Ser Gln Ser Arg Val Arg
                170                 175                 180

Asn Gln Gly Gly Leu Pro Gly Ala Val His Gln Asn Gly Arg Cys
                185                 190                 195

Arg Pro Glu Thr Gly Ala Val Gly Glu Asp Ser Asp Gly Cys Tyr
                200                 205                 210

Val Gln Leu Pro Arg Ser Arg Pro Ala Leu Glu Leu Thr Ala Leu
                215                 220                 225

Thr Ala Pro Gly Pro Gly Ser Gly Ser Arg Pro Thr Gln Ala Lys
                230                 235                 240

Leu Leu Ala Lys Lys Arg Val Val Arg Met Leu Leu Val Ile Val
                245                 250                 255

Val Leu Phe Phe Leu Cys Trp Leu Pro Val Tyr Ser Ala Asn Thr
                260                 265                 270

Trp Arg Ala Phe Asp Gly Pro Gly Ala His Arg Ala Leu Ser Gly
                275                 280                 285

Ala Pro Ile Ser Phe Ile His Leu Leu Ser Tyr Ala Ser Ala Cys
                290                 295                 300

Val Asn Pro Leu Val Tyr Cys Phe Met His Arg Arg Phe Arg Gln
                305                 310                 315

Ala Cys Leu Glu Thr Cys Ala Arg Cys Cys Pro Arg Pro Pro Arg
                320                 325                 330

Ala Arg Pro Arg Ala Leu Pro Asp Glu Asp Pro Pro Thr Pro Ser
                335                 340                 345

Ile Ala Ser Leu Ser Arg Leu Ser Tyr Thr Thr Ile Ser Thr Leu
                350                 355                 360

Gly Pro Gly
```

```
<210> SEQ ID NO 8
<211> LENGTH: 392
<212> TYPE: PRT
<213> ORGANISM: Homo sapiens
<220> FEATURE:
<221> NAME/KEY: misc_feature
```

-continued

<223> OTHER INFORMATION: Incyte ID No: 7506814CD1

<400> SEQUENCE: 8

```
Met Glu Leu Leu Lys Leu Asn Arg Ser Val Gln Gly Thr Gly Pro
  1               5                  10                  15

Gly Pro Gly Ala Ser Leu Cys Arg Pro Gly Ala Pro Leu Leu Asn
                 20                  25                  30

Ser Ser Ser Val Gly Asn Leu Ser Cys Glu Pro Pro Arg Ile Arg
                 35                  40                  45

Gly Ala Gly Thr Arg Glu Leu Glu Leu Ala Ile Arg Ile Thr Leu
                 50                  55                  60

Tyr Ala Val Ile Phe Leu Met Ser Val Gly Gly Asn Met Leu Ile
                 65                  70                  75

Ile Val Val Leu Gly Leu Ser Arg Arg Leu Arg Thr Val Thr Asn
                 80                  85                  90

Ala Phe Leu Leu Ser Leu Ala Val Ser Asp Leu Leu Leu Ala Val
                 95                 100                 105

Ala Cys Met Pro Phe Thr Leu Leu Pro Asn Leu Met Gly Thr Phe
                110                 115                 120

Ile Phe Gly Thr Ile Ile Cys Lys Ala Val Ser Tyr Leu Met Gly
                125                 130                 135

Val Ser Val Ser Val Ser Thr Leu Ser Leu Val Ala Ile Ala Leu
                140                 145                 150

Glu Arg Tyr Ser Ala Ile Cys Arg Pro Leu Gln Ala Arg Val Trp
                155                 160                 165

Gln Thr Arg Ser His Ala Ala Arg Val Ile Val Ala Thr Trp Leu
                170                 175                 180

Leu Ser Gly Leu Leu Met Val Pro Tyr Pro Val Tyr Thr Val Val
                185                 190                 195

Gln Pro Val Gly Pro Arg Val Leu Gln Cys Val His Arg Trp Pro
                200                 205                 210

Ser Ala Arg Val Arg Gln Thr Trp Ser Val Leu Leu Leu Leu Leu
                215                 220                 225

Leu Phe Phe Ile Pro Gly Val Val Met Ala Val Ala Tyr Gly Leu
                230                 235                 240

Ile Ser Arg Glu Leu Tyr Leu Gly Leu Arg Phe Asp Gly Asp Ser
                245                 250                 255

Asp Ser Asp Ser Gln Ser Arg Val Arg Asn Gln Gly Gly Leu Pro
                260                 265                 270

Gly Ala Lys Lys Arg Val Val Arg Met Leu Leu Val Ile Val Val
                275                 280                 285

Leu Phe Phe Leu Cys Trp Leu Pro Val Tyr Ser Ala Asn Thr Trp
                290                 295                 300

Arg Ala Phe Asp Gly Pro Gly Ala His Arg Ala Leu Ser Gly Ala
                305                 310                 315

Pro Ile Ser Phe Ile His Leu Leu Ser Tyr Ala Ser Ala Cys Val
                320                 325                 330

Asn Pro Leu Val Tyr Cys Phe Met His Arg Arg Phe Arg Gln Ala
                335                 340                 345

Cys Leu Glu Thr Cys Ala Arg Cys Cys Pro Arg Pro Pro Arg Ala
                350                 355                 360

Arg Pro Arg Ala Leu Pro Asp Glu Asp Pro Pro Thr Pro Ser Ile
                365                 370                 375
```

-continued

```
Ala Ser Leu Ser Arg Leu Ser Tyr Thr Thr Ile Ser Thr Leu Gly
                380                 385                 390

Pro Gly


<210> SEQ ID NO 9
<211> LENGTH: 125
<212> TYPE: PRT
<213> ORGANISM: Homo sapiens
<220> FEATURE:
<221> NAME/KEY: misc_feature
<223> OTHER INFORMATION: Incyte ID No: 7506852CD1

<400> SEQUENCE: 9

Met Pro Pro Ser Ile Ser Ala Phe Gln Ala Ala Tyr Ile Gly Ile
  1               5                  10                  15

Glu Val Leu Ile Ala Leu Val Ser Val Pro Gly Asn Val Leu Val
                 20                  25                  30

Ile Trp Ala Val Lys Val Asn Gln Ala Leu Arg Asp Ala Thr Phe
                 35                  40                  45

Cys Phe Ile Val Ser Leu Ala Val Ala Asp Val Ala Val Gly Ala
                 50                  55                  60

Leu Val Ile Pro Leu Ala Ile Leu Ile Asn Ile Gly Pro Gln Thr
                 65                  70                  75

Tyr Phe His Thr Cys Leu Met Val Ala Cys Pro Val Leu Ile Leu
                 80                  85                  90

Thr Gln Ser Ser Ile Leu Ala Leu Leu Ala Ile Ala Val Asp Arg
                 95                 100                 105

Tyr Leu Arg Val Lys Ile Pro Leu Arg Arg Ile Ser Gln Cys Met
                110                 115                 120

Ala Ser Thr Lys Ser
                125


<210> SEQ ID NO 10
<211> LENGTH: 728
<212> TYPE: PRT
<213> ORGANISM: Homo sapiens
<220> FEATURE:
<221> NAME/KEY: misc_feature
<223> OTHER INFORMATION: Incyte ID No: 7503782CD1

<400> SEQUENCE: 10

Met Leu Leu Pro Arg Ser Val Ser Ser Glu Arg Ala Pro Gly Val
  1               5                  10                  15

Pro Glu Pro Glu Glu Leu Trp Glu Ala Glu Met Glu Arg Leu Arg
                 20                  25                  30

Gly Ser Gly Thr Pro Val Arg Gly Leu Pro Tyr Ala Met Met Asp
                 35                  40                  45

Lys Arg Leu Ile Trp Gln Leu Arg Glu Pro Ala Gly Val Gln Thr
                 50                  55                  60

Leu Arg Trp Gln Arg Trp Gln Arg Arg Arg Gln Thr Val Glu Arg
                 65                  70                  75

Arg Leu Arg Glu Ala Ala Gln Arg Leu Ala Arg Gly Leu Gly Leu
                 80                  85                  90

Trp Glu Gly Ala Leu Tyr Glu Ile Gly Gly Leu Phe Gly Thr Gly
                 95                 100                 105

Ile Arg Ser Tyr Phe Thr Phe Leu Arg Phe Leu Leu Leu Leu Asn
                110                 115                 120

Leu Leu Ser Leu Leu Leu Thr Ala Ser Phe Val Leu Leu Pro Leu
```

-continued

```
                125                 130                 135

Val Trp Leu Arg Pro Pro Asp Pro Gly Pro Thr Leu Asn Leu Thr
                140                 145                 150

Leu Gln Cys Pro Gly Ser Arg Gln Ser Pro Pro Gly Val Leu Arg
                155                 160                 165

Phe His Asn Gln Leu Trp His Val Leu Thr Gly Arg Ala Phe Thr
                170                 175                 180

Asn Thr Tyr Leu Phe Tyr Gly Ala Tyr Arg Val Gly Pro Glu Ser
                185                 190                 195

Ser Ser Val Tyr Ser Ile Arg Leu Ala Tyr Leu Leu Ser Pro Leu
                200                 205                 210

Ala Cys Leu Leu Leu Cys Phe Cys Gly Thr Leu Arg Arg Met Val
                215                 220                 225

Lys Gly Leu Pro Gln Lys Thr Leu Leu Gly Gln Gly Tyr Gln Ala
                230                 235                 240

Pro Leu Ser Ala Lys Val Phe Ser Ser Trp Asp Phe Cys Ile Arg
                245                 250                 255

Val Gln Glu Ala Ala Thr Ile Lys Lys His Glu Ile Ser Asn Glu
                260                 265                 270

Phe Lys Val Glu Leu Glu Glu Gly Arg Arg Phe Gln Leu Met Gln
                275                 280                 285

Gln Gln Thr Arg Ala Gln Thr Ala Cys Arg Leu Leu Ser Tyr Leu
                290                 295                 300

Arg Val Asn Val Leu Ile Gly Leu Leu Val Val Gly Ala Ile Ser
                305                 310                 315

Ala Ile Phe Trp Ala Thr Lys Tyr Ser Gln Asp Asn Lys Glu Val
                320                 325                 330

Ser Gly Asn Cys Ile His Leu Ile Leu Ala Arg Thr Ala Gly Glu
                335                 340                 345

Ser Leu Phe Leu Leu Leu Gln Tyr Leu Pro Pro Gly Val Ile Ala
                350                 355                 360

Leu Val Asn Phe Leu Gly Pro Leu Leu Phe Thr Phe Leu Val Gln
                365                 370                 375

Leu Glu Asn Tyr Pro Pro Asn Thr Glu Val Asn Leu Thr Leu Ile
                380                 385                 390

Trp Cys Val Val Leu Lys Leu Ala Ser Leu Gly Met Phe Ser Val
                395                 400                 405

Ser Leu Gly Gln Thr Ile Leu Cys Ile Gly Arg Asp Lys Ser Ser
                410                 415                 420

Cys Glu Ser Tyr Gly Tyr Asn Val Cys Asp Tyr Gln Cys Trp Glu
                425                 430                 435

Asn Ser Val Gly Glu Glu Leu Tyr Lys Leu Ser Ile Phe Asn Phe
                440                 445                 450

Leu Leu Thr Val Ala Phe Ala Phe Leu Val Thr Leu Pro Arg Arg
                455                 460                 465

Leu Leu Val Asp Arg Phe Ser Gly Arg Phe Trp Ala Trp Leu Glu
                470                 475                 480

Arg Glu Glu Phe Leu Val Pro Lys Asn Val Leu Asp Ile Val Ala
                485                 490                 495

Gly Gln Thr Val Thr Trp Met Gly Leu Phe Tyr Cys Pro Leu Leu
                500                 505                 510

Pro Leu Leu Asn Ser Val Phe Leu Phe Leu Thr Phe Tyr Ile Lys
                515                 520                 525
```

-continued

```
Lys Tyr Thr Leu Leu Lys Asn Ser Arg Ala Ser Ser Arg Pro Phe
                530                 535                 540

Arg Ala Ser Ser Ser Thr Phe Phe Phe Gln Leu Val Leu Leu Leu
                545                 550                 555

Gly Leu Leu Leu Ala Ala Val Pro Leu Gly Tyr Val Val Ser Ser
                560                 565                 570

Ile His Ser Ser Trp Asp Cys Gly Leu Phe Thr Asn Tyr Ser Ala
                575                 580                 585

Pro Trp Gln Val Val Pro Glu Leu Val Ala Leu Gly Leu Pro Pro
                590                 595                 600

Ile Gly Gln Arg Ala Leu His Tyr Leu Gly Ser His Ala Phe Ser
                605                 610                 615

Phe Pro Leu Leu Ile Met Leu Arg Phe Ser Gly Gln Gln Gly Pro
                620                 625                 630

Trp Glu Gly Thr Pro Gly Gly Gly Gly Pro Ser Phe His Gly Gly
                635                 640                 645

Gly Glu Pro Val His Pro Gln Pro Gly Ala Arg Arg Arg Lys Pro
                650                 655                 660

Arg Glu Ala Gly Ala Ser Glu Lys Gln Glu Pro Pro Gly Pro Thr
                665                 670                 675

Leu Trp Ala Ala Met Gly Ile Ala Gly Ser Leu Gly Lys His Arg
                680                 685                 690

Val Trp Val Ala Ala Ala Ala Glu Leu Leu Val Leu Leu Cys Gln
                695                 700                 705

Arg Gly Gly Asp Glu Gly Leu Cys Glu Glu Gly Glu Glu Gly Pro
                710                 715                 720

Ile Leu Arg Tyr Ser Ser Val Gln
                725
```

<210> SEQ ID NO 11
<211> LENGTH: 61
<212> TYPE: PRT
<213> ORGANISM: Homo sapiens
<220> FEATURE:
<221> NAME/KEY: misc_feature
<223> OTHER INFORMATION: Incyte ID No: 7504647CD1

<400> SEQUENCE: 11

```
Met Ala Glu Thr Leu Phe Trp Thr Pro Leu Leu Val Val Leu Leu
  1               5                  10                  15

Ala Gly Leu Gly Asp Thr Glu Ala Gln Gln Thr Thr Leu His Pro
                 20                  25                  30

Leu Val Gly Arg Val Phe Val His Thr Leu Asp His Glu Thr Phe
                 35                  40                  45

Leu Ser Leu Pro Glu His Val Gly His Ser Leu Gln Ser Gly Gln
                 50                  55                  60

Leu
```

<210> SEQ ID NO 12
<211> LENGTH: 152
<212> TYPE: PRT
<213> ORGANISM: Homo sapiens
<220> FEATURE:
<221> NAME/KEY: misc_feature
<223> OTHER INFORMATION: Incyte ID No: 7500424CD1

<400> SEQUENCE: 12

-continued

```
Met Thr Pro Gln Ser Leu Leu Gln Thr Thr Leu Phe Leu Leu Ser
  1               5                  10                  15

Leu Leu Phe Leu Val Gln Gly Ala His Gly Arg Gly His Arg Glu
                 20                  25                  30

Asp Phe Arg Phe Cys Ser Gln Arg Asn Gln Thr His Arg Ser Ser
                 35                  40                  45

Leu His Tyr Lys Pro Thr Pro Asp Leu Arg Ile Ser Ile Glu Asn
                 50                  55                  60

Ser Glu Glu Ala Leu Thr Val His Ala Pro Phe Pro Ala Ala His
                 65                  70                  75

Pro Ala Ser Arg Ser Phe Pro Asp Pro Arg Gly Leu Tyr His Phe
                 80                  85                  90

Cys Leu Tyr Trp Asn Arg His Ala Gly Arg Leu His Leu Leu Tyr
                 95                 100                 105

Gly Lys Arg Asp Phe Leu Leu Ser Asp Lys Ala Ser Ser Leu Leu
                110                 115                 120

Cys Phe Gln His Gln Ala Arg Tyr Arg Cys Val Gly Trp Ala Arg
                125                 130                 135

Ser Leu Cys Pro Ser Gly Pro Leu Tyr Glu Leu His Cys Pro Cys
                140                 145                 150

Ser Pro


<210> SEQ ID NO 13
<211> LENGTH: 283
<212> TYPE: PRT
<213> ORGANISM: Homo sapiens
<220> FEATURE:
<221> NAME/KEY: misc_feature
<223> OTHER INFORMATION: Incyte ID No: 7500449CD1

<400> SEQUENCE: 13

Met Pro Pro Pro Pro Leu Leu Ser Leu Arg Arg Leu Gly Gly Gly
  1               5                  10                  15

Trp Ser Ala Val Thr Arg Leu Val Val Ala Ala Ala Gly Ala Arg
                 20                  25                  30

Ser Arg Gly Gly Arg Gly Gly Ser Arg Gly Ala Gly Gly Gly Gly
                 35                  40                  45

Arg Gly Gly Val Ala Arg Arg Arg Arg Leu Glu Leu Arg Ala Ala
                 50                  55                  60

Arg Ser Leu Leu Gly Ser Ser Leu Gln Glu Glu Cys Asp Tyr Val
                 65                  70                  75

Gln Met Ile Glu Val Gln His Lys Gln Cys Leu Glu Glu Ala Gln
                 80                  85                  90

Leu Glu Asn Glu Thr Ile Gly Cys Ser Lys Met Trp Asp Asn Leu
                 95                 100                 105

Thr Cys Trp Pro Ala Thr Pro Arg Gly Gln Val Val Val Leu Ala
                110                 115                 120

Cys Pro Leu Ile Phe Lys Leu Phe Ser Ser Ile Gln Gly Arg Asn
                125                 130                 135

Val Ser Arg Ser Cys Thr Asp Glu Gly Trp Thr His Leu Glu Pro
                140                 145                 150

Gly Pro Tyr Pro Ile Ala Cys Gly Leu Asp Asp Lys Ala Ala Ser
                155                 160                 165

Leu Asp Glu Gln Gln Thr Met Phe Tyr Gly Ser Val Lys Thr Gly
                170                 175                 180
```

-continued

```
Tyr Thr Ile Gly Tyr Gly Leu Ser Leu Ala Thr Leu Leu Val Ala
                185                 190                 195

Thr Ala Ile Leu Ser Leu Phe Arg Lys Leu His Cys Thr Arg Asn
                200                 205                 210

Tyr Ile His Met His Leu Phe Ile Ser Phe Ile Leu Arg Ala Ala
                215                 220                 225

Ala Val Phe Ile Lys Asp Leu Ala Leu Phe Asp Ser Gly Glu Ser
                230                 235                 240

Asp Gln Cys Ser Glu Gly Ser Gly Tyr Pro Ala His Ser Pro Trp
                245                 250                 255

Cys Gly Pro Ser Pro Gly Ser Ile Leu Arg Ile Met Val Cys Ser
                260                 265                 270

Gly Ala Gly Thr Pro Ser Thr Pro His Cys Gly Gly Ser
                275                 280


<210> SEQ ID NO 14
<211> LENGTH: 246
<212> TYPE: PRT
<213> ORGANISM: Homo sapiens
<220> FEATURE:
<221> NAME/KEY: misc_feature
<223> OTHER INFORMATION: Incyte ID No: 7503281CD1

<400> SEQUENCE: 14

Met Asp His Gln Asp Pro Tyr Ser Val Gln Ala Thr Ala Ala Ile
  1               5                  10                  15

Ala Ala Ala Ile Thr Phe Leu Ile Leu Phe Thr Ile Phe Gly Asn
                 20                  25                  30

Ala Leu Val Ile Leu Ala Val Leu Thr Ser Arg Ser Leu Arg Ala
                 35                  40                  45

Pro Gln Asn Leu Phe Leu Val Ser Leu Ala Ala Ala Asp Ile Leu
                 50                  55                  60

Val Ala Thr Leu Ile Ile Pro Phe Ser Leu Ala Asn Glu Leu Leu
                 65                  70                  75

Gly Tyr Trp Tyr Phe Arg Arg Thr Trp Cys Glu Val Tyr Leu Ala
                 80                  85                  90

Leu Asp Val Leu Phe Cys Thr Ser Ser Ile Val His Leu Cys Ala
                 95                 100                 105

Ile Ser Leu Asp Arg Tyr Trp Ala Val Ser Arg Ala Leu Glu Tyr
                110                 115                 120

Asn Ser Lys Arg Thr Pro Arg Arg Ile Lys Cys Ile Ile Leu Thr
                125                 130                 135

Val Trp Leu Ile Ala Ala Val Ile Ser Leu Pro Pro Leu Ile Tyr
                140                 145                 150

Lys Gly Asp Gln Gly Pro Gln Pro Arg Gly Arg Pro Gln Cys Lys
                155                 160                 165

Leu Asn Gln Glu Ala Trp Tyr Ile Leu Ala Ser Ser Ile Gly Ser
                170                 175                 180

Phe Phe Ala Pro Cys Leu Ile Met Ile Leu Val Tyr Leu Arg Ile
                185                 190                 195

Tyr Leu Ile Ala Lys Arg Ser Asn Arg Arg Gly Pro Arg Ala Lys
                200                 205                 210

Gly Gly Pro Gly Gln Ala Thr Ala Trp Ala Pro Ser Ala Arg Ser
                215                 220                 225

Thr Ala Arg Cys Pro Met Ala Ser Ser Ser Ser Ser Ser Gly Ser
                230                 235                 240
```

-continued

```
Ala Thr Ala Thr Ala His
                245


<210> SEQ ID NO 15
<211> LENGTH: 319
<212> TYPE: PRT
<213> ORGANISM: Homo sapiens
<220> FEATURE:
<221> NAME/KEY: misc_feature
<223> OTHER INFORMATION: Incyte ID No: 7503292CD1

<400> SEQUENCE: 15

Met Glu Thr Ser Ser Pro Arg Pro Pro Arg Pro Ser Ser Asn Pro
  1               5                  10                  15

Gly Leu Ser Leu Asp Ala Arg Leu Gly Val Asp Thr Arg Leu Trp
                 20                  25                  30

Ala Lys Val Leu Phe Thr Ala Leu Tyr Ala Leu Ile Trp Ala Leu
                 35                  40                  45

Gly Ala Ala Gly Asn Ala Leu Ser Val His Val Val Leu Lys Ala
                 50                  55                  60

Arg Ala Gly Arg Ala Gly Arg Leu Arg His His Val Leu Ser Leu
                 65                  70                  75

Ala Leu Ala Gly Leu Leu Leu Leu Leu Val Gly Val Pro Val Glu
                 80                  85                  90

Leu Tyr Ser Phe Val Trp Phe His Tyr Pro Trp Val Phe Gly Asp
                 95                 100                 105

Leu Gly Cys Arg Gly Tyr Tyr Phe Val His Glu Leu Cys Ala Tyr
                110                 115                 120

Ala Thr Val Leu Ser Val Ala Gly Leu Ser Ala Glu Arg Cys Leu
                125                 130                 135

Ala Val Cys Gln Pro Leu Arg Ala Arg Ser Leu Leu Thr Pro Arg
                140                 145                 150

Arg Thr Arg Trp Leu Val Ala Leu Ser Trp Ala Ala Ser Leu Gly
                155                 160                 165

Leu Ala Leu Pro Met Ala Val Ile Met Gly Gln Lys His Glu Leu
                170                 175                 180

Glu Thr Ala Asp Gly Glu Pro Glu Pro Ala Ser Arg Val Cys Thr
                185                 190                 195

Val Leu Val Ser Arg Thr Ala Leu Gln Val Phe Ile Gln Val Asn
                200                 205                 210

Val Leu Val Ser Phe Val Leu Pro Leu Ala Leu Thr Ala Phe Leu
                215                 220                 225

Asn Gly Val Thr Val Ser His Leu Leu Ala Leu Cys Ser Gln Val
                230                 235                 240

Pro Ser Thr Ser Thr Pro Gly Ser Ser Thr Pro Ser Arg Leu Glu
                245                 250                 255

Leu Leu Ser Glu Glu Gly Leu Leu Ser Phe Ile Val Trp Lys Lys
                260                 265                 270

Thr Phe Ile Gln Gly Gly Gln Glu Pro Ser Trp Ser Cys Met Ser
                275                 280                 285

Ser Ala Gly Cys Arg Thr Met Pro Ala Gly Ser Cys Thr Ala Thr
                290                 295                 300

Tyr Leu Met Thr Arg Gly Leu Thr His Cys Thr Ile Ser Thr Thr
                305                 310                 315

Thr Ser Thr Trp
```

<210> SEQ ID NO 16
<211> LENGTH: 284
<212> TYPE: PRT
<213> ORGANISM: Homo sapiens
<220> FEATURE:
<221> NAME/KEY: misc_feature
<223> OTHER INFORMATION: Incyte ID No: 7503311CD1

<400> SEQUENCE: 16

```
Met Thr Thr Ser Pro Ile Leu Gln Leu Leu Leu Arg Leu Ser Leu
  1               5                  10                  15

Cys Gly Leu Leu Leu Gln Arg Ala Glu Thr Gly Ser Lys Gly Gln
                 20                  25                  30

Thr Ala Gly Glu Leu Tyr Gln Arg Trp Glu Arg Tyr Arg Arg Glu
                 35                  40                  45

Cys Gln Glu Thr Leu Ala Ala Ala Glu Pro Pro Ser Gly Leu Ala
                 50                  55                  60

Cys Asn Gly Ser Phe Asp Met Tyr Val Cys Trp Asp Tyr Ala Ala
                 65                  70                  75

Pro Asn Ala Thr Ala Arg Ala Ser Cys Pro Trp Tyr Leu Pro Trp
                 80                  85                  90

His His His Val Ala Ala Gly Phe Val Leu Arg Gln Cys Gly Ser
                 95                 100                 105

Asp Gly Gln Trp Gly Leu Trp Arg Asp His Thr Gln Cys Glu Asn
                110                 115                 120

Pro Glu Lys Asn Glu Ala Phe Leu Asp Gln Arg Leu Ile Leu Glu
                125                 130                 135

Arg Leu Gln Val Met Tyr Thr Val Gly Tyr Ser Leu Ser Leu Ala
                140                 145                 150

Thr Leu Leu Leu Ala Leu Leu Ile Leu Ser Leu Phe Arg Arg Leu
                155                 160                 165

His Cys Thr Arg Asn Tyr Ile His Ile Asn Leu Phe Thr Ser Phe
                170                 175                 180

Met Leu Arg Ala Ala Ala Ile Leu Ser Arg Asp Arg Leu Leu Pro
                185                 190                 195

Arg Pro Gly Pro Tyr Leu Gly Asp Gln Ala Leu Ala Leu Trp Asn
                200                 205                 210

Gln Ala Leu Ala Ala Cys Arg Thr Ala Gln Ile Val Thr Gln Tyr
                215                 220                 225

Cys Val Gly Ala Asn Tyr Thr Trp Leu Leu Val Glu Gly Val Tyr
                230                 235                 240

Leu His Ser Leu Leu Val Leu Val Gly Gly Ser Glu Glu Gly His
                245                 250                 255

Phe Arg Tyr Tyr Leu Leu Leu Gly Trp Gly Ala Gly Ser Ala Thr
                260                 265                 270

Lys Ser Arg Pro Phe Gly Gly Leu Tyr Gly Pro Pro Ser Ser
                275                 280
```

<210> SEQ ID NO 17
<211> LENGTH: 400
<212> TYPE: PRT
<213> ORGANISM: Homo sapiens
<220> FEATURE:
<221> NAME/KEY: misc_feature
<223> OTHER INFORMATION: Incyte ID No: 7510384CD1

<400> SEQUENCE: 17

-continued

```
Met Asp Arg Arg Met Trp Gly Ala His Val Phe Cys Val Leu Ser
  1               5                  10                  15

Pro Leu Pro Thr Val Leu Gly His Met His Pro Glu Cys Asp Phe
                 20                  25                  30

Ile Thr Gln Leu Arg Glu Asp Glu Ser Ala Cys Leu Gln Ala Ala
                 35                  40                  45

Glu Glu Met Pro Asn Thr Thr Leu Gly Cys Pro Ala Thr Trp Asp
                 50                  55                  60

Gly Leu Leu Cys Trp Pro Thr Ala Gly Ser Gly Glu Trp Val Thr
                 65                  70                  75

Leu Pro Cys Pro Asp Phe Phe Ser His Phe Ser Ser Glu Ser Gly
                 80                  85                  90

Ala Val Lys Arg Asp Cys Thr Ile Thr Gly Trp Ser Glu Pro Phe
                 95                 100                 105

Pro Pro Tyr Pro Val Ala Cys Pro Val Pro Leu Glu Leu Leu Ala
                110                 115                 120

Glu Glu Glu Ser Tyr Phe Ser Thr Val Lys Ile Ile Tyr Thr Val
                125                 130                 135

Gly His Ser Ile Ser Ile Val Ala Leu Phe Val Ala Ile Thr Ile
                140                 145                 150

Leu Val Ala Leu Arg Arg Leu His Cys Pro Arg Asn Tyr Val His
                155                 160                 165

Thr Gln Leu Phe Thr Thr Phe Ile Leu Lys Ala Gly Ala Val Phe
                170                 175                 180

Leu Lys Asp Ala Ala Leu Phe His Ser Asp Asp Thr Asp His Cys
                185                 190                 195

Ser Phe Ser Thr Val Met Ala Met Gly Glu Gly Ala Gly Gln Val
                200                 205                 210

Gly Glu Arg Gly Gly Ser Met Gln Gly Leu Cys Gly Arg Leu Pro
                215                 220                 225

Phe Arg His His Asp Gln Leu Gln Leu Ala Val Gly Arg Ser Arg
                230                 235                 240

Leu Pro Glu Leu Pro Pro Gly Leu His Leu Pro Gln Leu Lys Glu
                245                 250                 255

Ser Leu Leu Val Ala Gly Ser Arg Trp Leu Gly Ala Ala Arg Ala
                260                 265                 270

Leu His Trp His Val Gly Glu Leu Gln Thr Gly Leu Arg Gly His
                275                 280                 285

Arg Val Leu Gly Pro Gly Arg His Leu Pro Leu Leu Val Asp His
                290                 295                 300

Gln Arg Ala His Cys Pro Leu Gly Arg Gly Glu Leu Trp Ala Phe
                305                 310                 315

Ser Gln Tyr Tyr Pro His Pro Gly Glu Glu Thr Gly Ala Ser Ser
                320                 325                 330

Gly Gln Pro Pro Tyr Pro Val Ser Val Leu Ala Ser Leu Gln Val
                335                 340                 345

Asp Thr Phe Pro Asp Pro Thr Leu Trp Asn Ser Leu His His Leu
                350                 355                 360

Gln Leu Pro Ala Arg Gln Cys Trp Pro Gly His Pro Pro Pro Pro
                365                 370                 375

Gly Ala Gly Thr Gly Phe Leu Pro Gly Leu His Cys Cys His Pro
                380                 385                 390
```

-continued

```
Leu Leu Leu Pro Gln Pro Arg Gly Glu Asp
                395                 400


<210> SEQ ID NO 18
<211> LENGTH: 893
<212> TYPE: PRT
<213> ORGANISM: Homo sapiens
<220> FEATURE:
<221> NAME/KEY: misc_feature
<223> OTHER INFORMATION: Incyte ID No: 7509976CD1

<400> SEQUENCE: 18

Met Pro Ser Val Cys Leu Leu Leu Leu Leu Phe Leu Ala Val Gly
  1               5                  10                  15

Gly Ala Leu Gly Asn Arg Pro Phe Arg Ala Phe Val Val Thr Asp
                 20                  25                  30

Thr Thr Leu Thr His Leu Ala Val His Arg Val Thr Gly Glu Val
                 35                  40                  45

Phe Val Gly Ala Val Asn Arg Val Phe Lys Leu Ala Pro Asn Leu
                 50                  55                  60

Thr Glu Leu Arg Ala His Val Thr Gly Pro Val Glu Asp Asn Ala
                 65                  70                  75

Arg Cys Tyr Pro Pro Pro Ser Met Arg Val Cys Ala His Arg Leu
                 80                  85                  90

Ala Pro Val Asp Asn Ile Asn Lys Leu Leu Leu Ile Asp Tyr Ala
                 95                 100                 105

Ala Arg Arg Leu Val Ala Cys Gly Ser Ile Trp Gln Gly Ile Cys
                110                 115                 120

Gln Phe Leu Arg Leu Asp Asp Leu Phe Lys Leu Gly Glu Pro His
                125                 130                 135

His Arg Lys Glu His Tyr Leu Ser Gly Ala Gln Glu Pro Asp Ser
                140                 145                 150

Met Ala Gly Val Ile Val Glu Gln Gly Gln Gly Pro Ser Lys Leu
                155                 160                 165

Phe Val Gly Thr Ala Val Asp Gly Lys Ser Glu Tyr Phe Pro Thr
                170                 175                 180

Leu Ser Ser Arg Lys Leu Ile Ser Asp Glu Asp Ser Ala Asp Met
                185                 190                 195

Phe Ser Leu Val Tyr Gln Asp Glu Phe Val Ser Ser Gln Ile Lys
                200                 205                 210

Ile Pro Ser Asp Thr Leu Ser Leu Tyr Pro Ala Phe Asp Ile Tyr
                215                 220                 225

Tyr Ile Tyr Gly Phe Val Ser Ala Ser Phe Val Tyr Phe Leu Thr
                230                 235                 240

Leu Gln Leu Asp Thr Gln Gln Thr Leu Leu Asp Thr Ala Gly Glu
                245                 250                 255

Lys Phe Phe Thr Ser Lys Ile Val Arg Met Cys Ala Gly Asp Ser
                260                 265                 270

Glu Phe Tyr Ser Tyr Val Glu Phe Pro Ile Gly Cys Ser Trp Arg
                275                 280                 285

Gly Val Glu Tyr Arg Leu Val Gln Ser Ala His Leu Ala Lys Pro
                290                 295                 300

Gly Leu Leu Leu Ala Gln Ala Leu Gly Val Pro Ala Asp Glu Asp
                305                 310                 315

Val Leu Phe Thr Ile Phe Ser Gln Gly Gln Lys Asn Arg Ala Ser
                320                 325                 330
```

-continued

```
Pro Pro Arg Gln Thr Ile Leu Cys Leu Phe Thr Leu Ser Asn Ile
                335                 340                 345

Asn Ala His Ile Arg Arg Arg Ile Gln Ser Cys Tyr Arg Gly Glu
                350                 355                 360

Gly Thr Leu Ala Leu Pro Trp Leu Leu Asn Lys Glu Leu Pro Cys
                365                 370                 375

Ile Asn Thr Pro Met Gln Ile Asn Gly Asn Phe Cys Gly Leu Val
                380                 385                 390

Leu Asn Gln Pro Leu Gly Gly Leu His Val Ile Glu Gly Leu Pro
                395                 400                 405

Leu Leu Ala Asp Ser Thr Asp Gly Met Ala Ser Val Ala Ala Tyr
                410                 415                 420

Thr Tyr Arg Gln His Ser Val Val Phe Ile Gly Thr Arg Ser Gly
                425                 430                 435

Ser Leu Lys Lys Val Arg Val Asp Gly Phe Gln Asp Ala His Leu
                440                 445                 450

Tyr Glu Thr Val Pro Val Val Asp Gly Ser Pro Ile Leu Arg Asp
                455                 460                 465

Leu Leu Phe Ser Pro Asp His Arg His Ile Tyr Leu Leu Ser Glu
                470                 475                 480

Lys Gln Val Ser Gln Leu Pro Val Glu Thr Cys Glu Gln Tyr Gln
                485                 490                 495

Ser Cys Ala Ala Cys Leu Gly Ser Gly Asp Pro His Cys Gly Trp
                500                 505                 510

Cys Val Leu Arg His Arg Cys Cys Arg Glu Gly Ala Cys Leu Gly
                515                 520                 525

Ala Ser Ala Pro His Gly Phe Ala Glu Glu Leu Ser Lys Cys Val
                530                 535                 540

Gln Val Arg Val Arg Pro Asn Asn Val Ser Val Thr Ser Pro Gly
                545                 550                 555

Val Gln Leu Thr Val Thr Leu His Asn Val Pro Asp Leu Ser Ala
                560                 565                 570

Gly Val Ser Cys Ala Phe Glu Ala Ala Ala Glu Asn Glu Ala Val
                575                 580                 585

Leu Leu Pro Ser Gly Glu Leu Leu Cys Pro Ser Pro Ser Leu Gln
                590                 595                 600

Glu Leu Arg Ala Leu Thr Arg Gly His Gly Ala Thr Arg Thr Val
                605                 610                 615

Arg Leu Gln Leu Leu Ser Lys Glu Thr Gly Val Arg Phe Ala Gly
                620                 625                 630

Ala Asp Phe Val Phe Tyr Asn Cys Ser Val Leu Gln Ser Cys Met
                635                 640                 645

Ser Cys Val Gly Ser Pro Tyr Pro Cys His Trp Cys Lys Tyr Arg
                650                 655                 660

His Thr Cys Thr Ser Arg Pro His Glu Cys Ser Phe Gln Glu Gly
                665                 670                 675

Arg Val His Ser Pro Glu Gly Cys Pro Glu Ile Leu Pro Ser Gly
                680                 685                 690

Asp Leu Leu Ile Pro Val Gly Val Met Gln Pro Leu Thr Leu Arg
                695                 700                 705

Ala Lys Asn Leu Pro Gln Pro Gln Ser Gly Gln Lys Asn Tyr Glu
                710                 715                 720
```

-continued

```
Cys Val Val Arg Val Gln Gly Arg Gln Gln Arg Val Pro Ala Val
                725                 730                 735

Arg Phe Asn Ser Ser Ser Val Gln Cys Gln Asn Ala Ser Tyr Ser
                740                 745                 750

Tyr Glu Gly Asp Glu His Gly Asp Thr Glu Leu Asp Phe Ser Val
                755                 760                 765

Val Trp Asp Gly Asp Phe Pro Ile Asp Lys Pro Pro Ser Phe Arg
                770                 775                 780

Ala Leu Leu Tyr Lys Cys Trp Ala Gln Arg Pro Ser Cys Gly Leu
                785                 790                 795

Cys Leu Lys Ala Asp Pro Arg Phe Asn Cys Gly Trp Cys Ile Ser
                800                 805                 810

Glu His Arg Cys Gln Leu Arg Thr His Cys Pro Ala Pro Lys Thr
                815                 820                 825

Asn Trp Met His Leu Ser Gln Lys Gly Thr Arg Cys Ser His Pro
                830                 835                 840

Arg Ile Thr Gln Ile His Pro Leu Val Gly Pro Lys Glu Gly Gly
                845                 850                 855

Thr Arg Val Thr Ile Val Gly Asp Asn Leu Gly Leu Leu Ser Arg
                860                 865                 870

Glu Val Gly Leu Arg Val Ala Gly Val Arg Cys Asn Ser Ile Pro
                875                 880                 885

Ala Glu Tyr Ile Ser Ala Glu Arg
                890
```

<210> SEQ ID NO 19
<211> LENGTH: 203
<212> TYPE: PRT
<213> ORGANISM: Homo sapiens
<220> FEATURE:
<221> NAME/KEY: misc_feature
<223> OTHER INFORMATION: Incyte ID No: 7510454CD1

<400> SEQUENCE: 19

```
Met Lys Ser Phe Leu Pro Gly Thr Cys Ile Leu Leu Cys Ser Ala
  1               5                  10                  15

Phe Asn Leu Met Phe Phe Ser Leu Phe Arg Leu Lys Tyr Asn Ile
                 20                  25                  30

Cys Ile Ile Leu Arg Ala Cys Asn Thr Met Leu Ser Ser Asn Thr
                 35                  40                  45

Ile Met Glu Ile Phe Phe Leu Ser His Ile Asp Ile Gly Ile Trp
                 50                  55                  60

Arg Asn Leu Leu Leu Leu Leu Met Pro Ile Tyr Thr Phe Leu Ile
                 65                  70                  75

Cys Pro Gln Gln Lys Lys Pro Met Gly Leu Leu Phe Leu His Leu
                 80                  85                  90

Ser Val Ala Asn Thr Met Thr Leu Leu Arg Lys Val Ile Pro Leu
                 95                 100                 105

Ala Val Lys Ser Phe Asn Thr Lys Asn Leu Leu Asn Tyr Thr Gly
                110                 115                 120

Cys Arg Glu Phe Glu Phe Leu Tyr Arg Val Ser Trp Gly Leu Pro
                125                 130                 135

Leu Cys Thr Thr Tyr Leu Leu Ser Met Val Gln Ala Leu Arg Gly
                140                 145                 150

Ser Pro Ser Lys Ser Arg Trp Thr Trp Leu Lys Asp Lys Met Leu
                155                 160                 165
```

-continued

```
Lys Thr Pro Leu Cys Phe Phe Leu His Ser Gly Ser Ser Thr Val
                170                 175                 180

Ser Ser Thr Ser Ser Leu Cys His Leu Leu Thr Leu Ser Asn Met
                185                 190                 195

Ala Val Ser Pro Arg Ile Ser Pro
                200


<210> SEQ ID NO 20
<211> LENGTH: 429
<212> TYPE: PRT
<213> ORGANISM: Homo sapiens
<220> FEATURE:
<221> NAME/KEY: misc_feature
<223> OTHER INFORMATION: Incyte ID No: 8017335CD1

<400> SEQUENCE: 20

Met Arg Val Ser Val Pro Gly Pro Ala Ala Ala Ala Ala Pro Ala
  1               5                  10                  15

Ala Gly Arg Glu Pro Ser Thr Pro Gly Gly Gly Ser Gly Gly Gly
                 20                  25                  30

Gly Ala Val Ala Ala Ala Ser Gly Ala Ala Val Pro Gly Ser Val
                 35                  40                  45

Gln Leu Ala Leu Ser Val Leu His Ala Leu Leu Tyr Ala Ala Leu
                 50                  55                  60

Phe Ala Phe Ala Tyr Leu Gln Leu Trp Arg Leu Leu Leu Tyr Arg
                 65                  70                  75

Glu Arg Arg Leu Ser Tyr Gln Ser Leu Cys Leu Phe Leu Cys Leu
                 80                  85                  90

Leu Trp Ala Ala Leu Arg Thr Thr Leu Phe Ser Ala Ala Phe Ser
                 95                 100                 105

Leu Ser Gly Ser Leu Pro Leu Leu Arg Pro Pro Ala His Leu His
                110                 115                 120

Phe Phe Pro His Trp Leu Leu Tyr Cys Phe Pro Ser Cys Leu Gln
                125                 130                 135

Phe Ser Thr Leu Cys Leu Leu Asn Leu Tyr Leu Ala Glu Val Ile
                140                 145                 150

Cys Lys Val Arg Cys Ala Thr Glu Leu Asp Arg His Lys Ile Leu
                155                 160                 165

Leu His Leu Gly Phe Ile Met Ala Ser Leu Leu Phe Leu Val Val
                170                 175                 180

Asn Leu Thr Cys Ala Met Leu Val His Gly Asp Val Pro Glu Asn
                185                 190                 195

Gln Leu Lys Trp Thr Val Phe Val Arg Ala Leu Ile Asn Asp Ser
                200                 205                 210

Leu Phe Ile Leu Cys Ala Ile Ser Leu Val Cys Tyr Ile Cys Lys
                215                 220                 225

Ile Thr Lys Met Ser Ser Ala Asn Val Tyr Leu Glu Ser Lys Gly
                230                 235                 240

Met Ser Leu Cys Gln Thr Val Val Val Gly Ser Val Val Ile Leu
                245                 250                 255

Leu Tyr Ser Ser Arg Ala Cys Tyr Asn Leu Val Val Val Thr Ile
                260                 265                 270

Ser Gln Asp Thr Leu Glu Ser Pro Phe Asn Tyr Gly Trp Asp Asn
                275                 280                 285

Leu Ser Asp Lys Ala His Val Glu Asp Ile Ser Gly Glu Glu Tyr
```

-continued

```
                290                 295                 300

Ile Val Phe Gly Met Val Leu Phe Leu Trp Glu His Val Pro Ala
                305                 310                 315

Trp Ser Val Val Leu Phe Phe Arg Ala Gln Arg Leu Asn Gln Asn
                320                 325                 330

Leu Ala Pro Ala Gly Met Ile Asn Ser His Ser Tyr Ser Ser Arg
                335                 340                 345

Ala Tyr Phe Phe Asp Asn Pro Arg Arg Tyr Asp Ser Asp Asp Asp
                350                 355                 360

Leu Pro Arg Leu Gly Ser Ser Arg Glu Gly Ser Leu Pro Asn Ser
                365                 370                 375

Gln Ser Leu Gly Trp Tyr Gly Thr Met Thr Gly Cys Gly Ser Ser
                380                 385                 390

Ser Tyr Thr Val Thr Pro His Leu Asn Gly Pro Met Thr Asp Thr
                395                 400                 405

Ala Pro Leu Leu Phe Thr Cys Ser Asn Leu Asp Leu Asn Asn His
                410                 415                 420

His Ser Leu Tyr Val Thr Pro Gln Asn
                425
```

<210> SEQ ID NO 21
<211> LENGTH: 101
<212> TYPE: PRT
<213> ORGANISM: Homo sapiens
<220> FEATURE:
<221> NAME/KEY: misc_feature
<223> OTHER INFORMATION: Incyte ID No: 7510197CD1

<400> SEQUENCE: 21

```
Met Asn Pro Phe Leu Ile Leu Ala Phe Val Gly Ala Ala Gly Glu
  1               5                  10                  15

Phe His Asp Leu Pro Gln Ala Pro Pro Thr Pro Phe Pro Gly Arg
                 20                  25                  30

His Met Pro Cys His Ser Cys His Leu Ser Ser Phe Asp Cys Ala
                 35                  40                  45

Leu Ile Phe Tyr Phe Leu His Leu Thr Tyr Leu Leu Pro Ile Leu
                 50                  55                  60

Leu Gly Leu Ser Leu Ser Leu Thr Cys Phe Thr Cys Ser Leu Ile
                 65                  70                  75

Ser Leu Pro Pro Leu Ser Phe Ile His Ile Arg Ala Val Leu Glu
                 80                  85                  90

Lys Leu Gly Arg Glu Thr Ser Cys Cys Pro Leu
                 95                 100
```

<210> SEQ ID NO 22
<211> LENGTH: 237
<212> TYPE: PRT
<213> ORGANISM: Homo sapiens
<220> FEATURE:
<221> NAME/KEY: misc_feature
<223> OTHER INFORMATION: Incyte ID No: 7510055CD1

<400> SEQUENCE: 22

```
Met Val Arg Leu Pro Leu Gln Cys Val Leu Trp Gly Cys Leu Leu
  1               5                  10                  15

Thr Ala Val His Pro Glu Pro Pro Thr Ala Cys Arg Glu Lys Gln
                 20                  25                  30

Tyr Leu Ile Asn Ser Gln Cys Cys Ser Leu Cys Gln Pro Gly Gln
```

-continued

```
                35                  40                  45

Lys Leu Val Ser Asp Cys Thr Glu Phe Thr Glu Thr Glu Cys Leu
                50                  55                  60

Pro Cys Gly Glu Ser Glu Phe Leu Asp Thr Trp Asn Arg Glu Thr
                65                  70                  75

His Cys His Gln His Lys Tyr Cys Asp Pro Asn Leu Gly Leu Arg
                80                  85                  90

Val Gln Gln Lys Gly Thr Ser Glu Thr Asp Thr Ile Cys Thr Cys
                95                 100                 105

Glu Glu Gly Trp His Cys Thr Ser Glu Ala Cys Glu Ser Cys Val
               110                 115                 120

Leu His Gly Ser Cys Ser Pro Gly Phe Gly Val Lys Gln Ile Ala
               125                 130                 135

Thr Gly Val Ser Asp Thr Ile Cys Glu Pro Cys Pro Val Gly Phe
               140                 145                 150

Phe Ser Asn Val Ser Ser Ala Phe Glu Lys Cys His Pro Trp Thr
               155                 160                 165

Ser Cys Glu Thr Lys Asp Leu Val Val Gln Gln Ala Gly Thr Asn
               170                 175                 180

Lys Thr Asp Val Val Cys Gly Glu Ser Trp Thr Met Gly Pro Gly
               185                 190                 195

Glu Ser Leu Gly Arg Ser Pro Gly Ser Ala Glu Ser Pro Gly Gly
               200                 205                 210

Asp Pro His His Leu Arg Asp Pro Val Cys His Pro Leu Gly Ala
               215                 220                 225

Gly Leu Tyr Gln Lys Gly Gly Gln Glu Ala Asn Gln
               230                 235


<210> SEQ ID NO 23
<211> LENGTH: 460
<212> TYPE: PRT
<213> ORGANISM: Homo sapiens
<220> FEATURE:
<221> NAME/KEY: misc_feature
<223> OTHER INFORMATION: Incyte ID No: 7501754CD1

<400> SEQUENCE: 23

Met Gly Ala Pro Pro Gly Tyr Arg Pro Ser Ala Trp Val His Leu
  1               5                  10                  15

Leu His Gln Leu Pro Arg Ala Asp Phe Gln Leu Arg Pro Val Pro
                20                  25                  30

Ser Val Phe Ala Pro Gln Glu Gln Glu Tyr Gln Gln Ala Leu Leu
                35                  40                  45

Leu Val Ala Ala Leu Ala Gly Leu Gly Leu Gly Leu Ser Leu Ile
                50                  55                  60

Phe Ile Ala Val Tyr Leu Ile Arg Phe Cys Cys Cys Arg Pro Pro
                65                  70                  75

Glu Pro Pro Gly Ser Lys Ile Pro Ser Pro Gly Gly Gly Cys Val
                80                  85                  90

Thr Trp Ser Cys Ile Val Ala Leu Leu Ala Gly Cys Thr Gly Ile
                95                 100                 105

Gly Ile Gly Phe Tyr Gly Asn Ser Glu Thr Ser Asp Gly Val Ser
               110                 115                 120

Gln Leu Ser Ser Ala Leu Leu His Ala Asn His Thr Leu Ser Thr
               125                 130                 135
```

-continued

```
Ile Asp His Leu Val Leu Glu Thr Val Glu Arg Leu Gly Glu Ala
                140                 145                 150

Val Arg Thr Glu Leu Thr Thr Leu Glu Glu Val Leu Glu Pro Arg
                155                 160                 165

Thr Glu Leu Val Ala Ala Ala Arg Gly Ala Arg Arg Gln Ala Glu
                170                 175                 180

Ala Ala Ala Gln Gln Leu Gln Gly Leu Ala Phe Trp Gln Gly Val
                185                 190                 195

Pro Leu Ser Pro Leu Gln Val Ala Glu Asn Val Ser Phe Val Glu
                200                 205                 210

Glu Tyr Arg Trp Leu Ala Tyr Val Leu Leu Leu Leu Leu Glu Leu
                215                 220                 225

Leu Val Cys Leu Phe Thr Leu Leu Gly Leu Ala Lys Gln Ser Lys
                230                 235                 240

Trp Leu Val Ile Val Met Thr Val Met Ser Leu Leu Val Leu Val
                245                 250                 255

Leu Ser Trp Gly Ser Met Gly Leu Glu Ala Ala Thr Ala Val Gly
                260                 265                 270

Leu Ser Asp Phe Cys Ser Asn Pro Asp Pro Tyr Val Leu Asn Leu
                275                 280                 285

Thr Gln Glu Glu Thr Gly Leu Ser Ser Asp Ile Leu Ser Tyr Tyr
                290                 295                 300

Leu Leu Cys Asn Arg Ala Val Ser Asn Pro Phe Gln Gln Arg Leu
                305                 310                 315

Thr Leu Ser Gln Arg Ala Leu Ala Asn Ile His Ser Gln Leu Leu
                320                 325                 330

Gly Leu Glu Arg Glu Ala Val Pro Gln Phe Pro Ser Ala Gln Lys
                335                 340                 345

Pro Leu Leu Ser Leu Glu Glu Thr Leu Asn Val Thr Glu Gly Asn
                350                 355                 360

Phe His Gln Leu Val Ala Leu Leu His Cys Arg Ser Leu His Lys
                365                 370                 375

Asp Tyr Gly Ala Ala Leu Arg Gly Leu Cys Glu Asp Ala Leu Glu
                380                 385                 390

Gly Leu Leu Phe Leu Leu Leu Phe Ser Leu Leu Ser Ala Gly Ala
                395                 400                 405

Leu Ala Thr Ala Leu Cys Ser Leu Pro Arg Ala Trp Ala Leu Phe
                410                 415                 420

Pro Pro Arg Asn Pro Ser Ala Leu Cys Ser Gly Ser Arg Leu Ser
                425                 430                 435

Glu Pro Leu Leu Pro Ala Gly Leu Glu Pro Gly Ser Pro Leu Arg
                440                 445                 450

Ser Phe Pro Gly Cys Arg Arg Arg Pro His
                455                 460


<210> SEQ ID NO 24
<211> LENGTH: 218
<212> TYPE: PRT
<213> ORGANISM: Homo sapiens
<220> FEATURE:
<221> NAME/KEY: misc_feature
<223> OTHER INFORMATION: Incyte ID No: 7510517CD1

<400> SEQUENCE: 24

Met Ser Thr Pro Gly Val Asn Ser Ser Ala Ser Leu Ser Pro Asp
  1               5                  10                  15
```

-continued

```
Arg Leu Asn Ser Pro Val Thr Ile Pro Ala Val Met Phe Ile Phe
                20                  25                  30

Gly Val Val Gly Asn Leu Val Ala Ile Val Val Leu Cys Lys Ser
                35                  40                  45

Arg Lys Glu Gln Lys Glu Thr Thr Phe Tyr Thr Leu Val Cys Gly
                50                  55                  60

Leu Ala Val Thr Asp Leu Leu Gly Thr Leu Leu Val Ser Pro Val
                65                  70                  75

Thr Ile Ala Thr Tyr Met Lys Gly Gln Trp Pro Gly Gly Gln Pro
                80                  85                  90

Leu Cys Glu Tyr Ser Thr Phe Ile Leu Leu Phe Phe Ser Leu Ser
                95                  100                 105

Gly Leu Ser Ile Ile Cys Ala Met Ser Val Glu Arg Tyr Leu Ala
                110                 115                 120

Ile Asn His Ala Tyr Phe Tyr Ser His Tyr Val Asp Lys Arg Leu
                125                 130                 135

Ala Gly Leu Thr Leu Phe Ala Val Tyr Ala Ser Asn Val Leu Phe
                140                 145                 150

Cys Ala Leu Pro Asn Met Gly Leu Gly Ser Ser Arg Leu Gln Tyr
                155                 160                 165

Pro Asp Thr Trp Cys Phe Ile Asp Trp Thr Thr Asn Val Thr Ala
                170                 175                 180

His Ala Ala Tyr Ser Tyr Ser Trp Cys Glu Tyr Ser Ser Thr Ser
                185                 190                 195

Tyr Ile Ser Gln Val Trp Ser Glu Lys Ser Val Lys Ile Gln Ile
                200                 205                 210

Cys Arg Pro Ser Glu Leu Leu Leu
                215
```

```
<210> SEQ ID NO 25
<211> LENGTH: 297
<212> TYPE: PRT
<213> ORGANISM: Homo sapiens
<220> FEATURE:
<221> NAME/KEY: misc_feature
<223> OTHER INFORMATION: Incyte ID No: 7511014CD1

<400> SEQUENCE: 25

Met Ser Met Asn Asn Ser Lys Gln Leu Val Ser Pro Ala Ala Ala
  1               5                  10                  15

Leu Leu Ser Asn Thr Thr Cys Gln Thr Glu Asn Arg Leu Ser Val
                20                  25                  30

Phe Phe Ser Val Ile Phe Met Thr Val Gly Ile Leu Ser Asn Ser
                35                  40                  45

Leu Ala Ile Ala Ile Leu Met Lys Ala Tyr Gln Arg Phe Arg Gln
                50                  55                  60

Lys Ser Lys Ala Ser Phe Leu Leu Leu Ala Ser Gly Leu Val Ile
                65                  70                  75

Thr Asp Phe Phe Gly His Leu Ile Asn Gly Ala Ile Ala Val Phe
                80                  85                  90

Val Tyr Ala Ser Asp Lys Glu Trp Ile Arg Phe Asp Gln Ser Asn
                95                  100                 105

Val Leu Cys Ser Ile Phe Gly Ile Cys Met Val Phe Ser Gly Leu
                110                 115                 120

Cys Pro Leu Leu Leu Gly Ser Val Met Ala Ile Glu Arg Cys Ile
```

-continued

```
                125                 130                 135

Gly Val Thr Lys Pro Ile Phe His Ser Thr Lys Ile Thr Ser Lys
                140                 145                 150

His Val Lys Met Met Leu Ser Gly Val Cys Leu Phe Ala Val Phe
                155                 160                 165

Ile Ala Leu Leu Pro Ile Leu Gly His Arg Asp Tyr Lys Ile Gln
                170                 175                 180

Ala Ser Arg Thr Trp Cys Phe Tyr Asn Thr Glu Asp Ile Lys Asp
                185                 190                 195

Trp Glu Asp Arg Phe Tyr Leu Leu Leu Phe Ser Phe Leu Gly Leu
                200                 205                 210

Leu Ala Leu Gly Val Ser Leu Leu Cys Asn Ala Ile Thr Gly Ile
                215                 220                 225

Thr Leu Leu Arg Val Lys Phe Lys Ser Gln Gln His Arg Gln Gly
                230                 235                 240

Arg Ser His His Leu Glu Met Val Ile Gln Leu Leu Ala Ile Met
                245                 250                 255

Cys Val Ser Cys Ile Cys Trp Ser Pro Phe Leu Gly Tyr Arg Ile
                260                 265                 270

Ile Leu Asn Gly Lys Glu Lys Tyr Lys Val Tyr Glu Glu Gln Ser
                275                 280                 285

Asp Phe Leu His Arg Leu Gln Trp Pro Thr Leu Glu
                290                 295


<210> SEQ ID NO 26
<211> LENGTH: 917
<212> TYPE: PRT
<213> ORGANISM: Homo sapiens
<220> FEATURE:
<221> NAME/KEY: misc_feature
<223> OTHER INFORMATION: Incyte ID No: 7506687CD1

<400> SEQUENCE: 26

Met Pro Ala Leu Gly Pro Ala Leu Leu Gln Ala Leu Trp Ala Gly
  1               5                  10                  15

Trp Val Leu Thr Leu Gln Pro Leu Pro Pro Thr Ala Phe Thr Pro
                 20                  25                  30

Asn Gly Thr Tyr Leu Gln His Leu Ala Arg Asp Pro Thr Ser Gly
                 35                  40                  45

Thr Leu Tyr Leu Gly Ala Thr Asn Phe Leu Phe Gln Leu Ser Pro
                 50                  55                  60

Gly Leu Gln Leu Glu Ala Thr Val Ser Thr Gly Pro Val Leu Asp
                 65                  70                  75

Ser Arg Asp Cys Leu Pro Pro Val Met Pro Asp Glu Cys Pro Gln
                 80                  85                  90

Ala Gln Pro Thr Asn Asn Pro Asn Gln Leu Leu Leu Val Ser Pro
                 95                 100                 105

Gly Ala Leu Val Val Cys Gly Ser Val His Gln Gly Val Cys Glu
                110                 115                 120

Gln Arg Arg Leu Gly Gln Leu Glu Gln Leu Leu Leu Arg Pro Glu
                125                 130                 135

Arg Pro Gly Asp Thr Gln Tyr Val Ala Ala Asn Asp Pro Ala Val
                140                 145                 150

Ser Thr Val Gly Leu Val Ala Gln Gly Leu Ala Gly Glu Pro Leu
                155                 160                 165
```

-continued

```
Leu Phe Val Gly Arg Gly Tyr Thr Ser Arg Gly Val Gly Gly Gly
                170                 175                 180

Ile Pro Pro Ile Thr Thr Arg Ala Leu Trp Pro Pro Asp Pro Gln
                185                 190                 195

Ala Ala Phe Ser Tyr Glu Glu Thr Ala Lys Leu Ala Val Gly Arg
                200                 205                 210

Leu Ser Glu Tyr Ser His His Phe Val Ser Ala Phe Ala Arg Gly
                215                 220                 225

Ala Ser Ala Tyr Phe Leu Phe Leu Arg Arg Asp Leu Gln Ala Gln
                230                 235                 240

Ser Arg Ala Phe Arg Ala Tyr Val Ser Arg Val Cys Leu Arg Asp
                245                 250                 255

Gln His Tyr Tyr Ser Tyr Val Glu Leu Pro Leu Ala Cys Glu Gly
                260                 265                 270

Gly Arg Tyr Gly Leu Ile Gln Ala Ala Ala Val Ala Thr Ser Arg
                275                 280                 285

Glu Val Ala His Gly Glu Val Leu Phe Ala Ala Phe Ser Ser Ala
                290                 295                 300

Ala Pro Pro Thr Val Gly Arg Pro Pro Ser Ala Ala Ala Gly Ala
                305                 310                 315

Ser Gly Ala Ser Ala Leu Cys Ala Phe Pro Leu Asp Glu Val Asp
                320                 325                 330

Arg Leu Ala Asn Arg Thr Arg Asp Ala Cys Tyr Thr Arg Glu Gly
                335                 340                 345

Arg Ala Glu Asp Gly Thr Glu Val Ala Tyr Ile Glu Tyr Asp Val
                350                 355                 360

Asn Ser Asp Cys Ala Gln Leu Pro Val Asp Thr Leu Asp Ala Tyr
                365                 370                 375

Pro Cys Gly Ser Asp His Thr Pro Ser Pro Met Ala Ser Arg Val
                380                 385                 390

Pro Leu Glu Ala Thr Pro Ile Leu Glu Trp Pro Gly Ile Gln Leu
                395                 400                 405

Thr Ala Val Ala Val Thr Met Glu Asp Gly His Thr Ile Ala Phe
                410                 415                 420

Leu Gly Asp Ser Gln Gly Gln Leu His Arg Val Tyr Leu Gly Pro
                425                 430                 435

Gly Ser Asp Gly His Pro Tyr Ser Thr Gln Ser Ile Gln Gln Gly
                440                 445                 450

Ser Ala Val Ser Arg Asp Leu Thr Phe Asp Gly Thr Phe Glu His
                455                 460                 465

Leu Tyr Val Met Thr Gln Ser Thr Leu Leu Lys Val Pro Val Ala
                470                 475                 480

Ser Cys Ala Gln His Leu Asp Cys Ala Ser Cys Leu Ala His Arg
                485                 490                 495

Asp Pro Tyr Cys Gly Trp Cys Val Leu Leu Gly Arg Cys Ser Arg
                500                 505                 510

Arg Ser Glu Cys Ser Arg Gly Gln Gly Pro Glu Gln Trp Leu Trp
                515                 520                 525

Ser Phe Gln Pro Glu Leu Gly Cys Leu Gln Val Ala Ala Met Ser
                530                 535                 540

Pro Ala Asn Ile Ser Arg Glu Glu Thr Arg Glu Val Phe Leu Ser
                545                 550                 555

Val Pro Asp Leu Pro Pro Leu Trp Pro Gly Glu Ser Tyr Ser Cys
```

-continued

```
                560                 565                 570

His Phe Gly Glu His Gln Ser Pro Ala Leu Leu Thr Gly Ser Gly
                575                 580                 585

Val Met Cys Pro Ser Pro Asp Pro Ser Glu Ala Pro Val Leu Pro
                590                 595                 600

Arg Gly Ala Asp Tyr Val Ser Val Ser Val Glu Leu Arg Phe Gly
                605                 610                 615

Ala Val Val Ile Ala Lys Thr Ser Leu Ser Phe Tyr Asp Cys Val
                620                 625                 630

Ala Val Thr Glu Leu Arg Pro Ser Ala Gln Cys Gln Ala Cys Val
                635                 640                 645

Ser Ser Arg Trp Gly Cys Asn Trp Cys Val Trp Gln His Leu Cys
                650                 655                 660

Thr His Lys Ala Ser Cys Asp Ala Gly Pro Met Val Ala Ser His
                665                 670                 675

Gln Ser Pro Leu Val Ser Pro Asp Pro Pro Ala Arg Gly Gly Pro
                680                 685                 690

Ser Pro Ser Pro Pro Thr Ala Pro Lys Ala Leu Ala Thr Pro Ala
                695                 700                 705

Pro Asp Thr Leu Pro Val Glu Pro Gly Ala Pro Ser Thr Ala Thr
                710                 715                 720

Ala Ser Asp Ile Ser Pro Gly Ala Ser Pro Ser Leu Leu Ser Pro
                725                 730                 735

Trp Gly Pro Trp Ala Gly Ser Gly Ser Ile Ser Ser Pro Gly Ser
                740                 745                 750

Thr Gly Ser Pro Leu His Glu Glu Pro Ser Pro Pro Ser Pro Gln
                755                 760                 765

Asn Gly Pro Gly Thr Ala Val Pro Ala Pro Thr Asp Phe Arg Pro
                770                 775                 780

Ser Ala Thr Pro Glu Asp Leu Leu Ala Ser Pro Leu Ser Pro Ser
                785                 790                 795

Glu Val Ala Ala Val Pro Pro Ala Asp Pro Gly Pro Glu Ala Leu
                800                 805                 810

His Pro Thr Val Pro Leu Asp Leu Pro Pro Ala Thr Val Pro Ala
                815                 820                 825

Thr Thr Phe Pro Gly Ala Met Gly Ser Val Lys Pro Ala Leu Asp
                830                 835                 840

Trp Leu Thr Arg Glu Gly Gly Glu Leu Pro Glu Ala Asp Glu Trp
                845                 850                 855

Thr Gly Gly Asp Ala Pro Ala Phe Ser Thr Ser Thr Leu Leu Ser
                860                 865                 870

Gly Arg Gly Asp Leu Gly Gly Lys Leu Leu Pro Leu Cys Gly Glu
                875                 880                 885

Arg Ser Gly Leu His Val Asp Ala Gly Pro Cys Gly Ala Gly Asn
                890                 895                 900

Pro Ala Ala Arg Gln Glu Pro Ala Pro Phe Pro Gly Trp Pro Arg
                905                 910                 915

Arg Gln
```

<210> SEQ ID NO 27
<211> LENGTH: 224
<212> TYPE: PRT
<213> ORGANISM: Homo sapiens
<220> FEATURE:

<221> NAME/KEY: misc_feature
<223> OTHER INFORMATION: Incyte ID No: 7510621CD1

<400> SEQUENCE: 27

```
Met Ala Val Glu Gly Gly Met Lys Cys Val Lys Phe Leu Leu Tyr
  1               5                  10                  15

Val Leu Leu Leu Ala Phe Cys Ala Cys Ala Val Gly Leu Ile Ala
                 20                  25                  30

Val Gly Val Gly Ala Gln Leu Val Leu Ser Gln Thr Ile Ile Gln
                 35                  40                  45

Gly Ala Thr Pro Gly Ser Leu Leu Pro Val Val Ile Ile Ala Val
                 50                  55                  60

Gly Val Phe Leu Phe Leu Val Ala Phe Val Gly Cys Cys Gly Ala
                 65                  70                  75

Cys Lys Glu Asn Tyr Cys Leu Met Ile Thr Phe Ala Ile Ala Gly
                 80                  85                  90

Tyr Val Phe Arg Asp Lys Val Met Ser Glu Phe Asn Asn Asn Phe
                 95                 100                 105

Arg Gln Gln Met Glu Asn Tyr Pro Lys Asn Asn His Thr Ala Ser
                110                 115                 120

Ile Leu Asp Arg Met Gln Ala Asp Phe Lys Cys Cys Gly Ala Ala
                125                 130                 135

Asn Tyr Thr Asp Trp Glu Lys Ile Pro Ser Met Ser Lys Asn Arg
                140                 145                 150

Val Pro Asp Ser Cys Cys Ile Asn Val Thr Val Gly Cys Gly Ile
                155                 160                 165

Asn Phe Asn Glu Lys Ala Ile His Lys Glu Gly Cys Val Glu Lys
                170                 175                 180

Ile Gly Gly Trp Leu Arg Lys Asn Val Leu Val Val Ala Ala Ala
                185                 190                 195

Ala Leu Gly Ile Ala Phe Val Glu Val Leu Gly Ile Val Phe Ala
                200                 205                 210

Cys Cys Leu Val Lys Ser Ile Arg Ser Gly Tyr Glu Val Met
                215                 220
```

<210> SEQ ID NO 28
<211> LENGTH: 114
<212> TYPE: PRT
<213> ORGANISM: Homo sapiens
<220> FEATURE:
<221> NAME/KEY: misc_feature
<223> OTHER INFORMATION: Incyte ID No: 7505533CD1

<400> SEQUENCE: 28

```
Met Glu Ala Val Val Phe Val Phe Ser Leu Leu Asp Cys Cys Ala
  1               5                  10                  15

Leu Ile Phe Leu Ser Val Tyr Phe Ile Ile Thr Leu Ser Asp Leu
                 20                  25                  30

Glu Cys Asp Tyr Ile Asn Ala Arg Ser Cys Cys Ser Lys Leu Asn
                 35                  40                  45

Lys Trp Val Ile Pro Glu Leu Ile Gly His Thr Ile Val Thr Val
                 50                  55                  60

Leu Leu Leu Met Ser Leu His Trp Phe Ile Phe Leu Leu Asn Leu
                 65                  70                  75

Pro Val Ala Thr Trp Asn Ile Tyr Arg Asn Thr Gln Ser Arg Ala
                 80                  85                  90
```

-continued

```
Ala Glu Val Thr His Glu Arg Ser His Asp Gln Ala Trp Phe Pro
                95                  100                 105

Leu Ala Leu Leu Leu His Val Ser Leu
                110


<210> SEQ ID NO 29
<211> LENGTH: 181
<212> TYPE: PRT
<213> ORGANISM: Homo sapiens
<220> FEATURE:
<221> NAME/KEY: misc_feature
<223> OTHER INFORMATION: Incyte ID No: 7511220CD1

<400> SEQUENCE: 29

Met Gly Ser Cys Ser Gly Arg Cys Ala Leu Val Val Leu Cys Ala
  1               5                  10                  15

Phe Gln Leu Val Ala Ala Leu Glu Arg Gln Val Phe Asp Phe Leu
                 20                  25                  30

Gly Tyr Gln Trp Ala Pro Ile Leu Ala Asn Phe Val His Ile Ile
                 35                  40                  45

Ile Val Ile Leu Gly Leu Phe Gly Thr Ile Gln Tyr Arg Leu Arg
                 50                  55                  60

Tyr Val Met Val Tyr Thr Leu Trp Ala Ala Val Trp Val Thr Trp
                 65                  70                  75

Asn Val Phe Ile Ile Cys Phe Tyr Leu Glu Val Gly Gly Leu Leu
                 80                  85                  90

Gln Asp Ser Glu Leu Leu Thr Phe Ser Leu Ser Arg His Arg Ser
                 95                 100                 105

Trp Trp Arg Glu Arg Trp Pro Gly Cys Leu His Glu Glu Val Pro
                110                 115                 120

Ala Val Gly Leu Gly Ala Pro His Gly Gln Ala Leu Val Ser Gly
                125                 130                 135

Ala Gly Cys Ala Leu Glu Pro Ser Tyr Val Glu Ala Leu His Ser
                140                 145                 150

Gly Leu Gln Ile Leu Ile Ala Leu Leu Gly Phe Val Cys Gly Cys
                155                 160                 165

Gln Val Val Ser Val Phe Thr Glu Glu Glu Asp Ser Cys Leu Arg
                170                 175                 180

Lys


<210> SEQ ID NO 30
<211> LENGTH: 1753
<212> TYPE: PRT
<213> ORGANISM: Homo sapiens
<220> FEATURE:
<221> NAME/KEY: misc_feature
<223> OTHER INFORMATION: Incyte ID No: 7510967CD1

<400> SEQUENCE: 30

Met Ser Val Leu Ile Ser Gln Ser Val Ile Asn Tyr Val Glu Glu
  1               5                  10                  15

Glu Asn Ile Pro Ala Leu Lys Ala Leu Leu Glu Lys Cys Lys Asp
                 20                  25                  30

Val Asp Glu Arg Asn Glu Cys Gly Gln Thr Pro Leu Met Ile Ala
                 35                  40                  45

Ala Glu Gln Gly Asn Leu Glu Ile Val Lys Glu Leu Ile Lys Asn
                 50                  55                  60

Gly Ala Asn Cys Asn Leu Glu Asp Leu Asp Asn Trp Thr Ala Leu
```

-continued

```
                65                  70                  75

Ile Ser Ala Ser Lys Glu Gly His Val His Ile Val Glu Glu Leu
                80                  85                  90

Leu Lys Cys Gly Val Asn Leu Glu His Arg Asp Met Gly Gly Trp
                95                  100                 105

Thr Ala Leu Met Trp Ala Cys Tyr Lys Gly Arg Thr Asp Val Val
                110                 115                 120

Glu Leu Leu Leu Ser His Gly Ala Asn Pro Ser Val Thr Gly Leu
                125                 130                 135

Gln Tyr Ser Val Tyr Pro Ile Ile Trp Ala Ala Gly Arg Gly His
                140                 145                 150

Ala Asp Ile Val His Leu Leu Leu Gln Asn Gly Ala Lys Val Asn
                155                 160                 165

Cys Ser Asp Lys Tyr Gly Thr Thr Pro Leu Val Trp Ala Ala Arg
                170                 175                 180

Lys Gly His Leu Glu Cys Val Lys His Leu Leu Ala Met Gly Ala
                185                 190                 195

Asp Val Asp Gln Glu Gly Ala Asn Ser Met Thr Ala Leu Ile Val
                200                 205                 210

Ala Val Lys Gly Gly Tyr Thr Gln Ser Val Lys Glu Ile Leu Lys
                215                 220                 225

Arg Asn Pro Asn Val Asn Leu Thr Asp Lys Asp Gly Asn Thr Ala
                230                 235                 240

Leu Met Ile Ala Ser Lys Glu Gly His Thr Glu Ile Val Gln Asp
                245                 250                 255

Leu Leu Asp Ala Gly Thr Tyr Val Asn Ile Pro Asp Arg Ser Gly
                260                 265                 270

Asp Thr Val Leu Ile Gly Ala Val Arg Gly Gly His Val Glu Ile
                275                 280                 285

Val Arg Ala Leu Leu Gln Lys Tyr Ala Asp Ile Asp Ile Arg Gly
                290                 295                 300

Gln Asp Asn Lys Thr Ala Leu Tyr Trp Ala Val Glu Lys Gly Asn
                305                 310                 315

Ala Thr Met Val Arg Asp Ile Leu Gln Cys Asn Pro Asp Thr Glu
                320                 325                 330

Ile Cys Thr Lys Asp Gly Glu Thr Pro Leu Ile Lys Ala Thr Lys
                335                 340                 345

Met Arg Asn Ile Glu Val Val Glu Leu Leu Leu Asp Lys Gly Ala
                350                 355                 360

Lys Val Ser Ala Val Asp Lys Lys Gly Asp Thr Pro Leu His Ile
                365                 370                 375

Ala Ile Arg Gly Arg Ser Arg Lys Leu Ala Glu Leu Leu Leu Arg
                380                 385                 390

Asn Pro Lys Asp Gly Arg Leu Leu Tyr Arg Pro Asn Lys Ala Gly
                395                 400                 405

Glu Thr Pro Tyr Asn Ile Asp Cys Ser His Gln Lys Ser Ile Leu
                410                 415                 420

Thr Gln Ile Phe Gly Ala Arg His Leu Ser Pro Thr Glu Thr Asp
                425                 430                 435

Gly Asp Met Leu Gly Tyr Asp Leu Tyr Ser Ser Ala Leu Ala Asp
                440                 445                 450

Ile Leu Ser Glu Pro Thr Met Gln Pro Pro Ile Cys Val Gly Leu
                455                 460                 465
```

-continued

Tyr Ala Gln Trp Gly Ser Gly Lys Ser Phe Leu Leu Lys Lys Leu
470 475 480

Glu Asp Glu Met Lys Thr Phe Ala Gly Gln Gln Ile Glu Pro Leu
485 490 495

Phe Gln Phe Ser Trp Leu Ile Val Phe Leu Thr Leu Leu Leu Cys
500 505 510

Gly Gly Leu Gly Leu Leu Phe Ala Phe Thr Val His Pro Asn Leu
515 520 525

Gly Ile Ala Val Ser Leu Ser Phe Leu Ala Leu Leu Tyr Ile Phe
530 535 540

Phe Ile Val Ile Tyr Phe Gly Gly Arg Arg Glu Gly Glu Ser Trp
545 550 555

Asn Trp Ala Trp Val Leu Ser Thr Arg Leu Ala Arg His Ile Gly
560 565 570

Tyr Leu Glu Leu Leu Leu Lys Leu Met Phe Val Asn Pro Pro Glu
575 580 585

Leu Pro Glu Gln Thr Thr Lys Ala Leu Pro Val Arg Phe Leu Phe
590 595 600

Thr Asp Tyr Asn Arg Leu Ser Ser Val Gly Gly Glu Thr Ser Leu
605 610 615

Ala Glu Met Ile Ala Thr Leu Ser Asp Ala Cys Glu Arg Glu Phe
620 625 630

Gly Phe Leu Ala Thr Arg Leu Phe Arg Val Phe Lys Thr Glu Asp
635 640 645

Thr Gln Gly Lys Lys Lys Trp Lys Lys Thr Cys Cys Leu Pro Ser
650 655 660

Phe Val Ile Phe Leu Phe Ile Ile Gly Cys Ile Ile Ser Gly Ile
665 670 675

Thr Leu Leu Ala Ile Phe Arg Val Asp Pro Lys His Leu Thr Val
680 685 690

Asn Ala Val Leu Ile Ser Ile Ala Ser Val Val Gly Leu Ala Phe
695 700 705

Val Leu Asn Cys Arg Thr Trp Trp Gln Val Leu Asp Ser Leu Leu
710 715 720

Asn Ser Gln Arg Lys Arg Leu His Asn Ala Ala Ser Lys Leu His
725 730 735

Lys Leu Lys Ser Glu Gly Phe Met Lys Val Leu Lys Cys Glu Val
740 745 750

Glu Leu Met Ala Arg Met Ala Lys Thr Ile Asp Ser Phe Thr Gln
755 760 765

Asn Gln Thr Arg Leu Val Val Ile Ile Asp Gly Leu Asp Ala Cys
770 775 780

Glu Gln Asp Lys Val Leu Gln Met Leu Asp Thr Val Arg Val Leu
785 790 795

Phe Ser Lys Gly Pro Phe Ile Ala Ile Phe Ala Ser Asp Pro His
800 805 810

Ile Ile Ile Lys Ala Ile Asn Gln Asn Leu Asn Ser Val Leu Arg
815 820 825

Asp Ser Asn Ile Asn Gly His Asp Tyr Met Arg Asn Ile Val His
830 835 840

Leu Pro Val Phe Leu Asn Ser Arg Gly Leu Ser Asn Ala Arg Lys
845 850 855

-continued

```
Phe Leu Val Thr Ser Ala Thr Asn Gly Asp Val Pro Cys Ser Asp
                860                 865                 870

Thr Thr Gly Ile Gln Glu Asp Ala Asp Arg Arg Val Ser Gln Asn
                875                 880                 885

Ser Leu Gly Glu Met Thr Lys Leu Gly Ser Lys Thr Ala Leu Asn
                890                 895                 900

Arg Arg Asp Thr Tyr Arg Arg Arg Gln Met Gln Arg Thr Ile Thr
                905                 910                 915

Arg Gln Met Ser Phe Asp Leu Thr Lys Leu Leu Val Thr Glu Asp
                920                 925                 930

Trp Phe Ser Asp Ile Ser Pro Gln Thr Met Arg Arg Leu Leu Asn
                935                 940                 945

Ile Val Ser Val Thr Gly Arg Leu Leu Arg Ala Asn Gln Ile Ser
                950                 955                 960

Phe Asn Trp Asp Arg Leu Ala Ser Trp Ile Asn Leu Thr Glu Gln
                965                 970                 975

Trp Pro Tyr Arg Thr Ser Trp Leu Ile Leu Tyr Leu Glu Glu Thr
                980                 985                 990

Glu Gly Ile Pro Asp Gln Met Thr Leu Lys Thr Ile Tyr Glu Arg
                995                 1000                1005

Ile Ser Lys Asn Ile Pro Thr Thr Lys Asp Val Glu Pro Leu Leu
                1010                1015                1020

Glu Ile Asp Gly Asp Ile Arg Asn Phe Glu Val Phe Leu Ser Ser
                1025                1030                1035

Arg Thr Pro Val Leu Val Ala Arg Asp Val Lys Val Phe Leu Pro
                1040                1045                1050

Cys Thr Val Asn Leu Asp Pro Lys Leu Arg Glu Ile Ile Ala Asp
                1055                1060                1065

Val Arg Ala Ala Arg Glu Gln Ile Ser Ile Gly Gly Leu Ala Tyr
                1070                1075                1080

Pro Pro Leu Pro Leu His Glu Gly Pro Pro Arg Ala Pro Ser Gly
                1085                1090                1095

Tyr Ser Gln Pro Pro Ser Val Cys Ser Ser Thr Ser Phe Asn Gly
                1100                1105                1110

Pro Phe Ala Gly Gly Val Val Ser Pro Gln Pro His Ser Ser Tyr
                1115                1120                1125

Tyr Ser Gly Met Thr Gly Pro Gln His Pro Phe Tyr Asn Arg Pro
                1130                1135                1140

Phe Phe Ala Pro Tyr Leu Tyr Thr Pro Arg Tyr Tyr Pro Gly Gly
                1145                1150                1155

Ser Gln His Leu Ile Ser Arg Pro Ser Val Lys Thr Ser Leu Pro
                1160                1165                1170

Arg Asp Gln Asn Asn Gly Leu Gly Ser Gly Pro Ala Pro Gly Pro
                1175                1180                1185

Val Val Leu Leu Asn Ser Leu Asn Val Asp Ala Val Cys Glu Lys
                1190                1195                1200

Leu Lys Gln Ile Glu Gly Leu Asp Gln Ser Met Leu Pro Gln Tyr
                1205                1210                1215

Cys Thr Thr Ile Lys Lys Ala Asn Ile Asn Gly Arg Val Leu Ala
                1220                1225                1230

Gln Cys Asn Ile Asp Glu Leu Lys Lys Glu Met Asn Met Asn Phe
                1235                1240                1245

Gly Asp Trp His Leu Phe Arg Ser Thr Val Leu Glu Met Arg Asn
```

-continued

```
                1250                1255                1260

Ala Glu Ser His Val Val Pro Glu Asp Pro Arg Phe Leu Ser Glu
                1265                1270                1275

Ser Ser Ser Gly Pro Ala Pro His Gly Glu Pro Ala Arg Arg Ala
                1280                1285                1290

Ser His Asn Glu Leu Pro His Thr Glu Leu Ser Ser Gln Thr Pro
                1295                1300                1305

Tyr Thr Leu Asn Phe Ser Phe Glu Glu Leu Asn Thr Leu Gly Leu
                1310                1315                1320

Asp Glu Gly Ala Pro Arg His Ser Asn Leu Ser Trp Gln Ser Gln
                1325                1330                1335

Thr Arg Arg Thr Pro Ser Leu Ser Ser Leu Asn Ser Gln Asp Ser
                1340                1345                1350

Ser Ile Glu Ile Ser Lys Leu Thr Asp Lys Val Gln Ala Glu Tyr
                1355                1360                1365

Arg Asp Ala Tyr Arg Glu Tyr Ile Ala Gln Met Ser Gln Leu Glu
                1370                1375                1380

Gly Gly Pro Gly Ser Thr Thr Ile Ser Gly Arg Ser Ser Pro His
                1385                1390                1395

Ser Thr Tyr Tyr Met Gly Gln Ser Ser Ser Gly Gly Ser Ile His
                1400                1405                1410

Ser Asn Leu Glu Gln Glu Lys Gly Lys Asp Ser Glu Pro Lys Pro
                1415                1420                1425

Asp Asp Gly Arg Lys Ser Phe Leu Met Lys Arg Gly Asp Val Ile
                1430                1435                1440

Asp Tyr Ser Ser Ser Gly Val Ser Thr Asn Asp Ala Ser Pro Leu
                1445                1450                1455

Asp Pro Ile Thr Glu Glu Asp Glu Lys Ser Asp Gln Ser Gly Ser
                1460                1465                1470

Lys Leu Leu Pro Gly Lys Lys Ser Ser Glu Arg Ser Ser Leu Phe
                1475                1480                1485

Gln Thr Asp Leu Lys Leu Lys Gly Ser Gly Leu Arg Tyr Gln Lys
                1490                1495                1500

Leu Pro Ser Asp Glu Asp Glu Ser Gly Thr Glu Glu Ser Asp Asn
                1505                1510                1515

Thr Pro Leu Leu Lys Asp Asp Lys Asp Arg Lys Ala Glu Gly Lys
                1520                1525                1530

Val Glu Arg Val Pro Lys Ser Pro Glu His Ser Ala Glu Pro Ile
                1535                1540                1545

Arg Thr Phe Ile Lys Ala Lys Glu Tyr Leu Ser Asp Ala Leu Leu
                1550                1555                1560

Asp Lys Lys Asp Ser Ser Asp Ser Gly Val Arg Ser Ser Glu Ser
                1565                1570                1575

Ser Pro Asn His Ser Leu His Asn Glu Val Ala Asp Asp Ser Gln
                1580                1585                1590

Leu Glu Lys Ala Asn Leu Ile Glu Leu Glu Asp Asp Ser His Ser
                1595                1600                1605

Gly Lys Arg Gly Ile Pro His Ser Leu Ser Gly Leu Gln Asp Pro
                1610                1615                1620

Ile Ile Ala Arg Met Ser Ile Cys Ser Glu Asp Lys Lys Ser Pro
                1625                1630                1635

Ser Glu Cys Ser Leu Ile Ala Ser Ser Pro Glu Glu Asn Trp Pro
                1640                1645                1650
```

-continued

```
Ala Cys Gln Lys Ala Tyr Asn Leu Asn Arg Thr Pro Ser Thr Val
               1655                1660                1665

Thr Leu Asn Asn Asn Ser Ala Pro Ala Asn Arg Ala Asn Gln Asn
               1670                1675                1680

Phe Asp Glu Met Glu Gly Ile Arg Glu Thr Ser Gln Val Ile Leu
               1685                1690                1695

Arg Pro Ser Ser Ser Pro Asn Pro Thr Thr Ile Gln Asn Glu Asn
               1700                1705                1710

Leu Lys Ser Met Thr His Lys Arg Ser Gln Arg Ser Ser Tyr Thr
               1715                1720                1725

Arg Leu Ser Lys Asp Pro Pro Glu Leu His Ala Ala Ala Ser Ser
               1730                1735                1740

Glu Ser Thr Gly Phe Gly Glu Glu Arg Glu Ser Ile Leu
               1745                1750


<210> SEQ ID NO 31
<211> LENGTH: 786
<212> TYPE: PRT
<213> ORGANISM: Homo sapiens
<220> FEATURE:
<221> NAME/KEY: misc_feature
<223> OTHER INFORMATION: Incyte ID No: 7511298CD1

<400> SEQUENCE: 31

Met Gly Gly Arg Val Phe Leu Ala Phe Cys Val Trp Leu Thr Leu
  1               5                  10                  15

Pro Gly Ala Glu Thr Gln Asp Ser Arg Gly Cys Ala Arg Trp Cys
                 20                  25                  30

Pro Gln Asn Ser Ser Cys Val Asn Ala Thr Ala Cys Arg Cys Asn
                 35                  40                  45

Pro Gly Phe Ser Ser Phe Ser Glu Ile Ile Thr Thr Pro Thr Glu
                 50                  55                  60

Thr Cys Asp Asp Ile Asn Glu Cys Ala Thr Pro Ser Lys Val Ser
                 65                  70                  75

Cys Gly Lys Phe Ser Asp Cys Trp Asn Thr Glu Gly Ser Tyr Asp
                 80                  85                  90

Cys Val Cys Ser Pro Gly Tyr Glu Pro Val Ser Gly Ala Lys Thr
                 95                 100                 105

Phe Lys Asn Glu Ser Glu Asn Thr Cys Gln Asp Val Asp Glu Cys
                110                 115                 120

Gln Gln Asn Pro Arg Leu Cys Lys Ser Tyr Gly Thr Cys Val Asn
                125                 130                 135

Thr Leu Gly Ser Tyr Thr Cys Gln Cys Leu Pro Gly Phe Lys Phe
                140                 145                 150

Ile Pro Glu Asp Pro Lys Val Cys Thr Asp Val Asp Glu Cys Ser
                155                 160                 165

Ser Gly Gln His Gln Cys Asp Ser Ser Thr Val Cys Phe Asn Thr
                170                 175                 180

Val Gly Ser Tyr Ser Cys Arg Cys Arg Pro Gly Trp Lys Pro Arg
                185                 190                 195

His Gly Ile Pro Asn Asn Gln Lys Asp Thr Val Cys Glu Asp Met
                200                 205                 210

Thr Phe Ser Thr Trp Thr Pro Pro Pro Gly Val His Ser Gln Thr
                215                 220                 225

Leu Ser Arg Phe Phe Asp Lys Val Gln Asp Leu Gly Arg Asp Ser
```

-continued

```
                230                 235                 240

Lys Thr Ser Ser Ala Glu Val Thr Ile Gln Asn Val Ile Lys Leu
                245                 250                 255

Val Asp Glu Leu Met Glu Ala Pro Gly Asp Val Glu Ala Leu Ala
                260                 265                 270

Pro Pro Val Arg His Leu Ile Ala Thr Gln Leu Leu Ser Asn Leu
                275                 280                 285

Glu Asp Ile Met Arg Ile Leu Ala Lys Ser Leu Pro Lys Gly Pro
                290                 295                 300

Phe Thr Tyr Ile Ser Pro Ser Asn Thr Glu Leu Thr Leu Met Ile
                305                 310                 315

Gln Glu Arg Gly Asp Lys Asn Val Thr Met Gly Gln Ser Ser Ala
                320                 325                 330

Arg Met Lys Leu Asn Trp Ala Val Ala Ala Gly Ala Glu Asp Pro
                335                 340                 345

Gly Pro Ala Val Ala Gly Ile Leu Ser Ile Gln Asn Met Thr Thr
                350                 355                 360

Leu Leu Ala Asn Ala Ser Leu Asn Leu His Ser Lys Lys Gln Ala
                365                 370                 375

Glu Leu Glu Glu Ile Tyr Glu Ser Ser Ile Arg Gly Val Gln Leu
                380                 385                 390

Arg Arg Leu Ser Ala Val Asn Ser Ile Phe Leu Ser His Asn Asn
                395                 400                 405

Thr Lys Glu Leu Asn Ser Pro Ile Leu Phe Ala Phe Ser His Leu
                410                 415                 420

Glu Ser Ser Asp Gly Glu Ala Gly Arg Asp Pro Pro Ala Lys Asp
                425                 430                 435

Val Met Pro Gly Pro Arg Gln Glu Leu Leu Cys Ala Phe Trp Lys
                440                 445                 450

Ser Asp Ser Asp Arg Gly Gly His Trp Ala Thr Glu Gly Cys Gln
                455                 460                 465

Val Leu Gly Ser Lys Asn Gly Ser Thr Thr Cys Gln Cys Ser His
                470                 475                 480

Leu Ser Ser Phe Ala Ile Leu Met Ala His Tyr Asp Val Glu Asp
                485                 490                 495

Trp Lys Leu Thr Leu Ile Thr Arg Val Gly Leu Ala Leu Ser Leu
                500                 505                 510

Phe Cys Leu Leu Leu Cys Ile Leu Thr Phe Leu Leu Val Arg Pro
                515                 520                 525

Ile Gln Gly Ser Arg Thr Thr Ile His Leu His Leu Cys Ile Cys
                530                 535                 540

Leu Phe Val Gly Ser Thr Ile Phe Leu Ala Gly Ile Glu Asn Glu
                545                 550                 555

Gly Gly Gln Val Gly Leu Arg Cys Arg Leu Val Ala Gly Leu Leu
                560                 565                 570

His Tyr Cys Phe Leu Ala Ala Phe Cys Trp Met Ser Leu Glu Gly
                575                 580                 585

Leu Glu Leu Tyr Phe Leu Val Val Arg Val Phe Gln Gly Gln Gly
                590                 595                 600

Leu Ser Thr Arg Trp Leu Cys Leu Ile Gly Tyr Gly Val Pro Leu
                605                 610                 615

Leu Ile Val Gly Val Ser Ala Ala Ile Tyr Ser Lys Gly Tyr Gly
                620                 625                 630
```

-continued

```
Arg Pro Arg Tyr Cys Trp Leu Asp Phe Glu Gln Gly Phe Leu Trp
                635                 640                 645

Ser Phe Leu Gly Pro Val Thr Phe Ile Ile Leu Cys Asn Ala Val
                650                 655                 660

Ile Phe Val Thr Thr Val Trp Lys Leu Thr Gln Lys Phe Ser Glu
                665                 670                 675

Ile Asn Pro Asp Met Lys Lys Leu Lys Lys Ala Arg Ala Leu Thr
                680                 685                 690

Ile Thr Ala Ile Ala Gln Leu Phe Leu Leu Gly Cys Thr Trp Val
                695                 700                 705

Phe Gly Leu Phe Ile Phe Asp Asp Arg Ser Leu Val Leu Thr Tyr
                710                 715                 720

Val Phe Thr Ile Leu Asn Cys Leu Gln Gly Ala Phe Leu Tyr Leu
                725                 730                 735

Leu His Cys Leu Leu Asn Lys Lys Val Arg Glu Glu Tyr Arg Lys
                740                 745                 750

Trp Ala Cys Leu Val Ala Gly Gly Ser Lys Tyr Ser Glu Phe Thr
                755                 760                 765

Ser Thr Thr Ser Gly Thr Gly His Asn Gln Thr Arg Ala Leu Arg
                770                 775                 780

Ala Ser Glu Ser Gly Ile
                785


<210> SEQ ID NO 32
<211> LENGTH: 1328
<212> TYPE: PRT
<213> ORGANISM: Homo sapiens
<220> FEATURE:
<221> NAME/KEY: misc_feature
<223> OTHER INFORMATION: Incyte ID No: 7510937CD1

<400> SEQUENCE: 32

Met Glu Phe Tyr Glu Ser Ala Tyr Phe Ile Val Leu Ile Pro Ser
  1               5                  10                  15

Ile Val Ile Thr Val Ile Phe Leu Phe Phe Trp Leu Phe Met Lys
                 20                  25                  30

Glu Thr Leu Tyr Asp Glu Val Leu Ala Lys Gln Lys Arg Glu Gln
                 35                  40                  45

Lys Leu Ile Pro Thr Lys Thr Asp Lys Lys Lys Ala Glu Lys Lys
                 50                  55                  60

Lys Asn Lys Lys Lys Glu Ile Gln Asn Gly Asn Leu His Glu Ser
                 65                  70                  75

Asp Ser Glu Ser Val Pro Arg Asp Phe Lys Leu Ser Asp Ala Leu
                 80                  85                  90

Ala Val Glu Asp Asp Gln Val Ala Pro Val Pro Leu Asn Val Val
                 95                 100                 105

Glu Thr Ser Ser Ser Val Arg Glu Arg Lys Lys Lys Glu Lys Lys
                110                 115                 120

Gln Lys Pro Val Leu Glu Glu Gln Val Ile Lys Glu Ser Asp Ala
                125                 130                 135

Ser Lys Ile Pro Gly Lys Lys Val Glu Pro Val Pro Val Thr Lys
                140                 145                 150

Gln Pro Thr Pro Pro Ser Glu Ala Ala Ala Ser Lys Lys Lys Pro
                155                 160                 165

Gly Gln Lys Lys Ser Lys Asn Gly Ser Asp Asp Gln Asp Lys Lys
```

-continued

```
                170                 175                 180

Val Glu Thr Leu Met Val Pro Ser Lys Arg Gln Glu Ala Leu Pro
                185                 190                 195

Leu His Gln Glu Thr Lys Gln Glu Ser Gly Ser Gly Lys Lys Lys
                200                 205                 210

Ala Ser Ser Lys Lys Gln Lys Thr Glu Asn Val Phe Val Asp Glu
                215                 220                 225

Pro Leu Ile His Ala Thr Thr Tyr Ile Pro Leu Met Asp Asn Ala
                230                 235                 240

Asp Ser Ser Pro Val Val Asp Lys Arg Glu Val Ile Asp Leu Leu
                245                 250                 255

Lys Pro Asp Gln Val Glu Gly Ile Gln Lys Ser Gly Thr Lys Lys
                260                 265                 270

Leu Lys Thr Glu Thr Asp Lys Glu Asn Ala Glu Val Lys Phe Lys
                275                 280                 285

Asp Phe Leu Leu Ser Leu Lys Thr Met Met Phe Ser Glu Asp Glu
                290                 295                 300

Ala Leu Cys Val Val Asp Leu Leu Lys Glu Lys Ser Gly Val Ile
                305                 310                 315

Gln Asp Ala Leu Lys Lys Ser Ser Lys Gly Glu Leu Thr Thr Leu
                320                 325                 330

Ile His Gln Leu Gln Glu Lys Asp Lys Leu Leu Ala Ala Val Lys
                335                 340                 345

Glu Asp Ala Ala Ala Thr Lys Asp Arg Cys Lys Gln Leu Thr Gln
                350                 355                 360

Glu Met Met Thr Glu Lys Glu Arg Ser Asn Val Val Ile Thr Arg
                365                 370                 375

Met Lys Asp Arg Ile Gly Thr Leu Glu Lys Glu His Asn Val Phe
                380                 385                 390

Gln Asn Lys Ile His Val Ser Tyr Gln Glu Thr Gln Gln Met Gln
                395                 400                 405

Met Lys Phe Gln Gln Val Arg Glu Gln Met Glu Ala Glu Ile Ala
                410                 415                 420

His Leu Lys Gln Glu Asn Gly Ile Leu Arg Asp Ala Val Ser Asn
                425                 430                 435

Thr Thr Asn Gln Leu Glu Ser Lys Gln Ser Ala Glu Leu Asn Lys
                440                 445                 450

Leu Arg Gln Asp Tyr Ala Arg Leu Val Asn Glu Leu Thr Glu Lys
                455                 460                 465

Thr Gly Lys Leu Gln Gln Glu Glu Val Gln Lys Lys Asn Ala Glu
                470                 475                 480

Gln Ala Ala Thr Gln Leu Lys Val Gln Leu Gln Glu Ala Glu Arg
                485                 490                 495

Arg Trp Glu Glu Val Gln Ser Tyr Ile Arg Lys Arg Thr Ala Glu
                500                 505                 510

His Glu Ala Ala Gln Gln Asp Leu Gln Ser Lys Phe Val Ala Lys
                515                 520                 525

Glu Asn Glu Val Gln Ser Leu His Ser Lys Leu Thr Asp Thr Leu
                530                 535                 540

Val Ser Lys Gln Gln Leu Glu Gln Arg Leu Met Gln Leu Met Glu
                545                 550                 555

Ser Glu Gln Lys Arg Val Asn Lys Glu Glu Ser Leu Gln Met Gln
                560                 565                 570
```

-continued

Val Gln Asp Ile Leu Glu Gln Asn Glu Ala Leu Lys Ala Gln Ile
575 580 585

Gln Gln Phe His Ser Gln Ile Ala Ala Gln Thr Ser Ala Ser Val
590 595 600

Leu Ala Glu Glu Leu His Lys Val Ile Ala Glu Lys Asp Lys Gln
605 610 615

Ile Lys Gln Thr Glu Asp Ser Leu Ala Ser Glu Arg Asp Arg Leu
620 625 630

Thr Ser Lys Glu Glu Glu Leu Lys Asp Ile Gln Asn Met Asn Phe
635 640 645

Leu Leu Lys Ala Glu Val Gln Lys Leu Gln Ala Leu Ala Asn Glu
650 655 660

Gln Ala Ala Ala Ala His Glu Leu Glu Lys Met Gln Gln Ser Val
665 670 675

Tyr Val Lys Asp Asp Lys Ile Arg Leu Leu Glu Glu Gln Leu Gln
680 685 690

His Glu Ile Ser Asn Lys Met Glu Glu Phe Lys Ile Leu Asn Asp
695 700 705

Gln Asn Lys Ala Leu Lys Ser Glu Val Gln Lys Leu Gln Thr Leu
710 715 720

Val Ser Glu Gln Pro Asn Lys Asp Val Val Glu Gln Met Glu Lys
725 730 735

Cys Ile Gln Glu Lys Asp Glu Lys Leu Lys Thr Val Glu Glu Leu
740 745 750

Leu Glu Thr Gly Leu Ile Gln Val Ala Thr Lys Glu Glu Glu Leu
755 760 765

Asn Ala Ile Arg Thr Glu Asn Ser Ser Leu Thr Lys Glu Val Gln
770 775 780

Asp Leu Lys Ala Lys Gln Asn Asp Gln Val Ser Phe Ala Ser Leu
785 790 795

Val Glu Glu Leu Lys Lys Val Ile His Glu Lys Asp Gly Lys Ile
800 805 810

Lys Ser Val Glu Glu Leu Leu Glu Ala Glu Leu Leu Lys Val Ala
815 820 825

Asn Lys Glu Lys Thr Val Gln Asp Leu Lys Gln Glu Ile Lys Ala
830 835 840

Leu Lys Glu Glu Ile Gly Asn Val Gln Leu Glu Lys Ala Gln Gln
845 850 855

Leu Ser Ile Thr Ser Lys Val Gln Glu Leu Gln Asn Leu Leu Lys
860 865 870

Gly Lys Glu Glu Gln Met Asn Thr Met Lys Ala Val Leu Glu Glu
875 880 885

Lys Glu Lys Asp Leu Ala Asn Thr Gly Lys Trp Leu Gln Asp Leu
890 895 900

Gln Glu Glu Asn Glu Ser Leu Lys Ala His Val Gln Glu Val Ala
905 910 915

Gln His Asn Leu Lys Glu Ala Ser Ser Ala Ser Gln Phe Glu Glu
920 925 930

Leu Glu Ile Val Leu Lys Glu Lys Glu Asn Glu Leu Lys Arg Leu
935 940 945

Glu Ala Met Leu Lys Glu Arg Glu Ser Asp Leu Ser Ser Lys Thr
950 955 960

-continued

```
Gln Leu Leu Gln Asp Val Gln Asp Glu Asn Lys Leu Phe Lys Ser
                965                 970                 975

Gln Ile Glu Gln Leu Lys Gln Gln Asn Tyr Gln Gln Ala Ser Ser
                980                 985                 990

Phe Pro Pro His Glu Glu Leu Leu Lys Val Ile Ser Glu Arg Glu
                995                 1000                1005

Lys Glu Ile Ser Gly Leu Trp Asn Glu Leu Asp Ser Leu Lys Asp
                1010                1015                1020

Ala Val Glu His Gln Arg Lys Lys Asn Asn Glu Arg Gln Gln Gln
                1025                1030                1035

Val Glu Ala Val Glu Leu Glu Ala Lys Glu Val Leu Lys Lys Leu
                1040                1045                1050

Phe Pro Lys Val Ser Val Pro Ser Asn Leu Ser Tyr Gly Glu Trp
                1055                1060                1065

Leu His Gly Phe Glu Lys Lys Ala Lys Glu Cys Met Ala Gly Thr
                1070                1075                1080

Ser Gly Ser Glu Glu Val Lys Val Leu Glu His Lys Leu Lys Glu
                1085                1090                1095

Ala Asp Glu Met His Thr Leu Leu Gln Leu Glu Cys Glu Lys Tyr
                1100                1105                1110

Lys Ser Val Leu Ala Glu Thr Glu Gly Ile Leu Gln Lys Leu Gln
                1115                1120                1125

Arg Ser Val Glu Gln Glu Glu Asn Lys Trp Lys Val Lys Val Asp
                1130                1135                1140

Glu Ser His Lys Thr Ile Lys Gln Met Gln Ser Ser Phe Thr Ser
                1145                1150                1155

Ser Glu Gln Glu Leu Glu Arg Leu Arg Ser Glu Asn Lys Asp Ile
                1160                1165                1170

Glu Asn Leu Arg Arg Glu Arg Glu His Leu Glu Met Glu Leu Glu
                1175                1180                1185

Lys Ala Glu Met Glu Arg Ser Thr Tyr Val Thr Glu Val Arg Glu
                1190                1195                1200

Leu Lys Asp Leu Leu Thr Glu Leu Gln Lys Lys Leu Asp Asp Ser
                1205                1210                1215

Tyr Ser Glu Ala Val Arg Gln Asn Glu Glu Leu Asn Leu Leu Lys
                1220                1225                1230

Ala Gln Leu Asn Glu Thr Leu Thr Lys Leu Arg Thr Glu Gln Asn
                1235                1240                1245

Glu Arg Gln Lys Val Ala Gly Asp Leu His Lys Ala Gln Gln Ser
                1250                1255                1260

Leu Glu Leu Ile Gln Ser Lys Ile Val Lys Ala Ala Gly Asp Thr
                1265                1270                1275

Thr Val Ile Glu Asn Ser Asp Val Ser Pro Glu Thr Glu Ser Ser
                1280                1285                1290

Glu Lys Glu Thr Met Ser Val Ser Leu Asn Gln Thr Val Thr Gln
                1295                1300                1305

Leu Gln Gln Leu Leu Gln Ala Val Asn Gln Gln Leu Thr Lys Glu
                1310                1315                1320

Lys Glu His Tyr Gln Val Leu Glu
                1325
```

<210> SEQ ID NO 33
<211> LENGTH: 355
<212> TYPE: PRT

-continued

<213> ORGANISM: Homo sapiens
<220> FEATURE:
<221> NAME/KEY: misc_feature
<223> OTHER INFORMATION: Incyte ID No: 7511852CD1

<400> SEQUENCE: 33

```
Met Ala Pro Val Ala Val Trp Ala Ala Leu Ala Val Gly Leu Glu
  1               5                  10                  15

Leu Trp Ala Ala Ala His Ala Leu Pro Ala Gln Val Ala Phe Thr
                 20                  25                  30

Pro Tyr Ala Pro Glu Pro Gly Ser Thr Cys Arg Leu Arg Glu Tyr
                 35                  40                  45

Tyr Asp Gln Thr Ala Gln Met Cys Cys Ser Lys Cys Ser Pro Gly
                 50                  55                  60

Gln His Ala Lys Val Phe Cys Thr Lys Thr Ser Asp Thr Val Cys
                 65                  70                  75

Asp Ser Cys Glu Asp Ser Thr Tyr Thr Gln Leu Trp Asn Trp Val
                 80                  85                  90

Pro Glu Cys Leu Ser Cys Gly Ser Arg Cys Ser Ser Asp Gln Val
                 95                 100                 105

Glu Thr Gln Ala Cys Thr Arg Glu Gln Asn Arg Ile Cys Thr Cys
                110                 115                 120

Arg Pro Gly Trp Tyr Cys Ala Leu Ser Lys Gln Glu Gly Cys Arg
                125                 130                 135

Leu Cys Ala Pro Leu Arg Lys Cys Arg Pro Gly Phe Gly Val Ala
                140                 145                 150

Arg Pro Gly Thr Glu Thr Ser Asp Val Val Cys Lys Pro Cys Ala
                155                 160                 165

Pro Gly Thr Phe Ser Asn Thr Thr Ser Ser Thr Asp Ile Cys Arg
                170                 175                 180

Pro His Gln Ile Cys Asn Val Val Ala Ile Pro Gly Asn Ala Ser
                185                 190                 195

Met Asp Ala Val Cys Thr Ser Thr Ser Pro Thr Arg Ser Met Ala
                200                 205                 210

Pro Gly Ala Val His Leu Pro Gln Pro Val Ser Thr Arg Ser Gln
                215                 220                 225

His Thr Gln Pro Thr Pro Glu Pro Ser Thr Ala Pro Ser Thr Ser
                230                 235                 240

Phe Leu Leu Pro Met Gly Pro Ser Pro Pro Ala Glu Gly Ser Thr
                245                 250                 255

Gly Asp Phe Ala Leu Pro Val Asp Ser Ser Pro Gly Gly His Gly
                260                 265                 270

Thr Gln Val Asn Val Thr Cys Ile Val Asn Val Cys Ser Ser Ser
                275                 280                 285

Asp His Ser Ser Gln Cys Ser Ser Gln Ala Ser Ser Thr Met Gly
                290                 295                 300

Asp Thr Asp Ser Ser Pro Ser Glu Ser Pro Lys Asp Glu Gln Val
                305                 310                 315

Pro Phe Ser Lys Glu Glu Cys Ala Phe Arg Ser Gln Leu Glu Thr
                320                 325                 330

Pro Glu Thr Leu Leu Gly Ser Thr Glu Glu Lys Pro Leu Pro Leu
                335                 340                 345

Gly Val Pro Asp Ala Gly Met Lys Pro Ser
                350                 355
```

-continued

<210> SEQ ID NO 34
<211> LENGTH: 295
<212> TYPE: PRT
<213> ORGANISM: Homo sapiens
<220> FEATURE:
<221> NAME/KEY: misc_feature
<223> OTHER INFORMATION: Incyte ID No: 7511077CD1

<400> SEQUENCE: 34

```
Met Gly Ala Cys Leu Gly Ala Cys Ser Leu Leu Ser Cys Ala Ser
  1               5                  10                  15

Cys Leu Cys Gly Ser Ala Pro Cys Ile Leu Cys Ser Cys Cys Pro
                 20                  25                  30

Ala Ser Arg Asn Ser Thr Val Ser Arg Leu Ile Phe Thr Phe Phe
                 35                  40                  45

Leu Phe Leu Gly Val Leu Val Ser Ile Ile Met Leu Ser Pro Gly
                 50                  55                  60

Val Glu Ser Gln Leu Tyr Lys Leu Pro Trp Val Cys Glu Glu Gly
                 65                  70                  75

Ala Gly Ile Pro Thr Val Leu Gln Gly His Ile Asp Cys Gly Ser
                 80                  85                  90

Leu Leu Gly Tyr Arg Ala Val Tyr Arg Met Cys Phe Ala Thr Ala
                 95                 100                 105

Ala Phe Phe Phe Phe Phe Thr Leu Leu Met Leu Cys Val Ser Ser
                110                 115                 120

Ser Arg Asp Pro Arg Ala Ala Ile Gln Asn Gly Phe Trp Phe Phe
                125                 130                 135

Lys Phe Leu Ile Leu Val Gly Leu Thr Val Gly Ala Phe Tyr Ile
                140                 145                 150

Pro Asp Gly Ser Phe Thr Asn Ile Trp Phe Tyr Phe Gly Val Val
                155                 160                 165

Gly Ser Phe Leu Phe Ile Leu Ile Gln Leu Val Leu Leu Ile Asp
                170                 175                 180

Phe Ala His Ser Trp Asn Gln Arg Trp Leu Gly Lys Ala Glu Glu
                185                 190                 195

Cys Asp Ser Arg Ala Trp Tyr Ala Gly Leu Phe Phe Phe Thr Leu
                200                 205                 210

Leu Phe Tyr Leu Leu Ser Ile Ala Ala Val Ala Leu Met Phe Met
                215                 220                 225

Tyr Tyr Thr Glu Pro Ser Gly Cys His Glu Gly Lys Val Phe Ile
                230                 235                 240

Ser Leu Asn Leu Thr Phe Cys Val Cys Val Ser Ile Ala Ala Val
                245                 250                 255

Leu Pro Lys Val Gln Ser Ala Leu Leu Arg Pro Pro Ala Gly Glu
                260                 265                 270

Gln Pro Asp Ala Asp Arg Gly Val Pro Thr Tyr Ala Arg Arg His
                275                 280                 285

Thr Ala Ala Ala Ala Ala Gly Gly Ser Leu
                290                 295
```

<210> SEQ ID NO 35
<211> LENGTH: 203
<212> TYPE: PRT
<213> ORGANISM: Homo sapiens
<220> FEATURE:
<221> NAME/KEY: misc_feature
<223> OTHER INFORMATION: Incyte ID No: 7511576CD1

-continued

<400> SEQUENCE: 35

```
Met Thr Ser Gln Pro Val Pro Asn Glu Thr Ile Ile Val Leu Pro
  1               5                  10                  15

Ser Asn Val Ile Asn Phe Ser Gln Ala Glu Lys Pro Glu Pro Thr
                 20                  25                  30

Asn Gln Gly Gln Asp Ser Leu Lys Lys His Leu His Ala Glu Ile
                 35                  40                  45

Lys Val Ile Gly Phe Ile Ile Ser Gly Ser Leu Ser Ile Ala Thr
                 50                  55                  60

Glu Lys Arg Leu Thr Lys Leu Leu Val His Ser Ser Leu Val Gly
                 65                  70                  75

Ser Ile Leu Ser Ala Leu Ser Ala Leu Val Gly Phe Ile Ile Leu
                 80                  85                  90

Ser Val Lys Gln Ala Thr Leu Asn Pro Ala Ser Leu Gln Cys Glu
                 95                 100                 105

Leu Asp Lys Asn Asn Ile Pro Thr Arg Ser Tyr Val Ser Tyr Phe
                110                 115                 120

Tyr His Asp Ser Leu Tyr Thr Thr Asp Cys Tyr Thr Ala Lys Ala
                125                 130                 135

Ser Leu Ala Gly Thr Leu Ser Leu Met Leu Ile Cys Thr Leu Leu
                140                 145                 150

Glu Phe Cys Leu Ala Val Leu Thr Ala Val Leu Arg Trp Lys Gln
                155                 160                 165

Ala Tyr Ser Asp Phe Pro Gly Ser Val Leu Phe Leu Pro His Ser
                170                 175                 180

Tyr Ile Gly Asn Ser Gly Met Ser Ser Lys Met Thr His Asp Cys
                185                 190                 195

Gly Tyr Glu Glu Leu Leu Thr Ser
                200
```

<210> SEQ ID NO 36
<211> LENGTH: 156
<212> TYPE: PRT
<213> ORGANISM: Homo sapiens
<220> FEATURE:
<221> NAME/KEY: misc_feature
<223> OTHER INFORMATION: Incyte ID No: 7511492CD1

<400> SEQUENCE: 36

```
Met Ala Ser Thr Ser Tyr Asp Tyr Cys Arg Val Pro Met Glu Asp
  1               5                  10                  15

Gly Asp Lys Arg Cys Lys Leu Leu Leu Gly Ile Gly Ile Leu Val
                 20                  25                  30

Leu Leu Ile Ile Val Ile Leu Gly Val Pro Leu Ile Ile Phe Thr
                 35                  40                  45

Ile Lys Ala Asn Ser Glu Ala Cys Arg Asp Gly Leu Arg Ala Val
                 50                  55                  60

Met Glu Cys Arg Asn Val Thr His Leu Leu Gln Gln Glu Leu Thr
                 65                  70                  75

Glu Ala Gln Lys Gly Phe Gln Asp Val Glu Ala Gln Ala Ala Thr
                 80                  85                  90

Cys Asn His Thr Val Lys Arg Lys Pro Gly Leu Lys Arg Glu Asn
                 95                 100                 105

Arg Gly Gln Glu Val Leu Pro Gln Leu Pro Gly Leu Gln Leu Arg
                110                 115                 120
```

-continued

```
Cys Gly Ala Pro Ala Ala Asp Cys Ala Ala Gly Pro Gln Arg Ser
                125                 130                 135

Ala Ala Val Arg Ser Gln Glu Ala Gly Thr Ser Trp Lys Val Arg
                140                 145                 150

Pro Ala Arg Leu Phe Ala
                155


<210> SEQ ID NO 37
<211> LENGTH: 170
<212> TYPE: PRT
<213> ORGANISM: Homo sapiens
<220> FEATURE:
<221> NAME/KEY: misc_feature
<223> OTHER INFORMATION: Incyte ID No: 7511141CD1

<400> SEQUENCE: 37

Met Arg Pro His Leu Ser Pro Pro Leu Gln Gln Leu Leu Leu Pro
  1               5                  10                  15

Val Leu Leu Ala Cys Ala Ala His Ser Thr Gly Ala Leu Pro Arg
                 20                  25                  30

Leu Cys Asp Val Leu Gln Val Leu Trp Glu Glu Gln Asp Gln Cys
                 35                  40                  45

Leu Gln Glu Leu Ser Arg Glu Gln Thr Gly Asp Leu Gly Thr Glu
                 50                  55                  60

Gln Pro Val Pro Gly Cys Glu Gly Met Trp Asp Asn Ile Ser Cys
                 65                  70                  75

Trp Pro Ser Ser Val Pro Gly Arg Met Val Glu Val Glu Cys Pro
                 80                  85                  90

Arg Phe Leu Arg Met Leu Thr Ser Arg Asn Gly Ser Leu Phe Arg
                 95                 100                 105

Asn Cys Thr Gln Asp Gly Trp Ser Glu Thr Phe Pro Arg Pro Asn
                110                 115                 120

Leu Ala Cys Gly Val Asn Val Asn Asp Ser Ser Asn Glu Lys Arg
                125                 130                 135

Glu Ala Pro Leu His Ser Gln Leu His Pro His Ala Pro Val Arg
                140                 145                 150

Val Leu His Pro Ser Cys Pro Val Gln Leu His Gln Gly Arg Arg
                155                 160                 165

Ala Leu Leu Leu Arg
                170


<210> SEQ ID NO 38
<211> LENGTH: 801
<212> TYPE: PRT
<213> ORGANISM: Homo sapiens
<220> FEATURE:
<221> NAME/KEY: misc_feature
<223> OTHER INFORMATION: Incyte ID No: 7511300CD1

<400> SEQUENCE: 38

Met Gly Gly Arg Val Phe Leu Ala Phe Cys Val Trp Leu Thr Leu
  1               5                  10                  15

Pro Gly Ala Glu Thr Gln Asp Ser Arg Gly Cys Ala Arg Trp Cys
                 20                  25                  30

Pro Gln Asn Ser Ser Cys Val Asn Ala Thr Ala Cys Arg Cys Asn
                 35                  40                  45

Pro Gly Phe Ser Ser Phe Ser Glu Ile Ile Thr Thr Pro Thr Glu
                 50                  55                  60
```

-continued

```
Thr Cys Asp Asp Ile Asn Glu Cys Ala Thr Pro Ser Lys Val Ser
                65                  70                  75

Cys Gly Lys Phe Ser Asp Cys Trp Asn Thr Glu Gly Ser Tyr Asp
                80                  85                  90

Cys Val Cys Ser Pro Gly Tyr Glu Pro Val Ser Gly Ala Lys Thr
                95                  100                 105

Phe Lys Asn Glu Ser Glu Asn Thr Cys Gln Asp Val Asp Glu Cys
                110                 115                 120

Gln Gln Asn Pro Arg Leu Cys Lys Ser Tyr Gly Thr Cys Val Asn
                125                 130                 135

Thr Leu Gly Ser Tyr Thr Cys Gln Cys Leu Pro Gly Phe Lys Phe
                140                 145                 150

Ile Pro Glu Asp Pro Lys Val Cys Thr Asp Val Asn Glu Cys Thr
                155                 160                 165

Ser Gly Gln Asn Pro Cys His Ser Ser Thr His Cys Leu Asn Asn
                170                 175                 180

Val Gly Ser Tyr Gln Cys Arg Cys Arg Pro Gly Trp Gln Pro Ile
                185                 190                 195

Pro Gly Ser Pro Asn Gly Pro Asn Asn Thr Val Cys Glu Asp Val
                200                 205                 210

Asp Glu Cys Ser Ser Gly Gln His Gln Cys Asp Ser Ser Thr Val
                215                 220                 225

Cys Phe Asn Thr Val Gly Ser Tyr Ser Cys Arg Cys Arg Pro Gly
                230                 235                 240

Trp Lys Pro Arg His Gly Ile Pro Asn Asn Gln Lys Asp Thr Val
                245                 250                 255

Cys Glu Asp Met Thr Phe Ser Thr Trp Thr Pro Pro Pro Gly Val
                260                 265                 270

His Ser Gln Thr Leu Ser Arg Phe Phe Asp Lys Val Gln Asp Leu
                275                 280                 285

Gly Arg Asp Ser Lys Thr Ser Ser Ala Glu Val Thr Ile Gln Asn
                290                 295                 300

Val Ile Lys Leu Val Asp Glu Leu Met Glu Ala Pro Gly Asp Val
                305                 310                 315

Glu Ala Leu Ala Pro Pro Val Arg His Leu Ile Ala Thr Gln Leu
                320                 325                 330

Leu Ser Asn Leu Glu Asp Ile Met Arg Ile Leu Ala Lys Ser Leu
                335                 340                 345

Pro Lys Gly Pro Phe Thr Tyr Ile Ser Pro Ser Asn Thr Glu Leu
                350                 355                 360

Thr Leu Met Ile Gln Glu Arg Gly Asp Lys Asn Val Thr Met Gly
                365                 370                 375

Gln Ser Ser Ala Arg Met Lys Leu Asn Trp Ala Val Ala Ala Gly
                380                 385                 390

Ala Glu Asp Pro Gly Pro Ala Val Ala Gly Ile Leu Ser Ile Gln
                395                 400                 405

Asn Met Thr Thr Leu Leu Ala Asn Ala Ser Leu Asn Leu His Ser
                410                 415                 420

Lys Lys Gln Ala Glu Leu Glu Glu Ile Tyr Glu Ser Ser Ile Arg
                425                 430                 435

Gly Val Gln Leu Arg Arg Leu Ser Ala Val Asn Ser Ile Phe Leu
                440                 445                 450
```

-continued

```
Ser His Asn Asn Thr Lys Glu Leu Asn Ser Pro Ile Leu Phe Ala
                455                 460                 465

Phe Ser His Leu Glu Ser Ser Asp Gly Glu Ala Gly Arg Asp Pro
                470                 475                 480

Pro Ala Lys Asp Val Met Pro Gly Pro Arg Gln Glu Leu Leu Cys
                485                 490                 495

Ala Phe Trp Lys Ser Asp Ser Asp Arg Gly Gly His Trp Ala Thr
                500                 505                 510

Glu Gly Cys Gln Val Leu Gly Ser Lys Asn Gly Ser Thr Thr Cys
                515                 520                 525

Gln Cys Ser His Leu Ser Ser Phe Ala Ile Leu Met Ala His Tyr
                530                 535                 540

Asp Val Glu Asp Trp Lys Leu Thr Leu Ile Thr Arg Val Gly Leu
                545                 550                 555

Ala Leu Ser Leu Phe Cys Leu Leu Leu Cys Ile Leu Thr Phe Leu
                560                 565                 570

Leu Val Arg Pro Ile Gln Gly Ser Arg Thr Thr Ile His Leu His
                575                 580                 585

Leu Cys Ile Cys Leu Phe Val Gly Ser Thr Ile Phe Leu Ala Gly
                590                 595                 600

Ile Glu Asn Glu Gly Gly Gln Val Gly Leu Arg Cys Arg Leu Val
                605                 610                 615

Ala Gly Leu Leu His Tyr Cys Phe Leu Ala Ala Phe Cys Trp Met
                620                 625                 630

Ser Leu Glu Gly Leu Glu Leu Tyr Phe Leu Val Val Arg Val Phe
                635                 640                 645

Gln Gly Gln Gly Leu Ser Thr Arg Trp Leu Cys Leu Ile Gly Tyr
                650                 655                 660

Gly Val Pro Leu Leu Ile Val Gly Val Ser Ala Ala Ile Tyr Ser
                665                 670                 675

Lys Gly Tyr Gly Arg Pro Arg Tyr Cys Trp Leu Asp Phe Glu Gln
                680                 685                 690

Gly Phe Leu Trp Ser Phe Leu Gly Pro Val Thr Phe Ile Ile Leu
                695                 700                 705

Cys Asn Ala Val Ile Phe Val Thr Thr Val Trp Lys Leu Thr Gln
                710                 715                 720

Lys Phe Ser Glu Ile Asn Pro Asp Met Lys Lys Leu Lys Lys Ala
                725                 730                 735

Arg Ala Leu Thr Ile Thr Ala Ile Ala Gln Leu Phe Leu Leu Gly
                740                 745                 750

Cys Thr Trp Val Phe Gly Leu Phe Ile Phe Asp Asp Arg Ser Leu
                755                 760                 765

Val Leu Thr Tyr Val Phe Thr Ile Leu Asn Cys Leu Gln Gly Ala
                770                 775                 780

Phe Leu Tyr Leu Leu His Cys Leu Leu Asn Lys Lys Ala Leu Arg
                785                 790                 795

Ala Ser Glu Ser Gly Ile
                800
```

<210> SEQ ID NO 39
<211> LENGTH: 2714
<212> TYPE: DNA
<213> ORGANISM: Homo sapiens
<220> FEATURE:
<221> NAME/KEY: misc_feature -continued
<223> OTHER INFORMATION: Incyte ID No: 3048626CB1

<400> SEQUENCE: 39

```
cgctcctacg cctaaaatga ccaatgtgtg atttcagtgg aataaatggc gtccaaagtc     60
acagatgcta tagtctggta tcaaaagaag attggagcat atgatcaaca aatatgggaa    120
aaatctgttg aacagagaga aatcaagggg ctaaggaata aaccaaagaa aacagcacat    180
gtgaaaccag acctcataga tgttgatctt gtaagagggt ctgcatttgc aaaggcaaag    240
cctgaaagtc cttggacttc tctgaccaga aagggaattg ttcgagttgt atttttcccc    300
tttttcttcc ggtggtggtt acaagtaaca tcaaaggtca tctttttctg gcttcttgtc    360
ctttatcttc ttcaagttgc tgcaatagta ttattctgct ccacttctag cccacacagc    420
atacctctga cagaggtgat tgggccgata tggctgatgc tgctcctggg aactgtgcat    480
tgccagattg tttccacaag aacacccaaa cctcctctaa gtacaggggg taaaagaaga    540
aggaaattaa gaaaagcagc ccatttggaa gtacataggg aaggagatgg ttctagtacc    600
acagataaca cacaagaggg agcagttcag aaccacggta caagcacctc tcacagcgtt    660
ggcactgtct tcagagatct ctggcatgct gctttctttt tatcaggatc aaagaaagca    720
aagaattcaa ttgataaatc aactgaaact gacaatggct atgtatccct tgatgggaag    780
aagactgtta aaagcggtga agatggaata caaaaccatg aacctcagtg tgaaactatt    840
cgaccagaag agacagcctg gaacacagga acactgagga atggtcctag caaagatacc    900
caaaggacaa taacaaatgt ctctgatgaa gtctccagtg aggaaggtcc tgaaacagga    960
tactcattac gtcgtcatgt ggacaggact tctgaaggtg ttcttcggaa tagaaagtca   1020
caccattata agaaacatta ccctaatgag gacgccccta aatcgggtac tagttgcagc   1080
tctcgctgtt caagttccag acaggattct gagagtgcaa ggccagaatc tgaaacagaa   1140
gatgtgttat gggaagactt gttacattgt gcagaatgcc attcatcttg taccagtgag   1200
acagatgtgg aaaatcatca gattaatcca tgtgtgaaaa aagaatatag agatgaccct   1260
tttcatcaga gtcatttgcc ctggctccat agttcccacc caggattaga aaaaataagt   1320
gctatagtat gggaaggtaa tgattgtaag aaagcagaca tgtctgtact tgaaatcagt   1380
ggaatgataa tgaacagagt gaacagccat ataccaggaa taggatacca gatttttgga   1440
aatgcagtct ctctcatact gggtttaact ccatttgttt tccgactttc tcaagctaca   1500
gacttggaac aactcacagc acattctgct tcagaacttt atgtgattgc atttggttct   1560
aatgaagatg tcatagttct ttctatggtt ataataagtt ttgtggttcg cgtgtctctt   1620
gtgtggattt tctttttttt gctctgtgta gcagaaagaa cttataaaca gcgattactt   1680
tttgcaaaac tctttggaca tttaacatct gcaaggaggg ctcgaaaatc tgaggttcct   1740
catttccggt tgaagaaagt acagaatata aaaatgtggc tatctctccg ttcctatctt   1800
aagcgtcgag gtcctcagcg atcagttgat gtaatagttt catctgcttt cttattgact   1860
atctcagttg tatttatctg ttgtgcccag gtgcttcatg tacacgagat cttccttgat   1920
tgtcactaca attgggaatt ggtaatctgg tgcatctcgt taacactttt tctcctaaga   1980
tttgttaccc ttggatcaga aacaagtaaa aaatatagta atacctcaat attacttact   2040
gaacagataa acctctactt gaaaatggag aaaaaaccta acaaaaagga ggaactgaca   2100
ctagtgaata atgttttaaa actggctact aaactgctaa aggagttgga cagtcctttt   2160
agattatatg ggcttacaat gaatccgctg ctttataaca tcacccaggt tgttatcctg   2220
tcagctgttt ctggtgttat cagtgacttg cttggattta atttaaagct atggaagatt   2280
```

-continued

```
aagtcatgac aattcaaaga aaagaagatg tagcctcttt tccagaataa gagtactgac   2340

taagctgcct gaaagcttgt cactgattcc ttgcttcaag agtctcagct aaggagttga   2400

agtggttaca tcagactggc ctgtggaaat cctaagatta atttaccggg tcaccttttt   2460

ttacaattaa tttagtcctt aaaattttaa ttttaaagct ttgaggtcct aaggtggtgg   2520

aaaggttgtt gaaccgggaa tcggattgct tgggaccctg gaaatgggcc agaaataatg   2580

ggcgaagtac caaatgttga aattagaggc catggctagg accggtttct ccaccaagcc   2640

ggaaacttgg catactttgg ggaaaatccg tgaacttgga aagtggcatg gagctgggca   2700

tgaccctaga agat                                                     2714
```

<210> SEQ ID NO 40
<211> LENGTH: 2858
<212> TYPE: DNA
<213> ORGANISM: Homo sapiens
<220> FEATURE:
<221> NAME/KEY: misc_feature
<223> OTHER INFORMATION: Incyte ID No: 2684425CB1

<400> SEQUENCE: 40

```
gaacgccgcg gggtcagggc gtgcagtctg ggacgcggga tgcttggcgc tctacctcgc     60

cgcccctgag ccttcccgtc cgcctcgcca cgcgcccgga cggcctgggg ttgctgcccg    120

tcagtctcga aaggtgtttt tggggaaaaa aatcacaatc tggacgtgag aaaggacatg    180

aggagactaa agacctggga ttttgtcaat cagaatgaaa ccaatgttga aagacttttc    240

aaatctattg ttggtggtac tctgtgacta tgttcttgga gaagctgaat atcttctctt    300

gagagagcca ggccatgtag cactaagcaa cgacacagtg tatgtggatt tccagtattt    360

tgatggtgct aatgggacac tgaggaatgt atctgtcctg ctgttggagg ccaacaccaa    420

tcagactgta actaccaagt acctcctgac caaccagtcc cagggaacac taaagtttga    480

gtgcttctat ttcaaggagg ctggtgacta ctggttcaca atgactccag aagcaacaga    540

caacagcact ccattcccct ggtgggagaa aagtgccttt ctgaaggtgg aatggcctgt    600

ctttcacgtt gacttgaata ggagtgccaa ggcagcagaa ggcaccttcc aagtgggcct    660

atttaccagt caaccactgt gcccgtttcc tgtggacaag cccaacattg tagtggatgt    720

catcttcacc aacagtcttc ctgaggcaag aagaaattca agacagccgc tggaaataag    780

aaccagcaaa aggacagaac ttgctcaagg tcagtgggtt gagtttggct gtgcaccctt    840

ggggccagaa gcctatgtca ccgtggtgct gaagctgctt gggcgagact cagtcattac    900

ctccacagga cccattgacc tggcccagaa atttggatac aaactggtga tggtgccaga    960

actcacatgt gagtccgggg tagaggtgac agtgctgcct ccaccatgca ccttcgtcca   1020

aggagtggtc actgtcttca aggaggcccc cagataccct gggaagagga ccattcactt   1080

ggctgaaaac agcctgcccc tgggagagag gaggacaatt tttaactgta ctttgtttga   1140

catggggaag aataagtact gctttgactt tggcatttca agcagaagcc atttttctgc   1200

aaaggaggag tgcatgctaa ttcagagaaa tacagctttc cagccatcca gcccatctcc   1260

tcttcagccc cagggtccag tgaagtccaa caacatcgtg actgtcactg gtatatcctt   1320

gtgcttgttc atcatcattg ccactgtgct catcacgctg tggaggaggt tcggccggcc   1380

agccaagtgc agcacacctg ctcgacacaa ctccatccac tcccccagct tccggaagaa   1440

ctcggacgag gagaatatct gcgagctgag cgagcagcgc gggagcttct cggatggggg   1500

agacgggccc acggggagtc caggggacac aggcatccct ctgacctaca ggcggagcgg   1560
```

-continued gccggtacct cccgaggatg atgcctctgg cagcgagagc ttccagtcca acgcccagaa 1620
gataatccca cctctgttca gctaccgcct tgcccagcag cagttaaagg agatgaaaaa 1680
gaaaggtctg acggaaacta ccaaagtgta tcacgtgtct cagagtcccc tgacagacac 1740
tgccattgat gcggccccca gcgctccctt agatttggaa agcccggaag aagctgcagc 1800
aaacaagttc cggatcaaat ccccatttcc ggagcagccc gcggtcagtg ccggggaaag 1860
gcctccctcc aggctggatc taaatgtgac tcaggccagt tgtgccataa gccccagcca 1920
gactctgatc cgcaagtcac aggcaaggca cgtgggcagc agagggggcc cgtccgaaag 1980
gagccatgcc aggaacgccc atttcaggag gacagcgagt ttccatgaag ccaggcaggc 2040
ccggccgttc cgagagagga gcatgtccac tctgactcca cggcaggccc ctgcctacag 2100
ctctaggacg cggacctgcg agcaggcaga ggacagattt aggcctcaga gtcgaggtgc 2160
ccacctgttt cctgaaaaac tggagcattt ccaagaggca agtggaaccc gtggtccatt 2220
aaaccctctc cctaaatcct acactttggg gcagcccttg aggaaaccag accttgggga 2280
tcaccaggca ggattagtgg ccggaattga gagaacagag ccccacagag ctcgtcgggg 2340
accgtccccc agtcacaaga gtgtctcaag gaagcagtct tctcccatat cccccaaaga 2400
taactaccag agggtcagtt ctctgagccc ttctcagtgt agaaaagaca agtgtcaaag 2460
cttccccact caccctgagt ttgccttcta tgacaatacg tcgtttggcc tcactgaggc 2520
tgagcagagg atgctggacc tcccaggata ttttgggtca aatgaagagg atgaaaccac 2580
aagtacactt agcgtggaga agctggtgat ctagactgag aatcagcctg agctttacac 2640
agctggggtc tgctactcgc gttttgtaga cttttgtgta actatttgta ccgtaggaca 2700
gaatgtgagg aggaagtaac acacagagga ggatgtgtgt gtatgcatgt gtttgaattc 2760
acaaggaaga aattatttat cttgagcttt ttcctttgtt attcaatttc tattgattta 2820
ttagtaataa caatgataat aaaatgtaaa tgagcaaa 2858

<210> SEQ ID NO 41
<211> LENGTH: 2445
<212> TYPE: DNA
<213> ORGANISM: Homo sapiens
<220> FEATURE:
<221> NAME/KEY: misc_feature
<223> OTHER INFORMATION: Incyte ID No: 7505960CB1

<400> SEQUENCE: 41
ctgagccatg gggggaaagc agcgggacga ggatgacgag gcctacggga agccagtcaa 60
atacgacccc tcctttcgag gccccatcaa gaacagaagc tgcacagatg tcatctgctg 120
cgtcctcttc ctgctcttca ttctaggtta catcgtggtg gggattgtgg cctggttgta 180
tggagacccc cggcaagtcc tctaccccag gaactctact ggggcctact gtggcatggg 240
ggagaacaaa gataagccgt atctcctgta cttcaacatc ttcagctgca tcctgtccag 300
caacatcatc tcagttgctg agaacggcct acagtgcccc acaccccagg tgtgtgtgtc 360
ctcctgcccg gaggacccat ggactgtggg aaaaaacgag ttctcacaga ctgttgggga 420
agtcttctat acaaaaaaca ggaacttttg tctgccaggg gtaccctgga atatgacggt 480
gatcacaagc ctgcaacagg aactctgccc cagtttcctc ctcccctctg ctccagctct 540
gggacgctgc tttccatgga ccaacattac tccaccggcg ctcccaggga tcaccaatga 600
caccaccata cagcagggga tcagcggtct tattgacagc ctcaatgccc gagacatcag 660
tgttaagatc tttgaagatt ttgcccagtc ctggtattgg attcttgttg ccctgggggt 720

-continued

```
ggctctggtc ttgagcctac tgtttatctt gcttctgcgc ctggtggctg ggcccctggt    780

gctggtgctg atcctgggag tgctgggcgt gctggcatac ggcatctact actgctggga    840

ggagtaccga gtgctgcggg acaagggcgc ctccatctcc cagctgggtt tcaccaccaa    900

cctcagtgcc taccagagcg tgcaggagac ctggctggcc gccctgatcg tgttggcggt    960

gcttgaagcc atcctgctgc tggtgctcat cttcctgcgg cagcggattc gtattgccat   1020

cgccctcctg aaggaggcca gcaaggctgt gggacagatg atgtctacca tgttctaccc   1080

actggtcacc tttgtcctcc tcctcatctg cattgcctac tgggccatga ctgctctgta   1140

cctggctaca tcggggcaac cccagtatgt gctctgggca tccaacatca gctcccccgg   1200

ctgtgagaaa gtgccaataa atacatcatg caaccccacg gcccaccttg tgaactcctc   1260

gtgcccaggg ctgatgtgcg tcttccaggg ctactcatcc aaaggcctaa tccctacctt   1320

ccccttaatc tctgccttca tccgcacact ccgttaccac actgggtcat tggcatttgg   1380

agccctcatc ctgacccttg tgcagatagc ccgggtcatc ttggagtata ttgaccacaa   1440

gctcagagga gtgcagaacc ctgtagcccg ctgcatcatg tgctgtttca agtgctgcct   1500

ctggtgtctg gaaaaattta tcaagttcct aaaccgcaat gcatacatca tgatcgccat   1560

ctacgggaag aatttctgtg tctcagccaa aaatgcgttc atgctactca tgcgaaacat   1620

tgtcagggtg gtcgtcctgg acaaagtcac agacctgctg ctgttctttg ggaagctgct   1680

ggtggtcgga ggcgtggggg tcctgtcctt ctttttttc tccggtcgca tcccggggct   1740

gggtaaagac tttaagagcc cccacctcaa ctattactgg ctgcccatca tgacctccat   1800

cctgggggcc tatgtcatcg ccagcggctt cttcagcgtt ttcggcatgt gtgtggacac   1860

gctcttcctc tgcttcctgg aagacctgga gcggaacaac ggctccctgg accggcccta   1920

ctacatgtcc aagagccttc taaagattct gggcaagaag aacgaggcgc ccccggacaa   1980

caagaagagg aagaagtgac agctccggcc ctgatccagg actgcacccc acccccaccg   2040

tccagccatc caacctcact tcgccttaca ggtctccatt ttgtggtaaa aaaaggtttt   2100

aggccaggcg ccgtggctca cgcctgtaat ccaacacttt gagaggctga ggcgggcgga   2160

tcacctgagt caggagttcg agaccagcct ggccaacatg gtgaaacctc cgtctctatt   2220

aaaaatacaa aaattagccg agagtggtgg catgcacctg tcatcccagc tactcgggag   2280

gctgaggcag gagaatcgct tgaacccggg aggcagaggt tgcagtgagc cgagatcgcg   2340

ccactgcact ccaacctggg tgacagactc tgtctccaaa acaaaacaaa caaacaaaaa   2400

gattttatta aagatatttt gttaactcag taaaaaaaaa aaaag                   2445
```

<210> SEQ ID NO 42
<211> LENGTH: 1248
<212> TYPE: DNA
<213> ORGANISM: Homo sapiens
<220> FEATURE:
<221> NAME/KEY: misc_feature
<223> OTHER INFORMATION: Incyte ID No: 7507021CB1

<400> SEQUENCE: 42

```
gcctggttac cgggagtggg gcgcccctcc tccttatccc ctcccctctt ccctgtcccc     60

tttcacagct ggctgtagct ggccaaggag ttctcgatta aagaggaagg ggcagtgctc    120

acatttctgg gcaggtgtct ggaaaatatg aggggccacc cctctctgct gctgctatat    180

atggcattaa ccacctgcct ggatacttca cccagtgagg agacagacca agaagtcttc    240

ctgggtcccc cagaggccca gagcttcctg agtagccata cccggattcc aagagccaac    300
```

-continued cactgggacc tggagctgct cacaccaggg aacctggaac gggagtgtct ggaagagagg 360
tgttcctggg aagaggccag ggagtatttt gaggacaaca ctctcacgga gcgcttttgg 420
gagagctaca tctacaatgg caaaggaggg cgtggacgag tggatgtggc cagcctggct 480
gtggggctga caggtggcat cctgctcatt gtcctggccg gcctgggagc cttttggtat 540
ctgcgctggc gacagcaccg aggccagcag ccctgtcccc aagagcctcc ccacctatga 600
gcaggcgctg gcagcctctg gggtacacga cgcacctcca ccccccctaca ccagcctcag 660 gaggcctcac tgaagagctg ctttcgagac ccggctctcc gaaccgtgcc cctgattcat 720
accggattcc ggaagccgct aggcctcata gacgccgaag ctggacttgg agtggggaat 780
ggtgggagta ggggtcatcc ggcccgaggc ctgccctggc acacgcgttt ccgccgcgta 840
tggatataca catgttttcg gcaacgtgtt cccgtgtcct ggcccctcac gggcccccac 900
actctcctga ccgtgagggc actggtcagt tccgcccccg tggtaggcag acgcgcgggg 960
aaattcggac ccaggagccc agccccggct gtgccatctt gtgtatgggc agatatgacc 1020
tgacagcccc ctccagtgcc acagggtacg cacacgcaga gccccgcctg tgcacacgcg 1080
tgtcttcgtg cactccccgt gcggtacagg ggcacttcgt aacccaggga aagggcgggg 1140
ggcatatttg caagcgcgct cggtgcgggc aggctcgcat tgcacccagg gagctggagt 1200
tgagctgttc ccctaaataa aaacccttcg gaaaggagac caaaaaaa 1248

<210> SEQ ID NO 43
<211> LENGTH: 1989
<212> TYPE: DNA
<213> ORGANISM: Homo sapiens
<220> FEATURE:
<221> NAME/KEY: misc_feature
<223> OTHER INFORMATION: Incyte ID No: 7509099CB1

<400> SEQUENCE: 43
gtagacgcac cctctgaaga tggtgactcc ctcctgagaa gctggacccc ttggtaaaag 60
acaaggcctt ctccaagaag aatatgaaag tgttactcag acttatttgt ttcatagctc 120
tactgatttc ttctctggag gctgataaat gcaaggaacg tgaagaaaaa ataattttag 180
tgtcatctgc aaatgaaatt gatgttcgtc cctgtcctct taacccaaat gaacacaaag 240
gcactataac ttggtataaa gatgacagca agacacctgt atctacagaa caagcctcca 300
ggattcatca acacaaagag aaactttggt ttgttcctgc taaggtggag gattcaggac 360
attactattg cgtggattgc aaacctctac ttcttgacaa tatacacttt agtggagtca 420
aagataggct catcgtgatg aatgtggctg aaaagcatag agggaactat acttgtcatg 480
catcctacac atacttgggc aagcaatatc ctattacccg ggtaatagaa tttattactc 540
tagaggaaaa caaacccaca aggcctgtga ttgtgagccc agctaatgag acaatggaag 600
tagacttggg atcccagata caattgatct gtaatgtcac cggccagttg agtgacattg 660
cttactggaa gtggaatggg tcagtaattg atgaagatga cccagtgcta ggggaagact 720
attacagtgt ggaaaatcct gcaaacaaaa gaaggagtac cctcatcaca gtgcttaata 780
tatcggaaat tgaaagtaga ttttataaac atccatttac ctgttttgcc aagaatacac 840
atggtataga tgcagcatat atccagttaa tatatccagt cactaatttc cagaagcaca 900
tgattggtat atgtgtcacg ttgacagtca taattgtgtg ttctgttttc atctataaaa 960
tcttcaagat tgacattgtg ctttggtaca gggattcctg ctatgatttt ctcccaataa 1020
aagcttcaga tggaaagacc tatgacgcat atatactgta tccaaagact gttggggaag 1080
ggtctacctc tgactgtgat atttttgtgt ttaaagtctt gcctgaggtc ttggaaaaac 1140
agtgtggata taagctgttc atttatggaa gggatgacta cgttggggaa gacattgttg 1200
aggtcattaa tgaaaacgta aagaaaagca gaagactgat tatcatttta gtcagagaaa 1260
catcaggctt cagctggctg ggtggttcat ctgaagagca aatagccatg tataatgctc 1320
ttgttcagga tggaattaaa gttgtcctgc ttgagctgga gaaaatccaa gactatgaga 1380
aaatgccaga atcgattaaa ttcattaagc agaaacatgg ggctatccgc tggtcagggg 1440
actttacaca gggaccacag tctgcaaaga caaggttctg gaagaatgtc aggtaccaca 1500
tgccagtcca gcgacggtca ccttcatcta aacaccagtt actgtcacca gccactaagg 1560
agaaactgca aagagaggct cacgtgcctc tcgggtagca tggagaagtt gccaagagtt 1620
ctttaggtgc ctcctgtctt atggcgttgc aggccaggtt atgcctcatg ctgacttgca 1680
gagttcatgg aatgtaacta tatcatcctt tatccctgag gtcacctgga atcagattat 1740
taagggaata agccatgacg tcaatagcag cccagggcac ttcagagtag agggcttggg 1800
aagatctttt aaaaaggcag taggcccggt gtggtggctc acgcctataa tcccagcact 1860
ttgggaggct gaagtgggtg gatcaccaga ggtcaggagt tcgagaccag cccagccaac 1920
atggcaaaac cccatctcta ctaaaaatac aaaaatgagc taggcatggt ggcacacgcc 1980
tgtaatccc 1989

<210> SEQ ID NO 44
<211> LENGTH: 1863
<212> TYPE: DNA
<213> ORGANISM: Homo sapiens
<220> FEATURE:
<221> NAME/KEY: misc_feature
<223> OTHER INFORMATION: Incyte ID No: 7509361CB1

<400> SEQUENCE: 44
tcccaccttc tctcccctcc tctctgcttt aattttctca gaattctctg gactgaggct 60
ccagttctgg cctttggggt tcaagatcac tgggaccagg ccgtgatctc tatgcccgag 120
tctcaaccct caactgtcac cccaaggcac ttgggacgtc ctggacagac cgagtcccgg 180
gaagccccag cactgccgct gccacactgc cctgagccca aatgggggag tgagaggcca 240
tagctgtctg gcatgggcct ctccaccgtg cctgacctgc tgctgccact ggtgctcctg 300
gagctgttgg tgggaatata cccctcaggg gttattggac tggtccctca cctaggggac 360
agggagaaga gagatagtgt gtgtccccaa ggaaaatata tccaccctca aaataattcg 420
atttgctgta ccaagtgcca caaaggaacc tacttgtaca atgactgtcc aggcccgggg 480
caggatacgg actgcaggga gtgtgagagc ggctccttca ccgcttcaga aaaccacctc 540
agacactgcc tcagctgctc caaatgccga aaggaaatgg gtcaggtgga gatctcttct 600
tgcacagtgg accgggacac cgtgtgtggc tgcaggaaga accagtaccg gcattattgg 660
agtgaaaacc ttttccagtg cttcaattgc agcctctgcc tcaatgggac cgtgcacctc 720
tcctgccagg agaaacagaa caccgtgtgc acctgccatg caggtttctt tctaagagaa 780
aacgagtgtg tctcctgtag taactgtaag aaaagcctgg agtgcacgaa gttgtgccta 840
ccccagattg agaatgttaa gggcactgag gactcagaga ggtggcacca ccctatcagg 900
gggctgaccc catccttgcg acagccctcg cctccgaccc catcccccaac cccccttcaga 960 agtgggagga cagcgcccac aagccacaga gcctagacac tgatgacccc gcgacgctgt 1020
acgccgtggt ggagaacgtg cccccgttgc gctggaagga attcgtgcgg cgcctagggc 1080

-continued

```
tgagcgacca cgagatcgat cggctggagc tgcagaacgg gcgctgcctg cgcgaggcgc   1140
aatacagcat gctggcgacc tggaggcggc gcacgccgcg gcgcgaggcc acgctggagc   1200
tgctgggacg cgtgctccgc gacatggacc tgctgggctg cctggaggac atcgaggagg   1260
cgctttgcgg ccccgccgcc ctcccgcccg cgcccagtct tctcagatga ggctgcgccc   1320
ctgcgggcag ctctaaggac cgtcctgcga gatcgccttc caaccccact tttttctgga   1380
aaggaggggt cctgcagggg caagcaggag ctagcagccg cctacttggt gctaacccct   1440
cgatgtacat agcttttctc agctgcctgc gcgccgccga cagtcagcgc tgtgcgcgcg   1500
gagagaggtg cgccgtgggc tcaagagcct gagtgggtgg tttgcgagga tgagggacgc   1560
tatgcctcat gcccgttttg ggtgtcctca ccagcaaggc tgctcggggg cccctggttc   1620
gtccctgagc ctttttcaca gtgcataagc agtttttttt gtttttgttt tgttttgttt   1680
tgtttttaaa tcaatcatgt tacactaata gaaacttggc actcctgtgc cctctgcctg   1740
gacaagcaca tagcaagctg aactgtccta aggcaggggc gagcacggaa caatggggcc   1800
ttcagctgga gctgtggact tttgtacata cactaaaatt ctgaagttaa aaaaaaaaaa   1860
aaa                                                                 1863
```

<210> SEQ ID NO 45
<211> LENGTH: 1734
<212> TYPE: DNA
<213> ORGANISM: Homo sapiens
<220> FEATURE:
<221> NAME/KEY: misc_feature
<223> OTHER INFORMATION: Incyte ID No: 7506815CB1

<400> SEQUENCE: 45

```
ggggcagggg gcagggagag gagggcggcg ggacgtgagc cggaatcgca gcgtgacgag     60
gtggagcctg cggtgggagc cgccgggtcg agctgagtaa ggcggctggg ctcggtgggg    120
gccatggagc tgctaaagct gaaccggagc gtgcagggaa ccggacccgg gccgggggct    180
tccctgtgcc gcccgggggc ccctctcctc aacagcagca gtgtgggcaa cctcagctgc    240
gagccccctc gcattcgcgg agccgggaca cgaggggtgt ctgtgagtgt gtccacgcta    300
agcctcgtgg ccatcgcact ggagcggtac agcgccatct gccgaccact gcaggcacga    360
gtgtggcaga cgcgctccca cgcggctcgc gtgattgtag ccacgtggct gctgtccgga    420
ctactcatgg tgccctaccc cgtgtacact gtcgtgcaac cagtggggcc tcgtgtgctg    480
cagtgcgtgc atcgctggcc cagtgcgcgg gtccgccaga cctggtccgt actgctgctt    540
ctgctcttgt tcttcatccc gggtgtggtt atggccgtgg cctacgggct tatctctcgc    600
gagctctact tagggcttcg ctttgacggc gacagtgaca gcgacagcca aagcagggtc    660
cgaaaccaag gcgggctgcc aggggctgtt caccagaacg ggcgttgccg gcctgagact    720
ggcgcggttg gcgaagacag cgatggctgc tacgtgcaac ttccacgttc ccggcctgcc    780
ctggagctga cggcgctgac ggctcctggg ccgggatccg gctcccggcc cacccaggcc    840
aagctgctgg ctaagaagcg cgtggtgcga atgttgctgg tgatcgttgt gctttttttt    900
ctgtgttggt tgccagttta tagtgccaac acgtggcgcg cctttgatgg cccgggtgca    960
caccgagcac tctcgggtgc tcctatctcc ttcattcact tgctgagcta cgcctcggcc   1020
tgtgtcaacc ccctggtcta ctgcttcatg caccgtcgct ttcgccaggc ctgcctggaa   1080
acttgcgctc gctgctgccc ccggcctcca cgagctcgcc ccagggctct tcccgatgag   1140
gaccctccca ctccctccat tgcttcgctg tccaggctta gctacaccac catcagcaca   1200
```

-continued

```
ctgggccctg gctgaggagt agaggggccg tgggggttga ggcagggcaa atgacatgca   1260

ctgacccttc cagacataga aaacacaaac cacaactgac acaggaaacc aacacccaaa   1320

gcatggacta accccaacgc acaggaaaag gtagcttacc tgacacaaga ggaataagaa   1380

tggagcagta catgggaaag gaggcatgcc tctgatatgg gactgagcct ggcccataga   1440

aacatgacac tgaccttgga gagacacagc gtccctagca gtgaactatt tctacacagt   1500

gggaactctg acaagggctg acctgcctct cacacacata gattaatggc actgattgtt   1560

ttagagacta tggagcctgg cacaggactg actctgggat gctcctagtt tgacctcaca   1620

gtgacccttc ccaatcagca ctgaaaatac catcaggcct aatctcatac ctctgaccaa   1680

caggctgttc tgcactgaaa aggttcttca tccctttcca gttaaggacc gtgg         1734
```

<210> SEQ ID NO 46
<211> LENGTH: 1786
<212> TYPE: DNA
<213> ORGANISM: Homo sapiens
<220> FEATURE:
<221> NAME/KEY: misc_feature
<223> OTHER INFORMATION: Incyte ID No: 7506814CB1

<400> SEQUENCE: 46

```
gtgagccgga atcgcagcgt gacgaggtgg agccgcggtg ggagcccgcc gggtcgagct     60

gagtaaggcg gcgggctcgg cgggggccat ggagctgcta aagctgaacc ggagcgtgca    120

gggaaccgga cccgggccgg gggcttccct gtgccgcccg gggcgcctc tcctcaacag    180

cagcagtgtg ggcaacctca gctgcgagcc ccctcgcatt cgcggagccg ggacacgaga    240

attggagctg gccattagaa tcactcttta cgcagtgatc ttcctgatga gcgttggagg    300

aaatatgctc atcatcgtgg tcctgggact gagccgccgc ctgaggactg tcaccaatgc    360

cttcctcctc tcactggcag tcagcgacct cctgctggct gtggcttgca tgcccttcac    420

cctcctgccc aatctcatgg gcacattcat ctttggcacc atcatctgca aggcggtttc    480

ctacctcatg gggtgtctg tgagtgtgtc cacgctaagc ctcgtggcca tcgcactgga    540

gcggtacagc gccatctgcc gaccactgca ggcacgagtg tggcagacgc gctcccacgc    600

ggctcgcgtg attgtagcca cgtggctgct gtccggacta ctcatggtgc cctaccccgt    660

gtacactgtc gtgcaaccag tggggcctcg tgtgctgcag tgcgtgcatc gctggcccag    720

tgcgcgggtc cgccagacct ggtccgtact gctgcttctg ctcttgttct tcatcccggg    780

tgtggttatg gccgtggcct acgggcttat ctctcgcgag ctctacttag ggcttcgctt    840

tgacggcgac agtgacagcg acagccaaag cagggtccga aaccaaggcg ggctgccagg    900

ggctaagaag cgcgtggtgc gaatgttgct ggtgatcgtt gtgctttttt ttctgtgttg    960

gttgccagtt tatagtgcca acacgtggcg cgcctttgat ggcccgggtg cacaccgagc   1020

actctcgggt gctcctatct ccttcattca cttgctgagc tacgcctcgg cctgtgtcaa   1080

ccccctggtc tactgcttca tgcaccgtcg ctttcgccag gcctgcctgg aaacttgcgc   1140

tcgctgctgc ccccggcctc cacgagctcg ccccagggct cttcccgatg aggaccctcc   1200

cactccctcc attgcttcgc tgtccaggct tagctacacc accatcagca cactgggccc   1260

tggctgagga gtagaggggc cgtgggggtt gaggcagggc aaatgacatg cactgaccct   1320

tccagacata gaaaacacaa accacaactg acacaggaaa ccaacaccca aagcatggac   1380

taaccccaac gcacaggaaa aggtagctta cctgacacaa gaggaataag aatggagcag   1440

tacatgggaa aggaggcatg cctctgatat gggactgagc ctggcccata gaaacatgac   1500
```

-continued

```
actgaccttg gagagacaca gcgtccctag cagtgaacta tttctacaca gtgggaactc   1560

tgacaagggc tgacctgcct ctcacacaca tagattaatg gcactgattg ttttagagac   1620

tatggagcct ggcacaggac tgactctggg atgctcctag tttgacctca cagtgaccct   1680

tcccaatcag cactgaaaat accatcaggc ctaatctcat acctctgacc aacaggctgt   1740

tctgcactga aaaggttctt catccctttc cagttaagga ccgtgg                  1786


<210> SEQ ID NO 47
<211> LENGTH: 2193
<212> TYPE: DNA
<213> ORGANISM: Homo sapiens
<220> FEATURE:
<221> NAME/KEY: misc_feature
<223> OTHER INFORMATION: Incyte ID No: 7506852CB1

<400> SEQUENCE: 47

gtccagagcc cagcccagcc ctaccgcgcg cggcccggag ctctgttccc tggaactttg     60

ggcactgcct ctgggacccc tgccggccag caggcaggat ggtgcttgcc tcgtgcccct    120

tggtgcccgt ctgctgatgt gcccagcctg tgcccgccat gccgccctcc atctcagctt    180

tccaggccgc ctacatcggc atcgaggtgc tcatcgccct ggtctctgtg cccgggaacg    240

tgctggtgat ctgggcggtg aaggtgaacc aggcgctgcg ggatgccacc ttctgcttca    300

tcgtgtcgct ggcggtggct gatgtggccg tgggtgccct ggtcatcccc ctcgccatcc    360

tcatcaacat tgggccacag acctacttcc acacctgcct catggttgcc tgtccggtcc    420

tcatcctcac ccagagctcc atcctggccc tgctggcaat tgctgtggac cgctacctcc    480

gggtcaagat ccctctccgg agaataagcc aatgcatggc aagcactaaa tcttagatcc    540

tgaagactca gccctcgagc aaaagacatg cacctcccca ctcaccgggc cctggaagag    600

gagggtgctc ctcttagagg cccctggagg ccaggcgtgc ctcagagggg cctttcgagg    660

cagctgggag gcagatcctc acactctgcc ctcctctccc ccaggtacaa gatggtggtg    720

accccccgga gggcggcggt ggccatagcc ggctgctgga tcctctcctt cgtggtggga    780

ctgaccccta tgtttggctg gaacaatctg agtgcggtgg agcgggcctg ggcagccaac    840

ggcagcatgg gggagcccgt gatcaagtgc gagttcgaga aggtcatcag catggagtac    900

atggtctact tcaacttctt tgtgtgggtg ctgcccccgc ttctcctcat ggtcctcatc    960

tacctggagg tcttctacct aatccgcaag cagctcaaca agaaggtgtc ggcctcctcc   1020

ggcgacccgc agaagtacta tgggaaggag ctgaagatcg ccaagtcgct ggccctcatc   1080

ctcttcctct ttgccctcag ctggctgcct ttgcacatcc tcaactgcat caccctcttc   1140

tgcccgtcct gccacaagcc cagcatcctt acctacattg ccatcttcct cacgcacggc   1200

aactcggcca tgaaccccat tgtctatgcc ttccgcatcc agaagttccg cgtcaccttc   1260

cttaagattt ggaatgacca tttccgctgc cagcctgcac ctcccattga cgaggatctc   1320

ccagaagaga ggcctgatga ctagaccccg ccttccgctc ccaccagccc acatccagtg   1380

gggtctcagt ccagtcctca catgcccgct gtcccagggg tctccctgag cctgccccag   1440

ctgggctgtt ggctgggggc atgggggagg ctctgaagag atacccacag agtgtggtcc   1500

ctccactagg agttaactac cctacacctc tgggccctgc aggaggcctg ggagggcaag   1560

ggtcctacgg agggaccagg tgtctagagg caacagtgtt ctgagccccc acctgcctga   1620

ccatcccatg agcagtccag agcttcaggg ctgggcaggt cctggggagg ctgagactgc   1680

agaggagcca cctgggctgg gagaaggtgc ttgggcttct gcggtgaggc aggggagtct   1740
```

-continued

```
gcttgtctta gatgttggtg gtgcagcccc aggaccaagc ttaaggagag gagagcatct   1800

gctctgagac ggatggaagg agagaggttg aggatgcact ggcctgttct gtaggagaga   1860

ctggccagag gcagctaagg ggcaggaatc aaggagcctc cgttcccacc tctgaggact   1920

ctggacccca ggccatacca ggtgctaggg tgcctgctct ccttgccctg ggccagccca   1980

ggattgtacg tgggagaggc agaaagggta ggttcagtaa tcatttctga tatttgctgg   2040

agtgctggct ccacgccctg ggagtgagc ttggtgcggt aggtgctggc ctcaaacagc   2100

cacgaggtgg tagctctgag ccctccttct tgccctgagc tttccgggga ggagccttgg   2160

agtgtaatta cctgtcatct gggccaccag ctc                                 2193
```

```
<210> SEQ ID NO 48
<211> LENGTH: 3696
<212> TYPE: DNA
<213> ORGANISM: Homo sapiens
<220> FEATURE:
<221> NAME/KEY: misc_feature
<223> OTHER INFORMATION: Incyte ID No: 7503782CB1

<400> SEQUENCE: 48
```

```
ctgtggcacc tcggcgtgcg gtcgctccgt ccagctttgt cttgtgcgtc tcgttcgtgt     60

cgcctggtct ctcggtgttc cgtgtccctc atcttctcag ctcctggccg gctcctgtct    120

atgcttccgc tcacgcttct ggggttttgg cggtatgctg cccctcggcc agcagtctct    180

gcagtccggt cgcgcatatt gtcctgctgg agtcgggagg cccgcttgtg cgtcacttgt    240

agtccccagg agcagaagac ggtgatggcg tggatgccag aggtgctgcc cacccggtag    300

ctctctccgt ttagagtgag ccatggctgt acaccaggat gatgcaggtg atcaagaagc    360

tcacgcccac agtggagagg taggcccagg cacaggtgga tacggggtgc agcaggtctt    420

ggctttcttt gcctgtgccg gtccagacgt ttctgtgccc tttggatctt tcaccccatt    480

tgacagatgg ggagactgag gccgtggctg tgtgtccctc tgagagttgg agcggggctg    540

ggcccgaatt cgaccgcagc aggattctct ctcatttctg agccccggag gtggcagagc    600

ggcagactcg ggcaagtgaa ccctagggct gcaggagccc aggccccgac gccggcgcag    660

aggggacgga agggcccgcc cccagcccag cgtgcacaga ggccatagcc aaggccttaa    720

ggctcatcca accggggact catatccccc ccaccggcag cccggcgccc cagcctctac    780

ccgtgcccgc cgagatgctg ctgccgcggt cggtgtcatc ggagcgggcc cctggggtgc    840

cggagccgga ggagctgtgg gaggcagaga tggagcggct gcgcggctct gggacgcccg    900

tgcgcgggct gccctatgcc atgatggaca agcgcctcat ctggcagctg cgggagcccg    960

cgggggtgca gaccttgcgc tggcagcggt ggcagcgccg gcggcagacg gtggaaaggc   1020

gcctgcggga ggcagcgcag cggctggccc ggggccttgg gctctgggag ggggcgctct   1080

acgagatcgg gggcctcttc ggcacaggaa ttcggtccta cttcaccttc ctccgcttcc   1140

tgctgctact caacctgctg agcctgctgc tcaccgcaag cttcgtgctg ctgcccctgg   1200

tctggctccg cccccctgac ccaggcccca ccctgaactt gaccctccag tgccctggta   1260

gccgccagtc cccgcctggc gttttgaggt tccacaatca actttggcat gttttgactg   1320

gcagggcctt caccaacacc tatctcttct acggtgcgta ccgagtgggg ccggagagca   1380

gctccgtgta cagcatccgc ctggcctacc tcctcagccc gctggcctgc ctgctcctct   1440

gcttctgtgg gactctgcgg cggatggtga aggggctgcc gcagaagact ctgctgggtc   1500

agggctatca ggcgcctctc agcgccaagg tcttctcctc atgggacttc tgcatccggg   1560
```

-continued

```
tgcaggaagc agccaccatc aagaagcatg agatcagcaa cgagttcaag gtggagctgg   1620
aggagggccg tcgcttccag ctgatgcagc agcagacccg ggcccagacg gcctgccgcc   1680
tgctctccta cctgcgggtc aacgtactca tcgggctcct ggtggttggg gccatcagcg   1740
ccatcttctg ggctaccaag tactcacagg acaacaagga ggtgtcaggc aactgcattc   1800
atttaatcct ggccagaact gcgggggagt ccctgtttct gctgctccag tacctgcccc   1860
ctggggtcat cgccctggtc aacttcctgg gtcccctgct gttcacattt ctggtccagc   1920
tggagaacta ccctcccaac acggaggtca acctcactct gatctggtgc gtggtgctga   1980
agctggccag cttggggatg ttctccgtct ccctgggtca gaccatactg tgcattggca   2040
gagacaagag cagctgtgag tcctacggct acaacgtttg tgactatcag tgctgggaga   2100
actccgtggg ggaggagctg tacaagctga gtatcttcaa cttcctcctc accgtggcct   2160
tcgccttcct ggtcaccctg cctcggaggc tgctggtgga ccggttctca ggccggttct   2220
gggcctggct ggaacgggag gagttcctgg tccccaagaa tgtgctggac atcgtggcgg   2280
ggcagacggt cacctggatg ggcctcttct actgcccccct gctgcccctg ctgaatagcg   2340
tcttcctctt cctcaccttc tacatcaaga agtacaccct cctgaagaac tccagggcat   2400
cttcgcggcc cttccgtgcc tccagctcca ccttcttctt ccagctagtg ctcctcctgg   2460
gcctgcttct ggctgcagtg cccctgggct atgtggtcag cagcatccac tcctcctggg   2520
actgcggcct cttcaccaac tactcagcac cctggcaagt ggtcccggag ctggtggccc   2580
ttgggctccc gcccattggc cagcgtgccc tccactacct gggctcccac gccttcagct   2640
tccccctcct catcatgctc aggttctcag ggcagcaggg gccatgggag gggacacctg   2700
gagggggagg tccttccttc catgggggtg gtgagcctgt gcacccccaa ccaggagcca   2760
gacgcagaaa gccaagggaa gcaggggcct ctgaaaagca ggaacctcct gggcccaccc   2820
tctgggctgc catggggatt gcaggatcac tggggaagca ccgtgtctgg gtggctgcag   2880
ctgctgagct attggtattg ctgtgccaga ggggagggga tgaggggctc tgcgaggaag   2940
gagaggaggg tcccatcctc agatacagca gtgtgcagtg agaagacccc agtaccgcgt   3000
attgtagaga ttgaggtggg gagagaggaa gtcagggaga ggcgcctgtg gccccagggg   3060
caactgacca cgaatcccct tcccacccaa gccttgtcct gacggtgtgc gtctcccaga   3120
cccaggccaa tgccagggcc atccacaggc tccggaagca gctggtgtgg gtgagtgtcc   3180
tcggggctgg tgaggggaca gcagcttcag tggaaaccct tccctatgtg tggccgaggg   3240
cctagaacac gtctgagcgg gtcaggtggg ttcttcccac tggagggcgt ggcctcaggc   3300
tgagagtgaa gacggggaag gggaggaaga gaacagctcg ggctcctgag accaggagcc   3360
agacctggta agtacatgac cttaggggct gggcctttgc ctgtaatccc aacgctttgg   3420
aggcccaggc aggaggatcg gatcacttga agccatgagt taaaaccagc ctgggcaaca   3480
aagcaagacc ctggtctcca ccaaaaataa gtaattaatt ttttaaaagg agaatgtggc   3540
cgggcgtggt gactcacgcc tgtaatccca gcactttcag aggccgaggt gggtggatca   3600
cctgaggtca ggagttcaag accagcctgg ccaaaatagc gaaaccccgt ctctacttaa   3660
aaaaaaaaaa aaaggggcgg gccggccaga atagtg                             3696
```

<210> SEQ ID NO 49
<211> LENGTH: 1283
<212> TYPE: DNA
<213> ORGANISM: Homo sapiens
<220> FEATURE:

-continued

<221> NAME/KEY: misc_feature
<223> OTHER INFORMATION: Incyte ID No: 7504647CB1

<400> SEQUENCE: 49

```
ggccgggcag ccatggctga gacactcttc tggactcctc tcctcgtggt tctcctggca     60
gggctggggg acaccgaggc ccagcagacc acgctacacc cacttgtggg ccgtgtcttt    120
gtgcacacct tggaccatga gacgtttctg agccttcctg agcatgtcgg tcacagccta    180
caatcgggac agctttgata ccactcggca gaggctggtg ctggagattg gggacccaga    240
aggcccccctg ctgccatacc aagccgagtt cctggtgcgc agccacgatg cggaggaggt    300
gctgccctca acacctgcca gccgcttcct ctcagccttg gggggactct gggagcccgg    360
agagcttcag ctgctcaacg tcacctctgc cttggaccgt gggggccgtg tccccccttcc    420
cattgagggc cgaaaagaag ggtatacat taaggtgggt tctgcctcac ctttttctac     480
ttgcctgaag atggtggcat cccccgatag ccacgcccgc tgtgcccagg gccagcctcc    540
acttctgtct tgctacgaca ccttggcacc ccacttccgc gttgactggt gcaatgtgac    600
cctggtggat aagtcagtgc cggagcctgc agatgaggtg cccaccccag gtgatgggat    660
cctggagcat gacccgttct tctgcccacc cactgaggcc ccagaccgtg acttcttggt    720
ggatgctctg gtcaccctcc tggtgcccct gctggtggcc ctgcttctca ccttgctgct    780
ggcctatgtc atgtgctgcc ggcgggaggg aaggctgaag agagacctgg ctacctccga    840
catccagatg gtccaccact gcaccatcca cgggaacaca gaggagctgc ggcagatggc    900
ggccagccgc gaggtgcccc ggccactctc caccctgccc atgttcaatg tgcacacagg    960
tgagcggctg cctccccgcg tggacagcgc ccaggtgccc ctcattctgg accagcactg   1020
acagcccagc cagtggttcc aggtccagcc ctgacttcat cctcccttct ctgtccacac   1080
cacgagtggc acatcccacc tgctgattcc agctcctggc cctcctggaa cccaggctct   1140
aaacaagcag ggagaggggg tggggtgggg tgagagtgtg tggagtaagg acattcagaa   1200
taaatatctg ctgctctgct caccaattgc tgctggcagc ctctcccgtc aaaaaaaaaa   1260
aaaaaaaaaa aaaaattgcg gtc                                           1283
```

<210> SEQ ID NO 50
<211> LENGTH: 1142
<212> TYPE: DNA
<213> ORGANISM: Homo sapiens
<220> FEATURE:
<221> NAME/KEY: misc_feature
<223> OTHER INFORMATION: Incyte ID No: 7500424CB1

<400> SEQUENCE: 50

```
ggaaggggag gagcaggcca cacaggcaca ggccggtgag ggacctgccc agacctggag     60
gtggtgactt ccaagagtga ctccgtcgga ggaaaatgac tccccagtcg ctgctgcaga    120
cgacactgtt cctgctgagt ctgctcttcc tggtccaagg tgcccacggc aggggccaca    180
gggaagactt tcgcttctgc agccagcgga accagacaca caggagcagc ctccactaca    240
aacccacacc agacctgcgc atctccatcg agaactccga agaggccctc acagtccatg    300
cccctttccc tgcagcccac cctgcttccc gatccttccc tgaccccagg ggcctctacc    360
acttctgcct ctactggaac cgacatgctg ggagattaca tcttctctat ggcaagcgtg    420
acttcttgct gagtgacaaa gcctctagcc tcctctgctt ccagcaccag gctcggtacc    480
gatgcgtggg ctgggctagg tccctctgtc catctgggcc tttgtatgag ctgcattgcc    540
cttgctcacc ctgaccaagc acacgcctca gaggggccct cagcctctcc tgaagccctc    600
```

-continued

```
ttgtggcaag aactgtggac catgccagtc ccgtctggtt tccatcccac cactccaagg     660
actgagactg acctcctctg gtgacactgg cctagagcct gacactctcc taagaggttc     720
tctccaagcc cccaaatagc tccaggcgcc ctcggccgcc catcatggtt aattctgtcc     780
aacaaacaca cacgggtaga ttgctggcct gttgtaggtg gtagggacac agatgaccga     840
cctggtcact cctcctgcca acattcagtc tggtatgtga ggcgtgcgtg aagcaagaac     900
tcctggagct acagggacag ggagccatca ttcctgcctg ggaatcctgg aagacttcct     960
gcaggagtca gcgttcaatc ttgaccttga agatgggaag gatgttcttt ttacgtacca    1020
attcttttgt cttttgatat taaaaagaag tacatgttca ttgtagagaa tttggaaact    1080
gtagaagaga atcaagaaga aaaataaaaa tcagctgttg taatcaccta gcaaaaaaaa    1140
aa                                                                   1142
```

<210> SEQ ID NO 51
<211> LENGTH: 1477
<212> TYPE: DNA
<213> ORGANISM: Homo sapiens
<220> FEATURE:
<221> NAME/KEY: misc_feature
<223> OTHER INFORMATION: Incyte ID No: 7500449CB1

<400> SEQUENCE: 51

```
cgccgcctcc gtcggagcct gcgggagggt ggtggtggtg gtggtggtgg ccctcgcccg      60
cctcactcat gcctcctcct cctctgctct cgctcaggcg cctcggtggc ggttggtcgg     120
cggttacgcg gctggtggtc gcggcggccg gggctcgctc tcggggaggc cggggcggat     180
ctcgcggcgc aggcggcggc ggccgaggtg gggtcgcgcg gcggaggcgg ctcgagcttc     240
gtgctgcgcg ctcgctcttg ggctcctcgc tgcaggagga gtgtgactat gtgcagatga     300
tcgaggtgca gcacaagcag tgcctggagg aggcccagct ggagaatgag acaataggct     360
gcagcaagat gtgggacaac ctcacctgct ggccagccac ccctcggggc caggtagttg     420
tcttggcctg tcccctcatc ttcaagctct tctcctccat tcaaggccgc aatgtaagcc     480
gcagctgcac cgacgaaggc tggacgcacc tggagcctgg cccgtacccc attgcctgtg     540
gtttggatga caaggcagcg agtttggatg agcagcagac catgttctac ggttctgtga     600
agaccggcta caccattggc tacggcctgt ccctcgccac ccttctggtc gccacagcta     660
tcctgagcct gttcaggaag ctccactgca cgcggaacta catccacatg cacctcttca     720
tatccttcat cctgagggct gccgctgtct tcatcaaaga cttggccctc ttcgacagcg     780
gggagtcgga ccagtgctcc gagggctcgg ggtacccagc acattcacca tggtgtggac     840
catcgccagg atccattttg aggattatgg tctgctcagg tgctgggaca ccatcaactc     900
ctcactgtgg tggatcataa agggccccat cctcacctcc atcttggtaa acttcatcct     960
gtttatttgc atcatccgaa tcctgcttca gaaactgcgg cccccagata tcaggaagag    1020
tgacagcagt ccatactcaa ggctagccag gtccacactc ctgctgatcc ccctgtttgg    1080
agtacactac atcatgttcg ccttctttcc ggacaatttt aagcctgaag tgaagatggt    1140
ctttgagctc gtcgtggggt ctttccaggg ttttgtggtg gctatcctct actgcttcct    1200
caatggtgag gtgcaggcgg agctgaggcg gaagtggcgg cgctggcacc tgcagggcgt    1260
cctgggctgg aaccccaaat accggcaccc gtcgggaggc agcaacggcg ccacgtgcag    1320
cacgcaggtt tccatgctga cccgcgtcag cccaggtgcc cgccgctcct ccagcttcca    1380
agccgaagtc tccctggtct gaccaccagg atcccagccc aagcggcccc tcccgcccct    1440
```

-continued

```
tcccactcgc agcagacgcc ggggacagag gcctgcc                          1477


<210> SEQ ID NO 52
<211> LENGTH: 1097
<212> TYPE: DNA
<213> ORGANISM: Homo sapiens
<220> FEATURE:
<221> NAME/KEY: misc_feature
<223> OTHER INFORMATION: Incyte ID No: 7503281CB1

<400> SEQUENCE: 52

aggggcgacg ctcttgtcta gccgagccgg gcagcgctgt cgtccacggt gcgcactggg     60

cgggcagcgc tccctctgcc cacctcccgc cccgtcatgg accaccagga cccctactcc    120

gtgcaggcca cagcggccat agcggcggcc atcaccttcc tcattctctt taccatcttc    180

ggcaacgctc tggtcatcct ggctgtgttg accagccgct cgctgcgcgc ccctcagaac    240

ctgttcctgg tgtcgctggc cgccgccgac atcctggtgg ccacgctcat catccctttc    300

tcgctggcca acgagctgct gggctactgg tacttccggc gcacgtggtg cgaggtgtac    360

ctggcgctcg acgtgctctt ctgcacctcg tccatcgtgc acctgtgcgc catcagcctg    420

gaccgctact gggccgtgag ccgcgcgctg gagtacaact ccaagcgcac cccgcgccgc    480

atcaagtgca tcatcctcac tgtgtggctc atcgccgccg tcatctcgct gccgcccctc    540

atctacaagg gcgaccaggg cccccagccg cgcgggcgcc cccagtgcaa gctcaaccag    600

gaggcctggt acatcctggc ctccagcatc ggatctttct ttgctccttg cctcatcatg    660

atccttgtct acctgcgcat ctacctgatc gccaaacgca gcaaccgcag aggtcccagg    720

gccaaggggg ggcctgggca ggctacagcc tgggcgccat ctgcccgaag cactgcaagg    780

tgccccatgg cctcttccag ttcttcttct ggatcggcta ctgcaacagc tcactgaacc    840

ctgttatcta caccatcttc aaccaggact tccgccgtgc cttccggagg atcctgtgcc    900

gcccgtggac ccagacggcc tggtgagccc gcctgcgctg cccctgtggg gttggtgcgg    960

tggcgccggg gtcaccctgc ttcttgccct gctgtgtgtg gctgcctccc ctgggctttc   1020

tgctccctgc ccagatcctg taggcctcat cttaggaacc ccttgggagg ggtgggcagg   1080

ggggctgcta gcaaggg                                                1097


<210> SEQ ID NO 53
<211> LENGTH: 1501
<212> TYPE: DNA
<213> ORGANISM: Homo sapiens
<220> FEATURE:
<221> NAME/KEY: misc_feature
<223> OTHER INFORMATION: Incyte ID No: 7503292CB1

<400> SEQUENCE: 53

ccggccgcgg gagcgggatg gaaaccagca gcccgcggcc cccgcggccc agctccaacc     60

cggggctgag cctggacgcc cggctgggcg tggacactcg cctctgggcc aaggtgctgt    120

tcaccgcgct ctacgcactc atctgggcgc tgggcgcggc gggcaatgcg ctgtccgtgc    180

acgtggtgct gaaggcgcgg gccgggcgcg cggggcgcct gcgccaccac gtgctcagcc    240

tggcgctcgc gggcctgctg ctgctgctgg tcggcgtgcc ggtggagctc tacagcttcg    300

tgtggttcca ctacccctgg gtcttcggcg acctgggctg ccgcggctac tacttcgtgc    360

acgagctgtg cgcctacgcc acggtgctga gcgtggcagg cctgagcgcc gagcgctgcc    420

tagccgtgtg ccagcccctg cgtgcccgca gcctgctgac gccacgccgg acccggtggc    480
```

-continued

```
tggtggcgct ctcgtgggcc gcctcgctcg gcctcgccct gcccatggcc gtcatcatgg    540

ggcagaagca cgaactcgag acggcggacg gggagccgga gcccgcctcg cgagtgtgca    600

cggtgctggt gagccgcacc gcgctccaag tctttatcca ggtgaatgtg ctggtgtcct    660

tcgtgctccc cttggcacta actgctttcc tgaatggggt cacagtgagc cacctgctgg    720

ccctctgctc ccaagtgccg tccacttcta ccccgggcag ctccaccccc agccgcctgg    780

agctgctgag tgaggagggt ctcctcagct tcatcgtatg gaagaagacc tttatccagg    840

gaggccagga gccatcgtgg tcatgtatgt catctgctgg ctgccgtacc atgcccgcag    900

gctcatgtac tgctacgtac ctgatgacgc gtggactgac ccactgtaca atttctacca    960

ctacttctac atggtgacca acacactttt ctacgtcagc tcagctgtga ctcctcttct   1020

ctacaacgcc gtgtcctcct ccttcagaaa actcttcctg gaagccgtca gctccctgtg   1080

tggagagcac caccccatga agcggttacc cccgaagccc cagagtccca ccctaatgga   1140

tacagcttca ggctttgggg atcccccaga aacccggacc tgaatgtaat gcaagaatga   1200

acagaacaag caaaatgacc agctgcttag tcacctggca aagcaggtga gcaacctcat   1260

cactaatcat tcaagcttcg cagccagggc gacttctatc aacccctgct ctgctgagaa   1320

ccatcaagcg cagggaagcc acgtgacccc tcctagcctc aggctccctc gtctgtgtag   1380

tggagataaa gaacagcacc catctcttag tgttgcctga gactaaagtg cttagcacag   1440

aacctggtgc gtagtagatg ctcaataaat ttttgctggc acgaaaaaaa aaaaaaaaaa   1500

a                                                                   1501
```

<210> SEQ ID NO 54
<211> LENGTH: 1613
<212> TYPE: DNA
<213> ORGANISM: Homo sapiens
<220> FEATURE:
<221> NAME/KEY: misc_feature
<223> OTHER INFORMATION: Incyte ID No: 7503311CB1

<400> SEQUENCE: 54

```
ggcagcggtg gcaggggctg caggagcaag tgaccaggag caggactggg gacaggcctg     60

atcgcccctg cacgaaccag acccttcgcc gccctcacga tgactacctc tccgatcctg    120

cagctgctgc tgcggctctc actgtgcggg ctgctgctcc agagggcgga gacaggctct    180

aaggggcaga cggcggggga gctgtaccag cgctgggaac ggtaccgcag ggagtgccag    240

gagaccttgg cagccgcgga accgccttca ggcctcgcct gtaacgggtc cttcgatatg    300

tacgtctgct gggactatgc tgcacccaat gccactgccc gtgcgtcctg cccctggtac    360

ctgccctggc accaccatgt ggctgcaggt ttcgtcctcc gccagtgtgg cagtgatggc    420

caatggggac tttggagaga ccatacacaa tgtgagaacc cagagaagaa tgaggccttt    480

ctggaccaaa ggctcatctt ggagcggttg caggtcatgt acactgtcgg ctactccctg    540

tctctcgcca cactgctgct agccctgctc atcttgagtt tgttcaggcg gctacattgc    600

actagaaact atatccacat caacctgttc acgtctttca tgctgcgagc tgcggccatt    660

ctcagccgag accgtctgct acctcgacct ggcccctacc ttggggacca ggcccttgcg    720

ctgtggaacc aggccctcgc tgcctgccgc acggcccaga tcgtgaccca gtactgcgtg    780

ggtgccaact acacgtggct gctggtggag ggcgtctacc tgcacagtct cctggtgctc    840

gtgggaggct ccgaggaggg ccacttccgc tactacctgc tcctcggctg ggggtgctggg   900

agcgcaacga agtcaaggcc atttggtgga ttatacggac cccatcctc atgaccatct    960
```

-continued

```
tgattaattt cctcattttt atccgcattc ttggcattct cctgtccaag ctgaggacac   1020
ggcaaatgcg ctgccgggat taccggctga ggctggctcg ctccacgctg acgctggtgc   1080
ccctgctggg tgtccacgag gtggtgtttg ctcccgtgac agaggaacag gcccggggcg   1140
ccctgcgctt cgccaagctc ggctttgaga tcttcctcag ctccttccag ggcttcctgg   1200
tcagcgtcct ctactgcttc atcaacaagg aggtgcagtc ggagatccgc cgtggctggc   1260
accactgccg cctgcgccgc agcctgggcg aggagcaacg ccagctcccg gagcgcgcct   1320
tccgggccct gccctccggc tccggcccgg gcgaggtccc caccagccgc ggcttgtcct   1380
cggggaccct cccagggcct gggaatgagg ccagccggga gttggaaagt tactgctagg   1440
gggcgggatc cccgtgtctg ttaagttagc atggatttat tgagtgccaa ctgcgtgcca   1500
ggcccagtac ggaggacgct ggggaaatgg tgaaggaaac agaaaaaagg tccctgccct   1560
tctggagatg acaactgagt ggggaaaaca gaccgtgaac acaaaacatc aag          1613
```

```
<210> SEQ ID NO 55
<211> LENGTH: 1523
<212> TYPE: DNA
<213> ORGANISM: Homo sapiens
<220> FEATURE:
<221> NAME/KEY: misc_feature
<223> OTHER INFORMATION: Incyte ID No: 7510384CB1

<400> SEQUENCE: 55
```

```
gaggctggtg gagggagcca ctgctgggct caccatggac cgccggatgt ggggggccca     60
cgtcttctgc gtgttgagcc cgttaccgac cgtattgggc cacatgcacc cagaatgtga    120
cttcatcacc cagctgagag aggatgagag tgcctgtcta caagcagcag aggagatgcc    180
caacaccacc ctgggctgcc ctgcgacctg ggatgggctg ctgtgctggc caacggcagg    240
ctctggcgag tgggtcaccc tcccctgccc ggatttcttc tctcacttca gctcagagtc    300
aggggctgtg aaacgggatt gtactatcac tggctggtct gagccctttc caccttaccc    360
tgtggcctgc cctgtgcctc tggagctgct ggctgaggag gaatcttact tctccacagt    420
gaagattatc tacaccgtgg gccatagcat ctctattgta gccctcttcg tggccatcac    480
catcctggtt gctctcagga ggctccactg cccccggaac tacgtccaca cccagctgtt    540
caccactttt atcctcaagg cgggagctgt gttcctgaag gatgctgccc ttttccacag    600
cgacgacact gaccactgca gcttctccac tgtaatggcc atgggtgaag ggctgggca     660
ggtgggggag agaggaggtt ctatgcaagg tctctgtggc cgcctcccat ttcgccacca    720
tgaccaactt cagctggctg ttggcagaag ccgtctacct gaactgcctc ctggcctcca    780
cctcccccag ctcaaggaga gccttctggt ggctggttct cgctggctgg gggctgcccg    840
tgctcttcac tggcacgtgg gtgagctgca aactggcctt cgaggacatc gcgtgctggg    900
acctggacga cacctccccc tactggtgga tcatcaaagg gcccattgtc ctctcggtcg    960
gggtgaactt tgggcttttt ctcaatatta tccgcatcct ggtgaggaaa ctggagccag   1020
ctcagggcag cctccatacc cagtctcagt attggcgtct ctccaagtcg acacttttcc   1080
tgatcccact ctttggaatt cactacatca tcttcaactt cctgccagac aatgctggcc   1140
tgggcatccg cctccccctg gagctgggac tgggttcctt ccagggcttc attgttgcca   1200
tcctctactg cttcctcaac caagaggtga ggactgagat ctcacggaag tggcatggcc   1260
atgaccctga gcttctgcca gcctggagga cccgtgctaa gtggaccacg ccttcccgct   1320
cggcggcaaa ggtgctgaca tctatgtgct aggctgcctc atcacgccac tggagtccac   1380
```

-continued

```
acttgaattt gggcagctac cacgggtctg ccatgctctg gaggagcaag ggggccacat   1440

ccccacccca gctgttaccc agcccggggc aggtgcagcc cttcctccct gtctctgcat   1500

ctgactctct tttgaggtcc ctg                                           1523


<210> SEQ ID NO 56
<211> LENGTH: 6826
<212> TYPE: DNA
<213> ORGANISM: Homo sapiens
<220> FEATURE:
<221> NAME/KEY: misc_feature
<223> OTHER INFORMATION: Incyte ID No: 7509976CB1

<400> SEQUENCE: 56

agtgtgtggg cggcggcggc ggcggctgcg cgcttggggc ccggggcgcg gggcgaggcc     60

gtggggacgt gcgagcgggg ccgcggtggg gctcgggggc gcgtccacgt ggccagaggg    120

cggccacccg gagccagcgg agggacaggc ctgtccccag gcgcggctgc cggccatgcc    180

ctctgtctgc ctcctcctgc tgctcttcct tgccgtgggg ggggccctgg gcaacaggcc    240

cttccgtgcc ttcgtggtga cagacaccac gcttacccac ctggctgtgc accgggtgac    300

tggggaggtg ttcgtgggcg cagtgaaccg agtctttaag ctggccccca acctgactga    360

gctgcgggcc catgtcacgg ggcccgtcga ggacaacgct cgctgctacc cgccccccag    420

catgcgcgtg tgtgcccacc gcctggcccc cgtggacaac atcaacaagc tgctgctcat    480

agactatgcg gcccgccgcc tggtggcctg cggcagcatc tggcagggca tctgccagtt    540

cctgcgtctg gacgacctct tcaagctggg tgagccgcac caccgcaagg agcactacct    600

gtcgggggcc caggagcccg actccatggc tggtgtcatt gtggagcagg gccaggggcc    660

cagcaagctg tttgtgggca ctgctgtcga cggcaagtcg gagtacttcc ccaccttgag    720

ctcccgcaag ctcatcagtg atgaagacag cgcggacatg ttcagtctcg tgtaccagga    780

tgagtttgtg tcctcccaga tcaagatccc ctcagacacg ctgtccttgt accctgcctt    840

tgacatctac tacatctacg gcttcgtcag cgcctccttc gtgtacttcc tgacgctgca    900

gctggacacc cagcagacgc tgttggacac agcgggcgag aaatttttca cgtccaagat    960

cgtgcgcatg tgcgcgggag actcagagtt ctactcatac gtggaattcc ccatcggctg   1020

ctcctggcgc ggcgtggagt accgcttggt gcagagcgcc cacctggcca agcctggcct   1080

gctgctggcc caggccctgg gcgtgccggc tgatgaggac gtcctcttca ccatcttctc   1140

tcagggccag aagaaccggg ccagcccacc ccggcagacc atcctctgcc tcttcaccct   1200

cagcaacatc aatgcccaca tccggcgccg catccagtcc tgctatcgtg gggagggcac   1260

tctggctctg ccctggctgc tgaacaagga gctgccctgc atcaacaccc ccatgcagat   1320

caacggcaac ttctgtgggc tggtgttgaa ccagcctctg ggaggcctgc atgtgatcga   1380

ggggctgccc ctgctggccg acagcaccga cggcatggcc agcgtggccg cctacaccta   1440

ccgccagcac tctgtggtct tcattggcac gcgcagcggc agcttgaaga aggtgcgggt   1500

cgatggcttc caggatgccc acctgtatga gacagtcccc gtggtggatg gcagccccat   1560

cctccgagac ctgctcttca gcccggacca ccggcacatc tatctcctga gtgagaagca   1620

ggtgagccag ctcccggtgg agacctgtga gcagtaccag agctgcgcag cctgcctggg   1680

ctccggggac ccgcactgtg gttggtgtgt gctgcgacac aggtgctgcc gcgaaggggc   1740

ctgtctgggc gcctctgccc cacacggctt tgctgaggag ctgagcaagt gtgtccaggt   1800

gcgggtccgg cccaacaatg tgtcagtgac gtcacctggg gtgcagctga ccgtcaccct   1860
```

-continued

```
gcacaacgtg ccagacctca gtgcgggcgt gagctgcgcc ttcgaggcgg cggcggagaa   1920
cgaggcggtc ctgctgccct ccggtgaact gctctgcccc tcaccctccc tccaggagct   1980
ccgagctctt accaggggc atggggccac ccgcactgtg cggctgcagc ttctctccaa   2040
ggagacaggc gtgaggtttg ccggtgctga ctttgtcttc tacaactgca gcgtcctcca   2100
gtcgtgcatg tcctgtgttg gcagccctta cccctgccac tggtgtaagt accgccacac   2160
gtgtaccagc cgcccccacg agtgctcctt ccaggagggc agggtccaca gccctgaggg   2220
ctgccctgag atcctgccca gtggggacct cctgatcccc gttggggtca tgcagcctct   2280
taccttgcgg gctaagaacc tacctcagcc gcagtcgggc cagaagaact atgagtgcgt   2340
ggtgcgggtg caggggcggc agcagcgggt gcctgccgtg cgcttcaaca gcagcagtgt   2400
gcagtgccag aacgcctcgt actcctatga aggtgatgag catggtgaca ccgagctgga   2460
cttctccgtg gtctgggatg gagacttccc catagacaag cctcccagct tccgagccct   2520
cctgtacaag tgctgggcgc agcggcccag ctgtggcctc tgcctcaagg ctgatccccg   2580
cttcaactgt ggctggtgca tctcagagca caggtgccag ctgcggaccc actgcccggc   2640
cccgaagacc aactggatgc acctgagcca gaagggcacc cggtgcagcc acccccgcat   2700
cacgcagatc caccctctcg tggggcccaa ggaaggaggc acccgggtca ccatcgtggg   2760
tgacaacctg ggcctcttgt cccgagaggt gggcctgcgg gtggctggcg tgcgttgcaa   2820
ctccattccg gccgagtaca tcagtgctga gaggtgagtg cggctctgtg ggtgcccggg   2880
ccgtatgtgg cctggccggc cctgacgctc tctgagccct aggatcgtgt gtgagatgga   2940
ggagtcgctg gtgcccagcc cgccgccggg gcccgtggag ctgtgtgtgg gtgactgttc   3000
agccgacttc cgcacgcagt cggagcaggt ctacagcttt gtgaccccaa cgtttgacca   3060
agtgagtccc agccgtggcc cggcgtccgg gggcacacgg cttaccatct caggcagctc   3120
tctggatgct ggcagcaggg tcacagtgac tgtgagggac agcgagtgcc agtttgtaag   3180
gagagatgcc aaggcgatcg tgtgcatctc acctctctcc accctgggcc ccagccaggc   3240
ccccatcaca cttgccattg accgggctaa catctccagc cccgggctca tctacaccta   3300
cactcaggac cccaccgtca cccgccttga gcccacctgg agcatcatca atggaagcac   3360
tgccatcact gtgagtggga cccacctgct gacggtccag gagccccggg tccgtgccaa   3420
gtaccgcggc attgagacca ccaatacatg ccaagtgatc aacgacactg ccatgctgtg   3480
taaggccccc ggcatctttc ttgggcggcc ccagcctcgg gcgcaaggcg agcaccctga   3540
tgagtttggc ttcctgctgg accacgtgca aacggcccgc tccctcaacc gctcctcctt   3600
tacctactac cctgatccca gctttgagcc gctggggccc tctggcgtgc tggacgtcaa   3660
accgggctcc cacgtggtgc tgaagggcaa gaacctgatt cccgcggcag ccggcagctc   3720
ccgcctcaac tacactgtgc tgataggagg ccagccgtgt tcgctcactg tctcggacac   3780
acaactcctg tgcgactcac ccagccagac tggccggcag cctgtcatgg tgctggtggg   3840
tggcctggag ttctggctgg gcaccctgca catctcggca gagcgggcgc tgaccctacc   3900
ggccatgatg ggctggcgg cggggggtgg gctcctgctg ctggccatca cagccgtgct   3960
ggtggcgtac aagcgcaaga ctcaggacgc ggaccgtacc ctcaagcgtc tgcagctgca   4020
gatggacaac ctggagtccc gtgtggccct ggagtgcaag gaagcttttg cagagctgca   4080
gacggacatc aatgagctga ctaaccacat ggacgaggtg cagatcccct tcctggacta   4140
ccggacttac gccgtgcgcg tgctcttccc gggcatcgag gcccacccgg tgctcaagga   4200
gctggatacg ccacccaacg tggagaaggc cctgcgcctc ttcgggcagc tgctgcacag   4260
```

-continued

```
ccgcgcgttc gtgcttacct tcatccacac gctggaggcc cagagcagct tctccatgcg   4320
cgaccgcggc accgtggcct cgctcaccat ggtggccctg cagagccggc tcgactatgc   4380
cacggggctg ctcaagcaac tgctggccga cctcatcgag aagaacctcg agagcaagaa   4440
ccaccccaag ctgctgctac gcaggacaga gtcagtggct gagaagatgc ttaccaactg   4500
gttcacgttc ctgctgcata agtttctgaa ggagtgtgct ggggagcctc tcttcctgct   4560
ttactgtgcc atcaagcagc agatggagaa gggccccatt gatgccatca cgggcgaggc   4620
acgatactcc ctgagcgagg acaagctcat ccgtcagcag atcgactaca agacactgac   4680
ccttcactgc gtgtgtccgg agaacgaggg cagcgcccag gtcccagtga aggttctcaa   4740
ctgtgacagc atcacccagg ccaaagataa gctgctggac actgtgtaca agggcattcc   4800
gtactcccag cgtcccaaag ctgaggacat ggacctggag tggcgccagg gccgcatgac   4860
tcgcatcatc ctccaggatg aggatgtcac caccaagatc gagtgtgact ggaagaggct   4920
caactcactg gcccactacc aggtgacaga cggttccttg gtggcattgg tgcccaaaca   4980
agtgtctgcc tataacatgg ccaactcctt caccttcacc cgctccctca gccgctacga   5040
gagcttgctc cgcacggcca gcagccctga tagcctccgc tcacgggcac ccatgattac   5100
gcctgaccag gagacaggca ccaaattgtg gcacctggtg aaaaaccacg accatgccga   5160
ccatcgcgag gggaccgtg gcagcaagat ggtctccgag atctacctga cacggctgct   5220
ggccaccaag ggcacactgc agaagttcgt ggatgacctc tttgagacag tgttcagcac   5280
agcccaccgg ggctcggccc tgcccctggc catcaagtac atgttcgact tcctggatga   5340
gcaggcggac cagcgccaga tcagcgaccc cgatgtgcgc cacacctgga agagcaactg   5400
cctgccgctg cgcttctggg tgaatgtgat caagaacccg cagttcgtgt tcgacatcca   5460
caagaacagc atcacggatg cctgcctgtc ggtggtagcc cagaccttca tggactcctg   5520
ctctacatcc gagcaccgcc tggggaagga ctcgccctcc aacaaactgc tctacgccaa   5580
ggacatcccc aactacaaga gctgggtgga gaggtattat cgagacattg caaagatggc   5640
atccatcagc gaccaggaca tggatgccta cctggtggag cagtcccgcc tccacgccag   5700
cgacttcagc gtcctgagtg cgctcaacga gctgtatttc tatgtcacca agtaccgcca   5760
ggagattctc acggctctgg accgagatgc ctcttgtcgg aagcataagt tgcggcagaa   5820
actggaacag atcatcagcc tcgtgtccag cgacagctaa ggtggtggaa tcggtgagga   5880
gggggcttct cagtcctgtg ccgtcctccc atccagggga gtggctggct caagcctggg   5940
tccccgggct gagccctgga ttgggtatcg tggggcaggt caccctggcc acgatgcccc   6000
cggcacaccc aggcccccctt cattagtgcc ttgctttggg ccctgcaggg ggaggggtga   6060
cagggcgagc ccccacccca gcagcagcaa tacccccacc ctcctgccct gtgcccaggt   6120
gttgggacag tcccaccctc cctgctattt atatccctct gcctatttat tgaatcgaac   6180
ttcgcctctg tctccatctg taaatatgtg tccccccacc ggatgtcgcc accctcactc   6240
acctgcctct tcttgagctg tcctgggccc tgccacccgt ctgggctcct ttgtgtagca   6300
ttatcagcct cggtctggcc tctggcacct caccttgcc atggctgacc ccacccattc   6360
caaggcgggg tcacggtacc agcagcactt ggggtgaggc ctccaaagct tcctcagaat   6420
tgtggctgtg ccacgctgga ccacagggtc cccctcaagc atctcggggc cctattctct   6480
ctgagcacct ggagggctgg actcaggctt gtgccagggc ctgacttggg cctgggggcc   6540
ctagaacact cctcctcctg agcctactgc caaacgtcct cagtgttgtc tgcacctgct   6600
```

-continued

```
ccgactcctt cagccgcccc attcagcgcc cgctccgtcc agtgcccgcc ctgtggggcc   6660

aaggcggccg tgccttacta ctctgtgtct tctgcctcct ctgaggaatc tggccctgtc   6720

tgacagtccc agaccccccg ttctctcctc tttagttgca tgagtttttc tttgttcatg   6780

gaatgttttt tcctgattaa atgttgggga aatgccaaaa aaaaaa                 6826
```

<210> SEQ ID NO 57
<211> LENGTH: 2481
<212> TYPE: DNA
<213> ORGANISM: Homo sapiens
<220> FEATURE:
<221> NAME/KEY: misc_feature
<223> OTHER INFORMATION: Incyte ID No: 7510454CB1

<400> SEQUENCE: 57

```
gacaagggtc tcactttgtt gcccaggttg gtctcgaact cccaggctcg agcggtcctc     60

ctgttttggc ctcccaaagc attgggatta caggcatgca ccacaattcc tgacctacag    120

ttttcttctt atgggctttg tacatttctt gcctcctggt atttttaagg aaatgtaaga    180

gtgtgaatca ggtactgatg gttttgactt cattatgatc agcatctttg gcttccatca    240

gagtagacac tgaacgtttt catccaaccg gatgatgagt gcattagaac tacataagag    300

atgaaatcct ttctccctgg gacatgtatc cttttgtgtt ctgcttttaa tttgatgttt    360

ttcagtcttt tcaggctgaa atataatatt tgtatcattc tgagagcctg taacaccatg    420

ctttccagca atacaattat ggaaattttt ttcctctctc atattgacat tgggatttgg    480

aggaacttac tgctactcct gatgcctatt tacacctttt tgatatgtcc ccagcagaag    540

aagcccatgg gcttgctttt ccttcacttg tctgttgcta atacgatgac acttctccgc    600

aaagttattc cattggcagt aaaatctttc aacactaaaa atcttttgaa ttatactgga    660

tgtagggaat ttgaattttt atatagagta tcttggggac ttccccctatg tacgacatac   720

ctcctaagca tggtgcaggc cctccgtggg agccccagca aatccaggtg gacgtggctg    780

aaagacaaaa tgctcaaaac accactgtgc ttcttcttac actctgggtc atcaacagtc    840

tcatctacat caagcttgtg ccatttgttg acactatcaa atatggcagt gtcaccaaga    900

atctctccat aaaaatgtgt ttagctacac cacacatggg taacacaatt gctgtctctc    960

atacgagtgt tatcacattc caggacttaa tttttctggt tctcatgagt tgagccagtg   1020

gctacttggt gattttcctt cacagacacc agaaaaataa tccacatctt cacaacaaca   1080

gctgttcctc tatagcctcc catgagaccg gaaccatcac gactgcgctg ctgcttatga   1140

tttgcttcgt tgtatttaat gtgagcaact cgtgccacag catttaccta agtacggtga   1200

agaaaaggga tcagttgtgg accatctcag atttgatttc ctcatgttac cccatttttt   1260

ggtccatttt tgctcattgg tagagaaagt cttatcctga attcaaaatc tatgaagtag   1320

agaaagtcgt cttatcccat agatatgtca aagtaaactt tcaccaatat aaactttttc   1380

caaaacaaca ttctataaag agttggtatt ctgaagaaat gatgggattt aggtctgaaa   1440

aatgagatat ttctcagttc actgcatgaa atataatcta atgaccttta ccttcagtaa   1500

agacaatatt gcatagctta gtatttaatg tttgtataca tagatataat catttaatag   1560

acaagtagat agataatttt tcatgtcaga tgttataatg gacttcttgc actagtcatt   1620

caatatccat atttttctta ctttaatttg tgttcagcat gaaaaatcat ttcaaaagga   1680

gatcagggac tccaggaagc agagcgtaac tccccacttc taaactgtgg gcttcacata   1740

atgacatcct accaagaaat cagtatagca aaggaggaaa aagagtaact tcgcattgga   1800
```

-continued

```
gaaacctaac aaacactgtc tcagccaggt gatcaaggcc actgtgagca gtgatcagtc   1860

aagtcgaaag tgcatatcat atgacaggat gagaatggca ttttacctcg acatcttccc   1920

tcccaaaact aataatccta ctacatcaga caaacctcag ctgagaaaca gtttccaaaa   1980

acacctgact agtaccccct aaaaccatca aggtcatcaa gaacaatgta gtcctgagaa   2040

atgatcacag ccgggaagaa cctaaggact tggtgtcctt tggtatcctg atatggaatc   2100

ctggagcaga aaaggacatt aagtaaaaac caaggaaata gaaataaagt ataaacttaa   2160

taatatatca atattaattc attaattgtg acaaatgtaa catagtaatg taagacatta   2220

aaatggggaa aattgggtat gatgtggagg agaactctgt gtattctatt tgcaactctt   2280

ctgtaaatgt aaacctattt gaacaattaa aaattttatt ttttcaaaac aaaaaaaaaa   2340

aaacaaaaca acaacaacac aaaaacacag aggggcgcgg cgaccaaaaa tatcaaacgg   2400

cccaccgcgg gggggccgcc ccacccataa agagataaac acacacggag gtaaaaaacg   2460

ggggaaagcg gtccctctcg c                                             2481
```

<210> SEQ ID NO 58
<211> LENGTH: 2512
<212> TYPE: DNA
<213> ORGANISM: Homo sapiens
<220> FEATURE:
<221> NAME/KEY: misc_feature
<223> OTHER INFORMATION: Incyte ID No: 8017335CB1

<400> SEQUENCE: 58

```
atgagggtgt ccgtgccggg tccggcggcc gctgccgccc ccgcagccgg ccgcgagccc     60

tccacgcccg gcgggggcag cggaggcgga ggcgccgtcg ctgcagcctc aggcgccgcg    120

gtgccgggct ccgtgcagtt ggcgctgagc gtcctgcacg ccctgctcta cgccgcgctg    180

ttcgcctttg cctacctgca gctgtggcgg ctgctcctgt accgcgagcg gcggctgagt    240

taccagagcc tctgcctctt cctctgtctc ctgtgggcag cgctcaggac caccctcttc    300

tccgccgcct tctcgctcag cggctccctg cccttgctcc ggccgcccgc tcacctgcac    360

ttcttccccc actggctgct ctactgcttc ccctcctgtc tccagttctc cacgctctgt    420

ctcctcaacc tctacctggc ggaggttata tgtaaagtca gatgtgccac tgaacttgac    480

agacacaaaa ttctactgca tttgggcttt ataatggcaa gcctgctctt tttagtggtg    540

aacttgactt gcgcaatgct agttcatgga gatgtcccag aaaatcagtt gaagtggact    600

gtgtttgttc gagcattaat taatgatagc ctgtttattc tttgtgccat ctctttagtg    660

tgttacatat gcaaaattac aaaaatgtca tcagctaatg tctacctcga atcaaagggt    720

atgtctctgt gccagactgt cgtcgtgggc tctgtagtca ttcttctgta ctcttccaga    780

gcttgttata atttggtggt ggtcaccata tctcaggata cattagaaag tccatttaat    840

tatggctggg ataatctttc agataaggct catgtagaag acataagtgg agaagagtat    900

atagtatttg gaatggtcct ctttctgtgg gaacatgtgc cagcatggtc ggtggtactg    960

tttttccggg cacagagatt aaaccagaat ttggcacctg ctggcatgat aaatagtcac   1020

agttatagtt ccagagctta ctttttcgac aatccaagac gatatgatag tgatgatgac   1080

ctgccaagac tgggaagttc aagagaagga agtttaccaa attcgcaaag tttgggctgg   1140

tatggcacca tgactgggtg tggcagcagc agttacacag tcactcccca cctgaatgga   1200

cctatgacag atactgctcc tttgctcttt acttgtagta atttagattt gaacaatcat   1260

catagcttat atgtgacacc acaaaactga cagcatcacc aagtcatgat tcttgagttg   1320
```

-continued

```
tttttcataa atgtgtatat tcaatgtgtt taaattccat ctacataaac attccattat   1380

ctgttgcaac tgaaaacaaa atctggaagt gtggctgtgt ttggtaaata acacagctat   1440

tatttttgac ctcttcatag taaaatgaag taaaatggaa agtttggagt aggagaaaag   1500

agagattaga tcttaaggca cttgatggcc tccaaaaatc ctgactttgg aacatcaaat   1560

gcatatgtgc acttttatct ttgttctgag tcactgcagt ccccaaagtc atatgccaat   1620

gttcacactg aaatactgta ttgtacacca aactggaagg caattttcct atgaaaatca   1680

aagccggtat attcattggt atgctctata cagatatctt aataaaaatt ttatagtgtg   1740

aacagtgcac agagttaagg cataaaaatg tatcattctt tataaaaatc tactgaaaat   1800

gtgtaatcat tgaagacagt tcttttaagc atgattttaa aatagcaact gaaattcaat   1860

cattttaaac aaatgatggt agtaatccat tagttatggc cagcagtgtt ctttggagag   1920

ccacaataat ttcaagagga aaatatacca gtgaaaattg tgtggctatt ttgagtagaa   1980

ttggtcagtt gattattttg tgtaattgag atatatgtag tagtttaagc atgattcttg   2040

aagaaagcaa tagtgacttt tgcataggga gattttggta gaaacttctt gggactaaac   2100

aagtttagag atgcatttaa gaattattca caaaatgtgt aattctaaat taaaacataa   2160

atatattttc aaaagcattt gatttctctg aagcatgata tagctggtct tacctagtga   2220

atcaggattg tcctcaggta aatgaaatca tgatacatta ttgcagtgaa ctcaagtgca   2280

atactttgta agacatataa ttcctatgat tttcacattt ttatatctta tatatgggaa   2340

aagccaaatt aaattgaatt cagattaatt ccagcattag actaaatgag caaacttaag   2400

taaatgtaca aactaggtaa gtataaaacc acaggttaac aatattggag tacttttaga   2460

attacattaa aactgtctta aatgtcctat cccaaatcta aaaaaaaaaa aa           2512
```

<210> SEQ ID NO 59
<211> LENGTH: 754
<212> TYPE: DNA
<213> ORGANISM: Homo sapiens
<220> FEATURE:
<221> NAME/KEY: misc_feature
<223> OTHER INFORMATION: Incyte ID No: 7510197CB1

<400> SEQUENCE: 59

```
catgaatcca ttcctgatcc ttgcctttgt gggagctgct ggcgagtttc atgacctgcc     60

tcaggcccca cccaccccct ttcctggcag acacatgccc tgccattctt gccacctctc    120

ctcttttgac tgcgctctga tattctattt cctccatctg acatatctcc ttcccatcct    180

ccttgggctc tctttaagcc tcacctgttt cacctgttcc ctcatttcac tcccaccact    240

gtcattcatc catatccgag ctgtgttgga gaagctggga agggagacca gttgctgtcc    300

cctttgacga tgatgacaag attgttgggg gctacacctg tgagaattct ctcccctacc    360

aggtgtccct gaattctggc tcccacttct gcggtggctc cctcatcagc gaacagtggg    420

tggtatcagc agctcactgc tacaagaccc gcatccaggt gagactggga gagcacaaca    480

tcaaagtcct ggaggggaat gagcagttca tcaatgcggc caagatcatc cgccacccta    540

aatacaacag ggacactctg gacaaaggac atcatgctga tcaaactctc ctcaactgcc    600

gtcatcaatt gcccgcgttg tccaccatct ctctgcccta ccgcccctcc agctgctggc    660

actgagtgcc tcatctccgg ttggggcaac actctgagcc tttgtggctg actacccaga    720

agagctgaag tgcctggatg ctccggtgct gacc                                754
```

<210> SEQ ID NO 60

-continued

<211> LENGTH: 1660
<212> TYPE: DNA
<213> ORGANISM: Homo sapiens
<220> FEATURE:
<221> NAME/KEY: misc_feature
<223> OTHER INFORMATION: Incyte ID No: 7510055CB1

<400> SEQUENCE: 60
gccaaggctg gggcagggga gtcagcagag gcctcgctcg ggcgcccagt ggtcctgccg 60
cctggtctca cctcgccatg gttcgtctgc ctctgcagtg cgtcctctgg ggctgcttgc 120
tgaccgctgt ccatccagaa ccacccactg catgcagaga aaaacagtac ctaataaaca 180
gtcagtgctg ttctttgtgc cagccaggac agaaactggt gagtgactgc acagagttca 240
ctgaaacgga atgccttcct tgcggtgaaa gcgaattcct agacacctgg aacagagaga 300
cacactgcca ccagcacaaa tactgcgacc ccaacctagg gcttcgggtc cagcagaagg 360
gcacctcaga aacagacacc atctgcacct gtgaagaagg ctggcactgt acgagtgagg 420
cctgtgagag ctgtgtcctg cacggctcat gctcgcccgg ctttggggtc aagcagattg 480
ctacaggggt ttctgatacc atctgcgagc cctgcccagt cggcttcttc tccaatgtgt 540
catctgcttt cgaaaaatgt caccccttgga caagctgtga gaccaaagac ctggttgtgc 600
aacaggcagg cacaaacaag actgatgttg tctgtggtga gtcctggaca atgggccctg 660
gagaaagcct aggaaggtcc ccaggatcgg ctgagagccc tggtggtgat ccccatcatc 720
ttcgggatcc tgtttgccat cctcttggtg ctggtcttta tcaaaaaggt ggccaagaag 780
ccaaccaata aggcccccca ccccaagcag gaaccccagg agatcaattt tcccgacgat 840
cttcctggct ccaacactgc tgctccagtg caggagactt tacatggatg ccaaccggtc 900
acccaggagg atggcaaaga gagtcgcatc tcagtgcagg agagacagtg aggctgcacc 960
cacccaggag tgtggccacg tgggcaaaca ggcagttggc cagagagcct ggtgctgctg 1020
ctgctgtggc gtgagggtga ggggctggca ctgactgggc atagctcccc gcttctgcct 1080
gcacccctgc agtttgagac aggagacctg gcactggatg cagaaacagt tcaccttgaa 1140
gaacctctca cttcaccctg gagcccatcc agtctcccaa cttgtattaa agacagaggc 1200
agaagtttgg tggtggtggt gttggggtat ggtttagtaa tatccaccag accttccgat 1260
ccagcagttt ggtgcccaga gaggcatcat ggtggcttcc ctgcgcccag gaagccatat 1320
acacagatgc ccattgcagc attgtttgtg atagtgaaca actggaagct gcttaactgt 1380
ccatcagcag gagactggct aaatatattc taattttatt tagccagtct cctgctgatg 1440
gacagttaag caggagactg gctaaataaa attagaatat atttatacaa cagaatctca 1500
aaaacactgt tgagtaagga aaaaaaggca tgctgctgaa tgatgggtat ggaacttttt 1560
aaaaaagtac atgcttttat gtatgtatat tgcctatgga tatatgtata aatacaatat 1620
gcatcatata ttgatataaa gatgtaaaga aaaaaggggc 1660

<210> SEQ ID NO 61
<211> LENGTH: 2118
<212> TYPE: DNA
<213> ORGANISM: Homo sapiens
<220> FEATURE:
<221> NAME/KEY: misc_feature
<223> OTHER INFORMATION: Incyte ID No: 7501754CB1

<400> SEQUENCE: 61
cccgcgccgc ccgcgccccg ctcgactccg gaggctcccg cagccccggc gtccgccccg 60
ctgccccctc ccccgggggc catgggggcg cccccgggct accggccctc agcttgggtg 120

-continued

```
catctcctcc accagctgcc ccgcgccgac ttccagctcc gcccggtgcc cagcgttttc    180
gcgccccaag agcaggaata ccagcaggcc ttgttgctgg tggcggcctt ggcgggcctg    240
ggcttgggcc tgagcctcat tttcatcgct gtctacctca tccgcttctg ctgctgccgg    300
ccccccgagc cccccgggtc caagatcccc tcgcccgggg gaggctgcgt cacctggagc    360
tgcattgtcg cccttctcgc cggctgcact ggcattggca tcggtttcta tggcaacagt    420
gagaccagtg atggggtgtc ccagctcagc tctgcgctgc tgcacgccaa ccacacactc    480
agcaccattg accacctggt gttggagacg gtggagaggc tgggcgaggc ggtgaggaca    540
gagctgacca ccctggagga ggtgctcgag ccgcgcacgg agctggtggc tgccgcccga    600
ggggctcgac ggcaggcgga ggctgcggcc cagcagctgc aggggctggc cttctggcag    660
ggagtgcccc tgagcccccct gcaggtggct gaaaatgtgt cctttgtgga ggagtacagg    720
tggctggcct acgtcctcct gctgctcctg gagctgctgg tctgcctctt caccctcctg    780
ggcctggcga agcagagcaa gtggctggtg atcgtgatga cagtcatgag tctcctggtt    840
ctcgtcctga gctggggctc catgggcctg gaggcagcca cggccgtggg cctcagtgac    900
ttctgctcca atccagaccc ttatgttctg aacctgaccc aggaggagac agggctcagc    960
tcagacatcc tgagctatta tctcctctgc aaccgggccg tctccaaccc cttccaacag   1020
aggctgactc tgtcccagcg agctctggcc aacatccact cccagctgct gggcctggag   1080
cgagaagctg tgcctcagtt cccttcagcg cagaagcctc tgctgtcctt ggaggagact   1140
ctgaatgtga cagaaggaaa tttccaccag ttggtggcac tgctacactg ccgcagcctg   1200
cacaaggact atggtgcagc cctgcggggc ctgtgcgaag acgccctgga aggcctgctc   1260
ttcctgctac tcttctccct gctgtctgca ggagcgctgg ccactgccct ctgcagcctg   1320
ccccgagcct gggccctctt cccacccagg aatccaagcg ctttgtgcag tggcagtcgt   1380
ctatctgagc ccctcctccc ggctggactg gagcctggct cccctcttcg ttccttccct   1440
ggctgccgga ggagacccca ctaacccagc ctgcctgggc tctgaccact aacactcttg   1500
gccatggaca gcctgcacag gaccgcctcc ctgctcttgg ccactgtgct cccatttctg   1560
tccttggcct tgggagtagc tgagggggca gactagggag tagggctggc aggggagggg   1620
gcagacagcc tcgcctcgca cccttcatcc ctggctgccg gtcccatcct tggagggact   1680
aagctggggg tgggggacat gagtcccccct gctgcccctg ccacatccca gtgggctctg   1740
accccctgat ctcaactcgt ggcactaact tggaaaaggg ttgatttaaa ataaaaggga   1800
agactatttt acaaaaaaaa aaaaaaaaaa aaaaaaaaaa aaaaaaaaaa aaaaaaaaaa   1860
aaaaaaaaaa aaaaaaaaaa aaaaaaaaaa aaaaaaaaaa aaaagagggg gggggggcaa   1920
gaaatgtatc ctcccccccg gataataaac tggcggagcg tccttgggga aaaacactac   1980
tccacaacag gggcacttaa aagcccgcgg aacattggtc aacatcctac ggtagtaaat   2040
atttcccgca cacaccaaga ttgagaaaaa catgagagat agcttaacag acatggtgat   2100
cgagatttat gcagagat                                                 2118
```

<210> SEQ ID NO 62
<211> LENGTH: 2800
<212> TYPE: DNA
<213> ORGANISM: Homo sapiens
<220> FEATURE:
<221> NAME/KEY: misc_feature
<223> OTHER INFORMATION: Incyte ID No: 7510517CB1

<400> SEQUENCE: 62

-continued

```
cttcactgac ccatcccgct gcacctcttg tttcccaagt ttttgaaagc tggcaactct     60
gacctcggtg tccaaaaatc gacagccact gagaccggct ttgagaagcc gaagatttgg    120
cagtttccag actgagcagg acaaggtgaa agcaggttgg aggcgggtcc aggacatctg    180
agggctgacc ctgggggctc gtgaggctgc caccgctgct gccgctacag acccagcctt    240
gcactccaag gctgcgcacc gccagccact atcatgtcca ctcccggggt caattcgtcc    300
gcctccttga gccccgaccg gctgaacagc ccagtgacca tcccggcggt gatgttcatc    360
ttcggggtgg tgggcaacct ggtggccatc gtggtgctgt gcaagtcgcg caaggagcag    420
aaggagacga ccttctacac gctggtatgt gggctggctg tcaccgacct gttgggcact    480
ttgttggtga gcccggtgac catcgccacg tacatgaagg gccaatggcc cgggggccag    540
ccgctgtgcg agtacagcac cttcattctg ctcttcttca gcctgtccgg cctcagcatc    600
atctgcgcca tgagtgtcga gcgctacctg gccatcaacc atgcctattt ctacagccac    660
tacgtggaca agcgattggc gggcctcacg ctctttgcag tctatgcgtc caacgtgctc    720
ttttgcgcgc tgcccaacat gggtctcggt agctcgcggc tgcagtaccc agacacctgg    780
tgcttcatcg actggaccac caacgtgacg gcgcacgccg cctactccta ctcgtggtgc    840
gagtattcgt caaccagtta tatcagccaa gtttggagcg agaagtcagt aaaaatccag    900
atttgcaggc catccgaatt gcttctgtga accccatcct agacccctgg atatatatcc    960
tcctgagaaa gacagtgctc agtaaagcaa tagagaagat caaatgcctc ttctgccgca   1020
ttggcgggtc ccgcagggag cgctccggac agcactgctc agacagtcaa aggacatctt   1080
ctgccatgtc aggccactct cgctccttca tctcccggga gctgaaggag atcagcagta   1140
catctcagac cctcctgcca gacctctcac tgccagacct cagtgaaaat ggccttggag   1200
gcaggaattt gcttccaggt gtgcctggca tgggcctggc ccaggaagac accacctcac   1260
tgaggacttt gcgaatatca gagacctcag actcttcaca gggtcaggac tcagagagtg   1320
tcttactggt ggatgaggct ggtgggagcg gcagggctgg gcctgcccct aaggggagct   1380
ccctgcaagt cacatttccc agtgaaacac tgaacttatc agaaaaatgt atataatagg   1440
caaggaaaga aatacagtac tgtttctgga cccttataaa atcctgtgca atagacacat   1500
acatgtcaca tttagctgtg ctcagaaggg ctatcatcat cctacaactc acattagaga   1560
acatcctggc ttttgagcac ttttcaaaca atcaagttga ctcacgtggg tcctgaggcc   1620
tgcagcacgt cggatgctac ccactatga cagaggattg tggtcacaac ttgatggctg   1680
cgaagaccta ccctccgttt ttctactaga taggaggatg gtagaagttt ggctgctgtc   1740
ataacatcca gagctttgtc gtatttggca cacagcagag gcccagatat tagaaaggct   1800
ctattccaat aaactatgag gactgcctta tggatgattt aagtgtctca ctaaagcatg   1860
aaatgtgaat ttttattgtt gtacatacga tttaaggtat ttaaagtatt ttcttctctg   1920
tgagaaggtt tattgttaat acaaggtata ataaaattat cgcaacccct ctccttccag   1980
tataaccagc tgaagttgca gatgttagat atttttcata aacaagttcg agtcaaagtt   2040
gaaaattcat agtaagattg atatctataa aatagatata aatttttaag agaaagaatt   2100
tagtattatc aaagggataa agaaaaaaat actatttaag atgtgaaaat tacagtccaa   2160
aatactgttc tttccaggct atgtataaaa tacatagtga aaattgttta gtgatattac   2220
atttatttat ccagaaaact gtgatttcag gagaacctaa catgctggtg aatattttca   2280
actttttccc tcactaattg gtacttttaa aaacataaca taaatttttt gaagtcttta   2340
```

-continued

```
ataaataacc cataattgaa gtgtataata taaaaaattt taaaaatcta agcagcttat   2400

tgtttctctg aaagtgtgtg tagttttact ttcctaagga attaccaaga atatccttta   2460

aaatttaaaa ggatggcaag ttgcatcaga aagctttatt ttgagatgta aaaagattcc   2520

caaacgtggt tacattagcc attcatgtat gtcagaagtg cagaattggg gcacttaatg   2580

gtcaccttgt aacagttttg tgtaactccc agtgatgctg tacacatatt tgaagggtct   2640

ttctcaaaga aatattaagc atgttttgtt gctcagtgtt tttgtgaatt gcttggttgt   2700

aattaaattc tgagcctgat attgatatgg ttttaagaag cagttgtacc aagtgaaatt   2760

attttggaga ttataataaa tatatacatt caaaaaaaaa                         2800


<210> SEQ ID NO 63
<211> LENGTH: 1750
<212> TYPE: DNA
<213> ORGANISM: Homo sapiens
<220> FEATURE:
<221> NAME/KEY: misc_feature
<223> OTHER INFORMATION: Incyte ID No: 7511014CB1

<400> SEQUENCE: 63

gccgcgcgcg ccccgcagtt tccgcgctaa gggaacgagt gcgcggaggg gacgagcggc     60

tggaccacag ccggcgcccg atcaggatct ccgcgctggg atcggtggaa cttgaggcag    120

cggcggcgcg gggcgccatg gcacaccgag cggctccgtc ttctgctcct cagagagccc    180

ggctggcggc ctgggatgac aagatgtctg gactgcaatc ctgcacagtt ttgagaggga    240

gatgacttga gtggttggct tttatctcca caacaatgtc catgaacaat tccaaacagc    300

tagtgtctcc tgcagctgcg cttctttcaa acacaacctg ccagacggaa aaccggcttt    360

ccgtattttt ttcagtaatc ttcatgacag tgggaatctt gtcaaacagc cttgccatcg    420

ccattctcat gaaggcatat cagagattta gacagaagtc caaggcatcg tttctgcttt    480

tggccagtgg cctggtaatc actgatttct ttggccatct catcaatgga gccatagcag    540

tatttgtata tgcttctgat aaagaatgga tccgctttga ccaatcaaat gtcctttgca    600

gtatttttgg tatctgcatg gtgttttctg gtctgtgccc acttcttcta ggcagtgtga    660

tggccattga gcggtgtatt ggagtcacaa aaccaatatt tcattctacg aaaattacat    720

ccaaacatgt gaaaatgatg ttaagtggtg tgtgcttgtt tgctgttttc atagctttgc    780

tgcccatcct tggacatcga gactataaaa ttcaggcgtc gaggacctgg tgtttctaca    840

acacagaaga catcaaagac tggaagata gattttatct tctacttttt tcttttctgg    900

ggctcttagc ccttggtgtt tcattgttgt gcaatgcaat cacaggaatt acacttttaa    960

gagttaaatt taaaagtcag cagcacagac aaggcagatc tcatcatttg gaaatggtaa   1020

tccagctcct ggcgataatg tgtgtctcct gtatttgttg gagcccattt ctgggataca   1080

gaataatttt gaatgggaaa gagaaatata aagtatatga agagcaaagt gatttcttac   1140

ataggttaca atggccaaca ttggaataaa tggaaatcat tctctggaaa cctgtgaaac   1200

aacacttttt gctctccgaa tggcaacatg gaatcaaatc ttagatcctt gggtatatat   1260

tcttctacga aaggctgtcc ttaagaatct ctataagctt gccagtcaat gctgtggagt   1320

gcatgtcatc agcttacata tttgggagct tagttccatt aaaaattcct taaaggttgc   1380

tgctatttct gagtcaccag ttgcagagaa atcagcaagc acctagctta ataggacagt   1440

aaatctgtgt ggggctagaa caaaattaag acatgtttgg caatatttca gttagttaaa   1500

tacctgtagc ctaactggaa aattcaggct tcatcatgta gtttgaagat actattgtca   1560
```

-continued

```
gattcaggtt ttgaaatttg tcaaataaac aggataactg tacatttttc acttgttttt   1620

gccaatggga ggtagacaca ataaaataat gccatgggag tcacactgaa agcaattttg   1680

agcttatctg tcttattatg ctttgagtga atcatctgtt gaggtctaat gcctttactt   1740

ggcctatttg                                                          1750


<210> SEQ ID NO 64
<211> LENGTH: 7106
<212> TYPE: DNA
<213> ORGANISM: Homo sapiens
<220> FEATURE:
<221> NAME/KEY: misc_feature
<223> OTHER INFORMATION: Incyte ID No: 7506687CB1

<400> SEQUENCE: 64

gcgtgcgaat atagtaatat aacactatga ttacatgcac gcgtcgtagc tcggaattgg     60

ctcgagcagc cggcctgcca ggtgaccatg cctgctctgg gcccagctct tctccaggct    120

ctctgggccg ggtgggtcct caccctccag ccccttccac caactgcatt cactcccaat    180

ggcacgtatc tgcagcacct ggcaagggac cccacctcag gcaccctcta cctgggggct    240

accaacttcc tgttccagct gagccctggg ctgcagctgg aggccacagt gtccaccggc    300

cctgtgctag acagcaggga ctgcctgcca cctgtgatgc ctgatgagtg cccccaggcc    360

cagcctacca acaacccgaa tcagctgctc ctggtgagcc caggggccct ggtggtatgc    420

gggagcgtgc accagggggt ctgtgaacag cggcgcctgg ggcagctcga gcagctgctg    480

ctgcggccag agcggcctgg ggacacacaa tatgtggctg ccaatgatcc tgcggtcagc    540

acggtggggc tggtagccca gggcttggca ggggagcccc tcctgtttgt ggggcgagga    600

tacaccagca ggggtgtggg gggtggcatt ccacccatca caacccgggc cctgtggccg    660

cccgaccccc aagctgcctt ctcctatgag gagacagcca agctggcagt gggccgcctc    720

tccgagtaca gccaccactt cgtgagtgcc tttgcacgtg gggccagcgc ctacttcctg    780

ttcctgcggc gggacctgca ggctcagtct agagcttttc gtgcctatgt atctcgagtg    840

tgtctccggg accagcacta ctactcctat gtggagttgc ctctggcctg cgaaggtggc    900

cgctacgggc tgatccaggc tgcagctgtg gccacgtcca gggaggtggc gcatggggag    960

gtgctctttg cagctttctc ctcggctgca ccccccactg tgggccggcc cccatcggcg   1020

gctgctgggg catctggagc ctctgccctc tgtgccttcc ccctggatga ggtggaccgg   1080

cttgctaatc gcacgcgaga tgcctgctac acccgggagg gtcgtgctga ggatgggacc   1140

gaggtggcct acatcgagta tgatgtcaat tctgactgtg cacagctgcc agtggacacc   1200

ctggatgctt atccctgtgg ctcagaccac acgcccagcc ccatggccag ccgggtcccg   1260

ctggaagcca caccaattct ggagtggcca gggattcagc taacagctgt ggcagtcacc   1320

atggaagatg gacacaccat cgctttcctg ggtgatagtc aagggcagct gcacagggtc   1380

tacttgggcc cagggagcga tggccaccca tactccacac agagcatcca gcaggggtct   1440

gcagtgagca gagacctcac ctttgatggg acctttgagc acctgtatgt catgacccag   1500

agcacacttc tgaaggttcc tgtggcttcc tgtgctcagc acctggactg tgcatcttgc   1560

cttgctcaca gggacccata ctgtgggtgg tgcgtgctcc ttggcaggtg cagtcgccgt   1620

tctgagtgct cgaggggcca gggcccagag cagtggctat ggagcttcca gcctgagctg   1680

ggctgtctgc aagtggcagc catgagtcct gccaacatca gccgagagga gacgagggag   1740

gttttcctat cagtgccaga cctgccaccc ctgtggccag ggagtcata ttcctgccac    1800
```

-continued

```
tttggggaac atcagagtcc tgccctgctg actggttctg gtgtgatgtg cccctcccca   1860
gaccctagtg aggccccagt gctgccgaga ggagccgact acgtatccgt gagcgtggag   1920
ctcagatttg gcgctgttgt gatcgccaaa acttccctct ctttctatga ctgtgtggcg   1980
gtcactgaac tccgcccatc tgcgcagtgc caggcctgtg tgagcagccg ctgggggtgt   2040
aactggtgtg tctggcagca cctgtgcacc cacaaggcct cgtgtgatgc tgggcccatg   2100
gttgcaagcc atcagagccc gcttgtctcc ccagaccctc ctgcaagagg tggacccagc   2160
ccctccccac ccacagcccc caaagccctg gccacccctg ctcctgacac ccttcccgtg   2220
gagcctgggg ctccctccac agccacagct tcggacatct cacctggggc tagtccttcc   2280
ctgctcagcc cctgggggcc atgggcaggt tctggctcca tatcttcccc tggctccaca   2340
gggtcgcctc tccatgagga gccctcccct cccagccccc aaaatggacc tggaaccgct   2400
gtccctgccc ccactgactt cagaccctca gccacacctg aggacctctt ggcctccccg   2460
ctgtcaccct cagaggtagc agcagtgccc cctgcagacc ctggccccga ggctcttcat   2520
cccacagtgc ccctggacct gcccccctgcc actgttcctg ccaccacttt cccaggggcc   2580
atgggctccg tgaagcccgc cctggactgg ctcacgagag aaggcggcga gctgcccgag   2640
gcggacgagt ggacgggggg tgacgcaccc gccttctcca cttccaccct cctctcagga   2700
agaggcgacc ttgggggcaa gctcctgccc ctgtgtggag agcgttcagg gctccacgtt   2760
gatgccggtc catgtggagc gggaaatccg gctgctaggc aggaacctgc accttttcca   2820
ggatggccca ggagacaatg agtgtgtgat ggagctggag ggcctcgagg tggtggttga   2880
ggcccgggtc gagtgtgagc cacctccaga tacccagtgc catgtcacct gccagcagca   2940
ccagctcagc tatgaggctc tgcagccgga gctccgtgtg gggctgtttc tgcgtcgggc   3000
cggccgtctg cgtgtggaca gtgctgaggg gctgcatgtg gtactgtatg actgttccgt   3060
gggacatgga gactgcagcc gctgccaaac tgccatgccc cagtatggct gtgtgtggtg   3120
tgagggggag cgtccacgtt gtgtgacccg ggaggcctgt ggtgaggctg aggctgtggc   3180
cacccagtgc ccagcgcccc tcatccactc ggtggagcca ctgactgggc ctgtagacgg   3240
aggcacccgt gtcaccatca ggggctccaa cctgggccag catgtgcagg atgtgctggg   3300
catggtcacg gtggctggag tgccctgtgc tgtggatgcc caggagtacg aggtctccag   3360
cagcctcgtg tgcatcaccg gggccagtgg ggaggaggtg gccggcgcca cagcggtgga   3420
ggtgccggga agaggacgtg gtgtctcaga acacgacttt gcctaccagg atccgaaggt   3480
ccattccatc ttcccggccc gcggccccag agctgggggc acccgtctca ccctgaatgg   3540
ctccaagctc ctgactgggc ggctggagga catccgagtg gtggttggag accagccttg   3600
tcacttgctg ccggagcagc agtcagaaca actgcggtgt gagaccagcc cacgccccac   3660
gcctgccacg ctccctgtgg ctgtgtggtt tggggccacg gagcggaggc ttcaacgcgg   3720
acagttcaag tataccttgg accccaacat cacctctgct ggccccacca agagcttcct   3780
cagtggagga cgtgagatat gcgtccgtgg ccagaatctg gacgtggtac agacgccaag   3840
aatccgggtg accgtggtct cgagaatgct gcagcccagc caggggcttg gacggaggcg   3900
tcgcgtggtc ccggagacgg catgttccct tggaccctcc tgcagtagcc agcaatttga   3960
ggagccgtgc catgtcaact cctcccagct catcacgtgc cgcacacctg ccctcccagg   4020
cctgcctgag gacccctggg tccgggtgga atttatcctt gacaacctgg tctttgactt   4080
tgcaacactg aaccccacac ctttctccta tgaggccgac cccaccctgc agccactcaa   4140
ccctgaggac cccaccatgc cattccggca caagcctggg agtgtgttct ccgtggaggg   4200
```

-continued

```
ggagaacctg gaccttgcaa tgtccaagga ggaggtggtg gctatgatag gggatggccc   4260
ctgtgtggtg aagacgctga cgcggcacca cctgtactgc gagccccccg tggagcagcc   4320
cctgccacgg caccatgccc tccgagaggc acctgactct ttgcctgagt tcacggtgca   4380
gatggggaac ttgcgcttct ccctgggtca cgtgcagtat gacggcgaga gccctggggc   4440
ttttcctgtg gcagcccagg tgggcttggg ggtgggcacc tctcttctgg ctctgggtgt   4500
catcatcatt gtcctcatgt acaggaggaa gagcaagcag gccctgaggg actataagaa   4560
ggttcagatc cagctggaga atctggagag cagtgtgcgg gaccgctgca agaaggaatt   4620
cacagacctc atgactgaga tgaccgatct caccagtgac ctcctgggca gcggcatccc   4680
cttcctcgac tacaaggtgt atgcggagag gatcttcttc cctgggcacc gcgagtcgcc   4740
cttgcaccgg gacctgggtg tgcctgagag cagacggccc actgtggagc aagggctggg   4800
gcagctctct aacctgctca acagcaagct cttcctcacc aagttcatcc acacgctgga   4860
gagccagcgc accttttcag ctcgggaccg tgcctacgtg gcatctctgc tcaccgtggc   4920
actgcatggg aagcttgagt atttcactga catcctccgc actctgctca gtgacctggt   4980
tgcccagtat gtggccaaga accccaagct gatgctgcgc aggacagaga ctgtggtgga   5040
gaagctgctc accaactgga tgtccatctg tctgtatacc ttcgtgaggg actccgtagg   5100
ggagcctctg tacatgctct ttcgagggat taagcaccaa gtggataagg ggccagtgga   5160
cagtgtgaca ggcaaggcca aatacacctt gaacgacaac cgcctgctca gagaggatgt   5220
ggagtaccgt cccctgacct tgaatgcact attggctgtg gggcctgggg caggagaggc   5280
ccagggcgtg cccgtgaagg tcctagactg tgacaccatc tcccaggcaa aggagaagat   5340
gctggaccag ctttataaag gagtgcctct cacccagcgg ccagaccctc gcacccttga   5400
tgttgagtgg cggtctgggg tggccgggca cctcattctt tctgacgagg atgtcacttc   5460
tgaggtccag ggtctgtgga ggcgcctgaa cacactgcag cattacaagg tcccagatgg   5520
agcaactgtg gccctcgtcc cctgcctcac caagcatgtg ctccgggaaa accaggatta   5580
tgtccctgga gagcggaccc caatgctgga ggatgtagat gagggggcca tccggccctg   5640
gcacctggtg aagccaagtg atgagccgga gccgcccagg cctcggaggg gcagccttcg   5700
gggcggggag cgtgagcgcg ccaaggccat ccctgagatc tacctgaccc gcctgctgtc   5760
catgaagggc accctgcaga agttcgtgga tgacctgttc caggtgattc tcagcaccag   5820
ccgccccgtg ccgctcgctg tgaagtactt ctttgacctg ctggatgagc aggcccagca   5880
gcatggcatc tccgaccagg acaccatcca catctggaag accaacagct tgcctctgag   5940
gttctggatc aatataataa aaaacccgca gtttgtgttc gacgtgcaaa catctgataa   6000
catggatgcg gtgctccttg tcattgcaca gaccttcatg gacgcctgca ccctggccga   6060
ccacaagctg ggccgggact ccccgatcaa caaacttctg tatgcacggg acattccccg   6120
gtacaagcgg atggtggaaa ggtactatgc agacatcaga cagactgtcc cagccagcga   6180
ccaagagatg aactctgtcc tggctgaact gtcctggaac tactccggag acctcggggc   6240
gcgagtggcc ctgcatgaac tctacaagta catcaacaag tactatgacc agatcatcac   6300
tgccctggag gaggatggca cggcccagaa gatgcagctg ggctatcggc tccagcagat   6360
tgcagctgct gtggaaaaca aggtcacaga tctataggaa cccaggagcc acggcctgct   6420
gttgcttcag cctggcctgg gcagccctgg aagctcggag gagaggccac cttcttaggt   6480
gcctgtagtg actgacaagc agagttagtg gaaggtgact cccagtctcc tggtggctct   6540
```

-continued ggcctcggcc ctgctggatc cacctcctag acccggggcc tcaaggctca tggggtagta 6600
cccagcctgc tccccgagtc cagcgaccct gtgacaccgg tctgcaggga gttggggact 6660
aagggcttcc agagagtggc tggaagagac tccaggcccc tggggagact gtactgttcc 6720
tgaacactgg ccttggccac actgggattc ggagaggaag gaggagagcc ccatgcttcc 6780
tgtctgcctc ctccaccatc cctgacctca gttgagctgc ctctggcctt gttgctgctg 6840
ccacatccta ggtctaagag ttgaacgcct ctcctaggcc actacaaact gacccctcag 6900
cagggctggc tgccacaggg ctgccctgcc tcataggtag ccatggtgag ggctatctgc 6960
tgcagggggg tcttggggag agtggtgact ccattgaccc agcttttcat taaaggataa 7020
cacactgcac tgagtctgat gtgtgagccc ggcctagccc ctggctacta ggaggacggc 7080
agctatgccc agcaggtacc aggggg 7106

<210> SEQ ID NO 65
<211> LENGTH: 1187
<212> TYPE: DNA
<213> ORGANISM: Homo sapiens
<220> FEATURE:
<221> NAME/KEY: misc_feature
<223> OTHER INFORMATION: Incyte ID No: 7510621CB1

<400> SEQUENCE: 65
ggaaaatgga gaagctgtgc taatagaggg gggccagaaa tccccactct agaatgctgt 60
agaatgttgg gagacaccca ggatgtgagc cagggacttt ctggaagtgt ttgttctggc 120
cccacccgac cccaggcagt ccccagctgt ctgcacagtc ggatggggag ggggcttgca 180
cagagttgga gccagaggag agagctggct catcccctac ggtaggatgg ggaaacctca 240
cagaccacat tgtcacccgg cctcagctct ccgccccggc gctcagaggg taactctcac 300
ccacctcgtc cgcttctctg aaccagagtg acccaggctg cgctccgccc cgctctccta 360
ccccgagttg gcacggaggc ccggcagcca tggcggtgga aggaggaatg aaatgtgtga 420
agttcttgct ctacgtcctc ctgctggcct tttgcgcctg tgcagtggga ctgattgccg 480
tgggtgtcgg ggcacagctt gtcctgagtc agaccataat ccagggggct accccctggct 540 ctctgttgcc agtggtcatc atcgcagtgg gtgtcttcct cttcctggtg gcttttgtgg 600
gctgctgcgg ggcctgcaag gagaactatt gtcttatgat cacgtttgcc attgctggct 660
atgtgtttag agataaggtg atgtcagagt ttaataacaa cttccggcag cagatggaga 720
attacccgaa aaacaaccac actgcttcga tcctggacag gatgcaggca gattttaagt 780
gctgtggggc tgctaactac acagattggg agaaaatccc ttccatgtcg aagaaccgag 840
tccccgactc ctgctgcatt aatgttactg tgggctgtgg gattaatttc aacgagaagg 900
cgatccataa ggagggctgt gtggagaaga ttgggggctg gctgaggaaa aatgtgctgg 960
tggtagctgc agcagccctt ggaattgctt ttgtcgaggt tttgggaatt gtctttgcct 1020
gctgcctcgt gaagagtatc agaagtggct acgaggtgat gtaggggtct ggtctcctca 1080
gcctcctcat ctgggggagt ggaatagtat cctcatctgg gggagtggaa tagtatcctc 1140
caggtttttc aattaaacgg attatttttt cagaccgaaa aaaaaaa 1187

<210> SEQ ID NO 66
<211> LENGTH: 570
<212> TYPE: DNA
<213> ORGANISM: Homo sapiens
<220> FEATURE:
<221> NAME/KEY: misc_feature
<223> OTHER INFORMATION: Incyte ID No: 7505533CB1

-continued

<400> SEQUENCE: 66
ttcggctcga gggcggcgac ggaggaggag gatggaggcg gtggtgttcg tcttctctct 60
cctcgattgt tgcgcgctca tcttcctctc ggtctacttc ataattacat tgtctgattt 120
agaatgtgat tacattaatg ctagatcatg ttgctcaaaa ttaaacaagt gggtaattcc 180
agaattgatt ggccatacca ttgtcactgt attactgctc atgtcattgc actggttcat 240
cttccttctc aacttacctg ttgccacttg gaatatatat cgaaatacac aatcgagggc 300
agctgaagtc acacatgaaa gaagccatga tcaagcttgg tttccacttg ctctgcttct 360
tcatgtatct ttatagtatg atcttagctt tgataaatga ctgaagctgg agaagccgtg 420
gttgaagtca gcctacacta cagtgcacag ttgaggagcc agagacttct taaatcatcc 480
ttagaaccgt gaccatagca gtatatattt tcctcttgga acaaaaaact atttttgctg 540
tatttttacc atataaagta tttaaaaaac 570

<210> SEQ ID NO 67
<211> LENGTH: 685
<212> TYPE: DNA
<213> ORGANISM: Homo sapiens
<220> FEATURE:
<221> NAME/KEY: misc_feature
<223> OTHER INFORMATION: Incyte ID No: 7511220CB1

<400> SEQUENCE: 67
ggccgagcgc ggggcacccg ggggcctcct gtataggcgg gcaccatggg ctcctgctcc 60
ggccgctgcg cgctcgtcgt cctctgcgct tttcagctgg tcgccgccct ggagaggcag 120
gtgtttgact tcctgggcta ccagtgggcg cccatcctgg ccaactttgt ccacatcatc 180
atcgtcatcc tgggactctt cggcaccatc cagtaccggc tgcgctacgt catggtgtac 240
acgctgtggg cagccgtctg ggtcacctgg aacgtcttca tcatctgctt ctacctggaa 300
gtcggtggcc tcttacagga cagcgagcta ctgaccttca gcctctcccg gcatcgctcc 360
tggtggcgtg agcgctggcc aggctgtctg catgaggagg tgccagcagt gggcctcggg 420
gccccccatg gccaggccct ggtgtcaggt gctggctgtg ccctggagcc cagctatgtg 480
gaggccctac acagtggcct gcagatcctg atcgcgcttc tgggctttgt ctgtggctgc 540
caggtggtca gcgtgtttac ggaggaagag gacagctgcc tgcgtaagtg aggaaacagc 600
tgatcctgct cctgtggcct ccagcctcag cgaccgacca gtgacaatga caggagctcc 660
caggccttgg gacgcgcccc caccc 685

<210> SEQ ID NO 68
<211> LENGTH: 5723
<212> TYPE: DNA
<213> ORGANISM: Homo sapiens
<220> FEATURE:
<221> NAME/KEY: misc_feature
<223> OTHER INFORMATION: Incyte ID No: 7510967CB1

<400> SEQUENCE: 68
tggccgccgg gtgtggtgag ggcgacgcgc ttgcagtcgc cgtctcttgc ttccccgtcc 60
tctgacatcg cctgcagccg agcgggcccg ttccgccgga gctgaggacc aggtattcaa 120
ataaagttaa ttgcagcttt ctgtgaaaat gtcagttttg atatcacaga gcgtcataaa 180
ttatgtagag gaagaaaaca ttcctgctct gaaagctctt cttgaaaaat gcaaagatgt 240
agatgagaga aatgagtgtg gccagactcc actgatgata gctgccgaac aaggcaatct 300

-continued

```
ggaaatagtg aaggaattaa ttaagaatgg agctaactgc aatctggaag atttggataa    360
ttggacagca cttatatctg catcgaaaga agggcatgtg cacatcgtag aggaactact    420
gaaatgtggg gttaacttgg agcaccgtga tatgggagga tggacagctc ttatgtgggc    480
atgttacaaa ggccgtactg acgtagtaga gttgcttctt tctcatggtg ccaatccaag    540
tgtcactggt ctgcagtaca gtgtttaccc aatcatttgg gcagcaggga gaggccatgc    600
agatatagtt catcttttac tgcaaaatgg tgctaaagtc aactgctctg ataagtatgg    660
aaccacccct ttagtttggg ctgcacgaaa gggtcatttg gaatgtgtga aacatttatt    720
ggccatggga gctgatgtgg atcaagaagg agctaattca atgactgcac ttattgtggc    780
agtgaaagga ggttacacac agtcagtaaa agaaattttg aagaggaatc caaatgtaaa    840
cttaacagat aaagatggaa atacagcttt gatgattgca tcaaaggagg gacatacgga    900
gattgtgcag gatctgctcg acgctggaac atatgtgaac atacctgaca ggagtgggga    960
tactgtgttg attggcgctg tcagaggtgg tcatgttgaa attgttcgag cgcttctcca   1020
aaaatatgct gatatagaca ttagaggaca ggataataaa actgctttgt attgggctgt   1080
tgagaaagga aatgcaacaa tggtgagaga tatcttacag tgcaatcctg acactgaaat   1140
atgcacaaag gatggtgaaa cgccacttat aaaggctacc aagatgagaa acattgaagt   1200
ggtggagctg ctgctagata aaggtgctaa agtgtctgct gtagataaga aaggagatac   1260
tcccttgcat attgctattc gtggaaggag ccggaaactg gcagaactgc ttttaagaaa   1320
tcccaaagat gggcgattac tttataggcc caacaaagca ggcgagactc cttataatat   1380
tgactgtagc catcagaaga gtattttaac tcaaatattt ggagccagac acttgtctcc   1440
tactgaaaca gacggtgaca tgcttggata tgatttatat agcagtgccc tggcagatat   1500
tctcagtgag cctaccatgc agccacccat ttgtgtgggg ttatatgcac agtggggaag   1560
tgggaaatct ttcttactca agaaactaga agacgaaatg aaaaccttcg ccggacaaca   1620
gattgagcct ctctttcagt tctcatggct catagtgttt cttaccctgc tactttgtgg   1680
agggcttggt ttattgtttg ccttcacggt ccacccaaat cttggaatag cagtgtcact   1740
gagcttcttg gctctcttat atatattctt tattgtcatt tactttggtg gacgaagaga   1800
aggagagagt tggaattggg cctgggtcct cagcactaga ttggcaagac atattggata   1860
tttggaactc ctccttaaat tgatgtttgt gaatccacct gagttgccag agcagactac   1920
taaagcttta cctgtgaggt tttgtttac agattacaat agactgtcca gtgtaggtgg   1980
agaaacttct ctggctgaaa tgattgcaac cctctcggat gcttgtgaaa gagagtttgg   2040
ctttttggca accaggcttt ttcgagtatt caagactgaa gatactcagg gtaaaaagaa   2100
atggaaaaaa acatgttgtc tcccatcttt tgtcatcttc ctttttatca ttggctgcat   2160
tatatctgga attactcttc tggctatatt tagagttgac ccaaagcatc tgactgtaaa   2220
tgctgtcctc atatcaatcg catctgtagt gggattggcc tttgtgttga actgtcgtac   2280
atggtggcaa gtgctggact cgctcctgaa ttcccaaaga aaacgcctcc ataatgcagc   2340
ctccaaactg cacaaattga aaagtgaagg attcatgaaa gttcttaaat gtgaagtgga   2400
attgatggcc aggatggcaa aaaccattga cagcttcact cagaatcaga caaggctggt   2460
ggtcatcatc gatggattag atgcctgtga gcaggacaaa gtccttcaga tgctggacac   2520
tgtccgagtt ctgttttcaa aaggcccgtt cattgccatt tttgcaagtg atccacatat   2580
tatcataaag gcaattaacc agaacctcaa tagtgtgctt cgggattcaa atataaatgg   2640
ccatgactac atgcgcaaca tagtccactt gcctgtgttc cttaatagtc gtggactaag   2700
```

-continued

```
caatgcaaga aaatttctcg taacttcagc aacaaatgga gacgttccat gctcagatac   2760
tacagggata caggaagatg ctgacagaag agtttcacag aacagccttg ggagatgac   2820
aaaacttggt agcaagacag ccctcaatag acgggacact taccgaagaa ggcagatgca   2880
gaggaccatc actcgccaga tgtcctttga tcttacaaaa ctgctggtta ccgaggactg   2940
gttcagtgac atcagtcccc agaccatgag aagattactt aatattgttt ctgtgacagg   3000
acgattactg agagccaatc agattagttt caactgggac aggcttgcta gctggatcaa   3060
ccttactgag cagtggccat accggacttc atggctcata ttatatttgg aagagactga   3120
aggtattcca gatcaaatga cattaaaaac catctacgaa agaatatcaa agaatattcc   3180
aacaactaag gatgttgagc cacttcttga aattgatgga gatataagaa attttgaagt   3240
gtttttgtct tcaaggaccc cagttcttgt ggctcgagat gtaaaagtct ttttgccatg   3300
cactgtaaac ctagatccca aactacggga aattattgca gatgttcgtg ctgccagaga   3360
gcagatcagt attggaggac tggcgtaccc cccgctccct ctacatgagg gtcctcctag   3420
ggcgccatca gggtacagcc agccccccatc cgtgtgctct tccacgtcct tcaatgggcc   3480
cttcgcaggt ggagtggtgt caccacagcc tcacagcagc tattacagcg gcatgacggg   3540
ccctcagcat cccttctaca acaggccatt ctttgcccca tacctttaca cgccaaggta   3600
ttaccctggc ggctcccaac atctcatctc acgtccatca gtaaaaacga gtttgcccag   3660
agatcagaac aatggcctag ggtcaggccc agccccaggc ccagtggtat tactgaattc   3720
actgaatgtg gatgcagtat gtgagaagct gaaacaaata gaagggctgg accagagtat   3780
gctgcctcag tattgtacca cgatcaaaaa ggcaaacata aatggccgtg tgttagctca   3840
gtgtaacatt gatgagctga agaaagagat gaatatgaat tttggagact ggcacctttt   3900
cagaagcaca gtactagaaa tgagaaacgc agaaagccac gtggtccctg aagacccacg   3960
tttcctcagt gagagcagca gtggcccagc cccgcacggt gagcctgctc gccgcgcttc   4020
ccacaacgag ctgcctcaca ccgagctctc cagccagacg ccctacacac tcaacttcag   4080
cttcgaagag ctgaacacgc ttggcctgga tgaaggtgcc cctcgtcaca gtaatctaag   4140
ttggcagtca caaactcgca gaaccccaag tctttcgagt ctcaattccc aggattccag   4200
tattgaaatt tcaaagctta ctgataaggt gcaggccgag tatagagatg cctatagaga   4260
atacattgct cagatgtccc agttagaagg gggccccggg tctacaacca ttagtggcag   4320
atcttctcca catagcacat attacatggg tcagagttca tcagggggct ctattcattc   4380
aaacctagag caagaaaagg ggaaggatag tgaaccaaag cccgatgatg ggaggaagtc   4440
ctttctaatg aagagggag atgttatcga ttattcatca tcaggggttt ccaccaacga   4500
tgcttccccc ctggatccta tcactgaaga agatgaaaaa tcagatcagt caggcagtaa   4560
gcttctccca ggcaagaaat cttccgaaag gtcaagcctc ttccagacag atttgaagct   4620
taagggaagt gggctgcgct atcaaaaact cccaagtgac gaggatgaat ctggcacaga   4680
agaatcagat aacactccac tgctcaaaga tgacaaagac agaaaagccg aagggaaagt   4740
agagagagtg ccgaagtctc cagaacacag tgctgagccg atcagaacct tcattaaagc   4800
caaagagtat ttatcggatg cgctccttga caaaaaggat tcatcggatt caggagtgag   4860
atccagtgaa agttctccca atcactctct gcacaatgaa gtggcggatg actcccagct   4920
tgaaaaggca aatctcatag agctggaaga tgacagtcac agcggaaagc ggggaatccc   4980
acatagcctg agtggcctgc aagatccaat tatagctcgg atgtccattt gttcagaaga   5040
```

-continued

```
caagaaaagc ccttccgaat gcagcttgat agccagcagc cctgaagaaa actggcctgc   5100

atgccagaaa gcctacaacc tgaaccgaac tcccagcacc gtgactctga acaacaatag   5160

tgctccagcc aacagagcca atcaaaattt cgatgagatg gagggaatta gggagacttc   5220

tcaagtcatt ttgaggccta gttccagtcc caacccaacc actattcaga atgagaatct   5280

aaaaagcatg acacataagc gaagccaacg ttcaagttac acaaggctct ccaaagatcc   5340

tccggagctc catgcagcag cctcttctga gagcacaggc tttggagaag aaagagaaag   5400

cattctttga gaaaaacaag caaaggagaa gagtgttact gtacccttat gacagaattg   5460

tcctggattt tgactccatc cacgcccatc acctttctac attttgctga cagataacta   5520

accgatgatg aggccgaggt aaaagagaca tctgcagtgt gacagaaggg agcatgaaaa   5580

gccatggttc acacaaggca agcttctgtg ggctttgtat tagaagcttt cgaactccac   5640

taatatatct gtggctttca ttggggcctt tccccataaa attttttgag accaggggcg   5700

accggggatt aaacaacggg cca                                           5723
```

<210> SEQ ID NO 69
<211> LENGTH: 3044
<212> TYPE: DNA
<213> ORGANISM: Homo sapiens
<220> FEATURE:
<221> NAME/KEY: misc_feature
<223> OTHER INFORMATION: Incyte ID No: 7511298CB1

<400> SEQUENCE: 69

```
agcctgtgga gacgggacag ccctgtccca ctcactcttt cccctgccgc tcctgccggc     60

agctccaacc atgggaggcc gcgtctttct cgcattctgt gtctggctga ctctgccggg    120

agctgaaacc caggactcca ggggctgtgc ccggtggtgc cctcagaact cctcgtgtgt    180

caatgccacc gcctgtcgct gcaatccagg gttcagctct tttctgaga tcatcaccac    240

cccgacggag acttgtgacg acatcaacga gtgtgcaaca ccgtcgaaag tgtcatgcgg    300

aaaattctcg gactgctgga acacagaggg gagctacgac tgcgtgtgca gcccgggata    360

tgagcctgtt tctggggcaa aaacattcaa gaatgagagc gagaacacct gtcaagatgt    420

ggacgaatgt cagcagaacc caaggctctg taaaagctac ggcacctgcg tcaacaccct    480

tggcagctat acctgccagt gcctgcctgg cttcaagttc atacctgagg atccgaaggt    540

ctgcacagat gtggacgagt gcagctccgg gcagcatcag tgtgacagct ccaccgtctg    600

cttcaacacc gtgggttcat acagctgccg ctgccgccca ggctggaagc ccagacacgg    660

aatcccgaat aaccaaaagg acactgtctg tgaagatatg actttctcca cctggacccc    720

gcccccctgga gtccacagcc agacgctttc ccgattcttc gacaaagtcc aggacctggg    780

cagagactcc aagacaagct cagccgaggt caccatccag aatgtcatca aattggtgga    840

tgaactgatg gaagctcctg gagacgtaga ggccctggcg ccacctgtcc ggcacctcat    900

agccacccag ctgctctcaa accttgaaga tatcatgagg atcctggcca agagcctgcc    960

taaaggcccc ttcacctaca tttccccttc gaacacagag ctgaccctga tgatccagga   1020

gcggggggac aagaacgtca ctatgggtca gagcagcgca cgcatgaagc tgaattgggc   1080

tgtggcagct ggagccgagg atccaggccc cgccgtggcg ggcatcctct ccatccagaa   1140

catgacgaca ttgctggcca atgcctcctt gaacctgcat tccaagaagc aagccgaact   1200

ggaggagata tatgaaagca gcatccgtgg tgtccaactc agacgcctct ctgccgtcaa   1260

ctccatcttt ctgagccaca acaacaccaa ggaactcaac tcccccatcc ttttcgcctt   1320
```

-continued

```
ctcccacctt gagtcctccg atggggaggc gggaagagac cctcctgcca aggacgtgat   1380

gcctgggcca cggcaggagc tgctctgtgc cttctggaag agtgacagcg acaggggagg   1440

gcactgggcc accgagggct gccaggtgct gggcagcaag aacggcagca ccacctgcca   1500

atgcagccac ctgagcagct ttgcgatcct tatggctcat tatgacgtgg aggactggaa   1560

gctgaccctg atcaccaggg tgggactggc gctgtcactc ttctgcctgc tgctgtgcat   1620

cctcactttc ctgctggtgc ggcccatcca gggctcgcgc accaccatac acctgcacct   1680

ctgcatctgc ctcttcgtgg gctccaccat cttcctggcc ggcatcgaga acgaaggcgg   1740

ccaggtgggg ctgcgctgcc gcctggtggc cgggctgctg cactactgtt tcctggccgc   1800

cttctgctgg atgagcctcg aaggcctgga gctctacttt cttgtggtgc gcgtgttcca   1860

aggccagggc ctgagtacgc gctggctctg cctgatcggc tatggcgtgc ccctgctcat   1920

cgtgggcgtc tcggctgcca tctacagcaa gggctacggc cgccccagat actgctggtt   1980

ggactttgag cagggcttcc tctggagctt cttgggacct gtgaccttca tcattttgtg   2040

caatgctgtc attttcgtga ctaccgtctg gaagctcact cagaagtttt ctgaaatcaa   2100

tccagacatg aagaaattaa agaaggcgag ggcgctgacc atcacggcca tcgcgcagct   2160

cttcctgttg ggctgcacct gggtctttgg cctgttcatc ttcgacgatc ggagcttggt   2220

gctgacctat gtgtttacca tcctcaactg cctgcagggc gccttcctct acctgctgca   2280

ctgcctgctc aacaagaagg ttcgggaaga ataccggaag tggcctgcc tagttgctgg    2340

ggggagcaag tactcagaat tcacctccac cacgtctggc actggccaca atcagacccg   2400

ggccctcagg gcatcagagt ccggcatatg aaggcgcatg gttctggacg gcccagcagc   2460

tcctgtggcc acagcagctt tgtacacgaa gaccatccat cctcccttcg tccaccactc   2520

tactccctcc accctccctc cctgatcccg tgtgccacca ggagggagtg gcagctatag   2580

tctggcacca aagtccagga cacccagtgg ggtggagtcg gagccactgg tcctgctgct   2640

ggctgcctct ctgctccacc ttgtgaccca gggtggggac aggggctggc ccagggctgc   2700

aatgcagcat gttgccctgg cacctgtggc cagtactcgg gacagactaa gggcgcttgt   2760

cccatcctgg acttttcctc tcatgtcttt gctgcagaac tgaagagact aggcgctggg   2820

gctcagcttc cctcttaagc taagactgat gtcagaggcc ccatggcgag gccccttggg   2880

gccactgcct gaggctcacg gtacagaggc ctgccctgcc tggccgggca ggaggttctc   2940

actgttgtga aggttgtaga cgttgtgtaa tgtgttttta tctgttaaaa tttttcagtg   3000

ttgacactta aaattaaaca catgcataca gaaaaaaaaa aaaa                    3044
```

<210> SEQ ID NO 70
<211> LENGTH: 4455
<212> TYPE: DNA
<213> ORGANISM: Homo sapiens
<220> FEATURE:
<221> NAME/KEY: misc_feature
<223> OTHER INFORMATION: Incyte ID No: 7510937CB1

<400> SEQUENCE: 70

```
cgacggcacc tgagcgactg ccgcggcggc ggcggcggcg gcggcgcctc ggagcgggcg     60

gcccgggctg tagtgccggc gccgccgcgt cttcccggtc tcctttcccg gccgcacagg    120

gttttatagg atcacattga caaaagtacc atggagtttt atgagtcagc atattttatt    180

gttcttattc cttcaatagt tattacagta attttcctct tcttctggct tttcatgaaa    240

gaaacattat atgatgaagt tcttgcaaaa cagaaaagag aacaaaagct tattcctacc    300
```

-continued

```
aaaacagata aaaagaaagc agaaaagaaa aagaataaaa agaaagaaat ccagaatgga    360
aacctccatg aatccgactc tgagagtgta cctcgagact ttaaattatc agatgctttg    420
gcagtagaag atgatcaagt tgcacctgtt ccattgaatg tcgttgaaac ttcaagtagt    480
gttagggaaa gaaaaaagaa ggaaaagaaa caaaagcctg tgcttgaaga gcaggtcatc    540
aaagaaagtg acgcatcaaa gattcctggc aaaaaagtag aacctgtccc agttactaaa    600
cagcccaccc ctccctctga agcagctgcc tcgaagaaga aaccagggca gaagaagtct    660
aaaaatggaa gcgatgacca ggataaaaag gtggaaactc tcatggtacc atcaaaaagg    720
caagaagcat tgcccctcca ccaagagact aaacaagaaa gtggatcagg gaagaagaaa    780
gcttcatcaa agaaacaaaa gacagaaaat gtcttcgtag atgaacccct tattcatgca    840
actacttata ttcctttgat ggataatgct gactcaagtc ctgtggtaga taagagagag    900
gttattgatt tgcttaaacc tgaccaagta gaagggatcc agaaatctgg gactaaaaaa    960
ctgaagaccg aaactgacaa agaaaatgct gaagtgaagt ttaaagattt tcttctgtcc   1020
ttgaagacta tgatgttttc tgaagatgag gctctttgtg ttgtagactt gctaaaggag   1080
aagtctggtg taatacaaga tgctttaaag aagtcaagta agggagaatt gactacgctt   1140
atacatcagc ttcaagaaaa ggacaagtta ctcgctgctg tgaaggaaga tgctgctgct   1200
acaaaggatc ggtgtaagca gttaacccag gaaatgatga cagagaaaga aagaagcaat   1260
gtggttataa caaggatgaa agatcgaatt ggaacattag aaaaggaaca taatgtattt   1320
caaaacaaaa tacatgtcag ttatcaagag actcaacaga tgcagatgaa gtttcagcaa   1380
gttcgtgagc agatggaggc agagatagct cacttgaagc aggaaaatgg tatactgaga   1440
gatgcagtca gcaacactac aaatcaactg gaaagcaagc agtctgcaga actaaataaa   1500
ctacgccagg attatgctag gttggtgaat gagctgactg agaaaacagg aaagctacag   1560
caagaggaag tccaaaagaa gaatgctgag caagcagcta ctcagttgaa ggttcaacta   1620
caagaagctg agagaaggtg ggaagaagtt cagagctaca tcaggaagag aacagcggaa   1680
catgaggcag cacagcaaga tttacagagt aaatttgtgg ccaaagaaaa tgaagtacag   1740
agtctgcata gtaagcttac agataccttg gtatcaaaac aacagttgga gcaaagacta   1800
atgcagttaa tggaatcaga gcagaaaagg gtgaacaaag aagagtctct acaaatgcag   1860
gttcaggata ttttggagca gaatgaggct ttgaaagctc aaattcagca gttccattcc   1920
cagatagcag cccagacctc cgcttcagtt ctagcagaag aattacataa agtgattgca   1980
gaaaaggata agcagataaa acagactgaa gattctttag caagtgaacg tgatcgttta   2040
acaagtaaag aagaggaact taaggatata cagaatatga atttcttatt aaaagctgaa   2100
gtgcagaaat tacaggccct ggcaaatgag caggctgctg ctgcacatga attggagaag   2160
atgcaacaaa gtgtttatgt taaagatgat aaaataagat tgctggaaga gcaactacaa   2220
catgaaattt caaacaaaat ggaagaattt aagattctaa atgaccaaaa caaagcatta   2280
aaatcagaag ttcagaagct acagactctt gtttctgaac agcctaataa ggatgttgtg   2340
gaacaaatgg aaaaatgcat tcaagaaaaa gatgagaagt taaagactgt ggaagaatta   2400
cttgaaactg gacttattca ggtggcaact aaagaagagg agctgaatgc aataagaaca   2460
gaaaattcat ctctgacaaa agaagttcaa gacttaaaag ctaagcaaaa tgatcaggtt   2520
tcttttgcct ctctagttga agaacttaag aaagtgatcc atgagaaaga tggaaagatc   2580
aagtctgtag aagagcttct ggaggcagaa cttctcaaag ttgctaacaa ggagaaaact   2640
gttcaggatt tgaaacagga aataaaggct ctaaaagaag aaataggaaa tgtccagctt   2700
```

-continued gaaaaggctc aacagttatc tatcacttcc aaagttcagg agcttcagaa cttattaaaa 2760
ggaaaagagg aacagatgaa taccatgaag gctgttttgg aagagaaaga gaaagaccta 2820
gccaatacag ggaagtggtt acaggatctt caagaagaaa atgaatcttt aaaagcacat 2880
gttcaggaag tagcacaaca taacttgaaa gaggcctctt ctgcatcaca gtttgaagaa 2940
cttgagattg tgttgaaaga aaaggaaaat gaattgaaga ggttagaagc catgctaaaa 3000
gagagggaga gtgatctttc tagcaaaaca cagctgttac aggatgtaca agatgaaaac 3060
aaattgttta agtcccaaat tgagcagctt aaacaacaaa actaccaaca ggcatcttct 3120 tttcccccctc atgaagaatt attaaaagta atttcagaaa gagagaaaga aataagtggt 3180
ctctggaatg agttagattc tttgaaggat gcagttgaac accagaggaa gaaaaacaat 3240
gaaaggcagc aacaggtgga agctgttgag ttggaggcta aagaagttct caaaaaatta 3300
tttccaaagg tgtctgtccc ttctaatttg agttatggtg aatggttgca tggatttgaa 3360
aaaaaggcaa aagaatgtat ggctggaact tcagggtcag aggaggttaa ggttctagag 3420
cacaagttga aagaagctga tgaaatgcac acattgttac agctagagtg tgaaaaatac 3480
aaatccgtcc ttgcagaaac agaaggaatt ttacagaagc tacagagaag tgttgagcaa 3540
gaagaaaata aatggaaagt taaggtcgat gaatcacaca agactattaa acagatgcag 3600
tcatcattta catcttcaga acaagagcta gagcgattaa gaagcgaaaa taaggatatt 3660
gaaaatctga gaagagaacg agaacatttg gaaatggaac tagaaaaggc agagatggaa 3720
cgatctacct atgttacaga agtcagagag ctgaaagatc tgttgactga attgcagaaa 3780
aaacttgatg attcatattc tgaagcagta agacagaatg aagagctaaa tttgttgaag 3840
gcacagttaa atgaaacact cacaaaactt agaactgaac aaaatgaaag acagaaggta 3900
gctggtgatt tgcataaggc tcaacagtca ctggagctta tccagtcaaa aatagtaaaa 3960
gctgctggag acactactgt tattgaaaat agtgatgttt ccccagaaac ggagtcttct 4020
gagaaggaga caatgtctgt aagtctaaat cagactgtaa cacagttaca gcagttgctt 4080
caggcggtaa accaacagct cacaaaggag aaagagcact accaggtgtt agagtgaagt 4140
aattgggaaa ctgttcattt gaggataaaa aaggcattgt attatatttt gccaaattaa 4200
agccttattt atgttttcac cctttctact ttgtcagaaa cactgaacag agttttgtct 4260
tttctaatcc ttgttagact actgatttaa agaaggaaaa aaaaaagcca actctgtaga 4320
caccttcaga gtttagtttt ataataaaaa ctgtttgaat aattagacct ttacattcct 4380
gaagataaac atgtaatctt ttatcttatt ttgctcaata aaattgttca gaagaaaaaa 4440
aaaaaaaaaa aaaaa 4455

<210> SEQ ID NO 71
<211> LENGTH: 1949
<212> TYPE: DNA
<213> ORGANISM: Homo sapiens
<220> FEATURE:
<221> NAME/KEY: misc_feature
<223> OTHER INFORMATION: Incyte ID No: 7511852CB1

<400> SEQUENCE: 71
tacccatggc gcccgtcgcc gtctgggccg cgctggccgt cggactggag ctctgggctg 60
cggcgcacgc cttgcccgcc caggtggcat ttacaccta cgccccggag cccgggagca 120
catgccggct cagagaatac tatgaccaga cagctcagat gtgctgcagc aaatgctcgc 180
cgggccaaca tgcaaaagtc ttctgtacca agacctcgga caccgtgtgt gactcctgtg 240

-continued

```
aggacagcac atacacccag ctctggaact gggttcccga gtgcttgagc tgtggctccc    300

gctgtagctc tgaccaggtg gaaactcaag cctgcactcg ggaacagaac cgcatctgca    360

cctgcaggcc cggctggtac tgcgcgctga gcaagcagga ggggtgccgg ctgtgcgcgc    420

cgctgcgcaa gtgccgcccg ggcttcggcg tggccagacc aggaactgaa acatcagacg    480

tggtgtgcaa gccctgtgcc ccggggacgt tctccaacac gacttcatcc acggatattt    540

gcaggcccca ccagatctgt aacgtggtgg ccatccctgg gaatgcaagc atggatgcag    600

tctgcacgtc cacgtccccc acccggagta tggccccagg ggcagtacac ttaccccagc    660

cagtgtccac acgatcccaa cacacgcagc caactccaga acccagcact gctccaagca    720

cctccttcct gctcccaatg ggccccagcc ccccagctga agggagcact ggcgacttcg    780

ctcttccagt tgattcttcc cctggtggcc atgggaccca ggtcaatgtc acctgcatcg    840

tgaacgtctg tagcagctct gaccacagct cacagtgctc ctcccaagcc agctccacaa    900

tgggagacac agattccagc ccctcggagt ccccgaagga cgagcaggtc cccttctcca    960

aggaggaatg tgcctttcgg tcacagctgg agacgccaga gaccctgctg gggagcaccg   1020

aagagaagcc cctgcccctt ggagtgcctg atgctgggat gaagcccagt taaccaggcc   1080

ggtgtgggct gtgtcgtagc caaggtgggc tgagccctgg caggatgacc ctgcgaaggg   1140

gccctggtcc ttccaggccc ccaccactag gactctgagg ctctttctgg gccaagttcc   1200

tctagtgccc tccacagccg cagcctccct ctgacctgca ggccaagagc agaggcagcg   1260

ggttgtggaa agcctctgct gccatggcgt gtccctctcg gaaggctggc tgggcatgga   1320

cgttcggggc atgctggggc aagtccctga ctctctgtga cctgccccgc ccagctgcac   1380

ctgccagcct ggcttctgga gcccttgggt tttttgtttg tttgtttgtt tgtttgtttg   1440

tttctccccc tgggctctgc cccagctctg gcttccagaa aaccccagca tccttttctg   1500

cagaggggct ttctggagag gagggatgct gcctgagtca cccatgaaga caggacagtg   1560

cttcagcctg aggctgagac tgcgggatgg tcctggggct ctgtgcaggg aggaggtggc   1620

agccctgtag ggaacggggt ccttcaagtt agctcaggag gcttggaaag catcacctca   1680

ggccaggtgc agtggctcac gcctatgatc ccagcacttt gggaggctga ggcgggtgga   1740

tcacctgagg ttaggagttc gagaccagcc tggccaacat ggtaaaaccc catctctact   1800

aaaaatacag aaattagccg ggcgtggtgg cgggcaccta tagtcccagc tactcagaag   1860

cctgaggctg ggaaatcgtt tgaacccggg aagcggaggt tgcagggagc cgagatcacg   1920

ccactgcact cgagactggc gacagaatc                                     1949
```

<210> SEQ ID NO 72
<211> LENGTH: 1322
<212> TYPE: DNA
<213> ORGANISM: Homo sapiens
<220> FEATURE:
<221> NAME/KEY: misc_feature
<223> OTHER INFORMATION: Incyte ID No: 7511077CB1

<400> SEQUENCE: 72

```
ccggcgccgg gcgcccgata ccgggagccg ccgccatggg ggcctgcctg ggagcctgct     60

ccctgctcag ctgcgcgtcc tgcctctgcg gctctgcccc ctgcatcctg tgcagctgct    120

gccccgccag ccgcaactcc accgtgagcc gcctcatctt cacgttcttc ctcttcctgg    180

gggtgctggt gtccatcatt atgctgagcc cgggcgtgga gagtcagctc tacaagctgc    240

cctgggtgtg tgaggagggg gccgggatcc ccaccgtcct gcagggccac atcgactgtg    300
```

-continued gctccctgct tggctaccgc gctgtctacc gcatgtgctt cgccacggcg gccttcttct 360
tctttttcac cctgctcatg ctctgcgtga gcagcagccg ggacccccgg gctgccatcc 420
agaatgggtt ttggttcttt aagttcctga tcctggtggg cctcaccgtg ggtgccttct 480
acatccctga cggctccttc accaacatct ggttctactt cggcgtcgtg ggctccttcc 540
tcttcatcct catccagctg gtgctgctca ttgactttgc gcactcctgg aaccagcggt 600
ggctgggcaa ggccgaggag tgcgattccc gtgcctggta cgcaggcctc ttcttcttca 660
ctctcctctt ctacttgctg tcgatcgcgg ccgtggcgct gatgttcatg tactacactg 720
agcccagcgg ctgccacgag ggcaaggtct tcatcagcct caacctcacc ttctgtgtct 780
gcgtgtccat cgctgctgtc ctgcccaagg tccagtctgc gctcctcaga ccaccggcag 840
gtgaacagcc tgatgcagac cgaggagtgc ccacctatgc tagacgccac acagcagcag 900
cagcagcagg tggcagcctg tgagggccgg gcctttgaca acgagcagga cggcgtcacc 960
tacagctact ccttcttcca cttctgcctg gtgctggcct cactgcacgt catgatgacg 1020
ctcaccaact ggtacaagcc cggtgagacc cggaagatga tcagcacgtg gaccgccgtg 1080
tgggtgaaga tctgtgccag ctgggcaggg ctgctcctct acctgtggac cctggtagcc 1140
ccactcctcc tgcgcaaccg cgacttcagc tgaggcagcc tcacagcctg ccatctggtg 1200
cctcctgcca cctggtgcct ctcggctcgg tgacagccac cctgccccct tcctggactt 1260
cgtgccttac tgagtctcta agactttttc taataaacaa gccagtgcgt gtaacaaaaa 1320
aa 1322

<210> SEQ ID NO 73
<211> LENGTH: 1381
<212> TYPE: DNA
<213> ORGANISM: Homo sapiens
<220> FEATURE:
<221> NAME/KEY: misc_feature
<223> OTHER INFORMATION: Incyte ID No: 7511576CB1

<400> SEQUENCE: 73
atttcacaaa tctacaatct gtgagtatca catcctgtat agctgtaaac actggaataa 60
ggaagggctg atgactttca gaagatgaag gtaagtagaa accgttgatg ggactgagaa 120
accagagtta aaacctcttt ggagcttctg aggactcagc tggaaccaac gggcacagtt 180
ggcaacacca tcatgacatc acaacctgtt cccaatgaga ccatcatagt gctcccatca 240
aatgtcatca acttctccca agcagagaaa cccgaaccca ccaaccaggg gcaggatagc 300
ctgaagaaac atctacacgc agaaatcaaa gttattgggt ttatcatctc tggctctcta 360
tcaatcgcca cagagaaaag gttaaccaag cttttggtgc atagcagcct ggttggaagc 420
attctgagtg ctctgtctgc cctggtgggt ttcattatcc tgtctgtcaa acaggccacc 480
ttaaatcctg cctcactgca gtgtgagttg gacaaaaata atataccaac aagaagttat 540
gtttcttact tttatcatga ttcactttat accacggact gctatacagc caaagccagt 600
ctggctggaa ctctctctct gatgctgatt tgcactctgc tggaattctg cctagctgtg 660
ctcactgctg tgctgcggtg gaaacaggct tactctgact tccctgggag tgtacttttc 720
ctgcctcaca gttacattgg taattctggc atgtcctcaa aatgactca tgactgtgga 780 tatgaagaac tattgacttc ttaagaaaaa agggagaaat attaatcaga aagttgattc 840
ttatgataat atggaaaagt taaccattat agaaaagcaa agcttgagtt tcctaaatgt 900
aagcttttaa agtaatgaac attaaaaaaa accattattt cactgtcatt taagatatgt 960

-continued

```
gttcattggg gatctcttga tttgcctgac attgacttca gcaaaagcac ggggctgtaa   1020

attaccattt actagattag ccaaatagtc tgaatttcca gaaaacaagg cagaatgatc   1080

attcccagaa acatttccca gaaaatgttt cccagaaaac tagacagaat gatcattcaa   1140

tggatcacag tgaagcaaag gacacaactt tttattgtac cccttaattg tcaacaggag   1200

ttaactgatt tgttgtggtg ctcagacttt tttatacagg tgctagtgtt ttatcctatg   1260

tattttaact cattagtgca taaaggcaag ccccatataa tgaagtctca gggtatatga   1320

aagtagctgg cttcaaaata aaatttttga gtgcaaaaaa aaaaaaaaaa aaaaaaaaaa   1380

g                                                                   1381
```

<210> SEQ ID NO 74
<211> LENGTH: 1027
<212> TYPE: DNA
<213> ORGANISM: Homo sapiens
<220> FEATURE:
<221> NAME/KEY: misc_feature
<223> OTHER INFORMATION: Incyte ID No: 7511492CB1

<400> SEQUENCE: 74

```
gaagattcca gcaccctccc ctaactccag gccagactcc tttcagctaa aggggagatc     60

tggatggcat ctacttcgta tgactattgc agagtgccca tggaagacgg ggataagcgc    120

tgtaagcttc tgctggggat aggaattctg gtgctcctga tcatcgtgat tctgggggtg    180

cccttgatta tcttcaccat caaggccaac agcgaggcct gccgggacgg ccttcgggca    240

gtgatggagt gtcgcaatgt cacccatctc ctgcaacaag agctgaccga ggcccagaag    300

ggctttcagg atgtggaggc ccaggccgcc acctgcaacc acactgtgaa gagaaaacca    360

ggtcttaagc gtgagaatcg cggacaagaa gtactacccc agctcccagg actccagctc    420

cgctgcggcg ccccagctgc tgattgtgct gctgggcctc agcgctctgc tgcagtgaga    480

tcccaggaag ctggcacatc ttggaaggtc cgtcctgctc ggcttttcgc ttgaacattc    540

ccttgatctc atcagttctg agcgggtcat ggggcaacac ggttagcggg gagagcacgg    600

ggtagccgga gaagggcctc tggagcaggt ctggaggggc catggggcag tcctgggtgt    660

ggggacacag tcgggttgac ccagggctgt ctccctccag agcctccctc cggacaagat    720

cccctctgtc ccaccgaaat ggcagggtgc ggtggggcag tccgctgtgt atggtctttt    780

gcggggggtg ctttcgggtc tgactcacaa aaaccccctt gagaaacacc taaaaaaaaa    840

aaaaaaacaa aaggggccaa aagccgaggg gcccccccga gaaaacaccc cccccagtgt    900

taaacccggg gaccgaaacc ccgcggggag ggcccccaaa aagcccggga caaatggtct    960

tgctcccccc ccgccgaagg ccggatagaa aaccagagac aatcctgtta acacccgccg   1020

ccccccc                                                             1027
```

<210> SEQ ID NO 75
<211> LENGTH: 3040
<212> TYPE: DNA
<213> ORGANISM: Homo sapiens
<220> FEATURE:
<221> NAME/KEY: misc_feature
<223> OTHER INFORMATION: Incyte ID No: 7511141CB1

<400> SEQUENCE: 75

```
gccgcaggtc gggtggctca gccatggctc ctcggggcgc agcggccggc cggagcccgg     60

gaccctgcgc ggggcgctga gctcccgagc gggcagaggg cacgggcagg cggacgtcgg    120
```

-continued

```
ggcgccctcg gggaacgtgc gggcaccatg cgtccccacc tgtcgccgcc gctgcagcag    180
ctactactgc cggtgctgct cgcctgcgcc gcgcactcga ctggagccct tccccgacta    240
tgtgacgtgc tacaagtgct gtgggaagag caagaccagt gcctgcagga actctccaga    300
gagcagacag gagacctggg cacggagcag ccagtgccag gttgtgaggg gatgtgggac    360
aacataagct gctggccctc ttctgtgccg ggccggatgg tggaggtgga atgcccgaga    420
ttcctccgga tgctcaccag cagaaatggt tccttgttcc gaaactgcac acaggatggc    480
tggtcagaaa ccttccccag gcctaatctg gcctgtggcg ttaatgtgaa cgactcttcc    540
aacgagaagc gggaggctcc actgcactcg caactacatc cacatgcacc tgttcgtgtc    600
cttcatcctt cgtgccctgt ccaacttcat caaggacgcc gtgctcttct cctcagatga    660
tgtcacctac tgcgatgccc acagggcggg ctgcaagctg gtcatggtgc tgttccagta    720
ctgcatcatg gccaactact cctggctgct ggtggaaggc ctctaccttc acacactcct    780
cgccatctcc ttcttctctg aaagaaagta cctccaggga tttgtggcat tcggatgggg    840
ttctccagcc atttttgttg ctttgtgggc tattgccaga cactttctgg aagatgttgg    900
gtaagctaac ggaaggagga taacaagaat gtatctgaca tcgtccagct tttcaaacag    960
catagttact tctttggagc tatctaggaa aggccttttt ctcaaagtag aggccacaga   1020
tgagttccct ggactgatgc tcactgcttc ccaggtgtgt ttccaggtgg gccgagcagc   1080
cttggccatg cctgcactgt cctggccttc ctgtcttctt gctgcctgtc cgctctgcat   1140
gtgggtcaga tgccagacaa gagctacggg gctccaggca ggtgttgctc catggaagaa   1200
actcaaggaa gggccagtcc agctttttct tcctcctggg atctccctcc tggatgcctc   1260
tctacccctg ggtgtttagg agccctgcag agccagactc taaagaagtc aggcattgag   1320
ggtggcagtg agcccagggg acgcacctgg gagtaggtac atgggaagca agcttaaaag   1380
aagctgggga agaggagagg cagcagggca gcagcgaggc agcggggcag catgggagtt   1440
gatttctcag gggcataatg acacaaccag gccaataagt ggatgaggtc aaatgagaca   1500
tccaagtgtc tatagtccaa atttagcccg aaataattgc ttcaaagtaa tttttgtatt   1560
gggtgaattc actttttcaa aaaatctgga ttttcagctt gtctagaaaa aaatggagag   1620
gtcctttaac acgttccatt tttccttgtg gcaaaaataa gctggagcag agctgcggct   1680
gtcttggaca gggcacatgc tccccagttt gctcagtacc ctccaggcct gatgtcccca   1740
gatcctgagg tcacatgtca gccatccacc acttctctta ctgatgtcat cttcctggct   1800
tctgttggta gctgagtttg ccaccgtgct cgctggtgaa ttctgacagt aagctaactt   1860
ttggatctgg gagtctcccg gctctcaggt tctcgcaggg agacaggtgg ccactccctc   1920
agccccagca gtgctcctgg gtggcaggag ggggtgttct aatggtgctg ggcacaccac   1980
tgcaggggct cagtgccaca aacacaggtc cttcatacca agggccacct cagggaacat   2040
gtccttgctg gttagcccag ctcccacagc tcccgctcat aaccatgccc agctgtccct   2100
cccttaggtg ctgggacatc aatgccaacg catccatctg gtggatcatt cgtggtcctg   2160
tgatcctctc catcctgatt aatttcatcc ttttcataaa cattctaaga atcctgatga   2220
gaaaacttag aacccaagaa acaagaggaa atgaagtcag ccattataag cgcctggcca   2280
ggtccactct cctgctgatc cccctctttg gcatccacta catcgtcttc gccttctccc   2340
cagaggacgc tatggagatc cagctgtttt ttgaactagc ccttggctca ttccagggac   2400
tggtggtggc cgtcctctac tgcttcctca acggggaggt gcagctggag gttcagaaga   2460
agtggcagca atggcacctc cgtgagttcc cactgcaccc cgtggcctcc ttcagcaaca   2520
```

-continued

```
gcaccaaggc cagccacttg gagcagagcc agggcacctg caggaccagc atcatctgag   2580

aggctggagc agggtcaccc atggacagag accaagagag gtcctgcgaa ggctgggcac   2640

tgctgtggga cagccagtct tcccagcaga caccctgtgt cctccttcag ctgaagatgc   2700

ccctccccag gccttggact cttccgaagg gatgtgaggc actgtggggc aggacaaggg   2760

cctgggattg gttcgttgct cttctgggaa gagaagttca ggggtcccat aaagggaccg   2820

cgaccttact atggtgcctg gatgagaaaa atgcgtgtaa gaaaagacac aaggaaatac   2880

ctgggctgca gggaagactc cgataattcc aaagataata tggcttacac taccgaacta   2940

cgagtgggta gacccgtata ccaaattact gcctagtagt gaggtcgata taagatctgc   3000

aacctgcgtg ttattacgcc gtcgacacct gggagcggcc                         3040
```

```
<210> SEQ ID NO 76
<211> LENGTH: 3158
<212> TYPE: DNA
<213> ORGANISM: Homo sapiens
<220> FEATURE:
<221> NAME/KEY: misc_feature
<223> OTHER INFORMATION: Incyte ID No: 7511300CB1

<400> SEQUENCE: 76

agcctgtgga gacgggacag ccctgtccca ctcactcttt cccctgccgc tcctgccggc     60

agctccaacc atgggaggcc gcgtctttct cgcattctgt gtctggctga ctctgccggg    120

agctgaaacc caggactcca ggggctgtgc ccggtggtgc cctcagaact cctcgtgtgt    180

caatgccacc gcctgtcgct gcaatccagg gttcagctct ttttctgaga tcatcaccac    240

cccgacggag acttgtgacg acatcaacga gtgtgcaaca ccgtcgaaag tgtcatgcgg    300

aaaattctcg gactgctgga acacagaggg gagctacgac tgcgtgtgca gcccgggata    360

tgagcctgtt tctggggcaa aaacattcaa gaatgagagc gagaacacct gtcaagatgt    420

ggacgaatgt cagcagaacc caaggctctg taaaagctac ggcacctgcg tcaacaccct    480

tggcagctat acctgccagt gcctgcctgg cttcaagttc atacctgagg atccgaaggt    540

ctgcacagat gtgaatgaat gcacctccgg acaaaacccg tgccacagct ccacccactg    600

cctcaacaac gtgggcagct atcagtgccg ctgccgcccg ggctggcaac cgattccggg    660

gtcccccaat ggcccaaaca ataccgtctg tgaagatgtg gacgagtgca gctccgggca    720

gcatcagtgt gacagctcca ccgtctgctt caacaccgtg ggttcataca gctgccgctg    780

ccgcccaggc tggaagccca gacacggaat cccgaataac caaaaggaca ctgtctgtga    840

agatatgact ttctccacct ggaccccgcc ccctggagtc cacagccaga cgctttcccg    900

attcttcgac aaagtccagg acctgggcag agactccaag acaagctcag ccgaggtcac    960

catccagaat gtcatcaaat tggtggatga actgatggaa gctcctggag acgtagaggc   1020

cctggcgcca cctgtccggc acctcatagc cacccagctg ctctcaaacc ttgaagatat   1080

catgaggatc ctggccaaga gcctgcctaa aggccccttc acctacattt cccctcgaa    1140

cacagagctg accctgatga tccaggagcg gggggacaag aacgtcacta tgggtcagag   1200

cagcgcacgc atgaagctga attgggctgt ggcagctgga gccgaggatc caggccccgc   1260

cgtggcgggc atcctctcca tccagaacat gacgacattg ctggccaatg cctccttgaa   1320

cctgcattcc aagaagcaag ccgaactgga ggagatatat gaaagcagca tccgtggtgt   1380

ccaactcaga cgcctctctg ccgtcaactc catctttctg agccacaaca acaccaagga   1440

actcaactcc cccatccttt tcgccttctc ccaccttgag tcctccgatg ggaggcgggg   1500
```

-continued

```
aagagaccct cctgccaagg acgtgatgcc tgggccacgg caggagctgc tctgtgcctt   1560
ctggaagagt gacagcgaca ggggagggca ctgggccacc gagggctgcc aggtgctggg   1620
cagcaagaac ggcagcacca cctgccaatg cagccacctg agcagctttg cgatccttat   1680
ggctcattat gacgtggagg actggaagct gaccctgatc accagggtgg gactggcgct   1740
gtcactcttc tgcctgctgc tgtgcatcct cactttcctg ctggtgcggc ccatccaggg   1800
ctcgcgcacc accatacacc tgcacctctg catctgcctc ttcgtgggct ccaccatctt   1860
cctggccggc atcgagaacg aaggcggcca ggtggggctg cgctgccgcc tggtggccgg   1920
gctgctgcac tactgtttcc tggccgcctt ctgctggatg agcctcgaag gcctggagct   1980
ctactttctt gtggtgcgcg tgttccaagg ccagggcctg agtacgcgct ggctctgcct   2040
gatcggctat ggcgtgcccc tgctcatcgt gggcgtctcg gctgccatct acagcaaggg   2100
ctacggccgc cccagatact gctggttgga ctttgagcag ggcttcctct ggagcttctt   2160
gggacctgtg accttcatca ttttgtgcaa tgctgtcatt ttcgtgacta ccgtctggaa   2220
gctcactcag aagttttctg aaatcaatcc agacatgaag aaattaaaga aggcgagggc   2280
gctgaccatc acggccatcg cgcagctctt cctgttgggc tgcacctggg tctttggcct   2340
gttcatcttc gacgatcgga gcttggtgct gacctatgtg tttaccatcc tcaactgcct   2400
gcagggcgcc ttcctctacc tgctgcactg cctgctcaac aagaaggccc tcagggcatc   2460
agagtccggc atatgaaggc gcatggttct ggacggccca gcagctcctg tggccacagc   2520
agctttgtac acgaagacca tccatcctcc cttcgtccac cactctactc cctccaccct   2580
ccctccctga tcccgtgtgc caccaggagg gagtggcagc tatagtctgg caccaaagtc   2640
caggacaccc agtggggtgg agtcggagcc actggtcctg ctgctggctg cctctctgct   2700
ccaccttgtg acccagggtg gggacagggg ctggcccagg gctgcaatgc agcatgttgc   2760
cctggcacct gtggccagta ctcgggacag actaagggcg cttgtcccat cctggacttt   2820
tcctctcatg tctttgctgc agaactgaag agactaggcg ctggggctca gcttccctct   2880
taagctaaga ctgatgtcag aggccccatg gcgaggcccc ttggggccac tgcctgaggc   2940
tcacggtaca gaggcctgcc ctgcctggcc gggcaggagg ttctcactgt tgtgaaggtt   3000
gtagacgttg tgtaatgtgt ttttatctgt taaaattttt cagtgttgac acttaaaatt   3060
aaacacatgc atacagaaaa aaaaaaaaaa aaaaaaaaaa aaaaaaaaaa aaaaaaaaaa   3120
aaaaaaaaaa aaaaaaaaaa aaaaaaaaaa aaaaaaaa                           3158
```